(12) United States Patent
Conner et al.

(10) Patent No.: US 7,655,641 B2
(45) Date of Patent: Feb. 2, 2010

(54) SULFONAMIDE DERIVATIVES AS PPAR MODULATORS

(75) Inventors: Scott Eugene Conner, Indianapolis, IN (US); Lynn Stacy Gossett, Indianapolis, IN (US); Jonathan Edward Green, Avon, IN (US); Winton Dennis Jones, Jr., Carmel, IN (US); Nathan Bryan Mantlo, Brownsburg, IN (US); Donald Paul Matthews, Indianapolis, IN (US); Daniel Ray Mayhugh, Carmel, IN (US); Daryl Lynn Smith, Fishers, IN (US); Jennifer Ann Vance, San Jose, CA (US); Xiaodong Wang, Carmel, IN (US); Alan M Warshawsky, Carmel, IN (US); Leonard Larry Winneroski, Jr., Greenwood, IN (US); Yanping Xu, Fishers, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 728 days.

(21) Appl. No.: 10/542,579

(22) PCT Filed: Feb. 10, 2004

(86) PCT No.: PCT/US2004/002015

§ 371 (c)(1),
(2), (4) Date: Jul. 15, 2005

(87) PCT Pub. No.: WO2004/073606

PCT Pub. Date: Sep. 2, 2004

(65) Prior Publication Data

US 2006/0217433 A1    Sep. 28, 2006

Related U.S. Application Data

(60) Provisional application No. 60/448,307, filed on Feb. 14, 2003.

(51) Int. Cl.
*A61K 31/66* (2006.01)
*A61K 31/38* (2006.01)
*C07D 409/12* (2006.01)
*C07D 209/04* (2006.01)

(52) U.S. Cl. .............. 514/141; 514/443; 548/467; 549/51; 549/52; 549/54; 549/55

(58) Field of Classification Search .............. 514/141, 514/443; 548/467; 549/51, 52, 54, 55
See application file for complete search history.

(56) References Cited

U.S. PATENT DOCUMENTS

| | | | |
|---|---|---|---|
| 5,089,514 A | 2/1992 | Hulin | |
| 5,232,945 A | 8/1993 | Hulin | |
| 5,306,726 A | 4/1994 | Hulin | |
| 5,902,726 A | 5/1999 | Kliewer et al. | |
| 5,994,554 A | 11/1999 | Kliewer et al. | |
| 6,248,781 B1 | 6/2001 | Jeppesen et al. | |
| 6,306,854 B1 | 10/2001 | Brown et al. | |
| 6,369,098 B1 | 4/2002 | Pershadsingh et al. | |
| 6,506,757 B1 | 1/2003 | Tajima et al. | |
| 6,518,290 B1 | 2/2003 | Sierra | |
| 7,071,220 B2 * | 7/2006 | Satoh et al. | 514/365 |

FOREIGN PATENT DOCUMENTS

| | | |
|---|---|---|
| EP | 0 930 229 | 7/1999 |
| EP | 1 167 357 | 2/2002 |
| EP | 1 216 980 | 6/2002 |
| GB | 2 359 082 | 8/2001 |
| WO | WO 97/28115 | 8/1997 |
| WO | WO 97/31907 | 9/1997 |
| WO | WO 01/00566 | 1/2001 |
| WO | WO 01/16120 | 3/2001 |
| WO | WO 02/16332 | 2/2002 |
| WO | WO 02/18355 | 3/2002 |
| WO | WO 02/100813 | 12/2002 |
| WO | WO 03/072099 | 9/2003 |

OTHER PUBLICATIONS

Sato, et al., "Synthesis and evaluation of novel fluorinated sulotroban-related sulfonamide derivatives as thromboxane A2 receptor antagonists," *Eur. J. Med. Chem.*, 30, pp. 403-414 (1995).
Sato, et al., "Asymmetric Synthesis of the Sulfoxide Metabolite of On-579 By The Kagan Protocol," *Bioorganic and Medicinal Chemistry Letters*, vol. 7 No. 19, pp. 2451-2454 (1997).
Shinozaki, et al., "Synthesis and thromboxane A2 antagonist activity of indane derivatives," *Bioorganic and Medicinal Chemistry Letters*, vol. 9, pp. 401-406 (1999).
Sato, et al., "Synthesis and evaluation of novel sulfonamide derivatives as thromboxane A2 receptor antagonists I," *Eur. J. Med. Chem.*, vol. 29, pp. 185-190 (1994).
Berlot, et al., "Preparation of a dansylated fibrate, a new fluorescent tool to study peroxisome proliferation. Effect on hepatic-derived cell lines," *Biochimie*, vol. 79, pp. 145-150 (1997).

(Continued)

*Primary Examiner*—Peter G O'Sullivan
(74) *Attorney, Agent, or Firm*—MaCharri Vorndran-Jones

(57) ABSTRACT

The present invention is directed to a compound of Formula (I): and pharmaceutically acceptable salts, solvates, hydrates or stereoisomers thereof, which are useful in treating or preventing disorders mediated by a peroxisome proliferator activated receptor (PPAR) such as syndrome X, type II diabetes, hyperglycemia, hyperlipidemia, obesity, coagaulopathy, hypertension, arteriosclerosis, and other disorders related to syndrome X and cardiovascular diseases.

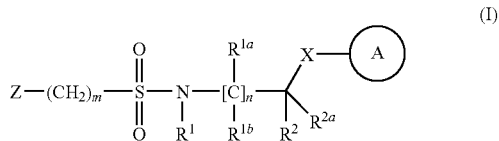

(I)

19 Claims, No Drawings

OTHER PUBLICATIONS

Liu, et al., "Identification of a Series of PPARγ/δ Dual Agonists Via Solid-Phase Parallel Synthesis," *Bioorganic and Medicinal Chemistry Letters*, vol. 11, pp. 2959-2962 (2001).

Sarges, et al., "Glucose Transport-Enhancing and Hypoglycemic Activity of 2-Methyl-2-phenoxy-3-phenylpropanoic Acids," J. Med. Chem., vol. 39, No. 24, pp. 4783-4802 (Nov. 22, 1996).

Cobb, et al., "N-(2-Benzoylphenyl)-L-tyrosine PPAR Agonists. 3. Structure-Activity Relationship and Optimization of the N-Aryl Substituent," J. Med. Chem., vol. 41, No. 25, pp. 5055-5069 (Dec. 3, 1998).

Bright, et al., "Competitive particle concentration fluorescence immunoassays for measuring anti-diabetic drug levels in mouse plasma," Journal of Immunological Methods, vol. 207, No. 1, pp. 23-31 (Aug. 2, 1997).

Brooks, et al., "Design and Synehesis of 2-Methyl-2-{4-[2-(5-methyl-2-aryloxazol-4-yl)ethoxy]phenoxy}propionic Acids: A New Class of Dual PPAR Agonists," J. Med. Chem., vol. 44, No. 13, pp. 2061-2064 (Jun. 21, 2001).

Shinkai, et al., "Isoxazolidine-3,5-dione and Noncyclic 1,3-Dicarbonyl Compounds as Hypoglycemic Agents," J. Med. Chem., vol. 41, No. 11, pp. 1927-1933 (May 21, 1998).

Murugesan, et al., "Biphenylsulfonamide Endohelin Receptor Antagonists. 2. Discovery of 4'-Oxazolyl biphenylsulfonamides as a New Class of Potent, Highly Selective $ET_A$ Antagonists," J. Med. Chem., vol. 43, No. 16, pp. 3111-3117 (Aug. 10, 2000).

Malamas, et al., "Azole Phenoxy Hydroxyureas as Selective and Orally Active Inhibitors of 5-Lipoxygenase," J. Med. Chem., vol. 39, No. 1, pp. 237-245 (Jan. 5, 1996).

Meguro, et al., "Studies on Antidiabetic Agents. VIII. Synthesis and Hypoglycemic Activity of 4-Oxazoleacetic Acid Derivatives," Chemical & Pharmaceutical Bulletin, vol. 34, No. 7, pp. 2840-2851 (1986).

Xu, Yanping, et al., "Design and Synthesis of α-Aryloxy-α-methylhydrocinnamic Acids: A Novel Class of Dual Peroxisome Proliferator-Activated Receptor α/γ Agonists," J. Med. Chem, vol. 47, No. 10, pp. 2422-2425 (2004).

\* cited by examiner

SULFONAMIDE DERIVATIVES AS PPAR MODULATORS

This Application claims the benefit of U.S. Provisional Application Ser. No. 60/448,307, filed 14 Feb. 2003, and PCT Application Serial No. PCT/US2004/002015, filed 10 Feb. 2004, each hereby incorporated by reference in its entirety.

FIELD OF THE INVENTION

The present invention relates to compounds of peroxisome proliferator activated receptor (PPAR) agonists, more specifically sulfonamide derivatives of PPAR agonists, which are useful for the treatment and/or prevention of disorders modulated by a PPAR agonist.

BACKGROUND OF THE INVENTION

The peroxisome proliferator activated receptors (PPARs) are members of the nuclear receptor gene family that are activated by fatty acids and fatty acid metabolites. The PPARs belong to the subset of nuclear receptors that function as heterodimers with the 9-cis retinoic acid receptor (RXR). Three subtypes, designated PPARα, PPARγ and PPARδ, are found in species ranging from *Xenopus* to humans.

PPARα is the main subtype in the liver and has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also involved with the activity of fibrates and fatty acids in rodents and humans. Fibric acid derivatives such as clofibrate, fenofibrate, benzafibrate, ciprofibrate, beclofibrate and etofibrate, as well as gemfibrozil, produce a substantial reduction in plasma triglycerides along with moderate reduction in low-density lipoprotein (LDL) cholesterol, and they are used particularly for the treatment of hypelriglyceridemia.

PPARγ is the main subtype in adipose tissue and involved in activating the program of adipocyte differentiation. PPARγ is not involved in stimulating peroxisome proliferation in the liver. There are two isomers of PPARγ: PPARγ1 and PPARγ2, which differ only in that PPARγ2 contains an additional 28 amino acids present at the amino terminus. The DNA sequences for the PPARγ receptors are described in Elbrecht. et. al., BBRC 224;431-437 (1996). Although peroxisome proliferators, including the fibrates and fatty acids, activate the transcriptional activity of PPAR's, only prostaglandin $J_2$ derivatives have been identified as natural ligands for PPARγ, which also binds the anti-diabetic agents thiazolidinediones with high affinity. The physiological functions of PPARα and PPARγ in lipid and carbohydrate metabolism were uncovered once it was recognized that they were the receptors for the fibrate and glitazone drugs, respectively.

PPARα and PPARγ receptors have been implicated in diabetes mellitus, cardiovascular disease, obesity, and gastrointestinal disease, such as inflammatory bowel disease and other inflammation related illnesses. Such inflammation related illnesses include, but are not limited to Alzheimer's disease, Crohn's disease, rheumatoid arthritis, psoriasis, and ischemia reprofusion injury.

By contrast, PPARδ (also referred to as PPARβ and NUC1) is not reported to be receptor for any known class of drug molecules, and its role in mammalian physiology has remained undefined. The human nuclear receptor gene PPARδ (hPPARδ) has been cloned from a human osteosarcoma cell cDNA library and is fully described in A. Schmidt et al., *Molecular Endocrinology*, 6:1634-1641 (1992).

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes, which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL (known as the "bad" cholesterol) which are risk factors in cardiovascular diseases. The constellation of symptoms which includes hyperinsulemia combined with hypertension, elevated body weight, elevated triglycerides and elevated LDL is known as Syndrome X.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. One form of hyperlipidemia is hypercholesterolemia, characterized by the existence of elevated LDL cholesterol levels. The initial treatment for hypercholesterolemia is often a diet low in fat and cholesterol coupled with appropriate physical exercise. Drug intervention is initiated if LDL-lowering goals are not met by diet and exercise alone. It is desirable to lower elevated levels of LDL cholesterol and increase levels of HDL cholesterol. Generally, it has been found that increased levels of HDL are associated with lower risk for coronary heart disease (CHD). See Gordon, et al., *Am. J. Med.*, 62, 707-714 (1977); Stampfer, et al., *N. England J. Med.*, 325, 373-381 (1991); and Kannel, et al., *Ann. Internal Med.*, 90, 85-91 (1979). An example of an HDL raising agent is nicotinic acid, but the quantities needed to achieve HDL elevation are associated with undesirable effects, such as flushing.

There are several treatments currently available for treating diabetes mellitus but these treatments still remain unsatisfactory and have limitations. While physical exercise and reduction in dietary intake of calories will improve the diabetic condition, compliance with this approach can be poor because of sedentary lifestyles and excess food consumption, in particular high fat-containing food. Therefore, treatment with hypoglycemics, such as sulfonylureas (e.g., chlorpropamide, tolbutamide, tolazamide and acetohexamide) and biguanides (e.g. phenformin and metformin) are often necessary as the disease progresses. Sulfonylureas stimulate the β cells of the pancreas to secrete more insulin as the disease progresses. However, the response of the β cells eventually fails and treatment with insulin injections is necessary. In addition, both sulfonylurea treatment and insulin injection have the life threatening side effect of hypoglycemic coma, and thus patients using these treatments must carefully control dosage.

It has been well established that improved glycemic control in patients with diabetes (Type I and Type II) is accompanied by decreased microvasclular complications (DCCT and UKPDS). Due to difficulty in maintaining adequate glycemic control over time in patients with Type II diabetes, the use of insulin sensitizers in the therapy of Type II diabetes is growing. There is also a growing body of evidence that PPARγ agonist, insulin sensitizer, may have benefits in the treatment of Type II diabetes beyond their effects in improving glycemic control.

In the last decade a class of compounds known as thiazolidinediones (e.g. U.S. Pat. Nos. 5,089,514; 4,342,771; 4,367,234; 4,340,605; and 5,306,726) have emerged as effective antidiabetic agents that have been shown to increase the sensitivity of insulin sensitive tissues, such as skeletal muscle, liver and adipose, to insulin. Increasing insulin sensitivity rather than the amount of insulin in the blood reduces the likelihood of hypoglycemic coma. Although thiazolidinediones have been shown to increase insulin sensitivity by binding to PPARγ receptors, this treatment also produces unwanted side effects such as weight gain and, for troglitazone, liver toxicity.

In view of the above, there exists a need for new pharmaceutical agents which modulate these receptors to prevent, treat and/or alleviate these diseases or conditions while ameliorating side effects of current treatments.

SUMMARY OF THE INVENTION

The present invention relates to a compound of novel peroxisome proliferator activated receptor (PPAR) agonist having a structural Formula I,

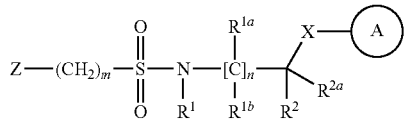

I and pharmaceutically acceptable salts, solvates, hydrates or stereoisomers thereof, wherein:

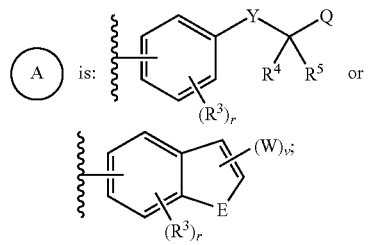

A is:

E is: O, S or $NR^{14}$;
W is:

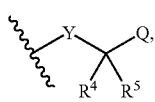

hydrogen, $C_1$-$C_6$ alkyl, $(CH_2)_{n'}C_3$-$C_6$ cycloalkyl, haloalkyl or acyl;
Q is: —$C(O)OR^6$ or $R^{6A}$;
X is: a bond, C, O, S or $S[O]_p$;

Y is: a bond, S, C or O;
Z is: a) aliphatic group,
b) aryl,
c) a 5- to 10-membered heteroaryl wherein the heteroaryl containing at least one heteroatom selected from N, O or S,
d) bi-aryl, wherein biaryl being defined as aryl substituted with another aryl or aryl substituted with heteroaryl,
e) bi-heteroaryl, wherein bi-heteroaryl being defined as heteroaryl substituted with another heteroaryl, or heteroaryl substituted with aryl, and
f) heterocyclyl;
wherein aliphatic group, aryl, heteroaryl, bi-aryl, bi-heteroaryl and heterocyclyl being optionally substituted with one or more groups independently selected from $R^{15}$;
m and n' are each independently: 0, 1, 2, 3 or 4;
n is: 0, 1, 2 or 3;
p is, 1 or 2;
r is: 1, 2, 3 or 4;
v is: 1 or 2;
$R^1$ is: hydrogen, wherein when Z is phenyl or naphthyl and $R^2$ is H, $R^1$ is not H, haloalkyl,
$C_1$-$C_6$ alkyl,
$C_1$-$C_6$ alkyl-$C_1$-$C_6$ alkoxy,
$C_1$-$C_6$ alkyl-aryl,
$C_2$-$C_6$ alkenyl,
$C_2$-$C_6$ alkynyl,
$(CH_2)_{n'}C_3$-$C_6$ cycloalkyl,
$C_1$-$C_6$ alkoxy,
aryl, or
$R^1$ and $R^2$ together being a 5- to 8-membered heterocyclyl ring, and wherein alkyl, aryl, alkenyl, alkynyl, cycloalkyl and alkoxy being optionally substituted with one or more groups independently selected from $R^{15}$;
$R^{1a}$ and $R^{1b}$ are each independently:
hydrogen,
$C_1$-$C_6$ alkyl, or
$R^1$ and $R^{1a}$, $R^1$ and $R^{1b}$, $R^2$ and $R^{1a}$, $R^2$ and $R^{1b}$ or $R^{1a}$ and $R^{1b}$ together being a 3- to 6-membered heterocyclyl or carbocyclyl ring where at least one of $R^{1a}$ and $R^{1b}$ is not hydrogen;
$R^2$ is: hydrogen,
haloalkyl,
$C_1$-$C_6$ alkyl,
$C_1$-$C_6$ alkyl-$C_1$-$C_6$ alkoxy,
$C_1$-$C_6$ alkyl-aryl,
$C_2$-$C_6$ alkenyl,
$C_2$-$C_6$ alkynyl,
$(CH_2)_{n'}C_3$-$C_6$ cycloalkyl,
$C_1$-$C_6$ alkoxy,
aryl, or
$R^1$ and $R^2$ together being a 5- to 8-membered heterocyclyl ring, and
wherein alkyl, aryl, alkenyl, alkynyl, cycloalkyl and alkoxy being optionally substituted with one or more groups independently selected from $R^{15}$;
$R^{2a}$ is: hydrogen, halo or $C_1$-$C_6$ alkyl and wherein $R^2$ and $R^{2a}$ together being a 3- to 8-membered ring; and wherein alkyl being optionally substituted with one or more groups independently selected from $R^{15}$;
$R^3$ is: hydrogen,
halo,
cyano,
haloalkyl,
$C_1$-$C_6$ alkyl,
$(CH_2)_{n'}C_3$-$C_6$ cycloalkyl, ($C_1$-$C_4$ alkyl)-heterocyclyl, wherein the heterocyclyl being optionally substituted with oxo,
($C_1$-$C_4$ alkyl)-$NR^7C(O)_pR^9$, and
wherein alkyl, cycloalkyl and heterocyclyl being optionally substituted with one or more groups independently selected from $R^{15}$;

$R^4$ and $R^5$ are each independently:
hydrogen,
halo,
$C_1$-$C_6$ alkyl
$C_1$-$C_6$ alkoxy;
aryloxy;
$N(R^8)_2$,
$SR^8$ or
$R^4$ and $R^5$ together being a 3- to 8-membered ring;
$R^6$ is: hydrogen, $C_1$-$C_6$ alkyl or aminoalkyl;
$R^{6A}$ is: carboxamide, $C_1$-$C_3$ alkylnitrile, sulfonamide, acylsulfonamide or tetrazole;
$R^7$ is: hydrogen or $C_1$-$C_6$ alkyl;
$R^8$ and $R^9$ are each independently:
hydrogen, $C_1$-$C_6$ alkyl, aryl, heteroaryl, or heterocyclyl, and
wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy;
$R^{14}$ is: hydrogen, aryl, $C_1$-$C_6$ alkyl, or $C_1$-$C_6$ alkyl-$COOR^6$, and
wherein aryl and alkyl being optionally substituted with one or more groups independently selected from $R^{15}$; and
$R^{15}$ is: hydrogen, nitro, cyano, hydroxyl, halo, haloalkyl, haloalkyloxy, aryloxy, oxo, $C_1$-$C_6$ alkyl, $C_1$-$C_6$ alkoxy, $N(R^8)_2$, $NR^8S(O)_2R^9$, $NR^8C(O)_pR^9$, $C(O)NR^8R^9$, $C(O)_pR^8$, $SR^8$, $S(O)_pR^8$ or $S(O)_2NR^8R^9$.

The compounds of the present invention are useful in the treatment or prevention of diseases or condition relates to hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component.

In one embodiment, the present invention also relates to pharmaceutical compositions which comprising at least one compound of the present invention, or a pharmaceutically acceptable salt, solvate, hydrate thereof and a pharmaceutically acceptable carrier. Within the scope of this invention also include a pharmaceutical composition containing additional therapeutic agent as well as at least one compound of the present invention, or a pharmaceutically acceptable salt, solvate, hydrate thereof and a pharmaceutically acceptable carrier.

In another embodiment, the present invention relates to a method of modulating a PPAR by contacting the receptor with at least one compound of the present invention, and pharmaceutically acceptable salts, solvates and hydrates thereof.

DETAILED DESCRIPTION OF THE INVENTION

The compounds of the present invention are directed to peroxisome proliferator activated receptor (PPAR) agonists, more specifically sulfonamide derivatives of PPAR agonists. The compounds of the present invention are also relates to PPAR γ/δ dual agonists, which are useful for the treatment and/or prevention of disorders modulated by a PPAR.

An embodiment of the present invention is a compound of novel peroxisome proliferator activated receptor (PPAR) agonists having a structural Formula I,

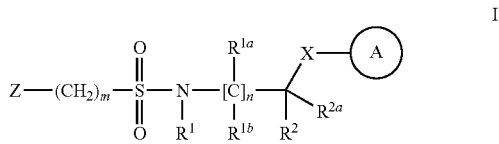

and pharmaceutically acceptable salts, solvates, hydrates or stereoisomers thereof, wherein:

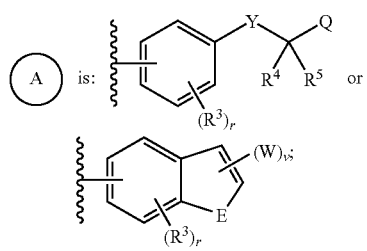

E is: O, S or $NR^{14}$;
W is:

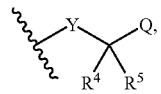

hydrogen, $C_1$-$C_6$ alkyl, $(CH_2)_{n'}C_3$-$C_6$ cycloalkyl, haloalkyl or acyl;
Q is: —$C(O)OR^6$ or $R^{6A}$;
X is: a bond, C, O, S or $S[O]_p$;
Y is: a bond, S, C or O:
Z is: a) aliphatic group,
  b) aryl,
  c) a 5- to 10-membered heteroaryl wherein the heteroaryl containing at least one heteroatom selected from N, O or S,
  d) bi-aryl, wherein biaryl being defined as aryl substituted with another aryl or aryl substituted with heteroaryl,
  e) bi-heteroaryl, wherein bi-heteroaryl being defined as heteroaryl substituted with another heteroaryl, or heteroaryl substituted with aryl, and
  f) heterocyclyl;
  wherein aliphatic group, aryl, heteroaryl, bi-aryl, bi-heteroaryl and heterocyclyl being optionally substituted with one or more groups independently selected from $R^{15}$;
m and n' are each independently: 0, 1, 2, 3 or 4;
n is: 0, 1, 2 or 3;
p is: 1 or 2;
r is: 1, 2, 3 or 4;
v is: 1 or 2;
$R^1$ is: hydrogen, wherein when Z is phenyl or naphthyl and $R^2$ is H, $R^1$ is not H,
haloalkyl,
$C_1$-$C_6$ alkyl, $C_1$-$C_6$ alkyl-$C_1$-$C_6$ alkoxy,
$C_1$-$C_6$ alkyl-aryl,
$C_2$-$C_6$ alkenyl,
$C_2$-$C_6$ alkynyl,
$(CH_2)_{n'}C_3$-$C_6$ cycloalkyl,
$C_1$-$C_6$ alkoxy,
aryl, or
$R^1$ and $R^2$ together being a 5- to 8-membered heterocyclyl ring, and
wherein alkyl, aryl, alkenyl, alkynyl, cycloalkyl and alkoxy being optionally substituted with one or more groups independently selected from $R^{15}$;

$R^{1a}$ and $R^{1b}$ are each independently:
hydrogen,
$C_1$-$C_6$ alkyl, or
$R^1$ and $R^{1a}$, $R^1$ and $R^{1b}$, $R^2$ and $R^{1a}$, $R^2$ and $R^{1b}$ or $R^{1a}$ and $R^{1b}$ together being a 3- to 6-membered heterocyclyl or carbocyclyl ring where at least one of $R^{1a}$ and $R^{1b}$ is not hydrogen;

$R^2$ is: hydrogen,
haloalkyl,
$C_1$-$C_6$ alkyl,
$C_1$-$C_6$ alkyl-$C_1$-$C_6$ alkoxy,
$C_1$-$C_6$ alkyl-aryl,
$C_2$-$C_6$ alkenyl,
$C_2$-$C_6$ alkynyl,
$(CH_2)_{n'}C_3$-$C_6$ cycloalkyl,
$C_1$-$C_6$ alkoxy,
aryl, or
$R^1$ and $R^2$ together being a 5- to 8-membered heterocyclyl ring, and
wherein alkyl, aryl, alkenyl, alkynyl, cycloalkyl and alkoxy being optionally substituted with one or more groups independently selected from $R^{15}$;

$R^{2a}$ is: hydrogen, halo or $C_1$-$C_6$ alkyl and wherein $R^2$ and $R^{2a}$ together being a 3- to 8-membered ring; and wherein alkyl being optionally substituted with one or more groups independently selected from $R^{15}$;

$R^3$ is: hydrogen,
halo,
cyano,
haloalkyl,
$C_1$-$C_6$ alkyl,
$(CH_2)_{n'}C_3$-$C_6$ cycloalkyl,
($C_1$-$C_4$ alkyl)-heterocyclyl, wherein the heterocyclyl being optionally substituted with oxo,
($C_1$-$C_4$ alkyl)-$NR^7C(O)_pR^9$, and
wherein alkyl, cycloalkyl and heterocyclyl being optionally substituted with one or more groups independently selected from $R^{15}$;

$R^4$ and $R^5$ are each independently:
hydrogen,
halo,
$C_1$-$C_6$ alkyl
$C_1$-$C_6$ alkoxy;
aryloxy;
$N(R^8)_2$,
$SR^8$ or
$R^4$ and $R^5$ together being a 3- to 8-membered ring:

$R^6$ is: hydrogen, $C_1$-$C_6$ alkyl or aminoalkyl;
$R^{6A}$ is: carboxamide, $C_1$-$C_3$ alkylnitrile, sulfonamide, acylsulfonamide or tetrazole;
$R^7$ is: hydrogen or $C_1$-$C_6$ alkyl;
$R^8$ and $R^9$ are each independently:
hydrogen, $C_1$-$C_6$ alkyl, aryl, heteroaryl, or heterocyclyl, and wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy;

$R^{14}$ is: hydrogen, aryl, $C_1$-$C_6$ alkyl, or $C_1$-$C_6$ alkyl-$COOR^6$, and wherein aryl and alkyl being optionally substituted with one or more groups independently selected from $R^{15}$; and $R^{15}$ is: hydrogen, nitro, cyano, hydroxyl, halo, haloalkyl, haloalkyloxy, aryloxy, oxo, $C_1$-$C_6$ alkyl, $C_1$-$C_6$ alkoxy, $(CH_2)_{n'}C_3$-$C_6$ cycloalkyl, $N(R^8)_2$, $NR^8S(O)_2R^9$, $NR^8C(O)_p R^9$, $C(O)NR^8R^9$, $C(O)_pR^8$, $SR^8$, $S(O)_pR^8$ or $S(O)_2NR^8R^9$.

A preferred embodiment of the present invention is a compound having a structural Formula II,

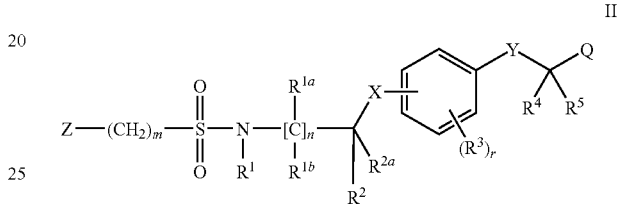

II and pharmaceutically acceptable salts, solvates, hydrates or stereoisomers thereof, wherein:

Q is: —$C(O)OR^6$ or $R^{6A}$;
X is: a bond, C, O, S or $S[O]_p$;
Y is: a bond, S, C or O;
Z is: a) aliphatic group,
  b) aryl,
  c) a 5- to 10-membered heteroaryl wherein the heteroaryl containing at least one heteroatom selected from N, O or S,
  d) bi-aryl, wherein biaryl being defined as aryl substituted with another aryl or aryl substituted with heteroaryl,
  e) bi-heteroaryl, wherein bi-heteroaryl being defined as heteroaryl substituted with another heteroaryl, or heteroaryl substituted with aryl, and
  f) heterocyclyl;
  wherein aliphatic group, aryl, heteroaryl, bi-aryl, bi-heteroaryl and heterocyclyl being optionally substituted with one or more groups independently selected from $R^{15}$;

m and n' are each independently: 0, 1, 2, 3 or 4;
n is: 0, 1, 2 or 3;
p is: 1 or 2;
r is: 1, 2, 3 or 4;
$R^1$ is: aryl
haloalkyl,
$C_1$-$C_6$ alkyl,
$C_1$-$C_6$ alkyl-$C_1$-$C_6$ alkoxy,
$C_1$-$C_6$ alkyl-aryl,
$C_2$-$C_6$ alkenyl,
$C_2$-$C_6$ alkynyl,
$(CH_2)_{n'}C_3$-$C_6$ cycloalkyl,
$C_1$-$C_6$ alkoxy or
$R^1$ and $R^2$ together being a 5- to 8-membered heterocycyl ring, and
wherein alkyl, aryl, alkenyl, alkynyl, cycloalkyl and alkoxy being optionally substituted with one or more groups independently selected from $R^{15}$;

$R^{1a}$ and $R^{1b}$ are each independently:
hydrogen,
$C_1$-$C_6$ alkyl, or
$R^1$ and $R^{1a}$, $R^1$ and $R^{1b}$, $R^2$ and $R^{1a}$, $R^2$ and $R^{1b}$ or $R^{1a}$ and $R^{1b}$ together being a 3- to 6-membered heterocyclyl or carbocyclyl ring where at least one of $R^{1a}$ and $R^{1b}$ is not hydrogen;

$R^2$ is: hydrogen,
haloalkyl,
$C_1$-$C_6$ alkyl,
$C_1$-$C_6$ alkyl-$C_1$-$C_6$ alkoxy,
$C_1$-$C_6$ alkyl-aryl,
$C_1$-$C_6$ alkenyl,
$C_2$-$C_6$ alkynyl,
$(CH_2)_n C_3$-$C_6$ cycloalkyl,
$C_1$-$C_6$ alkoxy,
aryl, or
$R^1$ and $R^2$ together being a 5- to 8-membered heterocyclyl ring, and
wherein alkyl, aryl, alkenyl, alkynyl, cycloalkyl and alkoxy being optionally substituted with one or more groups independently selected from $R^{15}$;

$R^{2s}$ is: hydrogen, halo or $C_1$-$C_6$ alkyl and wherein $R^2$ and $R^{2a}$ together being a 3- to 8-membered ring; and wherein alkyl being optionally substituted with one or more groups independently selected from $R^{15}$;

$R^3$ is: hydrogen,
halo,
cyano,
haloalkyl,
$C_1$-$C_6$ alkyl,
$(CH_2)_n C_3$-$C_6$ cycloalkyl,
$(C_1$-$C_4$ alkyl)-heterocyclyl, wherein the heterocyclyl being optionally substituted with oxo,
$(C_1$-$C_4$ alkyl)-$NR^7C(O)_p R^9$, and
wherein alkyl, cycloalkyl and heterocyclyl being optionally substituted with one or more groups independently selected from $R^{15}$, $R^4$ and $R^5$ are each independently:
hydrogen,
halo,
$C_1$-$C_6$ alkyl
$C_1$-$C_6$ alkoxy;
aryloxy;
$N(R^8)_2$,
$SR^8$ or
$R^4$ and $R^5$ together being a 3- to 8-membered ring:

$R^6$ is: hydrogen, $C_1$-$C_6$ alkyl or aminoalkyl;
$R^{6A}$ is: carboxamide, $C_1$-$C_3$ alkylnitrile, sulfonamide, acylsulfonamide or tetrazole;
$R^7$ is: hydrogen or $C_1$-$C_6$ alkyl;
$R^8$ and $R^9$ are each independently:
hydrogen, $C_1$-$C_6$ alkyl, aryl, heteroaryl, or heterocyclyl, and
wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy;

$R^{15}$ is: hydrogen, nitro, cyano, hydroxyl, halo, haloalkyl, haloalkyloxy, aryloxy, oxo, $C_1$-$C_6$ alkyl, $C_1$-$C_6$ alkoxy, $(CH_2)_n C_3$-$C_6$ cycloalkyl, $N(R^8)_2$, $NR^8S(O)_2R^9$, $NR^8C(O)_p R^9$, $C(O)NR^8R^9$, $C(O)_p R^8$, $SR^8$, $S(O)_p R^8$ or $S(O)_2 NR^8R^9$.

The compound as recited above, wherein X and Y are respectively S and O; S and C; or C and O.

The compounds of Formula I and II as recited above, wherein Z is $C_1$-$C_6$ alkyl, aryl or heteroaryl.

The compounds of Formula I and II as recited above, wherein Z is phenyl, naphthyl, thiophenyl, oxazolyl, isooxazolyl, pyridyl, benzothiophenyl, benzofuranyl, indolyl, isoindolyl, pyrazolyl, imidazolyl, 1,4benzodioxan, benzooxazolyl, benzothiazolyl, benzoimidazolyl, or 2,3-dihydrobenzofuranyl.

The compounds of Formula I and II as recited above, wherein $R^1$ is $C_3$-$C_6$ alkyl or $(CH_2)_n C_3$-$C_6$ cycloalkyl; $R^2$ and $R^3$ are each independently $C_1$-$C_3$ alkyl: and r is 1.

The compounds of Formula I and II as recited above, wherein X is positioned para to Y; and $R^3$ is positioned ortho to Y.

Another preferred embodiment of the present invention is a compound having a structural Formula III,

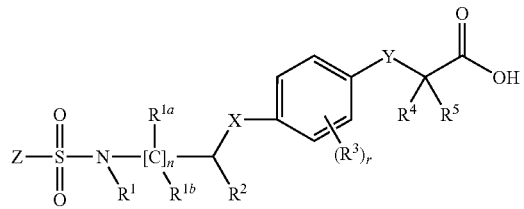

III and pharmaceutically acceptable salts, solvates, hydrates or stereoisomers thereof, wherein,
n is: 1 or 2;
r is: 1, 2, 3, or 4;
X is: S or C;
Y is: C or O;
Z is: aryl or a 5- to 10-membered heteroaryl,
wherein aryl and heteroaryl being optionally substituted with one or more groups independently selected from $R^{15}$;
$R^1$ and $R^2$ are each independently: $C_1$-$C_6$ alkyl or $(CH_2)_n C_3$-$C_6$ cycloalkyl; and
$R^{1a}$ and $R^{1b}$, $R^3$, $R^4$ and $R^5$ are each independently: hydrogen or $C_1$-$C_6$ alkyl.

Yet another preferred embodiment of the present invention is the compound having a structural Formula IV,

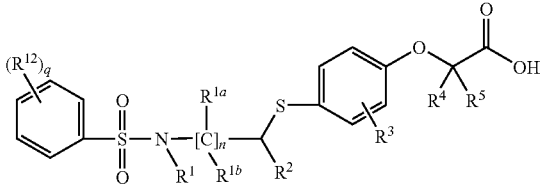

IV and pharmaceutically acceptable salts, solvates, hydrates or stereoisomers thereof, wherein:
q is 1, 2, 3, 4, or 5.
$R^8$ and $R^9$ are each independently:
hydrogen, $C_1$-$C_6$ alkyl, aryl, heteroaryl, or heterocyclyl,
wherein alkyl, aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy; and $R^{12}$ is: hydrogen, nitro, cyano, hydroxyl, halo, haloalkyl, haloalkyloxy, aryl, heteroaryl, aryloxy, oxo, $C_1$-$C_6$ alkyl, $C_1$-$C_6$ alkoxy, $(CH_2)_{n'}C_3$-$C_6$ cycloalkyl, $N(R^8)_2$, $NR^8 S(O)_2R^9$, $NR^8C(O)_pR^9$, $C(O)NR^8R^9$, $C(O)_pR^8$, $SR^8$, $S(O)_pR^8$ or $S(O)_2NR^8R^9$.

Yet another preferred embodiment of the present invention is the compound having a structural Formula V,

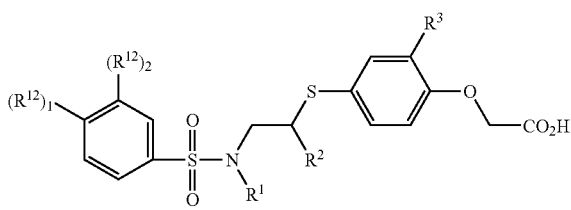

and pharmaceutically acceptable salts, solvates, hydrates or stereoisomers thereof, wherein: $R^1$ and $R^2$ are each independently $C_1$-$C_4$ alky or $(CH_2)_{n'}C_3$-$C_6$ cycloalkyl; $R^3$ is $C_1$-$C_4$ alky; $(R^{12})_1$ is halo, haloalkyl, or haloalkyloxy; and $(R^{12})_2$ is F, Cl or Br.

The compound as recited above, wherein $R^1$ is methyl, ethyl, propyl, clcylopropyl, cyploroylmethyl, cyclobutyl: $R^3$ is methyl and $(R^{12})_1$ is $OCF_3$.

Yet another embodiment of the present invention is a compound having a structural Formula VI,

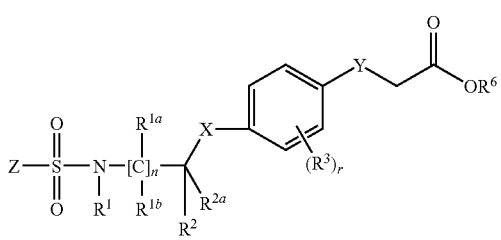

and pharmaceutically acceptable salts, solvates, hydrates or stereoisomers thereof, wherein:

X is: a bond, C, O, S or $S[O]_p$;
Y is: a bond, S, C or O;
Z is: heteroaryl wherein the heteroaryl containing at least one heteroatom selected from N, O or S, and wherein heteroaryl being optionally substituted with one or more groups selected from $R^{15}$;
n is: 0, 1, 2 or 3;
n' is: 0, 1, 2, 3 or 4;
p is: 1 or 2;
r is: 1, 2, 3 or 4;
$R^1$ is: hydrogen,
  haloalkyl,
  $C_1$-$C_6$ alkyl,
  $C_1$-$C_6$ alkyl-$C_1$-$C_6$ alkoxy,
  $C_1$-$C_6$ alkyl-aryl,
  $C_2$-$C_6$ alkenyl,
  $C_2$-$C_6$ alkynyl,
  $(CH_2)_{n'}C_3$-$C_6$ cycloalkyl,
  $C_1$-$C_6$ alkoxy,
  aryl, or
  $R^1$ and $R^2$ together being a 5- to 8-membered heterocyclyl ring, and
  wherein alkyl, aryl, alkenyl, alkynyl, cycloalkyl and alkoxy being optionally substituted with one or more groups independently selected from $R^{15}$;
$R^{1a}$ and $R^{1b}$ are each independently:
  hydrogen,
  $C_1$-$C_6$ alkyl, or
  $R^1$ and $R^{1a}$, $R^1$ and $R^b$, $R^2$ and $R^{1a}$, $R^2$ and $R^{1b}$ or $R^{1a}$ and $R^{1b}$ together being a 3- to 6-membered heterocyclyl or carbocyclyl ring where at least one of $R^{1a}$ and $R^{1b}$ is not hydrogen;
$R^2$ is: hydrogen,
  haloalkyl,
  $C_1$-$C_6$ alkyl,
  $C_1$-$C_6$ alkyl-$C_1$-$C_6$ alkoxy,
  $C_1$-$C_6$ alkyl-aryl,
  $C_2$-$C_6$ alkenyl,
  $C_2$-$C_6$ alkynyl,
  $(CH_2)_{n'}C_3$-$C_6$ cycloalkyl,
  $C_1$-$C_6$ alkoxy,
  aryl, or
  $R^1$ and $R^2$ together being a 5- to 8-membered heterocyclyl ring, and
  wherein alkyl, aryl, alkenyl, alkynyl, cycloalkyl and alkoxy being optionally substituted with one or more groups independently selected from $R^{15}$;
$R^{2a}$ is: hydrogen, halo or $C_1$-$C_6$ alkyl and wherein $R^2$ and $R^{2a}$ together being a 3- to 8-membered ring; and wherein alkyl being optionally substituted with one or more groups independently selected from $R^{15}$:
$R^3$ is: hydrogen,
  halo,
  cyano,
  haloalkyl,
  $C_1$-$C_6$ alkyl,
  $(CH_2)_{n'}C_3$-$C_6$ cycloalkyl,
  ($C_1$-$C_4$ alkyl)-heterocyclyl, wherein the heterocyclyl being optionally substituted with oxo,
  ($C_1$-$C_4$ alkyl)-$NR^7C(O)_pR^9$, and
  wherein alkyl, cycloalkyl and heterocyclyl being optionally substituted with one or more groups independently selected from $R^{15}$;
$R^6$ is: hydrogen, $C_1$-$C_6$ alkyl or aminoalkyl;
$R^7$ is: hydrogen or $C_1$-$C_6$ alkyl;
$R^8$ and $R^9$ are each independently:
  hydrogen, $C_1$-$C_6$ alkyl, aryl, heteroaryl, or heterocyclyl, and
  wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy; and
$R^{15}$ is: hydrogen, nitro, cyano, hydroxyl, halo, haloalkyl, haloalkyloxy, aryloxy, oxo, $C_1$-$C_6$ alkyl, $C_1$-$C_6$ alkoxy, $(CH_2)_{n'}C_3$-$C_6$ cycloalkyl, $N(R^8)_2$, $NR^8S(O)_2R^9$, $NR^8 C(O)_pR^9$, $C(O)NR^8R^9$, $C(O)_pR^8$, $SR^8$, $S(O)_pR^8$ or $S(O)_2 NR^8R^9$.

Yet another preferred embodiment of the present invention is the compound having a structural Formula VII,

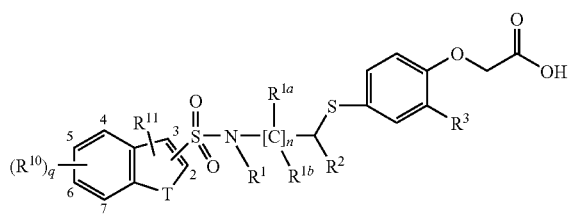

and pharmaceutically acceptable salts, solvates hydrates or stereoisomers thereof, wherein:

q is: 1, 2, 3, or 4;
T is: O, $NR^{1c}$ or S;
$R^{1c}$ is: hydrogen or $C_1$-$C_6$ alkyl;
$R^{10}$ and $R^{11}$ are each independently:
hydrogen, nitro, cyano, hydroxyl, halo, haloalkyl, haloalkyloxy, aryloxy, $C_1$-$C_6$ alkyl or $C_1$-$C_6$ alkoxy; and
wherein alkyl, aryloxy, and alkoxy being optionally substituted with one or more groups independently selected from $R^{15}$.

Yet another preferred embodiment of the present invention is the compound having a structural Formula VIII,

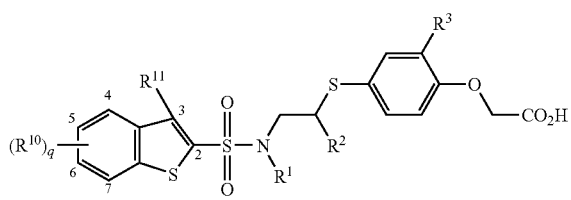

wherein:
q is: 1 or 2;
$R^1$ is: $C_3$-$C_5$ alky or $(CH_2)_{n'}C_3$-$C_6$ cycloalkyl;
$R^2$ and $R^3$ are each independently: $C_1$-$C_3$ alkyl;
$R^{10}$ is: halo, haloalkyl or $C_1$-$C_3$ alkyl, and
wherein $R^{10}$ being substituted at a position 5, or 6, or both 5 and 6 of benzothiophenyl ring; and
$R^{11}$ is: hydrogen or $C_1$-$C_6$ alkyl.

The compound as recited above, wherein $R^{10}$ is Cl, F, Br, $CH_3$ or $CF_3$ being substituted at a position 5 of benzothiophenyl ring.

Yet another preferred embodiment of the present invention is a compound having a structural Formula IX,

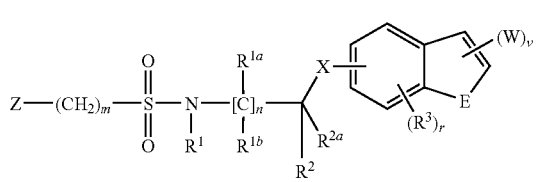

and pharmaceutically acceptable salts, solvates, hydrates or stereoisomers thereof, wherein:
E is: O, S or $NR^{14}$;

W is:

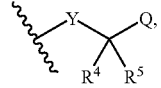

hydrogen, $C_1$-$C_6$ alkyl, $(CH_2)_{n'}C_3$-$C_6$ cycloalkyl, haloalkyl or acyl;
Q is: —C(O)$OR^6$ or $R^{64}$;
X is: a bond, C, O, S or $S[O]_p$;
Y is: a bond, S, C or O;
Z is: a) aliphatic group,
  b) aryl,
  c) a 5- to 10-membered heteroaryl wherein the heteroaryl containing at least one heteroatom selected from N, O or S,
  d) bi-aryl, wherein biaryl being defined as aryl substituted with another aryl or aryl substituted with heteroaryl,
  e) bi-heteroaryl, wherein bi-heteroaryl being defined as heteroaryl substituted with another heteroaryl, or heteroaryl substituted with aryl, and
  f) heterocyclyl;
  wherein aliphatic group, aryl, heteroaryl, bi-aryl, bi-heteroaryl and heterocyclyl being optionally substituted with one or more groups independently selected from $R^{15}$;
m and n' are each independently: 0, 1, 2, 3 or 4;
n is: 0, 1, 2 or 3;
p is: 1 or 2;
r is: 1, 2, 3 or 4;
v is: 1 or 2;
$R^1$ is: hydrogen,
  haloalkyl,
  $C_1$-$C_6$ alkyl,
  $C_1$-$C_6$ alkyl-$C_1$-$C_6$ alkoxy,
  $C_1$-$C_6$ alkyl-aryl,
  $C_2$-$C_6$ alkenyl,
  $C_2$-$C_6$ alkynyl,
  $(CH_2)_{n'}C_3$-$C_6$ cycloalkyl,
  $C_1$-$C_6$ alkoxy,
  aryl, or
  $R^1$ and $R^2$ together being a 5- to 8-membered heterocyclyl ring, and
  wherein alkyl, aryl, alkenyl, alkynyl, cycloalkyl and alkoxy being optionally substituted with one or more groups independently selected from $R^{15}$;
$R^{1a}$ and $R^{1b}$ are each independently:
  hydrogen,
  $C_1$-$C_6$ alkyl, or
  $R^1$ and $R^{1a}$, $R^1$ and $R^{1b}$, $R^2$ and $R^{1a}$, $R^2$ and $R^{1b}$ or $R^{1a}$ and $R^{1b}$ together being a 3- to 6-membered heterocyclyl or carbocyclyl ring where at least one of $R^{1a}$ and $R^{1b}$ is not hydrogen;
$R^2$ is: hydrogen,
  haloalkyl,
  $C_1$-$C_6$ alkyl,
  $C_1$-$C_6$ alkyl-$C_1$-$C_6$ alkoxy,
  $C_1$-$C_6$ alkyl-aryl,
  $C_2$-$C_6$ alkenyl,
  $C_2$-$C_6$ alkynyl,
  $(CH_2)_{n'}C_3$-$C_6$ cycloalkyl,
  $C_1$-$C_6$ alkoxy,
  aryl, or $R^1$ and $R^2$ together being a 5- to 8-membered heterocyclyl ring, and
wherein alkyl, aryl, alkenyl, alkynyl, cycloalkyl and alkoxy being optionally substituted with one or more groups independently selected from $R^{15}$;

$R^{2a}$ is: hydrogen, halo or $C_1$-$C_6$ alkyl and wherein $R^2$ and $R^{2a}$ together being a 3- to 8-membered ring; and wherein alkyl being optionally substituted with one or more groups independently selected from $R^{15}$;

$R^3$ is: hydrogen,
halo,
cyano,
haloalkyl,
$C_1$-$C_6$ alkyl,
$(CH_2)_n C_3$-$C_6$ cycloalkyl,
$(C_1$-$C_4$ alkyl)-heterocyclyl, wherein the heterocyclyl being optionally substituted with oxo,
$(C_1$-$C_4$ alkyl)-$NR^7C(O)_p R^9$, and
wherein alkyl, cycloalkyl and heterocyclyl being optionally substituted with one or more groups independently selected from $R^{15}$;

$R^4$ and $R^5$ are each independently:
hydrogen,
halo,
$C_1$-$C_6$ alkyl
$C_1$-$C_6$ alkoxy;
aryloxy;
$N(R^8)_2$,
$SR^8$ or
$R^4$ and $R^5$ together being a 3- to 8-membered ring;

$R^6$ is: hydrogen, $C_1$-$C_6$ alkyl or aminoalkyl:

$R^{6A}$ is: carboxamide, $C_1$-$C_3$-alkylnitrile, sulfonamide, acylsulfonamide or tetrazole;

$R^7$ is: hydrogen or $C_1$-$C_6$ alkyl;

$R^8$ and $R^9$ are each independently:
hydrogen, $C_1$-$C_6$ alkyl, aryl, heteroaryl, or heterocyclyl, and
wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy;

$R^{14}$ is: hydrogen, aryl, $C_1$-$C_6$ alkyl, or $C_1$-$C_6$ alkyl-$COOR^6$, and
wherein aryl and alkyl being optionally substituted with one or more groups independently selected from $R^{15}$; and $R^{15}$ is: hydrogen, nitro, cyano, hydroxyl, halo, haloalkyl, haloalkyloxy, aryloxy, oxo, $C_1$-$C_6$ alkyl, $C_1$-$C_6$ alkoxy, $(CH_2)_n C_3$-$C_6$ cycloalkyl, $N(R^8)_2$, $NR^8 S(O)_2 R^9$, $NR^8 C(O)_g R^9$, $C(O)NR^8 R^9$, $C(O)_p R^8$, $SR^8$, $S(O)_p R^8$ or $S(O)_2 NR^8 R^9$.

Yet another preferred embodiment of the present invention is the compound having a structural Formula X,

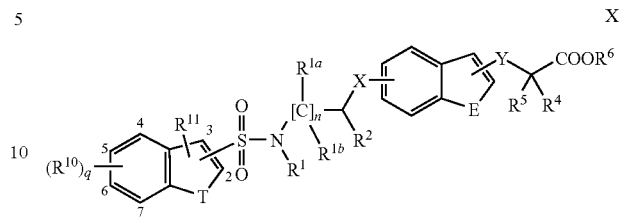

X and pharmaceutically acceptable salts, solvates, hydrates or stereoisomers thereof, wherein:
n and q are each independently: 1, 2, 3 or 4;
T is: O, $NR^{1c}$ or S;
X is: C, O or S;
$R^1$ is: hydrogen, $C_1$-$C_6$ alkyl or $(CH_2)_n C_3$-$C_6$ cycloalkyl;
$R^{1a}$, $R^{1b}$, $R^{1c}$ and $R^2$ are each independently: hydrogen or $C_1$-$C_6$ alkyl; and
$R^{10}$ and $R^{11}$ are each independently:
hydrogen, nitro, cyano, hydroxyl, halo, haloalkyl, haloalkyloxy, aryloxy, $C_1$-$C_6$ alkyl or $C_1$-$C_6$ alkoxy; and
wherein alkyl, alkoxy and aryloxy being optionally substituted with one or more groups selected from $R^{15}$.

Yet another preferred embodiment of the present invention is the compound having a structural Formula XI,

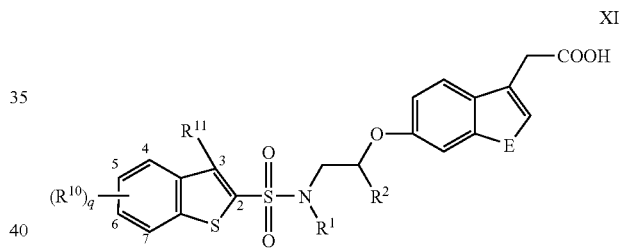

XI and pharmaceutically acceptable salts, solvates, hydrates or stereoisomers thereof, wherein:
q is 1 or 2;
E is O, S or $NR^{14}$;
$R^1$, $R^2$ and $R^{11}$ are each independently: $C_1$-$C_4$ alkyl;
$R^{10}$ is: Cl, F, Br, $CH_3$ or $CF_3$, and wherein $R^{10}$ being substituted at a position 5, or 6, or both 5 and 6 of benzothiophenyl ring; and
$R^{14}$ is: hydrogen, $C_1$-$C_6$ alkyl or aryl.

The most preferred embodiment of the present invention is the compounds listed below:

| No. | Structure | Name |
|---|---|---|
| 1 | ![structure] | 3-(4-{2-[(5-Fluoro-3-methyl-benzo[b]thiophene-2-sulfonyl)-propyl-amino]-ethylsulfanyl}-2-methyl-phenyl)-propionic acid |

-continued

| No. | Structure | Name |
|---|---|---|
| 2 | 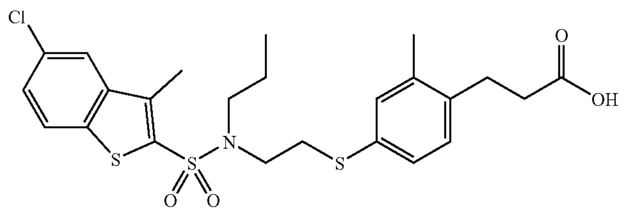 | 3-(4-{2-[(5-Chloro-3-methyl-benzo[b]thiophene-2-sulfonyl)-propyl-amino]-ethylsulfanyl}-2-methyl-phenyl)-propionic acid |
| 3 | 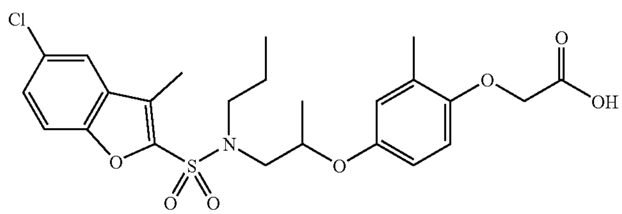 | (4-{2-[(5-Chloro-3-methyl-benzofuran-2-sulfonyl)-propyl-amino]-1-methyl-ethoxy}-2-methyl-phenoxy)-acetic acid |
| 4 | 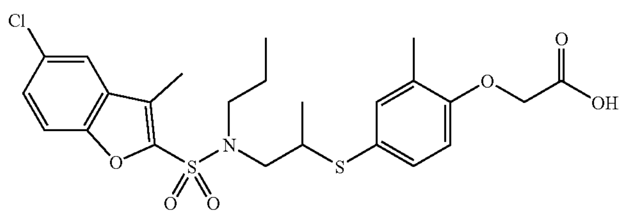 | (4-{2-[(5-Chloro-3-methyl-benzofuran-2-sulfonyl)-propyl-amino]-1-methyl-ethylsulfanyl}-2-methyl-phenoxy)-acetic acid |
| 5 | 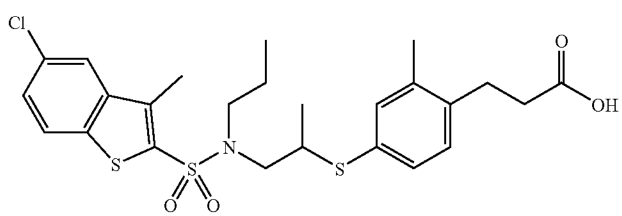 | 3-(4-{2-[(5-Chloro-3-methyl-benzo[b]thiophene-2-sulfonyl)-propyl-amino]-1-methyl-ethylsulfanyl}-2-methyl-phenyl)-propionic acid |
| 6 | 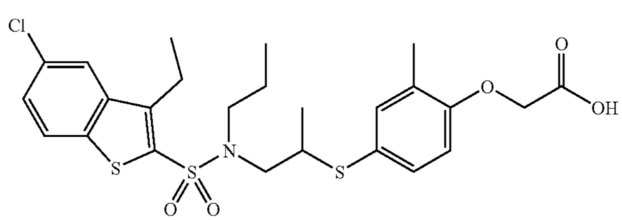 | (4-{2-[(5-Chloro-3-ethyl-benzo[b]thiophene-2-sulfonyl)-propyl amino]-1-methyl-ethylsulfanyl}-2-methyl-phenoxy)-acetic acid |
| 7 | 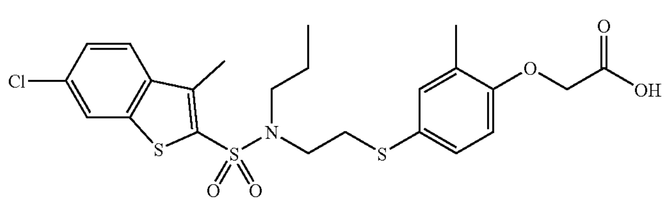 | 4-{2-[(6-Chloro-3-methyl-benzo[b]thiophene-2-sulfonyl)-propyl-amino]-ethylsulfanyl}-2-methyl-phenoxy)-acetic aci |
| 8 | 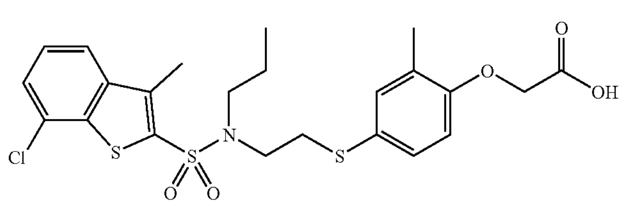 | 4-{2-[(7-Chloro-3-methyl-benzo[b]thiophene-2-sulfonyl)-propyl-amino]-ethylsulfanyl}-2-methyl-phenoxy)-acetic acid |

-continued

| No. | Structure | Name |
|---|---|---|
| 9 | 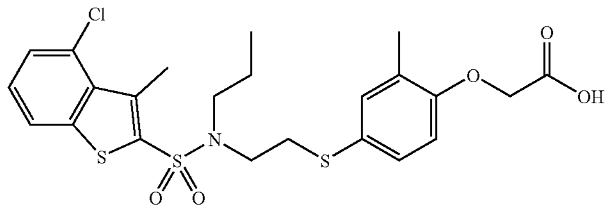 | (4-{2-[(4-Chloro-3-methyl-benzo[b]thiophene-2-sulfonyl)-propyl-amino]-ethylsulfanyl}-2-methyl-phenoxy)-acetic acid |
| 10 | 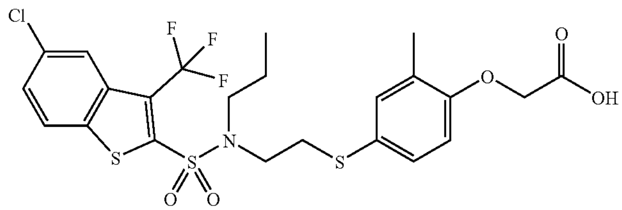 | (4-{2-[(5-Chloro-3-trifluoromethyl-benzo[b]thiophene-2-sulfonyl)-propyl-amino]-ethylsulfanyl}-2-methyl-phenoxy)-acetic acid |
| 11 | 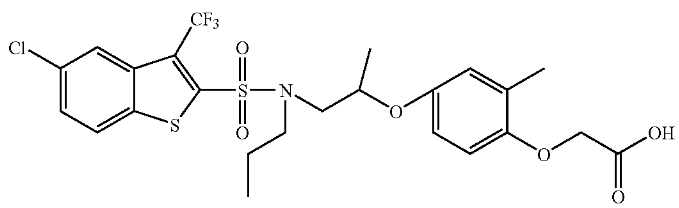 | (4-{2-[(5-Chloro-3-trifluoromethyl-benzo[b]thiophene-2-sulfonyl)-propyl-amino]-1-methyl-ethoxy}-2-methyl-phenoxy)-acetic acid |
| 12 | 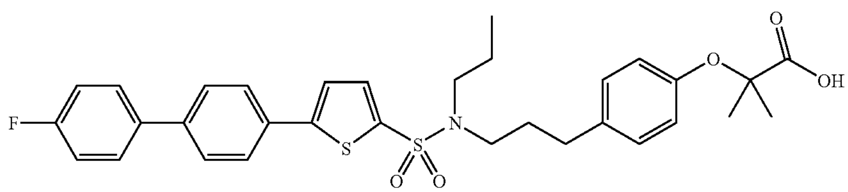 | 2-[4-(3-{[5-(4'-Fluoro-biphenyl-4-yl)-thiophene-2-sulfonyl]-propyl-amino}-propyl)-phenoxy]-2-methyl-propionic acid |
| 13 | 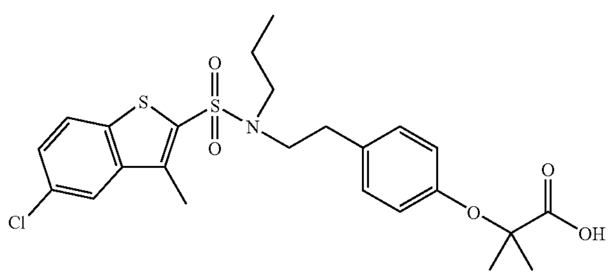 | 2-(4-{2-[(5-Chloro-3-methyl-benzo[b]thiophene-2-sulfonyl)-propy]-amino]-ethyl}-phenoxy)-2-methyl-propionic acid |
| 14 | 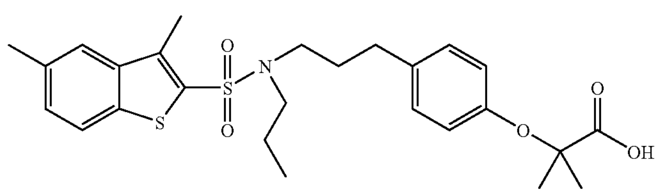 | 2-(4-{3-[(3,5-Dimethyl-benzo[b]thiophene-2-sulfonyl)-propyl-amino]-propyl}-phenoxy)-2-methyl-propionic acid |
| 15 | 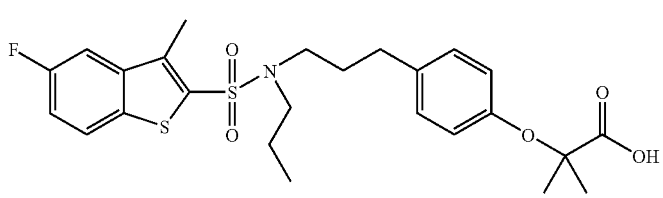 | 2-(4-{3-[(5-Fluoro-3-methyl-benzo[b]thiophene-2-sulfonyl)-propyl-amino]-propyl}-phenoxy)-2-methyl-propionic acid |

-continued

| No. | Structure | Name |
|---|---|---|
| 16 | 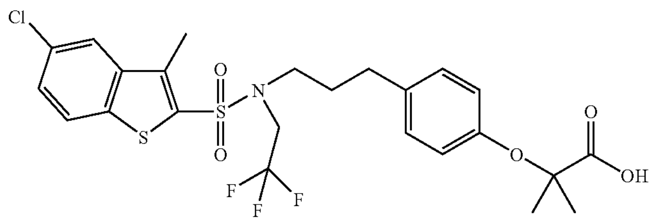 | 2-(4-{3-[(5-Chloro-3-methyl-benzo[b]thiophene-2-sulfonyl)-(2,2,2-trifluoro-ethyl)-amino]-propyl}-phenoxy)-2-methyl-propionic acid |
| 17 | 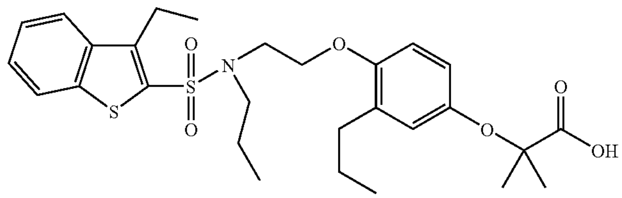 | 2-(4-{2-[(3-Ethyl-benzo[b]thiophene-2-sulfonyl)-propyl-amino]-ethoxy}-3-propyl-phenoxy)-2-methyl-propionic acid |
| 18 | 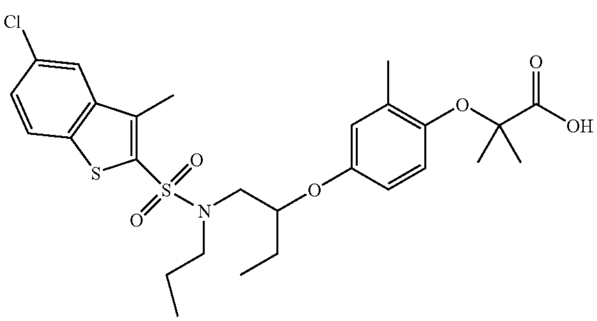 | 2-[4-(1-{[(5-Chloro-3-methyl-benzo[b]thiophene-2-sulfonyl)-propyl-amino]-methyl}-propoxy)-2-methyl-phenoxy]-2-methyl-propionic acid |
| 19 | 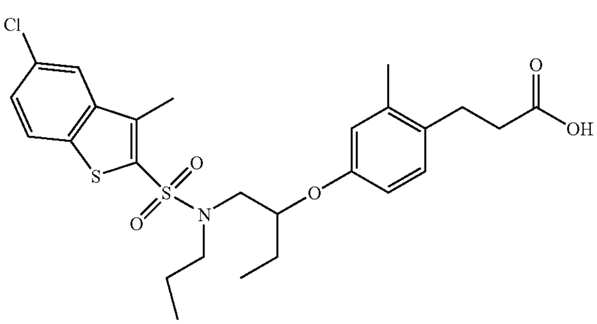 | 3-[4-(1-{[(5-Chloro-3-methyl-benzo[b]thiophene-2-sulfonyl)-propyl-amino]-methyl}-propoxy)-2-methyl-phenyl]-propionic acid |
| 20 | 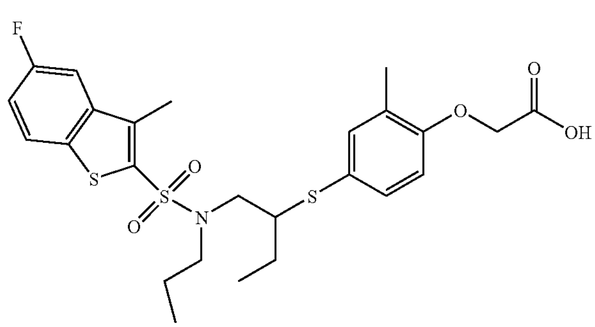 | [4-(1-{[(5-Fluoro-3-methyl-benzo[b]thiophene-2-sulfonyl)-propyl-amino]-methyl}-propylsulfanyl)-2-methyl-phenoxy]-acetic acid |

-continued

| No. | Structure | Name |
|---|---|---|
| 21 | 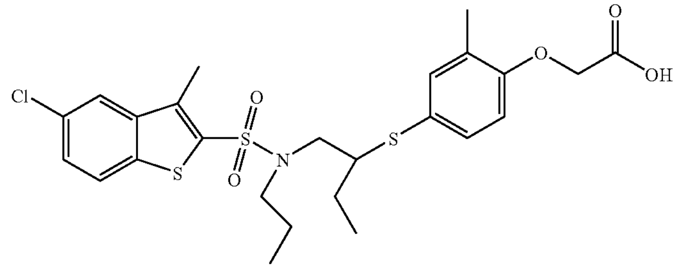 | [4-(1-{[(5-Chloro-3-methyl-benzo[b]thiophene-2-sulfonyl)-propyl-amino]-methyl}-propylsulfanyl)-2-methyl-phenoxy]-acetic acid |
| 22 | 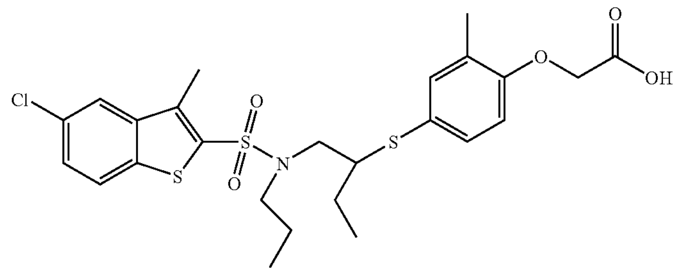 | [4-(1-{[(5-Chloro-3-methyl-benzo[b]thiophene-2-sulfonyl)-propyl-amino]-methyl}-propylsulfanyl)-2-methyl-phenoxy]-acetic acid |
| 23 | 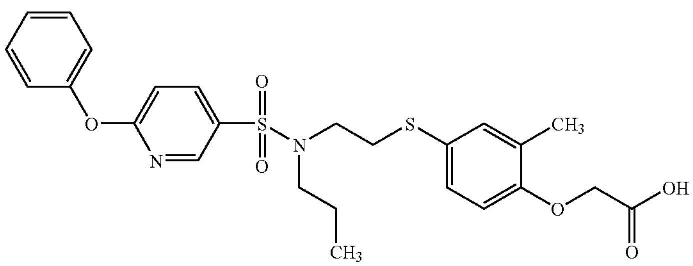 | (2-Methyl-4-{2-[(6-phenoxy-pyridine-3-sulfonyl)-propyl-amino]-ethylsulfanyl}phenoxy)-acetic acid |
| 24 | 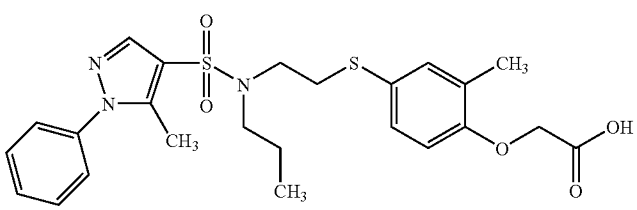 | (2-Methyl-4-{2-[(5-methyl-1-phenyl-1H-pyrazole-4-sulfonyl)-propyl-amino]-ethylsulfanyl}-phenoxy)-acetic acid |
| 25 | 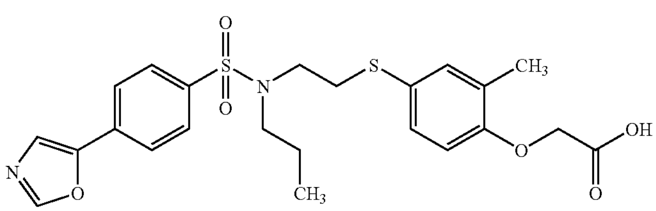 | (2-Methyl-4-{2-[(4-oxazol-5-yl-benzenesulfonyl)-propyl-amino]-ethylsulfanyl}-phenoxy)-acetic acid |
| 26 | 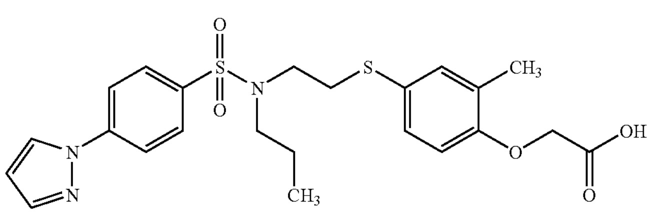 | (2-Methyl-4-{2-[propyl-(4-pyrazol-1-yl-benzenesulfonyl)-amino]-ethylsulfanyl}-phenoxy)-acetic acid |

-continued

| No. | Structure | Name |
|-----|-----------|------|
| 27 | 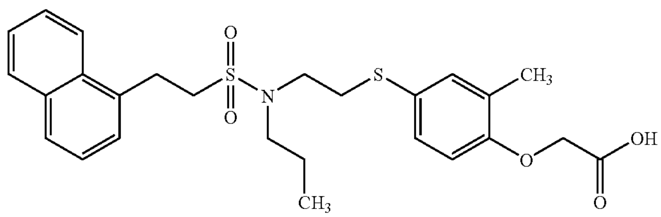 | (2-Methyl-4-{2-[(2-naphthalen-1-yl-ethanesulfonyl)-propyl-amino]-ethylsulfanyl}-phenoxy)-acetic acid |
| 28 | 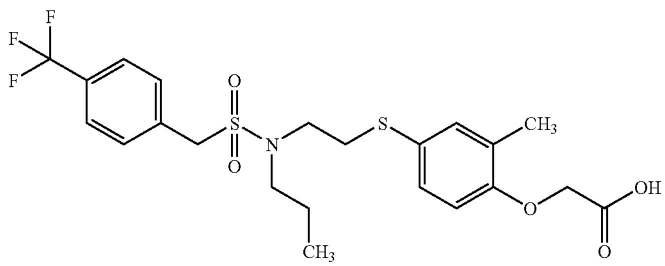 | (2-Methyl-4-{2-[propyl-(4-trifluoromethylphenyl-methanesulfonyl)-amino]-ethylsulfanyl)-phenoxy)-acetic acid |
| 29 | 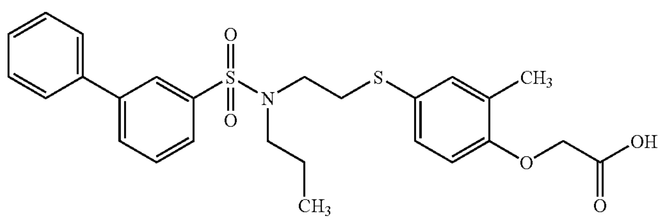 | (4-{2-[(Biphenyl-3-sulfonyl)-propyl-amino]-ethylsulfanyl}-2-methyl-phenoxy)-acetic acid |
| 30 | 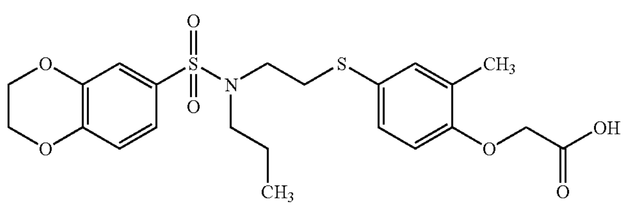 | (4-{2-[(2,3-Dihydro-benzo[1,4]dioxine-6-sulfonyl)-propyl-amino]-ethylsulfanyl}-2-methyl-phenoxy)-acetic acid |
| 31 | 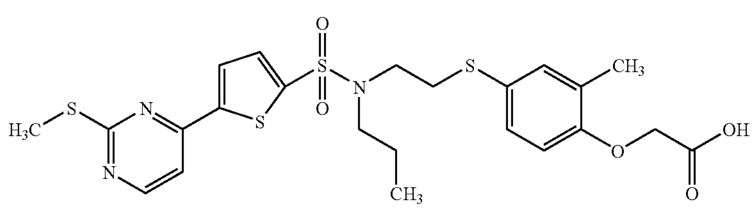 | [2-Methyl-4-(2-{[5-(2-methylsulfanyl-pyrimidin-4-yl)-thiophene-2-sulfonyl]-propyl-amino}-ethylsulfanyl)-phenoxy]-acetic acid |
| 32 | 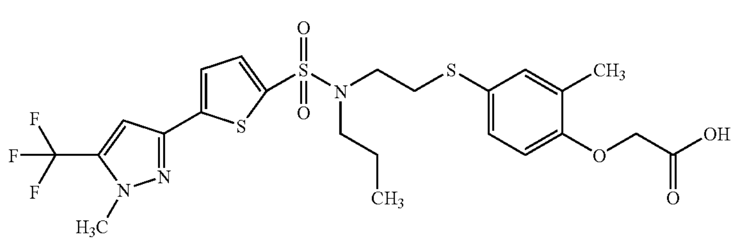 | [2-Methyl-4-(2-{[5-(1-methyl-5-trifluoromethyl-1H-pyrazol-3-yl)-thiophene-2-sulfonyl]-propyl-amino}-ethylsulfanyl)-phenoxy]-acetic acid |

-continued

| No. | Structure | Name |
|---|---|---|
| 33 | 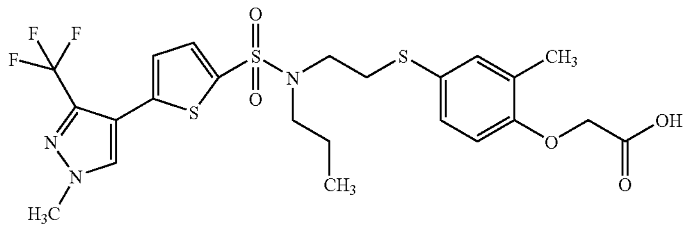 | [2-Methyl-4-(2-{[5-(1-methyl-3-trifluoromethyl-1H-pyrazol-4-yl)-thiophene-2-sulfonyl]-propyl-amino}-ethylsulfanyl)-phenoxy]-acetic acid |
| 34 | 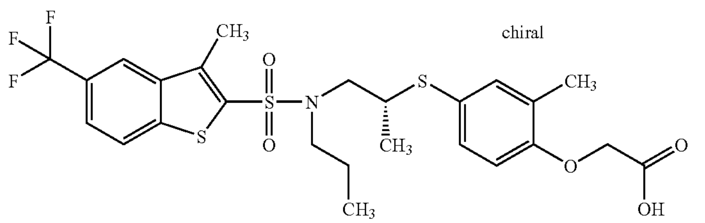 | (R)-(2-Methyl-4-{1-methyl-2-[(3-methyl-5-trifluoromethyl-benzo[b]thiophene-2-sulfonyl)-propyl-amino]-ethylsulfanyl}-phenoxy)-acetic acid |
| 35 | 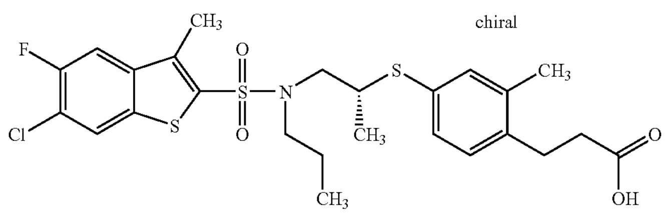 | (R)-3-(4-{2-[(6-Chloro-5-fluoro-3-methyl-benzo[b]thiophene-2-sulfonyl)-propyl-amino]-1-methyl-ethylsulfanyl}-2-methyl-phenyl)-propionic acid |
| 36 | 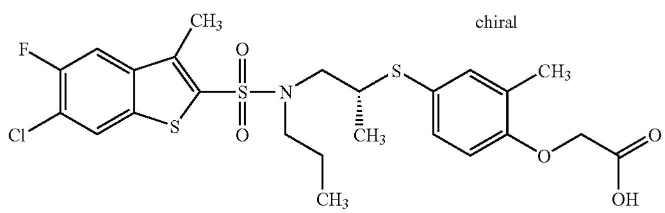 | (R)-(4-{2-[(6-Chloro-5-fluoro-3-methyl-benzo[b]thiophene-2-sulfony])-propyl-amino]-1-methyl-ethylsulfanyl}-2-methyl-phenoxy)-acetic acid |
| 37 | 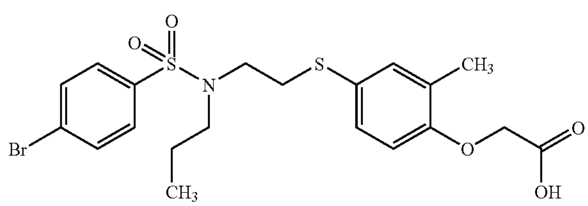 | (4-{2-[(4-Bromo-benzenesulfonyl)-propyl-amino]-ethylsulfanyl}-2-methyl-phenoxy)-acetic acid |
| 38 | 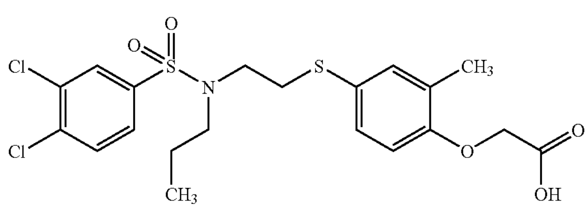 | (4-{2-[(3,4-Dichloro-benzenesulfonyl)-propyl-amino]-ethylsulfanyl}-2-methyl-phenoxy)-acetic acid |
| 39 | 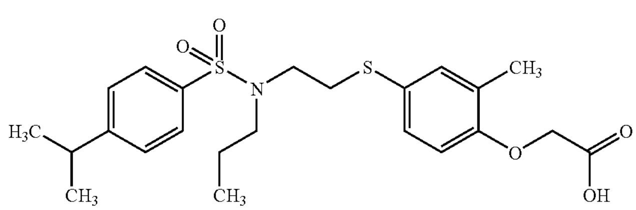 | (4-{2-[(4-Isopropyl-benzenesulfonyl)-propyl-amino]-ethylsulfanyl}-2-methyl-phenoxy)-acetic acid |

-continued

| No. | Structure | Name |
|---|---|---|
| 40 | 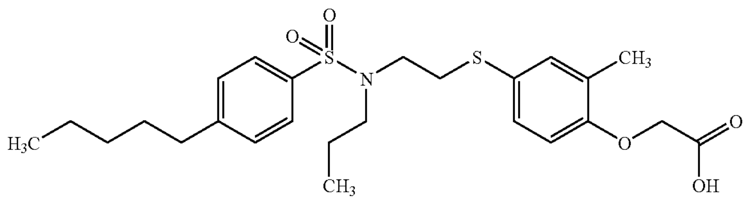 | (2-Methyl-4-{2-[(4-pentyl-benzenesulfonyl)-propyl-amino]-ethylsulfanyl}-phenoxy)-acetic acid |
| 41 | 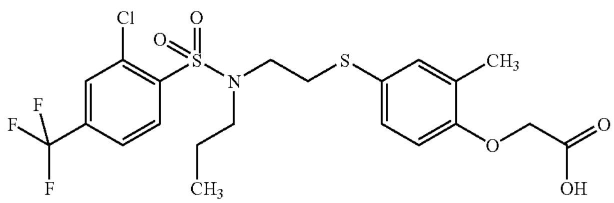 | (4-{2-[(2-Chloro-4-trifluoromethyl-benzenesulfonyl)-propyl-amino]-ethylsulfanyl}-2-methyl-phenoxy)-acetic acid |
| 42 | 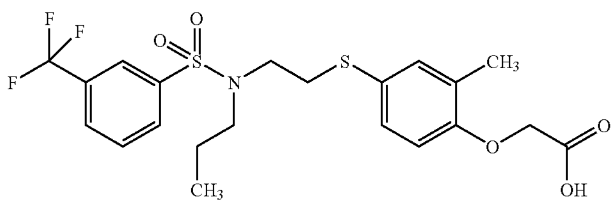 | (2-Methyl-4-{2-[propyl-(3-trifluoromethyl-benzenesulfonyl)-amino]-ethylsulfanyl}-phenoxy)-acetic acid |
| 43 | 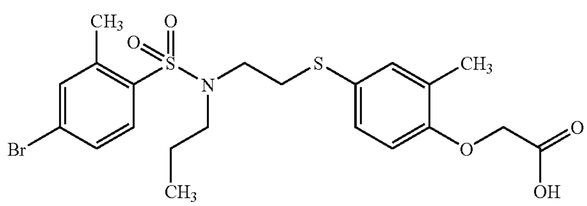 | (4-{2-[(4-Bromo-2-methyl-benzenesulfonyl)-propyl-amino]-ethylsulfanyl}-2-methyl-phenoxy)-acetic acid |
| 44 | 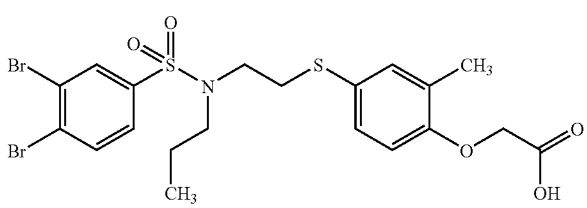 | (4-{2-[(3,4-Dibromo-benzenesulfonyl)-propyl-amino]-ethylsulfanyl}-2-methyl-phenoxy)-acetic acid |
| 45 | 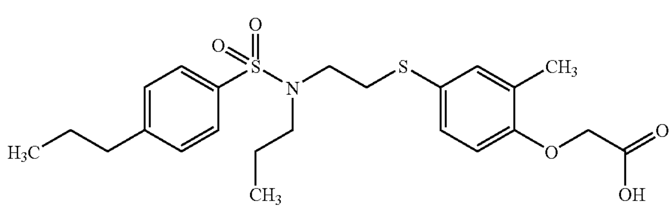 | (2-Methyl-4-{2-[propyl-(4-propyl-benzenesulfonyl)-amino]-ethylsulfanyl}-phenoxy)-acetic acid |
| 46 | 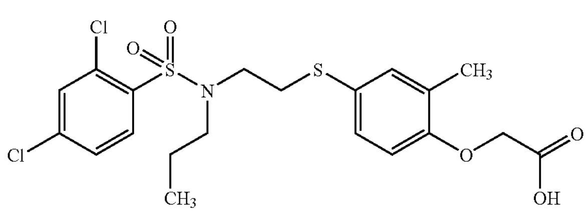 | (4-{2-[(2,4-Dichloro-benzenesulfonyl)-propyl-amino]-ethylsulfanyl}-2-methyl-phenoxy)-acetic acid |

-continued

| No. | Structure | Name |
|---|---|---|
| 47 | 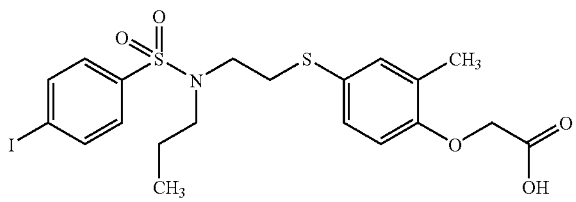 | (4-{2-[(4-Iodo-benzenesulfonyl)-propyl-amino]-ethylsulfanyl}-2-methyl-phenoxy)-acetic acid |
| 48 | 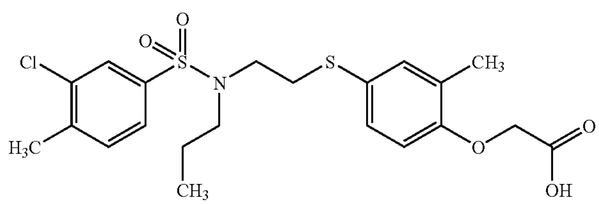 | (4-{2-[(3-Chloro-4-methyl-benzenesulfonyl)-propyl-amino]-ethylsulfanyl}2-methyl-phenoxy)-acetic acid |
| 49 | 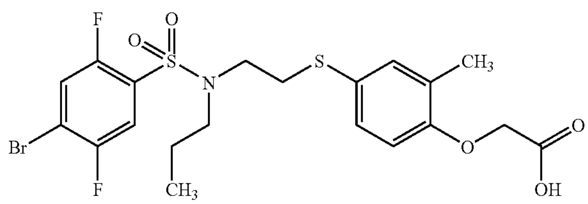 | (4-{2-[(4-Bromo-2,5-difluoro-benzenesulfonyl)-propyl-amino]-ethylsulfanyl}-2-methyl-phenoxy)-acetic acid |
| 50 | 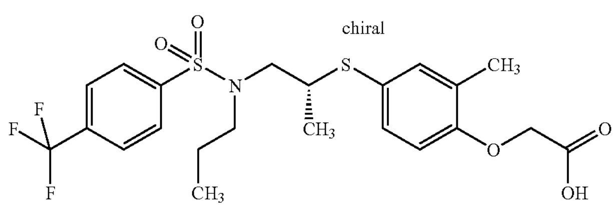 | (2-Methyl-4-{1-methyl-2-[propyl-(4-trifluoromethyl-benzenesulfonyl)-amino]-ethylsulfanyl}-phenoxy)-acetic acid |
| 51 | 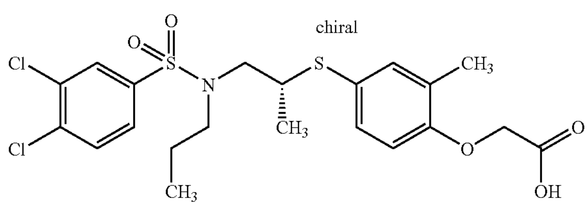 | (4-{2-[(3,4-Dichloro-benzenesulfonyl)-propyl-amino]-1-methyl-ethylsulfanyl}-2-methyl-phenoxy)-acetic acid |
| 52 | 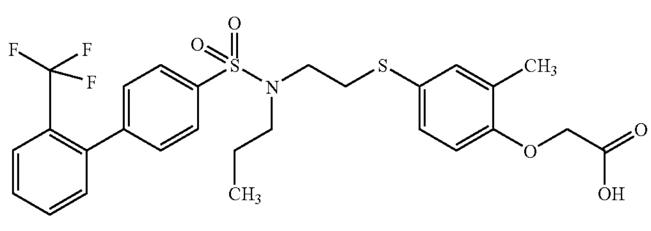 | (2-Methyl-4-{2-[propyl-(2'-trifluoromethyl-biphenyl-4-sulfonyl)-amino]-ethylsulfanyl}-phenoxy)-acetic acid |
| 53 | 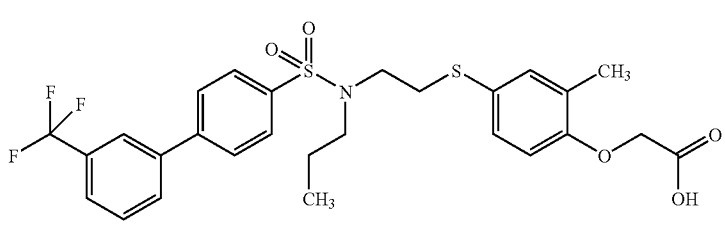 | (2-Methyl-4-{2-[propyl-(3'-trifluoromethyl-biphenyl-4-sulfonyl)-amino]-ethylsulfanyl}-phenoxy)-acetic acid |

-continued

| No. | Structure | Name |
|---|---|---|
| 54 | 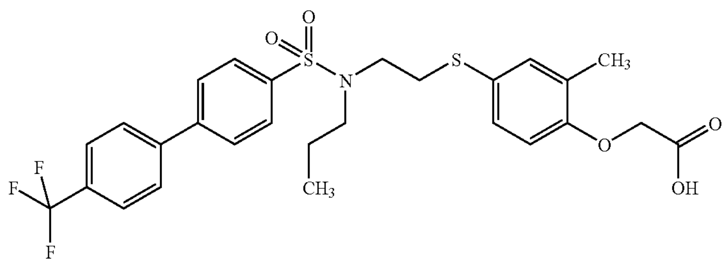 | (2-Methyl-4-{2-[propyl-(4'-trifluoromethyl-biphenyl-4-sulfony])-amino]-ethylsulfanyl}-phenoxy)-acetic acid |
| 55 | 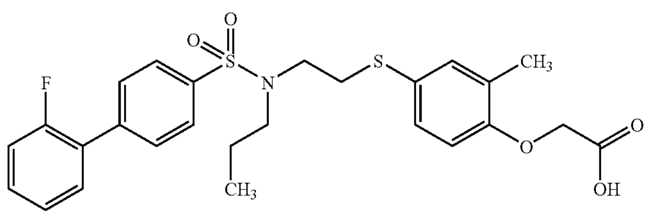 | (4-{2-[(2'-Fluoro-biphenyl-4-sulfonyl)-propyl-amino]-ethyl sulfanyl}-2-methyl-phenoxy)-acetic acid |
| 56 | 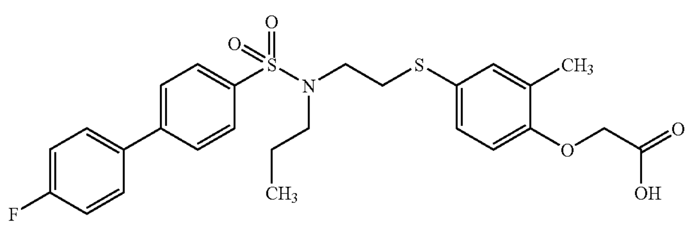 | (4-{2-[(4'-Fluoro-biphenyl-4-sulfonyl)-ethylsulfanyl}-2-methyl-phenoxy)-acetic acid |
| 57 | 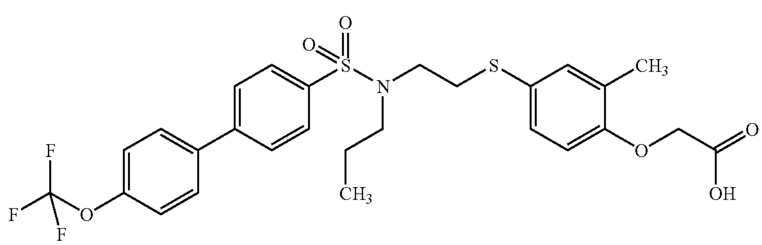 | (2-Methyl-4-{2-[propyl-(4'-trifluoromethoxy-biphenyl-4-sulfonyl)-amino]-ethylsulfanyl}-phenoxy)-acetic acid |
| 58 | 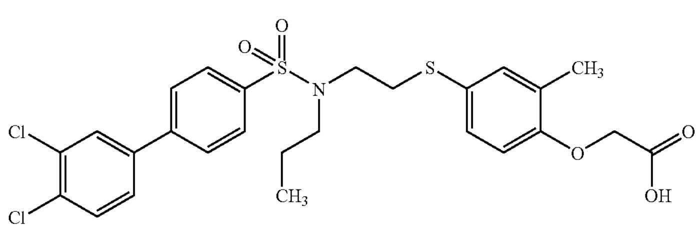 | (4-{2-[(3',4'-Dichloro-biphenyl-4-sulfonyl)-propyl-amino]-ethylsulfanyl}-2-methyl-phenoxy)-acetic acid |
| 59 | 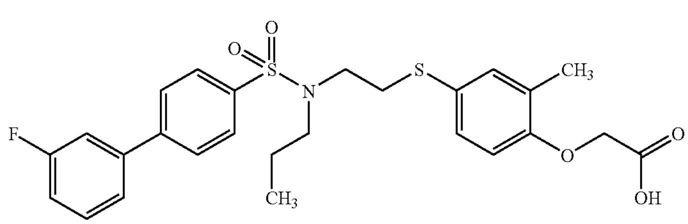 | (4-{2-[(3'-Fluoro-biphenyl-4-sulfonyl)-propyl-amino]-ethylsulfanyl}-2-methyl-phenoxy)-acetic acid |

-continued

| No. | Structure | Name |
|---|---|---|
| 60 | 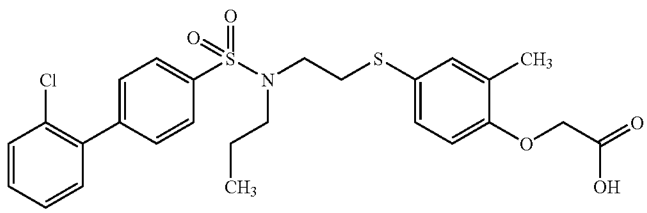 | (4-{2-[(2'-Chloro-biphenyl-4-sulfonyl)-propyl-amino]-ethylsulfanyl}-2-methyl-phenoxy)-acetic acid |
| 61 | 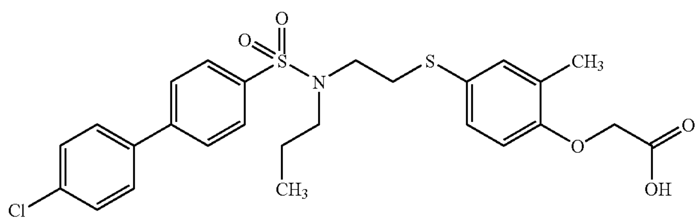 | (4-{2-[(4'-Methoxy-biphenyl-4-sulfonyl)-propyl-amino]-ethylsulfanyl}-2-methyl-phenoxy)-acetic acid |
| 62 | 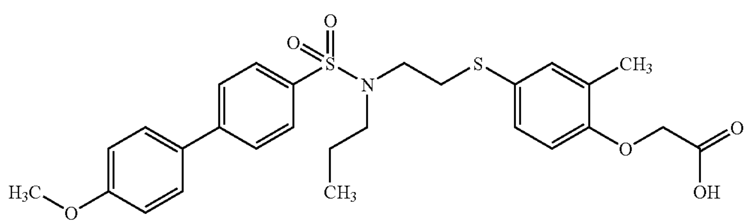 | (4-{2-[(4'-Methoxy-biphenyl-4-sulfonyl)-propyl-amino]-ethylsulfanyl}-2-methyl-phenoxy)-acetic acid |
| 63 | 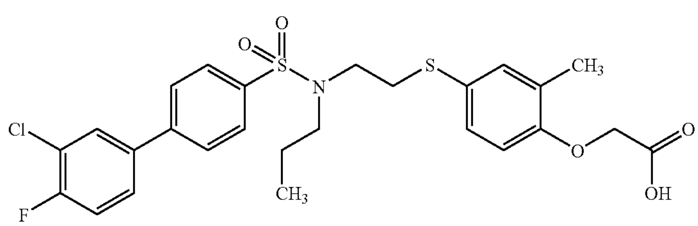 | (4-{2-[(3'-Chloro-4'-fluoro-bipheny]-4-sulfonyl)-propyl]-amino]-ethylsulfanyl}-2-methyl-phenoxy)-acetic acid |
| 64 | 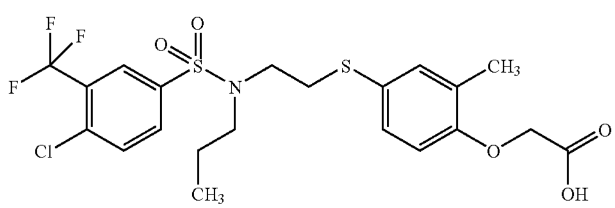 | (4-{2-[(4-Chloro-3-trifluoromethyl-benzenesulfonyl)-propyl-amino]-ethylsulfanyl}-2-methyl-phenoxy)-acetic acid |
| 65 | 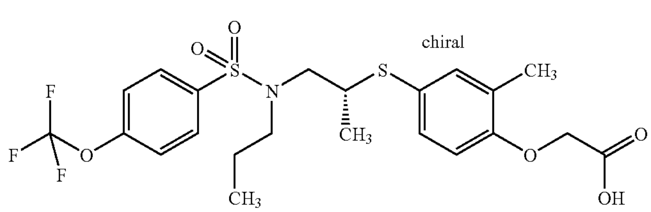 | (2-Methyl-4-{1-methyl-2-[propyl-(4-trifluoromethoxy-benzenesulfonyl)-amino]-ethylsulfanyl}-phenoxy)-acetic acid |
| 66 | 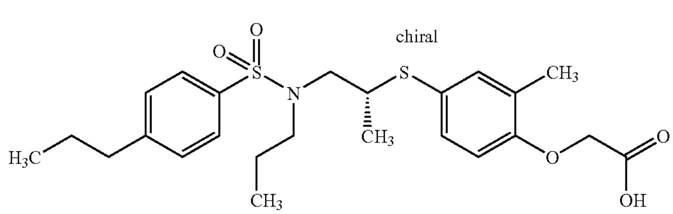 | (2-Methyl-4-{1-methyl-2-[propyl-(4-propyl-benzenesulfonyl)-amino]-ethylsulfanyl}-phenoxy)-acetic acid |

-continued

| No. | Structure | Name |
|---|---|---|
| 67 | 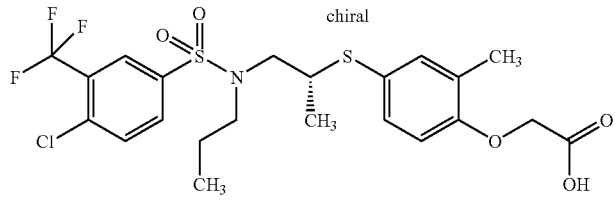 | (4-{2-[(4-Chloro-3-trifluoromethyl-benzenesulfonyl)-propyl-amino]-1-methyl-ethylsulfanyl}-2-methyl-phenoxy)-acetic acid |
| 68 | 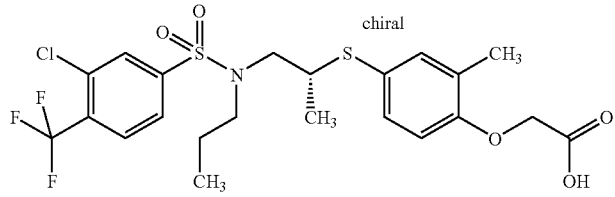 | (4-{2-[(3-Chloro-4-trifluoromethyl-benzenesulfonyl)-propyl-amino]-1-methyl-ethylsulfanyl}-2-methyl-phenoxy)-acetic acid |
| 69 | 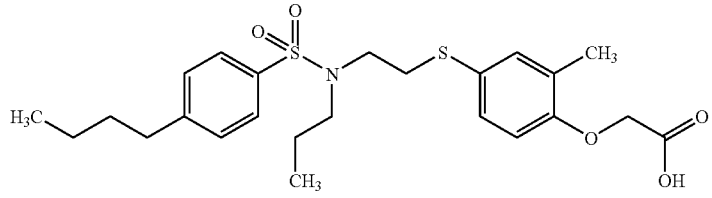 | (4-{2-[(4-Butyl-benzenesulfonyl)-propyl-amino]-ethylsulfanyl}-2-methyl-phenoxy)-acetic acid |
| 70 | 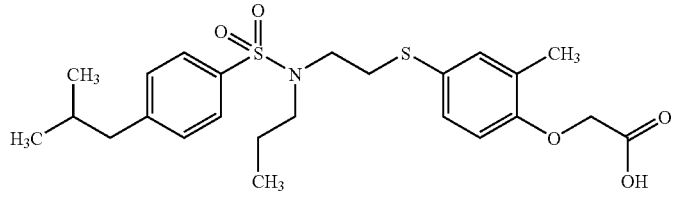 | (4-{2-[(4-Isobutyl-benzenesulfonyl)-propyl-amino]-ethylsulfanyl)-2-methyl-phenoxy)-acetic acid |
| 71 | 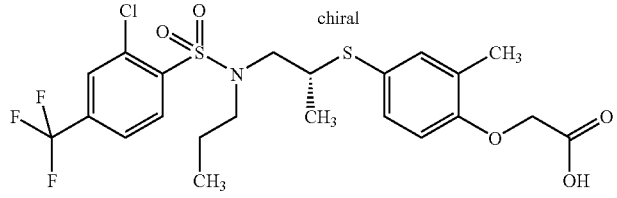 | (4-{2-[(2-Chloro-4-trifluoromethyl-benzenesulfonyl)-propyl-amino]-1-methyl-ethylsulfanyl}-2-methyl-phenoxy)-acetic acid |
| 72 | 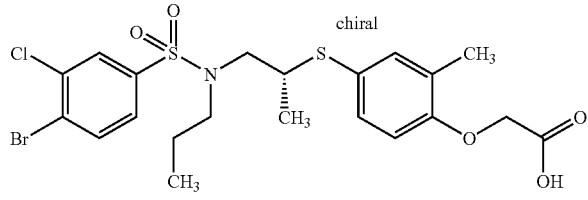 | (4-{2-[(4-Bromo-3-chloro-benzenesulfonyl)-propyl-amino}-1-methyl-ethylsulfanyl}-2-methyl-phenoxy)-acetic acid |
| 73 | 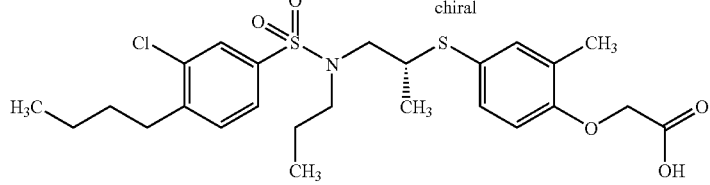 | (4-{2-[(4-Butyl-3-chloro-benzenesulfonyl)-propyl-amino]-1-methyl-ethylsulfanyl}-2-methyl-phenoxy)-acetic acid |

-continued

| No. | Structure | Name |
|---|---|---|
| 74 | 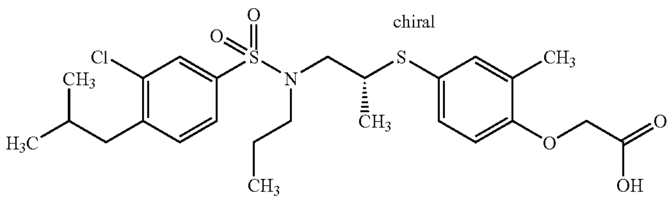 | (4-{2-[(3-Chloro-4-isobutyl-benzenesulfonyl)-propyl-amino]-1-methyl-ethylsulfanyl}-2-methyl-phenoxy)-acetic acid |
| 75 | 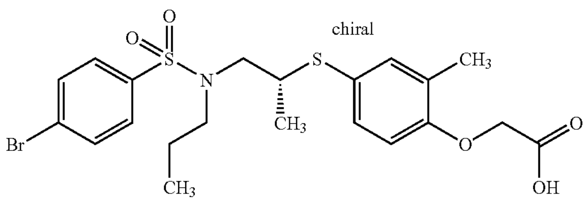 | (4-{2-[(4-Bromo-benzenesulfonyl)-propyl-amino]-1-methyl-ethylsulfanyl}-2-methyl-phenoxy)-acetic acid |
| 76 | 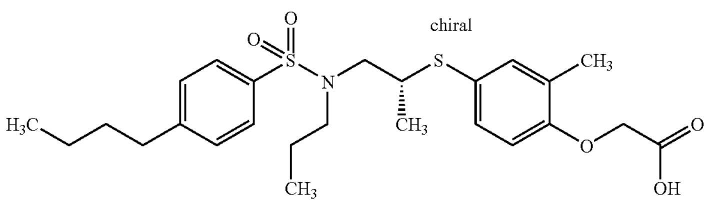 | (4-{2-[(4-Butyl-benzenesulfonyl)-propyl-amino]-1-methyl-ethylsulfanyl}-2-methyl-phenoxy)-acetic acid |
| 77 | 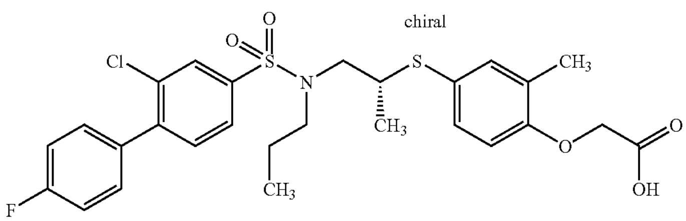 | (4-{2-[(2-Chloro-4'-fluoro-biphenyl-4-sulfonyl)-propyl-amino]-1-methyl-ethylsulfanyl}-2-methyl-phenoxy)-acetic acid |
| 78 | 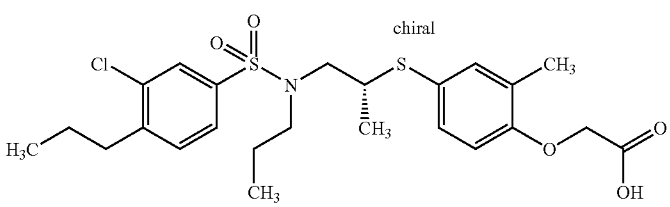 | (4-{2-[(3-Chloro-4-propyl-benzenesulfonyl)-propyl-amino]-1-methyl-ethylsulfanyl}-2-methyl-phenoxy)-acetic acid |
| 79 | 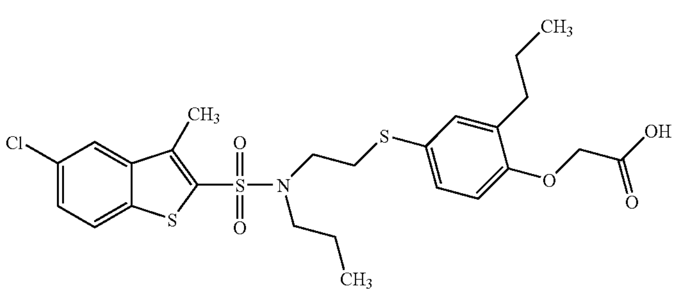 | (4-{2-[(5-Chloro-3-methyl-benzo[b]thiophene-2-sulfonyl)-propyl-amino]-ethylsulfanyl}-2-propyl-phenoxy)-acetic acid |
| 80 | 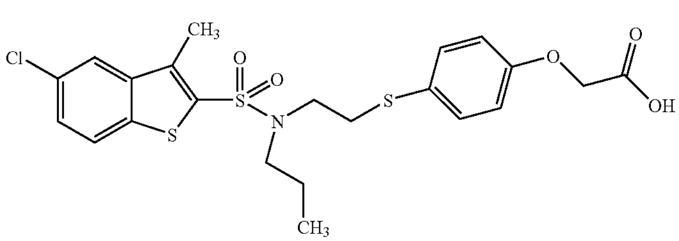 | (4-{2-[(5-Chloro-3-methyl-benzo[b]thiophene-2-sulfonyl)-propyl-amino]-ethylsulfanyl}-phenoxy)-acetic acid |

| No. | Structure | Name |
|---|---|---|
| 81 | 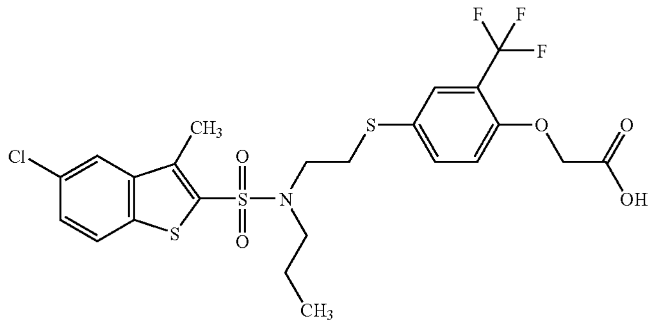 | (4-{2-[(5-Chloro-3-methyl-benzo[b]thiophene-2-sulfonyl)-propyl-amino]-ethylsulfanyl}-2-trifluoromethyl-phenoxy)-acetic acid |
| 82 | 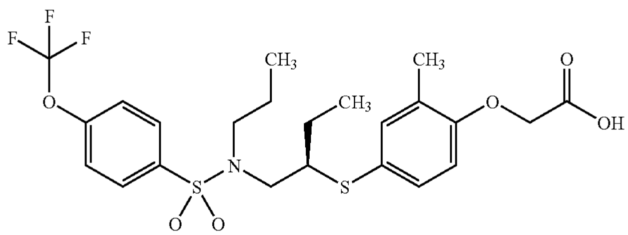 | [2-Methyl-4-(1-{[propyl-(4-trifluoromethoxy-benzenesulfonyl)-amino]-methyl}-propylsulfanyl)-phenoxy]-acetic acid |
| 83 | 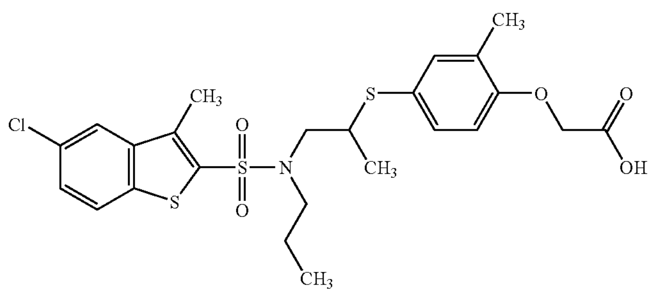 | (4-{2-[(5-Chloro-3-methyl-benzo[b]thiophene-2-sulfonyl)-propyl-amino]-1-methyl-ethylsulfanyl}-2-methyl-phenoxy)-acetic acid |
| 84 | 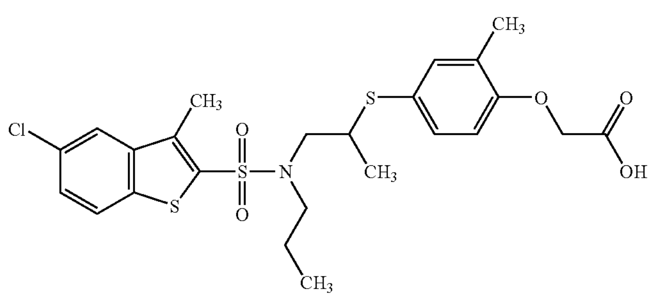 | (4-{2-[(5-Chloro-3-methyl-benzo[b]thiophene-2-sulfonyl)-propyl-amino]-1-methyl-ethylsulfanyl}-2-methyl-phenoxy)-acetic acid |
| 85 | 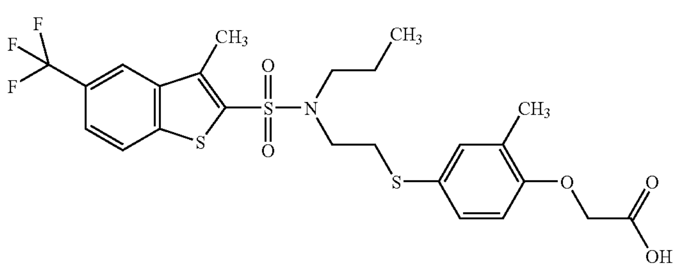 | (2-Methyl-4-{2-[(3-methyl-5-trifluoromethyl-benzo[b]thiophene-2-sulfonyl)-propyl-amino]-ethylsulfanyl}-phenoxy)-acetic acid |

-continued

| No. | Structure | Name |
|---|---|---|
| 86 | 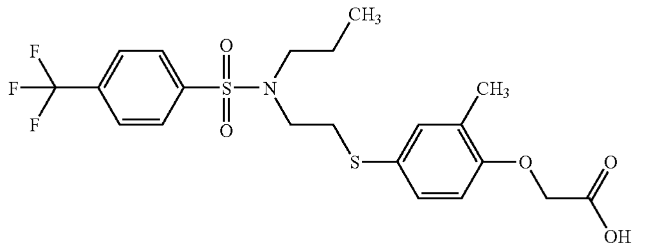 | (2-Methyl-4-{2-[propyl-(4-trifluoromethyl-benzenesulfonyl)-amino]-ethylsulfanyl}-phenoxy)-acetic acid |
| 87 | 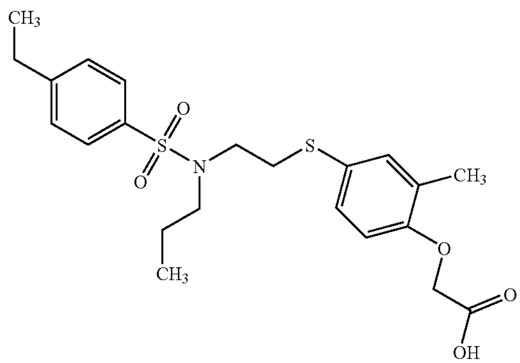 | (4-{2-[(4-Ethyl-benzenesulfonyl)-propyl-amino]-ethylsulfanyl}-2-methyl-phenoxy)-acetic acid |
| 88 | 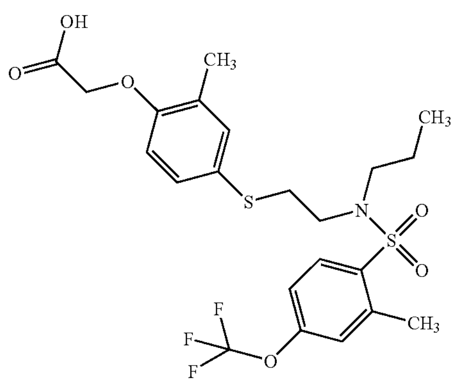 | (2-Methyl-4-{2-[(2-methyl-4-trifluoromethoxy-benzenesulfonyl)-propyl-amino]-ethylsulfanyl}-phenoxy)-acetic acid |
| 89 | 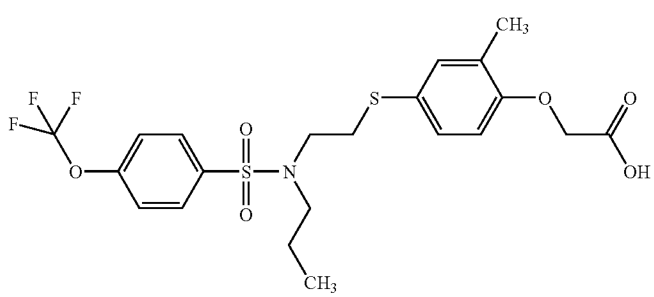 | (2-Methyl-4-{2-[propyl-(4-trifluoromethoxy-benzenesulfonyl)-amino]-ethylsulfanyl}-phenoxy)-acetic acid |
| 90 | 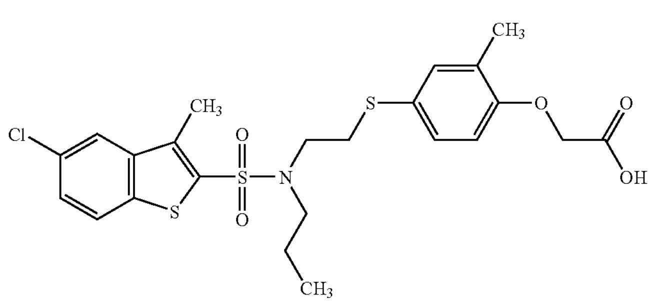 | (4-{2-[(5-Chloro-3-methyl-benzo[b]thiophene-2-sulfonyl)-propyl-amino]-ethylsulfanyl}-2-methyl-phenoxy)-acetic acid |

-continued

| No. | Structure | Name |
|---|---|---|
| 91 | 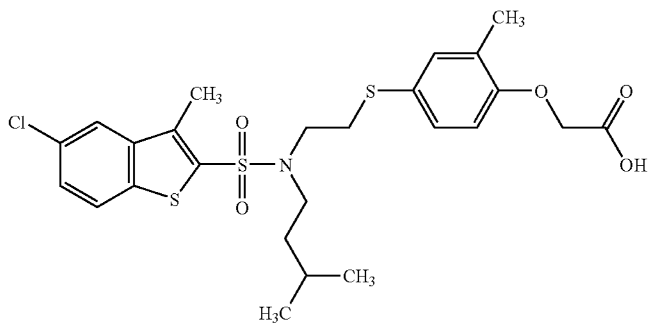 | (4-{2-[(5-Chloro-3-methyl-benzo[b]thiophene-2-sulfonyl)-(3-methyl-butyl)-amino]-ethylsulfanyl}-2-methyl-phenoxy)-acetic acid |
| 92 | 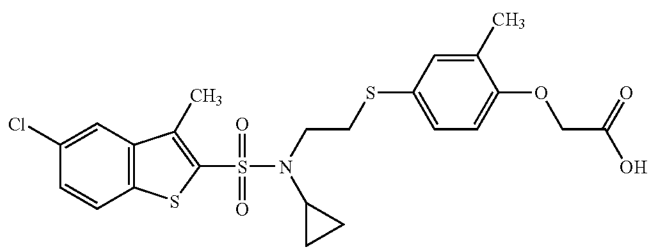 | (4-{2-[(5-Chloro-3-methyl-benzo[b]thiophene-2-sulfonyl)-cyclopropyl-amino]-ethylsulfanyl}-2-methyl-phenoxy)-acetic acid |
| 93 | 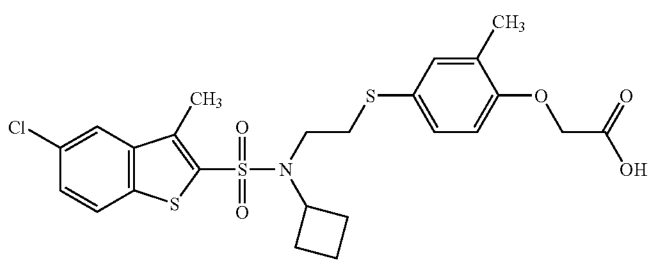 | (4-{2-[(5-Chloro-3-methyl-benzo[b]thiophene-2-sulfonyl)-cyclobutyl-amino]-ethylsulfanyl}-2-methyl-phenoxy)-acetic acid |
| 94 | 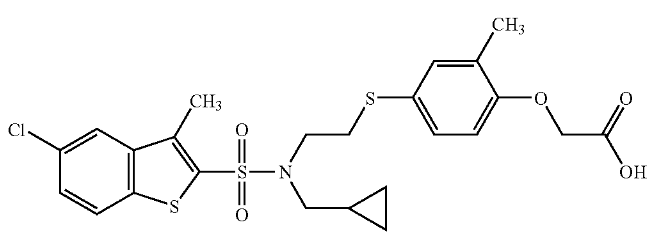 | (4-{2-[(5-Chloro-3-methyl-benzo[b]thiophene-2-sulfonyl)-cyclopropylmethyl-amino]-ethylsulfanyl}-2-methyl-phenoxy)-acetic acid |
| 95 | 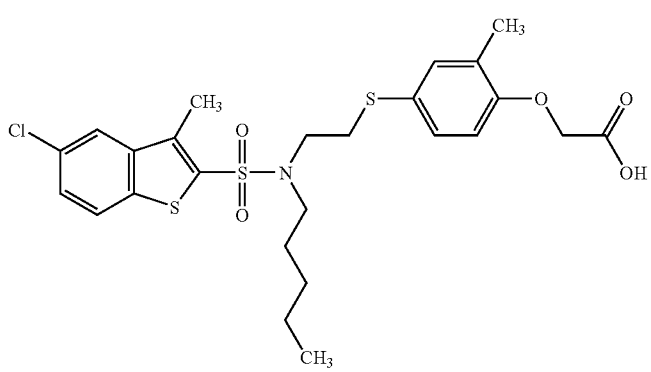 | (4-{2-[(5-Chloro-3-methyl-benzo[b]thiophene-2-sulfonyl)-pentyl-amino]-ethylsulfanyl}-2-methyl-phenoxy)-acetic acid |

-continued

| No. | Structure | Name |
|---|---|---|
| 96 | 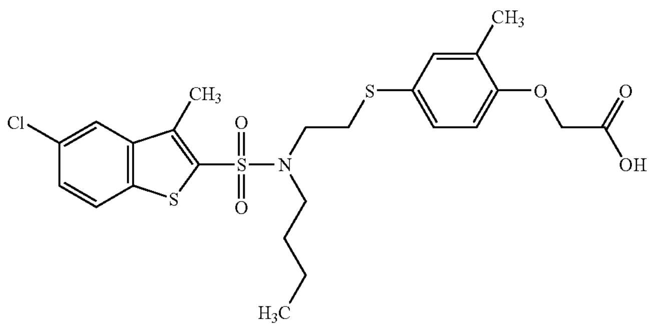 | (4-{2-[Butyl-(5-chloro-3-methyl-benzo[b]thiophene-2-sulfonyl)-amino]-ethylsulfanyl}-2-methyl-phenoxy)-acetic acid |
| 97 | 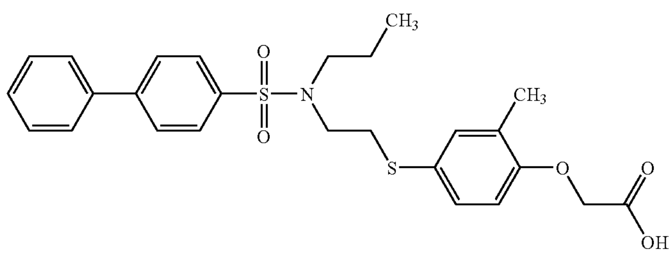 | (4-{2-[(Biphenyl-4-sulfonyl)-propyl-amino]-ethylsulfanyl}-2-methyl-phenoxy)-acid |
| 98 | 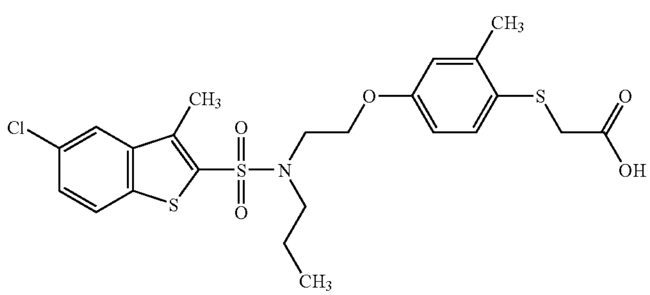 | (4-{2-[(5-Chloro-3-methyl-benzo[b]thiophene-2-sulfonyl)-propyl-amino]-ethoxy}-2-methyl-phenylsulfanyl)-acetic acid |
| 99 | 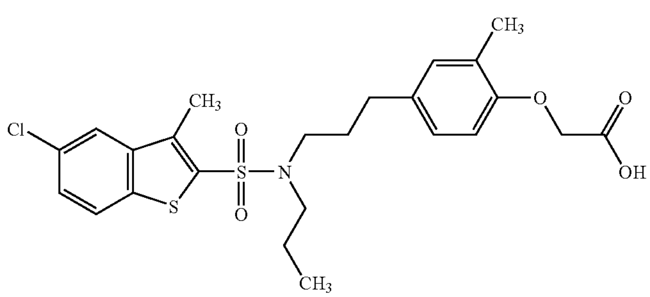 | (4-{3-[(5-Chloro-3-methyl-benzo[b]thiophene-2-sulfonyl)-propyl-amino]-propyl}-2-methyl-phenoxy)-acetic acid |
| 100 | 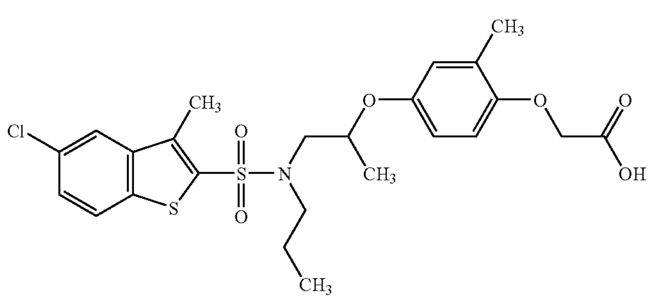 | (4-{2-[(5-Chloro-3-methyl-benzo[b]thiophene-2-sulfonyl)-propyl-amino]-1-methyl-ethoxy}-2-methyl-phenoxy)-acetic acid |

| No. | Structure | Name |
|---|---|---|
| 101 | 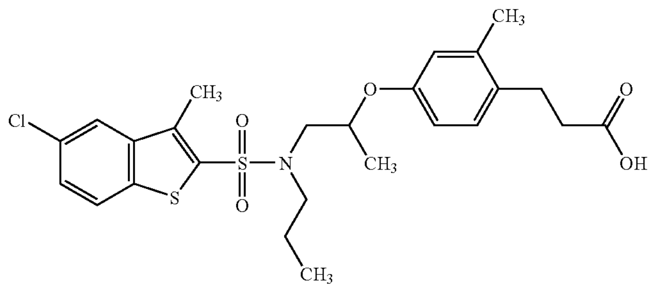 | 3-(4-{2-[(5-Chloro-3-methyl-benzo[b]thiophene-2-sulfonyl)-propyl-amino]-1-methyl-ethoxy}-2-methyl-phenyl)-propionic acid |
| 102 | 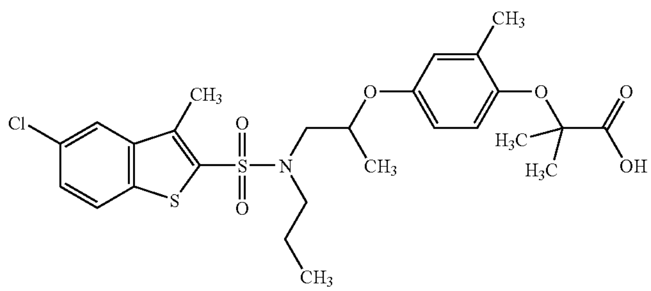 | 2-(4-{2-[(5-Chloro-3-methyl-benzo[b]thiophene-2-sulfonyl)-propyl-amino]-1-methyl-ethoxy}-2-methyl-phenoxy)-2-methyl-propionic acid |
| 103 | 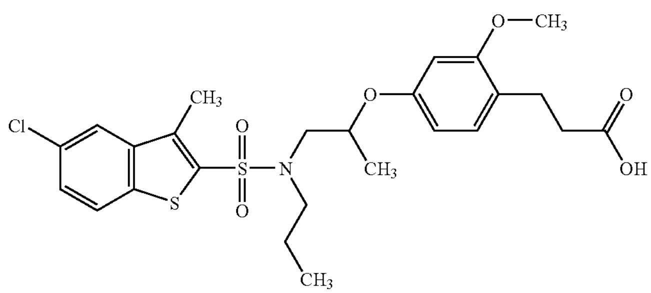 | 3-(4-{2-[(5-Chloro-3-methyl-benzo[b]thiophene-2-sulfonyl)-propyl-amino]-1-methyl-ethoxy}-2-methoxy-phenyl)-propionic acid |
| 104 | 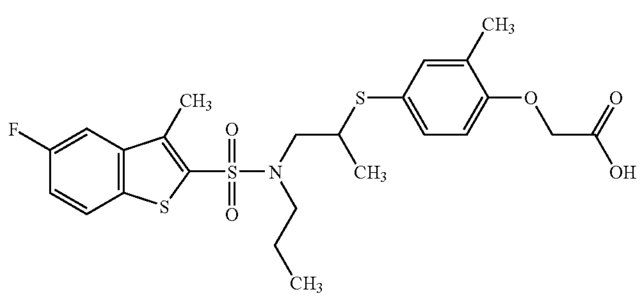 | (4-{2-[(5-Fluoro-3-methyl-benzo[b]thiophene-2-sulfonyl)-propyl-amino]-1-methyl-ethylsulfanyl}-2-methyl-phenoxy)-acetic acid |
| 105 | 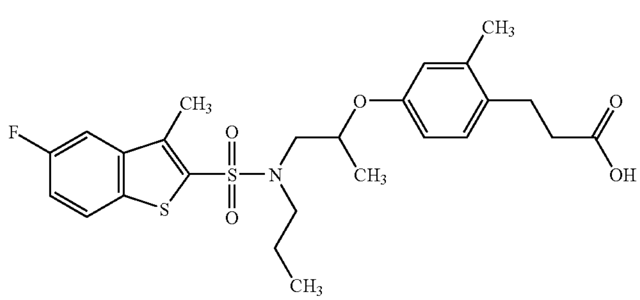 | 3-(4-{2-[(5-Fluoro-3-methyl-benzo[b]thiophene-2-sulfonyl)-propyl-amino]-1-methyl-ethoxy}-2-methyl-phenyl)-propionic acid |

-continued

| No. | Structure | Name |
|---|---|---|
| 106 | 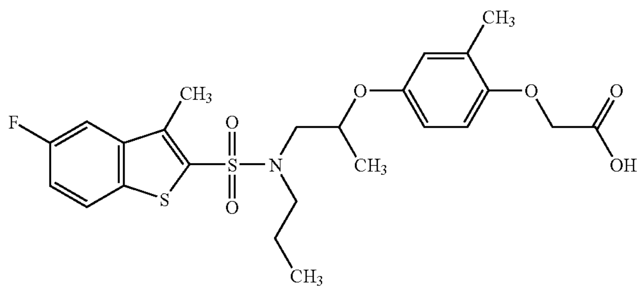 | (4-{2-[(5-Fluoro-3-methyl-benzo[b]thiophene-2-sulfonyl)-propyl-amino]-1-methyl-ethoxy}-2-methyl-phenoxy)-acetic acid |
| 107 | 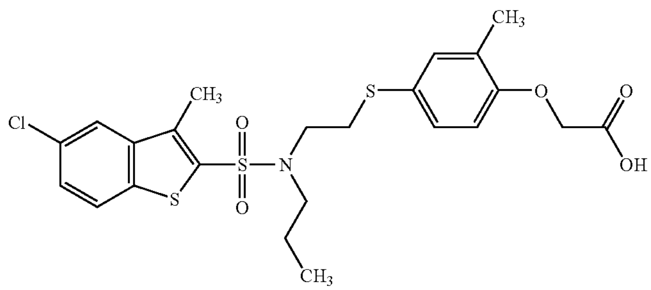 | (2-Chloro-4-{2-[(5-chloro-3-methyl-benzo[b]thiophene-2-sulfonyl)-propyl-amino]-ethylsulfanyl}-phenoxy)-acetic acid |
| 108 | 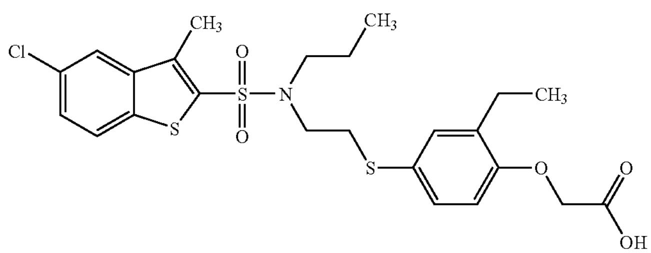 | (4-{2-[(5-Chloro-3-methyl-benzo[b]thiophene-2-sulfonyl)-propyl-amino]-ethylsulfanyl)-2-ethyl-phenoxy)-acetic acid |
| 109 | 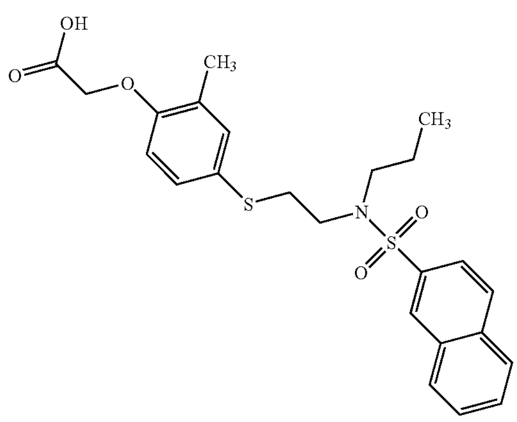 | (2-Methyl-4-{2-[(naphthalene-2-sulfonyl)-propyl-amino]-ethylsulfanyl}-phenoxy)-acetic acid |
| 110 | 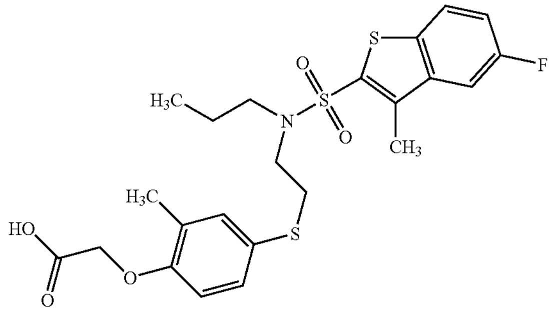 | (4-{2-[(5-Fluoro-3-methyl-benzo[b]thiophene-2-sulfonyl)-propyl-amino]-ethylsulfanyl}-2-methyl-phenoxy)-acetic acid |

-continued

| No. | Structure | Name |
|---|---|---|
| 111 | 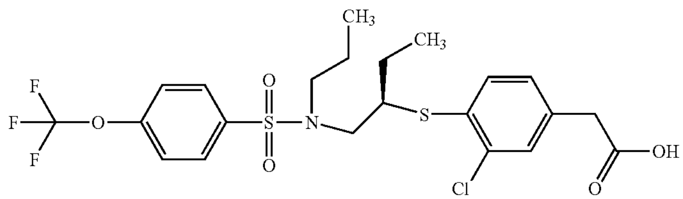 | [3-Chloro-4-(1-{[propyl-(4-trifluoromethoxy-benzenesulfonyl)-amino]-methyl}-propylsulfanyl)-phenyl]-acetic acid |
| 112 | Chiral | (R)-(3-Chloro-4-{2-[(5-chloro-3-methyl-benzo[b]thiophene-2-sulfonyl)-propyl-amino]-1-methyl-ethylsulfanyl}-phenyl)-acetic acid |
| 113 | 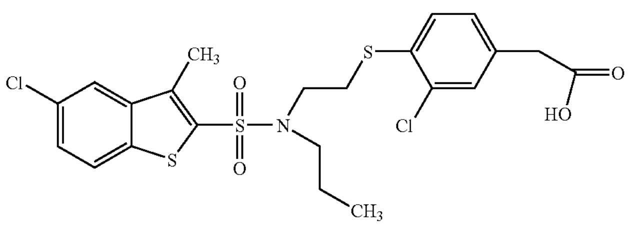 | (3-Chloro-4-{2-[(5-chloro-3-methyl-benzo[b]thiophene-2-sulfonyl)-propyl-amino]-ethylsulfanyl}-phenyl)-acetic acid |
| 114 | 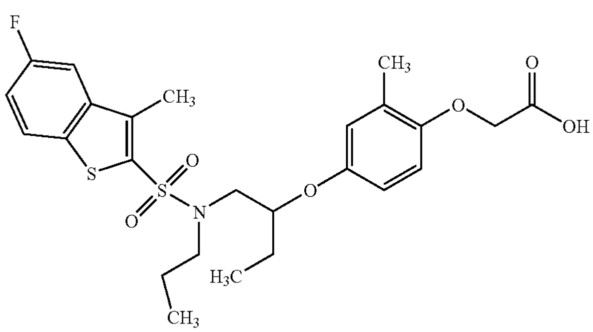 | [4-(1-{[(5-Fluoro-3-methyl-benzo[b]thiophene-2-sulfonyl)-propyl-amino]-methyl}-propoxy)-2-methyl-phenoxy]-acetic acid |
| 115 | 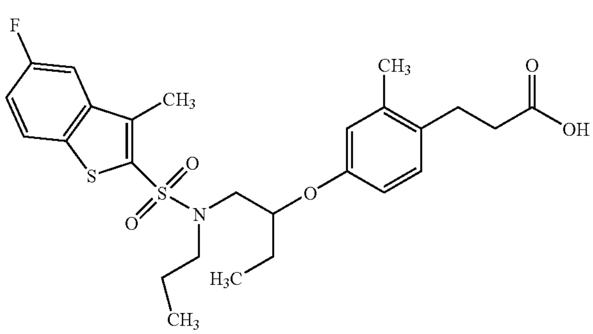 | 3-[4-(1-{[(5-Fluoro-3-methyl-benzo[b]thiophene-2-sulfonyl)-propyl-amino]-methyl}-propoxy)-2-methyl-phenyl]-propionic acid |

-continued

| No. | Structure | Name |
|---|---|---|
| 116 | 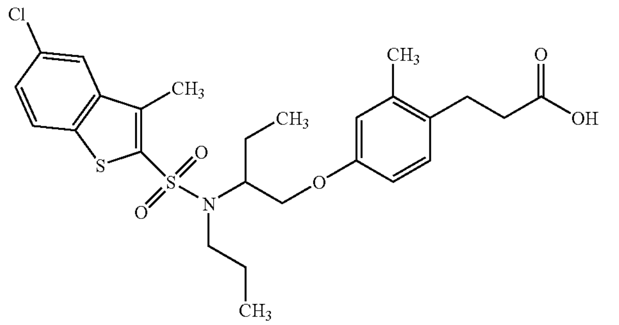 | 3-(4-{2-[(5-Chloro-3-methyl-benzo[b]thiophene-2-sulfonyl)-propyl-amino]-butoxy}-2-methyl-phenyl)-propionic acid |
| 117 | 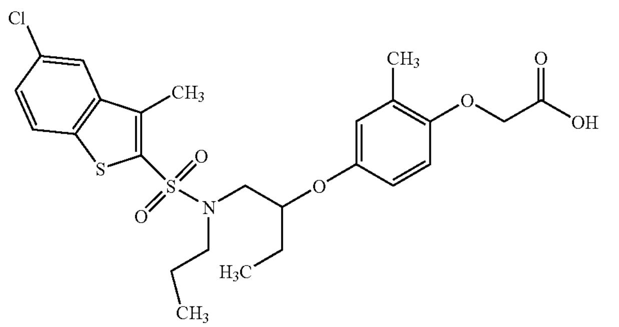 | [4-(1-{[(5-Chloro-3-methyl-benzo[b]thiophene-2-sulfonyl)-propyl-amino]-methyl}-propoxy)-2-methyl-phenoxy]-acetic acid |
| 118 | 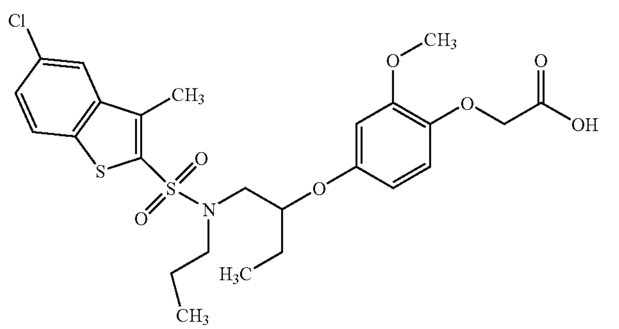 | [4-(1-{[(5-Chloro-3-methyl-benzo[b]thiophene-2-sulfonyl)-propyl-amino]-methyl}-propoxy)-2-methoxy-phenoxy]-acetic acid |
| 119 | 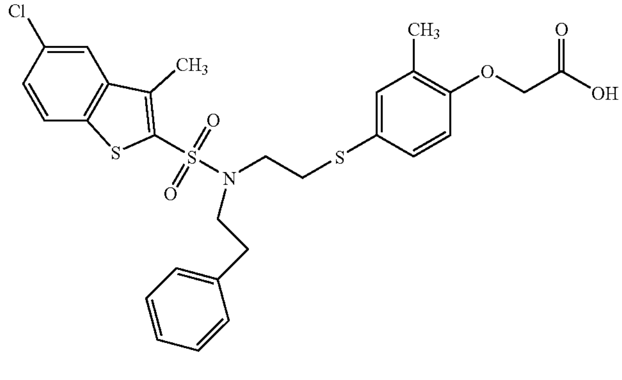 | (4-{2-[(5-Chloro-3-methyl-benzo[b]thiophene-2-sulfonyl)-phenethyl-amino]-ethylsulfanyl}-2-methyl-phenoxy)-acetic acid |

-continued

| No. | Structure | Name |
|---|---|---|
| 120 | 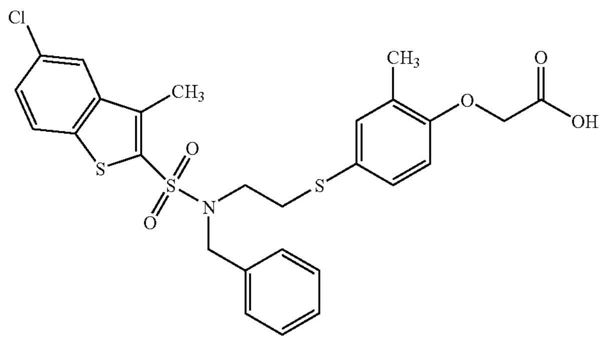 | (4-{2-[Benzyl-(5-chloro-3-methyl-benzo[b]thiophene-2-sulfonyl)-amino]-ethylsulfanyl}-2-methyl-phenoxy)-acetic acid |
| 121 | 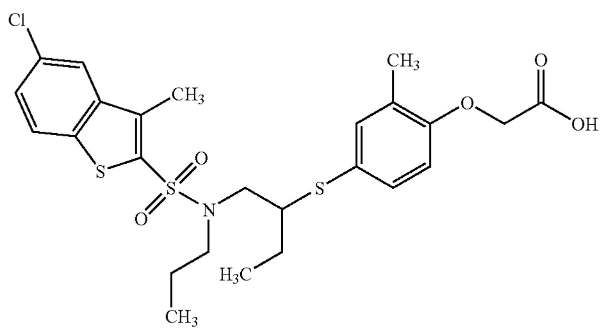 | [4-(1-{[(5-Chloro-3-methyl-benzo[b]thiophene-2-sulfonyl)-propyl-amino]-methyl}-propylsulfanyl)-2-methyl-phenoxy]-acetic acid |

Also encompassed by the present invention is a pharmaceutical composition, comprising a pharmaceutically acceptable carrier and at least one compound of the present invention or a pharmaceutically acceptable salt, solvate or hydrate thereof.

Also encompassed by the present invention is a pharmaceutical composition comprising: (1) at least one of compound of the present invention or a pharmaceutically acceptable salt, solvate, hydrate or stereoisomer thereof; (2) a second therapeutic agent selected from the group consisting of insulin sensitizers, sulfonylureas, biguanides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin; and (3) a pharmaceutically acceptable carrier.

Also encompassed by the present invention is a method of modulating a peroxisome proliferator activated receptor (PPAR), comprising the step of contacting the receptor with at least one compound of the present invention or a pharmaceutically acceptable salt, solvate or hydrate thereof.

The method recited above, wherein the PPAR is a gamma-receptor.

The method recited above, wherein the PPAR is a delta-receptor.

The method recited above, wherein the PPAR is a gamma and delta receptor.

Also encompassed by the present invention is a method for treating or preventing a PPAR-gamma mediated disease or condition in a mammal comprising the step of administering an effective amount of at least one compound of the present invention.

Also encompassed by the present invention is a method for treating or preventing a PPAR-delta mediated disease or condition in a mammal comprising the step of administering an effective amount of at least one compound of the present invention.

Also encompassed by the present invention is a method for treating or preventing a PPAR-gamma and delta mediated disease or condition in a mammal comprising the step of administering an effective amount of at least one compound of the present invention.

Also encompassed by the present invention is a method for lowering blood-glucose in a mammal comprising the step of administering an effective amount of at least one compound of the present invention.

Also encompassed by the present invention is a method of treating or preventing disease or condition in a mammal selected from the group consisting of hyperglycemia, dyslipidemia, Type II diabetes. Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component, comprising the step of administering an effective amount of a compound of at least one compound of the present invention.

Also encompassed by the present invention is a method of treating or preventing diabetes mellitus in a mammal comprising the step of administering to a mammal a therapeutically effective amount of at least one compound of the present invention.

Also encompassed by the present invention is a method of treating or preventing cardiovascular disease in a mammal comprising the step of administering to a mammal a therapeutically effective amount of at least one compound of the present invention, or a pharmaceutically acceptable salt, solvate, hydrate or stereoisomer thereof.

Also encompassed by the present invention is a method of treating or preventing syndrome X in a mammal, comprising the step of administering to the mammal a therapeutically effective amount of at least one compound of the present invention, or a pharmaceutically acceptable salt, solvate, hydrate or stereoisomer thereof.

Also encompassed by the present invention is a method of treating or preventing disease or condition in a mammal selected from the group consisting of hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component, comprising the step of administering an effective amount of at least one compound of the present invention, and an effective amount of second therapeutic agent selected from the group consisting of insulin sensitizers, sulfonylureas, biguanides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin.

Also encompassed by the present invention is use of a compound of the present invention and pharmaceutically acceptable salt, solvate, hydrate or stereoisomer thereof, for the manufacture of a medicament for the treatment of a condition modulated by a PPAR.

The terms used to describe the present invention have the following meanings unless otherwise indicated.

As used herein, the term "aliphatic" or "aliphatic group" is a non-aromatic, consisting solely of carbon and hydrogen and may optionally contain one or more units of saturation, e.g., double and/or triple bonds (also refer herein as "alkenyl" and "alkynyl"). An aliphatic or aliphatic group may be straight chained, branched (also refer herein as "alkyl") or cyclic (also refer herein as "cycloalkyl). When straight chained or branched, an aliphatic group typically contains between about 1 and about 10 carbon atoms, more typically between about 1 and about 6 carbon atoms. When cyclic, an aliphatic typically contains between about 3 and about 10 carbon atoms, more typically between about 3 and about 7 carbon atoms. Aliphatics are preferably $C_1$-$C_{10}$ straight chained or branched alkyl groups (i.e. completely saturated aliphatic groups), more preferably $C_1$-$C_6$ straight chained or branched alkyl groups. Examples include, but are not limited to methyl, ethyl, propyl, n-propyl, iso-propyl, n-butyl, sec-butyl, and tert-butyl. Additional examples include, but are not limited to, cyclopropyl, cyclopentyl, cyclohexyl, cyclopentyl, cyclohexylyl and the like.

The term "alkyl," unless otherwise indicated, refers to those alkyl groups of a designated number of carbon atoms of either a straight or branched saturated configuration. Examples of "alkyl" include, but are not limited to: methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above.

The term "alkenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with a designated number of substituents as set forth in the embodiment recited above.

The term "alkynyl" means hydrocarbon chain of a specified number of carbon atoms of either a straight or branched configuration and having at least one carbon-carbon triple bond, which may occur at any point along the chain. Example of alkynyl is acetylene. Alkynyl as defined above may be optionally substituted with a designated number of substituents as set forth in the embodiment recited above.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "alkyl-alkoxy" represents an alkyl group substituted with alkoxy group as defined above. Example of "alkyl-alkoxy" is $(CH_2)_nOCH_3$ (n=1 to 6) and the like. Alkyl-alkoxy as defined above may be optionally substituted with a designated number of substituents as set forth in the embodiment recited above.

The term "cycloalkyl" refers to a saturated or partially saturated carbocycle containing one or more rings of from 3 to 12 carbon atoms, more typically 3 to 6 carbon atoms. Examples of cycloalkyl includes, but are not limited to cyclopropyl, cyclobutyl, cyclopentyl, cyclohexyl and cycloheptyl, and the like. Cycloalkyl as defined above also includes a tricycle, such as adamantyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. Examples of haloalkyl group are trifluoromethyl, $CH_2CF_3$ and the like.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "aryl" includes carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl). The "aryl" as defined above may be optionally substituted with a designated number of substituents as set forth in the embodiment recited above.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from O, N, or S. The heteroaryl as defined above also includes heteroaryl fused with another heteroaryl, aryl fused with heteroaryl or aryl fused with heterocyclyl as defined herein. The "heteroaryl" may also be optionally substituted with a designated number of substituents as set forth in the embodiment recited above. Examples of heteroaryl are, but are not limited to: furanyl, thienyl (also referred to herein as "thiophenyl"), thiazolyl, imidazolyl, indolyl, isoindolyl, isooxazolyl, oxazoyl, pyrazolyl, pyrrolyl, pyrazinyl, pyridyl, pyrimidyl, pyrimidinyl and purinyl, cinnolinyl, benzofuranyl, benzothienyl (or benzothiophenyl), benzotriazolyl, benzoxazolyl, quinoline, isoxazolyl, isoquinoline 1,4benzodioxan, or 2,3-dihydrobenzofuranyl and the like.

The term "bi-aryl" is defined as aryl substituted with another aryl or aryl substituted with heteroaryl as defined above. Examples of "biaryl" are, but are not limited to: biphenyl where phenyl is substituted with another phenyl, and phenyl-pyridyl where phenyl is substituted with pyridyl. The "bi-aryl" as defined above may be optionally substituted with a designated number of substituents as set forth in the embodiment recited above.

The term "bi-heteroaryl" is defined as heteroaryl substituted with another heteroaryl, or heteroaryl substituted with aryl or biaryl as defined above. Examples of "bi-heteroaryl" are, but are not limited to: thienyl-pyrazolyl, thienyl-thienyl, thienyl-pyridyl, thienyl-phenyl, thienyl-biphenyl and the like. The "bi-heteroaryl" as defined above may be optionally substituted with a designated number of substituents as set forth in the embodiment recited above.

The term "heterocyclyl" refers to a non-aromatic ring which contains one or more heteroatoms selected from O, N or S, which includes a monocyclic, bicyclic or tricyclic ring of 5- to 14-carbon atoms containing one or more heteroatoms selected from O, N or S. The "heterocyclyl" as defined above may be optionally substituted with a designated number of substituents as set forth in the embodiment recited above. Examples of heterocyclyl include, but are not limited to, morpholine, piperidine, piperazine, pyrrolidine, and thiomorpholine.

The term "carbocyclyl" refers to carbocycly ring that is saturated or partially saturated ring. Examples of carbocyclyl are, but not limited to, cyclopentyl, cyclohexyl, cyclopentenyl, cyclohexenyl and the like.

An aryl-$C_1$-$C_6$-alkyl group, as used herein, is an aryl substituent that is linked to a compound by an alkyl group having from one to six carbon atoms. The aryl-$C_1$-$C_6$-alkyl group as defined above may be optionally substituted with a designated number of substituents as set forth in the embodiment recited above.

The "aminoalkyl" as used herein contains both a basic amino group ($NH_2$) and an alkyl group as defined above.

The term $R^{64}$ (or bioisosteres) as used herein includes carboxamide, $C_1$-$C_3$alkylnitrile, sulfonamide, acylsulfonamide and tetrazole, wherein these are optionally substituted with one or more suitable substituents selected from haloalkyl, aryl, heteroaryl, and $C_1$-$C_6$ alkyl. The heteroalkyl, aryl, heteroaryl and alkyl may further optionally substituted with one or more substituents selected from the list provided for $R^{15}$. The examples of $R^{64}$ (or bioisosteres) are, but not limited to, hydroxamic acid, acyl cyanamide, tetrazoles, sulfinylazole, sulfonylazole, 3-hydroxyisoxazole, hydroxythiadiazole, sulphonate and acylsulfonamide.

The term "acyl" means a R—C(O)— group where R is $C_1$-$C_6$ alkyl or aryl such as phenyl. Preferred acyl groups are those in which the alkyl group is lower alkyl such as acetyl.

The term "active ingredient" means the compounds generically described by Formula I as well as the salts, solvates and prodrugs of such compounds.

The term "pharmaceutically acceptable" means that the carrier, diluents, excipients and salt must be compatible with the other ingredients of the composition, and not deleterious to the recipient thereof. Pharmaceutical compositions of the present invention are prepared by procedures known in the art using well-known and readily available ingredients.

"Preventing" refers to reducing the likelihood that the recipient will incur or develop any of the pathological conditions described herein.

"Treating" refers to mediating a disease or condition, and preventing or mitigating its further progression or ameliorating the symptoms associated with the disease or condition.

"Pharmaceutically-effective amount" means that amount of a compound of the present invention, or of its salt, solvate, hydrate or prodrug thereof that will elicit the biological or medical response of a tissue, system or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount, which is sufficient to modulate a PPAR receptor such as a PPARα, PPARγ, PPARδ or PPARγ/δ receptor to mediate a disease or condition. Conditions mediated by PPAR receptors include, for example, diabetes mellitus, cardiovascular disease, Syndrome X, obesity and gastrointestinal disease. Additional conditions associated with the modulation of a PPAR receptor include inflammation related conditions, which include, for example, IBD (inflammatory bowel disease), rheumatoid arthritis, psoriasis, Alzheimer's disease, Chrohn's disease and ischemia reprofusion injury (stroke and miocardial infarction).

A "mammal" is an individual animal that is a member of the taxonomic class Mammalia. The class Mammalia includes humans, monkeys, chimpanzees, gorillas, cattle, swine, horses, sheep, dogs, cats, mice, rats and the like. Administration to a human is most preferred. A human to whom the compounds and compositions of the present invention are administered has a disease or condition in which control blood glucose levels are not adequately controlled without medical intervention, but wherein there is endogenous insulin present in the human's blood. Non-insulin dependent diabetes mellitus (NIDDM) is a chronic disease or condition characterized by the presence of insulin in the blood, even at levels above normal, but resistance or lack of sensitivity to insulin action at the tissues.

Those skilled in the art will recognize that stereocenters exist in compound of Formula I. Accordingly, the present invention includes all possible stereoisomers and geometric isomers of Formula I including racemic compounds and the optically active isomers.

The compounds of Formula I contain one or more chiral centers and exist in different optically active forms. When compounds of Formula I contain one chiral center, the compounds exist in two enantiomeric forms and the present invention includes both enantiomers and mixtures of enantiomers, such as racemic mixtures. Resolution of the final product, an intermediate or a starting material may be effected by any suitable method known in the art, for example by formation of diastereoisomeric salts which may be separated by crystallization; formation of diastereoisomeric derivatives or complexes which may be separated by crystallization and gas-liquid or liquid chromatography; selective reaction of one enantiomer with an enantiomer-specific reagent such as enzymatic esterification; and gas-liquid or liquid chromatography in a chiral environment such as on a chiral support, for example silica with a bound chiral ligand or in the presence of a chiral solvent. See also *Sterochemistry of Carbon Compounds* by E. L. Eliel (Mcgraw Hill, 1962) and *Tables of Resolving Agents* by S. H. Wilen. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula I has more than one chiral substituents, it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Formula I and mixtures thereof.

Certain compounds of Formula I may exist in different stable conformational forms, which may be separable. Torsional asymmetry due to restricted rotation about an asymmetric single bond, for example because of steric hindrance or ring strain, may permit separation of different conformers. The present invention includes each conformational isomer of compounds of Formula I and mixtures thereof.

Certain compound of Formula I may exist in zwitterionic form, and the present invention includes each zwitterionic form of compounds of Formula I and mixtures thereof.

Certain compounds of Formula I and their salts may exist in more than one crystal form. Polymorphs of compounds of Formula I form part of the present invention and may be prepared by crystallization of a compound of Formula I under different conditions, such as using different solvents or different solvent mixtures for recrystallization; crystallization at different temperatures; and various modes of cooling ranging from very fast to very slow cooling during crystallization. Polymorphs may also be obtained by heating or melting a compound of Formula I followed by gradual or fast cooling. The presence of polymorphs may be determined by solid probe NMR spectroscopy, IR spectroscopy, differential scanning calorimetry, powder X-ray diffraction or other available techniques.

Certain compounds of Formula I and their salts may exist in more than one crystal form, and the present invention includes each crystal form and mixtures thereof.

Certain compounds of Formula I and their salts may also exist in the form of solvates, for example hydrates, and the present invention includes each solvate and mixtures thereof.

"Pharmaceutically-acceptable salt" refers to salts of the compounds of Formula I, which are substantially non-toxic to mammals. Typical pharmaceutically acceptable salts include those salts prepared by reaction of the compounds of the present invention with a mineral, organic acid: an organic base or inorganic base. Such salts are known as base addition salts, respectively. It should be recognized that the particular counterion forming a part of any salt of the present invention is not of a critical nature so long as the salt as a whole is pharmaceutically acceptable and the counterion does not contribute undesired qualities to the salt as a whole.

By virtue of its acidic moiety, a compound of Formula I forms salts with pharmaceutically acceptable bases. Some examples of base addition salts include metal salts such as aluminum; alkali metal salts such as lithium, sodium or potassium; and alkaline earth metal salts such as calcium, magnesium, ammonium, or substituted ammonium salts. Examples of substituted ammonium salts include, for instance, those with lower alkylamines such as trimethylamine and triethylamine; hydroxyalkylamines such as 2-hydroxyethylamine, bis-(2-hydroxyethyl)-amine or tri-(2-hydroxyethyl)-amine; cycloalkylamines such as bicyclohexylamine or dibenzylpiperidine, N-benzyl-β-phenethylamine, dehydroabietylamine, N,N'-bisdehydro-abietylamine, glucamine, N-piperazine methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid. These salts may be prepared by methods known to those skilled in the art.

Certain compounds of Formula I and their salts may also exist in the form of solvates, for example hydrates, and the present invention includes each solvate and mixtures thereof.

The compounds of present invention, which bind to and activate the PPARs, lower one or more of glucose, insulin, triglycerides, fatty acids and/or cholesterol, and are therefore useful for the treatment and/or prevention of hyperglycemia, dyslipidemia and in particular Type II diabetes as well as other diseases including syndrome X, Type I diabetes, hypertriglyceridemia, insulin resistance, diabetic dyslipidemia, hyperlipidemia, hypercholesteremia, heart failure, coagaulopathy, hypertension, and cardiovascular diseases, especially arteriosclerosis. In addition, these compounds are indicated to be useful for the regulation of appetite and food intake in subjects suffering from disorders such as obesity, anorexia bulimia and anorexia nervosa.

The compounds and compositions of the present invention are also useful to treat acute or transient disorders in insulin sensitivity, which sometimes occurs following a surgery, trauma, myocardial infarction and the like. The compounds and compositions of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who can benefit from administration of the compounds and compositions of the present invention.

The present invention further provides a method for the treatment and/or prophylaxis of hyperglycemia in a human or non-human mammal which comprises administering an effective, non-toxic amount of a compound of Formula I, or a tautomeric form thereof and/or a pharmaceutically acceptable salt thereof and/or a pharmaceutically acceptable solvate thereof to a hyperglycemic human or non-human mammal in need thereof.

The compounds of the present invention are useful as therapeutic substances in preventing or treating Syndrome X, diabetes mellitus and related endocrine and cardiovascular disorders and diseases in human or non-human animals.

The present invention also relates to the use of a compound of Formula I as described above for the manufacture of a medicament for treating a PPARγ or PPARδ mediated condition, separately or in combination.

A therapeutically effective amount of a compound of Formula I can be used for the preparation of a medicament useful for treating Syndrome X, diabetes, treating obesity, lowering tryglyceride levels, raising the plasma level of high density lipoprotein, and for treating, preventing or reducing the risk of developing arteriosclerosis, and for preventing or reducing the risk of having a first or subsequent atherosclerotic disease event in mammals, particularly in humans. In general, a therapeutically effective amount of a compound of Formula I of the present invention typically reduces serum glucose levels, more specifically HbA1c, of a patient by about 0.7% or more;

typically reduces serum triglyceride levels of a patient by about 20% or more; and increases serum HDL levels in a patient.

Additionally, an effective amount of a compound of Formula I and a therapeutically effective amount of one or more active agents selected from antihyperlipidemic agent, plasma HDL-raising agents, antihypercholesterolemic agents, fibrates, vitamins, aspirin, insulin secretogogues, insulin and the like can be used together for the preparation of a medicament useful for the above described treatments.

Advantageously, compositions containing the compound of Formula I or the salts thereof may be provided in dosage unit form, preferably each dosage unit containing from about 1 to about 500 mg. It is understood that the amount of the compounds or compounds of Formula I that will be administered is determined by a physician considering of all the relevant circumstances.

Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially arteriosclerosis.

The compositions are formulated and administered in the same general manner as detailed herein. The compounds of the present invention may be used effectively alone or in combination with one or more additional active agents depending on the desired target therapy. Combination therapy includes administration of a single pharmaceutical dosage composition, which contains a compound of Formula I and one or more additional active agents, as well as administration of a compound of Formula I and each active agent in its own separate pharmaceutical dosage. For example, a compound of Formula I or thereof and an insulin secretogogue such as biguanides, thiazolidinediones, sulfonylureas, insulin or α-glucosidose inhibitors can be administered to the patient together in a single oral dosage composition such as a tablet or capsule, or each agent administered in separate oral dosage s. Where separate dosage s are used, a compound of Formula I and one or more additional active agents can be administered at essentially the same time, i.e., concurrently or at separately staggered times, i.e., sequentially; combination therapy is understood to include all these regimens.

An example of combination treatment or prevention of arteriosclerosis may involve administration of a compound of Formula I or salts thereof in combination with one or more of second active therapeutic agents: antihyperlipidemic agents; plasma HDL-raising agents; antihypercholesterolemic agents, fibrates, vitamins, aspirin and the like. As noted above, the compounds of Formula I can be administered in combination with more than one additional active agent.

Another example of combination therapy can be seen in treating diabetes and related disorders wherein the compounds of Formula I or salts thereof can be effectively used in combination with second active therapeutic, such as sulfonylureas, biguanides, thiazolidinediones, α-glucosidase inhibitors, other insulin secretogogues, insulin as well as the active agents discussed above for treating arteriosclerosis.

The examples of second therapeutic agents are insulin sensitizers, PPARγ agonists, glitazones, troglitazone, pioglitazone, englitazone, MCC-555, BRL 49653, biguanides, metformin, phenformin, insulin, insulin mimetics, sufonylureas, tolbutamide, glipizide, alpha-glucosidase inhibitors, acarbose, cholesterol lowering agent, HMG-CoA reductase inhibitors, lovastatin, simvastatin, pravastatin, fluvastatin, atrovastatin, rivastatin, other statins, sequestrates, cholestyramine, colestipol, dialkylaminoalkyl derivatives of a cross-linked dextran, nicotinyl alcohol, nicotinic acid: a nicotinic acid salt, PPARα agonists, fenofibric acid derivatives, gemfibrozil, clofibrate, fenofibrate, benzafibrate, inhibitors of cholesterol absorption, beta-sitosterol, acryl CoA:cholesterol acyltransferase inhibitors, melinamide, probucol PPARδ agonists, antiobesity compounds, fenfluramine, dexfenfluramine, phentiramine, sulbitramine, orlistat, neuropeptide Y5 inhibitors, $\beta_3$ adrenergic receptor agonists, and ileal bile acid transporter inhibitors.

The compounds of the present invention and the pharmaceutically acceptable salts, solvates and hydrates thereof have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper is dependent upon the route of administration chosen. Pharmaceutical compositions typically contain from about 1 to about 99 weight percent of the active ingredient, which is a compound of the present invention.

Preferably, the pharmaceutical formulation is in unit dosage form. A "unit dosage form" is a physically discrete unit containing a unit dose suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts considering various factors, such as without limitation, the species, age, weight, sex, medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses of two, three or more times per day. Where delivery is via transdermal forms, administration is continuous.

Suitable routes of administration of pharmaceutical compositions of the present invention include, for example, oral, eye drop, rectal, transmucosal, topical or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the present invention can also be administered in a targeted drug delivery system, such as in a liposome coated with endothelial cell-specific antibody.

For oral administration, the compounds of the present invention can be formulated readily by combining the active compounds with pharmaceutically acceptable carriers well known in the art. Such carriers enable the compounds of the present invention to be Formulated as tablets, pills, powders, sachets, granules, dragees, capsules, liquids, elixirs, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid: or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid: sodium oleate, sodium benzoate, sodium acetate, sodium chloride, talc, and the like. When a dosage unit form is a capsule, it may contain, in addition to materials of the above type, a liquid carrier such as a fatty oil.

Solid forms include powders, tablets and capsules. A solid carrier can be one or more substances, which may also act as flavoring agents, lubricants, solubilisers, suspending agents, binders, tablet disintegrating agents and encapsulating material.

In powders, the carrier is a finely divided solid, which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquids include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration, the compounds of the present invention or salts thereof can be combined with sterile aqueous or organic media to form injectable solutions or suspensions. Formulations for injection may be presented in unit dosage form, such as in ampoules or in multi-dose container with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks' solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the all. The active compounds can also be administered intranasally as, for example, liquid drops or spray.

For buccal administration, the compositions may take the form of tablets or lozenges Formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas, in the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier, which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing for example up to 10% by weight of the active compound. The compounds of the present invention are preferably formulated prior to administration.

In yet another embodiment of the present invention, the compound is radiolabelled, such as with carbon-14 or tritiated. Said radiolabelled or tritiated compounds are useful as reference standards for in vitro assays to identify new PPARγ/δ agonists.

Binding and Cotransfection Studies

The in vitro potency of compounds in modulating PPARγ, PPARα and PPARδ receptors are determined by the procedures detailed below. DNA-dependent binding (ABCD binding) is carried out using Scintillation Proximity Assay (SPA) technology with PPAR receptors. Tritium-labeled PPARα and PPARγ agonists are used as radioligands for generating displacement curves and $IC_{50}$ values with compounds of the present invention. Cotransfection assays are carried out in CV-1 cells. The reporter plasmid contains an acylCoA oxidase (AOX) PPRE and TK promoter upstream of the luciferase reporter cDNA. Appropriate PPARs and RXRα are constitutively expressed using plasmids containing the CMV promoter. Since for PPARα and PPARβ, interference by endogenous PPARγ in CV-1 cells is an issue, in order to eliminate such interference, a GAL4 chimeric system is used in which the DNA binding domain of the transfected PPAR is replaced by that of GAL4, and the GAL4 response element is utilized in place of the AOX PPRE. Receptor activation by compounds of the present invention is determined relative to PPARα agonist and PPARγ agonist reference molecules to obtain percent efficacies. EC50 values are determined by computer fit to a concentration-response curve. A typical range for concentration determination is from 1 nM to 10 μM. For binding or cotransfection studies with receptors other than PPARs, similar assays are carried out using appropriate ligands, receptors, reporter constructs and etc. for that particular receptor. In some cases, a single high concentration of agonist (10 μM) was used.

These studies are carried out to evaluate the ability of compounds of the present invention to bind to and/or activate various nuclear transcription factors, particularly huPPARα ("hu" indicates "human") huPPARγ and huPPARδ. These studies provide in-vitro data concerning efficacy and selectivity of compounds of the present invention. Furthermore, binding and cotransfection data for compounds of the present invention are compared with corresponding data for reference compounds that act on either huPPARα or huPPARγ. The typical range of concentration for binding is from 1 nM to 10 μM. The concentration of test compound required to effect 50% maximal activation of PPARα ($IC_{50}α$) and PPARγ ($IC_{50}γ$) is determined. The compounds of the present invention are, in general, found to have $IC_{50}$ or $EC_{50}$ in the range of about 1 nM to about 5 μM for PPAR alpha, gamma or delta.

Evaluation of Triglyceride and Cholesterol Level in HuapoA1 Transgenic Mice

Five to six week old male mice, transgenic for human apoA1 [C57B⅙-tgn (apoa1)1rub. Jackson Laboratory, Bar Harbor, Me.] are housed five per cage (10"×20"×8" with aspen chip bedding) with food (Purina 5001) and water available at all times. After an acclimation period of 2 weeks, animals are individually identified by ear notches, weighed and assigned to groups based on body weight. Beginning the following morning, mice are dosed daily by oral gavage for 7 days using a 20 gauge, 1½" curved disposable feeding needle. Treatments are test compounds (30 mg/kg), a positive control (fenofibrate, 100 mg/g) or vehicle [1% carboxymethylcellulose (w/v)/0.25% Tween80 (w/v); 0.2 ml/mouse]. Prior to termination on day 7, mice are weighed and dosed. Three hours after dosing, animals are anesthetized by inhalation of isoflurane (2-4%) and blood obtained via cardiac puncture (0.7-1.0 ml). Whole blood is transferred to serum separator tubes (Vacutainer SST), chilled on ice and permitted to clot. Serum is obtained after centrifugation at 4° C. and frozen until analysis for triglycerides, total cholesterol, compound levels and serum lipoprotein profile by fast protein liquid chromatography (FPLC) coupled to an inline detection system. After sacrifice by cervical dislocation, the liver, heart and epididymal fat pads are excised and weighed.

The animals dosed with vehicle have average triglycerides values of about 60 to 80 mg/dl, which are reduced by the positive control fenofibrate (33-58 mg/dl with a mean reduction of 37%). The animals dosed with vehicle have average total serum cholesterol values of about 140 to 180 mg/dl, which are increased by fenofibrate (about 190 to 280 mg/dl with a mean elevation of 41%). When subject to FPLC analysis, pooled sera from vehicle-treated hu apoA1 transgenic mice have a high-density lipoprotein cholesterol (HDLc) peak area, which ranges from 47v-sec to 62v-sec. Fenofibrate increases the amount of HDLc (68-96v-sec with a mean percent increase of 48%). Test compounds evaluated in terms of percent increase in the area under the curve. Representative compounds of the present invention are tested using the above methods or substantially similar methods.

Evaluation of Glucose Levels in db/db Mice

Five week old male diabetic (db/db) mice [C57BlKs/jm+/+Lepr(db), Jackson Laboratory, Bar Harbor, Me.] or lean littermates (db+) are housed 6 per cage (10"×20"×8" with aspen chip bedding) with food (Purina 5015) and water available at all times. After an acclimation period of 2 weeks, animals are individually identified by ear notches, weighed and bled via the tail vein for determination of initial glucose levels. Blood is collected (100 μl) from unfasted animals by wrapping each mouse in a towel, cutting the tip of the tail with a scalpel, and milking blood from the tail into a heparinized capillary tube balanced on the edge of the bench. Sample is discharged into a heparinized microtainer with gel separator (VWR) and retained on ice. Plasma is obtained after centrifugation at 4° C. and glucose is measured immediately. Remaining plasma is frozen until the completion of the experiment, and glucose and triglycerides are assayed in all samples. Animals are grouped based on initial glucose levels and body weights. Beginning the following morning, mice are dosed daily by oral gavage for 7 days using a 20 gauge, 1½" curved disposable feeding needle. Treatments are test compounds (30 mg/kg), a positive control agent (30 mg/cg) or vehicle [1% carboxymethylcellulose (w/v)/0.25% Tween80 (w/v); 0.3 ml/mouse]. On day 7, mice are weighed and bled (tail vein) for about 3 hours after dosing. Twenty-four hours after the $7^{th}$ dose (i.e., day 8), animals are bled again (tail vein). Samples obtained from conscious animals on days 0, 7 and 8 are assayed for glucose. After 24 hour bleed, animals are weighed and dosed for the final time. Three hours after dosing on day 8, animals are anesthetized by inhalation of isoflurane, and blood obtained is via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

The animals dosed with vehicle have average triglycerides values of about 170 to 230 mg/dl, which are reduced by the positive PPARγ control (about 70 to 120 mg/dl with a mean reduction of 50%). Male db/db mice are hyperglycemic (average glucose of about 680 to 730 mg/dl on the 7$^{th}$ day of treatment), while lean animals have average glucose levels between about 190 and 230 mg/dl. Treatment with the positive control agent reduces glucose significantly (about 350 to 550 mg/dl with a mean decrease towards normalization of 56%).

Glucose is measured colorimetrically by using commercially purchased reagents (Sigma #315-500). According to the manufacturers, the procedures are modified from published work (McGowan et al. *Clin Chem.* 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte coupled with a color reaction first described by Trinder (Trinder, P. *Ann Clin Biochem,* 6:24 (1969)). The absorbance of the dye produced is linearly related to the analyte in the sample. The assays are further modified for use in a 96 well format. Standards (Sigma #339-11, Sigma #16-11, and Sigma #CC0534 for glucose, triglycerides and total cholesterol, respectively), quality control plasma (Sigma # A2034), and samples (2 or 5 μl/well) are measured in duplicate using 200 μl of reagent. An additional aliquot of sample, pipetted to a third well and diluted in 200 μl water, provided a blank for each specimen. Plates are incubated at room temperature (18, 15, and 10 minutes for glucose, triglycerides and total cholesterol, respectively) on a plate shaker and absorbance read at 500 nm (glucose and total cholesterol) or 540 nm (triglycerides) on a plate reader. Sample absorbance is compared to a standard curve (100-800, 10-500, and 100-400 mg/dl for glucose, triglycerides and total cholesterol, respectively). Values for the quality control sample are consistently within the expected range and the coefficient of variation for samples is below 10%. All samples from an experiment are assayed at the same time to minimize inter-assay variability.

Serum lipoproteins are separated and cholesterol is quantitated with an in-line detection system. Sample is applied to a Superose® 6 HR$^{10}$/$_{30}$-size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min is mixed with the column effluent through a T-connection, and the mixture is passed through a 15 m×0.5 mm id knitted tubing reactor immersed in a 37° C. water bath. The colored product produced in the presence of cholesterol is monitored in the flow stream at 505 nm, and the analog voltage from the monitor is converted to a digital signal for collection and analysis. The change in voltage corresponding to change in cholesterol concentration is plotted against time, and the area under the curve corresponding to the elution of VLDL, LDL and HDL is calculated (Perkin Elmer Turbochrome software).

The compounds of the present invention can be prepared according to the procedures of the following schemes and examples, which may further illustrate details for the preparation of the compounds of the present invention. The compounds illustrated in the schemes and examples are, however, not to be construed as forming the only genus that is considered as the present invention.

General Reaction Scheme

The compounds of the present invention, in general, may be prepared according to the Reaction Schemes described below.

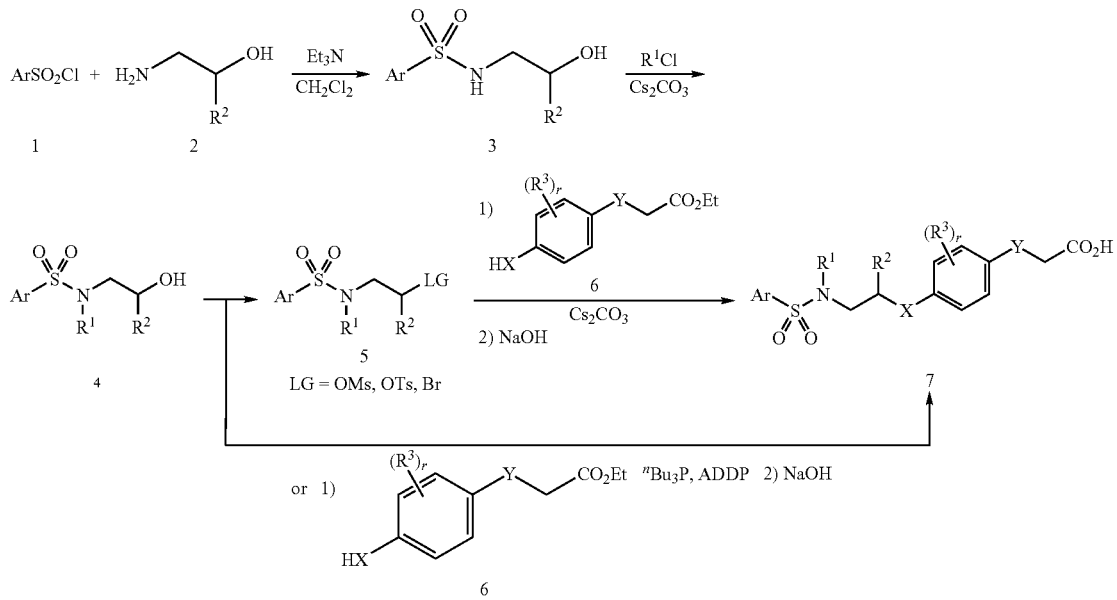

As shown in Reaction Scheme 1, a secondary sulfonamide 3 can be readily prepared from amino alcohol 2 treated with sulfonylchloride 1. Alkylation of 3 with alkyl halide ($R^1X$, where X is Br or Cl) provides alcohol 4, which is then converted to mesylate, tosylate or bromide 5. A nucleophilic substitution of 5 with phenol (or thiophenol) 6 followed by a hydrolysis yield the acid product 7. Alternatively, the acid 7 can be prepared by coupling alcohol 4 with phenol (thiophenol) 6 under a Mitsunobu reaction condition followed by the hydrolysis.

-continued

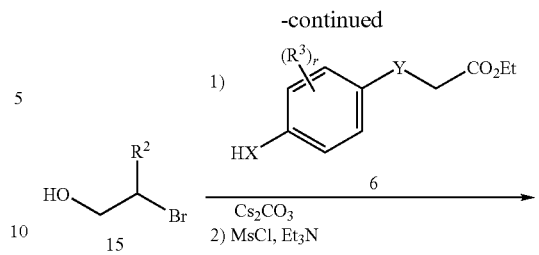

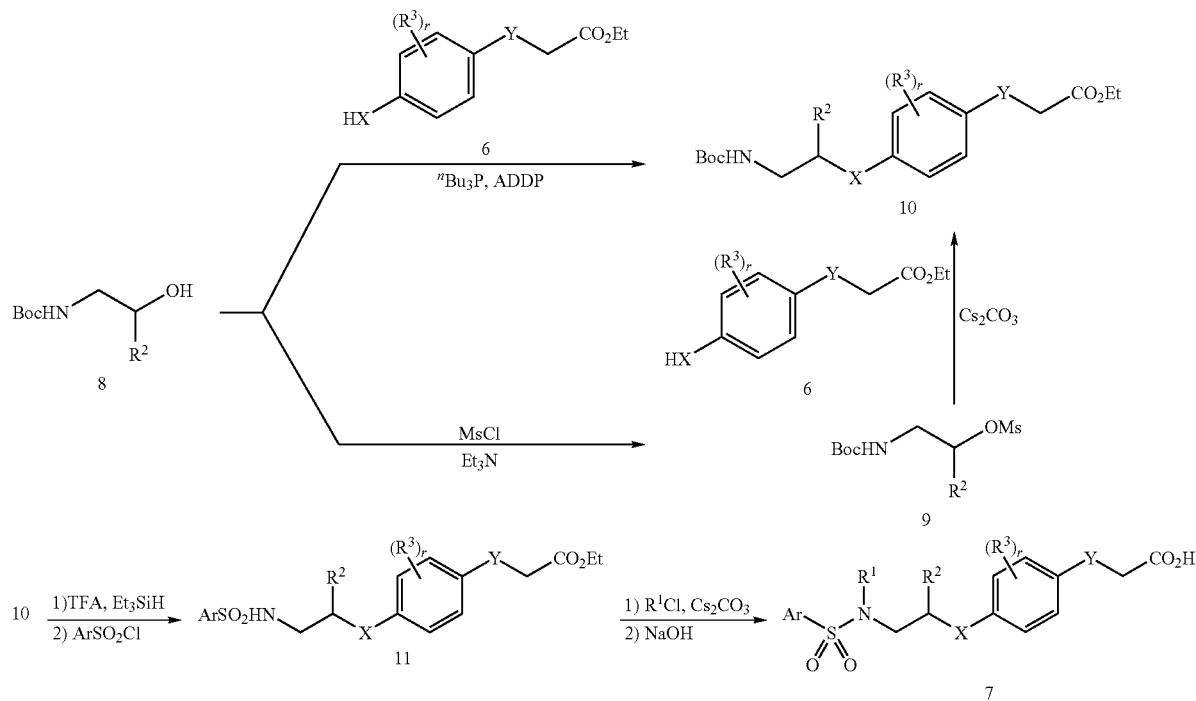

As shown in Reaction Scheme 2, a compound 10 can be prepared from alcohol 8 and phenol 6 under a Mitsnobu reaction condition. Alternatively, it can also be prepared from the $S_{N2}$ displacement of mesylate 9 with phenol 6. The mesylate 9 can be easily accessed from the parent alcohol 8 under the standard mesylation condition. The removal of the protecting group such as Boc group under the acidic condition followed by sulfonylation provides the sulfonamide 11. The N-alkylation using alkyl halide ($R^1X$, where X is Br or Cl) and subsequent hydrolysis afford the acid compound 7.

-continued

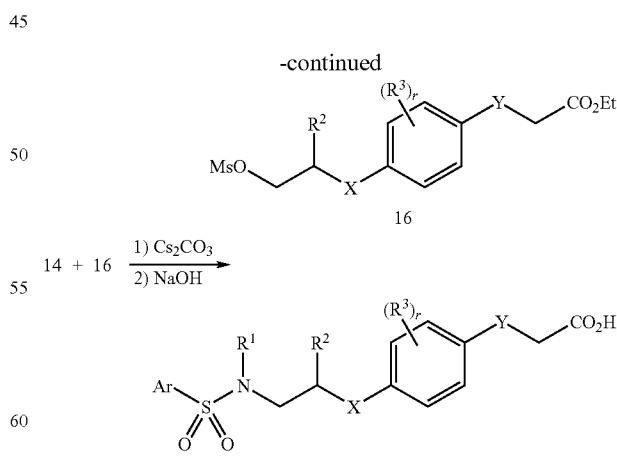

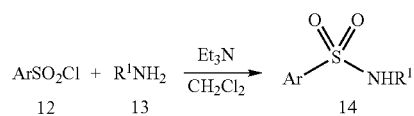

As shown in Reaction Scheme 3, the sulfonamide compound 14 can be prepared from sulfonyl chloride 12 and amine 13. Subsequent treatment of 14 with mesylate 16 followed by a saponification affords the acid compound 7. Mesylate 16, as shown above can be prepared by a $S_{N2}$ displacement of bromide 15 with phenol 6.

As shown in Reaction Scheme 5, sulfonamide compound 21 is prepared according to the method illustrated in Reaction Scheme 2. Various substitutions are introduced under palladium (Pd) mediated Suzuki and Negishi coupling conditions where a subsequent hydrolysis affords the acid compound 7.

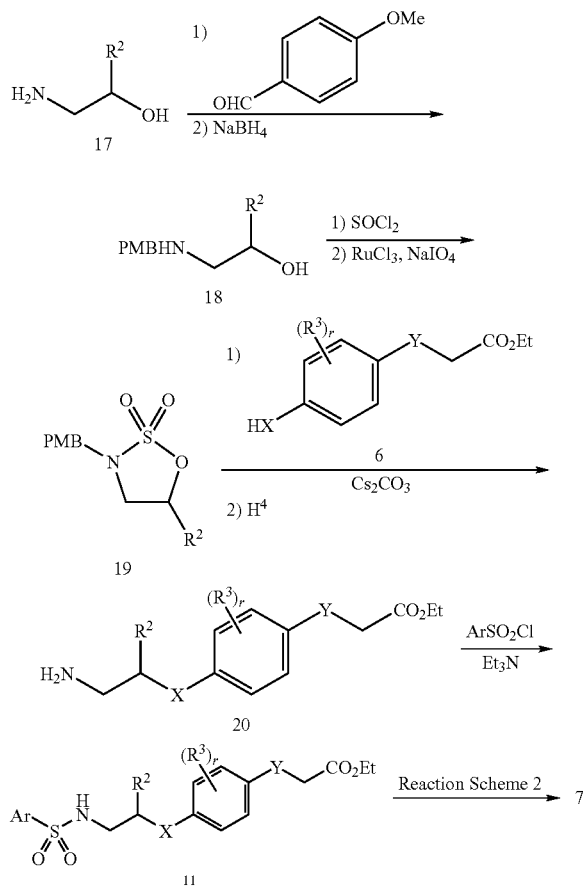

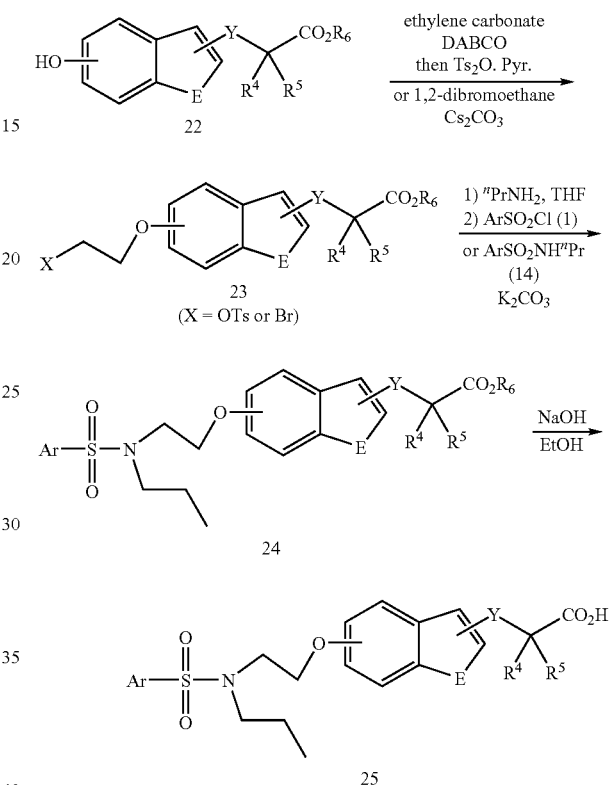

Reaction Scheme 4 illustrates another way to prepare the sulfonamide compound 7. A standard reductive amination converts 17 to amine 18. Cyclic sulfamidate 19 is achieved using a two-step procedure, which involves the formation of sulfamidite followed by oxidation in the presence of catalyst such as $RuCl_3$. Nucleophile ring opening of sulfamidate with phenol 6 followed by a subsequent acid workup affords the amine compound 20. The compound 20 is further converted to sulfonamide 11 under a standard sulfonylation condition. The compound 11 is then converted to the acid sing the same procedure as described in Reaction Scheme 2.

Reaction Scheme 6 illustrates a synthetic route to prepare sulfonamide compound 25. Phenol 22 can be treated with ethylene carbonate followed by a tosylation of the alcohol to afford compound 23. Alternatively, compound 23 can be obtained in a one step process by treating phenol 22 with 1,2-dibromoethane. Compound 23 is then converted to the secondary amine, which is treated with sulfonyl chloride (1) to afford ester 24. Compound 24 can also be obtained by treatment of 23 with arylsulfonamide (14) under a basic condition. Compound 24 undergoes a hydrolysis to afford acid product 25.

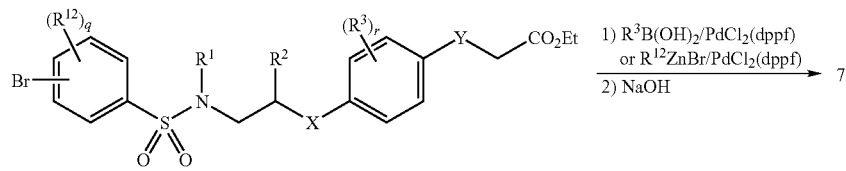

Reaction Scheme 7

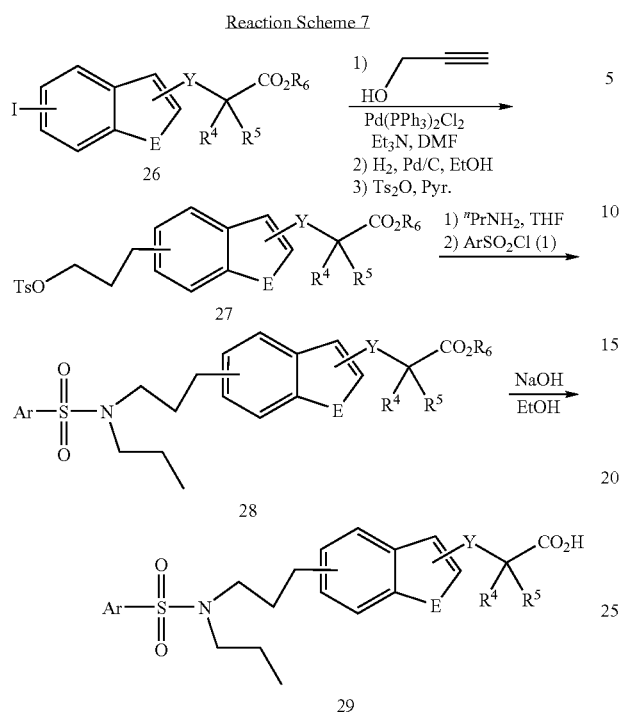

Reaction Scheme 7 illustrates a synthetic route to prepare sulfonamide compound 29. A palladium mediated coupling of aryl iodide 26 with propargyl alcohol provides a carbon-carbon bond formation, where the triple bond is reduced under the hydrogenation condition and alcohol is converted to its corresponding tosylate to provide compound 27. Compound 27 is converted to the secondary amine, which is then treated with sulfonyl chloride (1) to afford ester 28. Ester 28 undergoes a hydrolysis to afford acid product 29.

In the Schemes, Procedures and Examples between, various reagent symbols and abbreviations have the following meanings.

BINAP 2,2'-Bis(diphenylphosphino)-1,1-binaphthyl
Boc t-butoxycarbonyl
CBZ benzyloxycarbonyl
DCM dichloromethane
DEAD diethyl azodicarboxylate
DI deionized
DIAD diisopropyl azodicarboxylate
DIPEA diisopropylethylamine
DMAP 4-dimethylamino pyridine
DMF N,N-dimethylformamide
DMSO dimethylsulfoxide
eq. (equiv) equivalent(s)
EDC 1-(3-dimethylaminopropyl)-3-ethylcarbodiimide HCl
ESI-MS electron spray ion-mass spectroscopy
Et ethyl
EtOAc ethyl acetate
FMOC 9-Flurorenylmethyl carbamate
h hours
HOAc acetic acid
HPLC high performance liquid chromatography
HRMS high resolution mass
h hour(s)
LRMS low resolution mass
LAH lithium aluminum hydride
Me methyl
Ms methanesulfonyl
NBS N-bromosuccinimide
$Pd_2(dba)_3$, tris(dibenzylideneacetone) dipalladium(0)
Ph phenyl
Pr propyl
r.t. (RT) room temperature
TBAF tetrabutylammonium fluoride
TBS tertbutyldimethylsilyl
TFA trifluoroacetic acid
TEA triethylamine
THF tetrahydrofuran
TLC thin-layer chromatography

EXAMPLE 1

[5-(1-{[(5-Chloro-3-methyl-benzo[b]thiophene-2-sulfonyl)-propyl-amino]-methyl}-propoxy)-indol-1-yl]-acetic acid

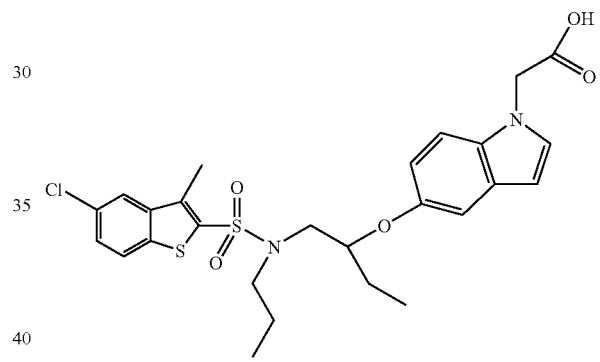

Step A

5-Chloro-3-methyl-benzo[b]thiophene-2-sulfonyl chloride

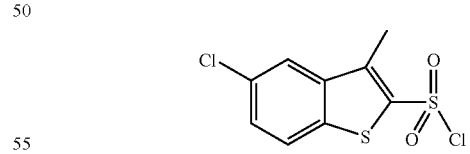

Chlorosulphonic acid (21.8 mL, 0.328 mol) was added via syringe to 0° C. dichloroethane (118 mL). 5-chloro-3-methylbenzothiophene (20.0 g, 0.109 mol) in dichloroethane (32 mL) was added dropwise to the solution. The resulting cranberry-colored solution was thickened to a slurry, which was stirred at room temperature. After 2 h, the reaction slurry was poured over an ice/water bath. The resulting precipitate was washed with copious amounts of water and dried overnight in a vacuum oven to provide 26.0 g (84%) of The title compound. $^1$H NMR (400 MHz, CDCl$_3$) δ 7.88 (d, 1H, J=8.6 Hz), 7.75 (d, 1H, J=2.0 Hz), 7.35 (dd, 1H, J=8.6 Hz, 2.0 Hz), 2.45 (s, 3H). $R_f$=0.53 in 33% acetone in hexanes.

Step B

5-Chloro-3-methyl-benzo[b]thiophene-2-sulfonic acid (2-hydroxy-butyl)-amide

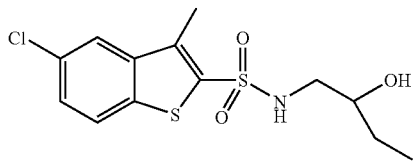

The compound of 5-chloro-3-methyl-benzo[b]thiophene-2-sulfonyl chloride (2.03 g, 7.22 mmol) in dichloromethane (20 mL) was added dropwise to a 0° C. solution of 1-amino-2-butanol (0.8 mL, 9.94 mmol) and triethylamine (2.0 mL, 14.4 mmol) in dichloromethane (80 mL). The resulting solution was stirred at ambient temperature for 1 h, then diluted with dichloromethane and washed with water. The organic layer was dried over $Na_2SO_4$ and concentrated in vacuo to provide a quantitative yield of the title compound. $^1$H NMR (400 MHz, $CDCl_3$) δ 7.79 (d, 1H, J=8.0 Hz), 7.45 (dd, 1H, J=8.0 Hz, 1.8 Hz), 3.69-3.64 (m, 1H), 3.24 (dd, 1H, J=13.3 Hz, 3.1 Hz), 3.92 (dd, 1H, J=13.3 Hz, 8.0 Hz), 2.66 (s, 3H), 1.53-1.41 (m, 2H), 0.91 (t, 3H, J=7.1 Hz). MS [EI+] 334 $(M+H)^+$. $R_f$=0.52 in 50% acetone in hexanes.

Step C

5-Chloro-3-methyl-benzo[b]thiophene-2-sulfonic acid (2-hydroxy-butyl)-propyl-amide

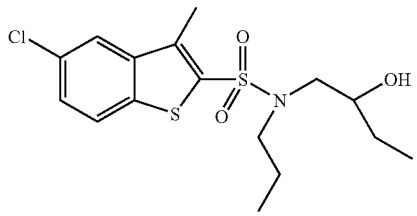

A solution of 5-chloro-3-methyl-benzo[b]thiophene-2-sulfonic acid (2-hydroxy-butyl)-amide (2.41 g, 7.22 mmol) and 1-iodopropane (0.92 mL, 9.38 mmol) in dimethylformamide (120 mL) was treated with cesium carbonate (3.06 g, 9.38 mmol). The resulting mixture was healed to 50° C. under $N_2$ until all of the 5-chloro-3-methyl-benzo[b]thiophene-2-sulfonic acid (2-hydroxy-butyl)-amide was consumed. The mixture was cooled to ambient temperature and diluted with diethyl ether. The organic layer was washed with 1N HCl and water, dried over $Na_2SO_4$, and concentrated in vacuo. The crude material was purified by flash chromatography, using 20% acetone in hexanes as eluent to provide 2.43 g (90%) of the title compound. $^1$H NMR (400 MHz, $CDCl_3$) δ 7.79 (D, 1 h, J=2.3 Hz), 7.74 (d, 1H, J=8.7 Hz), 7.46 (dd, 1H, J=8.7 Hz, 2.3 Hz), 3.83-3.76 (m, 1H), 3.35-3.16 (m, 4H), 2.69 (s, 3H), 2.33 (d, 1H, J=3.6 Hz), 1.67-1.57 (m, 2H), 1.53-1.42 (m, 2H), 0.98 (t, 3H, J=7.3 Hz), 0.82 (t, 3H, J=7.3 Hz). MS [EI+] 376 $(M+H)^+$. $R_f$=0.23 in 20% acetone in hexanes.

Step D

Toluene-4-sulfonic acid 1-{[(5-chloro-3-methyl-benzo[b]thiophene-2-sulfonyl)-propyl-amino]-methyl}-propyl ester

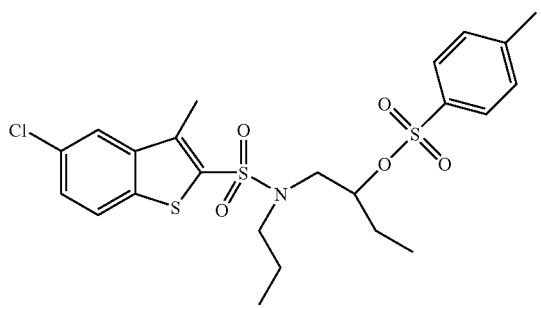

A solution of 5-chloro-3-methyl-benzo[b]thiophene-2-sulfonic acid (2-hydroxy-butyl)-propyl-amide (1.05 g, 2.79 m mL) and pyridine (0.90 mL, 11.2 mmol) in dichloromethane (140 mL) was treated with dimethylaminopyridine (0.136 g, 1.12 mmol) and p-toluenesulphonic anhydride (1.82 g, 5.59 mmol). The resultant mixture was stirred at ambient temperature for 48 h, then diluted with dichloromethane and washed with 1N HCl. The organic layers were combined, dried over $Na_2SO_4$, and concentrated in vacuo. The crude material was purified by flash chromatography, using 20% acetone in hexanes as eluent, to provide 1.29 g (87%) of the title compound. $^1$H NMR (400 MHz, $CDCl_3$) δ 7.77 (d, 2H, J=8.3 Hz), 7.74 (d, 2H, J=8.6 Hz). 7.46 (d, 1H, J=8.3 Hz, 1.8 Hz), 7.33 (d, 2H, J=7.7 Hz), 4.66-4.60 (m, 1H), 3.48 (q, 2H, J=5.4 Hz), 3.18, 3.14 (ABq, 2H, J=8.4 Hz), 2.66 (s, 3H), 2.44 (s, 3H), 1.85-1.78 (m, 1H), 1.69-1.62 (m, 1H), 1.51, 1.48 (ABq, 2H, J=7.4 Hz), 0.88 (t, 3H, J=6.8 Hz), 0.79 (td, 3H, J=7.7 Hz, 4.5 Hz). $R_f$=0.60 in 50% acetone in hexanes.

Step E

[1-(1-{[(5-Chloro-3-methyl-benzo[b]thiophene-2-sulfonyl)-propyl-amino]-methyl}-propoxy)-indol-1-yl]-acetic acid

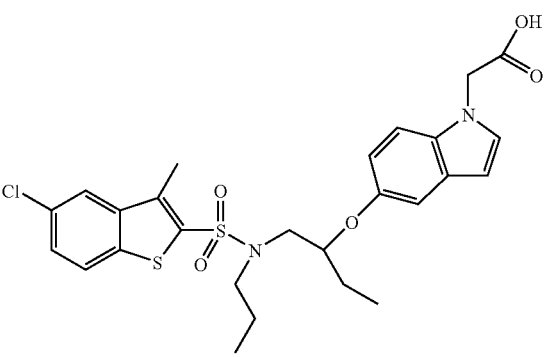

A solution of (5-hydroxy-indol-1-yl)-acetic acid ethyl ester (0.062 g, 0.28 mmol) and toluene-4-sulfonic acid 1-{[(5-chloro-3-methyl-benzo[b]thiophene-2-sulfonyl)-propyl-amino]-methyl}-propyl ester (0.165 g, 0.31 mmol) in dimethylformamide (5 mL) was treated with cesium carbonate (0.138 g, 0.42 mmol), heated to 60° C. under $N_2$ for 10 h. The resulting suspension was cooled to ambient temperature, diluted with diethyl ether, and washed with 1N HCl and water. The organic layer was dried over $Na_2SO_4$ and concentrated in vacuo. A solution of crude [5-(1-{[(5-chloro-3-methyl-benzo[b]thiophene-2-sulfonyl)-propyl-amino]-methyl}-propoxy)-indol-1-yl]-acetic acid methyl ester and 5N NaOH (1 mL) in ethanol (5 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. MS [EI−] 547 (M−H)+.

EXAMPLE 2

3-[3-(1-{[(5-Chloro-3-methyl-benzo[b]thiophene-2-sulfonyl)-propyl-amino]-methyl}-propoxy)-phenyl]-propionic acid

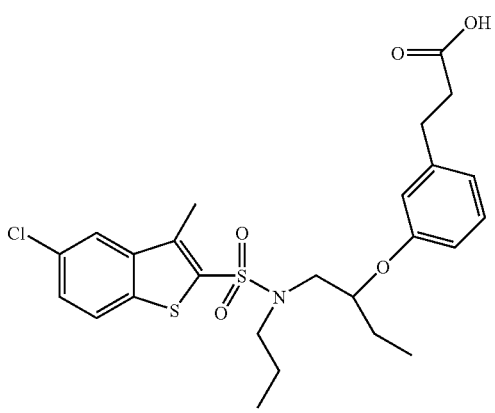

A solution of 3-(3-hydroxy-phenyl)-propionic acid methyl ester (0.055 g, 0.31 mmol) and toluene-4-sulfonic acid 1-{[(5-chloro-3-methyl-benzo[b]thiophene-2-sulfonyl)-propyl-amino]-methyl}-propyl ester (0.78 g, 0.34 mmol) in dimethylformamide (5 mL) was treated with cesium carbonate (0.149 g, 0.46 mmol), heated to 60° C. under $N_2$ for 10 h. The resulting suspension was cooled to ambient temperature, diluted with diethyl ether, and washed with 1N HCl and water. The organic layer was dried over $Na_2SO_4$ and concentrated in vacuo. A solution of crude 3-[3-(1-{[(5-chloro-3-methyl-benzo[b]thiophene-2-sulfonyl)-propyl-amino]-methyl}-propoxy)-phenyl]-propionic acid methyl esterand 5N NaOH (1 mL) in ethanol (5 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, CDCl$_3$) δ 7.70 (dd, 2H, J=5.4 Hz, 3.4 Hz), 7.42 (dd, 1H, J=8.6 Hz, 2.3 Hz), 7.08 (t, 1H, J=7.7 Hz). 6.73 (d, 1H, J=7.7 Hz), 6.60-6.58 (m, 2H), 4.44-4.38 (m, 1H), 3.59 (dd, 1H, J=15.0 Hz, 4.1 Hz), 3.40-3.25 (m, 3H), 2.84 (t, 2H, J=7.3 Hz), 2.64 (t, 2H, J=7.7 Hz), 2.60 (s, 3H), 1.70-1.54 (m, 4H), 0.95 (t, 3H, J=7.7 Hz), 0.83 (t, 3H, J=7.3 Hz). HRMS (ES+) m/z exact mass calculated for C25H31NO5S2Cl 524.1332, found 524.1332.

EXAMPLE 3

[4-(1-{[(5-Chloro-3-methyl-benzo[b]thiophene-2-sulfonyl)-propyl-amino]-methyl}-propoxy)-2-methyl-phenoxy]-acetic acid

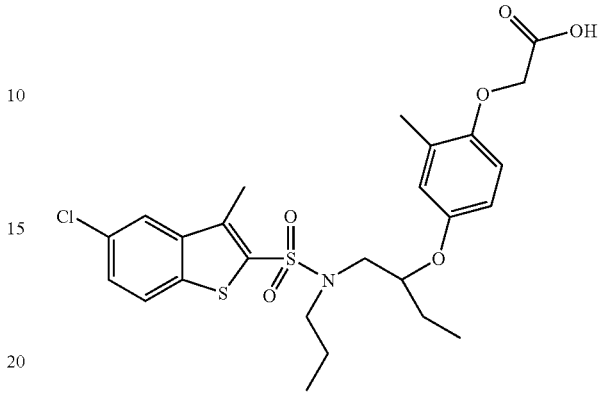

A solution of (4-hydroxy-2-methyl-phenoxy)-acetic acid methyl ester (0.050 g, 0.26 mmol) and toluene-4-sulfonic acid 1-{[(5-chloro-3-methyl-benzo[b]thiophene-2-sulfonyl)-propyl-amino]-methyl}-propyl ester (0.149 g, 0.28 mmol) in dimethylformamide (5 mL) was treated with cesium carbonate (0.125 g, 0.38 mmol), heated to 60° C. under $N_2$ for 10 h. The resulting suspension was cooled to ambient temperature, diluted with diethyl ether, and washed with 1N HCl and water. The organic layer was dried over $Na_2SO_4$ and concentrated in vacuo. A solution of crude [4-(1-{[(5-chloro-3-methyl-benzo[b]thiophene-2-sulfonyl)-propyl-amino]-methyl}-propoxy)-2-methyl-phenoxy]-acetic acid methyl esterand 5N NaOH (1 mL) in ethanol (5 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, CDCl$_3$) δ 7.71-7.69 (m, 2H), 7.42 (dd, 1H, J=7.9 Hz, 2.4 Hz), 6.55-6.47 (m, 3H), 4.58 (s, 2H), 4.32-4.28 (m, 1H), 3.57 (dd, 1H, J=15.1 Hz, 3.6 Hz), 3.41-3.26 (m, 2H), 2.59 (s, 3H0, 2.16 (s, 3H), 1.69-1.55 (m, 4H), 0.94 (t, 3H, J=7.3 Hz), 0.84 (t, 3H, J=7.3 Hz). HRMS (ES+) m/z exact mass calculated for C25H31NO6S2Cl 540.1281, found 540.1284.

EXAMPLE 4

[4-(1-{[(5-Chloro-3-methyl-benzo[b]thiophene-2-sulfonyl)-propyl-amino]-methyl}-propoxy)-2-methyl-phenoxy]-acetic acid

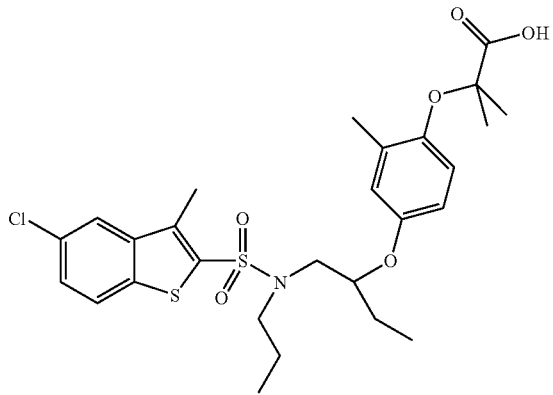

A solution of 2-(4-hydroxy-2-methyl-phenoxy)-2-methyl-propionic acid ethyl ester (0.051 g, 0.21 mmol) and toluene-4-sulfonic acid 1-{[(5-chloro-3-methyl-benzo[b]thiophene-2-sulfonyl)-propyl-amino]-methyl}-propyl ester (0.125 g, 0.24 mmol) in dimethylformamide (5 mL) was treated with cesium carbonate (0.105 g, 0.32 mmol), healed to 60° C. under $N_2$ for 10 h. The resulting suspension was cooled to ambient temperature, diluted with diethyl ether, and washed with 1N HCl and water. The organic layer was dried over $Na_2SO_4$ and concentrated in vacuo. A solution of crude 2-[4-(1-{[(5-chloro[b]thiophene-2-sulfonyl)-propyl-amino]-methyl}-propoxy)-2-methyl-phenoxy]-2-methyl-propionic acid ethyl ester and 5N NaOH (1 mL) in ethanol (5 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, $CDCl_3$) δ 7.73 (m, 2H), 7.44 (dd, 1H, J=8.7 Hz, 2.0 Hz), 6.69 (d, 1H, J=8.7 Hz), 6.54 (dd, 1H, J=3.3 Hz), 6.49 (dd, 1H, J=8.7 Hz, 2.7 Hz), 4.35-4.30 (m, 1H), 3.57 (dd, 1 Hz. J=15.6 Hz. 3.5 Hz), 3.38-3.28 (m, 3H), 2.60 (s, 3H), 2.13 (s, 3H), 1.68-1.56 (m, 4H), 1.54 (s, 6H), 0.95 (t, 3H, J=8.7 Hz), 0.84 (t, 3H, J=6.9 Hz). MS [EI+] 568 (M+H)$^+$.

EXAMPLE 5

3-[4-(1-{[(5-Chloro-3-methyl-benzo[b]thiophene-2-sulfonyl)-propyl-amino]-methyl}-propoxy)-2-methyl-phenyl]-propionic acid

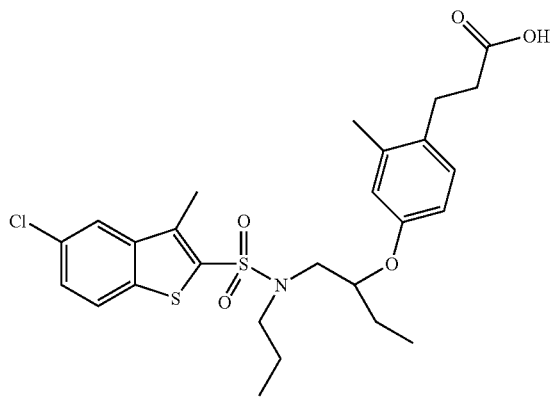

A solution of 3-(4-hydroxy-2-methyl-phenyl)-propionic acid methyl ester (0.065 g, 0.34 mmol) and toluene-4-sulfonic acid 1-{[(5-chloro-3-methyl-benzo[b]thiophene-2-sulfonyl)-propyl-amino]-methyl}-propyl ester (0.195 g, 0.39 mmol) in dimethylformamide (5 mL) was treated with cesium carbonate (0.164 g, 0.50 mmol), heated to 60° C. under $N_2$ for 10 h. The resulting suspension was cooled to ambient temperature, diluted with diethyl ether, and washed with 1N HCl and water. The organic layer was dried over $NaSO_4$ and concentrated in vacuo. A solution of crude 3-[4-(1-{[(5-chloro-3-methyl-benzo[b]thiophene-2-sulfonyl)-propyl-amino]-methyl}-propoxy)-2-methyl-phenyl])-propionic acid methyl esterand 5N NaOH (1 mL) in ethanol (5 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, $CDCl_3$) δ 7.70 (d, 2H, J=9.2 Hz), 7.42 (dd, 1H, J=8.5 Hz, 2.1 Hz), 6.90 (d, 1H, J=8.5 Hz), 6.49 (d, 2H, J=9.2 Hz), 4.38-4.32 (m, 1H), 3.59 (dd, 1H, J=15.2 Hz, 3.2 Hz), 3.42-3.29 (m, 3H), 2.84 (t, 2H, J=8.3 Hz), 2.59 (t, 2H, J=8.3 Hz), 2.58 (s, 3H), 2.18 (s, 3H), 1.68-1.58 (m, 4H), 0.94 (t, 3H, J=7.6 Hz), 0.85 (t, 3H, J=7.6 Hz). HRMS (ES+) m/z exact mass calculated for C26H33NO5S2Cl 538.1489, found 538.1465.

EXAMPLE 6

[4-(1-{[(5-Chloro-3-methyl-benzo[b]thiophene-2-sulfonyl)-propyl-amino]-methyl}-propoxy)-2-methoxy-phenoxy]-acetic acid

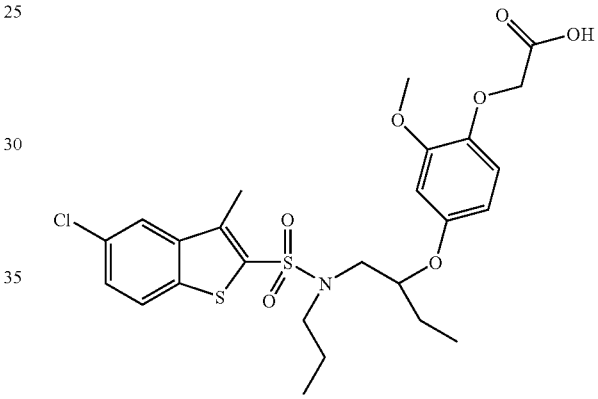

A solution of (4-hydroxy-2-methoxy-phenoxy)-acetic acid ethyl ester (0.055 g, 0.24 mmol) and toluene-4-sulfonic acid 1-{[(5-chloro-3-methyl-benzo[b]thiophene-2-sulfonyl)-propyl-amino]-methyl}-propyl ester (0.142 g, 0.27 mmol) in dimethylformamide (5 mL) was treated with cesium carbonate (0.213 g, 0.37 mmol), heated to 60° C. under $N_2$ for 10 h. The resulting suspension was cooled to ambient temperature, diluted with diethyl ether, and washed with 1N HCl and water. The organic layer was dried over $Na_2SO_4$ and concentrated in vacuo. A solution of crude [4-(1-{[(5-chloro-3-methyl-benzo[b]thiophene-2-sulfonyl)-propyl-amino]-methyl}-propoxy)-2-methoxy-phenoxy]-acetic acid ethyl esterand 5N NaOH (1 mL) in ethanol (5 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, $CDCl_3$) δ 7.70 (d, 2H, J=8.0 Hz), 7.43 (dd, 1H, J=8.7 Hz, 2.0 Hz), 6.91 (d, 1H, J=8.0 Hz), 6.34 (d, 1H, J=2.0 Hz), 6.26 (dd, 1H, J=8.7 Hz, 2.0 Hz), 4.42-4.37 (m, 1H), 3.72 (s, 3H), 3.56 (dd, 1H, J=15.3 Hz, 4.0 Hz), 2.84 (t, 2H, J=7.3 Hz), 2.62 (t, 2H, J=8.0 Hz), 2.60 (s, 3H), 1.71-1.55 (m, 2H), 0.96 (t, 3H, J=7.3 Hz), 0.84 (t, 3H, J=8.0 Hz). HRMS (ES+) m/z exact mass calculated for C26H32NO6S2ClNa 576.1257, found 576.1276.

EXAMPLE 7

[4-(1-{[(5-Fluoro-3-methyl-benzo[b]thiophene-2-sulfonyl)-propyl-amino]-methyl}-propylsulfanyl)-2-methyl-phenoxy]-acetic acid

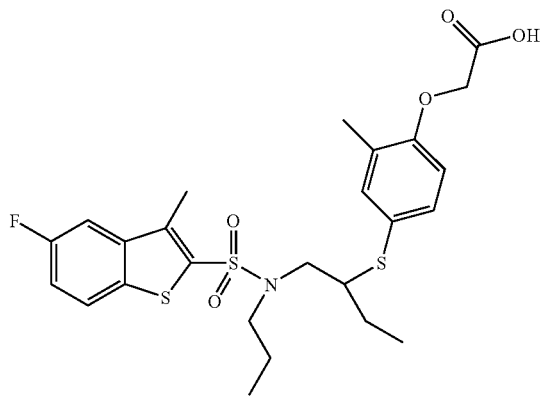

Step A

5-Fluoro-3-methyl-benzo[b]thiophene-2-sulfonic acid (2-hydroxy-butyl)-amide

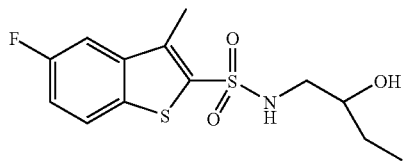

The compound of 5-fluoro-3-methyl-benzo[b]thiophene-2-sulfonyl chloride (1.0 g, 3.78 mmol) in dichloromethane (10 mL) was added dropwise to a 0° C. solution of 1-amino-2-butanol (0.4 mL, 4.2 mmol) and triethylamine (1.05 mL, 7.55 mmol) in dichloromethane (50 mL). The resulting solution was stirred at ambient temperature for 1 h, then diluted with dichloromethane and washed with water. The organic layer was dried over $Na_2SO_4$ and concentrated in vacuo to provide a quantitative yield of the title compound. $^1$H NMR (400 MHz, $CDCl_3$) δ 7.77 (q, 1H, J=4.5 Hz), 7.46 (dd, 1H, J=9.3 Hz, 2.6 Hz), 7.26 (td, H, J=9.3 Hz, 2.6 Hz), 3.70-3.64 (m, 1H), 3.25 (dd, 1H, J=12.7 Hz, 3.3 Hz), 2.92 (dd, 1H, J=12.7 Hz, 8.2 Hz), 2.65 (s, 3H), 1.51-1.43 (m, 2H), 1.04 (t, 3H, J=7.0 Hz), 0.91 (t, 3H, J=7.0 Hz). $R_f$=0.47 in 50% acetone in hexanes.

Step B

5-Fluoro-3-methyl-benzo[b]thiophene-2-sulfonic acid (2-hydroxy-butyl)-propyl-amide

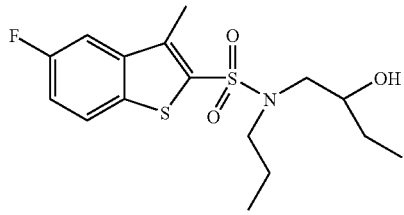

A solution of 5-fluoro-3-methyl-benzo[b]thiophene-2-sulfonic acid (2-hydroxy-butyl)-amide (1.2 g, 3.78 mmol) and 1-iodopropane (0.5 mL, 4.9 mmol) in dimethylformamide (60 mL) was treated with cesium carbonate (1.60 g, 4.9 mmol). The resulting mixture was heated to 50° C. under $N_2$ for 45 minutes. The reaction mixture was cooled to ambient temperature, and diluted with diethyl ether. The organic layer was washed with 1N HCl and water, dried over $Na_2SO_4$, and concentrated in vacuo. The crude material was purified by flash chromatography, using 20% acetone in hexanes as eluent, to provide 1.3 g (96%) of the title compound. $^1$H NMR (400 MHz, $CDCl_3$) δ 7.74 (dd, 1H, J=4.9 Hz, 3.7 Hz), 7.45 (dd, 1H, J=9.2 Hz, 2.4 Hz), 7.23 (td, 1H, J=9.2 Hz, 2.4 Hz), 3.82-3.75 (m, 1H), 3.29, 3.25 (ABq, 2H, J=7.9 Hz), 2.66 (s, 3H), 2.48 (d, 1H, J=3.7 Hz), 1.65-1.56 (m, 2H), 1.55-1.40 (m, 2H), 0.97 (t, 3H, J=7.3 Hz), 0.88 (t, 3H, J=7.3 Hz). MS [EI+] 360 (M+H)$^+$. $R_f$=0.57 in 50% acetone in hexanes.

Step C

Toluene-4-sulfonic acid 1-{[(5-fluoro-3-methyl-benzo[b]thiophene-2-sulfonyl)-propyl-amino]-methyl}-propyl ester

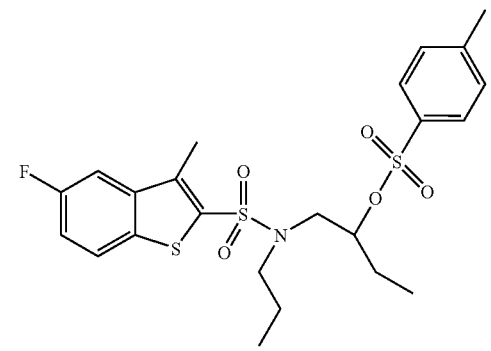

A solution of 5-fluoro-3-methyl-benzo[b]thiophene-2-sulfonic acid (2-hydroxy-butyl)-propyl-amide (0.611 g, 1.7 m mL) and pyridine (0.4 mL, 5.1 mmol) in dichloromethane (85 mL) was treated with dimethylaminopyridine (0.062 g, 0.51 mmol) and p-toluenesulphonic anhydride (0.83 g, 2.55 mmol). The resultant mixture was stirred at ambient temperature for 10 h, then diluted with dichloromethane and washed with 1N HCl. The organic layers were combined, dried over $Na_2SO_4$, and concentrated in vacuo. The crude material was purified by flash chromatography, using 13% acetone in hexanes as eluent, to provide quantitative yield of the title compound. $^1$H NMR (400 MHz, $CDCl_3$) δ 7.78-7.74 (m, 3H), 7.45 (dd, 1H, J=9.2 Hz, 2.7 Hz), 7.32 (d, 2H, J=8.1 Hz), 7.25 (td, 1H, J=9.2 Hz, 2.7 Hz), 4.66-4.060 (m, 1H), 3.49, 3.47 (ABq, 2H, J=6.0 Hz), 3.21-3.12 (m, 2H), 2.65 (s, 3H), 2.43 (s, 2H), 1.86-1.76 (m, 1H), 1.71-1.60 (m, 1H), 1.54-1.44 (m, 2H), 0.81-0.76 (m, 6H). MS [EI+] 514 (M+H)$^+$. $R_f$=0.20 in 20% acetone in hexanes.

Step D

[4-(1-{[(5-Fluoro-3-methyl-benzo[b]thiophene-2-sulfonyl)-propyl-amino]-methyl}-propylsulfanyl)-2-methyl-phenoxy]-acetic acid A solution of (4-mercapto-2-methyl-phenoxy)-acetic acid ethyl ester (0.11 g, 0.46 mmol) and toluene-4-sulfonic acid 1-{[(5-fluoro-3-methyl-benzo[b]thiophene-2-sulfonyl)-propyl-amino]-methyl}-propyl ester (0.12 g, 0.23 mmol) in dimethylformamide (2 mL) was treated with sodium hydride (0.02 g, 0.46 mmol) and stirred at ambient temperature under $N_2$. The resulting suspension was diluted with ethyl acetate, and washed with 1N HCl, water, and brine. The organic layer was dried over $Na_2SO_4$ and concentrated in vacuo. A solution of crude [4-(1-{[(5-fluoro-3-methyl-benzo[b]thiophene-2-sulfonyl)-propyl-amino]-methyl}-propylsulfanyl)-2-methyl-phenoxy]-acetic acid ethyl esterand 5N NaOH (1 mL) in ethanol (5 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, $CDCl_3$) δ 9.20 (s, 1H), 7.74 (dd, 1H, J=4.9 Hz, 3.6 Hz), 7.42 (dd, 1H, J=9.1 Hz, 2.4 Hz), 7.24-7.18 (m, 3H), 6.61 (d, 1H, J=8.5 Hz), 4.67 (s, 2H), 3.40, 3.26 (ABq, 1H, J=9.7 Hz), 3.37, 3.23 (ABq, 1H, J=9.7 Hz), 3.21-3.06 (m, 2H), 2.56 (s, 3H), 2.22 (s, 3H), 1.94-1.87 (m, 1H), 1.50-1.36 (m, 3H), 1.08 (t, 3H, J=7.3 Hz), 0.8 (t, 3H, J=7.3 Hz). HRMS (ES+) m/z exact mass calculated for $C_{25}H_{31}NO5FS_3$ 540.1348, found 540.1358.

EXAMPLE 8

3-[4-(1-{[(5-Fluoro-3-methyl-benzo[b]thiophene-2-sulfonyl)-propyl-amino]-methyl}-propoxy)-2-methyl-phenyl]-propionic acid

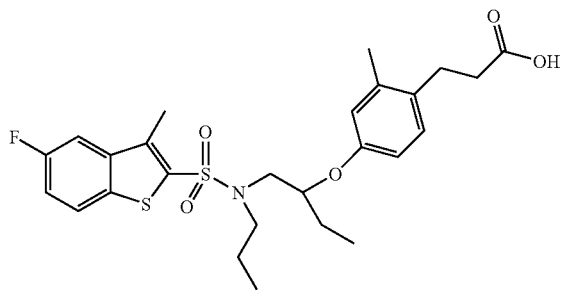

A solution of 3-(4-Hydroxy-2-methyl-phenyl)-propionic acid methyl ester (0.042 g, 0.22 mmol) and Toluene-4-sulfonic acid 1-{[(5-fluoro-3-methyl-benzo[b]thiophene-2-sulfonyl)-propyl-amino]-methyl}-propyl ester (0.122 g, 0.24 mmol) in acetonitrile (2 mL) was treated with cesium carbonate (0.23 g, 0.70 mmol), heated to 65° C. under $N_2$ for 18 h. The resulting suspension was cooled to ambient temperature, diluted with ethyl acetate, and washed with 1N HCl, water, and brine. The organic layer was dried over $Na_2SO_4$, concentrated in vacuo, and purified by flash chromatography, using 20% acetone in hexanes as eluent. $R_f$=0.14 in 20% acetone in hexanes. A solution of semicrude 3-[4-(1-{[(5-Fluoro-3-methyl-benzo[b]thiophene-2-sulfonyl)-propyl-amino]-methyl}-propoxy)-2-methyl-phenyl]-propionic acid methyl esterand 5N NaOH (0.5 mL) in ethanol (4 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, $CDCl_3$) δ 7.72 (dd, 1H, J=4.5 Hz), 7.38 (dd, 1H, J=9.8 Hz, 2.3 Hz), 7.22 (dd, 1H, J=9.0 Hz, 3.0 Hz), 6.92 (d, 1H, J=8.3 Hz), 6.53-6.51 (m, 2H), 3.59 (dd, 1H, J=15.0 Hz, 3.8 Hz), 3.41-3.26 (m, 3H), 2.84 (t, 2H, J=7.5 Hz), 2.59 (t, 2H, J=7.5 Hz), 2.58 (s, 3H), 2.19 (s, 3H), 1.69-1.58 (m, 4H), 0.95 (t, 3H, J=7.5 Hz), 0.85 (t, 3H, J=7.5 Hz). MS [EI+] 522 (M+H)$^+$.

EXAMPLE 9

[4-(1-{[(5-Fluoro-3-methyl-benzo[b]thiophene-2-sulfonyl)-propyl-amino]-methyl}-propoxy)-2-methyl-phenoxy]-acetic acid

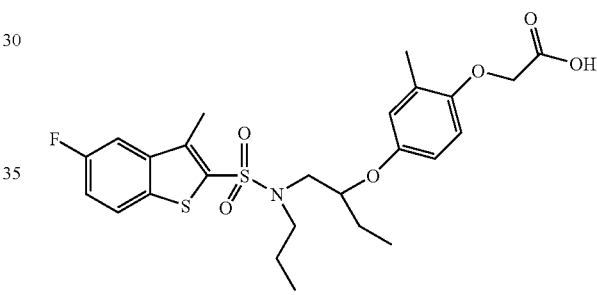

A solution of (4-hydroxy-2-methyl-phenoxy)-acetic acid methyl ester (0.05 g, 0.31 mmol) and toluene-4-sulfonic acid 1-{[(5-fluoro-3-methyl-benzo[b]thiophene-2-sulfonyl)-propyl-amino]-methyl}-propyl ester (0.173 g, 0.34 mmol) in dimethylformamide (2 mL) was treated with cesium carbonate (0.166 g, 0.51 mmol), heated to 60° C. under $N_2$ for 10 h. The resulting suspension was cooled to ambient temperature, diluted with ethyl acetate, and washed with 1N HCl, water, and brine. The organic layer was dried over $Na_2SO_4$ and concentrated in vacuo. A solution of crude [4-(1-{[(5-fluoro-3-methyl-benzo[b]thiophene-2-sulfonyl)-propyl-amino]-methyl}propoxy)-2-methyl-phenoxy]-acetic acid methyl esterand 5N NaOH (0.5 mL) in ethanol (4 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, $CDCl_3$) δ 8.75 (s, 1H), 7.73 (dd, 1H, J=86 Hz, 4.9 Hz), 7.39 (dd, 1H, J=9.8 Hz, 2.4 Hz), 7.23 (td, 1H, J=9.8 Hz, 2.4 Hz), 6.57-6.49 (m, 3H), 4.59 (s, 2H), 4.34-4.29 (m, 1H), 3.57 (dd, 1H, J=15.3 Hz, 3.7 Hz), 3.39-3.28 (m, 3H), 2.59 (s, 3H), 2.16 (s, 3H), 1.69-1.50 (m, 4H), 0.94 (t, 3H, J=7.3 Hz), 0.84 (t, 3H, J=7.3 Hz). HRMS (ES+) m/z exact mass calculated for $C_{25}H_{31}NO_6FS_2$ 524.1577, found 524.1569.

EXAMPLE 10

(4-{2-[(5-Chloro-3-methyl-benzo[b]thiophene-2-sulfonyl)-(3-phenyl-propyl)-amino]-ethylsulfanyl}-2-methyl-phenoxy)-acetic acid

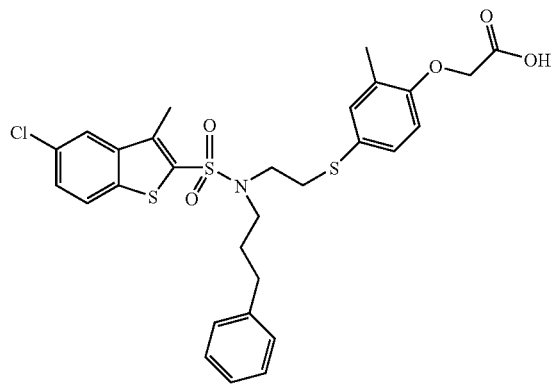

Step A

5-Chloro-3-methyl-benzo[b]thiophene-2-sulfonic acid (2-bromo-ethyl)-(3-phenyl-propyl)-amide

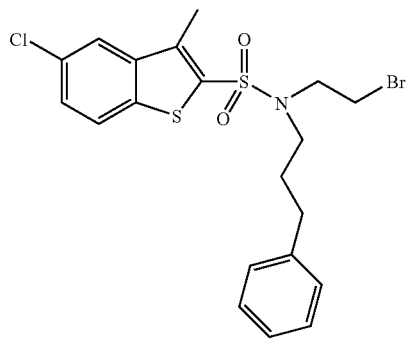

A solution of 5-chloro-3-methyl-benzo[b]thiophene-2-sulfonic acid (2-hydroxy-ethyl)-(3-phenyl-propyl)-amide (0.196 g, 0.46 mmol) and carbon tetrabromide (0.23 g, 0.69 mmol) in dichloromethane (5 mL) was treated with triphenylphosphine (0.18 g, 0.69 mmol). The resulting mixture was stirred at ambient temperature until all 5-chloro-3-methyl-benzo[b]thiophene-2-sulfonic acid (2-hydroxy-ethyl)-(3-phenyl-propyl)-amide was consumed, then adsorbed onto silica gel. The crude material was purified by flash chromatography, using 9% acetone in hexanes as eluent, to provide 0.151 g (67%) of the title compound. $^1$H NMR (400 MHz, CDCl$_3$) δ 7.78 (d, 1H, J=2.1 Hz), 7.74 (d, 1H, J=9.0 Hz), 7.46 (dd, 1H, J=9.0 Hz, 2.1 Hz), 7.26 (t, 2H, J=7.4 Hz), 7.20 (t, 1H, J=7.4 Hz), 7.11 (d, 2H J=8.2 Hz), 3.62-3.58 (m, 2H), 3.49-3.45 (m, 2H), 3.30 (t, 2H, J=7.4 Hz), 2.63 (t, 2H, J=7.4 Hz), 2.62 (s, 3H), 1.92 (p. 2H, J=7.4 Hz).

Step B (4-{2-[(5-Chloro-3-methyl-benzo[b]thiophene-2-sulfonyl)-(3-phenyl-propyl)-amino]-ethylsulfanyl}-2-methyl-phenoxy)-acetic acid A solution of (4-mercapto-2-methyl-phenoxy)-acetic acid ethyl ester (0.066 g, 0.29 mmol) and 5-chloro-3-methyl-benzo[b]thiophene-2-sulfonic acid (2-bromo-ethyl)-(3-phenyl-propyl)-amide (0.15 g, 0.32 mmol) in dimethylformamide (5 mL) was treated with cesium carbonate (0.143 g, 0.44 mmol) and heated at 60° C. under N$_2$ for 10 h. The resulting suspension was diluted with diethyl ether, and washed with 1N HCl and water. The organic layer was dried over Na$_2$SO$_4$ and concentrated in vacuo. A solution of crude (4-{2-[(5-chloro-3-methyl-benzo[b]thiophene-2-sulfonyl)-(3-phenyl-propyl)-amino]-ethylsulfanyl}-2-methyl-phenoxy)-acetic acid ethyl esterand 5N NaOH (1 mL) in ethanol (5 mL) was refluxed under nitrogen for 1 h, cooled to ambient temperature, and concentrated in vacuo. The residue was diluted with 1N HCl, extracted with CH$_2$Cl$_2$, dried through a Varian ChemElut cartridge, concentrated in vacuo, and purified by LCMS to provide the title compound. $^1$H NMR (400 MHz, CDCl$_3$) δ 7.74 (d, 1H, J=2.0 Hz), 7.71 (d, 1H, J=9.2 Hz), 7.44 (dd, 1H, J=9.2 Hz, 2.0 Hz), 7.27-7.24 (m, 2H), 7.20-7.08 (m, 5H), 6.62 (d, 1H, J=8.5 Hz), 4.66 (s, 2H), 3.34 (t, 2H, J=7.8 Hz), 3.26 (t, 2H, J=-7.8 hz), 3.00 (t, 2B, J=7.8 Hz), 2.59 (t, 2H, J=7.8 Hz), 2.52 (s, 3H), 2.23 (s, 3H), 1.83 (p, 2H, J=7.8 Hz). HRMS (ES+) m/z exact mass calculated for C$_{29}$H$_{30}$NO$_5$NaS$_3$Cl 626.0872, found 626.0866.

EXAMPLE 11

(4-{2-[(5-Chloro-3-methyl-benzo[b]thiophene-2-sulfonyl)-phenethyl-amino]-ethylsulfanyl}-2-methyl-phenoxy)-acetic acid

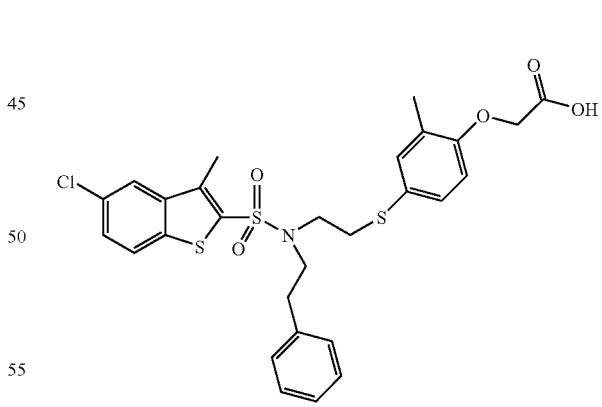

A solution of (4-mercapto-2-methyl-phenoxy)-acetic acid ethyl ester (0.061 g, 0.27 mmol) and 5-chloro-3-methyl-benzo[b]thiophene-2-sulfonic acid (2-bromo-ethyl)-phenethyl-amide (0.14 g, 0.30 mmol) in dimethylformamide (5 mL) was treated with cesium carbonate (0.132 g, 0.40 mmol) and heated at 60° C. under N$_2$ for 10 h. The resulting suspension was diluted with diethyl ether, and washed with 1N HCl and water. The organic layer was dried over Na$_2$SO$_4$ and concentrated in vacuo.

A solution of crude (4-{2-[(5-chloro-3-methyl-benzo[b]thiophene-2-sulfonyl)-phenethyl-amino]-ethylsulfanyl}-2-methyl-phenoxy)-acetic acid ethyl ester and 5N NaOH (1 mL) in ethanol (5 mL) was refluxed under nitrogen for 1 h, cooled to ambient temperature, and concentrated in vacuo. The residue was diluted with 1N HCl, extracted with CH$_2$Cl$_2$, dried through a Varian ChemElut cartridge, concentrated in vacuo, and purified by LCMS to provide the title compound. $^1$H NMR (400 MHz, CDCl$_3$) δ 7.73 (d, 1H, J=2.2 Hz), 7.71 (d, 1H, J=8.3 Hz), 7.44 (dd, 1H, J=8.9 Hz, 1.7 Hz), 7.23-7.16 (m, 1H), 7.07 (d, 2H, J=7.2 Hz), 6.65 (d, 1H, J=8.9 Hz), 4.68 (s, 2H), 3.47 (t, 2H, J=7.7 Hz), 3.37 (t, 2H, J=7.7 Hz), 2.95 (t, 2H, J=7.7 Hz), 2.82 (t, 2H, J=7.7 Hz), 2.52 (s, 3H), 2.26 (s, 3H). MS [EI+] 590 (M+H)$^+$.

EXAMPLE 12

(4-{2-[(5-Chloro-3-methyl-benzo[b]thiophene-2-sulfonyl)-phenethyl-amino]-ethoxy}-2-methyl-phenoxy)-acetic acid

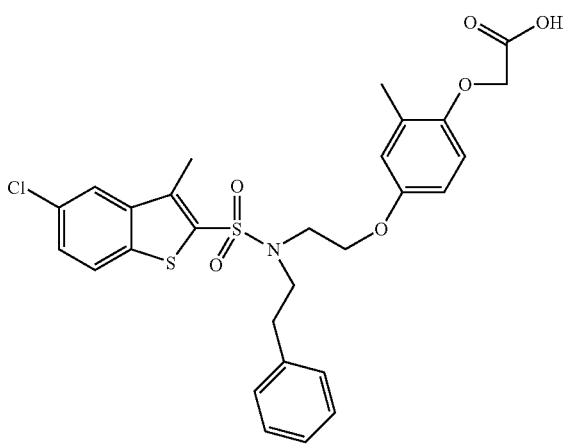

A solution of (4-hydroxy-2-methyl-phenoxy)-acetic acid methyl ester (0.052 g, 0.27 mmol) and 5-chloro-3-methyl-benzo[b]thiophene-2-sulfonic acid (2-bromo-ethyl)-phenethyl-amide (0.14 g, 0.29 mmol) in dimethylformamide (5 mL) was treated with cesium carbonate (0.132 g, 0.40 mmol) and heated at 60° C. under N$_2$ for 10 h. The resulting suspension was diluted with diethyl ether, and washed with 1 N HCl and water. The organic layer was dried over Na$_2$SO$_4$ and concentrated in vacuo. A solution of crude (4-{2-[(5-chloro-3-methyl-benzo[b]thiophene-2-sulfonyl)-phenethyl-amino]-ethoxy}-2-methyl-phenoxy)-acetic acid methyl ester and 5N NaOH (1 mL) in ethanol (5 mL) was refluxed under nitrogen for 1 h, cooled to ambient temperature, and concentrated in vacuo. The residue was diluted with 1N HCl, extracted with CH$_2$Cl$_2$, dried through a Varian ChemElut cartridge, concentrated in vacuo, and purified by LCMS to provide the title compound. HRMS (ES+) m/z exact mass calculated for C$_{28}$H$_{29}$NO$_6$S$_2$Cl 574.1125, found 574.1122.

EXAMPLE 13

3-(4-{2-[(5-Chloro-3-methyl-benzo[b]thiophene-2-sulfonyl)-phenethyl-amino]-ethoxy}-phenyl)-propionic acid

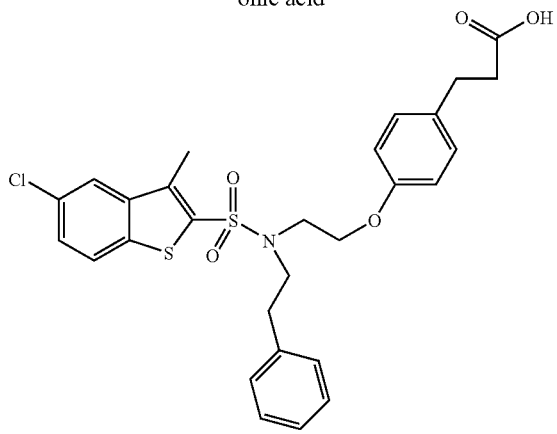

A solution of 3-(4-hydroxy-phenyl)-propionic acid methyl ester (0.064 g, 0.36 mmol) and 5-chloro-3-methyl-benzo[b]thiophene-2-sulfonic acid (2-bromo-ethyl)-phenethyl-amide (0.19 g, 0.39 mmol) in dimethylformamide (5 mL) was treated with cesium carbonate (0.174 g, 0.53 mmol) and heated at 60° C. under N$_2$ for 10 h. The resulting suspension was diluted with diethyl ether, and washed with 1N HCl and water. The organic layer was dried over Na$_2$SO$_4$ and concentrated in vacuo. A solution of crude 3-(4-{2-[(5-chloro-3-methyl-benzo[b]thiophene-2-sulfonyl)-phenethyl-amino]-ethoxy}-phenyl)-propionic acid methyl esterand 5N NaOH (1 mL) in ethanol (5 mL) was refluxed under nitrogen for 1 h, cooled to ambient temperature, and concentrated in vacuo. The residue was diluted with 1N HCl, extracted with CH$_2$Cl$_2$, dried through a Varian ChemElut cartridge, concentrated in vacuo, and purified by LCMS to provide the title compound. $^1$H NMR (400 MHz, CDCl$_3$) δ 7.71 (d, 2H, J=8.6 Hz), 7.44 (dd, 1H, J=8.6 Hz, 2.0 Hz), 7.26-7.13 (m, 7H), 6.78 (d, 1H, J=7.3 Hz), 6.63 (dd, 1H, J=8.6 Hz, 2.0 Hz), 6.63 (dd, 1H, J=8.6 Hz, 2.0 Hz), 6.58 (s, 1H), 4.08 (t, 2H, J=5.3 Hz), 3.71 (t, 2H, J=5.3 Hz), 3.63 (t, 2H, J=8.0 Hz), 2.99 (t, 2H, J=8.0 Hz), n2.87 (t, 2H, J=8.0 Hz), 2.64 (t, 2H, J=8.0 Hz), 2.62 (s, 3H). HRMS (ES+) m/z exact mass calculated for C$_{28}$H$_{28}$NO$_5$NaS$_2$Cl 580.0995, found 580.1000.

EXAMPLE 14

2-(4-{2-[(5-Chloro-3-methyl-benzo[b]thiophene-2-sulfonyl)-phenethyl-amino]-ethoxy}-2-methyl-phenoxy)-2-methyl-propionic acid

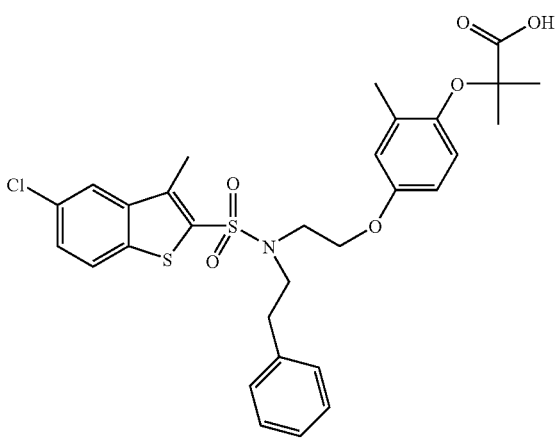

A solution of 2-(4-hydroxy-2-methyl-phenoxy)-2-methyl-propionic acid ethyl ester (0.062 g, 0.26 mmol) and 5-chloro-3-methyl-benzo[b]thiophene-2-sulfonic acid (2-bromo-ethyl)-phenethyl-amide (0.14 g, 0.29 mmol) in dimethylformamide (5 mL) was treated with cesium carbonate (0.127 g, 0.39 mmol) and heated at 60° C. under $N_2$ for 10 h. The resulting suspension was diluted with diethyl ether, and washed with 1 N HCl and water. The organic layer was dried over $Na_2SO_4$ and concentrated in vacuo.

A solution of crude 2-(4-{2-[(5-chloro-3-methyl-benzo[b]thiophene-2-sulfonyl)-phenethyl-amino]-ethoxy}-2-methyl-phenoxy)-2-methyl-propionic acid ethyl esterand 5N NaOH (1 mL) in ethanol (5 mL) was refluxed under nitrogen for 1 h, cooled to ambient temperature, and concentrated in vacuo. The residue was diluted with 1N HCl extracted with $CH_2Cl_2$, dried through a Varian ChemElut cartridge, concentrated in vacuo, and purified by LCMS to provide the title compound. $^1$H NMR (400 MHz, $CDCl_3$) δ 7.76-7.70 (m, 2H), 7.45 (dd, 2H, J=8.2 Hz, 2.1 Hz), 7.25-7.14 (m, 4H), 7.06 (dd, 1H, J=7.6 Hz. 1.4 Hz), 6.76 (d, 1H, J=8.2 Hz), 6.58-6.51 (m, 1H), 4.05 (t, 2H, J=6.2 Hz), 3.68 (t, 2H, J=6.2 Hz), 3.62 (t, 2H, J=8.2 Hz), 2.98 (t, 2H, J=8.2 Hz), 2.62 (s, 3H), 2.19 (s, 3H), 1.55 (s, 6H). HRMS (ES+) m/z exact mass calculated for $C_{30}H_{33}NO_6S_2Cl$ 602.1438, found 602.1422.

EXAMPLE 15

(5-{2-[(5-Chloro-3-methyl-benzo[b]thiophene-2-sulfonyl)-phenethyl-amino]-ethoxy}-indol-1-yl)-acetic acid

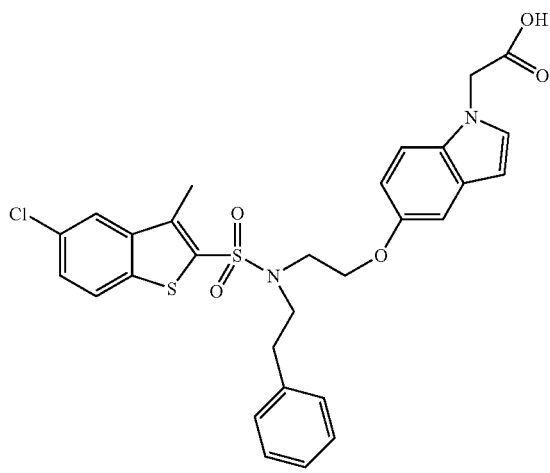

A solution of (5-hydroxy-indol-1-yl)-acetic acid ethyl ester (0.066 g, 0.30 mmol) and 5-chloro-3-methyl-benzo[b]thiophene-2-sulfonic acid (2-bromo-ethyl)-phenethyl-amide (0.16 g, 0.33 mmol) in dimethylformamide (5 mL) was treated with cesium carbonate (0.147 g, 0.45 mmol) and heated at 60° C. under $N_2$ for 10 h. The resulting suspension was diluted with diethyl ether, and washed with 1N HCl and water. The organic layer was dried over $Na_2SO_4$ and concentrated in vacuo. A solution of crude (5-{2-[(5-chloro-3-methyl-benzo[b]thiophene-2-sulfonyl)-phenethyl-amino]-ethoxy}-indol-1-yl)-acetic acid ethyl esterand 5N NaOH (1 mL) in ethanol (5 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. HRMS (ES+) m/z exact mass calcd. for $C_{29}H_{27}N_2O_5NaS_2Cl$ 605.0948, found 605.0956.

EXAMPLE 16

(4-{2-[Benzyl-(5-chloro-3-methyl-benzo[b]thiophene-2-sulfonyl)-amino]-ethylsulfanyl}-2-methyl-phenoxy)-acetic acid

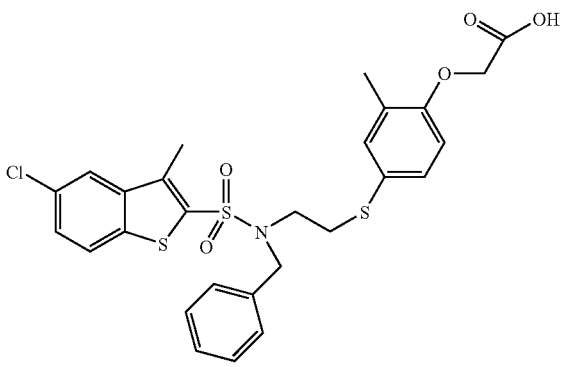

Step A

5-Chloro-3-methyl-benzo[b]thiophene-2-sulfonic acid (2-hydroxy-ethyl)-amide

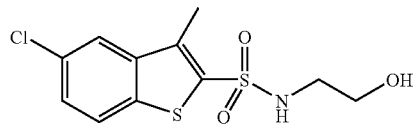

5-chloro-3-methyl-benzo[b]thiophene-2-sulfonyl chloride (2.02 g, 7.18 mmol) was added portion wise to a 0° C. solution of ethanolamine (0.5 mL, 7.90 mmol) and triethylamine (2.0 mL, 14.4 mmol) in dichloromethane (100 mL). The resulting solution was stirred at ambient temperature for 2 h, then diluted with dichloromethane and washed with water. The organic layer was dried over $Na_2SO_4$ and concentrated in vacuo. The crude material was purified by flash chromatography to provide 1.8 g (80%) of the title compound. $^1$H NMR (400 MHz, $CDCl_3$) δ 8.15 (t, 1H, J=5.9 Hz), 8.08 (d, 1H, J=8.8 Hz), 8.02 (d, 1H, J=2.3 Hz), 7.56 (dd, 1H, J=8.8 Hz, 2.3 Hz), 4.49 (s, 2H), 3.56 (t, 2H, J=8.2 Hz), 3.18 (t, 2H, J=7.8 Hz), 2.70 (s, 3H). $R_f$=0.35 in 50% acetone in hexanes.

Step B

5-Chloro-3-methyl-benzo[b]thiophene-2-sulfonic acid benzyl-(2-bromo-ethyl)-amide

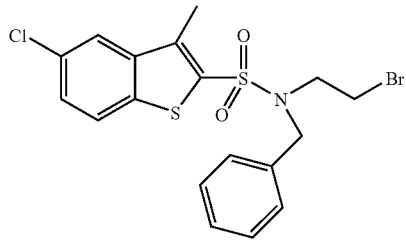

A solution of 5-chloro-3-methyl-benzo[b]thiophene-2-sulfonic acid (2-hydroxy-ethyl)-amide (1.0 g, 3.27 mmol) and benzyl bromide (0.51 mL, 4.25 mmol) in dimethylformamide (60 mL) was treated with cesium carbonate (1.39 g, 4.25 mmol). The resulting mixture was heated to 50° C. under N$_2$ for 2 h. The reaction mixture was cooled to ambient temperature, and diluted with diethyl ether. The organic layer was washed with 1N HCl and water, dried over Na$_2$SO$_4$, and concentrated in vacuo. The crude material was purified by flash chromatography, using 20% acetone in hexanes as eluent. R$_f$=0.52 in 50% acetone in hexanes.

A solution of 5-chloro-3-methyl-benzo[b]thiophene-2-sulfonic acid benzyl-(2-hydroxy-ethyl)-amide and carbon tetrabromide (1.63 g, 4.91 mmol) in dichloromethane (20 mL) was treated with triphenylphosphine (1.29 g, 4.93 mmol). The resulting mixture was stirred at ambient temperature for 10 h, then adsorbed onto silica gel. The crude material was purified by flash chromatography, using 10% acetone in hexanes as eluent, to provide 1.10 g (73%) of the title compound. $^1$H NMR (400 MHz, CDCl$_3$) δ 7.81 (d, 1H, J=2.2 Hz), 7.77 (d, 1H, J=8.6 Hz), 7.48 (dd, 3H, J=8.6 Hz, 2.2 Hz), 7.34-7.27 (m, 5H), 4.49 (s, 2H), 3.56 (t, 2H, J=8.2 Hz), 3.18 (t, 2H, J=8.2 Hz), 2.70 (s, 3H). R$_f$=0.66 in 50% acetone in hexanes.

Step C (4-{2-[Benzyl-(5-chloro-3-methyl-benzo[b]thiophene-2-sulfonyl-amino]-ethylsulfanyl}-2-methyl-phenoxy)-acetic acid A solution of (4-mercapto-2-methyl-phenoxy)-acetic acid ethyl ester (0.30 g, 0.13 mmol) and 5-chloro-3-methyl-benzo[b]thiophene-2-sulfonic acid benzyl-(2-bromo-ethyl)-amide (0.05 g, 0.10 mmol) in dimethylformamide (2 mL) was treated with sodium hydride (0.01 g, 0.13 mmol) and stirred at ambient temperature under N$_2$. The resulting suspension was diluted with ethyl acetate, and washed with 1N HCl, water, and brine. The organic layer was dried over Na$_2$SO$_4$ and concentrated in vacuo.

A solution of crude [4-(1-{[(5-chloro-3-methyl-benzo[b]thiophene-2-sulfonyl)-propyl-amino]-methyl}-propylsulfanyl)-2-methyl-phenoxy]-acetic acid ethyl ester and 5N NaOH (1 mL) in ethanol (4 mL) was refluxed under nitrogen for 1 h, cooled to ambient temperature, and concentrated in vacuo. The residue was diluted with 1N HCl, extracted with CH$_2$Cl$_2$, dried through a Varian ChemElut cartridge, concentrated in vacuo, and purified by LCMS to provide the title compound. $^1$H NMR (400 MHz, CDCl$_3$) δ 7.76 (d, 1H, J=1.9 Hz), 7.73 (d, 1H J=8.4 Hz), 7.45 (dd, 1H, J=8.4 Hz, 1.9 Hz), 7.28-7.19 (m, 5H), 7.02 (s, 1H), 6.95 (d, 1H, J=8.4 Hz), 6.54 (d, 1H, J=8.4 Hz), 4.65 (s, 2H), 4.40 (s, 2H), 3.29 (t, 2H, J=8.8 Hz), 2.73 (t, 2H, J=8.8 Hz), 2.57 (s, 3H), 2.19 (s, 3H). HRMS (ES+) m/z exact mass calculated for C$_{27}$H$_{27}$NO$_5$S$_3$Cl 576.0740, found 576.0751.

EXAMPLE 17

3-(4-{2-[Benzyl-(5-chloro-3-methyl-benzo[b]thiophene-2-sulfonyl)-amino]-ethoxy}-2-methyl-phenyl)-propionic acid

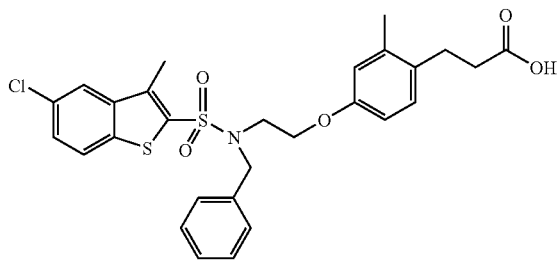

A solution of 3-(4-hydroxy-phenyl)-propionic acid methyl ester (0.056 g, 0.29 mmol) and 5-chloro-3-methyl-benzo[b]thiophene-2-sulfonic acid benzyl-(2-bromo-ethyl)-amide (0.145 g, 0.32 mmol) in dimethylformamide (2 mL) was treated with cesium carbonate (0.141 g, 0.43 mmol) and heated at 60° C. under N$_2$ for 10 h. The resulting suspension was diluted with ethyl acetate, and washed with 1N HCl and water. The organic layer was dried over Na$_2$SO$_4$ and concentrated in vacuo. A solution of crude 3-(4-{2-[benzyl-(5-chloro-3-methyl-benzo[b]thiophene-2-sulfonyl)-amino]-ethoxy}-2-methyl-phenyl)-propionic acid ethyl ester and 5N NaOH (1 mL) in ethanol (4 mL) was refluxed under nitrogen for 1 h, cooled to ambient temperature, and concentrated in vacuo. The residue was diluted with 1N HCl, extracted with CH$_2$Cl$_2$, dried through a Varian ChemElut cartridge, concentrated in vacuo, and purified by LCMS to provide the title compound. $^1$H NMR (400 MHz, CDCl$_3$) δ 7.71-7.70 (m, 2H), 7.48 (d, 1H, J=6.3 Hz, 2.3 Hz), 7.31-7.19 (m, 5H), 6.91 (d, 1H, J=8.6 Hz), 6.37 (d, 1H, J=8.6 Hz), 6.30 (d, 1H, J=2.3 Hz), 4.63 (s, 2H), 4.28 (d, 1H, J=6.3 Hz), 3.90 (t, 2H, J=5.8 Hz), 3.60 (t, 2H, J=5.8 Hz), 2.82 (t, 2H, J=8.1 Hz), 2.64 (s, 3H), 2.58 (t, 2H, J 8.1 Hz), 2.16 (s, 3H). HRMS (ES+) m/z exact mass calculated for C$_{28}$H$_{28}$NO$_5$NaS$_2$Cl 580.0995, found 580.0989.

EXAMPLE 18

3-(4-{2-[(5-Chloro-3-methyl-benzo[b]thiophene-2-sulfonyl)-(3-phenyl-propyl)-amino]-ethoxy}-2-methyl-phenyl)-propionic acid

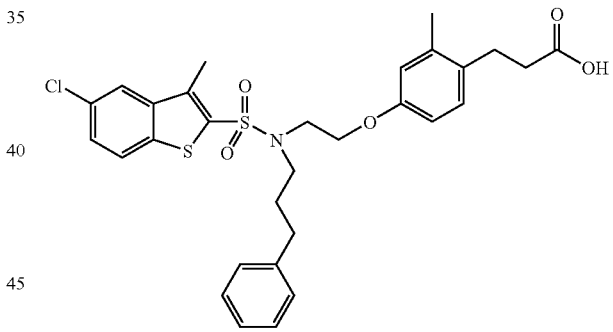

A solution of 3-(4-hydroxy-phenyl)-propionic acid methyl ester (0.054 g, 0.28 mmol) and 5-Chloro-3-methyl-benzo[b]thiophene-2-sulfonic acid (2-bromo-ethyl)-(3-phenyl-propyl)-amide (0.149 g, 0.31 mmol) in dimethylformamide (2 mL) was treated with cesium carbonate (0.149 g, 0.46 mmol) and heated at 60° C. under N$_2$ for 10 h. The resulting suspension was diluted with ethyl acetate, and washed with 1N HCl, water, and brine. The organic layer was dried over Na$_2$SO$_4$ and concentrated in vacuo. A solution of crude 3-(4-{2-[(5-chloro-3-methyl-benzo[b]thiophene-2-sulfonyl)-(3-phenyl-propyl)-amino]-ethoxy}-2-methyl-phenyl)-propionic acid ethyl ester and 5N NaOH (1 mL) in ethanol (4 mL) was refluxed under nitrogen for 1 h, cooled to ambient temperature, and concentrated in vacuo. The residue was diluted with 1N HCl, extracted with CH$_2$Cl$_2$, dried through a Varian ChemElut cartridge, concentrated in vacuo, and purified by LCMS to provide the title compound. $^1$H NMR (400 MHz, CDCl$_3$) δ 7.78-7.70 (m, 2H), 7.45 (dd, 2H, J=8.1 Hz, 1.8 Hz), 7.25-6.97 (m, 5H), 6.51 (dd, 1H, J=8.1 Hz, 1.8 Hz), 6.48 (s, 1H), 4.07 (t, 2H, J=6.1 Hz), 3.64 (t, 2H, J=6.1 Hz), 3.41 (t, 2H, J=7.3 Hz), 2.86 (t, 2H, J=7.3 Hz), 2.66-2.53 (m, 5H), 2.21 (s, 3H), 2.03-1.95 (m, 3H), 1.84 (p, 1H, J=7.3 Hz). HRMS (ES+) m/z exact mass calculated for $C_{30}H_{32}NO_5NaS_2Cl$ 608.1308, found 608.1312.

EXAMPLE 19

3-(4-{2-[(5-Chloro-3-methyl-benzo[b]thiophene-2-sulfonyl)-propyl-amino]-butoxy}-2-2-methyl-phenyl)-propionic acid

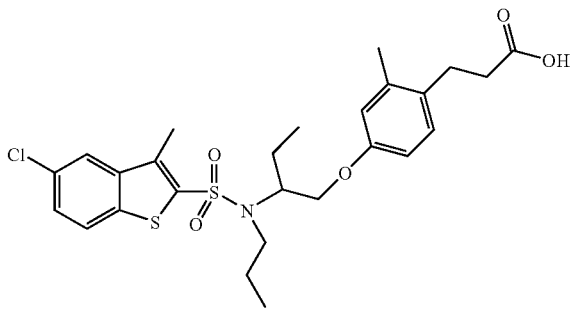

Step A

5-Chloro-3-methyl-benzo[b]thiophene-2-sulfonic acid (1-hydroxymethyl-propyl)-amide

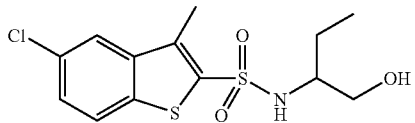

5-chloro-3-methyl-benzo[b]thiophene-2-sulfonyl chloride (1.08 g, 3.84 mmol) was added portion-wise to a 0° C. solution of 2-amino-1-butanol (0.4 mL, 4.22 mmol) and triethylamine (1.1 mL, 7.68 mmol) in dichloromethane (50 mL). The resulting solution was stirred at ambient temperature for 2 h, then diluted with chloroform and washed with water. The organic layer was dried over $Na_2SO_4$ and concentrated in vacuo to provide 1.25 g (98%) of the title compound. $^1$H NMR (400 MHz, CDCl$_3$) δ 7.74 (d, 1H, J=2.0 Hz), 7.71 (d, 1H, J=8.2 Hz), 7.41 (dd, 1H, J=8.2 Hz, 2.0 Hz), 3.53 (qd, 2H, J=10.0 Hz, 4.0 Hz), 3.34-3.30 (m, 1H), 2.64 (s, 3H), 1.58-1.44 (m, 2H), 0.99 (t, 3H, J=6.9 Hz). R$_f$=0.41 in 50% acetone in hexanes.

Step B

5-Chloro-3-methyl-benzo[b]thiophene-2-sulfonic acid (1-hydroxymethyl-propyl)-propyl-amide

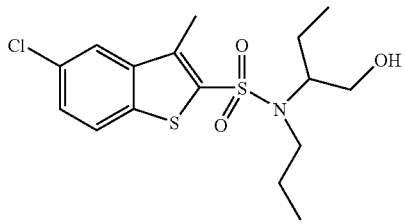

A solution of 5-chloro-3-methyl-benzo[b]thiophene-2-sulfonic acid (1-hydroxymethyl-propyl)-amide (1.25 g, 3.74 mmol) and 1-iodopropane (0.47 mL, 4.87 mmol) in dimethylformamide (60 mL) was treated with cesium carbonate (1.59 g, 4.87 mmol). The resulting mixture was heated to 50° C. under $N_2$ until all of the 5-chloro-3-methyl-benzo[b]thiophene-2-sulfonic acid (1-hydroxymethyl-propyl)-amide was consumed. The reaction mixture was cooled to ambient temperature, and diluted with diethyl ether. The organic layer was washed with 1N HCl, water, and brine. The organic layer was dried over $Na_2SO_4$ and concentrated in vacuo to provide quantitative yield of the title compound. $^1$H NMR (400 MHz, CDCl$_3$) δ 7.97 (s, 1H), 7.71 (d, 1H, J=1.7 Hz), 7.68 (d, 1H, J=8.4 Hz), 7.38 (dd, 1H, J=8.4 Hz, 1.7 Hz), 3.78-3.71 (m, 1H), 3.57 (td, 2H, J=10.4 Hz, 5.9 Hz), 3.29 (m, 1H), 3.13-3.045 (m, 1H), 2.63 (s, 3H), 1.71-1.61 (m, 2H), 1.58-1.46 (m, 1H), 1.41-1.30 (m, 1H), 0.85 (t, 3H, J=7.4 Hz), 0.70 (t, 3H, J=7.4 Hz). MS [EI+] 376 (M+H)$^+$. R$_f$=0.63 in 50% acetone in hexanes.

Step C

5-Chloro-3-methyl-benzo[b]thiophene-2-sulfonic acid (1-bromomethyl-propyl)-propyl-amide

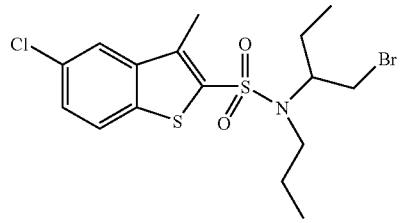

A solution of 5-chloro-3-methyl-benzo[b]thiophene-2-sulfonic acid (1-hydroxymethyl-propyl)-propyl-amide and carbon tetrabromide (1.86 g, 5.61 mmol) in dichloromethane (25 mL) was treated with triphenylphosphine (1.47 g, 5.61 mmol). The resulting mixture was stirred at ambient temperature until 5-chloro-3-methyl-benzo[b]thiophene-2-sulfonic acid (1-hydroxymethyl-propyl)-propyl-amide was consumed, then adsorbed onto silica gel. The crude material was purified by flash chromatography, using 10% acetone in hexanes as eluent, to provide 0.86 g (52% over two steps) of the title compound. $^1$H NMR (400 MHz, CDCl$_3$) δ 7.75 (t, 1H, J=2.7 Hz), 7.74 (dd, 1H, J=8.4 Hz, 3.4 Hz), 7.42 (dt, 1H, J=8.4 Hz, 3.4 Hz), 4.11 (t, 1H, J=8.1 Hz), 3.92 (t, 1H, J=8.1 Hz), 3.41-3.23 (m, 1H), 3.24-3.11 (m, 2H), 2.68 (s, 3H), 1.75-1.61 (m, 2H), 1.59-1.46 (m, 2H), 0.91-0.79 (m, 6H). R$_f$=0.70 in 50% acetone in hexanes.

Step D 3-(4-{2-[(5-Chloro-3-methyl-benzo[b]thiophene-2-sulfonyl)-propyl-amino]-butoxy}-2-methyl-phenyl)-propionic acid A solution of 3-(4-hydroxy-2-methyl-phenyl)-propionic acid ethyl ester (0.060 g, 0.31 mmol) and 5-chloro-3-methyl-benzo[b]thiophene-2-sulfonic acid (1-bromomethyl-propyl)-propyl-amide (0.149 g, 0.34 mmol) in dimethylformamide (2 mL) was treated with cesium carbonate (0.151 g, 0.46 mmol) and heated at 50° C. under $N_2$ for 10 h. The resulting suspension was diluted with ethyl acetate, and washed with 1N HCl, water, and brine. The organic layer was dried over $Na_2SO_4$ and concentrated in vacuo. A solution of crude 3-(4-{2-[(5- chloro-3-methyl-benzo[b]thiophene-2-sulfonyl)-propyl-amino]-butoxy}-2-methyl-phenyl)-propionic acid ethyl esterand 5N NaOH (1 mL) in ethanol (4 mL) was refluxed under nitrogen for 1 h, cooled to ambient temperature, and concentrated in vacuo. The residue was diluted with 1N HCl, extracted with $CH_2Cl_2$, dried through a Varian ChemElut cartridge, concentrated in vacuo, and purified by LCMS to provide the title compound. $^1$H NMR (400 MHz, $CDCl_3$) δ 7.72 (d, 1H, J=1.4 Hz), 7.71 (d, 1H, J=4.5 Hz), 7.43 (dd, 1H, J=8.8 Hz, 2.1 Hz), 6.91 (d, 1H, J=8.8 Hz), 6.38 (dd, 1H, J=8.2 Hz, 2.5 Hz), 6.16 (d, 1H, J=2.5 Hz), 4.08 (p, 1H, J=5.6 Hz), 3.95-3.86 (m, 2H), 3.45-3.19 (m, 2H), 2.82 (t, 2H, J=7.4 Hz), 2.65 (s, 3H), 2.55 (t, 2H, J=7.4 Hz), 2.11 (S, 3H), 1.82-1.60 (m, 4H), 0.94 (t, 3H, J=7.4 Hz), 0.89 (t, 3H, J=7.4 Hz). HRMS (ES+) m/z exact mass calculated for $C_{26}H_{33}NO_5S_2Cl$ 538.1489, found 538.1477.

EXAMPLE 20

[4-(1-{[(5-Chloro-3-methyl-benzo[b]thiophene-2-sulfonyl)-propyl-amino]-methyl}-propylsulfanyl)-2-methyl-phenoxy]-acetic acid

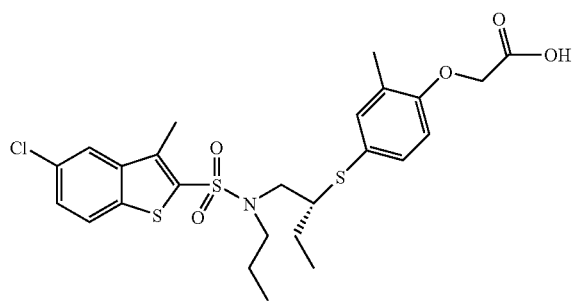

Step A 1-(4-Methoxy-benzylamino)-butan-2-ol

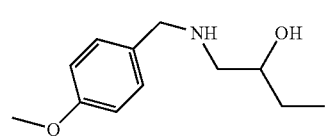

1-amino-2-butanol (15.0 mL, 0.157 mol) was added to a 0° C. suspension of p-anisaldehyde (21.0 mL, 0.172 mol) and sodium sulphate (26.68 g, 0.188 mol) in dry $CH_2Cl_2$ (150 mL). The resulting mixture was stirred at room temperature for one hour, filtered, and concentrated in vacuo. The residue was diluted with 4° A molecular sieve-dried ethanol (100 mL) and cooled to 0° C. Sodium borohydride (5.92 g, 0.157 mol) was added to the solution in two portions and the resulting mixture was stirred at room temperature for two hours. The resultant mixture was concentrated in vacuo, then partitioned between $CH_2Cl_2$ and 1 N NaOH. The organic layer was acidified to pH 10 with 1N HCl, dried over sodium sulphate, and concentrated in vacuo to give >99% yield of 1-(4-methoxy-benzylamino)-butan-2-ol. $^1$H NMR (400 MHz, $CDCl_3$) δ 7.25 (d, 2H, J=8.6 Hz), 6.85 (d, 2H, J=8.6 Hz), 3.78 s, 3H), 3.72, 3.68 (ABq, 2H, J=12.4 Hz), 3.56-3.50 (m, 1H), 2.71 (dd, 1H, J=12.3 Hz, 2.8 Hz), 2.49 (dd, 1H, J=12.3 Hz, 9.6 Hz), 1.46-1.38 (m, 2H), 0.92 t, 3H, J=7.4 Hz). MS [EI+] 210 $(M+H)^+$.

Step B

5-Ethyl-3-(4-methoxy-benzyl)-[1,2,3]oxathiazolidine 2-oxide

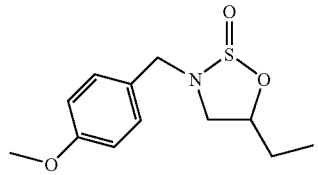

Thionyl chloride (21.1 mL, 0.29 mol) was added dropwise to a −78° C. solution of 1-(4-Methoxy-benzylamino)-butan-2-ol (32.75 g, 0.16 mol) and triethylamine (81.8 mL, 0.59 mol) in dry $CH_2Cl_2$. The resulting mixture was stirred at −78° C. for 40 minutes, then warmed to 0° C. for five hours. The reaction mixture was diluted with water and extracted with $CH_2Cl_2$. The organic layers were combined, dried over sodium sulphate, and concentrated in vacuo. The residue was purified by flash chromatography, using 11% acetone in hexanes as eluent, and gave 15.35 g (39%) of 5-ethyl-3-(4-methoxy-benzyl)-[1,2,3]oxathiazolidine 2-oxide. $^1$H NMR (400 MHz, $CDCl_3$) δ 7.28 (dd, 2H, J=8.5 Hz, 4.5 Hz), 6.87 (d, 2H, J=8.5 Hz), 5.02-4.96 (m, 1H), 4.54-4.47 (m, 1H), 4.24, 4.22 (ABq, 2H, J=5.9 Hz isomer 1), 3.91, 3.79 (ABq, 2H, J=13.3 Hz isomer 2), 3.79 s, 3H), 3.41, 3.39 (ABq, 1H, J=6.1 Hz isomer 1) 3.29, 3.27 (ABq, 1H, J=6.1 Hz isomer 2) 3.12, 3.10 (ABq, 1H, J=9.6 Hz isomer 1) 2.92, 2.90 (ABq, 1H, J=9.6 Hz isomer 2) 1.98-1.77 (m, 2H isomer 1), 1.76-1.57 (m, 2H isomer 2), 1.00 t, 3H, J=7.5 Hz, 0.94 t, 3H, J=7.5 Hz. $R_f$=0.31 in 33% acetone in hexanes.

Step C

5-Ethyl-3-(4-methoxy-benzyl)-[1,2,3]oxathiazolidine 2,2-dioxide

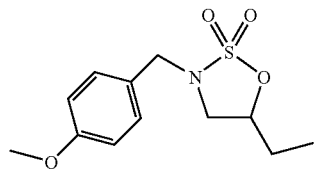

Ruthenium (III) chloride (0.27 g, 1.32 mmol) was added to a biphasic solution of 5-ethyl-3-(4-methoxy-benzyl)-[1,2,3] oxathiazolidine 2-oxide (15.35 g, 60.1 mmol), sodium periodate (25.7 g, 0.12 mol), $CCl_4$ (150 mL), $CH_3CN$ (150 mL), and water (180 mL). The resulting mixture was stirred at room temperature for three hours, and then filtered through a pad of celite. The filtrate was diluted with $CH_2Cl_2$ and washed with sodium thiosulphate solution and water. The residue was purified by flash chromatography, using 11% acetone in hexanes as eluent, and gave 14.33 g (88%) of 5-ethyl-3-(4-methoxy-benzyl)-[1,2,3]oxathiazolidine 2,2-dioxide. This material was resolved using chiral HPLC (Chiralpak OJ 4.6×150 nun, 30/70 alcohol/heptane, 0.6 mL/min, 240 nm UV setting) to give enantiomers: isomer 1, (>98% ee, R) and isomer 2, (>98% ee S). $^1$H NMR (400 MHz, $CDCl_3$) δ 7.27 (d, 2H, J=8.8 Hz), 6.88 (d, 2H, J=8.8 Hz), 4.69-4.62 (m, 1H), 4.23, 4.03 (ABq, 2H, J=13.4 Hz), 3.80 s, 3H), 3.35 (dd, 1H, J=9.5 Hz, 6.2 Hz) 3.03 (dd, 1H, J=9.5 Hz, 8.2 Hz) 1.92-1.81 (m, 1H), 1.75-1.65 (m, 1H), 0.98 t, 3H, J=7.5 Hz). $R_f$=0.31 in 33% acetone in hexanes.

Step D (4-{1-[(4-Methoxy-benzylamino)-methyl]-propylsulfanyl}-2-methyl-phenoxy)-acetic acid ethyl ester

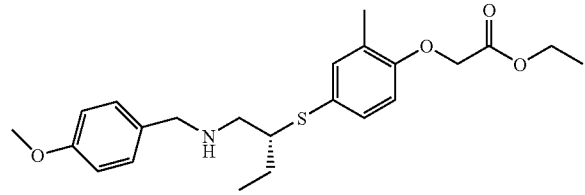

A 0° C. solution of (4-mercapto-2-methyl-phenoxy)-acetic acid ethyl ester (6.66 g, 29.43 mmol) in dimethylformamide (10 mL) was treated with sodium hydride (1.18 g, 29.43 mmol). The suspension was flushed with $N_2$ while stirring for 15 minutes at 0° C. 5-Ethyl-3-(4-methoxy-benzyl)-[1,2,3]oxathiazolidine 2,2-dioxide (5.32 g, 19.62 mmol) in dimethylformamide (10 mL) was added and the resulting mixture was heated at 50° C. for 4 h. The reaction mixture was cooled to ambient temperature, diluted with diethyl ether, and stirred with 1N HCl. After 8 h. the mixture was basified to pH7 with saturated aqueous sodium bicarbonate solution. The organic layer was washed with water and brine, dried over sodium sulphate, treated with trifluoroacetic acid (4.4 mL, 58.86 mmol), and concentrated in vacuo to provide 15.6 g (84%) of the title compound as a TFA salt. $^1$H NMR (400 MHz, CDCl$_3$) δ 7.20 (d, 2H, J=9.1 Hz), 6.95 (d, 1H, J=1.4 Hz), 6.87-6.84 (m, 1H), 6.85 (d, 2H, J=8.7 Hz), 6.43 (d, 1H, J=9.1 Hz), 4.55 (s, 2H), 4.20 (p, 2H, J=7.0 Hz), 4.20-4.06 (m, 2H), 3.74 (s, 3H0, 3.09-3.02 (m, 2H), 2.86-2.74 (m, 1H), 2.09 (s, 3H), 1.42 (p, 2H, J=7.0 Hz), 1.22 (t, 3H, J=7.0 Hz), 0.95 (t, 3H, J=7.0 Hz). MS [EI+] 418 (M+H)$^+$.

Step E (4-{1-[(5-Chloro-3-methyl-benzo[b]thiophene-2-sulfonylamino)-methyl]-propylsulfanyl}-2-methyl-phenoxy)-acetic acid ethyl ester

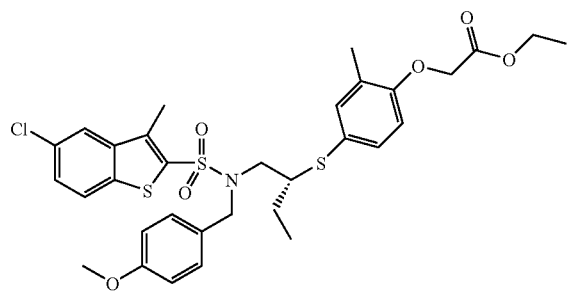

A 0° C. solution of (4-{1-[(4-methoxy-benzylamino)-methyl]-propylsulfanyl}-2-methyl-phenoxy)-acetic acid ethyl ester (9.43 g, 18.97 mmol) in dichloromethane (200 mL) was treated with triethylamine (21.2 mL, 151.76 mmol). Sulfonyl chloride (6.93 g, 24.6 mmol) was added all at once as a solid and the reaction mixture was warmed to ambient temperature for 1.5 h. The reaction mixture was diluted with dichloromethane and washed with 1N HCl. The organic layers were combined, dried over MgSO$_4$, and concentrated in vacuo. The crude material was purified by flash chromatography, using 11% acetone in hexanes, to provide 4.76 g (45%) of the title compound. $^1$H NMR (400 MHz, CDCl$_3$) δ 7.77 (d, 2H, J=1.7 Hz), 7.75 (d, 2H, J=8.7 Hz), 7.44 (dd, 1H, J=8.7 Hz, 1.7 Hz), 7.22 (dd, 1H, J=8.7 Hz, 2.1 Hz), 7.18-7.15 (m, 1H), 7.03 (d, 2H, J=8.7 Hz), 6.75 (d, 1H, J=8.7 Hz), 4.62 (s, 2H), 4.86, 4.08 (ABq, 2H, J=14.6 Hz), 4.27, 4.23 (ABq, 2H, J=6.9 Hz), 3.77 (s, 3H), 3.45, 3.43 (ABq, 1H, J=10.4 Hz), 3.17, 3.13 (ABq, 1H, J=5.0 Hz), 2.76-2.68 (m, 1H), 2.57 (s, 3H), 2.22 (s, 3H), 2.39 (t, 2H, J=5.0 Hz), 1.28 (td, 3H, J=7.3 Hz, 2.3 Hz), 0.86 (t, 3H, J=7.3 Hz). $R_f$=0.32 in 33% acetone in hexanes.

Step F

[4-(1-{[(5-Chloro-3-methyl-benzo[b]thiophene-2-sulfonyl)-propyl-amino]-methyl}-propylsulfanyl)-2-methyl-phenoxy]-acetic acid ethyl ester

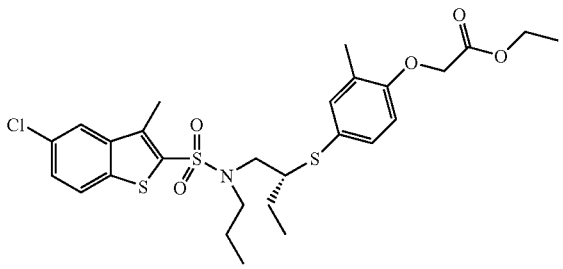

Trifluoroacetic acid (70 mL, 1 mmol) was added dropwise to a solution of (4-{1-[chloro-3-methyl-benzo[b]thiophene-2-sulfonylamino)-methyl]-propylsulfanyl}-2-methyl-phenoxy)-acetic acid ethyl ester and triethylsilane (23 mL, 144 mmol). The resulting solution was stirred at ambient temperature for 1 h, and then concentrated in vacuo. The reaction residue was diluted with diethyl ether and washed with saturated aqueous sodium bicarbonate and water. The organic layer was dried over sodium sulphate and concentrated in vacuo. $R_f$=0.27 in 33% acetone in hexanes.

1-Iodopropane (2.1 mL, 21.8 mmol) was added to a suspension of crude (4-{1-[(5-chloro-3-methyl-benzo[b]thiophene-2-sulfonylamino)-methyl]-propylsulfanyl}-2-methyl-phenoxy)-acetic acid ethyl ester and cesium carbonate (7.03 g, 21.8 mmol) in dimethylformamide (100 mL). The resulting mixture was heated to 50° C. for 2 h, then cooled to ambient temperature and diluted with diethyl ether. The organic layer was washed with 1N HCl, water, and brine, dried over MgSO$_4$, and concentrated in vacuo. The crude material was purified by trituration, using acetone and hexanes, to provide 2.16 g (53%) of the title compound. $R_f$=0.34 in 33% acetone in hexanes. $^1$H NMR (400 MHz, CDCl$_3$) δ7.77 (d, 1H, J=2.2 Hz), 7.73 (d, 1H J=8.6 Hz), 7.44 (dd, 1H, J=8.6 Hz, 2.2 Hz), 7.22 (d, 1H, J=1.4 Hz), 7.18 (dd, 1H, J=8.6 Hz, 2.9 Hz), 6.59 (d, 1H, J=8.6 Hz), 4.62 (s, 2H), 4.26 (q, 2H, J=7.2 Hz), 3.38 (dd, 1H, J=14.4 Hz, 9.4 Hz), 3.24 (dd, 1H, J=14.4 Hz, 5.8 Hz), 3.20-3.06 (m, 3H), 2.56 (s, 3H), 2.24 (s, 3H), 1.97-1.87 (m, 1H), 1.52-1.35 (m, 3H), 1.29 (t, 3H, J=7.2 Hz), 1.29 (t, 3H, J=7.2 Hz), 1.09 (t, 3H, J=7.2 Hz), 0.81 (t, 3H, J=7.2 Hz).

Step G

[4-(1-{[[(5-Chloro-3-methyl-benzo[b]thiophene-2-sulfonyl)-propyl-amino]-methyl}-propylsulfanyl)-2-methyl-phenoxy]-acetic acid A solution of [4-(1-{[(5-chloro-3-methyl-benzo[b]thiophene-2-sulfonyl)-propyl-amino]-methyl}-propylsulfanyl)-2-methyl-phenoxy]-acetic acid ethyl ester (2.16 g, 3.79 mmol) and 5N NaOH (2 mL) in ethanol (20 mL) was refluxed under nitrogen for 0.5 h, cooled to ambient temperature, and concentrated in vacuo. The residue was diluted with 1N HCl, extracted with $CH_2Cl_2$, dried over $Na_2SO_4$, and concentrated in vacuo to provide 2.08 g (99%) of the title compound. $^1$H NMR (400 MHz, CDCl$_3$) δ 7.74 (s, 1H), 7.71 (d, 1H, J=8.8 Hz, 1.5 Hz), 7.42 (d, 1H, J=8.8 Hz), 7.22 (s, 1H), 7.19 (d, 1H, J=8.8 Hz), 6.61 (d, 1H, J=8.8 Hz), 5.29 (d, 1H, J=2.2 Hz), 4.68 (s, 2H), 3.39 (dd, 1H, J=13.9 hz, 8.8 Hz), 3.25 (dd, 1H, J=15.4 Hz, 4.4 Hz), 3.20-3.07 (m, 3H), 2.57 (s, 3H), 2.22 (s, 3H), 1.96-1.86 (m, 1H), 1.53-1.35 (m, 3H), 1.09 (t, 3H, J=7.3 Hz), 0.81 (t, 3H, J=7.3 Hz). HRMS (ES+) m/z exact mass calculated for $C_{25}H_{31}NO_5S_3Cl$ 556.1053, found 556.1038.

EXAMPLE 21

(R)-[2-Methyl-4-(1-{[propyl-(4-trifluoromethoxy-benzenesulfonyl)-amino]-methyl}-propylsulfanyl)-phenoxy]-acetic acid

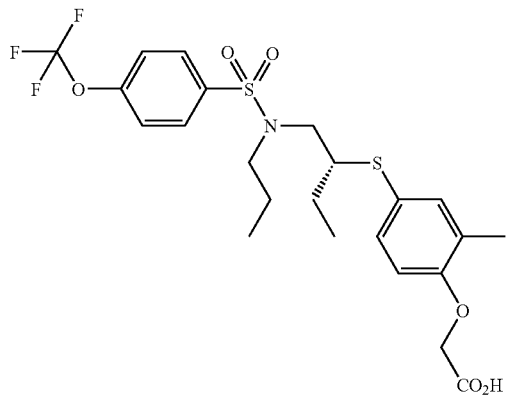

Step A

N-(2-hydroxy-butyl)-N-propyl-4-trifluoromethoxy-benzenesulfonamide

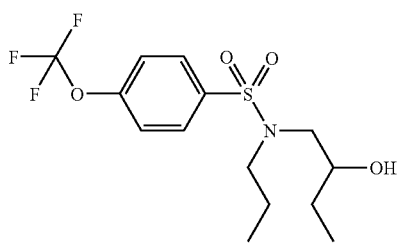

A 0° C. solution of 1-amino-2-butanol (3.57 g, 40.0 mmol) and triethylamine (7.38 g, 72.9 mmol) in $CH_2Cl_2$ (100 mL) was treated with 4-(trifluoromethoxy) benzenesulfonyl chloride (9.50 g, 36.5 mmol) and the reaction warmed to room temperature and stirred for 1 hour under $N_2$. The reaction was quenched with 1 N HCl (75 mL) and diluted with more $CH_2Cl_2$ and extracted with water. The organic layer was dried ($Na_2SO_4$) and the solvent was removed in vacuo to afford 11.86 g (100%) of crude N-(2-hydroxy-butyl)-4-trifluoromethoxy-benzenesulfonamide that was utilized without purification.

A solution of N-(2-hydroxy-butyl)-4-trifluoromethoxy-benzenesulfonamide (11.86 g, assume 36.5 mmol) and iodopropane (8.05 g, 47.4 mmol) in DMF (90 mL) was treated with cesium carbonate (15.44 g, 47.4 mmol) and the reaction mixture was stirred at room temperature for 17 hours under $N_2$. The reaction mixture was filtered using Et$_2$O to rinse the solids and the filtrate acidified with 1 N HCl (100 mL). The filtrate was diluted with more Et$_2$O and then extracted with water. The organic layer was dried ($Na_2SO_4$) and the solvent removed in vacuo to afford crude product that was absorbed on silica gel and then column purified using 5/1 hexanes/acetone to afford 11.25 g (87%). $R_f$=0.40 (1/1 hexanes/acetone). MS (ES$^+$) m/z mass calculated for $C_{14}H_{20}O_4F_3NS$ 355, found 356 (M+1, 100%).

Step B

N-(2-Bromo-butyl)-N-propyl-4-trifluoromethoxy-benzenesulfonamide

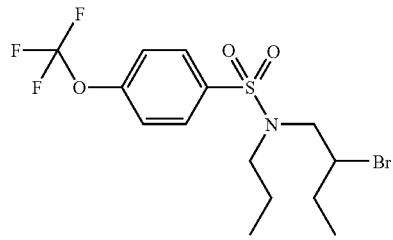

A solution of N-(2-hydroxy-butyl)-N-propyl-4-trifluoromethoxy-benzenesulfonamide (11.23 g, 31.6 mmol) in $CH_2Cl_2$ (100 mL) was treated with carbon tetrabromide (15.72, 47.4 mmol) and then triphenylphospine (12.43 g, 47.4 mmol). The reaction was stirred at room temperature under $N_2$ until the reaction was complete by TLC (2/1 hexanes/acetone). The solvent was removed in vacuo to afford crude product that was triturated in Et$_2$O and filtered to remove most of the triphenylphosphine oxide. The solvent was removed in vacuo give crude product that was absorbed oil silica gel and then column purified using 10/1 hexanes/acetone to afford 12.3 g (90%). $R_f$=0.41 (2/1 hexanes/acetone).

Step C

(R)-[2-Methyl-4-(1-{[propyl-(4-trifluoromethoxy-benzenesulfonyl)-amino]-methyl}-propylsulfanyl)-phenoxy]-acetic acid ethyl ester

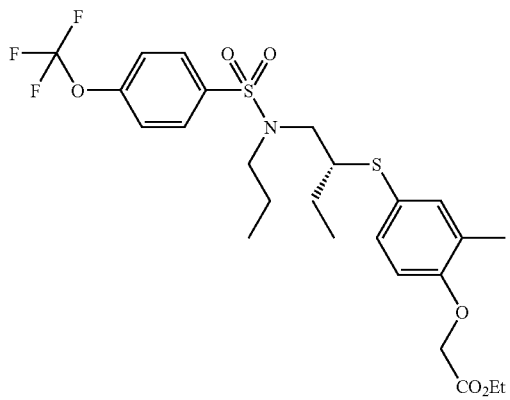

A solution of column purified (4-mercapto-2-methyl-phenoxy)-acetic acid ethyl ester (1.50 g, 6.62 mmol) in dry DMF (30 mL) was purged with $N_2$ and then 325 mesh $K_2CO_3$ (1.37 g, 9.91 mmol) was added and the resultant mixture purged with $N_2$ for 5 minutes more. A solution of (S)-N-(2-bromobutyl)-N-propyl-4-trifluoromethoxy-benzenesulfonamide (3.45 g, 8.25 mmol) in DMF (15 mL) was added dropwise to the reaction, which was stirred for 5 hours at room temperature under $N_2$. The reaction was acidified with 1 N HCl (20 mL), diluted with $Et_2O$ and then extracted twice with water. The organic layer was dried ($Na_2SO_4$) and the solvent was removed in vacuo to afford crude product that was absorbed on silica gel and then column purified using 8/1 hexanes/EtOAc to afford 3.1 g (73%) racemic. This material was resolved using preparative chiral HPLC (Chiralpak AD 8×34 cm, 95/5 heptane/EtOH, 375 ml/min, 230 nm UV setting) to give enantiomers (isomer 1, 99.3% ee, R; and isomer 2, 97.1% ee S). $R_f$ isomer 1/isomer 2=0.42 (2/1 hexanes/acetone). $^1$H NMR (400 MHz, $CDCl_3$); MS (ES$^+$) m/z mass calculated for $C_{25}H_{32}O_6F_3NS_2$ 563, found 564 (M+1, 100%).

Step D

(R)-[2-Methyl-4-(1-{[propyl-(4-trifluoromethoxy-benzenesulfonyl)-amino]-methyl}-propylsulfanyl)-phenoxy]-acetic acid A solution of (R)-[2-methyl-4-(1-{[propyl-(4-trifluoromethoxy-benzenesulfonyl)-amino]-methyl}-propylsulfanyl)-phenoxy]-acetic acid ethyl ester (1.40 g, 2.48 mmol) in EtOH (40 mL) was treated with 5 N NaOH (5 mL) and stirred at room temperature until saponification complete. The solvent was removed in vacuo to give a residue that was acidified with 1 N HCl and then diluted with EtOAc and extracted with water. The organic layer was dried ($Na_2SO_4$) and the solvent was removed in vacuo to afford 1.31 g (98%). $^1$H NMR (400 MHz, $CDCl_3$; HRMS (ES$^+$) m/z exact mass calculated for $C_{23}H_{28}O_6F_3NS_2Na$ 558.1200, found 558.1208.

EXAMPLE 22

(R)-(4-{2-[(5-Chloro-3-methyl-benzo[b]thiophene-2-sulfonyl)-propyl-amino]-1-methyl-ethylsulfanyl}-2-methyl-phenoxy)-acetic acid

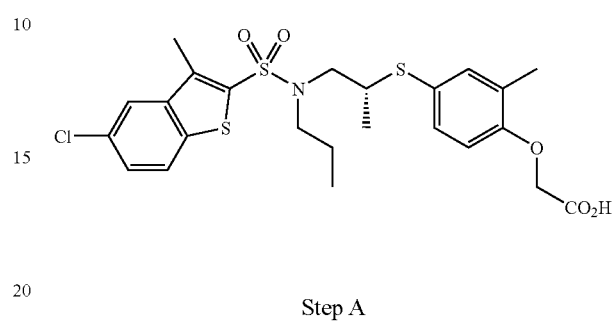

Step A

(S)-5-Chloro-3-methyl-benzo[b]thiophene-2-sulfonic acid (2-hydroxy-propyl)-propyl-amide

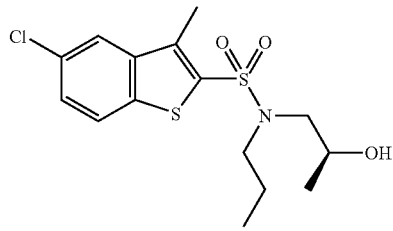

A 0° C. solution of (S)-(+)-1-amino-2-propanol (1.76 g, 23.4 mmol) and triethylamine (4.32 g, 42.7 mmol) in $CH_2Cl_2$ (100 mL) was treated with 5-chloro-3-methyl-benzo[b]thiophene-2-sulfonyl chloride (6.0 g, 21.3 mmol) and the reaction warmed to room temperature and stirred for 1 hour under $N_2$. The reaction was quenched with 1 N HCl (50 mL), diluted with more $CH_2Cl_2$ and extracted with water. The organic layer was dried ($Na_2SO_4$) and the solvent was removed in vacuo to afford 6.86 g (100%) of crude 5-chloro-3-methyl-benzo[b]thiophene-2-sulfonic acid (2-hydroxypropyl)-amide that was utilized without purification.

A solution of (S)-5-chloro-3-methyl-benzo[b]thiophene-2-sulfonic acid (2-hydroxy-propyl)-amide (6.86 g, assume 21.3 mmol) and iodopropane (4.72 g, 27.8 mmol) in DMF (90 mL) was treated with cesium carbonate (9.04 g, 27.7 mmol) and the reaction mixture was stirred at room temperature for 17 hours under $N_2$. The reaction mixture was filtered using $Et_2O$ to rinse the solids and the filtrate acidified with 1 N HCl (50 mL). The filtrate was diluted with more $Et_2O$ and then extracted with water. The organic layer was dried ($Na_2SO_4$) and the solvent removed in vacuo to afford crude product that was absorbed on silica gel and then column purified using 5/1 hexanes/acetone to afford 7.10 g (92%). $R_f$=0.44 (1/1 hexanes/acetone). $^1$H NMR (400 MHz, $CDCl_3$); MS (ES$^+$) m/z mass calculated for $C_{15}H_{20}O_3NS_2Cl$ 361, found 362 and 364 (M+1 and M+3, 100%).

Step B (S)-Methanesulfonic acid 2-[(5-chloro-3-methyl-benzo[b]thiophene-2-sulfonyl)-propyl-amino]-1-methyl-ethyl ester

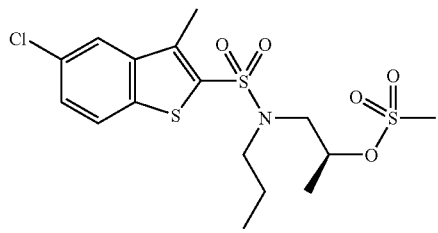

A 0° C. solution of 5-chloro-3-methyl-benzo[b]thiophene-2-sulfonic acid (2-hydroxy-propyl)-propyl-amide (7.10 g, 19.6 mmol) and triethylamine (3.0 g, 29.6 mmol) in $CH_2Cl_2$ (100 mL) was treated with methanesulfonyl chloride (2.69 g, 23.5 mmol) and the reaction stirred for 2 hours at 0° C. under $N_2$. The reaction was quenched with 1 N HCl (40 mL) and diluted with more $CH_2Cl_2$ and extracted with water. The organic layer was dried ($Na_2SO_4$) and the solvent removed in vacuo to afford 9.27 g (100%) that was utilized without purification. $R_f$=0.44 (1/1 hexanes/acetone). $^1$H NMR (400 MHz, $CDCl_3$); MS (ES$^+$) m/z mass calculated for $C_{16}H_{22}O_5NS_3Cl$ 439, found 440 and 442 (M+1 and M+3, 100%).

Step C (R)-(4-{2-[(5-Chloro-3-methyl-benzo[b]thiophene-2-sulfonyl)-propyl-amino]-1-methyl-ethylsulfanyl}-2-methyl-phenoxy)-acetic acid ethyl ester

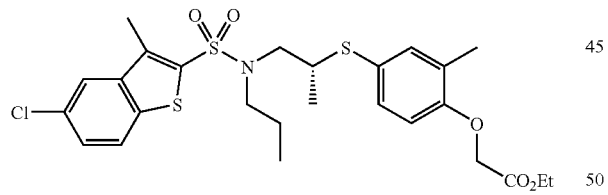

A solution of column purified (4-mercapto-2-methyl-phenoxy)-acetic acid ethyl ester (0.205 g, 0.906 mmol) in dry DMF (40 mL) was purged with $N_2$ and then 325 mesh $K_2CO_3$ (0.188 g, 1.36 mmol) was added and the resultant mixture purged with $N_2$ for 5 minutes more. A solution of (S)-methanesulfonic acid 2-[(5-chloro-3-methyl-benzo[b]thiophene-2-sulfonyl)-propyl-amino]-1-methyl-ethyl ester (0.478 g, 1.09 mmol) in DMF (2 mL) was added dropwise to the reaction, which was stirred for 17 hours at room temperature under $N_2$. The reaction was acidified with 1 N HCl (20 mL), diluted with $Et_2O$ and then extracted twice with water. The organic layer was dried ($Na_2SO_4$) and the solvent was removed in vacuo to afford crude product that was absorbed on silica gel and then column purified using 6/1 hexanes/EtOAc to afford 0.284 g (55%). $R_f$=0.38 (2/1 hexanes/EtOAc). $^1$H NMR (400 MHz, $CDCl_3$); MS (ES$^+$) m/z mass calculated for $C_{26}H_{32}O_5NClS_2$ 569, found 570 and 572 (M+1 and M+3, 100%).

Step D (R)-(4-{2-[(5-Chloro-3-methyl-benzo[b]thiophene-2-sulfonyl)propyl-amino]-1-methyl-ethylsulfanyl}-2-methyl-phenoxy)-acetic acid A solution of (R)-(4-{2-[(5-chloro-3-methyl-benzo[b]thiophene-2-sulfonyl)-propyl-amino]-1-methyl-ethylsulfanyl}-2-methyl-phenoxy)-acetic acid ethyl ester (0.284 g, 0.498 mmol) in EtOH (10 mL) was treated with 5 N NaOH (1 mL) and stirred at room temperature until saponification complete. The solvent was removed in vacuo to give a residue that was acidified with 1 N HCl and then diluted with EtOAc and extracted with water. The organic layer was dried ($Na_2SO_4$) and the solvent removed in vacuo to afford 0.281 g (100%). $^1$H NMR (400 MHz, $CDCl_3$); HRMS (ES$^+$) m/z exact mass calculated for $C_{24}H_{28}O_5NClS_2$ 541, found 542 and 544 (M+1 and M+3, 100%).

EXAMPLE 23

(R) and (S)-(4-{2-[(5-Chloro-3-methyl-benzo[b]thiophene-2-sulfonyl)-propyl-amino]-1-methyl-ethylsulfanyl}-2-methyl-phenoxy)-acetic acid

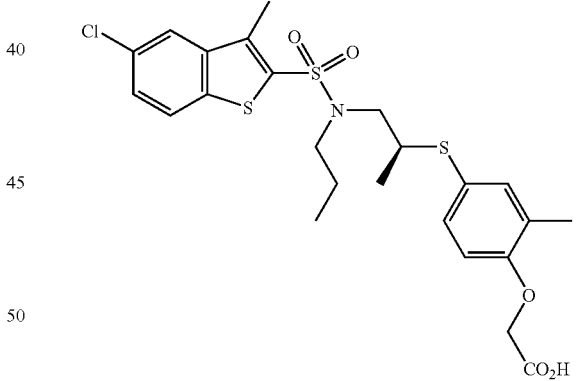

Racemic (4-{2-[(5-chloro-3-methyl-benzo[b]thiophene-2-sulfonyl)-propyl-amino]-1-methyl-ethylsulfanyl}-2-methyl-phenoxy)-acetic acid ethyl ester was prepared as described in Example 22 and was then resolved using preparative chiral HPLC (Chiralcel OD 8×34 cm, 90/10 heptane/IPA. 370 ml/min, 250 nm UV setting) to give enantiomers (0.155 g, isomer 1, 100% ee, R: and 0.176 g, isomer 2, 100% ee, S). These esters were saponified as described in Example 22, Step D to afford 0.136 g (93%, enantiomer 1) and 0.153 g (92%, enantiomer 2). $^1$H NMR (400 MHz, $CDCl_3$); HRMS (ES$^+$) m/z exact mass calcd for $C_{24}H_{28}O_5NClS_3Na$ 564.0716, found 564.0718.

EXAMPLE 24

(2-Methyl-4-{2-[(3-methyl-5-trifluoromethyl-benzo[b]thiophene-2-sulfonyl)-propyl-amino]-ethylsulfanyl}-phenoxy)-acetic acid

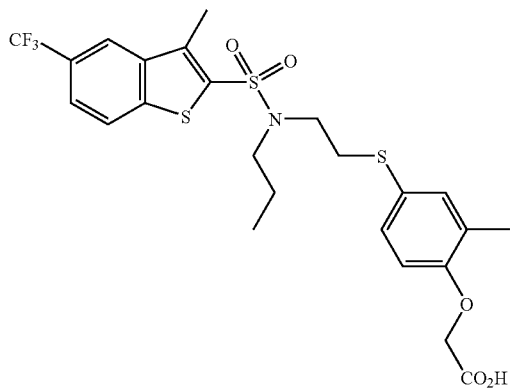

Step A (2-Hydroxy-ethyl)-propyl-carbamic acid tert-butyl ester

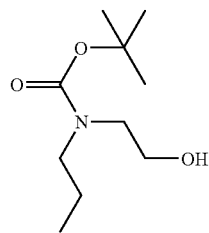

A 0° C. solution of 2-propylamino-ethanol (3.00 g, 29.1 mmol) and triethylamine (3.09 g, 30.5 mmol) in dry THF (60 mL) was treated dropwise with a solution of di-tert-butyl carbonate (6.66 g, 30.5 mmol) in THF (10 mL). The reaction was stirred and warmed to room temperature for 1.5 hours under $N_2$. The reaction was diluted with EtOAc and extracted with water. The organic layer was dried ($Na_2SO_4$) and the solvent was removed in vacuo to afford 6.11 g (100%) of crude product that was utilized without purification. $R_f$=0.46 (1/1 hexanes/acetone. CAM stain). $^1$H NMR (400 MHz, $CDCl_3$) δ 3.75-3.71 (m, 2H), 3.41, 3.37 (m, 2H), 3.18 (bt, 2H, J=6.85 Hz), 1.59-1.50 (m, 2H), 1.46 (s, 9H), 0.875 (t, 3H, J=7.33 Hz).

Step B

Methanesulfonic acid 2-(tert-butoxycarbonyl-propyl-amino)-ethyl ester

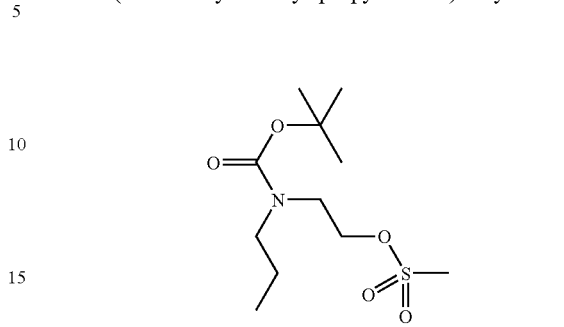

A 0° C. solution of (2-hydroxy-ethyl)-propyl-carbamic acid tert-butyl ester (3.0 g, 14.8 mmol) and triethylamine (2.40 g, 23.7 mmol) in $CH_2Cl_2$ (30 mL) was treated with methanesulfonyl chloride (2.22 g, 19.4 mmol) and the reaction stirred for 1.5 hours at 0° C. under $N_2$. The reaction was quenched with 1 N HCl (40 mL) and diluted with more $CH_2Cl_2$ and extracted with water. The organic layer was dried ($MgSO_4$) and the solvent was removed in vacuo to afford 4.11 g (99%) that was utilized without purification. $R_f$=0.58 (1/1 hexanes/acetone, CAM stain). $^1$H NMR (400 MHz, $CDCl_3$) δ 4.34-3.30 (m, 2H), 3.57-3.49 (m, 2H), 3.24-3.13 (m, 2H), 3.00 (s, 3H), 1.72-1.51 (m, 2H), 1.45 (s, 9H), 0.875 (t, 3H, J=7.58 Hz).

Step C ({4-[2-(tert-Butoxycarbonyl-propyl-amino)-ethylsulfanyl}-2-methyl-phenoxy]-acetic acid ethyl ester

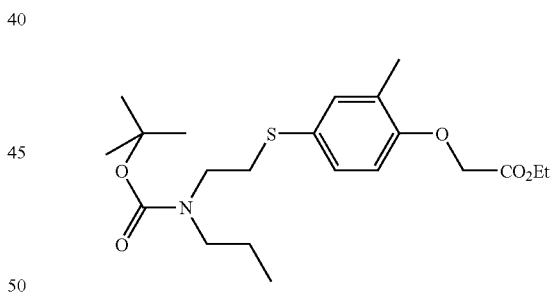

A solution of crude (4-mercapto-2-methyl-phenoxy)-acetic acid ethyl ester (3.95 g, 17.5 mmol) in dry DMF (35 mL) was purged with $N_2$ and then $Cs_2CO_3$ (7.12 g, 21.9 mmol) was added and the resultant mixture purged with $N_2$ for 5 minutes more. A solution of methanesulfonic acid 2-(tert-butoxycarbonyl-propyl-amino)-ethyl ester (4.10 g, 14.6 mmol) in DMF (5 mL) was added dropwise to the reaction and it was heated to 50° C. and stirred for 17 hours under $N_2$. The reaction was cooled and filtered using $Et_2O$ to rinse the solids. The filtrate was acidified with 1 N HCl (15 mL), diluted with $Et_2O$ and then extracted twice with water. The organic layer was dried ($Na_2SO_4$) and the solvent removed in vacuo to afford crude product that was absorbed on silica gel and then column purified using 6/1 hexanes/acetone to afford 3.25 g (54%). $R_f$=0.33 (2/1 hexanes/acetone).

Step D 1-(2-Methylsulfanyl-5-trifluoromethyl-phenyl)-ethanone

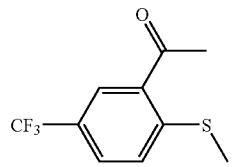

A solution of 2-fluoro-5-trifluoromethyl acetophenone (3.0 g, 14.5 mmol) in dry DMF (20 mL) was treated with sodium thiomethoxide (1.22 g, 17.4 mmol) and the reaction was stirred for 2 hours at room temperature under $N_2$. The reaction was quenched with 1 N HCl (10 mL), diluted with $Et_2O$ and then extracted twice with water. The organic layer was dried ($Na_2SO_4$) and the solvent removed in vacuo to afford crude product that was absorbed on silica gel and then column purified using 5/1 hexanes/acetone to afford 2.88 g (850%). $R_f$=0.57 (1/1 hexanes/acetone). $^1$H NMR (400 MHz, $CDCl_3$) δ 8.05 (s, 1H), 7.69 (d, 1H, J=8.31 Hz), 7.42 (d, 1H, J=8.80 Hz), 2.68 (s, 3H), 2.48 (s, 3H).

Step E

3-Methyl-5-trifluoromethyl-benzo[b]thiophene-2-carboxylic acid

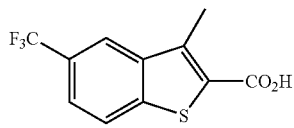

A mixture of 1-(2-methylsulfanyl-5-trifluoromethyl-phenyl)-ethanone (2.06 g, 8.79 mmol) and bromoacetic acid (7.33 g, 52.8 mmol) in acetic acid (20 mL) was heated to reflux and stirred for 20 hours under N. The reaction was cooled and water was added to form a slurry. The slurry was filtered and the solids rinsed with water to afford 1.59 g (69%) of the title compound after drying in a vacuum oven at 45° C. $R_f$=0.18 (1/1 hexanes/acetone). $^1$H NMR (400 MHz. $CDCl_3$). MS ($ES^+$) m/z mass calculated for $C_{11}H_7O_2SF_3$ 260, found 259 (M−1, 100%).

Step F

3-Methyl-5-trifluoromethyl-benzo[b]thiophene

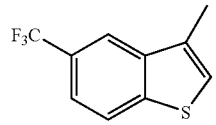

A mixture of 3-methyl-5-trifluoromethyl-benzo[b]thiophene-2-carboxylic acid (0.80 g, 3.07 mmol) and copper powder (0.164 g, 2.58 mmol) in quinoline (14 mL) was placed in a 200° C. oil bath and stirred for 20 minutes under $N_2$. The reaction was cooled, diluted with $CH_2Cl_2$ and filtered through hyflo. The filtrate was extracted twice with 1 N HCl (100 mL) then water. The organic layer was dried ($Na_2SO_4$) and the solvent was removed in vacuo to afford crude product that was column purified using 100% hexanes to afford 0.575 g (86%). $R_f$=0.62 (2/1 hexanes/acetone). $^1$H NMR (400 MHz, $CDCl_3$).

Step G

3-Methyl-5-trifluoromethyl-benzo[b]thiophene-2-sulfonyl chloride

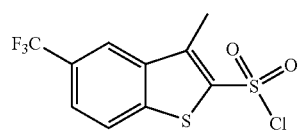

A 0° C. solution of 3-methyl-5-trifluoromethyl-benzo[b]thiophene (0.558 g, 2.58 mmol) in $CH_2Cl_2$ (4 mL) was treated dropwise with chlorosulfonic acid (0.894 g, 7.67 mmol) in $CH_2Cl_2$ (4 mL). The reaction was warmed to room temperature and stirred for 1.5 hours under $N_2$. The reaction was poured into ice water and the mixture extracted with $Et_2O$. The aqueous layer was re-extracted with $CH_2Cl_2$ and the combined organic layers were dried ($Na_2SO_4$) and the solvent was removed in vacuo to afford 0.22 g (27%) as a gray solid that was utilized without purification. $R_f$=0.46 (2/1 hexanes/acetone).

Step H (2-Methyl-4-{2-[(3-methyl-5-trifluoromethyl-benzo[b]thiophene-2-sulfonyl)-propyl-amino]-ethylsulfanyl}-phenoxy)-acetic acid ethyl ester

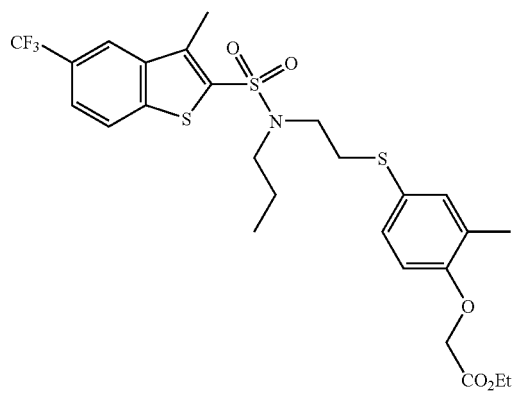

A 0° C. solution of ({4-[2-(tert-butoxycarbonyl-propyl-amino)-ethylsulfanyl]-2-methyl-phenoxy}-acetic acid ethyl ester (0.11 g, 0.266 mmol) and dimethylethyl silane (0.071 g, 0.805 mmol) in dry $CH_2Cl_2$ (3 mL) was treated with trifluoroacetic acid (0.5 mL) and warmed to room temperature and stirred for 1.5 hours under $N_2$. The solvent was removed in vacuo to afford the trifluoroacetic acid salt of [2-methyl-4-(2-propylamino-ethylsulfanyl)-phenoxy]-acetic acid ethyl ester, which was carried on without purification.

The [2-methyl-4-(2-propylamino-ethylsulfanyl)-phenoxy]-acetic acid ethyl ester-TFA salt was re-dissolved in $CH_2Cl$, (5 mL) and cooled to 0° C. Triethylamine (0.162 g, 1.60 mmol) was added dropwise to the reaction and then a solution of 3-methyl-5-trifluoromethyl-benzo[b]thiophene- 2-sulfonyl chloride (0.084 g, 0.266 mmol) in $CH_2Cl_2$ (3 mL) was added. The reaction was warmed to room temperature and stirred for 1 hour under $N_2$. The reaction was acidified with 1 N HCl (10 mL), diluted with $CH_2Cl_2$ and then extracted with water. The organic layer was dried ($Na_2SO_4$) and the solvent was removed in vacuo to afford crude product that was absorbed on silica gel and then column purified using 6/1 hexanes/acetone to afford 0.113 g (72%). $R_f$=0.18 (2/1 hexanes/acetone). $^1$H NMR (400 MHz, $CDCl_3$); MS ($ES^+$) 177/mass calculated for $C_{26}H_{30}O_5NS_3F_3$ 589, found 590 (M+1, 100%).

Step I (2-Methyl-4-{2-[(3-methyl-5-trifluoromethyl-benzo[b]thiophene-2-sulfonyl)-propyl-amino]-ethylsulfanyl}-phenoxy)-acetic acid A 0° C. solution of (2-methyl-4-{2-[(3-methyl-5-trifluoromethyl-benzo[b]thiophene-2-sulfonyl)-propyl-amino]-ethylsulfanyl}-phenoxy)-acetic acid ethyl ester (0.113 g, 0.192 mmol) in THF (6 mL) was treated with 1 N LiOH (0.57 mL) and stirred at room temperature until saponification complete. The mixture was acidified with 1 N HCl and then diluted with EtOAc and extracted with water. The organic layer was dried ($Na_2SO_4$) and the solvent was removed in vacuo to afford 0.079 g (73%). $^1$H NMR (400 MHz, $CDCl_3$); MS ($ES^+$) m/z mass calculated for $C_{24}H_{26}O_5NS_3F_3$ 561, found 562 (M+1, 100%).

EXAMPLE 25

(2-Methyl-4-{2-[propyl-(4-trifluoromethyl-benzenesulfonyl)-amino]-ethylsulfanyl-}-phenoxy)-acetic acid

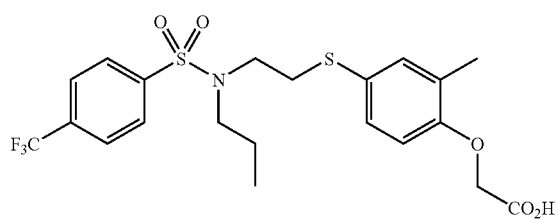

Step A ((2-Methyl-4-{2-[propyl-(4-trifluoromethylbenzenesulfonyl)-amino]-ethylsulfanyl}-phenoxy)acetic acid ethyl ester

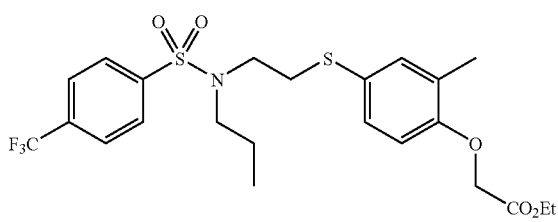

Procedure from Example 24, Step H was utilized with 4-trifluoromethyl-benzenesulfonyl chloride to afford 0.132 g (80%). $R_f$=0.34 (2/1 hexanes/acetone). $^1$H NMR (400 MHz, $CDCl_3$), MS ($ES^+$) m/z mass calculated for $C_{23}H_{28}O_5NS_2F_3$ 519, found 520 (M+1, 100%).

Step B (2-Methyl-4-{2-[propyl-(4-trifluoromethyl-benzenesulfonyl)-amino]-ethylsulfanyl}-phenoxy)-acetic acid Procedure from Example 24, Step 1 was utilized with ((2-methyl-4-{2-[propyl-(4-trifluoromethylbenzenesulfonyl-amino]-ethylsulfanyl}-phenoxy)-acetic acid ethyl ester to afford 0.094 g (76%) of the title compound. $^1$H NMR (400 MHz, $CDCl_3$); HRMS ($ES^+$) m/z exact mass calculated for $C_{21}H_{24}O_5NS_2F_3Na$ 514.0946, found 514.0928.

EXAMPLE 26

((4-{2-[(4-Chloro-benzenesulfonyl)-propyl-amino]-ethylsulfanyl}-2-methyl-phenoxy)-acetic acid

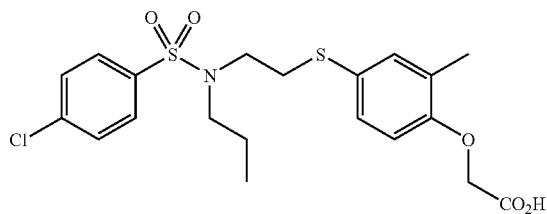

Procedure from Example 25 was utilized with 4-chloro-benzenesulfonyl chloride to afford 0.80 g (89%) of the title compound. $^1$H NMR (400 MHz, $CDCl_3$); HRMS ($ES^+$) m/z exact mass calculated for $C_{20}H_{24}O_5NS_2ClNa$ 480.0682, found 480.0683.

EXAMPLE 27

(4-{2-[(4-Methoxy-benzenesulfonyl)-propyl-amino]-ethylsulfanyl}-2-methyl-phenoxy)-acetic acid

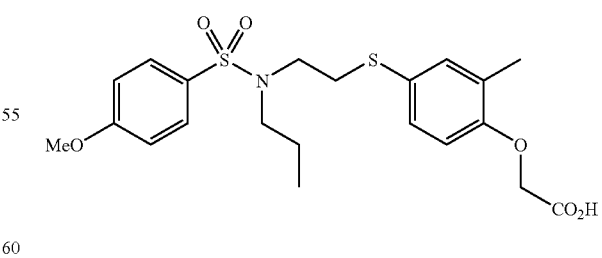

Procedure from Example 25 was utilized with 4-methoxy-benzenesulfonyl chloride to afford 0.105 g acid that was purified by preparative HPLC to afford 0.027 g (22%) of the title compound. $^1$H NMR (400 MHz. $CDCl_3$); MS ($ES^+$) m/z mass calculated for $C_{21}H_{27}O_6NS$, 453, found 454 (M+1, 100%).

EXAMPLE 28

(2-Methyl-4-{2-[propyl-(toluene-4-sulfonyl)-amino]-ethylsulfanyl}-phenoxy)-acetic acid

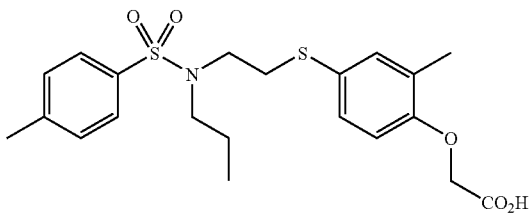

Procedure from Example 25 was utilized with 4-methyl-benzenesulfonyl chloride to afford 0.139 g acid that was purified by preparative HPLC to afford 0.040 g (34%) of the title compound. $^1$H NMR (400 MHz, CDCl$_3$); MS (ES$^+$) m/z mass calculated for $C_{21}H_{27}O_5NS_2$ 437, found 438 (M+1, 100%).

EXAMPLE 29

(4-{2-[(4-Fluoro-benzenesulfonyl)-propyl-amino]-ethylsulfanyl}-2-methyl-phenoxy)-acetic acid

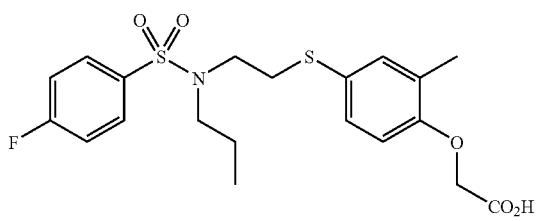

Procedure from Example 25 was utilized with 4-fluoro-benzenesulfonyl chloride to afford 0.146 g acid that was purified by preparative HPLC to afford 0.045 g (38%) of the title compound. $^1$H NMR (400 MHz, CDCl$_3$); MS (ES$^+$) m/z mass calculated for $C_{20}H_{24}O_5NS_2$ 441, found 442 (M+1, 100%).

EXAMPLE 30

(4-{2-[(4-Ethyl-benzenesulfonyl)-propyl-amino]-ethylsulfanyl}-2-methyl-phenoxy)-acetic acid

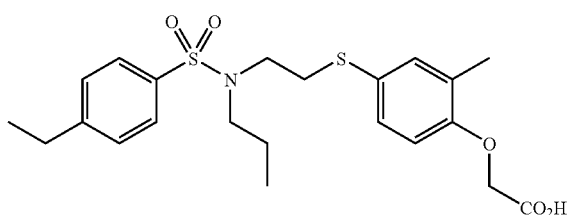

Procedure from Example 25 was utilized with 4-ethyl-benzenesulfonyl chloride to afford 0.086 g acid that was purified by preparative HPLC to afford 0.058 g (48%) of the title compound. $^1$H NMR (400 MHz, CDCl$_3$); MS (ES$^+$) m/z mass calculated for $C_{22}H_{30}O_5NS_2$ 452.1565, found 452.179.

EXAMPLE 31

(4-{2-[(2-Bromo-4-trifluoromethoxy-benzenesulfonyl)-propyl-amino]-ethylsulfanyl}-2-methyl-phenoxy)-acetic acid

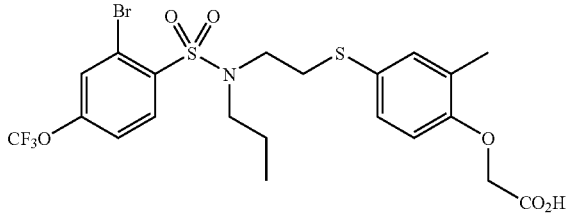

Step A

2-Bromo-4-trifluoromethoxy-benzenesulfonyl chloride

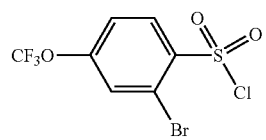

Chlorosulfonic acid (8 mL) was cooled to 0° C. and was treated with 1-bromo-3-(trifluoromethoxy)benzene (5.0 g, 20.7 mmol). The resultant mixture was stirred for 10 minutes at 0° C. and then warmed to room temperature and stirred for 1 hour under N$_2$. The reaction mixture was poured into ice water and then extracted twice with CH$_2$Cl$_2$. The organic layer was dried (MgSO$_4$) and the solvent was removed in vacuo to afford 2.69 g (38%) that was utilized without further purification. R$_f$=0.53 (2/1 hexanes/acetone).

Step B (4-{2-[(2-Bromo-4-trifluoromethoxy-benzenesulfonyl)-propyl-amino]-ethylsulfanyl}-2-methyl-phenoxy)-acetic acid ethyl ester

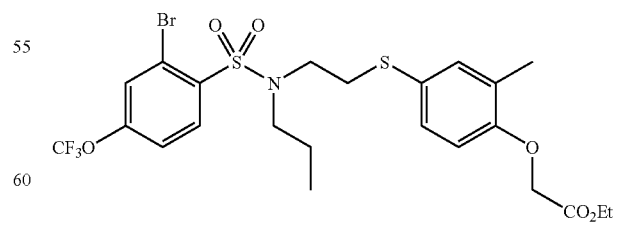

Procedure from Example 24, Step H was utilized with 2-bromo-4-trifluoromethoxy-benzenesulfonyl chloride to afford 0.65 g (87%) of the title compound. R$_f$=0.31 (2/1 hexanes/acetone). $^1$H NMR (400 MHz, CDCl$_3$); MS (ES$^+$)

m/z mass calculated for $C_{23}H_{27}O_6NS_2F_3Br$ 613, found 614 and 616 (M+1 and M+3, 100%).

Step C (4-{2-[(2-Bromo-4-trifluoromethoxy-benzenesulfonyl)-propyl-amino]-ethylsulfanyl}-2-methyl-phenoxy)-acetic acid A solution of (4-{2-[(2-bromo-4-trifluoromethoxy-benzenesulfonyl)-propyl-amino]-ethylsulfanyl-}-2-methyl-phenoxy)-acetic acid ethyl ester (0.056 g, 0.091 mmol) in EtOH (6 mL) was treated with 5 N NaOH (0.5 mL) and was stirred at room temperature for 3 hours. The solvent was removed in vacuo to give a residue that was acidified with 1 N HCl (10 mL), diluted with ethyl acetate and extracted with water. The organic layer was dried ($Na_2SO_4$) and the solvent removed in vacuo to afford 0.072 g of crude acid that was purified by preparative HPLC to afford 0.042 g (79%). $^1$H NMR (400 MHz, $CDCl_3$); HRMS (ES$^+$) m/z exact mass calculated for $C_{21}H_{24}NO_6S_2F_3Br$ 586.0181, found 586.0164.

EXAMPLE 32

((2-Methyl-4-{2-[(2-methyl-4-trifluoromethoxy-benzenesulfonyl)-propyl-amino]-ethylsulfanyl}-phenoxy)-acetic acid

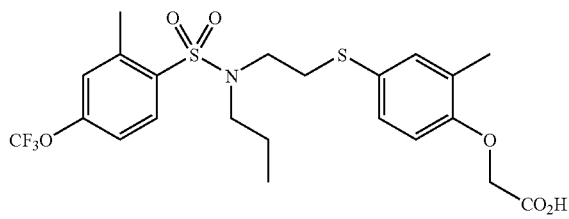

Step A (2-Methyl-4-{2-[(2-methyl-4-trifluoromethoxy-benzenesulfonyl)-propyl-amino]-ethylsulfanyl}-phenoxy)-acetic acid ethyl ester

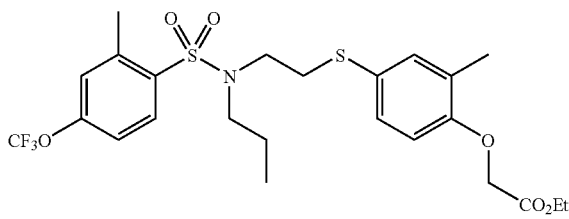

The compound of (4-{2-[(2-bromo-4-trifluoromethoxy-benzenesulfonyl)-propyl-amino]-ethylsulfanyl}-2-methyl-phenoxy)-acetic acid ethyl ester (Example 31, Step B) (0.100 g, 0.163 mmol), methyl boronic acid (0.029 g, 0.484 mmol) and cesium fluoride (0.087 g, 0.573 mmol) were combined in 1,4-dioxane (3 mL) and purged with $N_2$. The reaction was treated with 1,1'-bis(diphenylphosphino)ferrocene palladium (II)chloride, $CH_2Cl_2$ complex (0.018 g, 0.025 mmol) and heated in an oil bath at 80° C. for 2 hours under $N_2$. The reaction was cooled and the solvent was removed in vacuo to afford crude product that was absorbed on silica eel and column purified using 6/1 hexanes/acetone to afford 0.080 g (91%). $R_f$=0.22 (2/1 hexanes/acetone). $^1$H NMR (400 MHz, $CDCl_3$); MS (ES$^+$) m/z mass calculated for $C_{24}H_{30}O_6NS_2F_3$ 549, found 550 (M+1, 100%).

Step B ((2-Methyl-4-{2-[(2-methyl-4-trifluoromethoxy-benzenesulfonyl)-propyl-amino]-ethylsulfanyl}-phenoxy)-acetic acid A solution of (2-methyl-4-{2-[(2-methyl-4-trifluoromethoxy-benzenesulfonyl)-propyl-amino]-ethylsulfanyl}-phenoxy)-acetic acid ethyl ester (0.080 g, 0.156 mmol) in EtOH (6 mL) was treated with 5 N NaOH (0.5 mL) and was stirred at room temperature for 3 hours. The solvent was removed in vacuo to give a residue that was acidified with 1 N HCl (10 mL) and then diluted with ethyl acetate and extracted with water. The organic layer was dried ($Na_2SO_4$) and the solvent was removed in vacuo to afford 0.053 g of crude acid that was purified by preparative HPLC to afford 0.048 g (63%). $^1$H NMR (400 MHz, $CDCl_3$); HRMS (ES$^+$) m/z exact mass calculated for $C_{22}H_{27}NO_6S_2F_3$ 522.1232, found 522.1252.

EXAMPLE 33

(4-{2-[(2-Butyl-4-trifluoromethoxy-benzenesulfonyl)-propyl-amino]-ethylsulfanyl}-2-methyl-phenoxy)-acetic acid

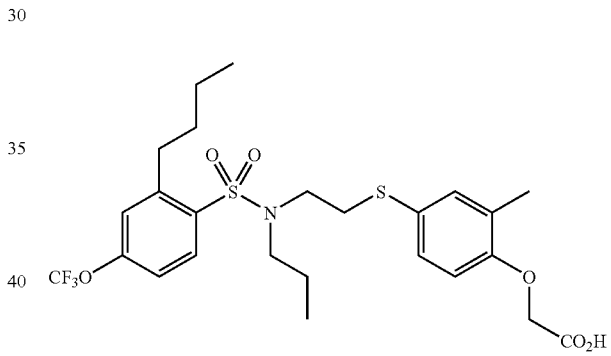

The compound of (4-{2-[(2-bromo-4-trifluoromethoxy-benzenesulfonyl)-propyl-amino]-ethylsulfanyl}-2-methyl-phenoxy)-acetic acid ethyl ester (Example 31, Step B) (0.126 g, 0.205 mmol), butyl boronic acid (0.063 g, 0.618 mmol) and cesium fluoride (0.109 g, 0.718 mmol) were combined in 1,4-dioxane (4 mL) and purged with $N_2$. The reaction was treated with 1,1'-bis(diphenylphosphino)ferrocene palladium (II)chloride, $CH_2Cl_2$ complex (0.023 g, 0.031 mmol) and heated in an oil bath at 80° C. for 4 hours under $N_2$. The reaction was cooled and the solvent removed in vacuo to afford 0.172 g (assume 0.205 mmol) of crude (4-{2-[(2-butyl-4-trifluoromethoxy-benzenesulfonyl)-propyl-amino]-ethylsulfanyl}-2-methyl-phenoxy)-acetic acid ethyl ester that was dissolved in EtOH (6 mL) and treated with 5 N NaOH (0.5 mL). The reaction mixture was stirred at room temperature for 3 hours. The solvent was removed in vacuo to give a residue that was acidified with 1 N HCl (10 mL) and then diluted with ethyl acetate and extracted with water. The organic layer was dried ($Na_2SO_4$) and the solvent was removed in vacuo to afford 0.133 g of crude acid that was purified by preparative HPLC to afford 0.011 g (9%). $^1$H NMR (400 MHz, $CDCl_3$); MS (ES$^+$) m/z mass calculated for $C_{25}H_{32}NO_6S_2F_3$ 563, found 564 (M+1, 100%).

EXAMPLE 34

[4-(2-Chloro-ethylsulfanyl)-2-methyl-phenoxy]-acetic acid ethyl ester

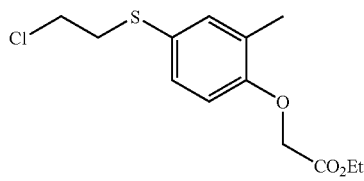

A solution of crude (4-mercapto-2-methyl-phenoxy)-acetic acid ethyl ester (1.64 g, 7.25 mmol) in dry DMF (20 mL) was purged with $N_2$ and then 325 mesh $K_2CO_3$ (1.50 g, 10.9 mmol) was added and the resultant mixture purged with $N_2$ for 5 minutes more. 1-Bromo-2-chloroethane (3.11 g, 21.7 mmol) was added dropwise to the reaction, which was stirred for 17 hours at room temperature under $N_2$. The reaction was acidified with 1 N HCl (20 mL), diluted with $Et_2O$ and then extracted twice with water. The organic layer was dried ($Na_2SO_4$) and the solvent was removed in vacuo to afford 1.60 g (77%) that was utilized without further purification. $R_f$=0.60 (1/1 hexanes/acetone). $^1$H NMR (400 MHz, $CDCl_3$); MS ($ES^+$) m/z mass calculated for $C_{13}H_{17}O_3ClS$ 288, found 289 and 291 (M+1 and M+3, 100%).

EXAMPLE 35

(2-Methyl-4-{2-[(naphthalene-1-sulfonyl)-propyl-amino]-ethylsulfanyl}-phenoxy)-acetic acid

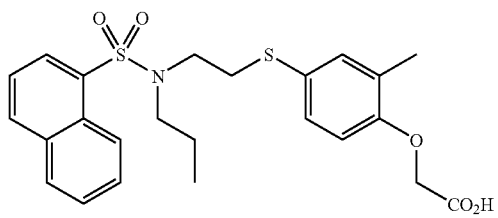

Step A

Naphthalene-1-sulfonic acid propylamide

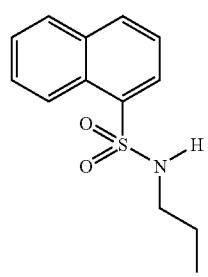

A solution of propyl amine (0.051 g, 0.862 mmol) and triethylamine (0.134 g, 1.32 mmol) in $CH_2Cl_2$ (6 mL) was treated with naphthalene-1-sulfonyl chloride (0.150 g, 0.660 mmol) and stirred overnight at room temperature under $N_2$. The reaction mixture was gravity filtered through a Varian Extube Extraction Column (ChemElut 1005) that bad been pre-treated with 4 mL 1 N HCl. The extraction column was washed with $CH_2Cl_2$ (4×), and the solvent was removed from the filtrate in vacuo to afford 0.157 g (95%) that was utilized without further purification. $R_f$=0.47 (1/1 hexanes/acetone). $^1$H NMR (400 MHz, $CDCl_3$); MS ($ES^+$) m/z mass calculated for $C_{13}H_{15}O_2NS$ 249, found 250 (M+1, 100%).

Step B (2-Methyl-4-{2-[(naphthalene-1-sulfonyl)-propyl-amino]-ethylsulfanyl}-phenoxy)-acetic acid A mixture of [4-(2-chloro-ethylsulfanyl)-2-methyl-phenoxy]-acetic acid ethyl ester (0.097 g, 0.334 mmol), naphthalene-1-sulfonic acid propyl amide (0.084 g. 0.337 mmol) and $Cs_2CO_3$ (0.143 g, 0.439 mmol) in DMF (5 mL) was stirred for 18 hours at 60° C. The reaction was cooled to room temperature and treated with 5 N NaOH (1.5 mL) and stirred for 2 hours at room temperature. The reaction was acidified with 1 N HCl (20 mL), diluted with $Et_2O$ and then extracted with water. The organic layer was dried ($Na_2SO_4$) and the solvent was removed in vacuo to afford 0.237 g crude product that was purified by preparative HPLC to afford 0.013 g (8%) of the title compound. $^1$H NMR (400 MHz, $CDCl_3$); HRMS ($ES^+$) m/z exact mass calculated for $C_{24}H_{28}O_5NS_2$ 474.1409, found 474.1412.

EXAMPLE 36

(4-{2-[(5-Chloro-naphthalene-2-sulfonyl)-propyl-amino]-ethylsulfanyl}-2-methyl-phenoxy)-acetic acid

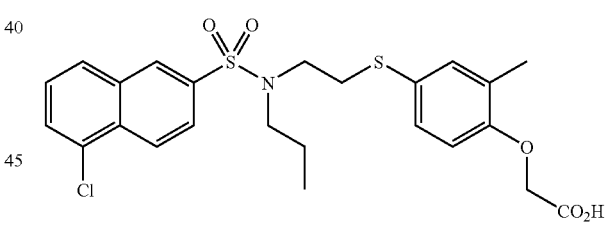

Step A

5-Chloro-naphthalene-2-sulfonic acid propylamide

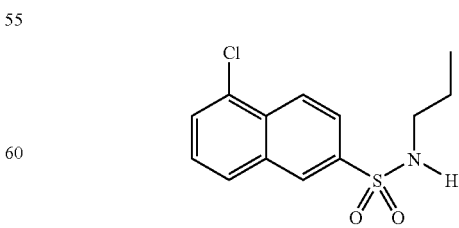

Procedure from Example 35. Step A was utilized with 5-chloro-naphthalene-2-sulfonyl chloride to afford 0.160 g (98%) that was utilized without further purification. $R_f$=0.53

(1/1 hexanes/acetone). $^1$H NMR (400 MHz, CDCl$_3$); MS (ES$^+$) m/z mass calcd for C$_{13}$H$_{14}$O$_2$NClS 283, found 284 and 286 (M+1 and M+3, 100%).

Step B (4-{2-[(5-Chloro-naphthalene-2-sulfonyl)-propyl-amino]-ethylsulfanyl}-2-methyl-phenoxy)-acetic acid Procedure from Example 35, Step B was utilized to afford 0.009 g (7%) of the title compound. $^1$H NMR (400 MHz, CDCl$_3$); HRMS (ES$^+$) m/z exact mass calculated for C$_{24}$H$_{27}$O$_5$NS$_2$Cl 508.1019, found 508.1000.

EXAMPLE 37

(2-Methyl-4-{2-[propyl-(4-trifluoromethoxybenzenesulfonyl)-amino]-ethylsulfanyl}-phenoxy)-acetic acid

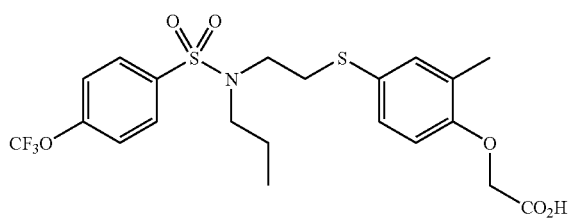

Step A

N-Propyl-4-trifluoromethoxy-benzenesulfonamide

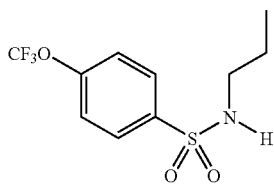

Procedure from Example 35, Step A was utilized with 4-trifluoromethoxy-benzenesulfonyl chloride to afford 0.154 g (94%) that was utilized without further purification. R$_f$=0.53 (1/1 hexanes/acetone). $^1$H NMR (400 MHz, CDCl$_3$); MS (ES$^+$) m/z mass calcd for C$_{10}$H$_{12}$O$_3$NSF$_3$ 283, found 284 (M+1, 100%).

Step B (2-Methyl-4-{2-[propyl-(4-trifluoromethoxybenzenesulfonyl)-amino]-ethylsulfanyl}-phenoxy)-acetic acid Procedure from Example 35, Step B was utilized to afford 0.008 g (6%) of the title compound. $^1$H NMR (400 MHz, CDCl$_3$); HRMS (ES$^4$) m/z exact mass calculated for C$_{21}$H$_{25}$O$_6$NS$_2$F, 508.1075, found 508.1100.

EXAMPLE 38

{4-[2-(Benzenesulfonyl-propyl-amino)-ethylsulfanyl]-2-methyl-phenoxy}-acetic acid

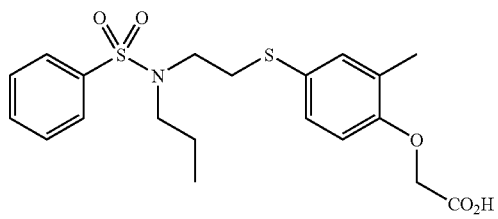

Step A

N-Propyl-benzenesulfonamide

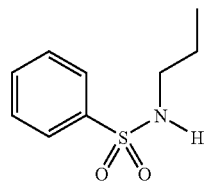

Procedure from Example 35, Step A was utilized with benzenesulfonyl chloride to afford 0.169 g (100%) that was utilized without further purification. R$_f$=0.48 (1/1 hexanes/acetone). $^1$H NMR (400 MHz, CDCl$_3$); MS (ES$^+$) m/z mass calculated for C$_9$H$_{13}$O$_2$NS 199, found 200 (M+1, 100%).

Step B

{4-[2-(Benzenesulfonyl-propyl-amino)-ethylsulfanyl]-2-methyl-phenoxy}-acetic acid Procedure from example 15, Step B utilized to afford 0.008 g (4%) of the title compound. $^1$H NMR (400 MHz, CDCl$_3$); HRMS (ES$^+$) m/z exact mass calculated for C$_{20}$H$_{26}$O$_5$S$_2$ 424.1252, found 424.1241.

EXAMPLE 39

(2-Methyl-4-{2-[propyl-(toluene-2-sulfonyl)-amino]-ethylsulfanyl}-phenoxy)-acetic acid

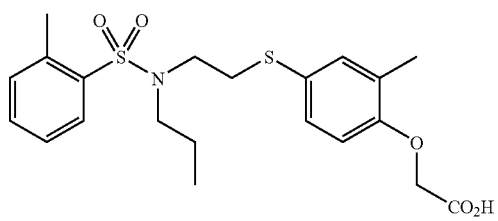

Step A

2-Methyl-N-propyl-benzenesulfonamide

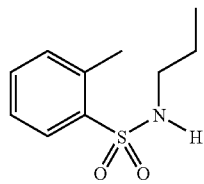

Procedure from Example 35, Step A was utilized with 2-methyl benzenesulfonyl chloride to afford 0.167 g (100%) that was utilized without further purification. $R_f$=0.48 (1/1 hexanes/acetone). $^1$H NMR (400 MHz, CDCl$_3$); MS (ES$^+$) m/z mass calcd for C$_{10}$H$_{15}$O$_2$NS 213, found 214 (M+1, 100%).

Step B

(2-Methyl-4-{2-[propyl-(toluene-2-sulfonyl)-amino]-ethylsulfanyl}-phenoxy)-acetic acid Procedure from Example 35, Step B utilized to afford 0.011 g (6%) of the title compound. $^1$H NMR (400 MHz, CDCl$_3$); HRMS (ES$^+$) m/z exact mass calculated for C$_{21}$H$_{28}$O$_5$NS$_2$ 438.1409, found 438.1427.

EXAMPLE 40

(2-Methyl-4-{2-[propyl-(2-trifluoromethyl-benzene-sulfonyl)-amino]-ethylsulfanyl}-phenoxy)-acetic acid

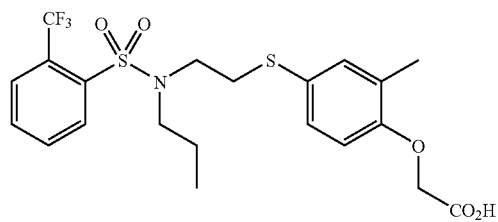

Step A

N-Propyl-2-trifluoromethyl-benzenesulfonamide

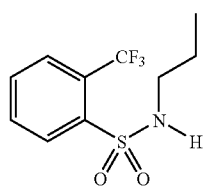

Procedure from Example 35, Step A was utilized with 2-trifluoromethyl-benzenesulfonyl chloride to afford 0.164 g (100%) that was utilized without further purification. $R_f$=0.48 (1/1 hexanes/acetone). $^1$H NMR (400 MHz, CDCl$_3$); MS (ES$^+$) m/z mass calcd for C$_{10}$H$_{12}$O$_2$NSF$_3$ 267, found 268 (M+1, 100%).

Step B

(2-Methyl-4-{2-[propyl-(2-trifluoromethyl-benzene-sulfonyl)-amino]-ethylsulfanyl}-phenoxy)-acetic acid Procedure from Example 35, Step B utilized to afford 0.010 g (9%) of title compound. $^1$H NMR (400 MHz, CDCl$_3$); HRMS (ES$^+$) m/z exact mass calculated for C$_{21}$H$_{25}$O$_5$NS$_2$F$_3$ 492.1126, found 492.1146.

EXAMPLE 41

(2-Methyl-4-{2-[propyl-(2,4,6-triisopropylbenzene-sulfonyl)-amino]-ethylsulfanyl}-phenoxy)-acetic acid

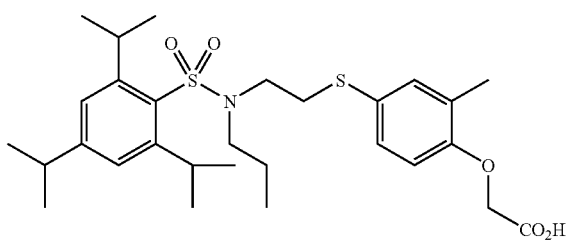

Step A

2,4,6-Triisopropyl-N-propyl-benzenesulfonamide

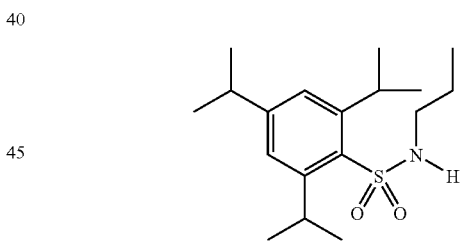

Procedure from Example 35, Step A was utilized with 2,4,6-triisopropyl-benzenesulfonyl chloride to afford 0.161 g (100%) that was utilized without further purification. $R_f$=0.63 (1/1 hexanes/acetone). $^1$H NMR (400 MHz, CDCl$_3$); MS (ES$^+$) m/z mass calculated for C$_{18}$H$_{31}$O$_2$NS 325, found 326 (M+1, 100%).

Step B

(2-Methyl-4-{2-[propyl-(2,4,6-triisopropylbenzene-sulfonyl)-amino]-ethylsulfanyl}-phenoxy)-acetic acid Procedure from Example 35, Step B utilized to afford 0.009 g (7%) of the title compound. $^1$H NMR (400 MHz, CDCl$_3$); HRMS (ES$^+$) m/z exact mass calculated for C$_{29}$H$_{44}$O$_5$NS$_2$ 550.2661, found 550.2667.

EXAMPLE 42

(2-Methyl-4-{2-[propyl-(2,4,6-trimethyl-benzene-sulfonyl)-amino]-ethylsulfanyl}-phenoxy)-acetic acid

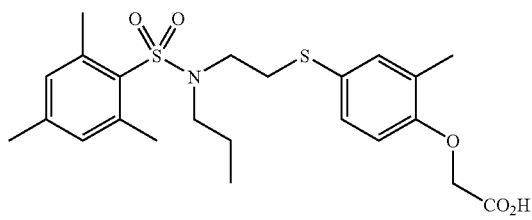

Step A 2,4,6-Trimethyl-N-propyl-benzenesulfonamide

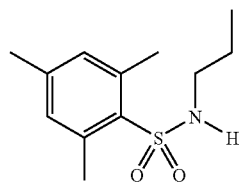

Procedure from Example 35, Step A was utilized with 2,4,6-trimethyl-benzenesulfonyl chloride to afford 0.165 g (100%) that was utilized without further purification. $R_f$=0.51 (1/1 hexanes/acetone). $^1$NMR (400 MHz, CDCl$_3$); MS (ES$^+$) m/z mass calculated for $C_{12}H)_9O_2NS$ 241, found 242 (M+1, 100%).

Step B (2-Methyl-4-{2-[propyl-(2,4,6-trimethyl-benzene-sulfonyl)-amino]-ethylsulfanyl}phenoxy)-acetic acid Procedure from Example 35, Step B utilized to afford 0.012 g (9%) of the title compound. $^1$H NMR (400 MHz, CDCl$_3$); HRMS (ES$^+$) 7 m/z exact mass calculated for $C_{23}H_{32}O_5NS_2$ 466.1722, found 466.1735.

EXAMPLE 43

(2-Methyl-4-{2-[propyl-(2-trifluoromethoxybenze-nesulfonyl)-amino]-ethylsulfanyl}-phenoxy)-acetic acid

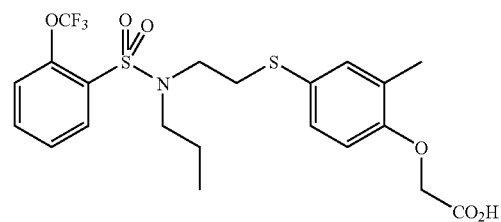

Step A

N-Propyl-2-trifluoromethoxy-benzenesulfonamide

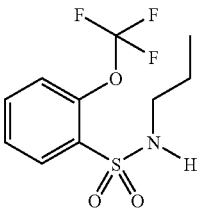

Procedure from Example 35, Step A was utilized with 2-trifluoromethoxy-benzenesulfonyl chloride to afford 0.163 g (100%) that was utilized without further purification. $R_f$=0.51 (1/1 hexanes/acetone). $^1$H NMR (400 MHz, CDCl$_3$); MS (ES$^+$) m/z mass calculated for $C_{10}H_{12}O_2NSF_3$ 283, found 284 (M+1, 100%).

Step B (2-Methyl-4-{2-[propyl-(2-trifluoromethoxybenze-nesulfonyl)-amino]-ethylsulfanyl}-phenoxy)-acetic acid Procedure from Example 35, Step B utilized to afford 0.008 g (7%) of the title compound. $^1$H NMR (400 MHz, CDCl$_3$); HRMS (ES$^+$) m/z exact mass calculated for $C_{21}H_{24}O_6NS_2F_3Na$ 530.0895, found 530.0889.

EXAMPLE 44

(4-{2-[(5-Chloro-naphthalene-1-sulfonyl)-propyl-amino]-ethylsulfanyl}-2-methyl-phenoxy)-acetic acid

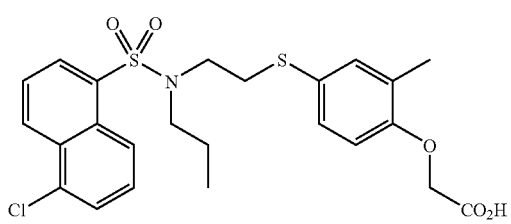

Step A

5-Chloro-naphthalene-1-sulfonic acid propylamide

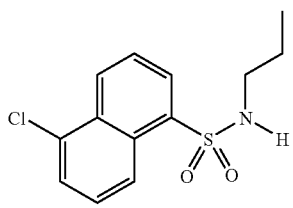

Procedure from Example 35, Step A was utilized with 5-chloro-naphthalene-1-sulfonyl chloride to afford 0.163 g (100%) that was utilized without further purification. $R_f$=0.54 (1/1 hexanes/acetone). $^1$H NMR (400 MHz, CDCl$_3$); MS (ES$^+$) m/z mass calculated for C$_{13}$H$_{14}$O$_2$NSCl 283, found 284 and 286 (M+1 and M+3, 100%).

Step B (4-{2-[(5-Chloro-naphthalene-1-sulfonyl)-propyl-amino]-ethylsulfanyl}-2-methyl-phenoxy)-acetic acid Procedure from Example 35, Step B utilized to afford 0.011 g (9%) of the title compound. $^1$H NMR (400 MHz, CDCl$_3$); HRMS (ES$^+$) m/z exact mass calculated for C$_{24}$H$_{27}$O$_5$NS$_2$Cl 508.1019, found 508.1021.

EXAMPLE 45

(2-Methyl-4-{2-[(4-nitro-benzenesulfonyl)-propyl-amino]-ethylsulfanyl}-phenoxy)-acetic acid

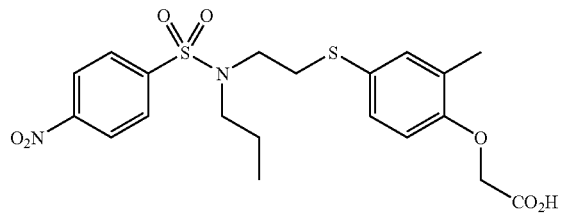

Step A

4-Nitro-N-propyl-benzenesulfonamide

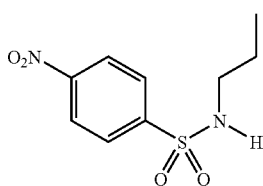

Procedure from Example 35, Step A was utilized with 4-nitro-benzenesulfonyl chloride to afford 0.165 g (100%) that was utilized without further purification. $R_f$=0.49 (1/1 hexanes/acetone). $^1$H NMR (400 MHz, CDCl$_3$); MS (ES$^-$) m/z mass calcd for C$_9$H$_{12}$O$_3$N$_2$S 244, found 243 (M−1, 100%).

Step B (2-Methyl-4-{2-[(4-nitro-benzenesulfonyl)-propyl-amino]-ethylsulfanyl}-phenoxy)-acetic acid Procedure from Example 35, Step B utilized to afford 0.008 g (6%) of the title compound. $^1$H NMR (400 MHz, CDCl$_3$); HRMS (ES$^+$) m/z exact mass calculated for C$_{20}$H$_{25}$O$_7$N$_2$S$_2$ 469.1103, found 469.1113.

EXAMPLE 46

(4-{2-[(2-Chloro-5-trifluoromethyl-benzenesulfo-nyl)-propyl-amino]-ethylsulfanyl}-2-methyl-phe-noxy)-acetic acid

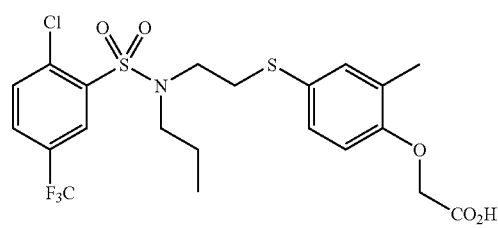

Step A

2-Chloro-N-propyl-5-trifluoromethyl-benzene-sulfonamide

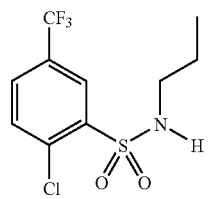

Procedure from Example 35, Step A was utilized with 2-chloro-5-trifluoromethyl-benzenesulfonyl chloride to afford 0.162 g (94%) that was utilized without further purification. $R_f$=0.53 (1/1 hexanes/acetone). $^1$H NMR (400 MHz, CDCl$_3$); MS (ES$^+$) m/z mass calculated for C$_{10}$H$_{11}$O$_2$NSClF$_3$ 301, found 302 and 304 (M+1 and M+3, 100%).

Step B (4-{2-[(2-Chloro-5-trifluoromethyl-benzenesulfo-nyl)-propyl-amino]-ethylsulfanyl}-2-methyl-phe-noxy)-acetic acid Procedure from Example 35, Step B utilized to afford 0.014 g (12%) of the title compound. $^1$H NMR (400 MHz, CDCl$_3$); HRMS (ES$^+$) m/z exact mass calculated for C$_{21}$H$_{24}$O$_5$NS$_2$F$_3$Cl 526.0737, found 526.0724.

EXAMPLE 47

(4-{2-[(5-Chloro-3-methyl-benzo[b]thiophene-2-sulfonyl)-propyl-amino]-ethylsulfanyl}-2-methyl-phenoxy)-acetic acid

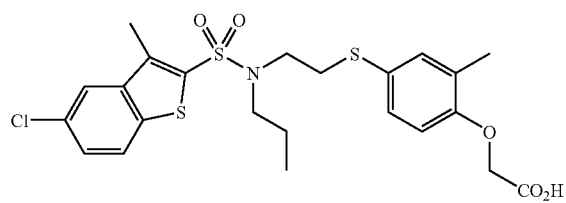

Step A

5-Chloro-3-methyl-benzo[b]thiophene-2-sulfonic acid propylamide

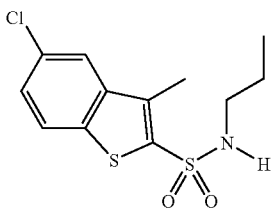

A 0° C. solution of propylamine (0.35 g, 5.92 mmol) and triethylamine (1.08 g, 10.7 mmol) in $CH_2Cl_2$ (75 mL) was treated with 5-chloro-3-methyl-benzo[b]thiophene-2-sulfonylchloride (1.50 g, 5.33 mmol) and stirred at room temperature under $N_2$. When the reaction was complete by TLC (1/1 hexanes/acetone) the reaction was quenched with 1 N HCl (21 mL), diluted with water and extracted with $CH_2Cl_2$. The organic layer was dried ($Na_2SO_4$) and the solvent was removed in vacuo to afford 1.61 g (99%) that was utilized without further purification. $R_f$=0.53 (1/1 hexanes/acetone). $^1H$ NMR (400 MHz, $CDCl_3$); MS (ES$^+$) m/z mass calculated for $C_{32}H_{14}O_2NS_2Cl$ 303, found 304 and 306 (M+1 and M+3, 100%).

Step B (4-{2-[(5-Chloro-3-methyl-benzo[b]thiophene-2-sulfonyl)-propyl-amino]-ethylsulfanyl}-2-methyl-phenoxy)-acetic acid A mixture of [4-(2-chloro-ethylsulfanyl)-2-methyl-phenoxy]-acetic acid ethyl ester (0.116 g, 0.401 mmol), 5-chloro-3-methyl-benzo[b]thiophene-2-sulfonic acid propylamide (0.122 g, 0.401 mmol) and $Cs_2CO_3$ (0.170 g, 0.520 mmol) in DMF (6 mL) was stirred for 17 hours at room temperature under $N_2$. The reaction was heated to 40° C. for 4 hours more and then cooled to room temperature. The reaction mixture was treated with 5 N NaOH (1.5 mL) and stirred for 2 hours at room temperature. The reaction was acidified with 1 N HCl (20 mL), diluted with $Et_2O$ and then extracted with water. The organic layer was dried ($Na_2SO_4$) and the solvent was removed in vacuo to afford 0.282 g crude product that was purified by preparative HPLC to afford 0.013 g (7%). $^1H$ NMR (400 MHz, $CDCl_3$); HRMS (ES$^+$) m/z exact mass calculated for $C_{23}H_{26}O_5NClS_3Na$ 550.0559, found 550.0563.

EXAMPLE 48

(4-{2-[(5-Chloro-3-methyl-benzo[b]thiophene-2-sulfonyl)-methyl-amino]-ethylsulfanyl}-2-methyl-phenoxy)-acetic acid

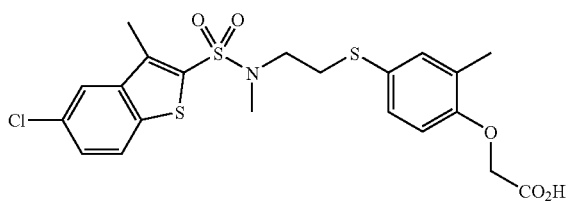

Step A

5-Chloro-3-methyl-benzo[b]thiophene-2-sulfonic acid methylamide

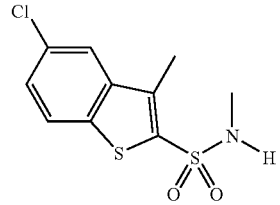

A solution of triethylamine (1.38 g. 7.17 mmol) and 5-chloro-3-methyl-benzo[b]thiophene-2-sulfonyl chloride (1.00 g. 3.56 mmol) in THF (10 mL) was treated with a 2 M solution of methylamine in THF (2.67 mL, 5.35 mmol) and stirred at room temperature under $N_2$ for 30 minutes. When the reaction was complete by TLC (1/1 hexanes/acetone) the reaction was quenched with 1 N HCl (14 mL), diluted with water and extracted with ethyl acetate. The organic layer was dried ($Na_2SO_4$) and the solvent was removed in vacuo to afford 0.97 g (99%) that was utilized without further purification. $R_f$=0.47 (1/1 hexanes/acetone). $^1H$ NMR (400 MHz, $CDCl_3$); MS (ES$^-$) m/z mass calculated for $C_{10}H_{10}O_2NS_2Cl$ 275, found 274 and 276 (M−1 and M+1, 100%).

Step B (4-{2-[(5-Chloro-3-methyl-benzo[b]thiophene-2-sulfonyl)-methyl-amino]-ethylsulfanyl}-2-methyl-phenoxy)-acetic acid A mixture of [4-(2-chloro-ethylsulfanyl)-2-methyl-phenoxy]-acetic acid ethyl ester (0.116 g, 0.401 mmol), 5-chloro-3-methyl-benzo[b]thiophene-2-sulfonic acid methylamide (0.110 g. 0.401 mmol) and $Cs_2CO_3$ (0.170 g, 0.520 mmol) in DMF (6 mL) was stirred for 17 hours at room temperature under $N_2$. The reaction was heated to 40° C. for 4 hours more and then cooled to loom temperature. The reaction mixture was treated with 5 N NaOH (1.5 mL) and stirred for 2 hours at room temperature. The reaction was acidified with 1 N HCl

EXAMPLE 49

(4-{2-[(5-Chloro-3-methyl-benzo[b]thiophene-2-sulfonyl)-(3-methyl-butyl)-amino]-ethylsulfanyl}-2-methyl-phenoxy)-acetic acid

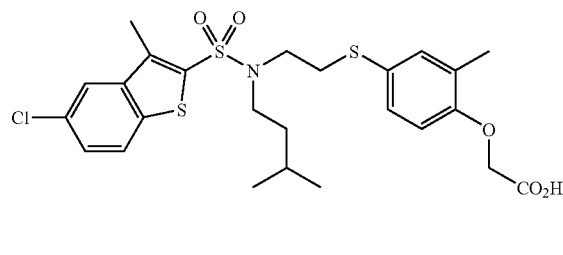

Step A

5-Chloro-3-methyl-benzo[b]thiophene-2-sulfonic acid (3-methyl-butyl)-amide

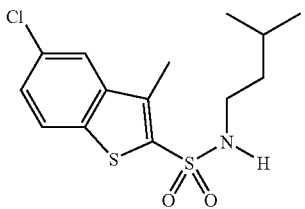

A solution of 3-methyl-butylamine (0.102 g, 1.17 mmol) and triethylamine (0.118 g, 1.17 mmol) in $CH_2Cl_2$ (10 mL) was treated with 5-chloro-3-methyl-benzo[b]thiophene-2-sulfonyl chloride (0.300 g, 1.07 mmol) and stirred at room temperature under $N_2$. The reaction mixture was gravity filtered through a Varian Extube Extraction Column (ChemElut 1005) that had been pre-treated with 4 mL 1 N HCl. The extraction column was washed with $CH_2Cl_2$ (4×) and the solvent was removed from the filtrate in vacuo to afford 0.325 g (92%) that was utilized without further purification. $R_f$=0.26 (2/1 hexanes/acetone). $^1$H NMR (400 MHz, $CDCl_3$); MS (ES$^+$) m/z mass calculated for $C_{14}H_{18}ClNO_2S_2$ 331, found 332 and 334 (M+1 and M+3, 100%).

Step B (4-{2-[(5-Chloro-3-methyl-benzo[b]thiophene-2-sulfonyl)-(3-methyl-butyl)-amino]-ethylsulfanyl}-2-methyl-phenoxy)-acetic acid A mixture of [4-(2-chloro-ethylsulfanyl)-2-methyl-phenoxy]-acetic acid ethyl ester (0.160 g, 0.554 mmol), 5-chloro-3-methyl-benzo[b]thiophene-2-sulfonic acid (3-methyl-butyl)-amide (0.183 g, 0.551 mmol) and $Cs_2CO_3$ (0.234 g, 0.718 mmol) in DMF (7 mL) was stirred at 45° C. for 22 hours. The reaction mixture was cooled and then treated with 5 N NaOH (1.5 mL) and stirred for 4 hours at room temperature. The reaction was acidified with 1 N HCl (20 mL), diluted with $Et_2O$ and then extracted with water. The organic layer was dried ($Na_2SO_4$) and the solvent was removed in vacuo to afford 0.72 g crude product that was purified by preparative HPLC to afford 0.018 g (6%). $^1$H NMR (400 MHz, $CDCl_3$); HRMS (ES$^+$) m/z exact mass calculated for $C_{25}H_{30}O_5NClS_3Na$ 578.0872, found 578.0900.

EXAMPLE 50

(4-{2-[(5-Chloro-3-methyl-benzo[b]thiophene-2-sulfonyl)-(3,3-dimethyl-butyl)-amino]-ethylsulfanyl}-2-methyl-phenoxy)-acetic acid

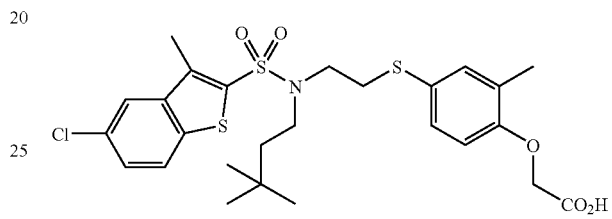

Step A

5-Chloro-3-methyl-benzo[b]thiophene-2-sulfonic acid (3,3-dimethyl-butyl)-amide

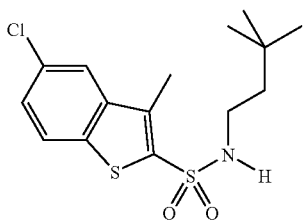

Procedure from Example 49, Step A was utilized with 3,3-dimethyl butylamine to afford 0.354 g (96%) that was utilized without further purification. $R_f$=0.24 (2/1 hexanes/acetone). $^1$H NMR (400 MHz, $CDCl_3$); MS (ES$^+$) m/z mass calculated for $C_{15}H_{20}ClNO_2S_2$ 345, found 346 and 348 (M+1 and M+3, 100%).

Step B (4-{2-[(5-Chloro-3-methyl-benzo[b]thiophene-2-sulfonyl)-(3,3-dimethyl-butyl)-amino]-ethylsulfanyl}-2-methyl-phenoxy)-acetic acid Procedure from Example 49, Step B was utilized to afford 0.62 g crude product that was purified by preparative HPLC to afford 0.032 g (16%) of the title compound. $^1$H NMR (400 MHz, $CDCl_3$); HRMS (ES$^+$) m/z exact mass calculated for $C_{26}H_{33}O_5NClS_3$ 570.1209, found 570.1202.

(20 mL), diluted with $Et_2O$ and then extracted with water. The organic layer was dried ($Na_2SO_4$) and the solvent was removed in vacuo to afford 0.45 g crude product that was purified by preparative HPLC to afford 0.023 g (12%). $^1$H NMR (400 MHz, $CDCl_3$); HRMS (ES$^+$) m/z exact mass calculated for $C_{21}H_{23}O_5NClS_3$ 500.0427, found 500.0428.

EXAMPLE 51

(4-{2-[(5-Chloro-3-methyl-benzo[b]thiophene-2-sulfonyl)cyclopropyl-amino]-ethylsulfanyl}-2-methyl-phenoxy)-acetic acid

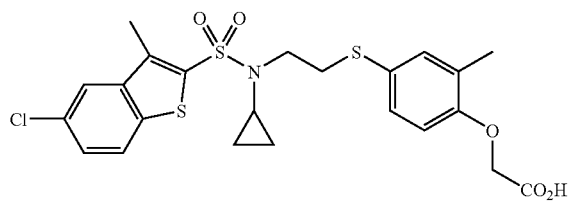

Step A

5-Chloro-3-methyl-benzo[b]thiophene-2-sulfonic acid cyclopropylamide

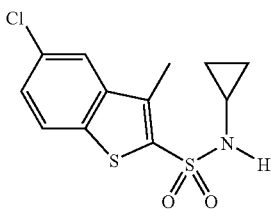

Procedure from Example 49, Step A was utilized with cyclopropylamine to afford 0.321 g (99%) that was utilized without further purification. $R_f$=0.16 (2/1 hexanes/acetone). $^1$H NMR (400 MHz, CDCl$_3$); MS (ES$^+$) m/z mass calculated for C$_{12}$H$_{12}$ClNO$_2$S$_2$ 301, found 302 and 304 (M+1 and M+3, 100%).

Step B (4-{2-[(5-Chloro-3-methyl-benzo[b]thiophene-2-sulfonyl)cyclopropyl-amino]ethylsulfanyl}-2-methyl-phenoxy)-acetic acid Procedure from Example 49, Step B was utilized to afford 0.38 g crude product that was purified by preparative HPLC to afford 0.027 g (9%) of the title compound. $^1$H NMR (400 MHz, CDCl$_3$); HRMS (ES$^+$) m/z exact mass calculated for C$_{23}$H$_{24}$O$_5$NClS$_3$Na 548.0403, found 548.0403.

EXAMPLE 52

(4-{2-[(5-Chloro-3-methyl-benzo[b]thiophene-2-sulfonyl)-(1-ethyl-propyl)-amino]-ethylsulfanyl}-2-methyl-phenoxy)-acetic acid

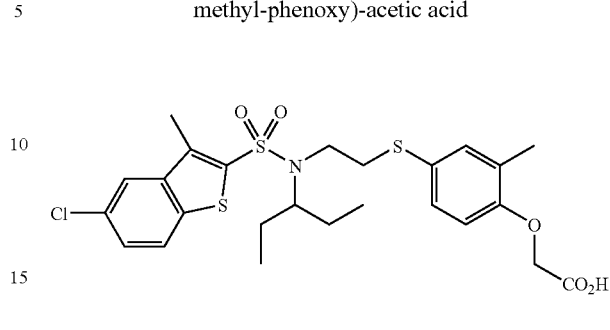

Step A

5-Chloro-3-methyl-benzo[b]thiophene-2-sulfonic acid (1-ethyl-propyl)-amide

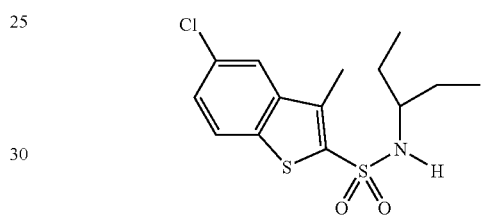

Procedure from Example 49, Step A was utilized with 1-ethyl-propylamine to afford 0.343 g (97%) that was utilized without further purification. $R_f$=0.26 (2/1 hexanes/acetone). $^1$H NMR (400 MHz, CDCl$_3$): MS (ES$^+$) m/z mass calculated for C$_{14}$H$_{18}$ClNO$_2$S$_2$ 331 found 332 and 334 (M+1 and M+3, 100%).

Step B (4-{2-[(5-Chloro-3-methyl-benzo[b]thiophene-2-sulfonyl)-(1-ethyl-propyl)-amino]-ethylsulfanyl}-2-methyl-phenoxy)-acetic acid Procedure from Example 49. Step B was utilized to afford 0.007 g (2%) of the title compound. $^1$H NMR (400 MHz, CDCl$_3$): HRMS (ES$^+$) m/z exact mass calculated for C$_{25}$H$_{30}$O$_5$ClS$_3$Na 578.0872, found 578.0920.

EXAMPLE 53

(4-{2-[(5-Chloro-3-methyl-benzo[b]thiophene-2-sulfonyl)-cyclobutyl-amino]-ethylsulfanyl}-2-methyl-phenoxy)-acetic acid

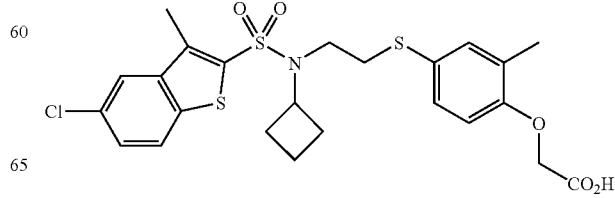

Step A

5-Chloro-3-methyl-benzo[b]thiophene-2-sulfonic acid cyclobutylamide

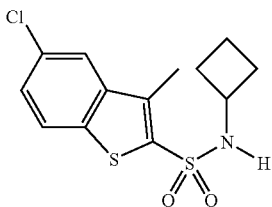

Procedure from Example 49, Step A was utilized with cyclobutylamine to afford 0.365 g (100%) that was utilized without further purification. $R_f$=0.20 (2/1 hexanes/acetone). $^1$H NMR (400 MHz, CDCl$_3$); MS (ES$^+$) m/z mass calculated for C$_{13}$H$_{14}$ClNOS$_2$ 315, found 316 and 318 (M+1 and M+3, 100%).

Step B

(4-{2-[(5-Chloro-3-methyl-benzo[b]thiophene-2-sulfonyl)-cyclobutyl-amino]-ethylsulfanyl}-2-methyl-phenoxy)-acetic acid

Procedure from Example 49, Step B was utilized to afford 0.024 g (8%) of the title compound. $^1$H NMR (400 MHz, CDCl$_3$); HRMS (ES$^+$) m/z exact mass calculated for C$_{24}$H$_{26}$O$_5$NClS$_3$Na 562.0559, found 562.0535.

EXAMPLE 54

(4-{2-[(5-Chloro-3-methyl-benzo[b]thiophene-2-sulfonyl)-cyclopentyl-amino]-ethylsulfanyl}-2-methyl-phenoxy)-acetic acid

Step A

5-Chloro-3-methyl-benzo[b]thiophene-2-sulfonic acid cyclopentylamide

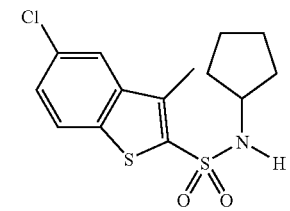

Procedure from Example 49, Step A was utilized with cyclopentylamine to afford 0.403 g (100%) that was utilized without further purification. $R_f$=0.20 (2/1 hexanes/acetone). $^1$H NMR (400 MHz, CDCl$_3$); MS (ES$^+$) m/z mass calculated for C$_{14}$H$_{16}$ClNO$_2$S$_2$ 329, found 330 and 332 (M+1 and M+3, 100%).

Step B

(4-{2-[(5-Chloro-3-methyl-benzo[b]thiophene-2-sulfonyl)-cyclopentyl-amino]-ethylsulfanyl}-2-methyl-phenoxy)-acetic acid

Procedure from Example 49, Step B was utilized to afford 0.011 g (4%) of the title compound. $^1$H NMR (400 MHz, CDCl$_3$); MS (ES$^+$) m/z mass calculated for C$_{25}$H$_{28}$O$_5$NClS$_3$ 553, found 552 and 554 (M−1 and M+1, 100%).

EXAMPLE 55

(4-{2-[(5-Chloro-3-methyl-benzo[b]thiophene-2-sulfonyl)-cyclopropylmethyl-amino]-ethylsulfanyl}-2-methyl-phenoxy)-acetic acid

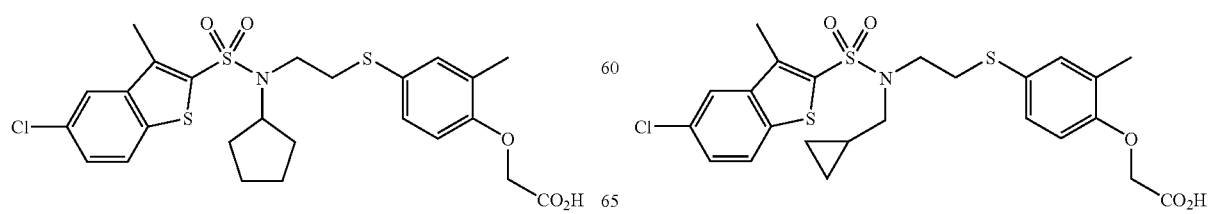

137

Step A

5-Chloro-3-methyl-benzo[b]thiophene-2-sulfonic acid cyclopropylmethyl-amide

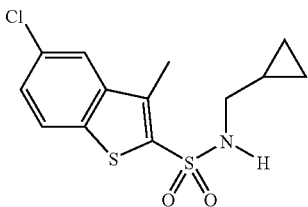

Procedure from Example 49, Step A was utilized with cyclopropylmethylamine to afford 0.333 g (99%) that was utilized without further purification. $R_f$=0.20 (2/1 hexanes/acetone). $^1$H NMR (400 MHz, CDCl$_3$); MS (ES$^+$) m/z mass calculated for $C_{13}H_{14}ClNO_2S_2$ 315, found 316 and 318 (M+1 and M+3, 100%).

Step B (4-{2-[(5-Chloro-3-methyl-benzo[b]thiophene-2-sulfonyl)-cyclopropylmethyl-amino]-ethylsulfanyl}-2-methyl-phenoxy)-acetic acid Procedure from Example 49, Step B was utilized to afford 0.332 g crude product that was purified by preparative HPLC to afford 0.020 g (7%) of the title compound. $^1$H NMR (400 MHz, CDCl$_3$); HRMS (ES$^+$) m/z exact mass calculated for $C_{24}H_{27}O_5NClS_3$ 540.0740, found 540.0739.

EXAMPLE 56

(4-{2-[(5-Chloro-3-methyl-benzo[b]thiophene-2-sulfonyl)-pentyl-amino]-ethylsulfanyl}-2-methyl-phenoxy)-acetic acid

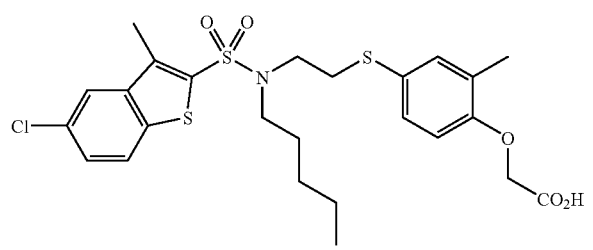

138

Step A

5-Chloro-3-methyl-benzo[b]thiophene-2-sulfonic acid pentylamide

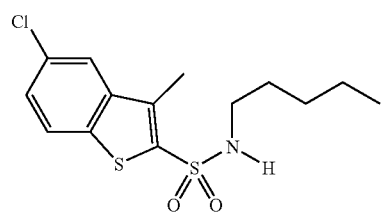

Procedure from Example 49. Step A was utilized with n-pentylamine to afford 0.379 g (100%) that was utilized without further purification. $R_f$=0.22 (2/1 hexanes/acetone). $^1$H NMR (400 MHz, CDCl$_3$): MS (ES$^+$) m/z mass calculated for $C_{14}H_{18}ClNO_2S_2$ 331, found 332 and 334 (M+1 and M+3, 100%).

Step B (4-{2-[(5-Chloro-3-methyl-benzo[b]thiophene-2-sulfonyl)-pentyl-amino]-ethylsulfanyl}-2-methyl-phenoxy)-acetic acid Procedure from Example 49, Step B was utilized to afford 0.045 g (15%) of the title compound. $^1$H NMR (400 MHz. CDCl$_3$): MS (ES$^-$) m/z exact mass calculated for $C_{25}H_{28}O_5NClS_3$ 555, found 554 and 556 (M−1 and M+1, 100%).

EXAMPLE 57

(4-{2-[Butyl-(5-chloro-3-methyl-benzo[b]thiophene-2-sulphonyl)-amino]-ethylsulfanyl}-2-methyl-phenoxy)-acetic acid

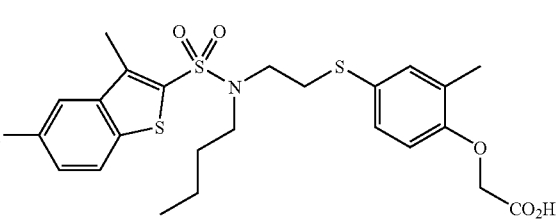

Step A

5-Chloro-3-methyl-benzo[b]thiophene-2-sulfonic acid butylamide

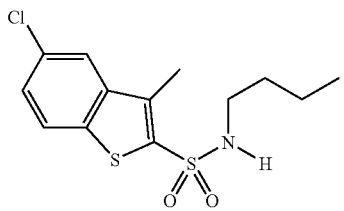

Procedure from Example 49, Step A was utilized with n-butylamine to afford 0.352 g (100%) that was utilized without further purification. $R_f$=0.24 (2/1 hexanes/acetone). $^1$H NMR (400 MHz, CDCl$_3$); MS (ES$^+$) m/z mass calculated for $C_{13}H_{16}ClNO_2S_2$ 317, found 318 and 320 (M+1 and M+3, 100%).

Step B

(4-{2-[Butyl-(5-chloro-3-methyl-benzo[b]thiophene-2-sulfonyl)-amino]-ethylsulfanyl}-2-methyl-phenoxy)-acetic acid Procedure from Example 49, Step B was utilized to afford 0.030 g (10%) of the title compound. $^1$H NMR (400 MHz, CDCl$_3$); HRMS (ES$^+$) m/z exact mass calculated for $C_{24}H_{28}O_5NClS_3Na$ 564.0716, found 564.0740.

EXAMPLE 58

(4-{2-[(5-Chloro-3-methyl-benzo[b]thiophene-2-sulfonyl)-(2-dimethylamino-ethyl)-amino]-ethylsulfanyl}-2-methyl-phenoxy)-acetic acid; trifluoro-acetic acid

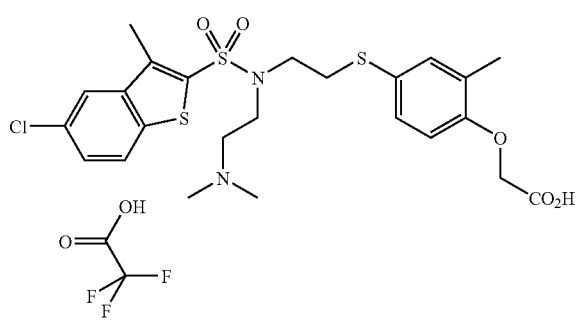

Step A

5-Chloro-3-methyl-benzo[b]thiophene-2-sulfonic acid (2-dimethylamino-ethyl)-amide

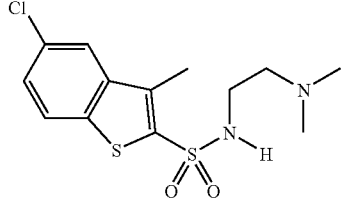

A 0° C. solution of N,N-dimethylethylenediamine (0.086 g, 0.976 mmol) and triethylamine (0.134 g, 1.32 mmol) in CH$_2$Cl$_2$ (10 mL) was treated with 5-chloro-3-methyl-benzo[b]thiophene-2-sulfonyl chloride (0.250 g. 0.889 mmol) and stirred at room temperature under N$_2$ until complete by TLC (2/1 hexanes/acetone). The reaction was neutralized with 1 N HCl, diluted with water and then extracted with CH$_2$Cl$_2$. The organic layer was dried (Na$_2$SO$_4$) and the solvent was removed in vacuo to afford 0.290 g (98%) that was utilized without further purification. $R_f$=0.05 (2/1 hexanes/acetone). $^1$H NMR (400 MHz, CDCl$_3$); MS (ES$^+$) m/z mass calculated for $C_{13}H_{17}ClN_2O_2S_2$ 332, found 333 and 335 (M+1 and M+3, 100%).

Step B

(4-{2-[(5-Chloro-3-methyl-benzo[b]thiophene-2-sulfonyl)-(2-dimethylamino-ethyl)-amino]-ethylsulfanyl}-2-methyl-phenoxy)-acetic acid; trifluoro-acetic acid (2076995)

Procedure from Example 49, Step B was utilized to afford 0.033 g (7%) of the title compound. $^1$H NMR (400 MHz. CDCl$_3$); MS (ES$^+$) m/z mass calculated for $C_{24}H_{29}O_5N_2ClS_3$ 556 (free-base), found 557 and 559 (M+1 and M+3, 100%).

EXAMPLE 59

[4-(3-Chloro-propylsulfanyl)-2-methyl-phenoxy]-acetic acid ethyl ester

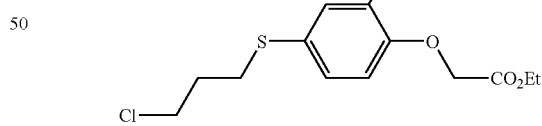

A solution of crude (4-mercapto-2-methyl-phenoxy)-acetic acid ethyl ester (5.26 g, 23.2 mmol) in dry DMF (50 mL) was purged with N$_2$ and then 325 mesh K$_2$CO$_3$ (4.82 g, 34.9 mmol) was added and the resultant mixture purged with N$_2$ for 5 minutes more. 1-Bromo-3-chloropropane (10.98 g, 69.8 mmol) was added dropwise to the reaction which was stirred for 17 hours at room temperature under N$_2$. The reaction was filtered and the solids washed with Et$_2$O. The filtrate was acidified with 1 N HCl (70 mL), diluted with Et$_2$O and then extracted with water (4×). The organic layer was dried (Na$_2$SO$_4$) and the solvent was removed in vacuo to afford crude product that was purified by column chromatography using 5/1 hexanes/acetone to afford 5.73 g (82%). $R_f$=0.62 (1/1 hexanes/acetone). $^1$H NMR (400 MHz, CDCl$_3$); MS (ES$^+$) m/z mass calculated for C$_{14}$H$_{19}$O$_3$ClS 302, found 303 and 305 (M+1 and M+3, 100%).

EXAMPLE 60

(4-{3-[(5-Chloro-3-methyl-benzo[b]thiophene-2-sulfonyl)-propyl-amino]-propylsulfanyl}-2-methyl-phenoxy)-acetic acid

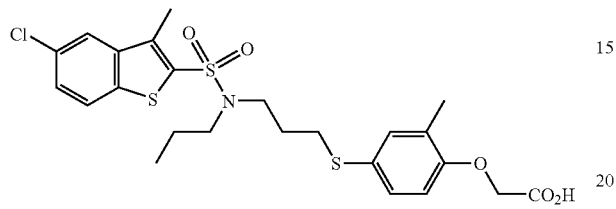

A mixture of [4-(3-chloro-propylsulfanyl)-2-methyl-phenoxy]-acetic acid ethyl ester (0.100 g, 0.330 mmol), 5-chloro-3-methyl-benzo[b]thiophene-2-sulfonic acid propylamide (0.100 g, 0.329 mmol) and Cs$_2$CO$_3$ (0.140 g, 0.430 mmol) in DMF (7 mL) was stirred at 55° C. for 8 hours. The reaction mixture was cooled and acidified with 1 HCl (10 mL). The mixture was diluted with water and then extracted with Et$_2$O. The organic layer was dried (Na$_2$SO$_4$) and the solvent was removed in vacuo to afford 0.183 g crude product that was dissolved in THF (6 mL) and treated with 1 N LiOH (1.6 mL). The reaction mixture was stirred for 4 hours at room temperature. The reaction was acidified with 1 N HCl (10 mL), diluted with ethyl acetate and then extracted with water. The organic layer was dried (Na$_2$SO$_4$) and the solvent removed in vacuo to afford 0.164 g crude product that was purified by preparative HPLC to afford 0.095 g (53%). $^1$H NMR (400 MHz, CDCl$_3$); MS (ES$^+$) m/z mass calculated for C$_{24}$H$_{28}$O$_5$NClS$_3$ 541, found 542 and 544 (M+1 and M+3, 100%).

EXAMPLE 61

(2-Methyl-4-{3-[(naphthalene-1-sulfonyl)-propyl-amino]-propylsulfanyl}-phenoxy)-acetic acid

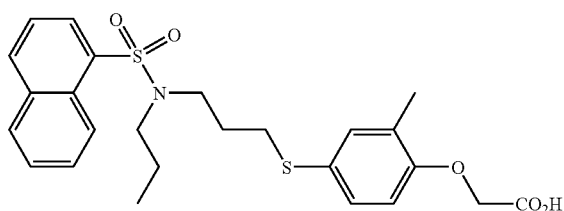

A mixture of [4-(3-chloro-propylsulfanyl)-2-methyl-phenoxy]-acetic acid ethyl ester (0.108 g, 0.357 mmol), naphthalene-1-sulfonic acid propylamide (0.089 g, 0.357 mmol) and Cs$_2$CO$_3$ (0.151 g, 0.463 mmol) in DMF (6 mL) was stirred for 21 hours at 45° C. The reaction was cooled to room temperature and treated with 5 N NaOH (1.5 mL) and stirred for 2 hours at room temperature. The reaction was acidified with 1 N HCl (20 mL), diluted with Et$_2$O and then extracted with water. The organic layer was dried (Na$_2$SO$_4$) and the solvent was removed in vacuo to afford 0.389 g crude product that was purified by preparative HPLC to afford 0.077 g (44%). $^1$H NMR (400 MHz, CDCl$_3$); HRMS (ES$^+$) m/z exact mass calculated for C$_{25}$H$_{30}$O$_5$NS$_2$ 488.1565, found 488.1559.

EXAMPLE 62

((4-{3-[(5-Chloro-naphthalene-2-sulfonyl)-propyl-amino]-propylsulfanyl}-2-methyl-phenoxy)-acetic acid

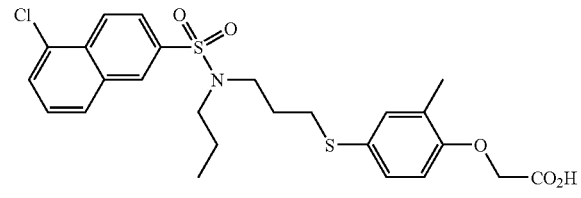

Procedure from Example 61 was utilized to afford 0.076 g (54%) of the title compound. $^1$H NMR (400 MHz, CDCl$_3$); HRMS (ES$^+$) m/z exact mass calculated for C$_{25}$H$_{29}$O$_5$NS$_2$Cl 522.1176, found 522.1213.

EXAMPLE 63

(2-Methyl-4-{3-[propyl-(4-trifluoromethoxybenzenesulfonyl)-amino]-propylsulfanyl}-phenoxy)-acetic acid

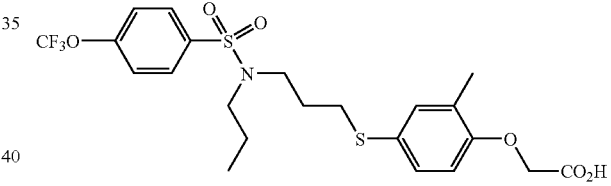

Procedure from Example 61 was utilized to afford 0.077 g (53%) of the title compound. $^1$H NMR (400 MHz, CDCl$_3$); HRMS (ES$^+$) m/z exact mass calculated for C$_{22}$H$_{27}$O$_6$NS$_2$F$_3$ 522.1232, found 522.134.

EXAMPLE 64

{4-[3-(Benzenesulfonyl-propyl-amino)-propylsulfanyl]-2-methyl-phenoxy}-acetic acid

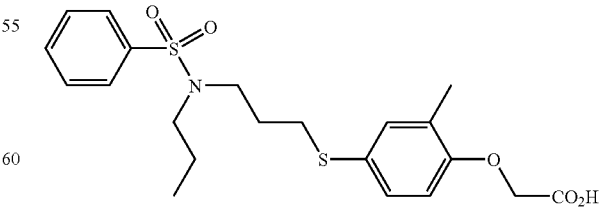

Procedure from Example 61 was utilized to afford 0.147 g (65%) of the title compound. $^1$H NMR (400 MHz, CDCl$_3$); HRMS (ES$^+$) m/z exact mass calculated for C$_{21}$H$_{28}$O$_5$NS$_2$ 438.1409, found 438.1404.

EXAMPLE 65

(2-Methyl-4-{3-[propyl-(toluene-2-sulfonyl)-amino]-propylsulfanyl}-phenoxy)-acetic acid

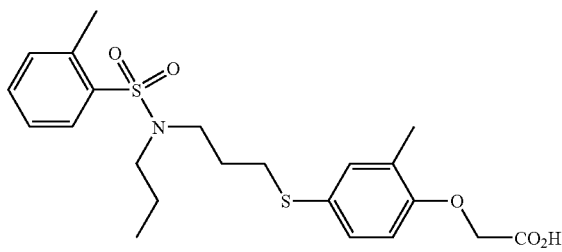

Procedure from Example 61 was utilized to afford 0.126 g (67%) of the title compound. $^1$H NMR (400 MHz, CDCl$_3$); HRMS (ES$^+$) m/z exact mass calculated for C$_{22}$H$_{30}$O$_5$NS$_2$ 452.1565, found 452.1600.

EXAMPLE 66

(2-Methyl-4-{3-[propyl-(2-trifluoromethyl-benzene-sulfonyl)-amino]-propylsulfanyl}-phenoxy)-acetic acid

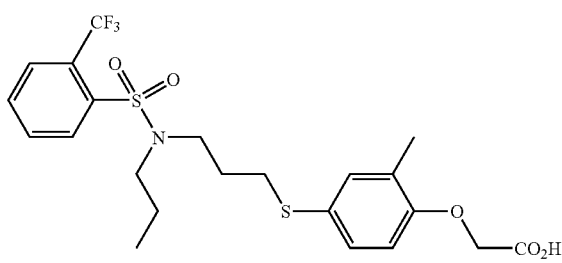

Procedure from Example 61 was utilized to afford 0.070 g (35%) of the title compound. $^1$H NMR (400 MHz, CDCl$_3$); HRMS (ES$^+$) m/z exact mass calculated for C$_{22}$H$_{27}$O$_5$NS$_2$F$_3$ 506.1283, found 506.1288.

EXAMPLE 67

(2-Methyl-4-{3-[propyl-(2,4,6-triisopropylbenzene-sulfonyl)-amino]-propylsulfanyl}-phenoxy)-acetic acid

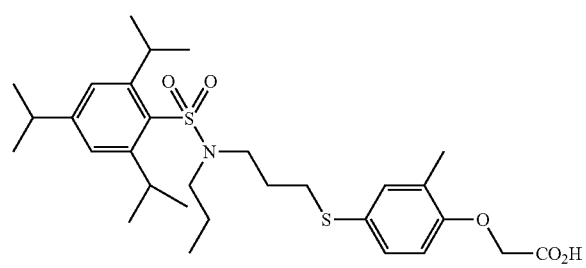

Procedure from Example 61 was utilized to afford 0.096 g (55%) of the title compound. $^1$H NMR (400 MHz, CDCl$_3$); HRMS (ES$^+$) m/z exact mass calculated for C$_{30}$H$_{46}$O$_5$NS$_2$ 564.2817, found 564.2922.

EXAMPLE 68

(2-Methyl-4-{3-[propyl-(2,4,6-trimethyl-benzene-sulfonyl)-amino]-propylsulfanyl}-phenoxy)-acetic acid

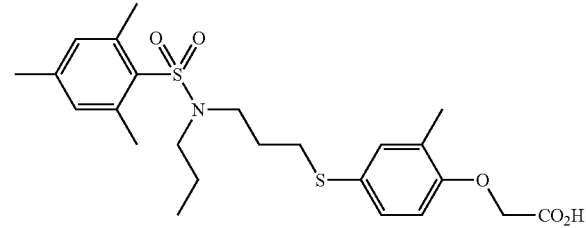

Procedure from Example 61 was utilized to afford 0.111 g (48%) of the title compound. $^1$H NMR (400 MHz, CDCl$_3$); HRMS (ES$^+$) m/z exact mass calculated for C$_{24}$H$_{34}$O$_5$NS$_2$ 480.1878, found 480.1887.

EXAMPLE 69

(2-Methyl-4-{3-[propyl-(2-trifluoromethoxybenzenesulfonyl)-amino]-propylsulfanyl}-phenoxy)-acetic acid

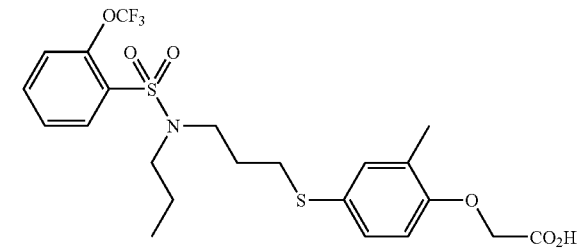

Procedure from Example 61 was utilized to afford 0.106 g (56%) of the title compound. $^1$H NMR (400 MHz, CDCl$_3$); HRMS (ES$^+$) m/z exact mass calculated for C$_{22}$H$_{27}$O$_6$NS$_2$F$_3$ 522.1232, found 522.1260.

EXAMPLE 70

(4-{3-[(5-Chloro-naphthalene-1-sulfonyl)-propyl-amino]-propylsulfanyl}-2-methyl-phenoxy)-acetic acid Procedure from Example 61 was utilized to afford 0.103 g (56%) of the title compound. $^1$H NMR (400 MHz, CDCl$_3$): HRMS (ES$^+$) m/z exact mass calculated for C$_{25}$H$_{29}$O$_5$NS$_2$Cl 522.1176, found 522.1155.

EXAMPLE 71

(2-Methyl-4-{3-[(4-nitro-benzenesulfonyl)-propyl-amino]-propyl sulfanyl}-phenoxy)-acetic acid

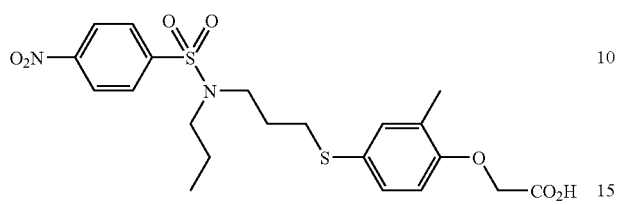

Procedure from Example 61 was utilized to afford 0.088 g (39%) of the title compound. $^1$H NMR (400 MHz, CDCl$_3$); HRMS (ES$^+$) m/z exact mass calculated for C$_{21}$H$_{26}$O$_7$N$_2$S$_2$Na 505.1079, found 505.1090.

EXAMPLE 72

((4-{3-[(2-Chloro-5-trifluoromethyl-benzenesulfonyl)-propyl-amino]-propylsulfanyl}-2-methyl-phenoxy)-acetic acid

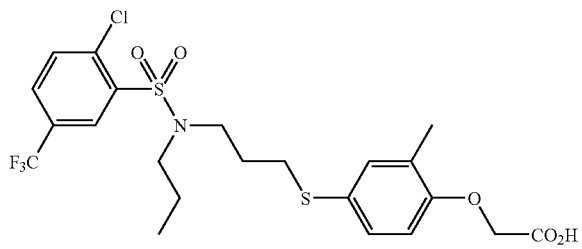

Procedure from Example 61 was utilized to afford 0.053 g (34%) of the title compound. $^1$H NMR (400 MHz, CDCl$_3$); HRMS (ES$^+$) m/z exact mass calculated for C$_{22}$H$_{26}$O$_5$N$_2$S$_2$F$_3$Na 562.0712, found 562.0704.

EXAMPLE 73

(4-{4-[(5-Chloro-3-methyl-benzo[b]thiophene-2-sulfonyl)-propyl-amino]-butylsulfanyl}-2-methyl-phenoxy)-acetic acid

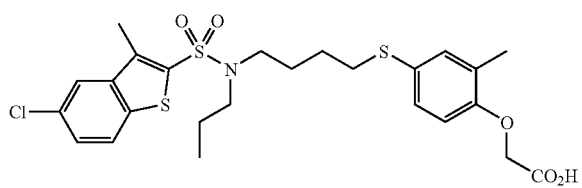

Step A

[4-(4-Chloro-butylsulfanyl)-2-methyl-phenoxy]-acetic acid ethyl ester

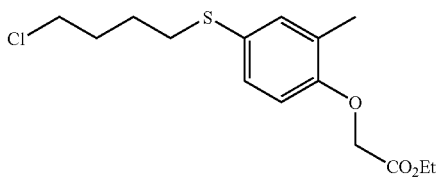

A solution of crude (4-mercapto-2-methyl-phenoxy)-acetic acid ethyl ester (1.40 g, 6.21 mmol) in dry DMF (15 mL) was purged with N$_2$ and then 325 mesh K$_2$CO$_3$ (1.29 g, 9.33 mmol) was added, and the resultant mixture was purged with N$_2$ for 5 minutes more. 1-Bromo-4-chlorobutane (3.12 g, 18.2 mmol) was added dropwise to the reaction which was stirred for 17 hours at room temperature under N$_2$. The reaction was acidified with 1 N HCl (20 mL), diluted with Et$_2$O and then extracted four times with water. The organic layer was dried (Na$_2$SO$_4$) and the solvent was removed in vacuo to afford crude product that was purified by column chromatography using 10/1 hexanes/acetone to afford 1.14 g (58%). R$_f$=0.31 (2/1 hexanes/acetone). $^1$H NMR (400 MHz, CDCl$_3$); MS (ES$^+$) m/z mass calculated for C$_{15}$H$_{21}$ClS 316, found 317 and 319 (M+1 and M+3, 100%)

Step B (4-{4-[(5-Chloro-3-methyl-benzo[b]thiophene-2-sulfonyl)-propyl-amino]-butylsulfanyl}-2-methyl-phenoxy)-acetic acid A mixture of [4-(4-chloro-butylsulfanyl)-2-methyl-phenoxy]-acetic acid ethyl ester (0.102 g, 0.322 mmol). 5-chloro-3-methyl-benzo[b]thiophene-2-sulfonic acid propylamide (0.098 g, 0.322 mmol) and Cs$_2$CO$_3$ (0.136 g, 0.417 mmol) in DMF (7 mL) was stirred at 50° C. for 22 hours. The reaction mixture was cooled and then treated with 5 N NaOH (1.5 mL) and stirred for 4 hours at room temperature. The reaction was acidified with 1 N HCl (20 mL), diluted with Et$_2$O and then extracted with water. The organic layer was dried (Na$_2$SO$_4$) and the solvent was removed in vacuo to afford 0.464 g crude product that was purified by preparative HPLC to afford 0.068 g (38%) of the title compound. $^1$H NMR (400 MHz, CDCl$_3$); MS (ES$^+$) m/z mass calculated for C$_{25}$H$_{30}$O$_5$NClS$_3$ 555, found 556 and 558 (M+1 and M+3, 100%).

EXAMPLE 74

(4-{2-[(5-Chloro-3-methyl-benzo[b]thiophene-2-sulfonyl)-propyl-amino]-ethoxy}-2-methyl-phenoxy)-acetic acid

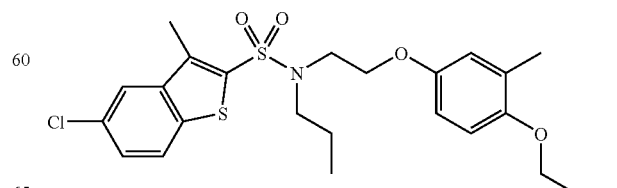

Step A

5-Chloro-3-methyl-benzo[b]thiophene-2-sulfonic acid (2-hydroxy-ethyl)-propyl-amide

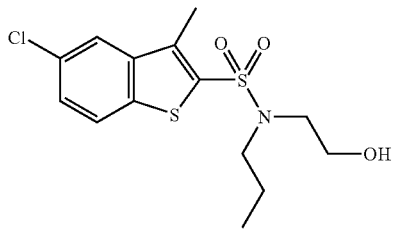

A 0° C. solution of 2-(propylamino)ethanol (0.605 g, 5.86 mmol) and triethylamine (1.08 g, 10.7 mmol) in $CH_2Cl_2$ (25 mL) was treated with 5-chloro-3-methyl-benzo[b]thiophene-2-sulfonyl chloride (1.50 g, 5.33 mmol) and the reaction was warmed to room temperature and stirred for 2 hours under $N_2$. The reaction was quenched with 1 N HCl (20 mL) and diluted with more $CH_2Cl_2$ and extracted with water. The organic layer was dried ($Na_2SO_4$) and the solvent was removed in vacuo to afford 1.82 g (98%) of the title compound. $R_f$=0.38 (1/1 hexanes/acetone). MS (ES$^+$) m=1 mass calculated for $C_{14}H_{18}O_3NS_2Cl$ 347, found 348 and 350 (M+1 and M+3, 100%).

Step B

Toluene-4-sulfonic acid 2-[(5-chloro-3-methyl-benzo[b]thiophene-2-sulfonyl)-propyl-amino]-ethyl ester

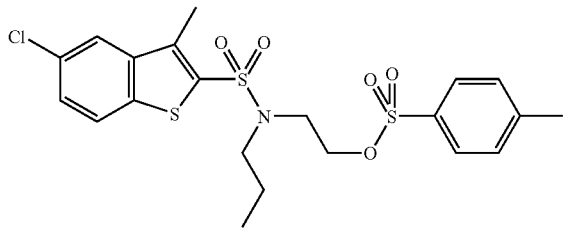

A solution of 5-chloro-3-methyl-benzo[b]thiophene-2-sulfonic acid (2-hydroxy-ethyl)-propyl-amide (1.82 g, 5.23 mmol), pyridine (1.66 g. 20.9 mmol) and N,N-dimethylaminopyridine (0.19 g, 1.55 mmol) in $CH_2Cl_2$ (50 mL) was treated with p-toluenesulfonic anhydride (3.42 g, 10.5 mmol), and the reaction stirred at room temperature under $N_2$ until complete by TLC (2/1 hexanes/acetone). The reaction was quenched with 1 N HCl (30 mL) and diluted with more $CH_2Cl_2$ and extracted with water. The organic layer was dried ($Na_2SO_4$) and the solvent was removed in vacuo to afford crude product that was absorbed on silica gel and purified by column chromatography using a gradient of 9/1 to 4/1 hexanes/acetone to afford 2.76 g (100%) of the title compound. $R_f$=0.35 (2/1 hexanes/acetone). MS (ES$^+$) m/z mass calculated for $C_{21}H_{24}O_5NS_3Cl$ 501, found 502 and 504 (M+1 and M+3, 100%).

Step C

(4-{2-[(5-Chloro-3-methyl-benzo[b]thiophene-2-sulfonyl)-propyl-amino]-ethoxy}-2-methyl-phenoxy)-acetic acid A mixture of (4-hydroxy-2-methyl-phenoxy)-acetic acid ethyl ester (0.060 g, 0.306 mmol), toluene-4-sulfonic acid 2-[(5-chloro-3-methyl-benzo[b]thiophene-2-sulfonyl)-propyl-amino]-ethyl ester (0.153 g. 0.305 mmol) and $Cs_2CO_3$ (0.149 g, 0.457 mmol) in dry DMF (7 mL) was stirred at 50° C. for 17 hours under $N_2$. The reaction was cooled and then treated with 5 N NaOH (2 mL) and stirred at room temperature for 4 hours. The reaction was quenched with 1 N BC) (25 mL), diluted with $Et_2O$ and then extracted with water. The organic layer was dried ($Na_2SO_4$) and the solvent was removed in vacuo to afford 0.447 g of crude product that was purified by preparative HPLC to afford 0.087 g (55%) of the title compound. HRMS (ES$^+$) m/z exact mass calculated for $C_{23}H_{27}O_6NClS_2$ 512.0968, found 512.0972.

EXAMPLE 75

3-(4-{2-[(5-Chloro-3-methyl-benzo[b]thiophene-2-sulfonyl)-propyl-amino]-ethoxy}-2-methyl-phenyl)-propionic acid

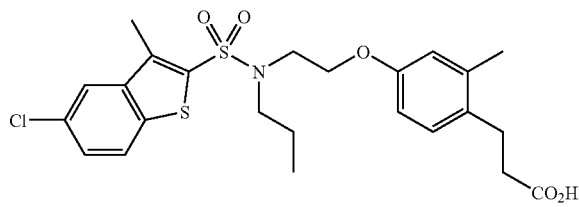

A mixture of 3-(4-hydroxy-2-methyl-phenyl)-propionic acid methyl ester (0.052 g, 0.268 mmol), toluene-4-sulfonic acid 2-[(5-chloro-3-methyl-benzo[b]thiophene-2-sulfonyl)-propyl-amino]-ethyl ester (0.134 g, 0.267 mmol) and $Cs_2CO_3$ (0.131 g, 0.402 mmol) in dry DMF (7 mL) was stirred at 50° C. for 17 hours under $N_2$. The reaction was cooled and then treated with 5 N NaOH (2 mL) and stirred at room temperature for 4 hours. The reaction was quenched with 1 N HCl (25 mL), diluted with $Et_2O$ and then extracted with water. The organic layer was dried ($Na_2SO_4$) and the solvent was removed in vacuo to afford 0.548 g of crude product that was purified by preparative HPLC to afford 0.075 g (55%) of the title compound. 3H NMR (400 MHz, $CDCl_3$); HRMS (ES$^+$) m/z exact mass calculated for $C_{24}H_{28}O_5NClS_2Na$ 532.0995, found 532.1003.

EXAMPLE 76

(4-{2-[(Biphenyl-4-sulfonyl)-propyl-amino]-ethylsulfanyl}-2-methyl-phenoxy)-acetic acid

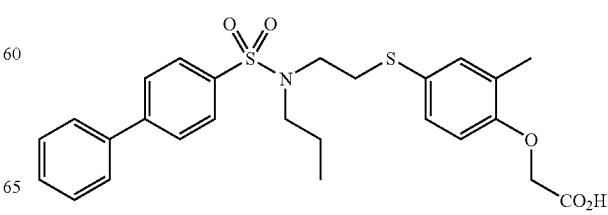

Step A

Biphenyl-4-sulfonic acid (2-hydroxy-ethyl)-propyl-amide

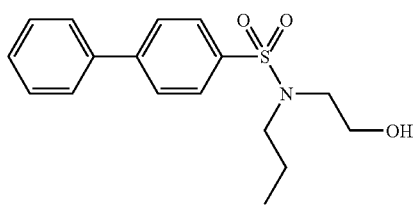

Procedure from Example 74, Step A was utilized with biphenyl-4-sulfonyl chloride to afford 3.34 g (88%) the title compound. $R_f$=0.38 (1/1 hexanes/acetone). MS (ES$^+$) m/z mass calculated for $C_{17}H_{21}O_3NS$ 319, found 320 (M+1, 100%).

Step B

Toluene-4-sulfonic acid 2-[(biphenyl-4-sulfonyl)-propyl-amino]-ethyl ester

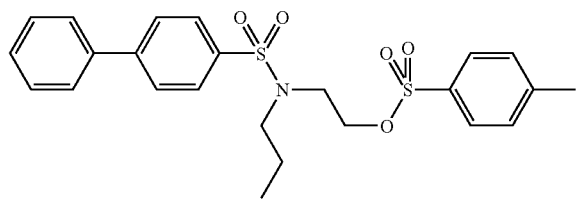

Procedure from Example 74, Step B was utilized with biphenyl-4-sulfonic acid (2-hydroxy-ethyl)-propyl-amide to afford 2.23 g (45%) of the title compound. $R_f$=0.46 (1/1 hexanes/acetone). MS (ES$^+$) m/=mass calculated for $C_{24}H_{27}O_5 NS_2$ 473, found 474 (M+1, 100%).

Step C

(4-{2-[(Biphenyl-4-sulfonyl)-propyl-amino]-ethyl-sulfanyl}-2-methyl-phenoxy)-acetic acid ethyl ester

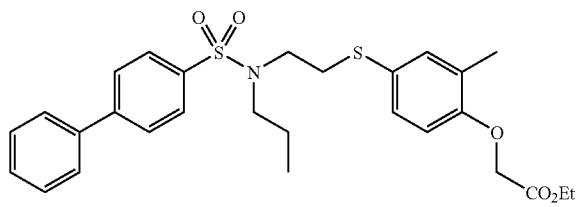

A solution of (4-mercapto-2-methyl-phenoxy)-acetic acid ethyl ester (0.51 g, 2.25 mmol) in dry DMF (8 mL) was purged with $N_2$ and then $Cs_2CO_3$ (0.80 g, 2.46 mmol) was added, and the resultant mixture purged with $N_2$ for 5 minutes more. Toluene-4-sulfonic acid 2-[(biphenyl-4-sulfonyl)-propyl-amino]-ethyl ester (0.53 g, 1.12 mmol) was added to the reaction, which was heated to 50° C. and stirred for 17 hours under $N_2$. The reaction was cooled, acidified with 1 N HCl (20 mL), diluted with $Et_2O$ and then extracted with water. The organic layer was dried ($Na_2SO_4$), and the solvent was removed in vacuo to afford crude product that was absorbed on silica gel and then column purified using 6/1 hexanes/ethyl acetate to afford 0.414 g (70%) of the title compound. $R_f$=0.24 (2/1 hexanes/ethyl acetate). MS (ES$^+$) m/z mass calculated for $C_{28}H_{33}O_2NS_2$ 527, found 528 (M+1, 100%).

Step D

(4-{2-[(Biphenyl-4-sulfonyl)-propyl-amino]-ethyl-sulfanyl}-2-methyl-phenoxy)-acetic acid A solution of (4-{2-[(biphenyl-4-sulfonyl)-propyl-amino]-ethylsulfanyl}-2-methyl-phenoxy)-acetic acid ethyl ester (0.414 g, 0.784 mmol) in THF (8 mL) was treated with 1 N LiOH (3.1 mL) and stirred at room temperature for 2.5 hours. The mixture was acidified with 1 N HCl (20 mL) and then diluted with EtOAc and extracted with water. The organic layer was dried ($Na_2SO_4$) and the solvent was removed in vacuo to afford 0.450 g (100%) of the title compound. HRMS (ES$^+$) m/z exact mass calculated for $C_{26}H_{29}O_5NS_2Na$ 522.1385, found 522.1392.

EXAMPLE 77

(2-Methyl-4-{2-[(4-phenoxy-benzenesulfonyl)-propyl-amino]-ethylsulfanyl}-phenoxy)-acetic acid

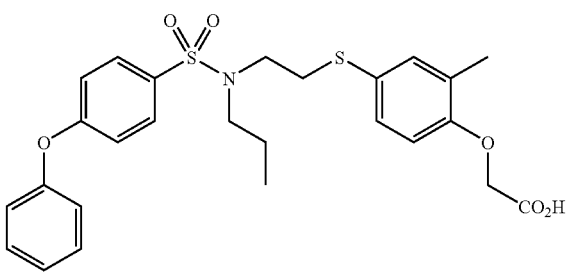

Step A

N-(2-Hydroxy-ethyl)-4-phenoxy-N-propyl-benzene-sulfonamide

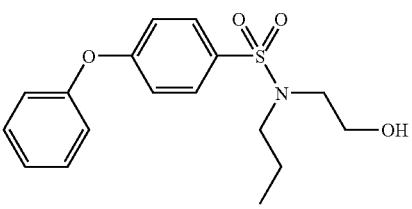

Procedure from Example 74, Step A was utilized with 4-phenoxy-benzenesulfonyl chloride to afford 4.07 g (100%) of the title compound. $R_f$=0.33 (1/1 hexanes/acetone). MS (ES$^+$) m/z mass calculated for $C_{17}H_{21}O_4NS$ 335, found 336 (M+1, 100%).

151

Step B

Toluene-4-sulfonic acid 2-[(4-phenoxy-benzenesulfonyl)-propyl-amino]-ethyl ester

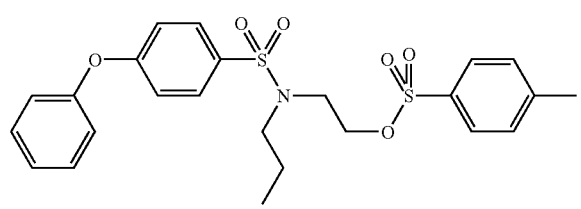

Procedure from Example 74, Step B was utilized with N-(2-hydroxy-ethyl)-4-phenoxy-N-propyl-benzenesulfonamide to afford 5.10 g (86%) of the title compound. $R_f$=0.48 (1/1 hexanes/acetone). MS (ES$^+$) m/z mass calculated for $C_{24}H_{27}O_6NS_2$ 489, found 490 (M+1, 100%).

Step C (2-Methyl-4-{2-[(4-phenoxy-benzenesulfonyl)-propyl-amino]-ethylsulfanyl}-phenoxy)-acetic acid ethyl ester

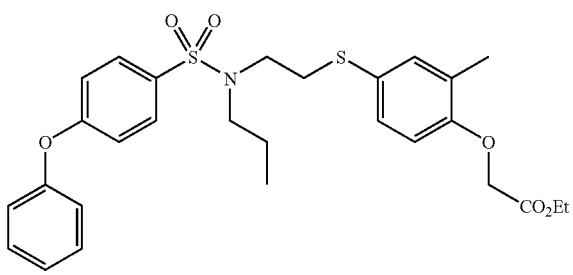

Procedure from Example 76. Step C was utilized with toluene-4-sulfonic acid 2-[(4-phenoxy-benzenesulfonyl)-propyl-amino]-ethyl ester to afford 0.163 g (27%) of the title compound. $R_f$=0.28 (2/1 hexanes/ethyl acetate). MS (ES$^+$) m/z mass calculated for $C_{28}H_{33}O_6NS_2$ 543, found 544 (M+1, 100%).

Step D (2-Methyl-4-{2-[(4-phenoxy-benzenesulfonyl)-propyl-amino]-ethylsulfanyl}-phenoxy)-acetic acid Procedure from Example 76. Step D was utilized with (2-methyl-4-{2[(4-phenoxy-benzenesulfonyl)-propyl-amino]-ethylsulfanyl}-phenoxy)-acetic acid ethyl ester to afford 0.13 g (85%) of the title compound. HRMS (ES$^+$) nm/Z exact mass calculated for $C_{26}H_{30}O_6NS_2Na$ 516.1515, found 516.1528.

152

EXAMPLE 78

(2-Methyl-4-{2-[propyl-(3-trifluoromethoxybenzenesulfonyl)-amino]-ethylsulfanyl}-phenoxy)-acetic acid

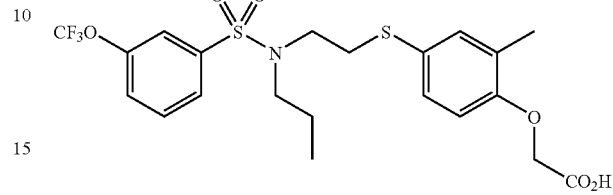

Step A

N-(2-Hydroxy-ethyl)-N-propyl-3-trifluoromethoxy-benzenesulfonamide

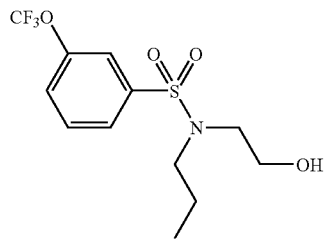

Procedure from Example 74, Step A was utilized with 3-trifluoromethoxy-benzenesulfonyl chloride to afford 1.19 g (95%) of the title compound. $R_f$=0.40 (1/1 hexanes/acetone). MS (ES$^+$) m/z mass calculated for $C_{12}H_{16}O_4NSF_3$ 327, found 328 (M+1, 100%).

Step B

Toluene-4-sulfonic acid 2-[propyl-(3-trifluoromethoxy-benzenesulfonyl)-amino]-ethyl ester

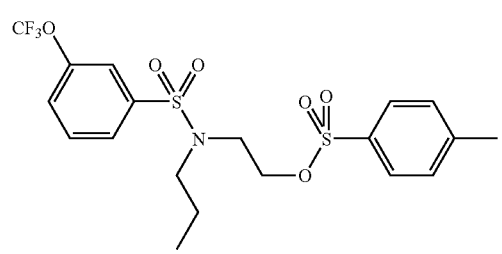

Procedure from Example 74. Step B was utilized with N-(2-hydroxy-ethyl)-N-propyl-3-trifluoromethoxy-benzenesulfonamide to afford 1.56 g (90%) of the title compound. $R_f$=0.48 (1/1 hexanes/acetone). MS (ES$^+$) m/z mass calculated for $C_{19}H_{22}O_6NS_2F_3$ 481, found 482 (M+1, 100%).

Step C (2-Methyl-4-{2-[propyl-(3-trifluoromethoxybenzenesulfonyl)-amino]-ethylsulfanyl}-phenoxy)-acetic acid ethyl ester

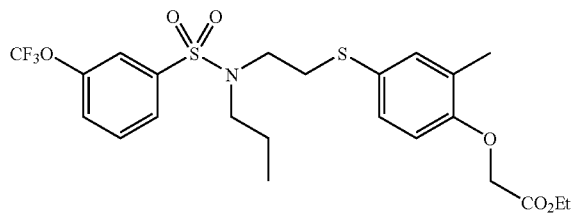

Procedure from Example 76, Step C was utilized with toluene-4-sulfonic acid toluene-4-sulfonic acid 2-[propyl-(3-trifluoromethoxy-benzenesulfonyl)-amino]-ethyl ester to afford 0.425 g (72%) of the title compound. $R_f$=0.26 (2/1 hexanes/ethyl acetate). MS (ES$^+$) m/z mass calculated for $C_{23}H_{28}O_6NS_2F_3$ 535, found 536 (M+1, 100%).

Step D (2-Methyl-4-{2-[propyl-(3-trifluoromethoxybenzenesulfonyl)-amino]-ethylsulfanyl}-phenoxy)-acetic acid Procedure from Example 76, Step D was utilized with (2-methyl-4-{2-[propyl-(3-trifluoromethoxybenzenesulfonyl)-amino]-ethylsulfanyl}-phenoxy)-acetic acid ethyl ester to afford 0.438 g (100%) of the title compound. HRMS (ES$^+$) m/z exact mass calculated for $C_{21}H_{24}O_6NS_2F_3Na$ 530.0895, found 530.0902.

EXAMPLE 79

3-(4-{2-[(5-Fluoro-3-methyl-benzo[b]thiophene-2-sulfonyl)-propyl-amino]-ethoxy}-2-methyl-phenyl)-propionic acid

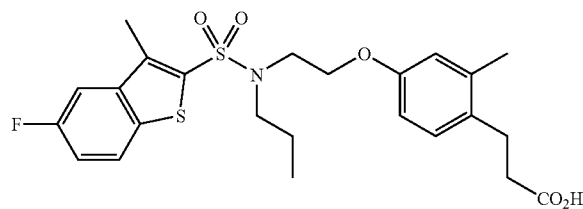

Step A

Toluene-4-sulfonic acid 2-[(5-fluoro-3-methyl-benzo[b]thiophene-2-sulfonyl)-propyl-amino]-ethyl ester

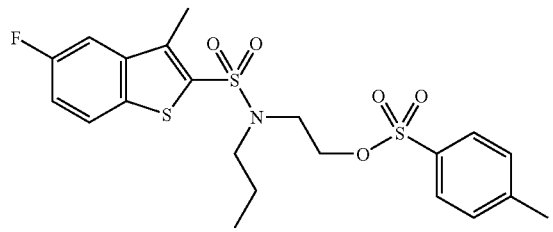

The procedure for Example 74, Steps A and B were utilized to afford 0.479 g (87%) of the title compound. $R_f$=0.53 (1/1 hexanes/acetone).

Step B 3-(4-{2-[(5-Fluoro-3-methyl-benzo[b]thiophene-2-sulfonyl)-propyl-amino]-ethoxy}-2-methyl-phenyl)-propionic acid methyl ester

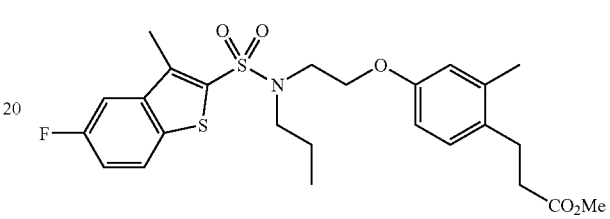

A mixture of 3-(4-hydroxy-2-methyl-phenyl)-propionic acid methyl ester (0.040 g, 0.206 mmol), toluene-4-sulfonic acid 2-[(5-fluoro-3-methyl-benzo[b]thiophene-2-sulfonyl)-propyl-amino]-ethyl ester (0.100 g, 0.206 mmol) and $Cs_2CO_3$ (0.100 g, 0.307 mmol) in dry DMF (10 mL) was stirred at 65° C. for 3 hours under $N_2$. The reaction was cooled and quenched with 1 N HCl (10 mL). The mixture was diluted with water and extracted with $Et_2O$. The organic layer was dried ($Na_2SO_4$) and the solvent was removed in vacuo to afford crude product that was purified by column chromatography using 8/1 hexanes/acetone to afford 0.097 g (92%) of the title compound. $R_f$=0.53 (1/1 hexanes/acetone). HRMS (ES$^+$) m/z exact mass calculated for $C_{25}H_{30}O_5NS_2F$ 507, found 508 (M+1, 100%).

Step C 3-(4-{2-[(5-Fluoro-3-methyl-benzo[b]thiophene-2-sulfonyl)-propyl-amino]-ethoxy}-2-methyl-phenyl)-propionic acid A solution of 3-(4-{2-[(5-fluoro-3-methyl-benzo[b]thiophene-2-sulfonyl)-propyl-amino]-ethoxy}-2-methyl-phenyl)-propionic acid methyl ester (0.096, 0.189 mmol) in EtOH (10 mL) was treated with 5 N NaOH (0.5 mL) and heated to reflux for 2 hours. The reaction was cooled and the solvent removed in vacuo to afford a residue that was quenched with 1 N HCl (10 mL). The mixture was diluted with water and then extracted with $CH_2Cl_2$. The organic layer was dried ($Na_2SO_4$) and the solvent was removed in vacuo to afford 0.077 g (83%) of the title compound. HRMS (ES$^-$) m/z exact mass calculated for $C_{24}H_{27}O_5NS_2F$ 492.1315, found 492.1317.

EXAMPLE 80

(4-{2-[(5-Fluoro-3-methyl-benzo[b]thiophene-2-sulfonyl)-propyl-amino]-ethoxy}-2-methyl-phenoxy)-acetic acid

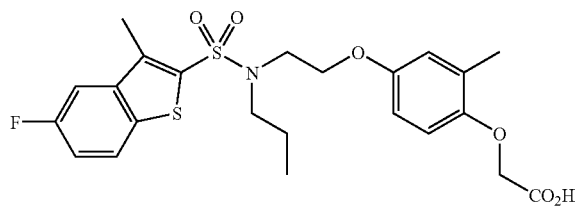

Step A (4-{2-[(5-Fluoro-3-methyl-benzo[b]thiophene-2-sulfonyl)-propyl-amino]-ethoxy}-2-methyl-phenoxy)-acetic acid methyl ester

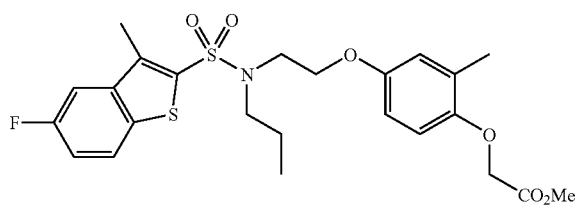

A mixture of (4-hydroxy-2-methyl-phenoxy)-acetic acid methyl ester (0.050 g, 0.255 mmol), toluene-4-sulfonic acid 2-[(5-fluoro-3-methyl-benzo[b]thiophene-2-sulfonyl)-propyl-amino]-ethyl ester (0.115 g, 0.237 mmol) and $Cs_2CO_3$ (0.116 g, 0.356 mmol) in dry DMF (10 mL) was stirred at 65° C. for 3 hours under $N_2$. The reaction was cooled and quenched with 1 N HCl (10 mL). The mixture was diluted with water and extracted with $Et_2O$. The organic layer was dried ($Na_2SO_4$) and the solvent was removed in vacuo to afford crude product that was purified by column chromatography using 8/1 hexanes/acetone to afford 0.084 g (68%) of the title compound. $R_f$=0.56 (1/1 hexanes/acetone). MS ($ES^+$) m/z mass calculated for $C_{24}H_{28}O_6NS_2F$ 509, found 510 (M+1, 100%).

Step B (4-{2-[(5-Fluoro-3-methyl-benzo[b]thiophene-2-sulfonyl)-propyl-amino]-ethoxy}-2-methyl-phenoxy)-acetic acid A solution of (4-{2-[(5-fluoro-3-methyl-benzo[b]thiophene-2-sulfonyl)-propyl-amino]-ethoxy}-2-methyl-phenoxy)-acetic acid methyl ester (0.084, 0.165 mmol) in EtOH (10 mL) was treated with 5 N NaOH (0.5 mL) and heated to reflux for 2 hours. The reaction was cooled and the solvent was removed in vacuo to afford a residue that was quenched with 1 N HCl (10 mL). The mixture was diluted with water and then extracted with $CH_2Cl_2$. The organic layer was dried ($Na_2SO_4$) and the solvent removed in vacuo to afford 0.072 g (88%) of the title compound. HRMS ($ES^+$) m/z exact mass calculated for $C_{23}H_{27}O_6NS_2F$ 496.1264, found 496.1274.

EXAMPLE 81

3-(4-{2-[(5-Fluoro-3-methyl-benzo[b]thiophene-2-sulfonyl)-propyl-amino]-ethoxy}-phenyl)-2-methoxy-propionic acid

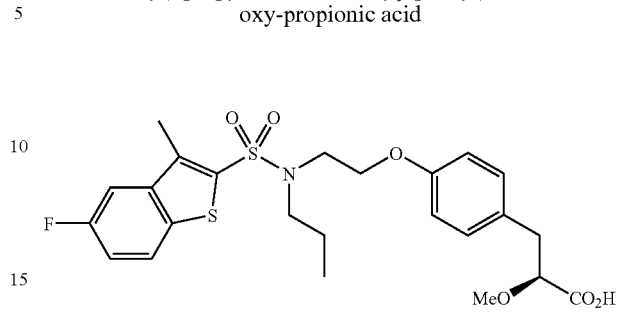

Step A 3-(4-{2-[(5-Fluoro-3-methyl-benzo[b]thiophene-2-sulfonyl)-propyl-amino]-ethoxy}-phenyl)-2-methoxy-propionic acid ethyl ester

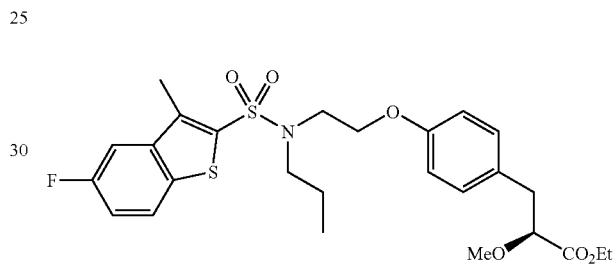

A mixture of 3-(4-hydroxy-phenyl)-2-methoxy-propionic acid ethyl ester (0.037 g, 0.165 mmol), toluene-4-sulfonic acid 2-[(5-fluoro-3-methyl-benzo[b]thiophene-2-sulfonyl)-propyl-amino]-ethyl ester (0.080 g, 0.165 mmol) and $Cs_2CO_3$ (0.080 g, 0.246 mmol) in dry DMF (10 mL) was stirred at 45° C. for 17 hours under $N_2$. The reaction was cooled and quenched with 1 N HCl (10 mL). The mixture was diluted with water and extracted with $Et_2O$. The organic layer was dried ($Na_2SO_4$) and the solvent was removed in vacuo to afford crude product that was purified by column chromatography using 6/1 hexanes/acetone to afford 0.072 g (82%) of the title compound. $R_f$=0.56 (1/1 hexanes/acetone). MS ($ES^+$) 777/z mass calculated for $C_{26}H_{32}O_6NS_2F$ 537, found 538 (M+1,100%).

Step B 3-(4-{2-[(5-Fluoro-3-methyl-benzo[b]thiophene-2-sulfonyl)-propyl-amino]-ethoxy}-phenyl)-2-methoxy-propionic acid A solution of 3-(4-{2-[(5-fluoro-3-methyl-benzo[b]thiophene-2-sulfonyl)-propyl-amino]-ethoxy}phenyl)-2-methoxy-propionic acid ethyl ester (0.072, 0.134 mmol) in EtOH (6 mL) was treated with 5 N NaOH (0.25 mL) and stirred at room temperature for 4 hours. The reaction was cooled and the solvent was removed in vacuo to afford a residue that was quenched with 1 N HCl (10 mL). The mixture was diluted with water and then extracted with ethyl acetate. The organic layer was dried ($Na_2SO_4$) and the solvent was removed in vacuo to afford 0.058 g (85%) of the title compound. MS (ES⁺) m/z mass calculated for C$_{24}$H$_{28}$O$_6$NS$_2$F 509, found 510 (M+1, 100%).

EXAMPLE 82

(4-{2-[(4-tert-Butyl-benzenesulfonyl)-propyl-amino]-ethoxy}-2-methyl-phenylsulfanyl)-acetic acid

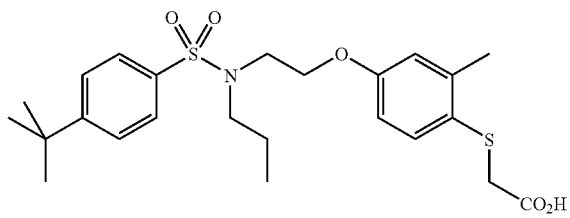

Step A

Toluene-4-sulfonic acid 2-[(4-tert-butyl-benzene-sulfonyl)-propyl-amino]-ethyl ester

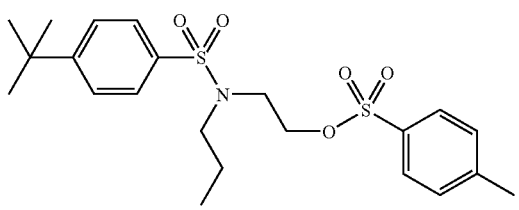

The procedure for Example 74, Steps A and B were utilized to afford 2.81 g (100%) of the title compound. R$_f$=0.57 (1/1 hexanes/acetone). MS (ES⁺) m/z mass calculated for C$_{22}$H$_{31}$O$_5$NS$_2$ 453, found 454 (M+1, 100%).

Step B (4-{2-[(4-tert-Butyl-benzenesulfonyl)propyl-amino]-ethoxy}-2-methyl-phenylsulfanyl)-acetic acid methyl ester

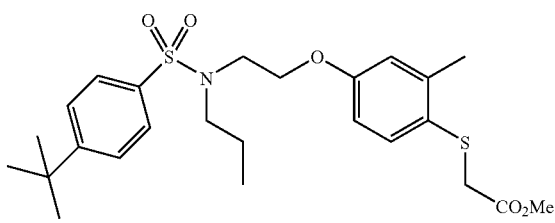

A mixture of (4-mercapto-2-methyl-phenoxy)-acetic acid ethyl ester (0.39 g, 1.72 mmol), toluene-4-sulfonic acid 2-[(4-tert-butyl-benzenesulfonyl)-propyl-amino]-ethyl ester (0.703 g, 1.55 mmol) and Cs$_2$CO$_3$ (0.720 g. 2.21 mmol) in dry DMF (10 mL) was purged with N$_2$ and then stirred at room temperature for 17 hours and then heated to 50° C. for 1 hour under N, The reaction was cooled and acidified with 1 N HCl. The mixture was diluted with water and extracted with Et$_2$O. The organic layer was dried (Na$_2$SO$_4$) and the solvent was removed in vacuo to afford crude product that was absorbed on silica gel and purified by column chromatography using 6/1 hexanes/acetone to afford 0.206 g (26%) of the title compound. R$_f$=0.51 (1/1 hexanes/acetone). MS(ES⁺) m/z mass calculated for C$_{26}$H$_{37}$O$_5$NS$_2$ 507, found 508 (M+1, 100%).

Step C (4-{2-[(4-tert-Butyl-benzenesulfonyl)-propyl-amino]-ethoxy}-2-methyl-phenylsulfanyl)-acetic acid A solution of (4-{2-[(4-tert-butyl-benzenesulfonyl)-propyl-amino]-ethoxy}-2-methyl-phenylsulfanyl)-acetic acid methyl ester (0.206, 0.406 mmol) in THF (10 mL) was treated with 1 N LiOH (2 mL) was stirred at room temperature for 2.5 hours. The reaction was acidified with 1 N HCl, the mixture was diluted with water, and the mixture extracted with ethyl acetate. The organic layer was dried (Na$_2$SO$_4$) and the solvent was removed in vacuo to afford 0.210 g (100%) of the title compound. HRMS (ES⁺) m/z exact mass calculated for C$_{24}$H$_{33}$O$_5$NS$_2$Na 502.1698, found 502.1700.

EXAMPLE 83

(4-{2-[(5-Chloro-3-methyl-benzo[b]thiophene-2-sulfonyl)-propyl-amino]-ethoxy}-2-methyl-phenyl-sulfanyl)-acetic acid

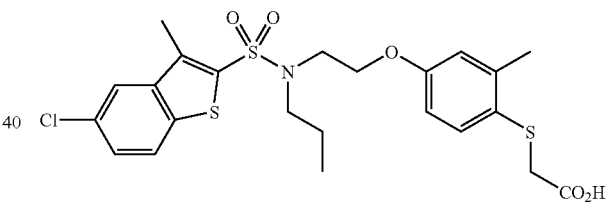

Step A 4-benzyloxy-2-methyl-1-methylsulfanyl-benzene

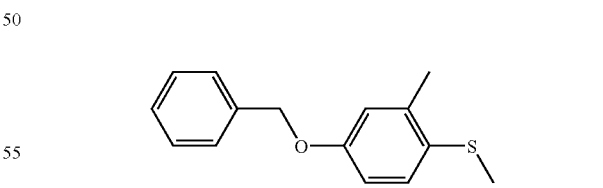

A mixture of 4-(methylthio)-m-cresol (10 g, 64.8 mmol) and 325 mesh K$_2$CO$_3$ (11.65 g. 84.3 mmol) in DMF (100 mL) was treated with benzyl bromide (12.22 g. 71.5 mmol) and stirred at room temperature for 17 hr under N$_2$. The mixture was filtered using Et$_2$O to rinse the solids and the filtrate was acidified with 1 N HCl (65 mL). The filtrate was diluted with more Et$_2$O and then extracted with twice with water and brine. The organic layer was dried (Na$_2$SO$_4$) and the solvent was removed in vacuo to afford 17.03 g (100%) crude title compound, which was carried on without purification. R$_f$=0.66 (1/1 hexanes/acetone).

Step B

1-Methanesulfinyl-4-benzyloxy-2-methyl-benzene

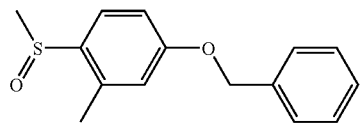

A 0° C. solution of crude compound obtained in Step A (17.03 g, 64.8 mmol) in chloroform (300 mL) was treated with about 77% m-chloroperbenzoic acid (14.53 g, 64.8 mmol) in portions over 10 minutes. The reaction was stirred at 0° C. for 20 minutes and monitored closely by TLC (1/1 hexanes/acetone) until the crude compound (Step A) was gone (R$_f$=0.66) and the sulfoxide formed (R$_f$=0.27). The reaction mixture was extracted with saturated NaHCO$_3$ and then saturated NaHSO$_3$. The organic layer was dried (MgSO$_4$) and the solvent was removed in vacuo to afford 18.32 g (100%) crude title compound that was carried on without purification. R$_f$=0.27 (1/1 hexanes/acetone).

Step C (4-benzyloxy-2-methyl-phenylsulfanyl)-acetic acid ethyl ester

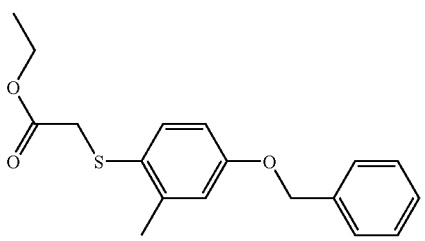

A solution of crude Step B (18.32 g, 64.8 mmol) in CH$_2$Cl$_2$ (250 mL) was treated with trifluoroacetic anhydride (27.2 g, 0.130 mol) and the resultant purple solution was heated to reflux for 30 minutes under N$_2$ to afford a brown colored solution. The reaction was cooled and the solvent was removed in vacuo to give 25.21 g (100%) of Pummerer product that was carried on without purification. R$_f$=0.66 (1/1 hexanes/acetone).

The crude α-trifluoroacetoxy sulfide (25.21 g, assume 64.8 mmol) was combined with bromoethyl acetate (59.02 g. 0.353 mol) in EtOH (230 mL) and purged with N$_2$ for 5 minutes. Potassium carbonate (325 mesh, 32.56 g, 0.236 mol) was added and the reaction mixture stirred for 17 hours at room temperature under N$_2$. The reaction mixture was filtered using Et$_2$O to rinse the solids and the filtrate was acidified with 1 N HCl (100 mL). The filtrate was diluted with more Et$_2$O and extracted with water. The organic layer was dried (Na$_2$SO$_4$) and the solvent was removed in vacuo to afford crude product that was absorbed on silica gel and purified by flash chromatography using 10/1 hexanes/acetone to afford 6.45 g (35%) of the title compound. R$_f$=0.43 (2/1 hexanes/acetone).

Step D (4-Hydroxy-2-methyl-phenylsulfanyl)-acetic acid ethyl ester

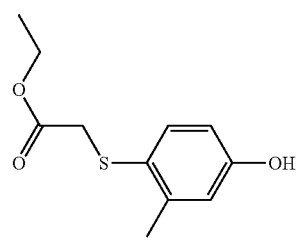

A −78° C. solution of Step C (6.44 g, 20.4 mmol) and dimethylethylsilane (17.96 g, 0.203 mol) in CH$_2$Cl$_2$ (150 mL) was treated dropwise with a 1 M solution of TiCl$_4$ in CH$_2$Cl$_2$ (20.4 mL, 20.4 mmol). The reaction mixture was warmed to 0° C. and then room temperature for 3 hours. The reaction was quenched with water and extracted with EtOAc. The organic layer was dried (Na$_2$SO$_4$) and the solvent was removed in vacuo to afford crude product that was absorbed on silica gel and purified by flash chromatography using 98/2 CH$_2$Cl$_2$/acetonitrile to afford 2.96 g (64%) of the title compound. R$_f$=0.28 (2/1 hexanes/acetone).

Step E (4-{2-[(5-Chloro-3-methyl-benzo[b]thiophene-2-sulfonyl)-propyl-amino]-ethoxy}-2-methyl-phenyl-sulfanyl)-acetic acid ethyl ester

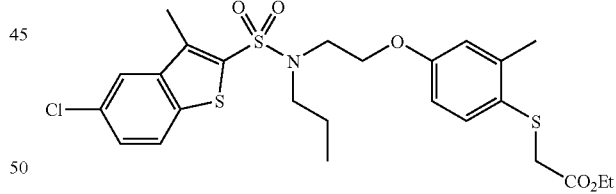

A mixture of (4-hydroxy-2-methyl-phenylsulfanyl)-acetic acid ethyl ester (0.090 g, 0.398 mmol), toluene-4-sulfonic acid 2-[(5-chloro-3-methyl-benzo[b]thiophene-2-sulfonyl)-propyl-amino]-ethyl ester (0.219 g, 0.436 mmol) and Cs$_2$CO$_3$ (0.194 g, 0.595 mmol) in dry DMF (10 mL) was stirred at 50° C. for 17 hours under N$_2$. The reaction was cooled, quenched with 1 N HCl (10 mL), diluted with water and extracted with Et$_2$O. The organic layer was dried (Na$_2$SO$_4$) and the solvent was removed in vacuo to afford crude product that was absorbed on silica gel and purified by column chromatography using 6/1 hexanes/acetone afford 0.131 g (59%) of the title compound. R$_f$=0.23 (2/1 hexanes/acetone). MS (ES$^+$) m/z mass calculated for C$_{25}$H$_{30}$O$_5$NClS$_3$ 555, found 556 and 558 (M+1 and M+3, 100%).

Step F (4-{2-[(5-Chloro-3-methyl-benzo[b]thiophene-2-sulfonyl)-propyl-amino]-ethoxy}-2-methyl-phenyl-sulfanyl)-acetic acid A solution of (4-{2-[(5-chloro-3-methyl-benzo[b]thiophene-2-sulfonyl)-propyl-amino]-ethoxy}-2-methyl-phenylsulfanyl)-acetic acid ethyl ester (0.131 g, 0.236 mmol) in THF (8 mL) was treated with 1 N LiOH (1.5 mL) and stirred at room temperature for 4 hours. The reaction was quenched with 1 N HCl (20 mL), diluted with ethyl acetate and then extracted with water. The organic layer was dried ($Na_2SO_4$) and the solvent was removed in vacuo to afford 0.128 g (100%) of the title compound that was further purified by preparative HPLC to afford 0.059 pure title compound (48%). MS (ES$^+$) m/z mass calculated for $C_{23}H_{26}O_5NClS_3$ 527, found 526 and 528 (M−1 and M+1, 100%).

EXAMPLE 84

(4-{3-[(5-Chloro-3-methyl-benzo[b]thiophene-2-sulfonyl)-propyl-amino]-propyl}-phenoxy)-acetic acid

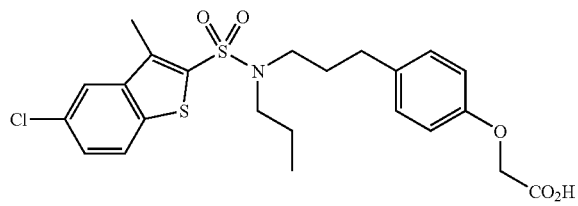

Step A

[4-(3-Hydroxy-propyl)-phenoxy]-acetic acid ethyl ester ethyl ester

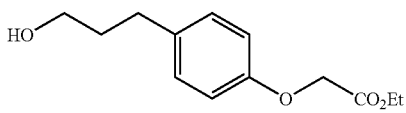

A mixture of 3-(4-hydroxyphenyl)-1-propanol (10.0 g, 65.7 mmol), ethylbromoacetate (32.9 g, 0.197 mol) and 325 mesh $K_2CO_3$ (13.6 g, 98.4 mmol) in ethanol (150 mL) was heated to reflux for 1.5 hours under $N_2$. The reaction was cooled, filtered and the filtrate was quenched with 1 N HCl (100 mL). The filtrate was diluted with water and extracted with ethyl acetate. The organic layer was dried ($Na_2SO_4$) and the solvent was removed in vacuo to afford crude product that was purified by column chromatography using 6/1 hexanes/acetone afford 13.13 g (84%) of the title compound. $R_f$=0.33 (1/1 hexanes/acetone).

Step B

{4-[3-(Toluene-4-sulfonyloxy)-propyl]-phenoxy}-acetic acid ethyl ester

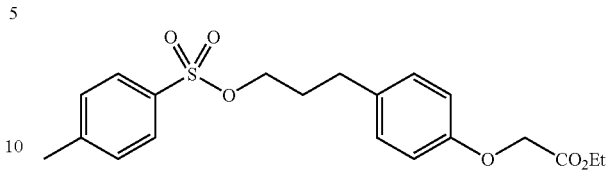

A solution of [4-(3-hydroxy-propyl)-phenoxy]-acetic acid ethyl ester ethyl ester (2.00 g, 8.39 mmol), pyridine (2.66 g, 33.6 mmol) and N,N-dimethylaminopyridine (0.31 g. 2.54 mmol) in $CH_2Cl_2$ (75 mL) was treated with p-toluenesulfonic anhydride (5.48 g. 16.8 mmol) and the reaction stirred at room temperature under $N_2$ for 3 hours. The reaction was quenched with 1 N HCl (50 mL) and diluted with more $CH_2Cl_2$ and extracted with water. The organic layer was dried ($Na_2SO_4$) and the solvent was removed in vacuo to afford crude product that was purified by column chromatography using 6/1 hexanes/acetone to afford 2.78 g (84%) of the title compound. $R_f$=0.47 (1/1 hexanes/acetone).

Step C (4-{3-[(5-Chloro-3-methyl-benzo[b]thiophene-2-sulfonyl)-propyl-amino]-propyl}-phenoxy)-acetic acid A mixture of {4-[3-(toluene-4-sulfonyloxy)-propyl]-phenoxy}-acetic acid ethyl ester (0.26 g, 0.662 mmol), 5-chloro-3-methyl-benzo[b]thiophene-2-sulfonic acid propylamide (0.200 g, 0.662 mmol) and $Cs_2CO_3$ (0.280 g, 0.859 mmol) in DMF (10 mL) was stirred at 50° C. for 4 hours. The reaction mixture was cooled and acidified with 1 HCl (10 mL). The mixture was diluted with water and then extracted with $Et_2O$. The organic layer was dried ($Na_2SO_4$) and the solvent was removed in vacuo to afford crude product that was dissolved in EtOH (15 mL) and treated with 5 N NaOH (1 mL). The reaction mixture was stirred for 2 hours at room temperature. The solvent was removed in vacuo to afford a residue that was acidified with 1 N HCl (10 mL). The mixture was diluted with $CH_2Cl_2$ and then extracted with water. The organic layer was dried ($Na_2SO_4$) and the solvent was removed in vacuo to afford crude product that was purified by column chromatography using a gradient of 3/1 hexanes/acetone then 100% acetone to afford 0.070 g (21%) of the title compound. HRMS (ES$^+$) 77/exact mass calculated for $C_{23}H_{27}O_5NClS_2$ 496.1019, found 496.1031.

EXAMPLE 85

(4-{3-[(5-Chloro-3-methyl-benzo[b]thiophene-2-sulfonyl)-propyl-amino]-propyl}-2-methyl-phenoxy)-acetic acid

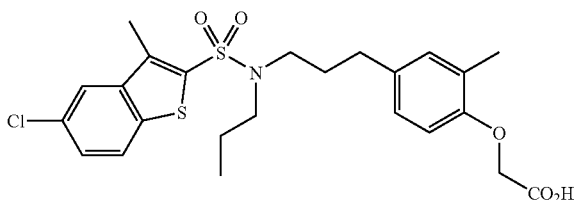

Step A

[4-(3-Hydroxy-propyl)-2-iodo-phenoxy]-acetic acid ethyl ester

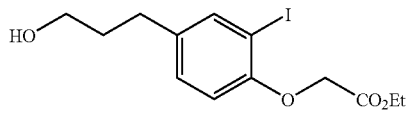

A mixture of [4-(3-hydroxy-propyl)-phenoxy]-acetic acid ethyl ester ethyl ester (0.50 g, 2.09 mmol), silver sulfate (1.31 g, 4.20 mol) and iodine (1.07 g, 4.22 mmol) in ethanol (10 mL) was stirred at room temperature for 17 hours under $N_2$. The reaction mixture was filtered the solvent was removed in vacuo to afford crude product that was purified by column chromatography using 3/1 hexanes/acetone afford 0.24 g (31%) of the title compound. $R_f$=0.21 (2/1 hexanes/acetone).

Step B

[4-(3-Hydroxy-propyl)-2-methyl-phenoxy]-acetic acid ethyl ester

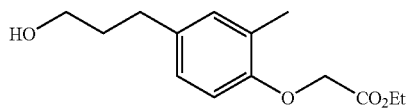

A mixture of [4-(3-hydroxy-propyl)-2-iodo-phenoxy]-acetic acid ethyl ester (0.23 g, 0.632 mmol), methylboronic acid (0.113 g. 1.89 mol) and cesium fluoride (0.34 g, 2.24 mmol) in 1,4-dioxane (4 mL) was stirred at room temperature and purged with $N_2$ for 3 minutes. The reaction was treated with 1,1' bis(diphenylphosphino) ferrocene palladium (II) chloride, $CH_2Cl_2$ complex (0.040 g) and then stirred at 80° C. for 1 hour under $N_2$. The reaction mixture was cooled and the solvent was removed in vacuo to afford crude product that was absorbed on silica gel and purified by column chromatography using 3/1 hexanes/acetone afford 0.086 g (54%) of the title compound. $R_f$=0.37 (1/1 hexanes/acetone).

Step C

{2-Methyl-4-[3-(toluene-4-sulfonyloxy)-propyl]-phenoxy}-acetic acid ethyl ester

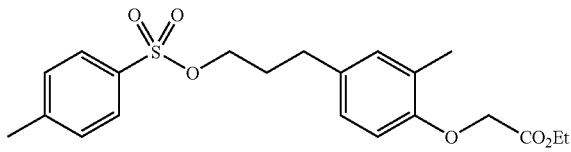

A solution of [4-(3-hydroxy-propyl)-2-methyl-phenoxy]-acetic acid ethyl ester (0.086 g, 0.341 mmol), pyridine (0.108 g, 1.36 mmol) and N,N-dimethyl-aminopyridine (0.012 g, 0.098 mmol) in $CH_2Cl_2$ (8 mL) was treated with p-toluene-sulfonic anhydride (0.222 g, 0.680 mmol) and the reaction stirred at room temperature for 1 hour under 2. The reaction was quenched with 1 N HCl (5 mL) and diluted with more $CH_2Cl_2$ and extracted with water. The organic layer was dried ($Na_2SO_4$) and the solvent was removed in vacuo to afford crude product that was purified by column chromatography using 6/1 hexanes/acetone to afford 0.117 g (84%) of the title compound. $R_f$=0.49 (1/1 hexanes/acetone). MS (ES$^+$) m/z mass calculated for $C_{21}H_{26}O_6S$ 406, found 424 (M+NH$_4$).

Step D (4-{3-[(5-Chloro-3-methyl-benzo[b]thiophene-2-sulfonyl)-propyl-amino]-propyl}-2-methyl-phenoxy)-acetic acid A mixture of {2-methyl-4-[3-(toluene-4-sulfonyloxy)-propyl]-phenoxy}-acetic acid ethyl ester (0.117 g, 0.288 mmol), 5-chloro-3-methyl-benzo[b]thiophene-2-sulfonic acid propylamide (0.087 g, 0.286 mmol) and $Cs_2CO_3$ (0.122 g, 0.374 mmol) in DMF (8 mL) was stirred at 50° C. for 3 hours. The reaction mixture was cooled and acidified with 1 HCl (10 mL). The mixture was diluted with water and then extracted with $Et_2O$. The organic layer was dried ($Na_2SO_4$) and the solvent was removed in vacuo to afford 0.495 g of crude product that was dissolved in EtOH (10 mL) and treated with 5 N NaOH (1.5 mL). The reaction mixture was stirred for 2 hours at room temperature. The solvent was removed in vacuo to afford a residue that was acidified with 1 N HCl (10 mL). The mixture was diluted with $Et_2O$ and then extracted with water. The organic layer was dried ($Na_2SO_4$) and the solvent was removed in vacuo to afford 0.162 g of crude product that was purified by preparative HPLC to afford 0.049 g (33%) of the title compound. HRMS (ES$^+$) m/z exact mass calculated for $C_{24}H_{29}O_5NClS_2$ 510.1176, found 510.1184.

EXAMPLE 86

(4-{3-[(5-Chloro-3-methyl-benzo[b]thiophene-2-sulfonyl)-methyl-amino]-propyl}-2-methyl-phenoxy)-acetic acid

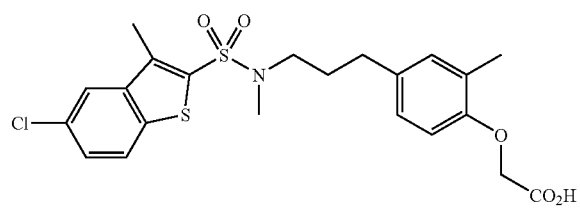

Step A (4-{3-[(5-Chloro-3-methyl-benzo[b]thiophene-2-sulfonyl)-methyl-amino]-propyl}-2-methyl-phenoxy)-acetic acid ethyl ester

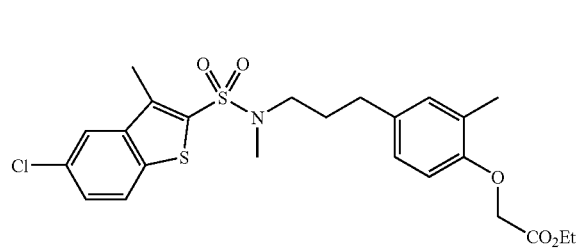

A mixture of {2-methyl-4-[3-(toluene-4-sulfonyloxy)-propyl]-phenoxy}-acetic acid ethyl ester (0.120 g, 0.295 mmol). 5-chloro-3-methyl-benzo[b]thiophene-2-sulfonic acid methylamide (0.081 g, 0.294 mmol) and Cs$_2$CO$_3$ (0.125 g, 0.384 mmol) in DMF (8 mL) was stirred at 50° C. for 4 hours. The reaction mixture was cooled and acidified with 1 HCl (3 mL). The mixture was diluted with water and then extracted with Et$_2$O. The organic layer was dried (Na$_2$SO$_4$) and the solvent was removed in vacuo to afford crude product that was purified by column chromatography using 6/1 hexanes/acetone to afford 0.127 g (85%) of the title compound. R$_f$=0.54 (1/1 hexanes/acetone). MS (ES$^+$) m/z mass calculated for C$_{24}$H$_{28}$O$_5$NClS$_2$ 509, found 510 and 512 (M+1 and M+3, 100%).

Step B (4-{3-[(5-Chloro-3-methyl-benzo[b]thiophene-2-sulfonyl)-methyl-amino]-propyl}-2-methyl-phenoxy)-acetic acid A solution of (4-{3-[(5-chloro-3-methyl-benzo[b]thiophene-2-sulfonyl)-methyl-amino]-propyl}-2-methyl-phenoxy)-acetic acid ethyl ester (0.124 g, 0.243 mmol) in THF (6 mL) and treated with 1 N LiOH (1.2 mL). The reaction mixture was stirred for 2 hours at room temperature. The mixture was acidified with 1 N HCl (10 mL), dilute with water, and extracted with ethyl acetate. The organic layer was dried (Na$_2$SO$_4$) and the solvent was removed in vacuo to afford 0.118 g (100%) of the title compound. HRMS (ES$^+$) m/z mass calculated for C$_{22}$H$_{25}$O$_5$NClS$_2$ 482.0863, found 482.0874.

EXAMPLE 87

{4-[3-(5-Chloro-3-methyl-benzo[b]thiophene-2-sulfonylamino)-propyl]-2-methyl-phenoxy}-acetic acid

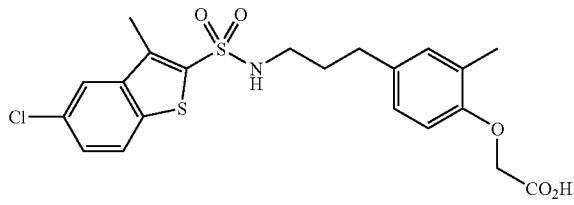

Step A

5-Chloro-3-methyl-benzo[b]thiophene-2-sulfonic acid amide

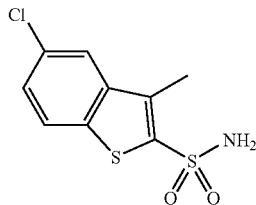

A solution of 29% ammonium hydroxide (5 mL) in THF (30 mL) was treated with 5-chloro-3-methyl-benzo[b]thiophene-2-sulfonyl chloride (1.50 g, 5.33 mmol) and stirred at room temperature for 30 minutes under N. The mixture was diluted with water and extracted with ethyl acetate. The organic layer was dried (Na$_2$SO$_4$) and the solvent was removed in vacuo to afford 1.37 g (98%) of the title compound that was utilized without further purification. R$_f$=0.46 (1/hexanes/acetone). MS (ES$^-$) m/z mass calculated for C$_9$H$_8$O$_2$NS$_2$Cl 261, found 260 and 262 (M−1 and M+1, 100%).

Step B

{4-[3-(5-Chloro-3-methyl-benzo[b]thiophene-2-sulfonylamino)-propyl]-2-methyl-phenoxy}-acetic acid ethyl ester

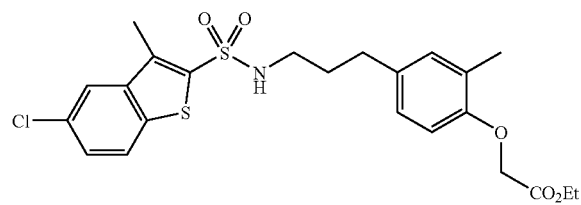

A mixture of {2-methyl-4-[3-(toluene-4-sulfonyloxy)-propyl]-phenoxy}-acetic acid ethyl ester (0.259 g, 0.637 mmol), 5-chloro-3-methyl-benzo[b]thiophene-2-sulfonic acid amide (0.167 g, 0.637 mmol) and Cs$_2$CO$_3$ (0.270 g, 0.829 mmol) in DMF (20 mL) was stirred at 50° C. for 17 hours. The reaction mixture was cooled and acidified with 1 HCl (20 mL). The mixture was diluted with water and then extracted with Et$_2$O. The organic layer was dried (Na$_2$SO$_4$) and the solvent removed in vacuo to afford 0.495 g of crude product that was purified by column chromatography using a gradient of 8/1 to 4/1 hexanes/acetone to afford 0.129 g (41%). MS (ES$^-$) m/z mass calculated for C$_{22}$H$_{26}$O$_5$NClS$_2$ 495, found 494 and 496 (M−1 and M+1, 100%).

Step C

{4-[3-(5-Chloro-3-methyl-benzo[b]thiophene-2-sulfonylamino)-propyl]-2-methyl-phenoxy}-acetic acid A solution of (4-{3-[(5-chloro-3-methyl-benzo[b]thiophene-2-sulfonyl)-propyl-amino]-propyl}-2-methyl-phenoxy)-acetic acid (0.095 g, 0.192 mmol) in THF (4 ml) and treated with 1 N LiOH (1 mL). The reaction mixture was stirred for 2 hours at room temperature. The mixture was acidified with 1 N HCl (6 mL), dilute with water, and extracted with ethyl acetate. The organic layer was dried (Na$_2$SO$_4$) and the solvent was removed in vacuo to afford 0.092 g (100%) of the title compound. MS (ES$^+$) m/z mass calculated for C$_{21}$H$_{22}$O$_5$NClS$_2$ 467, found 468 and 470 (M+1 and M+3, 100%).

EXAMPLE 88

(4-{2-[(5-Chloro-3-methyl-benzo[b]thiophene-2-sulfonyl)-propyl-amino]-1-methyl-ethoxy}-2-methyl-phenoxy)-acetic acid

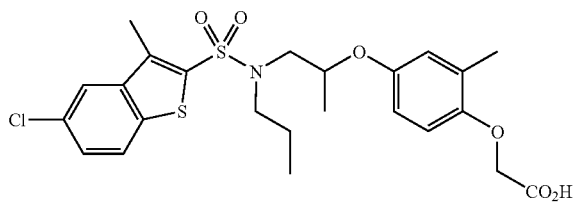

Step A

5-Chloro-3-methyl-benzo[b]thiophene-2-sulfonic acid (2-hydroxy-propyl)-propyl-amide

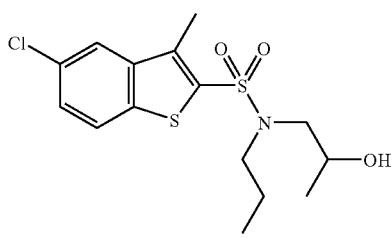

A 0° C. solution of 1-amino-2-propanol (0.59 g, 7.86 mmol) and triethylamine (1.44 g, 14.2 mmol) in CH$_2$Cl$_2$ (75 mL) was treated with 5-chloro-3-methyl-benzo[b]thiophene-2-sulfonyl chloride (2.0 g, 7.11 mmol) and the mixture was warmed to room temperature and stirred for 1 hour under N$_2$. The reaction was quenched with 1 N HCl (20 mL) and diluted with more CH$_2$Cl$_2$ and extracted with water. The organic layer was dried (Na$_2$SO$_4$) and the solvent was removed in vacuo to afford 2.27 g (100%) of crude 5-chloro-3-methyl-benzo[b]thiophene-2-sulfonic acid (2-hydroxy-propyl)-amide that was utilized without purification.

A solution of 5-chloro-3-methyl-benzo[b]thiophene-2-sulfonic acid (2-hydroxy-propyl)-amide (2.27 g, assume 7.11 mmol) and iodopropane (1.57 g, 9.24 mmol) in DMF (50 mL) was treated with cesium carbonate (3.01 g, 9.24 mmol) and the reaction mixture was stirred at 50° C. for 2.5 hours under N$_2$. The reaction mixture was cooled and quenched with 1 N HCl (30 mL). The mixture was diluted with more Et$_2$O and then extracted with water. The organic layer was dried (Na$_2$SO$_4$) and the solvent was removed in vacuo to afford crude product that was column purified using 4/1 hexanes/acetone to afford 2.48 g (96%) of the title compound. R$_f$=0.58 (1/1 hexanes/acetone). MS (ES$^+$) m/z mass calculated for C$_{15}$H$_{20}$O$_3$NS$_2$Cl 361, found 362 and 364 (M+1 and M+3, 100%).

Step B

Toluene-4-sulfonic acid 2-[(5-chloro-3-methyl-benzo[b]thiophene-2-sulfonyl)-propyl-amino]-1-methyl-ethyl ester

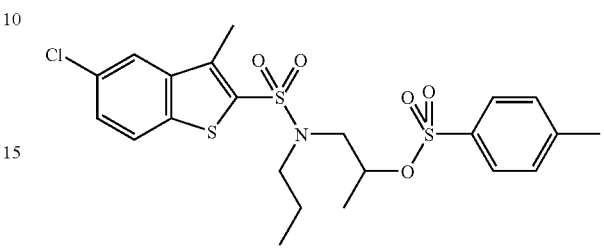

A 0° C. solution of 5-chloro-3-methyl-benzo[b]thiophene-2-sulfonic acid (2-hydroxy-propyl)-propyl-amide (2.48 g, 6.85 mmol) pyridine (2.17 g, 27.4 mmol) and N,N-dimethylaminopyridine (0.33 g, 2.70 mmol) in CH$_2$Cl$_2$ (75 mL) was treated with p-toluenesulfonic anhydride (4.47 g, 13.7 mmol), and the mixture was stirred at room temperature under N$_2$ for 6 hours. The reaction was quenched with 1 N HCl (50 mL) and diluted with more CH$_2$Cl$_2$ and extracted with water. The organic layer was dried (Na$_2$SO$_4$) and the solvent was removed in vacuo to afford crude product that was purified by column chromatography using 9/1 hexanes/acetone to afford 3.59 g (100%) of the title compound. R$_f$=0.56 (1/1 hexanes/acetone).

Step C (4-{2-[(5-Chloro-3-methyl-benzo[b]thiophene-2-sulfonyl)-propyl-amino]-1-methyl-ethoxy}-2-methyl-phenoxy)-acetic acid A mixture of (4-hydroxy-2-methyl-phenoxy)-acetic acid methyl ester (0.046 g, 0.235 mmol), toluene-4-sulfonic acid 2-[(5-chloro-3-methyl-benzo[b]-thiophene-2-sulfonyl)-propyl-amino]-1-methyl-ethyl ester (0.133 g, 0.258 mmol) and Cs$_2$CO$_3$ (0.115 g, 0.353 mmol) in DMF (7 mL) was stirred at 60° C. for 20 hours under N$_2$. The reaction was cooled acidified with 1 N HCl (10 mL), diluted with Et$_2$O and then extracted twice with water. The organic layer was dried (Na$_2$SO$_4$) and the solvent was removed in vacuo to afford crude ester that was dissolved in EtOH (8 mL), treated with 5 N NaOH (1 mL), stirred at 50° C. for 20 minutes and then cooled and stirred at room temperature for 3 hours. The solvent was removed in vacuo to give a residue that was acidified with 1 N HCl (10 mL) and then diluted with Et$_2$O and extracted with water. The organic layer was dried (Na$_2$SO$_4$) and the solvent was removed in vacuo to afford 0.103 g of crude acid that was purified by preparative HPLC to afford 0.028 g (22%) of the title compound. HRMS (ES$^+$) m/z exact mass calculated for C$_{24}$H$_{29}$O$_6$NClS$_2$ 526.1125, found 526.1113.

EXAMPLE 89

3-(4-{2-[(5-Chloro-3-methyl-benzo[b]thiophene-2-sulfonyl)-propyl-amino]-1-methyl-ethoxy}-2-methyl-phenyl)-propionic acid

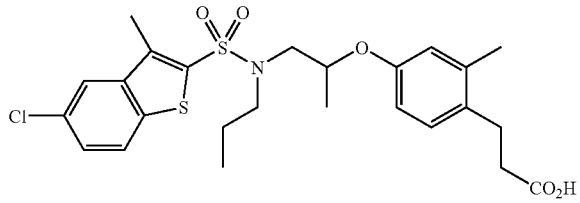

The title compound was prepared by following the procedure of Example 88, Step C utilizing 3-(4-hydroxy-2-methyl-phenyl)-propionic acid methyl ester to afford 0.032 g (25%). HRMS (ES+) m/z exact mass calculated for $C_{25}H_{31}O_5NClS_2$ 524.1332, found 524.1342.

EXAMPLE 90

2-(4-{2-[(5-Chloro-3-methyl-benzo[b]thiophene-2-sulfonyl)-propyl-amino]-1-methyl-ethoxy}-2-methyl-phenoxy)-2-methyl-propionic acid

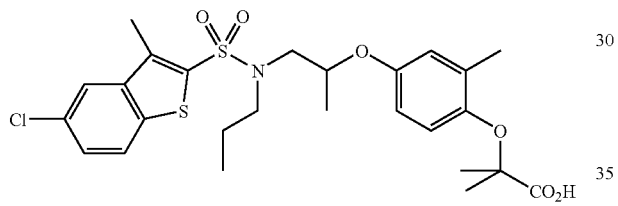

The title compound was prepared by following the procedure of Example 88, Step C utilizing 2-(4-hydroxy-2-methyl-phenoxy)-2-methyl-propionic acid ethyl ester to afford 0.041 g (28%). HRMS (ES+) m/=exact mass calculated for $C_{26}H_{33}O_6NClS_2$ 554.1438, found 554.1436.

EXAMPLE 91

3-(3-{2-[(5-Chloro-3-methyl-benzo[b]thiophene-2-sulfonyl)-propyl-amino]-1-methyl-ethoxy}-phenyl)-propionic acid

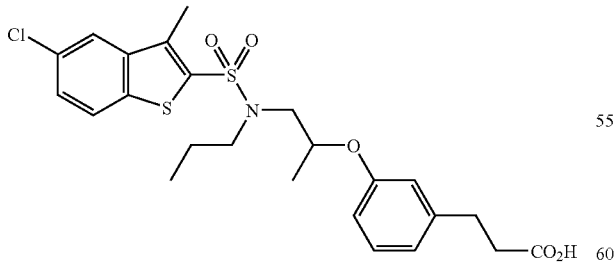

The title compound was prepared by following the procedure of Example 88, Step C utilizing 3-(3-hydroxy-phenyl)-propionic acid methyl ester to afford 0.036 g (30%). HRMS (ES+) m/z exact mass calculated for $C_{24}H_{29}O_5ClS_2$ 510.1176, found 510.1181.

EXAMPLE 92

3-(4-{2-[(5-Chloro-3-methyl-benzo[b]thiophene-2-sulfonyl)-propyl-amino]-1-methyl-ethoxy}-2-methoxy-phenyl)-propionic acid

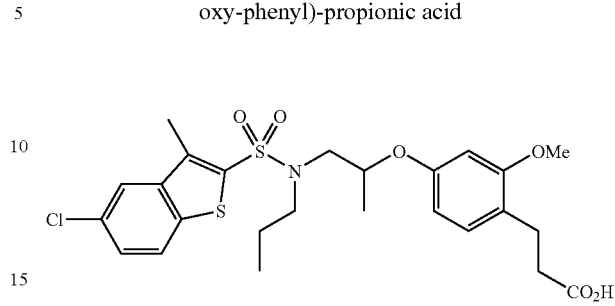

The title compound was prepared by following the procedure of Example 88, Step C utilizing 3-(4-hydroxy-2-methoxy-phenyl)-propionic acid ethyl ester to afford 0.028 g (22%). HRMS (ES+) m/z exact mass calculated for $C_{25}H_{31}O_6NClS_2$ 540.1281, found 540.1290.

EXAMPLE 93

(5-{2-[(5-Chloro-3-methyl-benzo[b]thiophene-2-sulfonyl)-propyl-amino]-1-methyl-ethoxy}-indol-1-yl)-acetic acid

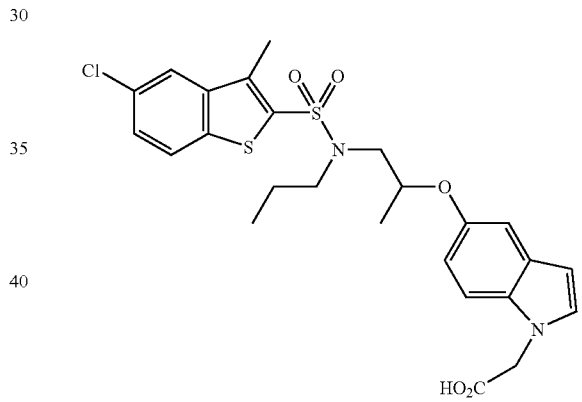

The title compound was prepared by following the procedure of Example 88, Step C utilizing (5-hydroxy-indol-1-yl)-acetic acid ethyl ester to afford 0.048 g (33%). $^1$H NMR (400 MHz, CDCl$_3$).

EXAMPLE 94

(4-{2-[(5-Chloro-3-methyl-benzo[b]thiophene-2-sulfonyl)-propyl-amino]-propylsulfanyl}-2-methyl-phenoxy)-acetic acid

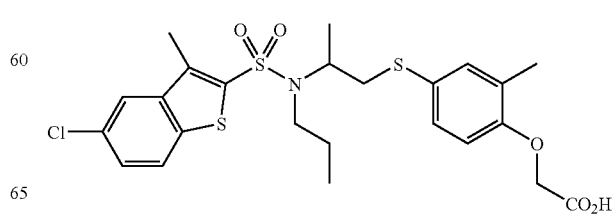

Step A

5-Chloro-3-methyl-benzo[b]thiophene-2-sulfonic acid (2-hydroxy-1-methyl-ethyl)-propyl-amide

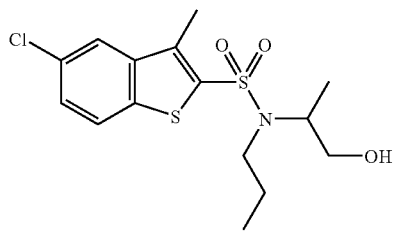

A 0° C. solution of D,L-2-amino-1-propanol (0.59 g, 7.86 mmol) and triethylamine (1.44 g, 14.2 mmol) in CH$_2$Cl$_2$ (75 mL) was treated with 5-chloro-3-methyl-benzo[b]thiophene-2-sulfonyl chloride (2.0 g. 7.11 mmol), and the mixture was warmed to room temperature and stirred for 1 hour under N$_2$. The reaction was quenched with 1 N HCl (30 mL) and diluted with more CH$_2$Cl$_2$ and extracted with water. The organic layer was dried (Na$_2$SO$_4$) and the solvent was removed in vacuo to afford 2.34 g (100%) of crude 5-chloro-3-methyl-benzo[b]thiophene-2-sulfonic acid (2-hydroxy-1-methyl-ethyl)-amide that was utilized without purification.

A solution of 5-chloro-3-methyl-benzo[b]thiophene-2-sulfonic acid (2-hydroxy-1-methyl-ethyl)-amide (2.347 g, assume 7.11 mmol) and iodopropane (1.57 g, 9.24 mmol) in DMF (50 mL) was treated with cesium carbonate (3.01 g, 9.24 mmol) and the reaction mixture was stirred at 50° C. for 2.5 hours under N$_2$. The reaction mixture was cooled and quenched with 1 N HCl (20 mL). The mixture was diluted with more Et$_2$O and then extracted with water. The organic layer was dried (Na$_2$SO$_4$) and the solvent was removed in vacuo to afford crude product that was column purified using 4/1 hexanes/acetone to afford 2.27 g (88%) of the title compound. R$_f$=0.45 (1/1 hexanes/acetone). MS (ES$^+$) m/z mass calculated for C$_{15}$H$_{20}$O$_3$NS$_2$Cl 361, found 362 and 364 (M+1 and M+3, 100%).

Step B

Toluene-4-sulfonic acid 2-[(5-chloro-3-methyl-benzo[b]thiophene-2-sulfonyl)-propyl-amino]-propyl ester

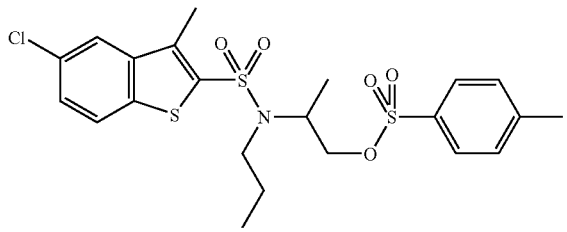

A 0° C. solution of 5-chloro-3-methyl-benzo[b]thiophene-2-sulfonic acid (2-hydroxy-1-methyl-ethyl)-propyl-amide (2.27 g, 6.27 mmol) pyridine (1.98 g, 25.0 mmol) and N,N-dimethylaminopyridine (0.23 g. 1.88 mmol) in CH$_2$Cl$_2$ (50 mL) was treated with p-toluenesulfonic anhydride (4.09 g, 12.5 mmol), and the mixture was stirred at room temperature under N$_2$ for 1 hour. The reaction was quenched with 1 N HCl (50 mL) and diluted with more CH$_2$Cl$_2$ and extracted with water. The organic layer was dried (Na$_2$SO$_4$), and the solvent was removed in vacuo to afford crude product that was absorbed on silica gel and then purified by column chromatography using a gradient of 9/1 hexanes/acetone then 100% acetone to afford 2.00 g (62%) of the title compound. R$_f$=10.51 (1/1 hexanes/acetone).

Step C (4-{2-[(5-Chloro-3-methyl-benzo[b]thiophene-2-sulfonyl)-propyl-amino]-propylsulfanyl}-2-methyl-phenoxy)-acetic acid ethyl ester

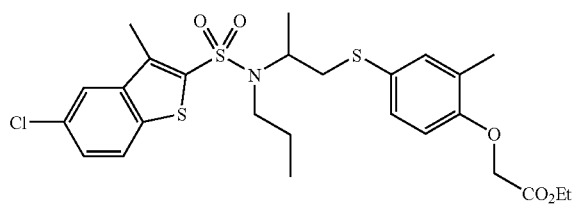

A solution of (4-mercapto-2-methyl-phenoxy)-acetic acid ethyl ester (0.296 g, 1.31 mmol) in dry DMF (8 mL) was treated with a 60% oil suspension of NaH (0.052 g, 0.130 mmol), and the resultant mixture was stirred at room temperature for 5 minutes under N$_2$. The mixture was cooled to 0° C. and then treated dropwise with a solution of toluene-4-sulfonic acid 2-[(5-chloro-3-methyl-benzo[b]thiophene-2-sulfonyl)-propyl-amino]-propyl ester (0.607 g, 1.17 mmol) in DMF (7 mL). The mixture was stirred at room temperature for 17 hours under N. The reaction was acidified with 1 N HCl (10 mL), diluted with Et$_2$O and then extracted twice with water. The organic layer was dried (Na$_2$SO$_4$) and the solvent was removed in vacuo to afford crude ester that was absorbed on silica gel and column purified using a gradient of 10/1 to 6/1 hexane/acetone to afford 0.403 g (61%) of the title compound. MS (ES$^+$) m/z mass calculated for C$_{26}$H$_{32}$O$_5$NClS$_3$ 569, found 570 and 572 (M+1 and M+3, 100%).

Step D (4-{2-[(5-Chloro-3-methyl-benzo[b]thiophene-2-sulfonyl)-propyl-amino]-propylsulfanyl}-2-methyl-phenoxy)-acetic acid A solution of (4-{2-[(5-chloro-3-methyl-benzo[b]thiophene-2-sulfonyl)-propyl-amino]propylsulfanyl}-2-methyl-phenoxy)-acetic acid ethyl ester (0.129 g, 0.226 mmol) in EtOH (10 mL) was treated with 5 N NaOH (1.5 mL) and stirred at room temperature until saponification was completed. The solvent was removed in vacuo to give a residue that was acidified with 1 N HCl (10 mL) and then diluted with Cl$_2$Cl$_2$ and extracted with water. The organic layer was dried (Na$_2$SO$_4$) and the Solvent was removed in vacuo 10 afford 0.114 g (93%) of the title compound. HRMS (ES$^+$) m/z exact mass calculated for C$_{24}$H$_{29}$O$_5$NS$_3$Cl 542.0896, found 542.0891.

EXAMPLE 95

(4-{2-[(5-Chloro-3-methyl-benzo[b]thiophene-2-sulfonyl)-propyl-amino]-propylsulfanyl}-2-methyl-phenoxy)-acetic acid (enantiomers 1 and 2)

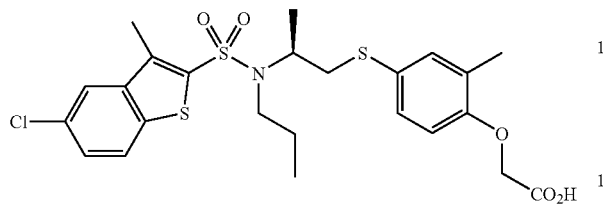

The compound of (4-{2-[(5-chloro-3-methyl-benzo[b]thiophene-2-sulfonyl)propyl-amino]-propylsulfanyl}-2-methyl-phenoxy)-acetic acid ethyl ester (Example 94, Step C) was resolved using chiral HPLC (Chiralcel OD 8×34 cm, 90/10 heptane/3A EtOH, 370 ml/min, 240 nm WV setting) to give enantiomers of isomer 1 (0.122 g, isomer 1, 100% ee) and isomer 2 (0.106 g, isomer 2, 100% ee). These esters were saponified as described in Example 94, Step D to afford 0.087 g (75%) of the title compound (enantiomer 1) and 0.077 g (76%) of the title compound (enantiomer 2). MS (ES$^+$) m/z exact mass calculated for $C_{24}H_{29}O_5NS_3Cl$ 541, found 542 and 544 (M+1 and M+3, 100%).

EXAMPLE 96

(4-{2-[(5-Chloro-3-methyl-benzo[b]thiophene-2-sulfonyl)-propyl-amino]-propoxy}-2-methyl-phenoxy)-acetic acid

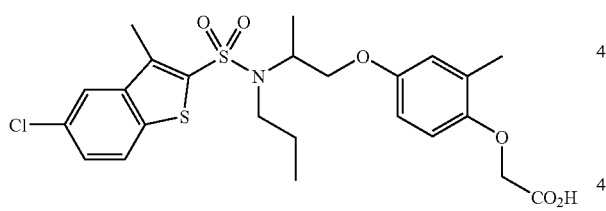

A mixture of (4-hydroxy-2-methyl-phenoxy)-acetic acid methyl ester (0.124 g, 0.235 mmol), toluene-4-sulfonic acid toluene-4-sulfonic acid 2-[(5-chloro-3-methyl-benzo[b]thiophene-2-sulfonyl)-propyl-amino]-propyl ester (0.326 g, 0.632 mmol) and $Cs_2CO_3$ (0.309 g, 0.948 mmol) in DMF (8 mL) was stirred at 55° C. for 20 hours under $N_2$. The mixture was cooled, acidified with 1 N HCl (10 mL), diluted with $Et_2O$ and extracted twice with water. The organic layer was dried ($Na_2SO_4$), and the solvent was removed in vacuo to afford 1.12 g of crude ester. The crude ester was dissolved in EtOH (10 mL), treated with 5 N NaOH (1.5 mL) and stirred at 50° C. for 5 minutes, which was then cooled and stirred at room temperature for 2 hours. The solvent was removed in vacuo to give a residue that was acidified with 1 N HCl (10 mL) and then diluted with $CH_2Cl_2$ and extracted with water. The organic layer was dried ($Na_2SO_4$) and the solvent was removed in vacuo to afford 0.416 g of crude acid that was purified by preparative HPLC to afford 0.161 g (48%) of the title compound. HRMS (ES$^+$) m/z exact mass calculated for $C_{24}H_{29}O_6NClS_2$ 526.1125, found 526.1124.

EXAMPLE 97

3-(4-{2-[(5-Chloro-3-methyl-benzo[b]thiophene-2-sulfonyl)-propyl-amino]-propoxy}-2-methyl-phenyl)-propionic acid

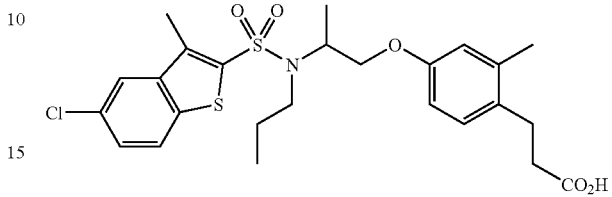

The title compound was prepared by following the procedure as described in Example 96 utilizing 3-(4-hydroxy-2-methyl-phenyl)-propionic acid methyl ester to afford 0.112 g (57%). HRMS (ES$^+$) m/z exact mass calculated for $C_{25}H_{31}O_5NClS_2$ 524.1332, found 524.1340.

EXAMPLE 98

2-(4-{2-[(5-Chloro-3-methyl-benzo[b]thiophene-2-sulfonyl)-propyl-amino]-propoxy}-2-methyl-phenoxy)-2-methyl-propionic acid

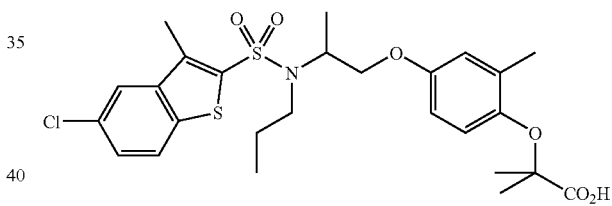

The title compound was prepared by following the procedure described in Example 96 utilizing 2-(4-hydroxy-2-methyl-phenoxy)-2-methyl-propionic acid ethyl ester to afford 0.055 g (42%). HRMS (ES$^+$) m/z exact mass calculated for $C_{26}H_{33}O_6NClS_2$ 554.1438, found 554.1444.

EXAMPLE 99

(4-{2-[(5-Fluoro-3-methyl-benzo[b]thiophene-2-sulfonyl)-propyl-amino]-1-methyl-ethylsulfanyl}-2-methyl-phenoxy)-acetic acid

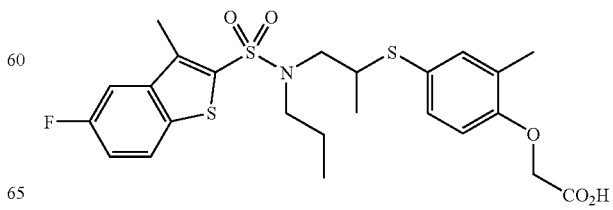

Step A

5-Fluoro-3-methyl-benzo[b]thiophene-2-sulfonic acid (2-hydroxy-propyl)-propyl-amide

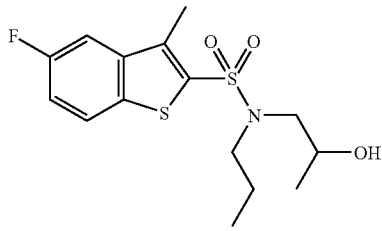

A 0° C. solution of 1-amino-2-propanol (0.312 g, 4.15 mmol) and triethylamine (0.76 g. 7.51 mmol) in $CH_2Cl_2$ (50 mL) was treated with 5-fluoro-3-methyl-benzo[b]thiophene-2-sulfonyl chloride (1.0 g. 3.77 mmol), and the mixture was warmed to room temperature and stirred for 1 hour under $N_2$. The mixture was acidified with 1 N HCl and diluted with more $CH_2Cl_2$ and extracted with water. The organic layer was dried ($Na_2SO_4$) and the solvent was removed in vacuo to afford 1.12 g (98%) of crude 5-fluoro-3-methyl-benzo[b]thiophene-2-sulfonic acid (2-hydroxy-propyl)-amide that was utilized without purification.

A solution of 5-fluoro-3-methyl-benzo[b]thiophene-2-sulfonic acid (2-hydroxy-propyl)-amide (1.12 g, assume 3.69 mmol) and iodopropane (0.835 g, 4.91 mmol) in DMF (40 mL) was treated with cesium carbonate (1.60 g, 4.91 mmol), and the reaction mixture was stirred at 50° C. for 2 hours under $N_2$. The reaction mixture was cooled and acidified with 1 N HCl (20 mL). The filtrate was diluted with $Et_2O$ and then extracted with water. The organic layer was dried ($Na_2SO_4$) and the solvent was removed in vacuo to afford crude product, which was column purified using 4/1 hexanes/acetone to afford 1.15 g (88%) of the title compound. $R_f$=0.43 (1/1 hexanes/acetone). MS (ES$^+$) m/z mass calculated for $C_{15}H_{20}O_3NS_2F$ 345, found 346 (M+1, 100%).

Step B

Toluene-4-sulfonic acid 2-[(5-fluoro-3-methyl-benzo[b]thiophene-2-sulfonyl)-propyl-amino]-1-methyl-ethyl ester

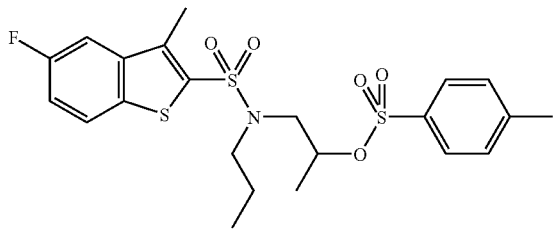

A 0° C. solution of 5-fluoro-3-methyl-benzo[b]thiophene-2-sulfonic acid (2-hydroxy-propyl)-propyl-amide (0.375 g. 1.13 mmol), pyridine (0.36 g, 4.55 mmol) and N,N-dimethylaminopyridine (0.041 g, 0.336 mmol) in $CH_2Cl_2$ (20 mL) was treated with p-toluenesulfonic anhydride (0.74 g, 2.27 mmol), and the mixture was stirred at room temperature under $N_2$ for 1 hour. The reaction was quenched with 1 N HCl (10 mL) and diluted with more $CH_2Cl_2$ and extracted with water. The organic layer was dried ($Na_2SO_4$) and the solvent was removed in vacuo to afford crude product that was purified by column chromatography using 9/1 hexanes/acetone to afford 0.479 g (87%) of the title compound. $R_f$=0.53 (1/1 hexanes/acetone). $^1$H NMR (400 MHz. CDCl$_3$). MS (ES$^+$) m/z mass calcd for $C_{22}H_{26}O_5NS_3F$ 499, found 500 (M+1, 100%).

Step C

(4-{2-[(5-Fluoro-3-methyl-benzo[b]thiophene-2-sulfonyl)-propyl-amino]-1-methyl-ethylsulfanyl}-2-methyl-phenoxy)-acetic acid A solution of (4-mercapto-2-methyl-phenoxy)-acetic acid ethyl ester (0.250 g, 1.10 mmol) in dry DMF (8 mL) was treated with a 60% oil suspension of NaH (0.044 g, 1.10 mmol), and the resultant mixture was stirred at room temperature for 5 minutes under $N_2$. The mixture was cooled to 0° C. and then treated dropwise with a solution of toluene-4-sulfonic acid 2-[(5-fluoro-3-methyl-benzo[b]thiophene-2-sulfonyl)-propyl-amino]-1-methyl-ethyl ester (0.266 g, 0.532 mmol) in DMF (3 mL). The mixture was stirred at room temperature for 17 hours under $N_2$. The reaction was acidified with 1 N HCl (10 mL), diluted with $Et_2O$ and then extracted with water. The organic layer was dried ($Na_2SO_4$) and the solvent was removed in vacuo to afford 0.82 g crude ester. The solid was dissolved in EtOH (15 mL) and treated with 5 N NaOH (1 mL). The solution was then heated and stirred at reflux for 10 minutes. The reaction was cooled, and the solvent was removed in vacuo to give a residue. The residue was acidified with 1 N HCl (10 mL), diluted with $CH_2Cl_2$ and extracted with water. The organic layer was dried ($Na_2SO_4$) and the solvent was removed in vacuo to afford 0.387 g crude acid, which was purified by preparative HPLC to afford 0.066 g (23%) of the title compound. HRMS (ES$^+$) m/z exact mass calculated for $C_{24}H_{29}O_5NS_3F$ 526.1192, found 526.1222.

EXAMPLE 100

(3-(4-{2-[(5-Fluoro-3-methyl-benzo[b]thiophene-2-sulfonyl)-propyl-amino]-1-methyl-ethoxy}-2-methyl-phenyl)-propionic acid

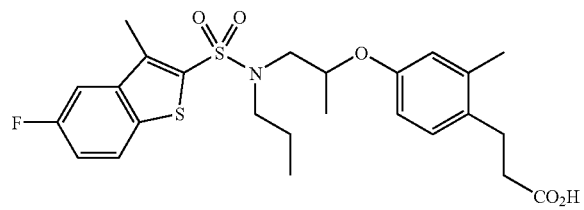

Step A

3-(4-{2-[(5-Fluoro-3-methyl-benzo[b]thiophene-2-sulfonyl)-propyl-amino]-1-methyl-ethoxy}-2-methyl-phenyl)-propionic acid methyl ester

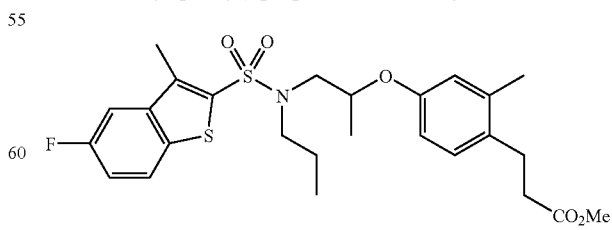

A mixture of 3-(4-hydroxy-2-methyl-phenyl)-propionic acid methyl ester (0.048 g, 0.247 mmol), and toluene-4-sulfonic acid 2-[(5-fluoro-3-methyl-benzo[b]thiophene-2-sulfonyl)-propyl-amino]-1-methyl-ethyl ester (Example 79, Step B) (0.133 g, 0.266 mmol) and $Cs_2CO_3$ (0.121 g, 0.371 mmol) in DMF (8 mL) was stirred at 50° C. for 17 hours under $N_2$. The mixture was cooled, acidified with 1 N HCl, diluted with $Et_2O$ and extracted with water. The organic layer was dried ($Na_2SO_4$) and the solvent was removed in vacuo to afford crude ester, which was purified by flash chromatography using 7/1 hexanes/acetone to afford 0.053 g (41%) of the title compound. $R_f$=0.62 (1/1 hexanes/acetone). MS (ES$^+$) m/z mass calculated for $C_{26}H_{32}O_5NS_2F$ 521, found 522 (M+1, 100%).

Step B (3-(4-{2-[(5-fluoro-3-methyl-benzo[b]thiophene-2-sulfonyl)-propyl-amino]-1-methyl-ethoxy}-2-methyl-phenyl)-propionic acid A solution of 3-(4-{2-[(5-fluoro-3-methyl-benzo[b]thiophene-2-sulfonyl)-propyl-amino]-1-methyl-ethoxy}-2-methyl-phenyl)-propionic acid methyl ester (0.053 g. 0.102 mmol) in EtOH (8 mL) was treated with 5 N NaOH (0.25 mL), and the mixture was stirred at room temperature for 6 hours. The solvent was removed in vacuo to give a residue, which was acidified with 1 N HCl, diluted with ethyl acetate and extracted with water. The organic layer was dried ($Na_2SO_4$), and the solvent was removed in vacuo to afford 0.038 g of crude acid that was purified by preparative HPLC to afford 0.023 g (45%) of the title compound. HRMS (ES$^+$) m/z exact mass calculated for $C_{25}H_{31}O_5NS_2F$ 508.1628, found 508.1624.

EXAMPLE 101

((4-{2-[(5-Fluoro-3-methyl-benzo[b]thiophene-2-sulfonyl)-propyl-amino]-1-methyl-ethoxy}-2-methyl-phenoxy)-acetic acid

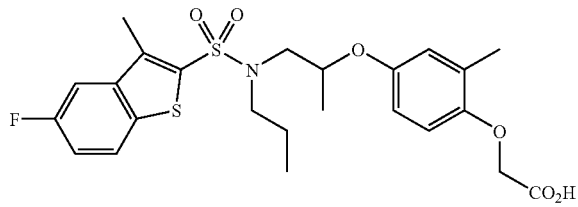

A mixture of (4-hydroxy-2-methyl-phenoxy)-acetic acid methyl ester (0.035 g, 0.178 mmol), toluene-4-sulfonic acid 2-[(5-fluoro-3-methyl-benzo[b]thiophene-2-sulfonyl)-propyl-amino]-1-methyl-ethyl ester (Example 99, Step B) (0.097 g, 0.194 mmol) and $Cs_2CO_3$ (0.089 g, 0.273 mmol) in DMF (6 mL) was stirred at 60° C. for 20 hours under $N_2$. The mixture was cooled, acidified with 1 N HCl, diluted with $Et_2O$ and extracted with water. The organic layer was dried ($Na_2SO_4$) and the solvent was removed in vacuo to afford crude ester, which was then dissolved in EtOH (8 mL). The solution was treated with 5 N NaOH (1 mL), stirred at 50° C. for 5 minutes, cooled and then stirred at room temperature for 2 hours. The solvent was removed in vacuo to give a residue. The residue was acidified with 1 N HCl (10 ml), diluted with $CH_2Cl_2$ and extracted with water. The organic layer was dried ($Na_2SO_4$) and the solvent was removed in vacuo to afford 0.416 g of crude acid, which was purified by preparative HPLC to afford 0.020 g (22%) of the title compound. MS (ES$^+$) m/z mass calculated for $C_{24}H_{28}O_6NS_2F$ 509, found 510 (M+1, 100%).

EXAMPLE 102

(2-Chloro-4-{2-[(5-chloro-3-methyl-benzo[b]thiophene-2-sulfonyl)-propyl-amino]-ethylsulfanyl}-phenoxy)-acetic acid

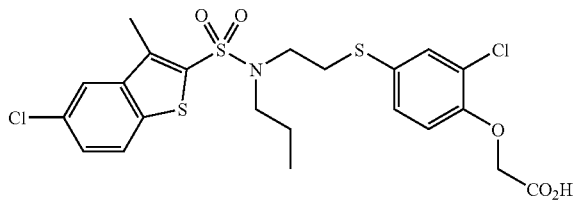

Step A (2-Chloro-4-mercapto-phenoxy)-acetic acid ethyl ester

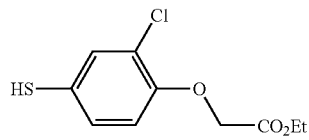

A mixture of (2-chloro-4-chlorosulfonyl-phenoxy)-acetic acid ethyl ester (1.0 g, 3.19 mmol) and 325 mesh tin powder (1.89 g, 15.9 mmol) in EtOH (5 mL) was treated dropwise with a 4 M solution of HCl in dioxane (5 mL). The reaction mixture was allowed to exotherm and then stirred at reflux for 1.5 hours under $N_2$. The mixture was cooled to room temperature and the resultant white slurry was filtered through hyflo using $CH_2Cl_2$ to rinse the solids. The filtrate was washed with water and the organic layer was dried ($Na_2SO_4$), and the solvent was removed in vacuo to afford 0.74 g (95%) of crude product that was utilized without purification. $R_f$=0.36 (1/1 hexanes/acetone). MS (ES$^+$) m/z mass calculated for $C_{10}H_{11}O_3SCl$ 246, found 247 and 249 (M+1 and M+3, 100%).

Step B (2-Chloro-4-{2-[(5-chloro-3-methyl-benzo[b]thiophene-2-sulfonyl)-propyl-amino]-ethylsulfanyl}-phenoxy)-acetic acid ethyl ester

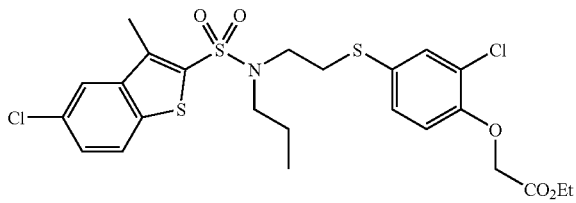

A solution of (2-chloro-4-mercapto-phenoxy)-acetic acid ethyl ester (0.34 g, 1.38 mmol) in dry DMF (10 mL) was purged with $N_2$ and then $Cs_2CO_3$ (0.584 g, 1.79 mmol) was added, and the resultant mixture was purged with N₂ for 5 minutes more. Solid toluene-4-sulfonic acid 2-[(5-chloro-3-methyl-benzo[b]thiophene-2-sulfonyl)-propyl-amino]-ethyl ester (0.55 g, 1.09 mmol) was added to the mixture, which was then stirred for 17 hours at room temperature under N₂. The mixture was acidified with 1 N HCl (20 mL), diluted with Et₂O and then extracted with water. The organic layer was dried (Na₂SO₄) and the solvent was removed in vacuo to afford crude product that was absorbed on silica gel and then column purified using 6/1 hexanes/acetone to afford 0.156 g (25%) of the title compound. $R_f$=0.59 (1/1 hexanes/EtOAc). MS (ES⁺) m/z mass calculated for $C_{24}H_{27}O_5NCl_2S_3$ 575, found 576 and 578 (M+1 and M+3, 100%).

Step C (2-Chloro-4-{2-[(5-chloro-3-methyl-benzo[b]thiophene-2-sulfonyl)-propyl-amino]-ethylsulfanyl}-phenoxy)-acetic acid A solution of (2-chloro-4-{2-[(5-chloro-3-methyl-benzo[b]thiophene-2-sulfonyl)-propyl-amino]-ethylsulfanyl}-phenoxy)-acetic acid ethyl ester (0.150 g, 0.260 mmol) in THF (8 mL) was treated with 1 N LiOH (1 mL) and the mixture was stirred at room temperature for 2.5 hours. The mixture was acidified with 1 N HCl, diluted with EtOAc and extracted with water. The organic layer was dried (Na₂SO₄) and the solvent was removed in vacuo to afford 0.150 g (100%) of the title compound. MS (ES⁺) m/z mass calculated for $C_{22}H_{23}O_5NCl_2S_3$ 547, found 548 and 550 (M+1 and M+3, 100%).

EXAMPLE 103

(4-{2-[(5-Chloro-3-methyl-benzo[b]thiophene-2-sulfonyl)-propyl-amino]-ethylsulfanyl}-2-ethyl-phenoxy)-acetic acid

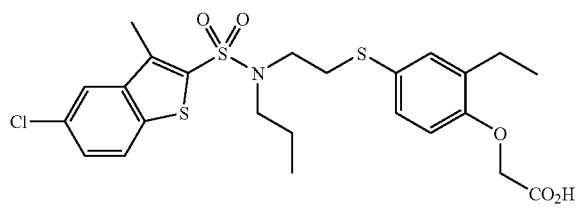

Step A (2-Ethyl-4-mercapto-phenoxy)-acetic acid ethyl ester

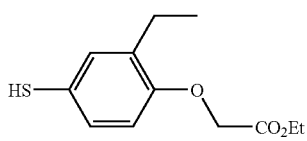

A mixture of (4-chlorosulfonyl-2-ethyl-phenoxy)-acetic acid ethyl ester (1.0 g, 3.25 mmol) and 325 mesh tin powder (1.92 g, 16.3 mmol) in EtOH (5 mL) was treated dropwise with a 4 M solution of HCl in dioxane (5 mL). The reaction mixture was allowed to exotherm and then stirred at reflux for 1.5 hours under N₂. The reaction was cooled to room temperature and the resultant white slurry was filtered through hyflo using CH₂Cl₂ to rinse the solids. The filtrate was washed with water and the organic layer was dried (Na₂SO₄) and the solvent was removed in vacuo to afford 0.85 g (100%) of crude product that was utilized without purification. MS (ES⁺) m/z mass calculated for $C_{12}H_{16}O_3S$ 240, found 241 and 243 (M+1 and M+3, 100%).

Step B (4-{2-[(5-Chloro-3-methyl-benzo[b]thiophene-2-sulfonyl)-propyl-amino]-ethylsulfanyl}-2-ethyl-phenoxy)-acetic acid ethyl ester

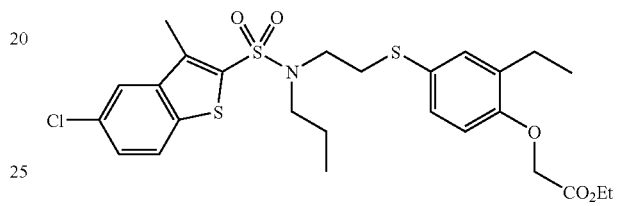

A solution of (2-ethyl-4-mercapto-phenoxy)-acetic acid ethyl ester (0.30 g, 1.25 mmol) in dry DMF (7 mL) was purged with N₂ and then Cs₂CO₃ (0.53 g, 1.63 mmol) was added, and the resultant mixture was pureed with N₂ for 5 minutes more. Solid toluene-4-sulfonic acid 2-[(5-chloro-3-methyl-benzo[b]thiophene-2-sulfonyl)-propyl-amino]-ethyl ester (0.313 g, 0.623 mmol) was added to the reaction mixture, which was heated to 50° C. and stirred for 3.5 hours under N₂. The reaction was cooled, acidified with 1 N HCl (20 mL), diluted with Et₂O and extracted with water. The organic layer was dried (Na₂SO₄) and the solvent was removed in vacuo to afford crude product, which was absorbed on silica gel and then column purified using 6/1 hexanes/acetone to afford 0.371 g (100%) of partially purified title compound. $R_f$=0.67 (1/1 hexanes/acetone). MS (ES⁺) m/z mass calculated for $C_{26}H_{32}O_5NClS_3$ 569, found 570 and 572 (M+1 and M+3, 100%).

Step C (4-{2-[(5-Chloro-3-methyl-benzo[b]thiophene-2-sulfonyl)-propyl-amino]-ethylsulfanyl}-2-ethyl-phenoxy)-acetic acid A solution of (4-{2-[(5-chloro-3-methyl-benzo[b]thiophene-2-sulfonyl)-propyl-amino]-ethylsulfanyl}-2-ethyl-phenoxy)-acetic acid ethyl ester (0.371 g, assume 0.262 mmol) in THF (10 mL) was treated with 1 N LiOH (2.5 mL), and the mixture was stirred at room temperature for 2.5 hours. The mixture was acidified with 1 N HCl, diluted with EtOAc and extracted with water. The organic layer was dried (Na₂SO₄) and the solvent was removed in vacuo to afford 0.391 g crude acid, which was purified by preparative HPLC to afford 0.217 g (64%) of the title compound. HRMS (ES⁺) m/z exact mass calculated for $C_{24}H_{28}O_5NClS_3Na$ 564.0716, found 564.0709.

EXAMPLE 104

(2-Methyl-4-{1-[(4-trifluoromethoxy-benzenesulfonylamino)-methyl]-propylsulfanyl}-phenoxy)-acetic acid

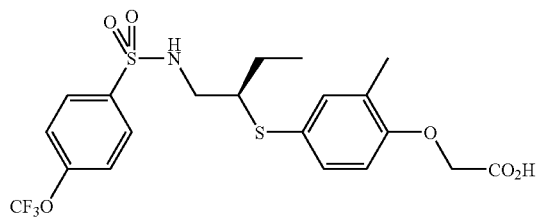

Step A

[4-(1-{4-(1-[(4-Methoxy-benzyl)-(4-trifluoromethoxy-benzenesulfonyl)-amino]-methyl}-propylsulfanyl)-2-methyl-phenoxy]-acetic acid ethyl ester

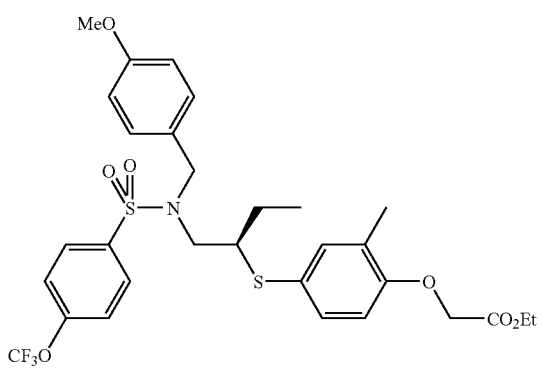

A 0° C. solution of (4-{1-[(4-Methoxy-benzylamino)-methyl]-propylsulfanyl}-2-methyl-phenoxy)-acetic acid ethyl ester trifluoro-acetic acid salt (6.14 g, 9.70 mmol) in $CH_2Cl_2$ (150 mL) was treated dropwise with triethylamine (7.84 g, 77.5 mmol) and then 4-(trifluoromethoxy)benzenesulfonyl chloride (3.07 g. 11.8 mmol). The reaction mixture was warmed to room temperature and stirred for 1 hour under $N_2$. The reaction was quenched with 1 N HCl (100 mL), diluted with water and extracted with $CH_2C)_2$. The organic layer was dried ($Na_2SO_4$) and the solvent was removed in vacuo to afford crude product that was absorbed on silica gel and column purified with 8/1 hexanes/acetone to afford 3.17 g (51%) of the title compound. $R_f$=0.20 (2/1 hexanes/acetone). MS (ES$^+$) m/z mass calculated for $C_{30}H_{34}NO_7S_2F_3$ 641, found 642 (M+1, 100%).

Step B (2-Methyl-4-{1-[(4-trifluoromethoxy-benzenesulfonylamino)-methyl]-propylsulfanyl}-phenoxy)-acetic acid ethyl ester

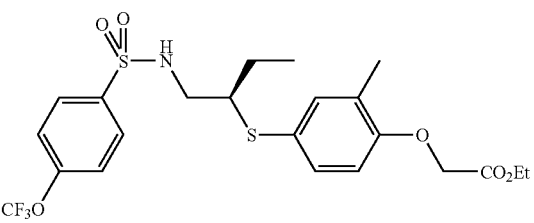

A mixture of [4-(1-{[(4-methoxybenzyl)-(4-trifluoromethoxy-benzenesulfonyl)-amino]-methyl}-propylsulfanyl)-2-methyl-phenoxy]-acetic acid ethyl ester (3.17 g, 4.94 mmol) and triethylsilane (11.5 g, 98.9 mmol) was treated trifluoroacetic acid (50 mL), and the mixture was stirred at room temperature for 3 hours under $N_2$. The solvent was removed in vacuo to afford a residue, which was diluted with $Et_2O$ and extracted with water. The organic layer was dried ($Na_2SO_4$) and the solvent was removed in vacuo to afford crude product, which was absorbed on silica gel and column purified with 99/1 $CH_2Cl_2$/acetonitrile to afford 1.13 g (44%) of the title compound. $R_f$=0.56 (98/2 $CH_2Cl_2$/acetonitrile). MS (ES$^-$) m/z mass calculated for $C_{22}H_{26}NO_6S_2F_3$ 521, found 520 (M−1, 100%).

Step C (2-Methyl-4-{1-[(4-trifluoromethoxy-benzenesulfonylamino)-methyl]-propylsulfanyl}-phenoxy)-acetic acid A solution of (2-methyl-4-{1-[(4-trifluoromethoxy-benzenesulfonylamino)-methyl]-propylsulfanyl}-phenoxy)-acetic acid ethyl ester (0.050 g, 0.096 mmol) in EtOH (6 mL) was treated with 5 N NaOH (0.5 mL), and the mixture was stirred at room temperature for 2.5 hours. The solvent was removed in vacuo to give a residue, which was acidified with 1 N HCl (10 mL), diluted with ethyl acetate and extracted, with water. The organic layer was dried ($Na_2SO_4$) and the solvent was removed in vacuo to afford 0.043 g (91%) of the title compound. HRMS (ES$^+$) m/z exact mass calculated for $C_{20}H_{22}NO_6S_2F_3Na$ 516.0738, found 516.0731.

EXAMPLE 105

General Procedure (1)

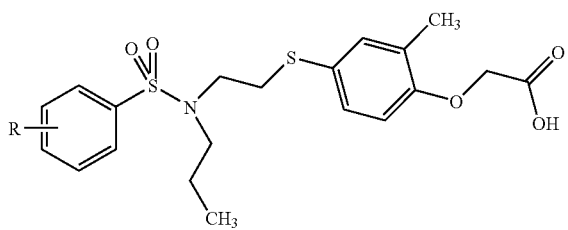

Step A

[2-Methyl-4-(2-propylamino-ethylsulfanyl)-phenoxy]-acetic acid ethyl ester; compound with trifluoroacetic acid

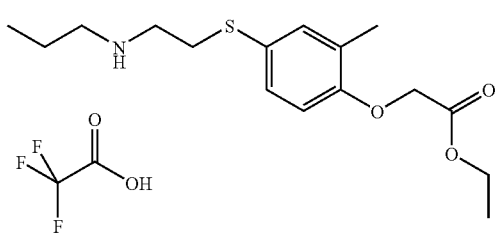

Trifluoroacetic acid (25.0 ml) was added dropwise to a mixture of ({4-[2-(tert-butoxycarbonyl-propyl-amino)-ethylsulfanyl]-2-methyl-phenoxy}-acetic acid ethyl ester (Example 24, Step C) (5.10 g, 12.4 mmol) and dimethylethyl silane in methylene chloride (100 ml) at room temperature. The mixture was stirred for 2 hours, and the solvents were evaporated on a rotavapor to give the title compound, which was used for the next step directly without purification.

Step B

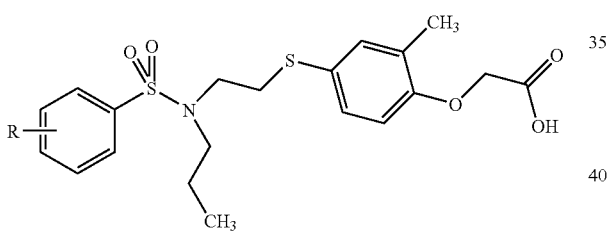

Trifluoroacetic acid salt of [2-methyl-4-(2-propylamino-ethylsulfanyl)-phenoxy]-acetic acid ethyl ester (Step A) (0.300 mmol) was added to a mixture of substituted benzene sulfonyl chloride (0.300 mmol) and Et$_3$N in methylene chloride (2.00 ml). After shaking or standing the reaction at room temperature overnight, the solvents were removed in vacuo. The resulting product was purified by column chromatography by eluting with ethyl acetate:hexane (1:4 to 1:2). Evaporation of the solvent afforded the sulfonamide as an ethyl ester. The ethyl ester was then dissolved in THF/MeOH (1:1, 2 ml) and 5.0N NaOH (1.0 ml) was added and let stand at room temperature overnight. The organic solvents were evaporated in vacuo and adjusted to pH 2 to 3 with concentrated HCl. The water was removed using ChemElut CE1005. The ChemElut tube was washed with ethyl acetate (40 ml) and the solution was concentrated to dryness. Purification by preparative HPLC (UV-2), eluting with 0.1% TFA in acetonitrile and lyophilization afforded the title compound.

The following Examples 106-137 were prepared by following the General Procedure (1) as described above by using the appropriate starting material.

EXAMPLE 106

(4-{2-[(4-Methanesulfonyl-benzenesulfonyl)-propyl-amino]-ethylsulfanyl}-2-methyl-phenoxy)-acetic acid

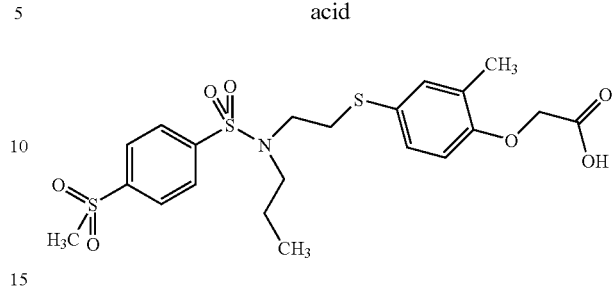

MS (ES): 500 (M−H)$^-$.

EXAMPLE 107

(4-{2-[(4-Bromo-benzenesulfonyl)-propyl-amino]-ethylsulfanyl}-2-methyl-phenoxy)-acetic acid

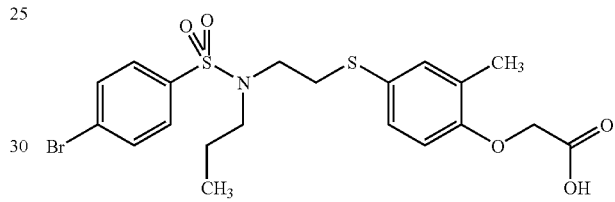

Mass found: 502

EXAMPLE 108

(4-{2-[(3,4-Difluoro-benzenesulfonyl)-propyl-amino]-ethylsulfanyl}-2-methyl-phenoxy)-acetic acid

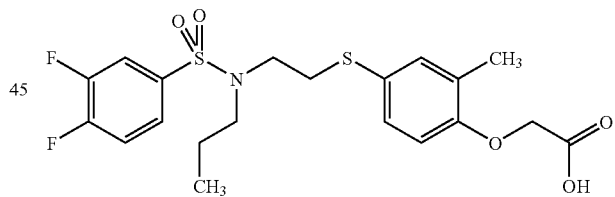

Mass found: 459

EXAMPLE 109

(2-Methyl-4-{2-[(4-pentyl-benzenesulfonyl)-propyl-amino]-ethylsulfanyl}-phenoxy)-acetic acid

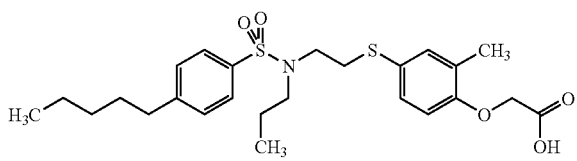

Mass found: 493

EXAMPLE 110

(4-{2-[(2-Chloro-4-trifluoromethyl-benzenesulfonyl)-propyl-amino]-ethylsulfanyl}-2-methyl-phenoxy)-acetic acid

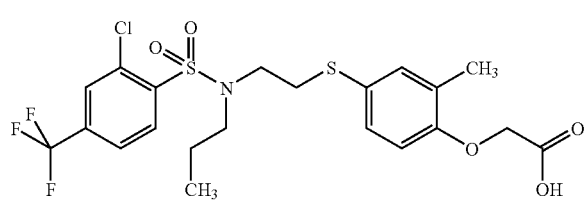

Mass found: 526

EXAMPLE 111

(4-{2-[(3,4-Dimethoxy-benzenesulfonyl)-propyl-amino]-ethylsulfanyl}-2-methyl-phenoxy)-acetic acid

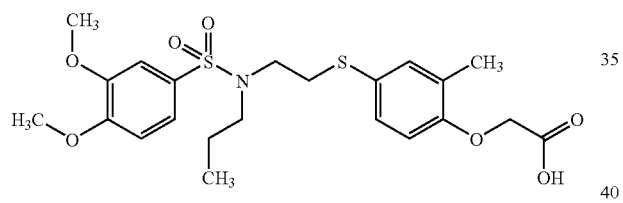

Mass found: 483

EXAMPLE 112

(4-{2-[(3,4-Dichloro-benzenesulfonyl)-propyl-amino]-ethylsulfanyl}-2-methyl-phenoxy)-acetic acid

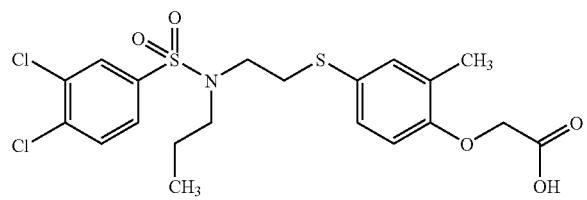

Mass found: 492

EXAMPLE 113

(4-{2-[(3,5-Dichloro-benzenesulfonyl)-propyl-amino]-ethylsulfanyl}-2-methyl-phenoxy)-acetic acid

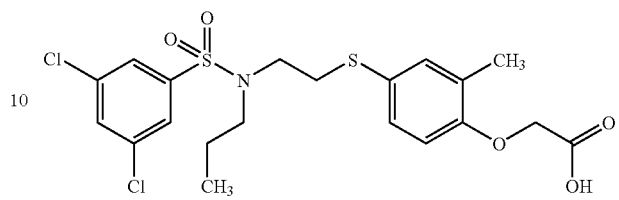

Mass found: 492

EXAMPLE 114

(4-{2-[(2-Methoxy-4-methyl-benzenesulfonyl)-propyl-amino]-ethylsulfanyl}-2-methyl-phenoxy)-acetic acid

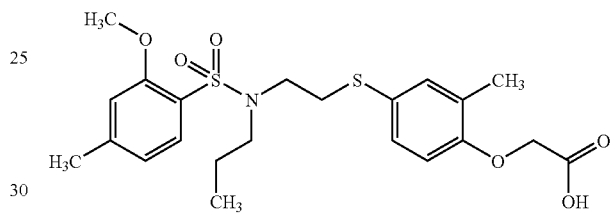

Mass found: 467

EXAMPLE 115

(4-{2-[(4-Isopropyl-benzenesulfonyl)-propyl-amino]-ethylsulfanyl}-2-methyl-phenoxy)-acetic acid

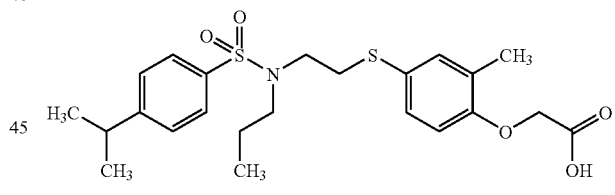

Mass found: 465

EXAMPLE 116

[4-(2-{[4-(1,1-Dimethyl-propyl)-benzenesulfonyl]propyl-amino}-ethylsulfanyl)-2-methyl-phenoxy]-acetic acid

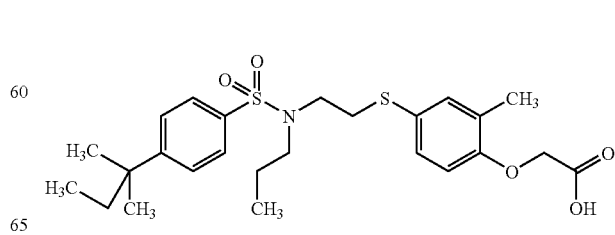

Mass found: 493

EXAMPLE 117

(2-Methyl-4-{2-[propyl-(3-trifluoromethyl-benzene-sulfonyl)-amino]-ethylsulfanyl}-phenoxy)-acetic acid

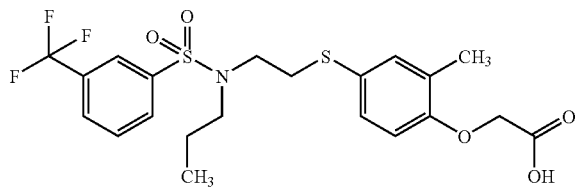

Mass spectrum (ES): 492 (M+H)$^+$, 490 (M–H)$^-$.

EXAMPLE 118

(4-{2-[(3-Chloro-benzenesulfonyl)-propyl-amino]-ethylsulfanyl}-2-methyl-phenoxy)-acetic acid

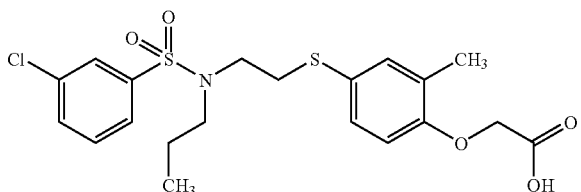

Mass spectrum (ES): 458 (M+H)$^+$, 456 (M–H)$^-$.

EXAMPLE 119

(4-{2-[(3,4-Dibromo-benzenesulfonyl)-propyl-amino]-ethylsulfanyl}-2-methyl-phenoxy)-acetic acid

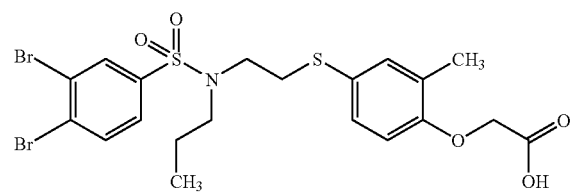

Mass spectrum (ES): 580, 582 (M+H)$^+$, 578, 580 (M–H)$^-$.

EXAMPLE 120

(4-{2-[(2,3-Dichloro-benzenesulfonyl)-propyl-amino]-ethylsulfanyl}-2-methyl-phenoxy)-acetic acid

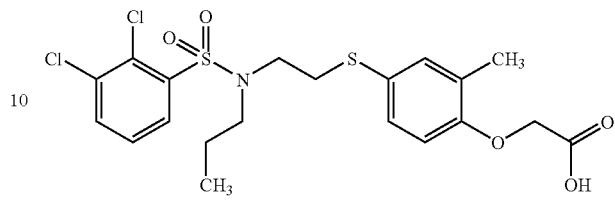

Mass spectrum (ES): 492 (M+H)$^+$, 490 (M–H)$^-$.

EXAMPLE 121

(2-Methyl-4-{2-[propyl-(toluene-3-sulfonyl)-amino]-ethylsulfanyl}-phenoxy)-acetic acid

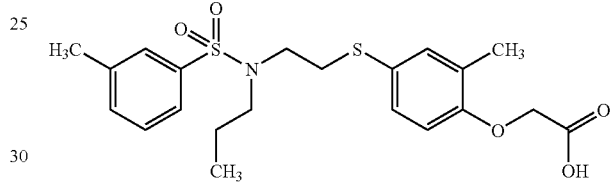

Mass spectrum (ES): 438 (M+H)$^+$, 436 (M–H)$^-$.

EXAMPLE 122

(4-{2-[(4-Acetyl-benzenesulfonyl)-propyl-amino]-ethylsulfanyl}-2-methyl-phenoxy)-acetic acid

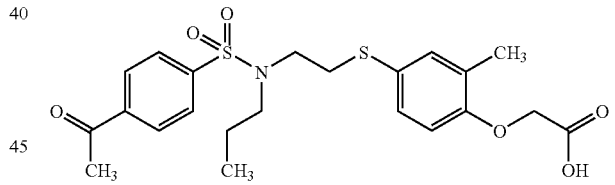

Mass spectrum (ES): 466 (M+H)$^+$, 464 (M–H)$^-$.

EXAMPLE 123

(4-{2-[(4-Bromo-2-methyl-benzenesulfonyl)-propyl-amino]-ethylsulfanyl}-2-methyl-phenoxy)-acetic acid

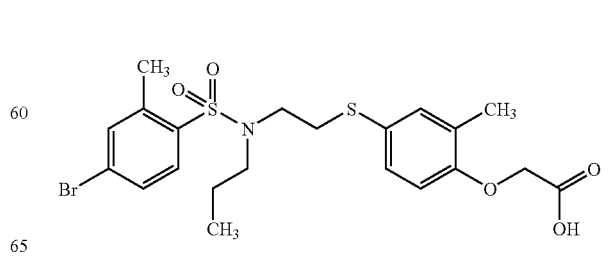

Mass spectrum (ES): 516, 518 (M+H)$^+$, 514, 516 (M–H)$^-$.

EXAMPLE 124

(2-Methyl-4-{2-[propyl-(4-propyl-benzenesulfonyl)-amino]-ethylsulfanyl}-phenoxy)-acetic acid

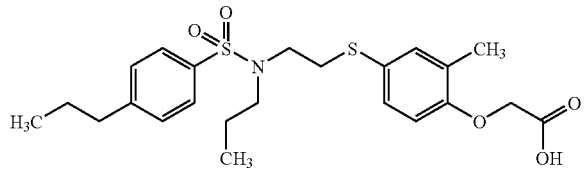

Mass spectrum (ES): 466 (M+H)$^+$, 464 (M−H)$^−$.

EXAMPLE 125

(4-{2-[(4-Bromo-2-trifluoromethoxy-benzenesulfonyl)-propyl-amino]-ethylsulfanyl}-2-methyl-phenoxy)-acetic acid

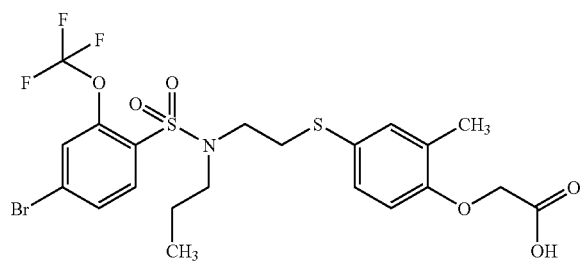

Mass spectrum (ES): 586, 588 (M+H)$^+$, 584, 585 (M−H)$^−$.

EXAMPLE 126

(4-{2-[(2,4-Dichloro-benzenesulfonyl)-propyl-amino]-ethylsulfanyl}-2-methyl-phenoxy)-acetic acid

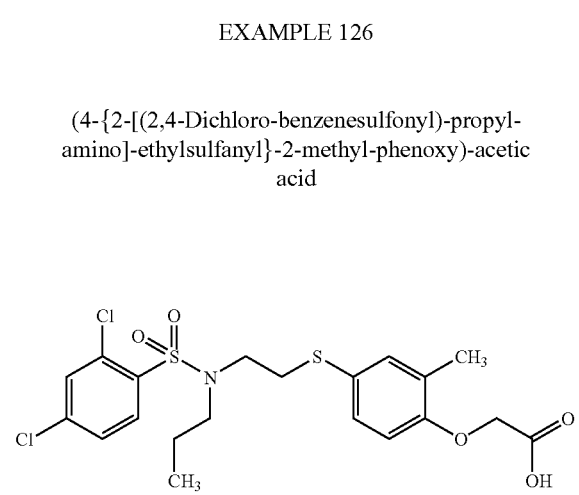

Mass spectrum (ES): 492 (M+H)$^+$, 490 (M−H)$^−$.

EXAMPLE 127

(4-{2-[(4-Iodo-benzenesulfonyl)-propyl-amino]-ethylsulfanyl}-2-methyl-phenoxy)-acetic acid

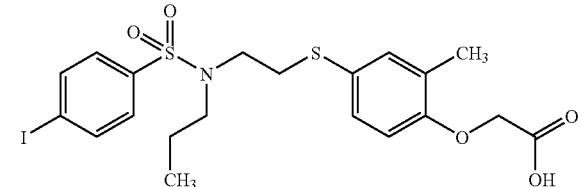

Mass spectrum (ES): 550 (M+H)$^+$, 548 (M−H)$^−$.

EXAMPLE 128

(4-{2-[(2-Chloro-benzenesulfonyl)-propyl-amino]-ethylsulfanyl}-2-methyl-phenoxy)-acetic acid

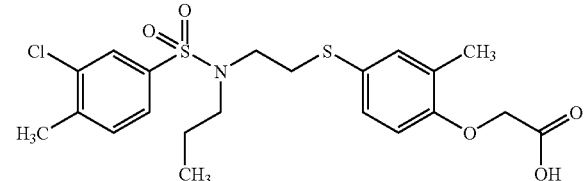

Mass spectrum (ES): 458 (M+H)$^+$, 456 (M−H)$^−$.

EXAMPLE 129

(4-{2-[(3-Chloro-4-methyl-benzenesulfonyl)-propyl-amino]-ethylsulfanyl}-2-methyl phenoxy)-acetic acid Mass spectrum (ES): 472 (M+H)$^+$, 470 (M−H)$^−$.

EXAMPLE 130

(4-{2-[(2-Bromo-benzenesulfonyl)-propyl-amino]-ethylsulfanyl}-2-methyl-phenoxy)-acetic acid

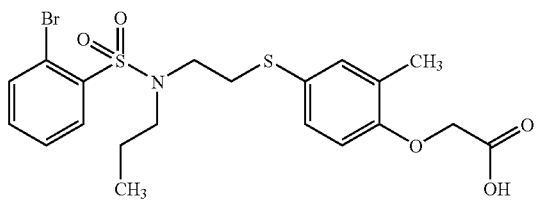

Mass spectrum (ES): 502, 504 (M+H)$^+$, 500, 502 (M−H)$^−$.

EXAMPLE 131

(4-{2-[(4-Bromo-2-ethyl-benzenesulfonyl)-propyl-amino]-ethylsulfanyl}-2-methyl-phenoxy)-acetic acid

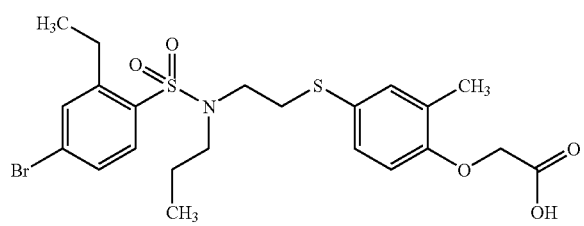

Mass spectrum (ES): 530, 532 (M+H)$^+$, 528, 530 (M−H)$^−$.

EXAMPLE 132

(4-{2-[(4-Bromo-2,5-difluoro-benzenesulfonyl)-propyl-amino]-ethylsulfanyl}-2-methyl-phenoxy)-acetic acid

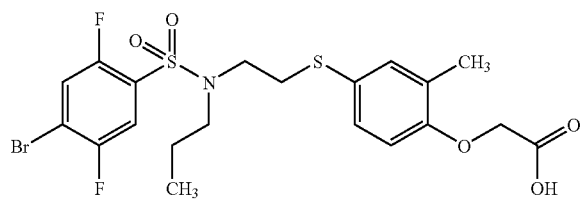

Mass spectrum (ES): 538, 540 (M+H)$^+$, 536, 538 (M−H)$^−$.

EXAMPLE 133

(4-{2-[(3-Chloro-2-methyl-benzenesulfonyl)-propyl-amino]-ethylsulfanyl}-2-methyl-phenoxy)-acetic acid

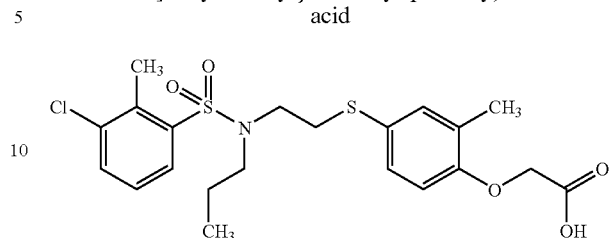

Mass spectrum (ES): 472 (M+H)$^+$, 470 (M−H)$^−$.

EXAMPLE 134

(4-{2-[(4-Butyl-benzenesulfonyl)-propyl-amino]-ethylsulfanyl}-2-methyl-phenoxy)-acetic acid

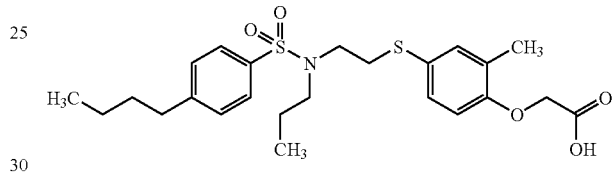

Mass spectrum (ES): 480 (M+H)$^+$, 478 (M−H)$^−$.

EXAMPLE 135

(4-{2-[(4-Isobutyl-benzenesulfonyl)-propyl-amino]-ethylsulfanyl}-2-methyl-phenoxy)-acetic acid

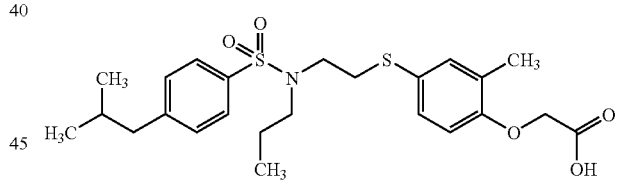

Mass spectrum (ES): 480 (M+H)$^+$, 478 (M−H)$^−$.

EXAMPLE 136

(4-{2-[(3-Chloro-4-methoxy-benzenesulfonyl)-propyl-amino]-ethylsulfanyl}-2-methyl-phenoxy)-acetic acid

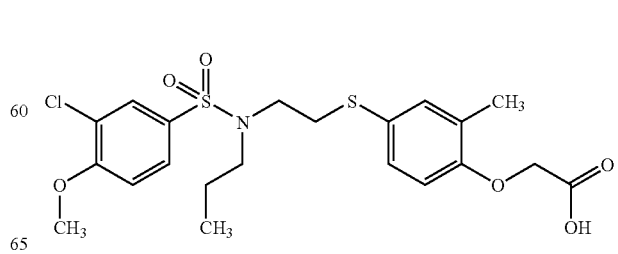

Mass spectrum (ES): 488 (M+H)$^+$, 486 (M−H)$^−$.

EXAMPLE 137

(4-{2-[(4-Chloro-3-trifluoromethyl-benzenesulfonyl)-propyl-amino]-ethylsulfanyl}-2-methyl-phenoxy)-acetic acid

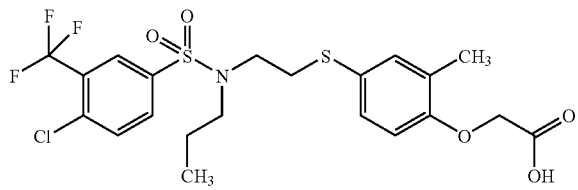

Mass spectrum (ES): 526 (M+H)$^+$, 524 (M−H)$^−$.

EXAMPLE 138

4-Chloro-3-trifluoromethyl-benzenesulfonyl chloride

Add a solution of NaNO$_{2(aq)}$ (10.0 mmole, 1.50 ml) into a suspension of 4-chloro-3-trifluoromethyl aniline (10.0 mmole) in concentrated HCl/glacial acetic acid (3.50:1.00, 4.50 ml) at 0° C. Stir for an hour. Transfer the diazonium salt formed above into a saturated solution of SO$_2$ in glacial HOAc (15.0 ml) at 0° C., then warm up to room temperature for an hour. Pour the reaction mixture into ice water (100 ml), extract with 3×50.0 ml ethyl ether. Wash the combined organics with 3×100 ml NaHCO$_{3(aq)}$, 3×100 ml brine, dried over Na$_2$SO$_4$ and concentrated. Purified by chromatography, eluting with ethyl acetate/hexane (1:9).

EXAMPLE 139

General Procedure (2)

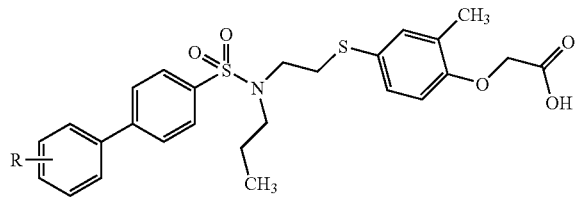

Step A (4-{2-[(4-Bromo-benzenesulfonyl)-propyl-amino]-ethylsulfanyl}-2-methyl-phenoxy)-acetic acid ethyl ester

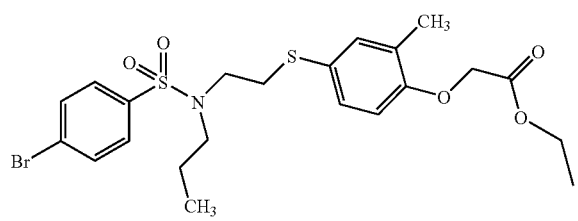

Triethyl amine (0.836 ml, 6.00 mmol) was added to a mixture of 4-bromo-benzenesulfonyl chloride (0.511 g, 2.00 mmole) trifluoroacetic acid salt of [2-methyl-4-(2-propylamino-ethylsulfanyl)-phenoxy]-acetic acid ethyl ester (Example 105, General Procedure (1), Step A) (0.850 g, 2.00 mmol) in methylene chloride (10.0 ml). The reaction was stirred at room temperature overnight. The mixture was diluted with more methylene chloride (10.0 ml) and washed with brine (20.0 ml). The aqueous layer was extracted with 2×20.0 ml methylene chloride. The organic extracts were combined, dried over sodium sulfate and concentrated under reduced pressure. Purification by column chromatography, eluting with ethyl acetate:hexane (1:9 to 1:4) and evaporation of solvents afforded the title compound.

Step B

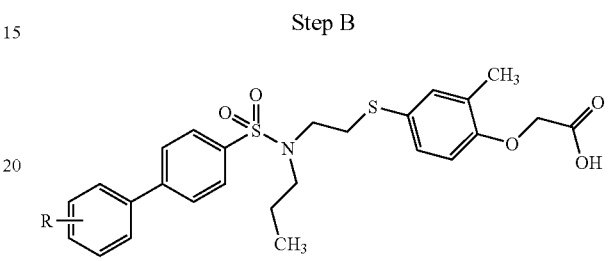

The compound of (4-{2-[(4-Bromo-benzenesulfonyl)-propyl-amino]-ethylsulfanyl}-2-methyl-phenoxy)-acetic acid ethyl ester (Step A) (0.100 mmol), corresponding substituted benzene boronic acid (0.300 mmol) and cesium fluoride were added to dioxane (2.00 ml). The mixture with was degassed with nitrogen for 15 minutes, and the catalyst PdCl$_2$(dppf) (0.0200 mmol) was added. The mixture was healed up to 100° C. for 16 hours. The catalyst was then removed through a celite pad and the solvent was evaporated in vacuo. Purification by column chromatography, eluting with ethyl acetate:hexane (1:9 to 1:4) and evaporation of solvents afforded the substituted biphenyl sulfonamide as an ethyl ester. The ethyl ester obtained above was dissolved in MeOH (2.00 ml) and 5.0N NaOH (1.00 ml) was added, and let it stand at room temperature overnight. The organic solvents were evaporated in vacuo and the mixture was adjusted to pH 2 to 3 with concentrated HCl. The water was removed using ChemElut CE1005. The ChemElut tube was washed with ethyl acetate (40 ml) and the solution was concentrated to dryness. Purification by preparative HPLC (UV-2), eluting with 0.1% TFA in acetonitrile and lyophilization yielded the title compound.

The following Examples 140-151 were prepared according to the General Procedure (2) as described above by using the appropriate starting material.

EXAMPLE 140

(2-Methyl-4-{2-[propyl-(2'-trifluoromethyl-biphenyl-4-sulfonyl)-amino]-ethylsulfanyl}-phenoxy)-acetic acid

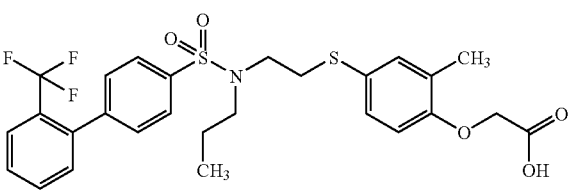

Mass spectrum (ES): 568 (M+H)$^+$, 566 (M−H).

EXAMPLE 141

(2-Methyl-4-{2-[propyl-(3'-trifluoromethyl-biphenyl-4-sulfonyl)-amino]-ethylsulfanyl}-phenoxy)-acetic acid

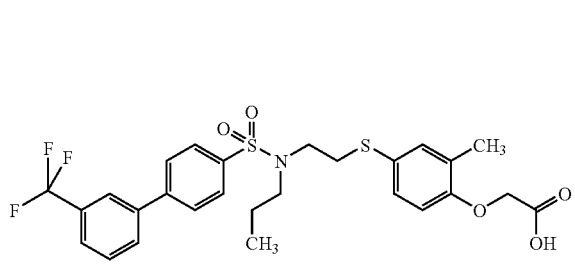

Mass spectrum (ES): 568 (M+H)$^+$, 566 (M−H)$^−$.

EXAMPLE 142

(2-Methyl-4-{2-[propyl-(4'-trifluoromethyl-biphenyl-4-sulfonyl)-amino]-ethylsulfanyl}-phenoxy)-acetic acid

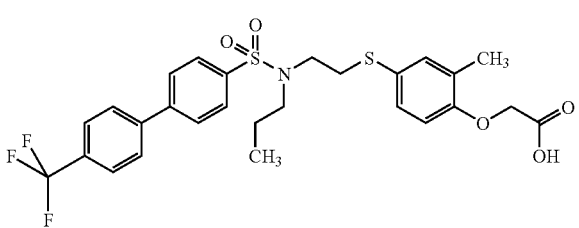

Mass spectrum (ES): 568 (M+H)$^+$, 566 (M−H)$^−$.

EXAMPLE 143

(4-{2-[(2'-Fluoro-biphenyl-4-sulfonyl)-propyl-amino]-ethylsulfanyl}-2-methyl-phenoxy)-acetic acid

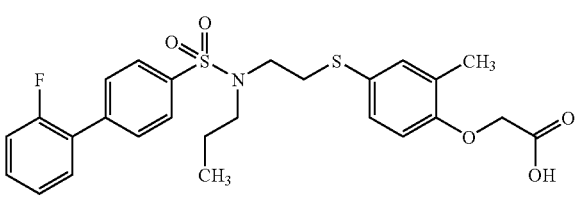

Mass spectrum (ES): 518 (M+H)$^+$, 516 (M−H)$^−$.

EXAMPLE 144

(4-{2-[(4'-Fluoro-biphenyl-4-sulfonyl)-propyl-amino]-ethylsulfanyl}-2-methyl-phenoxy)-acetic acid

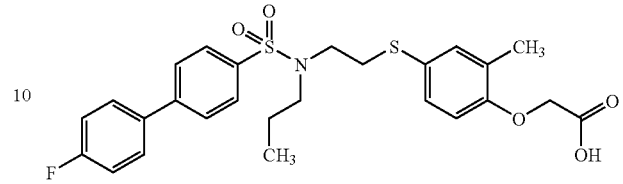

Mass spectrum (ES): 518 (M+H)$^+$, 536 (M−H)$^−$.

EXAMPLE 145

(2-Methyl-4-{2-[propyl-(4'-trifluoromethoxy-biphenyl-4-sulfonyl)-amino]-ethylsulfanyl}-phenoxy)-acetic acid

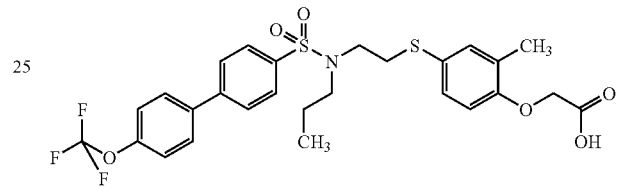

Mass spectrum (ES): 584 (M+H)$^+$, 582 (M−H)$^−$.

EXAMPLE 146

(4-{2-[(3',4'-Dichloro-biphenyl-4-sulfony)-propyl-amino]-ethylsulfanyl}-2-methyl-phenoxy)-acetic acid

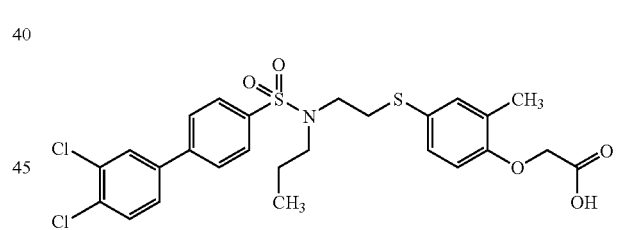

Mass spectrum (ES): 568, 570 (M+H)$^+$, 566, 568 (M−H)$^−$.

EXAMPLE 147

(4-{2-[(3'-Fluoro-biphenyl-4-sulfonyl)-propyl-amino]-ethylsulfanyl}-2-methyl-phenoxy)-acetic acid

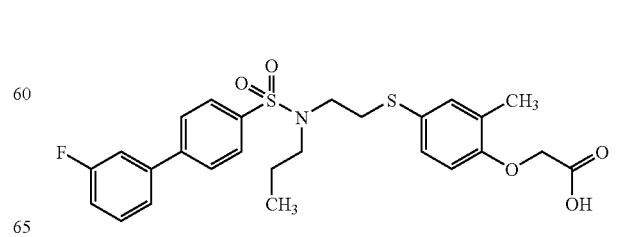

Mass spectrum (ES): 518 (M+H)$^+$, 516 (M−H)$^−$.

EXAMPLE 148

(4-{2-[(2'-Chloro-biphenyl-4-sulfonyl)-propyl-amino]-ethylsulfanyl}-2-methyl-phenoxy)-acetic acid

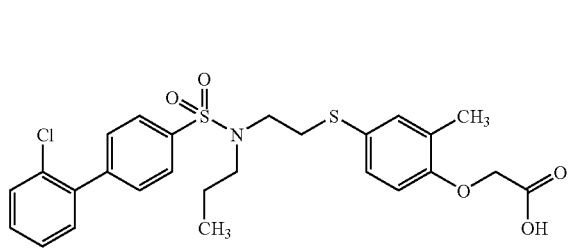

Mass spectrum (ES): 534 (M+H)$^+$, 532 (M−H)$^−$.

EXAMPLE 149

(4-{2-[(4'-Chloro-biphenyl-4-sulfonyl)-propyl-amino]-ethylsulfanyl}-2-methyl-phenoxy)-acetic acid

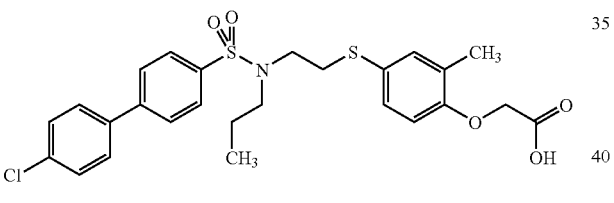

Mass spectrum (ES): 534 (M+H)$^+$, 532 (M−H)$^−$.

EXAMPLE 150

(4-{2-[(4'-Methoxy-biphenyl-4-sulfonyl)-propyl-amino]-ethylsulfanyl}-2-methyl phenoxy)-acetic acid (2123707, NH1-A03057-182-4)

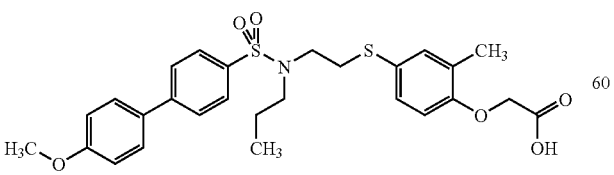

Mass spectrum (ES): 530 (M+H)$^+$, 528 (M−H)$^−$.

EXAMPLE 151

(4-{2-[(3'-Chloro-4'-fluoro-biphenyl-4-sulfonyl)-propyl-amino]-ethylsulfanyl}-2-methyl-phenoxy)-acetic acid

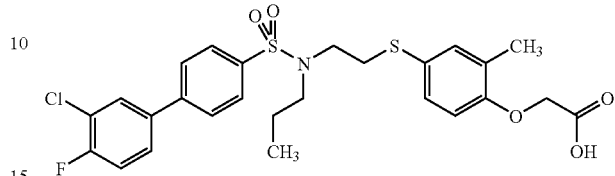

Mass spectrum (ES): 552 (M+H)$^+$, 550 (M−H)$^−$.

EXAMPLE 152

General Procedure (3a)

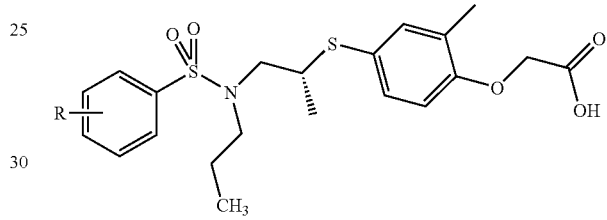

Step A

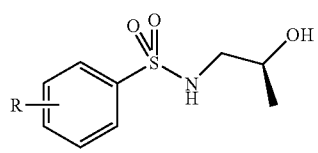

A solution of substituted benzenesulfonyl chloride (5.00 mmol) in methylene chloride (20.0 ml) was added into a mixture of (S)-(+)-amino-2-propanol (5.00 mmol) and triethyl amine (15.0 mmol) in methylene chloride (80.0 ml). The mixture was stirred at room temperature for 16 hours. The mixture was washed with 1.0N HCl (100 ml) and brine (2×100 ml). The organic layer was dried over sodium sulfate and concentrated in vicuo to give the title compound, which was used for the next step without further purification.

Step B

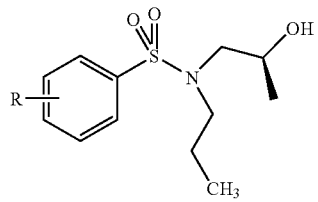

The primary sulfonamide (see Step A) (5.00 mmole) was dissolved in DMF (25.0 ml) and then cesium carbonate (1.95 g, 6.00 mmol) and 1-iodopropane (0.585 ml, 6.00 mmol) were added. The mixture was stirred for 16 hours and then diluted with ethyl acetate (100 ml). The solid was removed through filtration, and the mother liquid was washed with saturated aqueous NH₄Cl (100 ml). The aqueous was extracted back with more ethyl acetate (100 ml). The combined organics were washed with 3×200 ml brine, dried over sodium sulfate and concentrated under reduced pressure to provide the title compound.

Step C

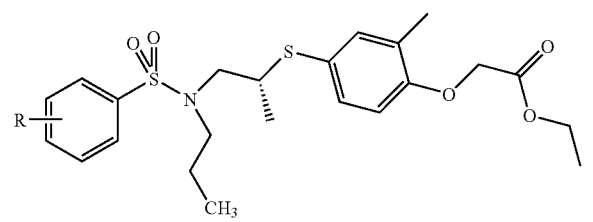

Methanesulfonyl chloride (1.20 mmol) was added dropwise to a mixture of the alcohol obtained from Step B (1.00 mmol) and triethyl amine (1.50 mmol) in DCM (10.0 ml) at 0° C., and the mixture was stirred at 0° C. for 2 hours. The mixture was quenched with 1N HCl (100 ml). The aqueous was extracted with DCM (50.0 ml), and the combined organics were washed with 3×100 ml brine, dried over sodium sulfate and concentrated under reduced pressure to give a mesylate. The mesylate (1.00 mmol) was dissolved in DMF (3.00 ml). The solution of mesylate was added into a mixture of (4-mercapto-2-methyl-phenoxy)-acetic acid ethyl ester (thiophenol headpiece) (1.20 mmol) and potassium carbonate (1.50 mmol) in DMF (3.00 ml) at room temperature, and the mixture was stirred for 16 hours. The mixture was diluted with ethyl acetate (50.0 ml), and the solids were removed by filtration. The mother liquid was washed with saturated aqueous NH₄Cl (50.0 ml), and the aqueous was extracted back with more ethyl acetate (20.0 ml). The combined organics were washed with 3×70.0 ml brine, dried over sodium sulfate and concentrated under reduced pressure. Purification by flash chromatography, eluting with ethyl acetate:hexane (0-1:4) and concentration of fractions afforded the title compound.

Alternatively, the title compound was prepared by the following procedure. The alcohol obtained from Step B (1.00 mmol) and (4-mercapto-2-methyl-phenoxy)-acetic acid ethyl ester (thiophenol headpiece) (1.00 mmol) were mixed in anhydrous toluene (5.00 ml), and the mixture was cooled to 0° C. Tri-n-butylphosphine (1.20 mmol) and a solution of 1,1'-(azodicarbonyl)-dipiperidine (1.20 mmol) in toluene (5.00 ml) were added to the mixture, which was warmed up to room temperature and stirred for 16 hours. The precipitate was removed through filtration, and concentrated under reduced pressure. Purification by flash chromatography, eluting with ethyl acetate:hexane (0-1:4) and concentration of fractions afforded the title compound.

Step D

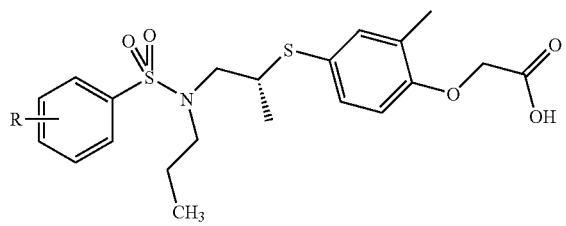

The ethyl ester (Step C, 0.200 mmol) was dissolved in MeOH (2.00 ml) and 5.0N NaOH (1.00 ml) was added, and the mixture was let stand at room temperature overnight The organic solvents were evaporated in vacuo, and adjusted to pH 2 to 3 with concentrated HCl. The water was removed using ChemElut CE 1005, and the Chem elut tube was washed with ethyl acetate (40.0 ml). The solution was concentrated to dryness afford the title compound.

EXAMPLE 153

General Procedure (3b)

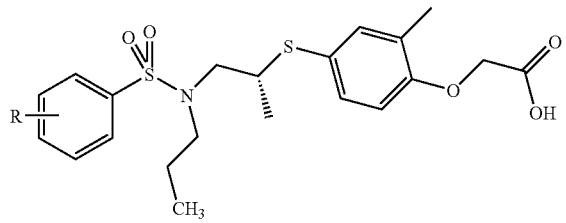

Step A (2-Hydroxy-propyl)-carbamic acid tert-butyl ester

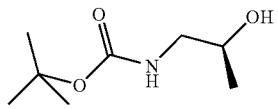

Triethyl amine (22.0 mmol) was added to a mixture of di-tert-butyl dicabonate (20.0 mmole) and (S)-(+)-1-aminopropanol (20.0 mmol) in MeOH (100 ml). The mixture was stirred at room temperature for 16 hours. The methanol was evaporated, the residue was re-dissolved in ethyl acetate (100 ml) and washed with brine (3×100 ml). The organic layer was dried over sodium sulfate and concentrated in vacuo to give the title compound, which was used for the next step without further purification.

Step B

[4-(2-tert-Butoxycarbonylamino-1-methyl-ethylsulfanyl)-2-methyl-phenoxy]-acetic acid ethyl ester

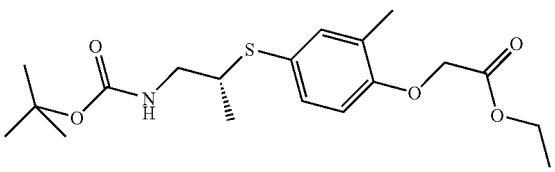

(2-Hydroxy-propyl)-carbamic acid tert-butyl ester (Step B, (10.0 mmol) and (4-mercapto-2-methyl-phenoxy)-acetic acid ethyl ester (thiophenol headpiece) (10.5 mmol) were mixed in anhydrous toluene (25.0 ml), and the mixture was cooled to 0° C. Tri-n-butylphosphine (12.0 mmol) and a solution of 1,1'-(azodicarbonyl)-dipiperidine (12.0 mmol) in toluene (25.0 ml) were added to the mixture, which was warmed up to room temperature and stirred for 16 hours. The precipitate was removed through filtration, and concentrated under reduced pressure. Purification by flash chromatography, eluting with ethyl acetate:hexane (0-1:4) and concentration of fractions afforded the title compound.

Step C

[4-(2-Amino-1-methyl-ethylsulfanyl)-2-methyl-phenoxy]-acetic acid ethyl ester

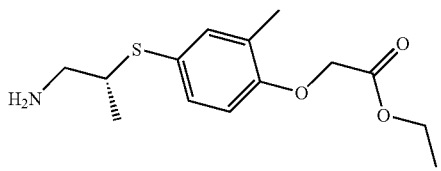

Trifluoroacetic acid (17 ml) was added dropwise to a mixture of [4-(2-tert-butoxycarbonylamino-1-methyl-ethylsulfanyl)-2-methyl-phenoxy]-acetic acid ethyl ester (Step B, 10.0 mmol) and dimethylethyl silane (30.0 mmol) in methylene chloride (100 ml) at room temperature. The mixture was stirred for 2 hours, which was then washed with saturated NaHCO$_3$ (3×100 ml), dried over Na$_2$SO$_4$ and concentrated on a rota-vapor to give the title compound. The compound was used for the next step directly without purification.

Step D

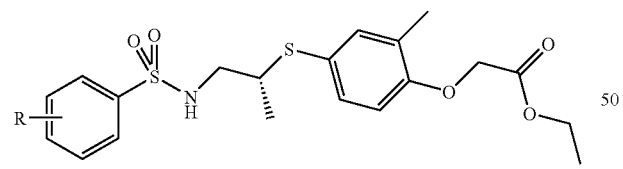

A solution of substituted benzene sulfonyl chloride (5.00 mmole) was added to a mixture of [4-(2-amino-1-methyl-ethylsulfanyl)-2-methyl-phenoxy]-acetic acid ethyl ester (Step C, 5.00 mmol) and Et$_3$N (15.0 mmol) in methylene chloride (40.0 ml) at 0° C., and the mixture was warmed up and stirred the reaction at room temperature for 16 hours. The mixture was washed with 1N HCl (50.0 ml) and brine (3×50.0 ml), dried over sodium sulfate and concentrated under reduced pressure. Purification by column chromatography, eluting with ethyl acetate:hexane (2:3) and evaporation of solvents afforded the title compound.

Step E

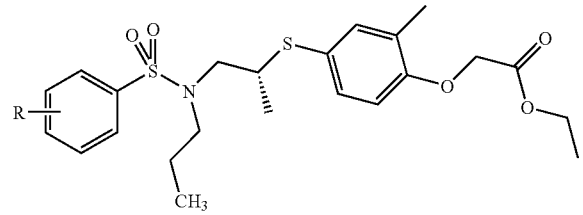

The primary sulfonamide (see Step D) (5.00 mmol) was dissolved in DMF (25.0 ml), and cesium carbonate (1.95 g, 6.00 mmol) and 1-iodopropane (0.585 ml, 6.00 mmol) were added. The mixture was stirred for 16 hours, and then diluted with ethyl acetate (100 ml). The solid was removed through filtration, and the mother liquid was washed with saturated aqueous NH$_4$Cl (100 ml). The aqueous was extracted back with more ethyl acetate (100 ml). The combined organics were washed with 3×200 ml brine, dried over sodium sulfate and concentrated under reduced pressure. Purification by flash chromatography, eluting with ethyl acetate:hexane (0-1:4) and concentration of fractions afforded the title compound.

Step F

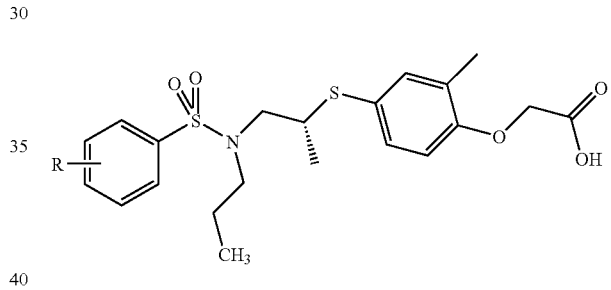

The ethyl ester (1.00 mmol) obtained from Step E was dissolved in MeOH (10.0 ml) and 5.0N NaOH (5.00 ml) was added and the mixture was let stand at room temperature overnight. The organic solvents were evaporated in vacuo, and adjusted to pH 2 to 3 with concentrated HCl. The water was removed using ChemElut CE1010, which was washed with ethyl acetate (200 ml). The solution was then concentrated to dryness give the title compound.

EXAMPLE 154

General Procedure (3c)

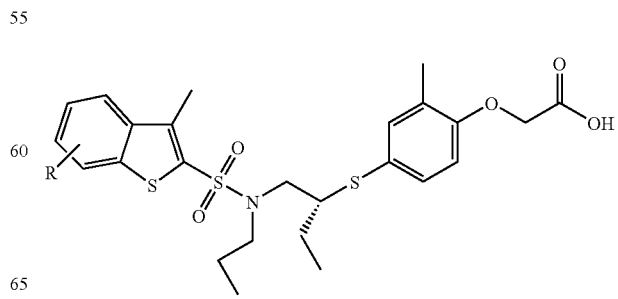

Step A

1-(4-Methoxy-benzylamino)-butan-2-ol

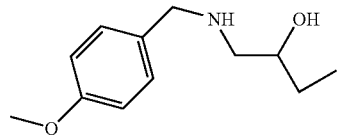

1-amino-2-butanol (0.157 mol) was added to a 0° C. suspension of p-anisaldehyde (0.172 mol) and sodium sulphate (0.188 mol) in dry $CH_2Cl_2$ (150 mL). The resulting mixture was stirred at room temperature for one hour, filtered, and concentrated in vacuo. The residue was diluted with 4 Å molecular sieve-dried ethanol (100 mL) and cooled to 0° C. Sodium borohydride (0.157 mol) was added to the solution in two portions and the resulting mixture was stirred at room temperature for two hours. The resultant mixture was concentrated in vacuo, and then partitioned between $CH_2Cl_2$ and 1 N NaOH. The organic layer was acidified to pH 10 with 1N HCl, dried over sodium sulphate, and concentrated in vacuo to give >99% yield of 1-(4-methoxy-benzylamino)-butan-2-ol. $^1$H NMR (400 MHz, $CDCl_3$) δ 7.25 (d, 2H, J=8.6 Hz), 6.85 (d, 2H, J=8.6 Hz). 3.78 s. 3H), 3.72, 3.68 (ABq, 2H, J=12.4 Hz) 3.56-3.50 (m, 1H), 2.71 (dd, 1H, J=12.3 Hz, 2.8 Hz), 2.49 (dd, 1H, J=12.3 Hz, 9.6 Hz) 1.46-1.38 (m, 2H), 0.92 t, 3H, J=7. 4 Hz). MS [EI+] 210 (M+H)$^+$.

Step B

5-Ethyl-3-(4-methoxy-benzyl)-[1,2,3]oxathiazolidine 2-oxide

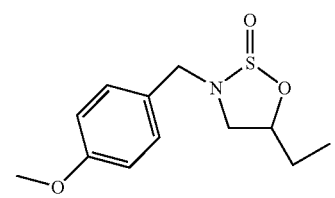

Thionyl chloride (20.29 mol) was added dropwise to a −78° C. solution of 1-(4-methoxy-benzylamino)-butan-2-ol (0.16 mol) and triethylamine (0.59 mol) in dry $CH_2Cl_2$. The resulting mixture was stirred at −78° C. for 40 minutes, and then warmed to 0° C. for five hours. The mixture was diluted with water and extracted with $CH_2Cl_2$. The organic layers were combined, dried over sodium sulphate, and concentrated in vacuo. The residue was purified by flash chromatography using 11% acetone in hexanes as eluent, and gave 15.35 g (39%) of 5-ethyl-3-(4-methoxy-benzyl)-[1,2,3]oxathiazolidine 2-oxide. $^1$H NMR (400 MHz. $CDCl_3$) δ 7.28 (dd, 2H, J=8.5 Hz, 4.5 Hz), 6.87 (d, 2H, J=8.5 Hz), 5.02-4.96 (m, 1H), 4.54-4.47 (m, 1H), 4.24, 4.22 (ABq, 2H, J=5.9 Hz isomer 1), 3.91, 3.79 (ABq, 2H, J=13.3 Hz isomer 2), 3.79 s, 3H), 3.41, 3.39 (ABq, 1H, J=6.1 Hz isomer 1) 3.29, 3.27 (ABq 1H, J=6.1 Hz isomer 2) 3.12, 3.10 (ABq, 1H, J=9.6 Hz isomer 1) 2.92, 2.90 (ABq, 1H, J=9.6 Hz isomer 2) 1.98-1.77 (m, 2H isomer 1), 1.76-1.57 (m, 2H isomer 2), 1.00 t, 3H, J=7.5 Hz), 0.94(t, 3H, J=7.5 Hz). $R_f$=0.31 in 33% acetone in hexanes.

Step C

5-Ethyl-3-(4-methoxy-benzyl)-[1,2,3]oxathiazolidine 2,2-dioxide

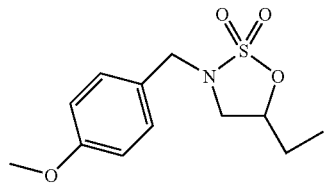

Ruthenium (III) chloride (1.32 mmol) was added to a biphasic solution of 5-ethyl-3-(4-methoxy-benzyl)-[1,2,3] oxathiazolidine 2-oxide (15.35 g, 60.1 mmol), sodium periodate (0.12 mol), $CCl_4$ (150 mL), $CH_3CN$ (150 mL), and water (180 mL). The resulting mixture was stirred at room temperature for three hours, and then filtered through a pad of celite. The filtrate was diluted with $CH_2Cl_2$ and washed with sodium thiosulphate solution and water. The residue was purified by flash chromatography, using 11% acetone in hexanes as eluent, and gave 14.33 g (88%) of 5-ethyl-3-(4-methoxy-benzyl)-[1,2,3]oxathiazolidine 2,2-dioxide. This material was resolved using chiral HPLC (Chiralpak OJ 4.6×150 mm, 30/70 alcohol/heptane, 0.6 mL/min, 240 nm UV setting) to give enantiomers: isomer 1, (>98% ee, R) and isomer 2, (>98% ee S). $^1$H NMR (400 MHz, $CDCl_3$) δ 7.27 (d, 2H, J=8.8 Hz), 6.88 (d, 2H, J=8.8 Hz), 4.69-4.62 (m, 1H), 4.23, 4.03 (ABq, 2H, J=13.4 Hz), 3.80 s, 3H), 3.35 (dd, 1H, J=9.5 Hz, 6.2 Hz) 3.03 (dd, 1H, J=9.5 Hz, 8.2 Hz) 1.92-1.81 (m, 1H), 1.75-1.65 (m, 1H), 0.98 t, 3H, J=7.5 Hz). $R_f$=0.31 in 33% acetone in hexanes.

Step D

(4-{1-[(4-Methoxy-benzylamino)-methyl]-propylsulfanyl}-2-methyl-phenoxy)-acetic acid ethyl ester

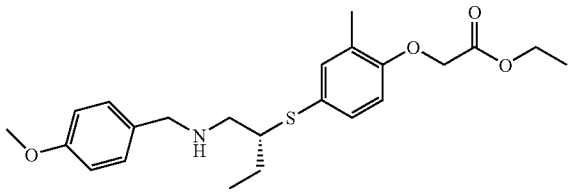

A 0° C. solution of (4-mercapto-2-methyl-phenoxy)-acetic acid ethyl ester (29.43 mmol) in dimethylformamide (10 mL) was treated with sodium hydride (29.43 mmol). The suspension was flushed with $N_2$ while stirring for 15 minutes at 0° C. 5-Ethyl-3-(4-methoxy-benzyl)-[1,2,3]oxathiazolidine 2,2-dioxide (19.62 mmol) in dimethylformamide (10 mL) was added and the resulting mixture was heated at 50° C. for 4 h. The mixture was cooled to ambient temperature, diluted with diethyl ether, and stirred with 1N HCl. After 8 h, the mixture was basified to pH7 with saturated aqueous sodium bicarbonate solution. The organic layer was washed with water and brine, dried over sodium sulphate. treated with trifluoroacetic acid (58.86 mmol), and concentrated in vacuo to provide 15.6 g (84%) of the title compound as a TFA salt. $^1$H NMR (400 MHz, CDCl$_3$) δ 7.20 (d, 2H, J=9.1 Hz), 6.95 (d, 1H J=1.4 Hz), 6.87-6.84 (m, 1H), 6.85 (d, 2H, J=8.7 Hz), 6.43 (d, 1H, J=9.1 Hz), 4.55 (s, 2H), 4.20 (p, 2H, J=7.0 Hz), 4.20-4.06 (m, 2H), 3.74 (s, 3H0. 3.09-3.02 (m, 2H), 2.86-2.74 (m, 1H), 2.09 (s, 3H), 1.42 (p, 21, J=7.0 Hz), 1.22 (t, 31. J=7.0 Hz), 0.95 (t, 3H) J=7.0 Hz). MS [EI+] 418 (M+H)$^+$.

Step E

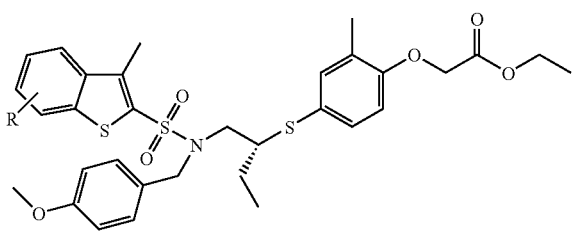

A 0° C. solution of (4-{1-[(4-methoxy-benzylamino)-methyl]-propylsulfanyl}-2-methyl-phenoxy)-acetic acid ethyl ester (18.97 mmol) in dichloromethane (200 mL) was treated with triethylamine (151.76 mmol). An appropriately substituted sulfonyl chloride (24.6 mmol) was added all at once and the reaction mixture was warmed to ambient temperature for 1.5 h. The reaction mixture was diluted with dichloromethane and washed with 1N HCl. The organic layers were combined, dried over MgSO$_4$, and concentrated in vacuo. The crude material was purified by flash chromatography to provide the title compound.

Step F

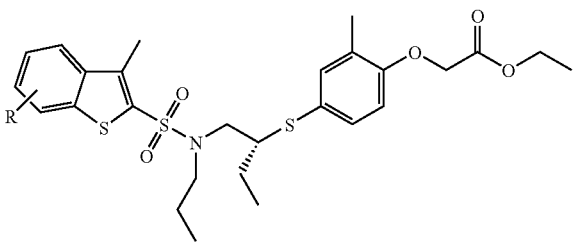

Trifluoroacetic acid (70 mL, 1 mmol) was added dropwise to a solution of the benzylamine (7.19 mmol) and triethylsilane (144 mmol). The resulting solution was stirred at ambient temperature for 1 h, then concentrated in vacuo. The reaction residue was diluted with diethyl ether and washed with saturated aqueous sodium bicarbonate and water. The organic layer was dried over sodium sulphate and concentrated in vacuo.

1-Iodopropane (21.8 mmol) was added to a suspension of the crude amine (21.8 mmol) in dimethylformamide (100 mL). The resulting mixture was healed to 50° C. for 2 h, and then cooled to ambient temperature and diluted with diethyl ether. The organic layer was washed with 1N HCl, water, and brine, dried over MgSO$_4$, and concentrated in vacuo to provide the title compound.

Step G

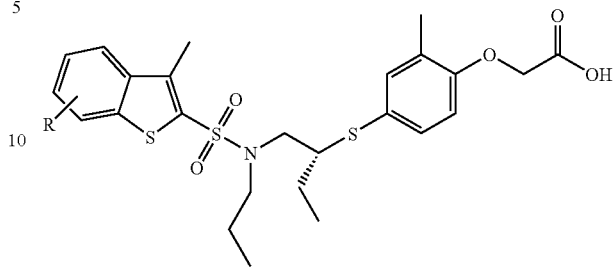

A solution of the ethyl ester (3.79 mmol) and 5N NaOH (2 mL) in ethanol (20 mL) was refluxed under nitrogen for 0.5 h, cooled to ambient temperature, and concentrated in vacuo. The residue was diluted with 1N HCl, extracted with CH$_2$Cl$_2$, dried over Na$_2$SO$_4$, and concentrated in vacuo to provide the title compound.

The following Examples 155 to) 60 were prepared according to the General Procedures (3a), (3b) and (3c) as described above in Examples 152 to 154 by using an appropriate starting material.

EXAMPLE 155

{2-Methyl-4-[1-methyl-2-(4-trifluoromethyl-benzenesulfonylamino)-ethylsulfanyl]-phenoxy}-acetic acid

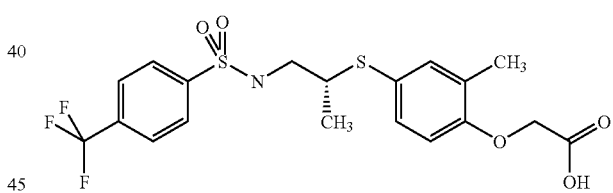

Mass spectrum (ES): 464 (M+H)$^+$, 462 (M−H)$^−$.

EXAMPLE 156

(2-Methyl-4-{1-methyl-2-[propyl-(4-trifluoromethyl-benzenesulfonyl)-amino]-ethylsulfanyl}-phenoxy)-acetic acid

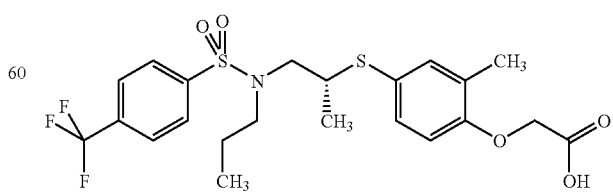

Mass spectrum (ES): 506 (M+H)$^+$, 504 (M−H)$^−$.

EXAMPLE 157

(4-{2-[(3,4-Dichloro-benzenesulfonyl)-propyl-amino]-1-methyl-ethylsulfanyl}-2-methyl-phenoxy)-acetic acid

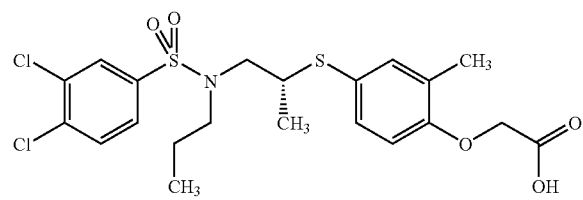

Mass spectrum (ES): 506 (M+H)+, 504 (M-H)-.

EXAMPLE 158

(2-Methyl-4-{1-methyl-2-[propyl-(4-trifluoromethoxy-benzenesulfonyl)-amino]-ethylsulfanyl}-phenoxy)-acetic acid

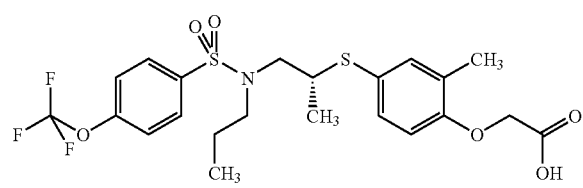

Mass spectrum (ES): 522 (M+H)+, 520 (M-H)-.

EXAMPLE 159

(2-Methyl-4-{1-methyl-2-[propyl-(4-propyl-benzenesulfonyl)-amino]-ethylsulfanyl}-phenoxy)-acetic acid

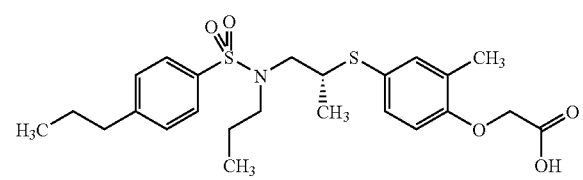

Mass spectrum (ES): 480 (M+H)+, 478 (M-H)-.

EXAMPLE 160

(4-{2-[(4-Chloro-3-trifluoromethyl-benzenesulfonyl)-propyl-amino]-1-methyl-ethylsulfanyl}-2-methyl-phenoxy)-acetic acid

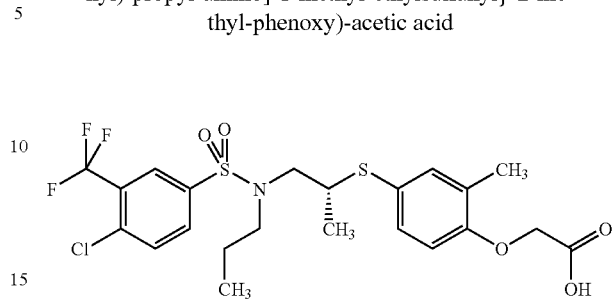

Mass spectrum (ES): 540 (M+H)+, 538 (M-H)-.

EXAMPLE 161

(4-{2-[(3-Chloro-4-trifluoromethyl-benzenesulfonyl)-propyl-amino]-1-methyl-ethylsulfanyl}-2-methyl-phenoxy)-acetic acid

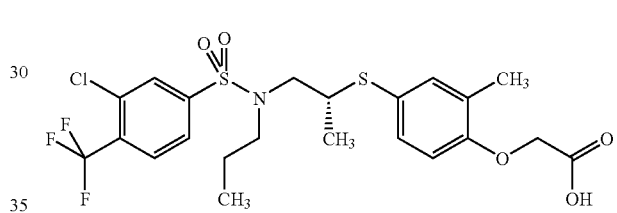

Mass spectrum (ES): 540 (M+H)+, 538 (M-H)-.

The title compound was prepared by using the intermediate 3-chloro-4-trifluoromethyl-benzenesulfonyl chloride, which was prepared as described below and following General Procedure 3(a) or 3(b) as described in Examples 152 and 153.

Step A

2-Chloro-4-nitro-1-trifluoromethyl-benzene

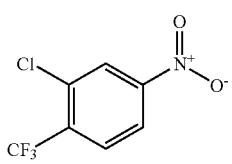

1-Bromo-2-chloro-4-nitrobenzene (1.86 g. 7.86 mmol) and CuI (0.225 g, 1.18 mmole) were mixed in anhydrous DMF (50 ml), and degassed with nitrogen for 15 minutes. Methyl fluorosulphonyl difluoroacetate (3.53 g, 23.6 mmol) was added, and the mixture was heated at 80° C. for 16 hours. After cooling to room temperature, the reaction mixture was partitioned between ethyl acetate (100 ml) and brine (100 ml). The aqueous layer was extracted with more ethyl acetate (100 ml). The combined organics were washed with 3×200 ml brine, dried over Na₂SO₄, concentrated, and purified by chromatography, eluting with ethyl acetate/hexane (1:9).

Step B

3-Chloro-4-trifluoromethyl-phenylamine

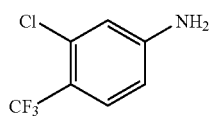

Tin(II) chloride dihydrate (4.97 mmol) in one portion was added to a solution of 2-chloro-4-nitro-1-trifluoromethyl-benzene (4.14 mmole) in methanol at room temperature, and the mixture was stirred for 16 hours. The mixture was concentrated in vacuo, and purified by chromatography, eluting with ethyl acetate/hexane (1:4 to 2:3) to give the title compound.

Step C

3-Chloro-4-trifluoromethyl-benzenesulfonyl chloride

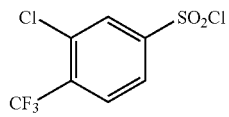

A solution of NaNO$_{2(aq)}$ (4.00 mmole, 1.00 ml) was added to a suspension of 3-chloro-4-trifluoromethyl aniline (Step B) (4.00 mmole) in concentrated HCl/glacial acetic acid (3.50: 1.00, 4.50 ml) at 0° C., and the mixture was stirred for an hour. The diazonium salt formed above was transferred into a saturated solution of SO₂ in glacial HOAc (15.0 ml) at 0° C., and the mixture was warmed up to room temperature for an hour. The mixture was poured into ice water (100 ml) and extracted with 3×50.0 ml ethyl ether. The combined organics were washed with 3×100 ml NaHCO$_{3(aq)}$, 3×100 ml brine, dried over Na₂SO₄, concentrated, and purified by chromatography, eluting with ethyl acetate/hexane (1:9).

EXAMPLE 162

General Procedure (4)

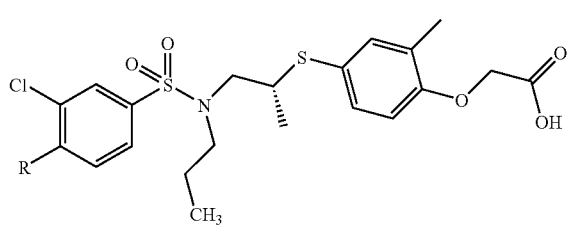

Step A (4-{2-[(4-Bromo-3-chloro-benzenesulfonyl)-propyl-amino]-1-methyl-ethylsulfanyl}-2-methyl-phenoxy)-acetic acid ethyl ester

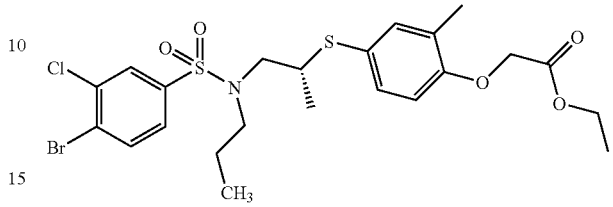

The titled compound can be prepared following General Procedure (3b), Steps A-E as described in Example 153.

Step B

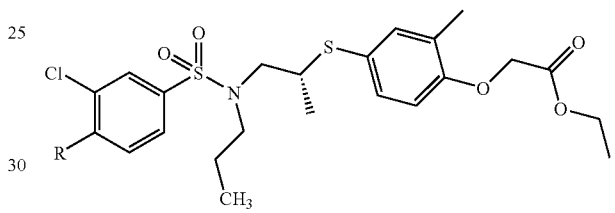

Dissolve (4-{2-[(4-bromo-3-chloro-benzenesulfonyl)-propyl-amino]-1-methyl-ethylsulfanyl}-2-methyl-phenoxy)-acetic acid ethyl ester (0.200 mmol) in THF (2.00 ml) at room temperature. Degas the solution with nitrogen gas for 15 minutes, then add the catalyst PdCl₂(dppf) (0.0100 mmol) and CuI (0.0120 mmol) subsequently. Inject corresponding alkyl zinc bromide in THF (0.5M 0.6 ml) and then stir for 3 hours. Remove the solvent on rota vapor. Partition the residue between ethyl acetate (20 ml) and 1N HCl$_{(aq)}$ (20 ml), wash the organic layer with brine (3×20 ml), dried over Na₂SO₄ and concentrated. Purification by column chromatography, eluting with ethyl acetate:hexane (1:4) to provide the title compound.

Step C

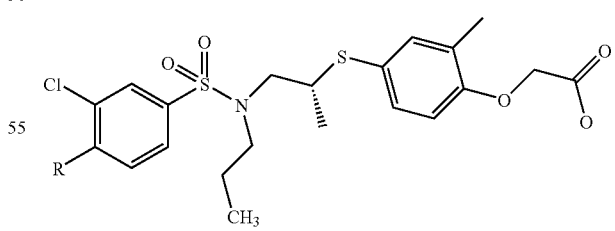

Dissolve the ethyl ester (1.00 mmol) obtained from Step B in MeOH (10.0 ml) and add 5.0N NaOH (5.00 ml), stand at room temperature overnight. Evaporate the organic solvents in vacuo, adjust pH=2 to 3 with concentrated HCl. Remove the water using ChemElut CE1010. Wash the Chem elut tube with ethyl acetate (100 ml) and concentrate the solution to dryness give the title compound.

EXAMPLE 163

(4-{2-[(4-sec-Butyl-3-chloro-benzenesulfonyl)-propyl-amino]-1-methyl-ethylsulfanyl}-2-methyl-phenoxy)-acetic acid

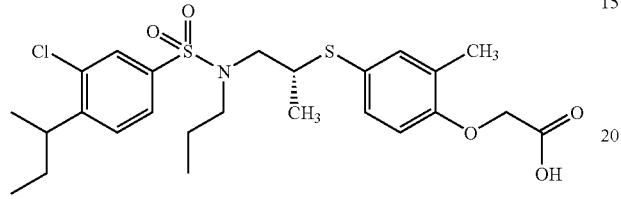

Mass spectrum (ES): 528 (M+H)+, 526 (M−H)−.

EXAMPLE 164

(4-{2-[(3-Chloro-4-cyclopentyl-benzenesulfonyl)-propyl-amino]-1-methyl-ethylsulfanyl}-2-methyl-phenoxy)-acetic acid

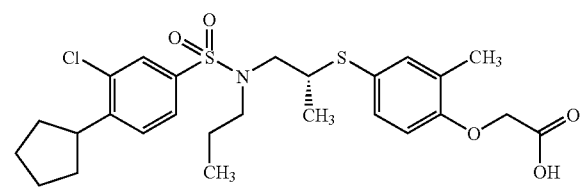

Mass spectrum (ES): 540 (M+H)+, 538 (M−H)−.

EXAMPLE 165

(4-{2-[(3-Chloro-4-cyclohexyl-benzenesulfonyl)-propyl-amino]-1-methyl-ethylsulfanyl}-2-methyl-phenoxy)-acetic acid

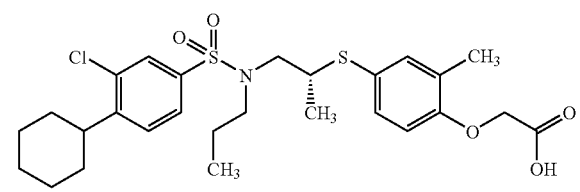

Mass spectrum (ES): 554 (M+H)+, 552 (M−H)−.

EXAMPLE 166

(2-Methyl-4-{1-methyl-2-[propyl-(4-trifluoromethoxy-benzenesulfonyl)-amino]-1-ethylsulfanyl}-phenoxy)-acetic acid

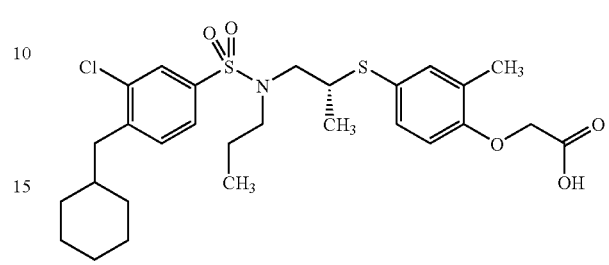

Mass spectrum (ES): 568 (M+H)+, 566 (M−H)−.

EXAMPLE 167

(2-Methyl-4-{1-methyl-2-[propyl-(4-trifluoromethoxy-benzenesulfonyl)-amino]-ethoxy}-phenylsulfanyl)-acetic acid

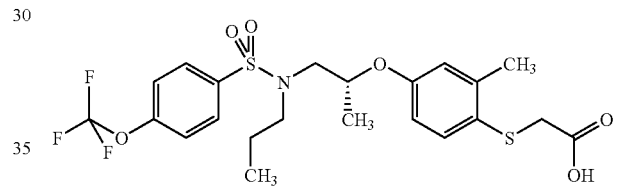

The title compound was prepared according to General Procedure (3a) as described in Example 152 using (4-hydroxy-2-methyl-phenylsulfanyl)-acetic acid ethyl ester instead of (4-mercapto-2-methyl-phenoxy)-acetic acid ethyl ester (thiophenol headpiece). MS (ES): 522 (M+H)+, 520 (M−H)−.

EXAMPLE 168

3-(2-Methyl-4-{1-methyl-2-[propyl-(4-trifluoromethoxy-benzenesulfonyl)-amino]-ethylsulfanyl}-phenyl)-propionic acid

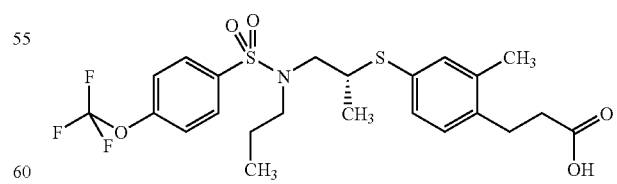

The title compound was prepared according to General Procedure (3a) as described in Example 152 using 3-(4-mercapto-2-methyl-phenyl)-propionic acid methyl ester instead of (4-mercapto-2-methyl-phenoxy)-acetic acid ethyl ester (thiophenol headpiece). MS (ES): 520 (M+H)+, 518 (M−H)−.

EXAMPLE 169

3-(2-Methyl-4-{1-methyl-2-[propyl-(4-trifluoromethoxy-benzenesulfonyl)-amino]-ethoxy}-phenyl)-propionic acid

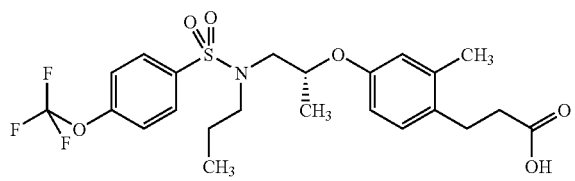

The title compound was prepared according to General Procedure (3a) as described in Example 152 using 3-(4-hydroxy-2-methyl-phenyl)-propionic acid methyl ester instead of (4-mercapto-2-methyl-phenoxy)-acetic acid ethyl ester (thiophenol headpiece). MS (ES): 504 (M+H)+, 502 (M−H)−.

EXAMPLE 170

(2-Methyl-4-{1-methyl-2-[propyl-(4-trifluoromethoxy-benzenesulfonyl)-amino]-ethoxy}-phenoxy)-acetic acid

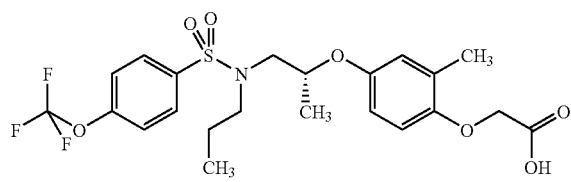

The title compound was prepared according to General Procedure (3a) as described in Example 152 using (4-hydroxy-2-methyl-phenoxy)-acetic acid methyl ester instead of (4-mercapto-2-methyl-phenoxy)-acetic acid ethyl ester (thiophenol headpiece). MS (ES): 506 (M+H)+, 504 (M−H)−.

EXAMPLE 171

(4-{2-[(2-Chloro-4-trifluoromethyl-benzenesulfonyl)-propyl-amino]-1-methyl-ethylsulfanyl}-2-methyl-phenoxy)-acetic acid

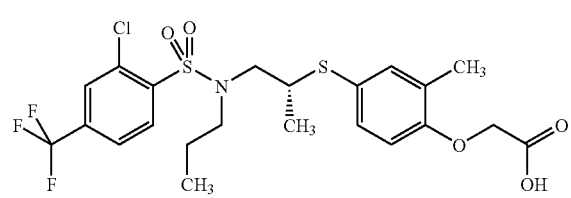

MS (ES): 540 (M+H)+, 538 (M−H)−.

EXAMPLE 172

(4-{2-[(4-Bromo-3-chloro-benzenesulfonyl)-propyl-amino]-1-methyl-ethylsulfanyl}-2-methyl-phenoxy)-acetic acid

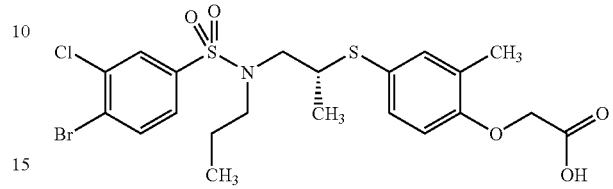

MS (ES): 550, 552 (M+H)+, 548, 550 (M−H)−.

The following Examples 173 and 174 were prepared according to the General Procedure (3b), Step A to Step E as described in Example 153 and the General Procedure (2) as described in Example 139 using (4-{2-[(4-bromo-3-chloro-benzenesulfonyl)-propyl-amino]-1-methyl-ethylsulfanyl}-2-methyl-phenoxy)-acetic acid ethyl ester instead of (4-{2-[(4-bromo-benzenesulfonyl)-propyl-amino]-ethylsulfanyl}-2-methyl-phenoxy)-acetic acid ethyl ester.

EXAMPLE 173

(4-{2-[(4-Butyl-3-chloro-benzenesulfonyl)-propyl-amino]-1-methyl-ethylsulfanyl}-2-methyl-phenoxy)-acetic acid

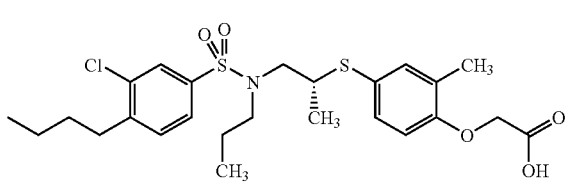

MS (ES): 528 (M+H)+, 526 (M−H)−.

EXAMPLE 174

(4-{2-[(3-Chloro-4-isobutyl-benzenesulfonyl)-propyl-amino]-1-methyl-ethylsulfanyl}-2-methyl-phenoxy)-acetic acid

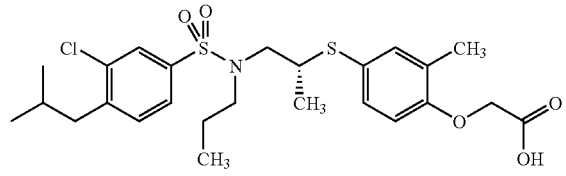

Mass spectrum (ES): 528 (M+H)+, 526 (M−H)−.

The following Examples 175 to 183 were prepared according to General Procedure (1) as described in Example 105.

EXAMPLE 175

(2-Methyl-4-{2-[(6-phenoxy-pyridine-3-sulfonyl)-propyl-amino]-ethylsulfanyl}phenoxy)-acetic acid

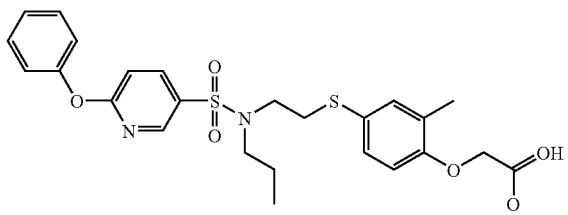

The title compound was prepared from 6-phenoxy-pyridine-3-sulfonyl chloride to afford 155 mg (64%). MS (ES+) m/z; 517 (M+1).

EXAMPLE 176

(2-Methyl-4-{2-[(5-methyl-1-phenyl-1H-pyrazole-4-sulfonyl)-propyl-amino]-ethylsulfanyl}-phenoxy)-acetic acid

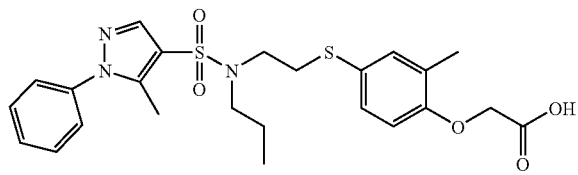

The title compound was prepared from 5-methyl-1-phenyl-1H-pyrazole-4-sulfonyl chloride to afford 175 mg (74%). MS (ES+) m/z: 504 (M+1).

EXAMPLE 177

(2-Methyl-4-{2-[(6-morpholin-4-yl-pyridine-3-sulfonyl)-propyl-amino]-ethylsulfanyl}-phenoxy)-acetic acid

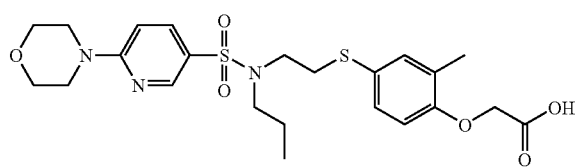

The title compound was prepared from 6-morpholin-4-yl-pyridine-3-sulfonyl chloride to afford 153 mg (64%). MS (ES+) m/z: 510 (M+1).

EXAMPLE 178

(2-Methyl-4-{2-[(4-oxazol-5-yl-benzenesulfonyl)-propyl-amino]-ethylsulfanyl}-phenoxy)-acetic acid

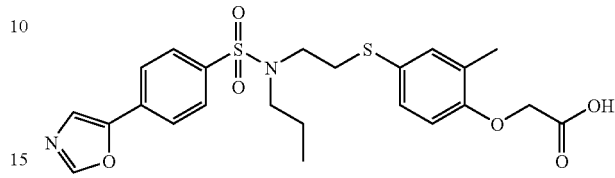

The title compound was prepared from 4-oxazol-5-yl-benzenesulfonyl chloride to afford 154 mg (67%). MS (ES+) m/z: 491 (M+1).

EXAMPLE 179

(4-{2-[(4-Benzenesulfonyl-thiophene-2-sulfonyl)-propyl-amino]-ethylsulfanyl}-2-methyl-phenoxy)-acetic acid

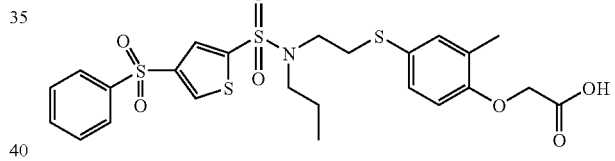

The title compound was prepared from 4-Benzenesulfonyl-thiophene-2-sulfonyl chloride to afford 182 mg (68%). MS (ES+) m/z: 570 (M+1).

EXAMPLE 180

(2-Methyl-4-{2-[propyl-(4-pyrazol-1-yl-benzenesulfonyl)-amino]-ethylsulfanyl}-phenoxy)-acetic acid

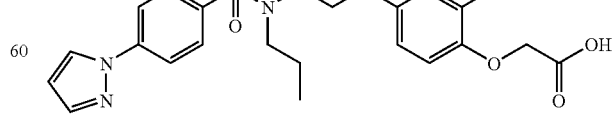

The title compound was prepared from 4-pyrazol-1-yl-benzenesulfonyl chloride to afford 148 mg (64%). MS (ES+) m/z: 490 (M+1).

EXAMPLE 181

(4-{2-[(2,4-Dimethyl-thiazole-5-sulfonyl)-propyl-amino]-ethylsulfanyl}-2-methyl-phenoxy)-acetic acid

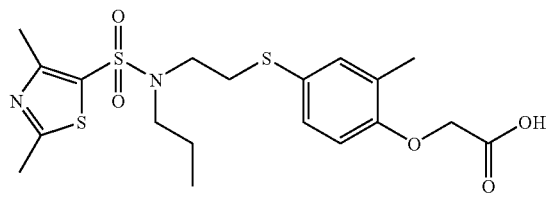

The title compound was prepared from 2,4-dimethyl-thiazole-5-sulfonyl chloride to afford 80 mg (37%). MS (ES$^+$) m/z: 459 (M+1).

EXAMPLE 182

(4-{2-[(2,3-Dihydro-benzo[1,4]dioxine-6-sulfonyl)-propyl-amino]-ethylsulfanyl}-2-methyl-phenoxy)-acetic acid

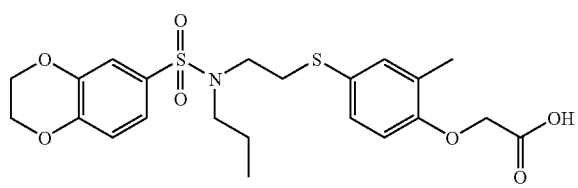

The title compound was prepared from 2,3-dihydro-benzo[1,4]dioxine-6-sulfonyl chloride to afford 38 mg (17%). MS (ES$^-$) m/z: 480 (M−1).

EXAMPLE 183

(2-Methyl-4-{2-[(2-naphthalen-1-yl-ethanesulfonyl)-propyl-amino]-ethylsulfanyl}-phenoxy)-acetic acid

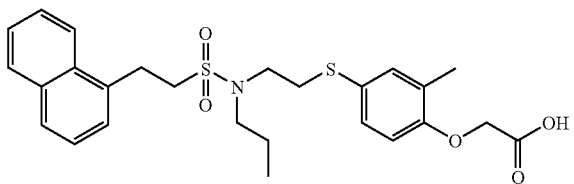

The title compound was prepared from 2-Naphthalen-1-yl-ethanesulfonyl chloride to afford 26 mg (12%). MS (ES$^-$) m/z: 500 (M−1).

EXAMPLE 184

{2-Methyl-4-[2-(propyl-p-tolylmethanesulfonyl-amino)-ethylsulfanyl]-phenoxy}-acetic acid

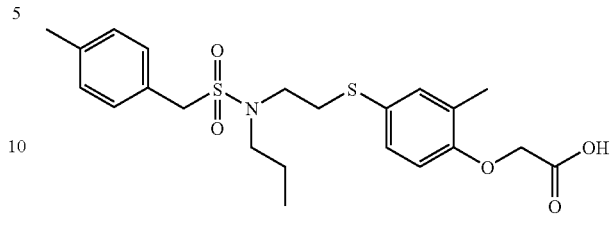

Step A

{2-Methyl-4-[2-(propyl-p-tolylmethanesulfonyl-amino)-ethylsulfanyl]-phenoxy}-acetic acid ethyl ester

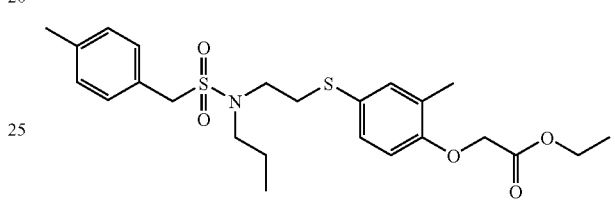

To a cooled (0° C.) solution of the trifluoroacetic acid salt of [2-methyl-4-(2-propylamino-ethylsulfanyl)-phenoxy]-acetic acid ethyl ester (175 mg, 0.41 mmol) in methylene chloride (2 ml) was added 1,8-diazabicyclo[5.4.0]undec-7-ene (0.13 ml, 0.86 mmol) followed by p-tolyl-methanesulfonyl chloride (84 mg, 0.41 mmol). The mixture was stirred for 1 hour at 0° C., then stirred at room temperature for 20 hours. The mixture was diluted with methylene chloride (5 ml), then washed with 1N HCl, water and brine, and then dried (Na$_2$SO$_4$) and concentrated to an oil. The crude product was purified by silica chromatography to provide about 40 mg of the title compound (20%). MS (ES$^+$) m/z: 480 (M+1).

Step B

{2-Methyl-4-[2-(propyl-p-tolylmethanesulfonyl-amino)-ethylsulfanyl]-phenoxy}-acetic acid

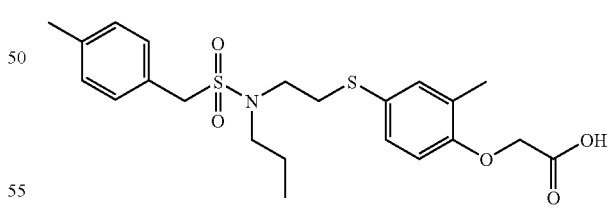

To a solution of {2-methyl-4-[2-propyl-p-tolylmethanesulfonyl-amino)-ethylsulfanyl]-phenoxy}-acetic acid ethyl ester (40 mg, 0.08 mmol) in methanol (2 ml) at room temperature was added aqueous 5N NaOH (0.2 ml, 1 mmol), and the mixture was stirred for 18 hours. The mixture was concentrated to give a residue, which was dissolved in water (10 ml) and CH$_2$Cl$_2$ (15 ml). The mixture was adjusted to pH 4 with 6N HCl. After extracting the aqueous layer with CH$_2$Cl$_2$ (2×10 ml), the combined organic extracts were washed with brine, dried (Na$_2$SO$_4$) and concentrated to an oil, which was purified by preparative reverse-phase HPLC (elution with 1%

TFA in acetonitrile) to afford about 34 mg (93%) of the title compound as a solid after lyophilization. MS (ES⁻) m/z: 450 (M−1).

The following Examples 185 to 193 were prepared according to the method as described in Example 184.

EXAMPLE 185

(2-Methyl-4-{2-[propyl-(4-trifluoromethyl phenyl-methanesulfonyl)-amino]-ethylsulfanyl}-phenoxy)-acetic acid

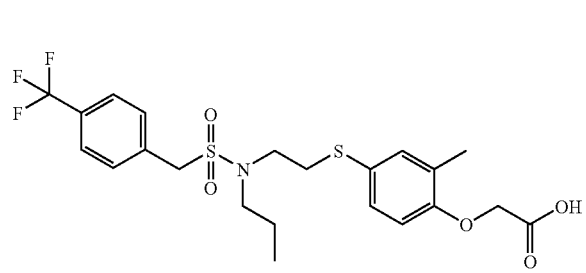

The title compound was prepared from (4-trifluoromethyl-phenyl)-methanesulfonyl chloride to afford 31 mg (15%). MS (ES⁻) m/z: 504 (M−1).

EXAMPLE 186

(4-{2-[(3,4-Dichloro-phenylmethanesulfonyl)-propyl-amino]-ethylsulfanyl}-2-methyl-phenoxy)-acetic acid

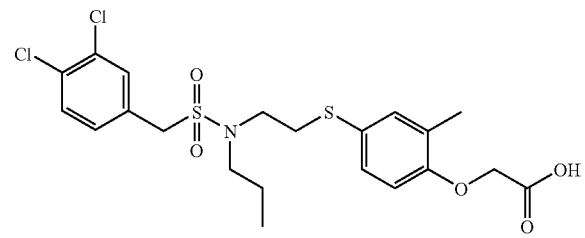

The title compound was prepared from (3,4-dichloro-phenyl)-methanesulfonyl chloride to afford 17 mg (8%). MS (ES⁻) m/z: 505 (M−1).

EXAMPLE 187

{2-Methyl-4-[2-(phenylmethanesulfonyl-propyl-amino) ethylsulfanyl]-phenoxy}-acetic acid

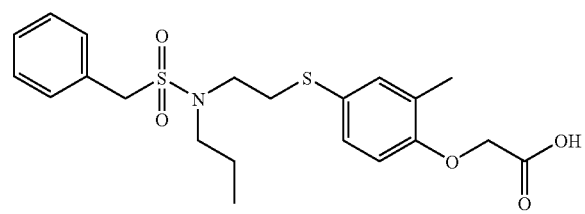

The title compound was prepared from phenyl-methanesulfonyl chloride to afford 24 mg (13%). MS (ES⁻) m/z: 436 (M−1).

EXAMPLE 188

(2-Methyl-4-{2-[(2-nitro-phenylmethanesulfonyl)-propyl-amino]-ethylsulfanyl}-phenoxy)-acetic acid

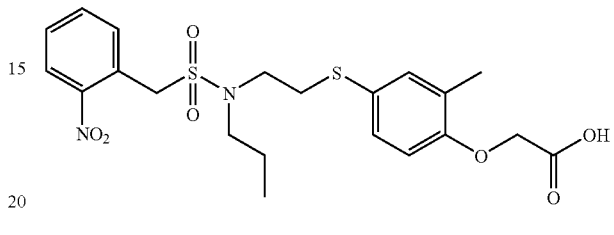

The title compound was prepared from (2-nitro-phenyl)-methanesulfonyl chloride to afford 12 mg (6%). MS (ES⁻) m/z: 481 (M−1).

EXAMPLE 189

(4-{2-[(Biphenyl-3-sulfonyl)-propyl-amino]-ethyl-sulfanyl}-2-methyl-phenoxy)-acetic acid

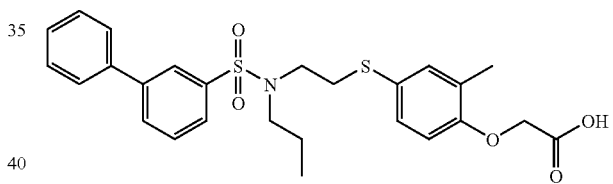

The title compound was prepared from biphenyl-3-sulfonyl chloride to afford 30 mg (15%). MS (ES⁻) m/z: 498 (M−1).

EXAMPLE 190

[2-Methyl-4-(2-{[5-(2-methylsulfanyl-pyrimidin-4-yl)-thiophene-2-sulfonyl]-propyl-amino}-ethylsulfanyl)-phenoxyl]-acetic acid

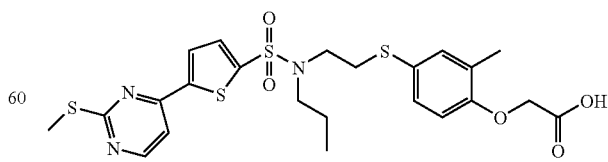

The title compound was prepared from 5-(2-methylsulfanyl-pyrimidin-4-yl)-thiophene-2-sulfonyl chloride to afford 39 mg (26%). MS (ES⁺) m/z: 554 (M+1).

EXAMPLE 191

[2-Methyl-4-(2-{[5-(1-methyl-5-trifluoromethyl-1H-pyrazol-3-yl)-thiophene-2-sulfonyl]-propyl-amino}-ethylsulfanyl)-phenoxy]-acetic acid

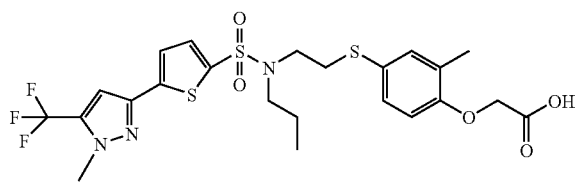

The title compound was prepared from 5-(1-methyl-5-trifluoromethyl-1H-pyrazol-3-yl)-thiophene-2-sulfonyl chloride to afford 47 mg (30%). MS (ES+) m/z: 578 (M+1).

EXAMPLE 192

[2-Methyl-4-(2-{[5-(1-methyl-3-trifluoromethyl-1H-pyrazol-4-yl)-thiophene-2-sulfonyl]-propyl-amino}-ethylsulfanyl)-phenoxy]-acetic acid

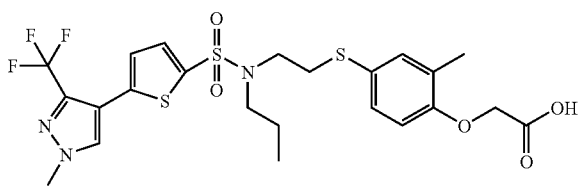

The title compound was prepared from 5-(1-methyl-3-trifluoromethyl-1H-pyrazol-4-yl)-thiophene-2-sulfonyl chloride to afford 60 mg (38%). MS (ES+) m/z: 578 (M+1).

EXAMPLE 193

(4-{2-[(2,3-Dihydro-benzofuran-5-sulfonyl)-propyl-amino]-ethylsulfanyl}-2-methyl-phenoxy)-acetic acid

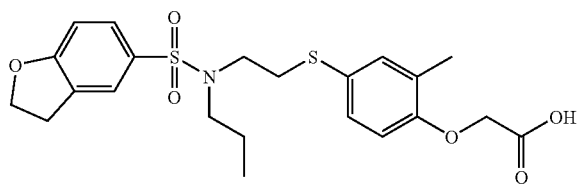

The title compound was prepared from 2,3-dihydro-benzofuran-5-sulfonyl chloride to afford 55 mg (44%). MS (ES−) m/z: 464 (M−1).

EXAMPLE 194

[4-(2-{[3-(6-Methoxy-pyridin-3-yl)-benzenesulfonyl]-propyl-amino}-ethylsulfanyl)-2-methyl-phenoxy]-acetic acid

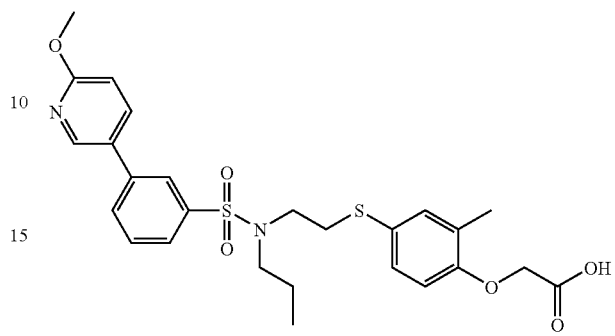

Step A (4-{2-[(3-Bromo-benzenesulfonyl)-propyl-amino]-ethylsulfanyl}-2-methyl-phenoxy)-acetic acid ethyl ester

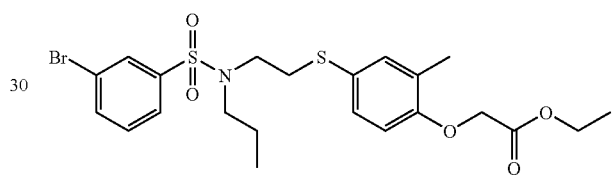

To a solution of the trifluoroacetic acid salt of [2-methyl-4-(2-propylamino-ethylsulfanyl)-phenoxy]-acetic acid ethyl ester (429 mg, 1.37 mmol) in CH$_2$Cl$_2$ (6 ml) at 22° C. was added triethylamine (0.77 ml, 5.5 mmol) followed by 3-bromo-benzenesulfonyl chloride (511 mg, 2.0 mmol) dropwise over two minutes. The mixture was stirred at room temperature for 18 hours, and then diluted with CH$_2$Cl$_2$ (20 ml) and 1 N HCl) (25 ml). After the aqueous layer was extracted with CH$_2$Cl$_2$ (10 ml), the organic layers were washed with water (20 ml), brine (20 ml), and then dried (Na$_2$SO$_4$) and concentrated to an oil which was purified by silica chromatography using 10:1 hexanes:ethyl acetate to provide about 510 mg as an oil (96%). MS (ES+) m/z: 532 (M+1).

Step B

[4-(2-{[3-(6-Methoxy-pyridin-3-yl)-benzenesulfonyl]-propyl-amino}-ethylsulfanyl)-2-methyl-phenoxy]-acetic acid ethyl ester

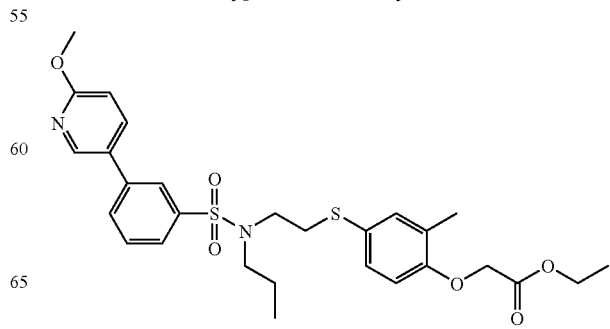

To a solution of (4-{2-[(3-bromo-benzenesulfonyl)-propyl-amino]-ethylsulfanyl}-2-methyl-phenoxy)-acetic acid ethyl ester (125 mg, 0.23 mmol) in acetonitrile (2 ml) under N₂ at room temperature was added palladium acetate (6 mg, 0.023 mmol) followed by 2-methoxy-5-pyridine boronic acid (105 mg, 0.69 mmol), tricyclohexylphosphine (10 mg, 0.035 mmol), and cesium fluoride (314 mg, 2.07 mmol). The mixture was heated at 90° C. for 6 hours, cooled to room temperature and concentrated to a solid. Purification by silica chromatography using 5:1 hexanes:acetone provided about 105 mg as a solid (82%). MS (ES⁺) m/z: 559 (M+1).

Step C

[4-(2-{[3-(6-Methoxy-pyridin-3-yl)-benzenesulfonyl]-propyl-amino}-ethylsulfanyl)-2-methyl-phenoxy]-acetic acid To a solution of [4-(2-{[3-(6-methoxy-pyridin-3-yl)-benzenesulfonyl]-propyl-amino}-ethylsulfanyl)-2-methyl-phenoxy]-acetic acid ethyl ester (95 mg, 0.17 mmol) in methanol (2 ml) at room temperature was added aqueous 5N NaOH (0.10 ml, 0.5 mmol), and the mixture was stirred for 18 hours. The mixture was concentrated to give a residue, which was dissolved in water (10 ml) and CH₂Cl₂ (15 ml). The mixture was adjusted to pH 4 with 6N HCl. After extracting the aqueous layer with CH₂Cl₂ (2×10 ml), the combined organic extracts were washed with brine, dried (Na₂SO₄) and concentrated to provide about 75 mg of the title compound as a solid (83%). MS (ES⁺) m/z: 531 (M+1).

EXAMPLE 195

(R)-(2-Methyl-4-{1-methyl-2-[(3-methyl-5-trifluoromethyl-benzo[b]thiophene-2-sulfonyl)-propyl-amino]-ethylsulfanyl}-phenoxy)-acetic acid

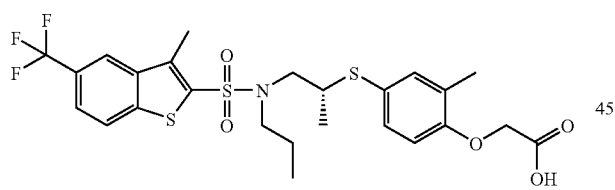

Step A

3-Methyl-5-trifluoromethyl-benzo[b]thiophene-2-carboxylic acid ethyl ester

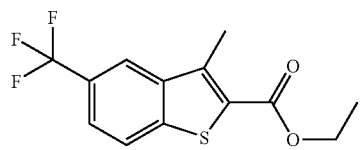

To a solution of 2-fluoro-5-(trifluoromethyl)acetophenone (6.4 g, 31 mmol) and ethyl 2-mercaptoacetate (3.72 g, 31 mmol) in DMF (60 ml) was added cesium carbonate (20.2 g, 62 mmol), and the resulting mixture was heated at 80° C. for 5 hours, which was then cooled to room temperature while stirring for 16 hours. The reaction mixture was diluted with water (600 ml) and extracted with diethyl ether (3×110 ml). The combined organic extracts were washed with brine (200 ml), dried (Na₂SO₄), and concentrated to provide the title compound as a solid, 8.16 g (92%), which was used without further purification.

Step B

3-Methyl-5-trifluoromethyl-benzo[b]thiophene-2-carboxylic acid

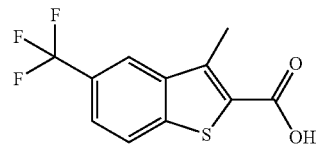

To a solution of 3-methyl-5-trifluoromethyl-benzo[b]thiophene-2-carboxylic acid ethyl ester (8.1 g, 28 mmol) in methanol (125 ml) at 45° C. was added aqueous 5N NaOH (17 ml, 85 mmol), and the mixture was stirred for 6 hours while cooling to room temperature. The mixture was concentrated to give a residue, which was dissolved in water (100 ml) and ethyl acetate (150 ml). The mixture was adjusted to pH 3 with 1N HCl. After extracting the aqueous layer with ethyl acetate (2×40 ml), the combined organic extracts were washed with brine, dried (Na₂SO₄) and concentrated to provide the title compound as a solid, 7.1 g (97%), which was used without further purification. MS (ES⁻) m/z: 259 (M−1).

Step C

3-Methyl-5-trifluoromethyl-benzo[b]thiophene

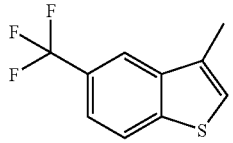

To a solution of 3-methyl-5-trifluoromethyl-benzo[b]thiophene-2-carboxylic acid (6.1 g, 23.4 mmol) in quinoline (200 ml) was added copper powder (0.89 g, 14 mmol), and the mixture was heated at 200° C. for one hour, which was then cooled to room temperature while stirring for 16 hours. The mixture was filtered through celite, and the filtrate was diluted with diethyl ether (300 ml). The filtrate was treated with ice (200 g), and the mixture was adjusted to pH 4 with concentrated hydrochloric acid. After extracting the aqueous layer with diethyl ether (2×100 ml), the combined ether extracts were washed with brine, dried (Na₂SO₄), and concentrated to an oil, which was purified by silica chromatography using hexanes to provide the title compound as a oil, 4.66 g (92%).

Step D

3-Methyl-5-trifluoromethyl-benzo[b]thiophene-2-sulfonic acid sodium salt

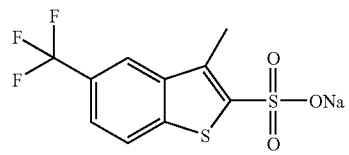

To a cooled solution of 3-methyl-5-trifluoromethyl-benzo[b]thiophene (3.83 g, 17.7 mmol) in trifluoroacetic acid (40 ml) at 5° C. was added chlorosulfonic acid (1.2 ml, 17.7 mmol) dropwise over 5 minutes. The thick suspension was stirred for 5 minutes, warmed to 15° C. and treated with additional chlorosulfonic acid (2.33 ml, 35.4 mmol) dropwise over 10 minutes. The mixture was stirred at 22° C. for 2 hours, and then carefully poured into a mix of ice/water (375 g). After stirring for 15 minutes, the solution was filtered, and the filtrate extracted with diethyl ether (6×100 ml). To the combined ether extracts was added brine (250 ml), which affected the precipitation of a solid. The resulting suspension was filtered to give the title compound as a solid, 2.8 g, after drying. The filtrate was again extracted with ethyl ether (200 ml), and the organic extract was treated with brine (120 ml). Subsequent filtration and drying afforded about 1.3 g of the title compound, which was used without further purification. The combined yield was 73%. MS (ES$^-$) m/z: 295 (M−1).

Step E

3-Methyl-5-trifluoromethyl-benzo[b]thiophene-2-sulfony) chloride

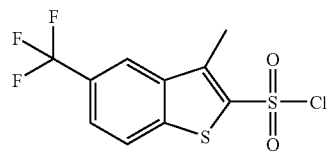

To a suspension of 3-Methyl-5-trifluoromethylbenzo[b]thiophene-2-sulfonic acid sodium salt (2.14 g, 6.72 mmol) in chloroform (12 ml) at room temperature was added chlorosulfonic acid (1.34 ml, 20.2 mmol) dropwise over 10 minutes. The resulting suspension was heated at 60° C. for 4.5 hours, cooled to room temperature and carefully poured into a mix of ice/water (250 g). The mixture was extracted with chloroform (3×20 ml), and the combined organic extracts were washed with cold water (0° C.), dried (Na$_2$SO$_4$), and concentrated to provide the title compound as a solid, 1.45 g (69%), which was used without further purification.

Step F

(S)-3-Methyl-5-trifluoromethyl-benzo[b]thiophene-2-sulfonic acid (2-hydroxy-propyl)-amide

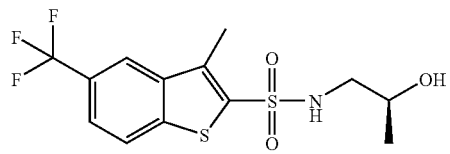

To a cooled solution of (S)-1-amino-propan-2-ol (0.34 g, 4.6 mmol) in methylene chloride (3 ml) at 0° C. was added triethylamine (1.92 ml, 13.8 mmol) followed by a dropwise addition of a solution of 3-methyl-5-trifluoromethyl-benzo[b]thiophene-2-sulfonyl chloride (1.45 g, 4.6 mmol) in methylene chloride (15 ml) over 3 minutes. The mixture was removed from the cooling bath and stirred for 1.5 hours, which was then diluted with 1N HCl (50 ml) and methylene chloride (20 ml). The aqueous layer was extracted with methylene chloride (20 ml), and the combined organic layers were washed with brine (40 ml), dried (Na$_2$SO$_4$), and concentrated to provide the title compound as a solid, 1.51 g (92%) which was used without further purification. MS (ES$^+$) m/z: 354 (M+1).

Step G

(S)-3-Methyl-5-trifluoromethyl-benzo[b]thiophene-2-sulfonic acid (2-hydroxy-propyl)-propyl-amide

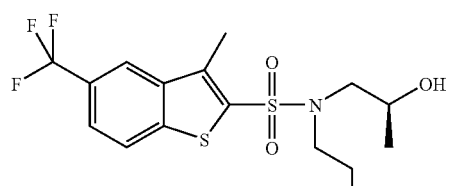

To a solution of (S)-3-methyl-5-trifluoromethyl-benzo[b]thiophene-2-sulfonic acid (2-hydroxy-propyl)-amide (1.5 g, 4.24 mmol) in N,N-dimethylformamide (15 ml) at room temperature was added n-propyl iodide (0.49 ml, 5.0 mmol) followed by cesium carbonate (1.65 g, 5 mmol), and the resulting mixture stirred for 18 hours. The mixture was diluted with water (120 ml) and ethyl acetate (70 ml), and the aqueous layer was extracted with ethyl acetate (3×30 ml). The combined organic extracts were washed with water (100 ml), brine (120 ml), dried (Na$_2$SO$_4$), and concentrated to a solid. Purification by silica chromatography using 4:1 hexanes:acetone provided the title compound as a solid, 1.49 g (89%). MS (ES$^+$) m/z: 396 (M+1).

Step H (S)-Methanesulfonic acid 1-methyl-2-[(3-methyl-5-trifluoromethyl-benzo[b]thiophene-2-sulfonyl)-propyl-amino]-ethyl ester

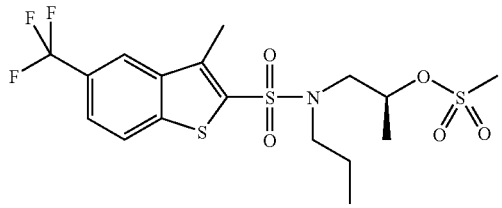

To a cooled (0° C.) solution of (S)-3-methyl-5-trifluoromethyl-benzo[b]thiophene-2-sulfonic acid (2-hydroxy-propyl)-propyl-amide (1.0 g, 2.52 mmol) and triethylamine (0.53 ml, 3.78 mmol) in methylene chloride (11 ml) was added methanesulfonyl chloride (0.23 ml, 3 mmol) dropwise over 2 minutes. The mixture was stirred at 0° C. for 2 hours, diluted with additional methylene chloride (25 ml), and then washed with 1N HCl (50 ml). The aqueous layer was back-extracted with methylene chloride (2×20 ml), and the combined organic extracts were washed with brine (75 ml), dried ($Na_2SO_4$), and concentrated to afford the title compound as an oil, 1.1 g (100%), which was used without further purification. MS (ES$^+$) m/z: 474 (M+1).

Step I (R)-(2-Methyl-4-{1-methyl-2-[(3-methyl-5-trifluoromethyl-benzo[b]thiophene-2-sulfonyl)-propyl-amino]-ethylsulfanyl}-phenoxy)-acetic acid ethyl ester

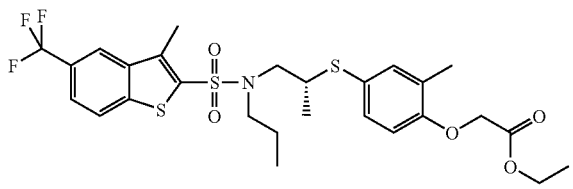

A solution of (4-mercapto-2-methyl-phenoxy)-acetic acid ethyl ester (0.57 g, 2.51 mmol) in N,N-dimethylformamide (12 ml) at room temperature was purged with $N_2$ gas, and potassium carbonate (520 mg, 3.76 mmol) was added followed by a solution of (S)-methanesulfonic acid 1-methyl-2-[(3-methyl-5-trifluoromethyl-benzo[b]thiophene-2-sulfonyl)-propyl-amino]-ethyl ester (1.19 g, 2.51 mmol) in N,N-dimethylformamide (7 ml) dropwise over 2 minutes. The mixture was stirred at room temperature for 24 hours, diluted with diethyl ether (50 ml), and washed with 1N HCl (2×25 ml) and brine (60 ml), and then dried ($Na_2SO_4$). Concentration in vacuo produced a crude oil, which was purified by silica chromatography using 8:1 hexanes:ethyl acetate to afford the title compound as a oil, 0.79 g (52%). MS (ES$^+$) m/z: 604 (M+1).

Step J (R)-(2-Methyl-4-{1-methyl-2-[(3-methyl-5-trifluoromethyl-benzo[b]thiophene-2-sulfonyl)-propyl-amino]-ethylsulfanyl}-phenoxy)-acetic acid To a solution of (R)-(2-methyl-4-{1-methyl-2-[(3-methyl-5-trifluoromethyl-benzo[b]thiophene-2-sulfonyl)-propyl-amino]-ethylsulfanyl}-phenoxy)-acetic acid ethyl ester (790 mg, 1.30 mmol) in ethanol (10 ml) at room temperature was added aqueous 5N NaOH (1.3 ml, 6.5 mmol), and the mixture was stirred for 3 hours. The mixture was concentrated to give a residue, which was dissolved in water (50 ml) and ethyl acetate (70 ml), and the mixture was adjusted to pH 3 with 1N HCl. After extracting the aqueous layer with ethyl acetate (20 ml). The combined organic extracts were washed with water (40 ml) and brine (50 ml), dried ($Na_2SO_4$) and concentrated to provide the title compound as a foam, 710 mg (95%). MS (ES$^-$) m/z: 574 (M−1).

EXAMPLE 196

(R)-3-(2-Methyl-4-{1-methyl-2-[(3-methyl-5-trifluoromethyl-benzo[b]thiophene-2-sulfonyl)-propyl-amino]-ethylsulfanyl}-phenyl)-propionic acid

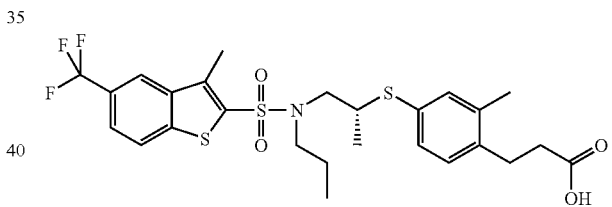

Using the method as described in Example 195, (S)-methanesulfonic acid 1-methyl-2-[(3-methyl-5-trifluoroethyl-benzo[b]thiophene-2-sulfonyl)-propyl-amino]-ethyl ester (Example 21, Step H) and 3-(4-mercapto-2-methyl-phenyl)-propionic acid methyl ester afforded the title compound. MS (ES$^-$) m/z: 572 (M−1).

EXAMPLE 197

(R)-(4-{2-[(6-Chloro-5-fluoro-3-methyl-benzo[b]thiophene-2-sulfonyl)-propyl-amino]-1-methyl-ethylsulfanyl}-2-methyl-phenoxy)-acetic acid

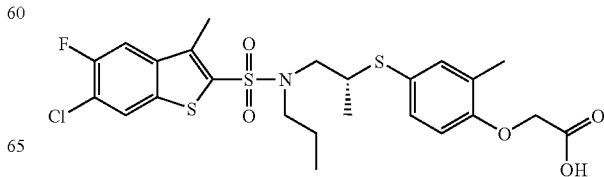

Step A

6-Chloro-5-fluoro-3-methyl-benzo[b]thiophene-2-carboxylic acid ethyl ester

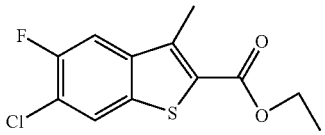

To a solution of 1-(4-chloro-2,5-difluoro-phenyl)-ethanone (4.9 g, 25.7 mmol) and ethyl 2-mercaptoacetate (2.81 g, 23.4 mmol) in DMF (50 ml) was added cesium carbonate (15.2 g, 46.8 mmol) and the resulting mixture was heated at 80° C. for 5 hours, and then cooled to room temperature wile stirring for 16 hours. The reaction mixture was diluted with water (500 ml) and extracted with diethyl ether (2×100 ml). The combined organic extracts were washed with brine (200 ml), dried ($Na_2SO_4$), and concentrated to give an oil which was purified by silica chromatography using 8:1 hexanes: ethyl acetate to afford the title compound as a solid, 1.4 g (22%).

Step B

6-Chloro-5-fluoro-3-methyl-benzo[b]thiophene-2-carboxylic acid

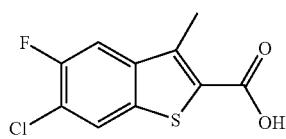

To a solution of 6-chloro-5-fluoro-3-methyl-benzo[b]thiophene-2-carboxylic acid ethyl ester (3.3 g, 12.2 mmol) in ethanol (110 ml) at room temperature was added aqueous 5N NaOH (7.3 ml, 36.6 mmol), and the mixture was stirred for 24 hours. The mixture was concentrated to give a residue, which was suspended in water (50 ml) and ethyl acetate (75 ml), which was then adjusted to pH 3 with 6N HCl. The suspension was filtered and the filtered solid was washed with ethyl acetate, and dried to afford the title compound as a solid, 1.3 g. A second crop was obtained from the filtrate after extracting the aqueous layer with ethyl acetate (3×40 ml), and then the combined organic extracts were washed with brine, dried ($Na_2SO_4$) and concentrated to provide the title compound as a solid, 1.1 g (77% combined yield) which was used without further purification. MS (ES) m/z: 243 (M−1).

Step C

6-Chloro-5-fluoro-3-methyl-benzo[b]thiophene

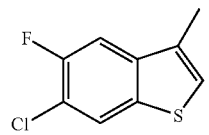

To a solution of 6-chloro-5-fluoro-3-methyl-benzo[b]thiophene-2-carboxylic acid (2.3 g, 9.4 mmol) in quinoline (55 ml) was added copper powder (0.36 g, 5.64 mmol), and the mixture was heated at 200° C. for 40 minutes and cooled to room temperature. The reaction mixture was diluted with diethyl ether (70 ml) and filtered through celite. The filtrate was washed with 5N HCl (4×100 ml), water (100 ml) and brine (150 ml), and then dried ($Na_2SO_4$) and concentrated 100 an oil, which was purified by silica chromatography using hexanes to provide the title compound as a solid, 1.64 g (92%). HRMS (EI$^+$) m/z exact mass calculated for $C_9H_6ClFS$ 199.9863, found 199.9836.

Step D 6-chloro-5-fluoro-3-methyl-benzo[b]thiophene-2-sulfonate sodium salt

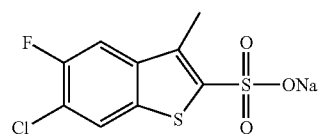

To a cooled solution of 6-chloro-5-fluoro-3-methyl-benzo[b]thiophene (1.43 g, 7.1 mmol) in trifluoroacetic acid (3 ml) and 1,2-dichloroethane (3 ml) at 5° C. was added chlorosulfonic acid (0.47 ml, 7.1 mmol) dropwise over 10 minutes. The thick suspension was stirred for 5 minutes, warmed to 15° C. and treated with additional chlorosulfonic acid (0.95 ml, 14.2 mmol) dropwise over 10 minutes. The mixture was stirred at room temperature for 5 hours, and then carefully poured into a mix of ice/water (300 g). After stirring for 10 minutes, the mixture was extracted with chloroform (3×50 ml). The aqueous layer was diluted with brine (350 ml), which affected the precipitation of a solid over the course of 2 days. The resulting suspension was filtered, and the filtered solid was dried to give the title compound as a solid, 0.97 g (45%), which was used without further purification. MS (ES$^-$) m/z: 279 (M−1).

Step E

6-Chloro-5-fluoro-3-methyl-benzo[b]thiophene-2-sulfonyl chloride

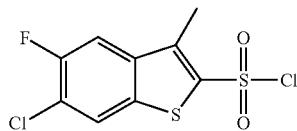

To a suspension of 6-chloro-5-fluoro-3-methyl-benzo[b]thiophene-2-sulfonate sodium salt (1.44 g, 4.75 mmol) in chloroform (12 ml) at room temperature was added chlorosulfonic acid (0.94 ml, 14.3 mmol) dropwise over 10 minutes. The resulting suspension was heated at 55° C. for 3.5 hours, cooled to room temperature, diluted with chloroform (35 ml), and carefully poured into a mix of ice/water (200 g). The mixture was extracted with chloroform (3×20 ml), and the combined organic extracts were washed with cold water (0° C.) (3×75 ml), dried ($Na_2SO_4$) and concentrated to provide the title compound as a solid. 1 g (70%) which was used without further purification.

Step F

(S)-6-Chloro-5-fluoro-3-methyl-benzo[b]thiophene-2-sulfonic acid (2-hydroxy-propyl)-amide

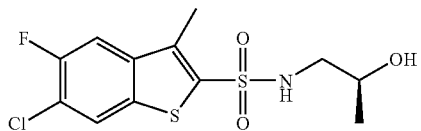

To a cooled solution of (S)-1-amino-propan-2-ol (0.25 g, 3.34 mmol) in methylene chloride (2 ml) at 0° C. was added triethylamine (1.4 ml, 10 mmol) followed by dropwise addition of a solution of 6-chloro-5-fluoro-3-methyl-benzo[b]thiophene-2-sulfonyl chloride (1 g, 3.34 mmol) in methylene chloride (10 ml) over 10 minutes. The mixture was removed from the cooling bath and stirred for 18 hours, and then diluted with 1N HCl (50 ml) and methylene chloride (35 ml). The resulting suspension was filtered to provide the title compound as a solid, 0.8 g (71%), which was used without further purification. MS ($ES^+$) m/z: 338 (M+1).

Step G

(S)-6-Chloro-5-fluoro-3-methyl-benzo[b]thiophene-2-sulfonic acid (2-hydroxy-propyl)-propyl-amide

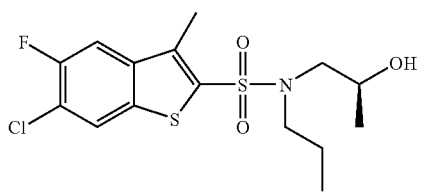

To a solution of (S)-6-chloro-5-fluoro-3-methyl-benzo[b]thiophene-2-sulfonic acid (2-hydroxy-propyl)-amide (0.79 g. 2.36 mmol) in N,N-dimethylformamide (6 ml) at room temperature was added n-propyl iodide (0.27 ml, 2.83 mmol) followed by cesium carbonate (922 mg, 2.83 mmol), and the resulting mixture was stirred for 18 hours. The mixture was diluted with 1N HCl (50 ml) and ethyl acetate (25 ml), and the aqueous layer was extracted with ethyl acetate (2×20 ml). The combined organic extracts were washed with water (40 ml) and brine (40 ml), and then dried ($Na_2SO_4$) and concentrated to a solid, which was purified by silica chromatography using 3:1 hexanes:ethyl acetate to provide the title compound as a solid, 0.87 g (98%). MS ($ES^+$) m/z: 381 (M+1).

Step H

(R)-(4-{2-[(6-Chloro-5-fluoro-3-methyl-benzo[b]thiophene-2-sulfonyl)-propyl-amino]-1-methyl-ethylsulfanyl}-2-methyl-phenoxy)-acetic acid ethyl ester

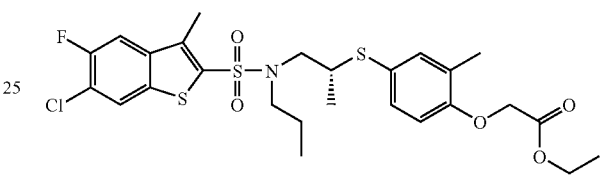

To a cooled solution of (S)-6-chloro-5-fluoro-3-methyl-benzo[b]thiophene-2-sulfonic acid (2-hydroxy-propyl)-propyl-amide (299 mg, 0.78 mmol) and (4-mercapto-2-methyl-phenoxy)-acetic acid ethyl ester 2064321 (176 mg, 0.78 mmol) in toluene (4 ml) at 0° C. was added tri-n-butylphosphine (0.23 ml, 0.94 mmol) over 2 minutes followed by the dropwise addition of a solution of 1,1'-(azodicarbonyl)dipiperidine (237 mg, 0.94 mmol) in toluene (4 ml) over 5 minutes. The suspension was stirred in an ice bath for 18 hours. The mixture was filtered, and the filtrate was concentrated to give an oil. Purification by silica chromatography using 8:1 hexanes:ethyl acetate provided the title compound as an oil, 338 mg (74%). MS ($ES^+$) m/z: 588 (M+1).

Step I

(R)-(4-{2-[(6-Chloro-5-fluoro-3-methyl-benzo[b]thiophene-2-sulfonyl)-propyl-amino]-1-methyl-ethylsulfanyl}-2-methyl-phenoxy)-acetic acid To a solution of (R)-(4-{2-[(6-chloro-5-fluoro-3-methyl-benzo[b]thiophene-2-sulfonyl)-propyl-amino]-1-methyl-ethylsulfanyl}-2-methyl-phenoxy)-acetic acid ethyl ester (334 mg, 0.56 mmol) in methanol (40 ml) at 45° C. was added aqueous 5N NaOH (2 ml, 10 mmol), and the mixture was stirred for 18 hours while cooling to room temperature. The mixture was concentrated to give a residue, which was dissolved in water (40 ml) and ethyl acetate (30 ml), and the mixture was adjusted to pH 3 with 5N HCl. After extracting the aqueous layer with ethyl acetate (20 ml), the combined organic extracts were washed with water (100 ml) and brine (100 ml), and then dried ($Na_2SO_4$) and concentrated to provide the title compound as a solid, 293 mg (94%). MS ($ES^-$) m/z: 558 (M−1).

EXAMPLE 198

(R)-3-(4-{2-[(6-Chloro-5-fluoro-3-methyl-benzo[b]thiophene-2-sulfonyl)-propyl-amino]-1-methyl-ethylsulfanyl}-2-methyl-phenyl)-propionic acid

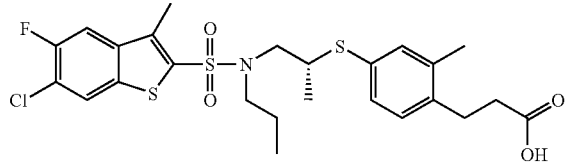

Using the method as described in Example 197, (S)-6-chloro-5-fluoro-3-methyl-benzo[b]thiophene-2-sulfonic acid (2-hydroxy-propyl)-propyl-amide (Example 23, Step G) and 3-(4-mercapto-2-methyl-phenyl)-propionic acid methyl ester afforded the title compound. MS (ES⁻) m/z: 556 (M−1).

EXAMPLE 199

3-(4-{2-[(5-Fluoro-3-methyl-benzo[b]thiophene-2-sulfonyl)-propyl-amino]-ethylsulfanyl}-2-methyl-phenyl)-propionic acid

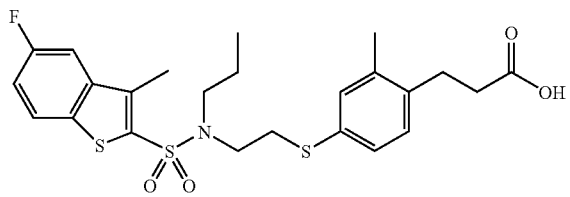

Sodium hydride (60% in mineral oil; about 30 mg, about 18 mg NaH, about 0.75 mmol) was added to a solution of 3-(4-mercapto-2-methyl-phenyl)-propionic acid methyl ester (50 mg, 0.24 mmol) in anhydrous DMF (2 mL). After stirring for about 15 min, toluene-4-sulfonic acid 2-[(5-fluoro-3-methyl-benzo[b]thiophene-2-sulfonyl)-propyl-amino]-ethyl ester (97 mg, 0.20 mmol, 1 equiv) was added followed by additional anhydrous DMF (2 mL) to rinse. The mixture was stirred for 3 hours and then quenched with 1 M aq HCl (6 mL). The mixture was extracted with Et₂O (2×5 mL), dried with anhydrous MgSO₄, and evaporated (50° C.) to give 97 mg of crude methyl ester as a yellow oil, which was eluted (50 mL 5% EtOAc/hex. 100 mL 10% EtOAc/hex) through a chromatotron (1 mm plate) yielding 42 mg of the purified methyl ester. This material was dissolved in EtOH (4 mL) and 5 M aq NaOH (0.4 mL) and rotary evaporated. The resultant residue was acidified with 5 M aq HCl (2 mL) and then extracted with CH₂Cl₂ (5 mL). The organic layer was dried (anhydrous MgSO₄) and rotary evaporated (50° C.) to yield 30 mg (29%) of the acid as a yellow oil. Calculated for $C_{24}H_{28}FNO_4S_3$: m/z 510.1243. Found: 510.1241

EXAMPLE 200

(4-{2-[(5-Fluoro-3-methyl-benzo[b]thiophene-2-sulfonyl)-propyl-amino]-1-methyl-ethoxy}-2,6-dimethyl-phenoxy)-acetic acid

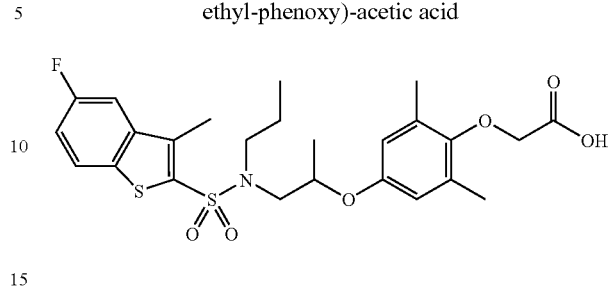

Step A

Acetic acid 4-hydroxy-3,5-dimethyl-phenyl ester

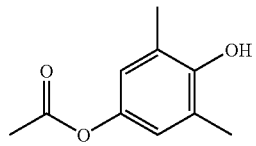

Acetic anhydride (1.5 mL, 1.6 g, 16 mmol, 1.1 equiv) was added dropwise over a period of 3 min to a hazy solution of 2,6-dimethylhydroquinone (2.00 g, 14.5 mmol, 1 equiv) and diisopropylethylamine (2.8 mL, 2.1 g, 16 mmol, 1.1 equiv) in CH₂Cl₂ (80 mL). Within 5 min after the addition, the reaction solution was completely clear. After stirring for about 18 h, the solution was evaporated (50° C.) to give 4.57 g of a brown oil, which was then take up in Et₂O (80 mL), washed with 0.2 M aq HCl (2×40 mL), dried (anhydrous Na₂SO₄), and rotary evaporated (50° C.) to afford about 2.43 g of a red-brown oil. The oil was eluted (100 mL 10% EtOAc/hex, 200 mL 20% EtOAc/hex, 200 mL 30% EtOAc/hex) through a chromatotron (6 mm plate) yielding 1.31 g (50.2%) of product as a yellow crystalline solid.

Step B (4-Hydroxy-2,6-dimethyl-phenoxy)-acetic acid methyl ester

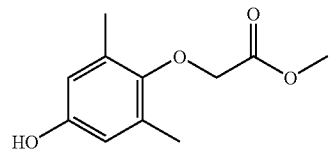

Potassium carbonate (220 mg, 1.6 mmol, 3.0 equiv) was added to a solution of acetic acid 4-hydroxy-3,5-dimethyl-phenyl ester (96 mg, 0.53 mmol, 1 equiv) in anhydrous DMF (5 mL) followed by tert-butyl bromoacetate (100 μL, 130 mg, 0.68 mmol, 0.3 equiv). The mixture was stirred at 80° C. for 2 h, which was then poured into H₂O (25 mL) and extracted with EtOAc (10 mL). The organic layer was washed with H₂O (2×5 mL), dried (anhydrous MgSO₄), and rotary evaporated (75° C.) giving 127 mg (81%) of phenylacetate intermediate as an orange-brown oil. The oil was dissolved in EtOH (2 mL) and 5 M aq NaOH (2 mL) was added. The mixture was rotary evaporated, acidified with 1 M aq HCl (10 mL), and extracted with EtOAc (2×5 mL). The combined organic layers were dried (anhydrous MgSO₄) and rotary evaporated to afford 64 mg (61%) of phenol acid as a brown crystalline solid, which was dissolved in $CH_2Cl_2$ (2 mL) and MeOH (0.5 mL) and (trimethylsilyl)diazomethane (2.0 M in hexanes; 0.5 mL) was added. After stirring for 5 min, the mixture was evaporated (50° C.; azeotrope 2× with $CH_2Cl_2$) to give about 67 mg (60%) of methyl ester phenol as a brown oil. Calculated for $C_{25}H_{30}FNO_6S_2$: m/z 210.0892. Found: 210.0884

Step C (4-{2-[(5-Fluoro-3-methyl-benzo[b]thiophene-2-sulfonyl)-propyl-amino]-1-methyl-ethoxy}-2,6-dimethyl-phenoxy)-acetic acid Cesium carbonate (260 mg. 0.80 mmol, 3.0 equiv) was added to a solution of (4-hydroxy-2,6-dimethyl-phenoxy)-acetic acid methyl ester (56 mg, 0.27 mmol, 1.0 equiv) and toluene-4-sulfonic acid 2-[(5-fluoro-3-methyl-benzo[b]thiophene-2-sulfonyl)-propyl-amino]-1-methyl-ethyl ester (133 mg, 0.27 mmol, 1 equiv) in anhydrous DMF (3 mL). The mixture was stirred at 50° C. for 16 h, which was poured into $H_2O$ (15 mL) and extracted with $Et_2O$ (10 mL). The organic layer was dried (anhydrous $MgSO_4$) and evaporated (50° C.) giving 111 mg of crude methyl ester as a yellow oil. The oil was eluted (100 mL 5% EtOAc/hex, 100 mL 10% EtOAc/hex, 100 mL 20% EtOAc/hex) through a chromatotron (1 mm plate) to yield 18 mg of the purified methyl ester, which was then dissolved in EtOH (2 mL) and 5 M aq NaOH (0.2 mL). The solution was evaporated, acidified with 5 M aq HCl (2 mL), and then extracted with $CH_2Cl_2$ (5 mL). The organic layer was dried (anhydrous $MgSO_4$) and evaporated (50° C.) to afford about 12 mg (8.6%) of the acid as a colorless oil.

Calculated for $C_{25}H_{30}FNO_6S_2$: m/z 546.1396. Found: 546.1403.

EXAMPLE 201

(4-{2-[(5-Chloro-3-methyl-benzo[b]thiophene-2-sulfonyl)-propyl-amino]-1-methyl-ethoxy}-2,6-dimethyl-phenoxy)-acetic acid

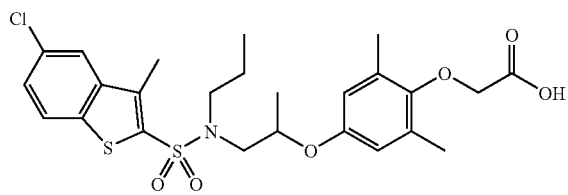

Step A (4-Hydroxy-2,6-dimethyl-phenoxy)-acetic acid tert-butyl ester

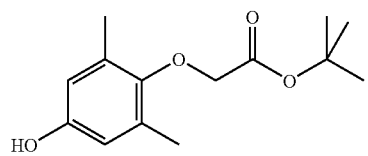

Potassium carbonate (2.7 g, 20 mmol, 3.0 equiv) was added to a solution of acetic acid 4-hydroxy-3,5-dimethyl-phenyl ester (1.19 g, 6.60 mmol, 1 equiv) in anhydrous DMF (60 mL) followed by tert-butyl bromoacetate (1.0 mL, 1.3 g, 6.8 mmol, 1.3 equiv). The mixture was stirred at 80° C. for 2 h and then at 20° C. for 14 h, which was poured into $H_2O$ (300 mL) and extracted with EtOAc (100 mL). The organic layer was washed with $H_2O$ (2×50 mL), dried (anhydrous $Na_2SO_4$), and rotary evaporated (75° C.) giving 1.63 g (84%) of phenylacetate intermediate as an orange-brown oil. The oil was dissolved in 10% N,N-diisopropylethyamine in MeOH (80 mL) and stirred for 4 h. The solution was evaporated to give a brown oil, which was dissolved in $Et_2O$ (50 mL) and washed with 1 M aq HCl (25 mL). The organic layer was dried (anhydrous $Na_2SO_4$) and rotary evaporated (65° C.) giving 1.27 g (76%) of crude product as a brown oil. The oil was eluted (100 mL 10% EtOAc/hex. 400 mL 20% EtOAc/hex) through a chromatotron (4 mm plate) yielding 263 mg (16%) of the pure compound as a cream-colored crystalline solid and another 382 mg of less-pure material.

Step B

5-Chloro-3-methyl-benzo[b]thiophene-2-sulfonic acid (2-hydroxy-propyl)-propyl-amide

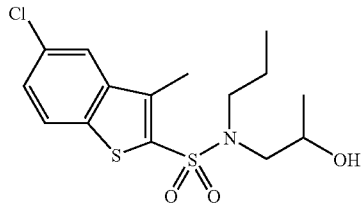

The compound of 5-chloro-3-methyl-benzo[b]thiophene-2-sulfonyl chloride (1.35 g, 4.80 mmol, 1 equiv) in one portion was added to a solution of 1-amino-2-propanol (0.45 mL, 0.44 g, 5.8 mmol, 1.2 equiv) and triethylamine (1.4 mL, 1.0 g, 10 mmol, 2.1 equiv) in anhydrous $CH_2Cl_2$ (50 mL) cooled to 0° C. After stirring foe 2 h, the solution was washed with 1 M aq HCl (25 mL), dried (anhydrous $Na_2SO_4$), and rotary evaporated (50° C.) giving 1.46 g (95%) of the secondary amide as an off-white solid. The solid was dissolved in anhydrous DMF (30 mL), and cesium carbonate (2.0 g, 6.1 mmol, 1.3 equiv) was added followed by 1-iodopropane (0.62 mL, 1.1 g, 6.4 mmol, 1.3 equiv). The mixture was stirred at 50° C. After 1 h, the mixture was poured into 1 M aq HCl (60 mL) and extracted with $Et_2O$ (60 mL). The organic layer was dried (anhydrous $Na_2SO_4$) and rotary evaporated (50° C.) to afford about 1.58 g (91%) of tertiary amide as a yellow crystalline solid. The solid was eluted (100 mL 20% EtOAc/hex, 100 mL 30% EtOAc/hex, 100 mL 40% EtOAc/hex, 150 mL 50% EtOAc/hex) through a chromatotron (4 mm plate) yielding 1.35 g (78%) of the purified material as an off-white crystalline solid.

Step C (4-{2-[(5-Chloro-3-methyl-benzo[b]thiophene-2-sulfonyl)-propyl-amino]-1-methyl-ethoxy}-2,6-dimethyl-phenoxy)-acetic acid tert-butyl ester

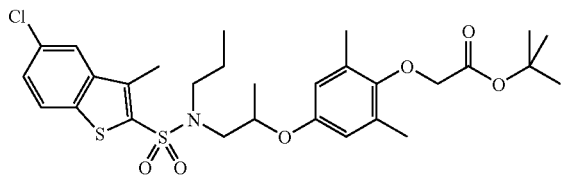

The compound of diisopropyl azodicarboxylate (50 μL, 51 mg, 0.25 mmol, 1.0 equiv) was added over a period of 1 min to a solution of (4-hydroxy-2,6-dimethyl-phenoxy)-acetic acid tert-butyl ester (63 mg, 0.25 mmol, 1 equiv), 5-chloro-3-methyl-benzo[b]thiophene-2-sulfonic acid (2-hydroxy-propyl)-propyl-amide (90 mg, 0.25 mmol, 1.0 equiv), and triphenylphosphine (66 mg, 0.25 mmol, 1.0 equiv) in toluene (3 mL). The reaction solution was stirred for 16 h. and rotary evaporated. The resultant yellow oil was eluted (100 mL 5% EtOAc/hex, 150 mL 10% EtOAc/hex) through a chromatotron (1 mm plate) yielding 100 mg (67%) of the desired product as a colorless oil. Calculated for $C_{29}H_{38}ClNNaO_6S_2$: m/z 618.1727. Found: 618.1713

Step D (4-{2-[(5-Chloro-3-methyl-benzo[b]thiophene-2-sulfonyl)-propyl-amino]-1-methyl-ethoxy}-2,6-dimethyl-phenoxy)-acetic acid The compound of (4-{2-[(5-Chloro-3-methyl-benzo[b]thiophene-2-sulfonyl)-propyl-amino]-1-methyl-ethoxy}-2,6-dimethyl-phenoxy)-acetic acid tert-butyl ester (100 mg, 0.168 mmol) was dissolved in 4 M HCl in 1,4-dioxane (5 mL), and the mixture was stirred for 17 h and then rotary evaporated (50° C.; azeotrope with $CH_2Cl_2$) yielding 96 mg (100%) to give the title compound as an off-white foam. Calculated for $C_{25}H_{30}ClNO_6S_2$: m/z 540.1281. Found: 540.1290.

EXAMPLE 202

3-(4-{2-[(5-Chloro-3-methyl-benzo[b]thiophene-2-sulfonyl)-propyl-amino]-ethylsulfanyl}-2-methyl-phenyl)-propionic acid

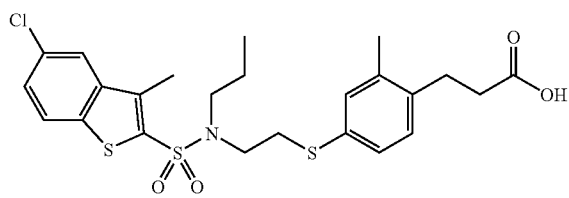

A mixture of 3-(4-mercapto-2-methyl-phenyl)-propionic acid methyl ester (53 mg, 0.25 mmol, 1 equiv), toluene-4-sulfonic acid 2-[(5-chloro-3-methyl-benzo[b]thiophene-2-sulfonyl)-propyl-amino]-ethyl ester (127 mg, 0.25 mmol, 1.0 equiv), and cesium carbonate (250 mg, 0.77 mmol, 3.0 equiv) in anhydrous DMF (5 mL) was stirred at 60° C. for 13 h. The mixture was poured into $H_2O$ (30 mL) and extracted with $Et_2O$ (3×15 mL). The organic layer was dried (anhydrous $MgSO_4$) and rotary evaporated (50° C.) giving 68 mg of a yellow oil, which was then dissolved in EtOH (5 mL) and 5 M aq NaOH (0.5 mL). After 15 h, the solution was rotary evaporated, acidified with 5 M aq HCl (2 mL) and extracted with $CH_2Cl_2$ (5 mL). The organic layer was dried (anhydrous $MgSO_4$) and rotary evaporated (50° C.) yielding 99 mg of the crude acid as a yellow oil, which was purified by reverse-phase chromatography to afford about 25 mg (19%) of the acid as a white crystalline solid. Calculated for $C_{24}H_{28}ClNNaO_4S_3$: m/z 548.0767. Found: 548.0767.

EXAMPLE 203

(4-{2-[(5-Chloro-3-methyl-benzofuran-2-sulfonyl)-propyl-amino]-1-methyl-ethoxy}-2-methyl-phenoxy)-acetic acid

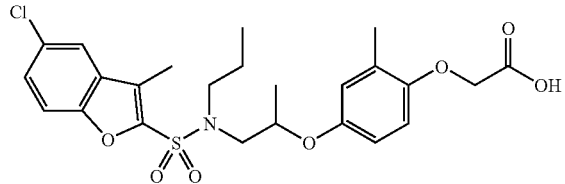

Step A

5-Chloro-3-methyl-benzofuran

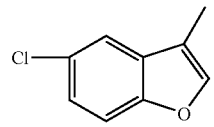

2-Acetyl-4-chlorophenoxy acetic acid (2.06 g, 9.0 mmol) and NaOAc (4.43 g, 54 mmol) was added to $Ac_2O$ (45.0 mL) and the mixture was heated at 110° C. under $N_2$ for 3 hours. The mixture was cooled to ambient temperature and poured into $H_2O$ (200 mL) and stirred overnight. The aqueous mixture was extracted with $Et_2O$ (450 mL) and the $Et_2O$ layer was separated. The $Et_2O$ was extracted with $H_2O$ (5×100 mL), washed with brine and dried ($MgSO_4$) and filtered. The filtrate was evaporated and the resulting oil was chromatographed on the chromatron using a 4 mm plate and eluted with EtOAc/hexane (5:95) to give about 0.98 g (65%). NMR $CDCl_3$ δ 7.45 (m, 1H), 7.42 (m, 1H), 7.38 (d, 1H), 7.25 (m, 1H), 2.22 (S, 3H).

Step B

5-Chloro-3-methyl-benzofuran-2-sulfonyl chloride

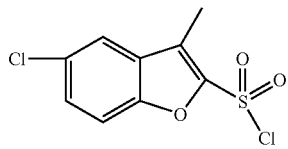

n-BuLi 2.5 M (1.20 mL, 3.0 mmol) was added to 5-chloro-3-methyl-benzofuran (0.40 g, 2.40 mmol) in dry THF (4.0 mL) under $N_2$ at −5° C. over 15 minutes. The light brown solution was stirred for 30 minutes at −5° C. to 0° C. This mixture was added by syringe to a stirring solution of $SO_2Cl_2$ (0.23 mL. 2.9 mmol) in hexane (4.0 Ml) at −5° C. to 0° C. and stirred for 1 hour. The mixture to was warmed to ambient temperature and diluted with 120 (10 mL), neutralized with solid $NaHCO_3$ and diluted with hexane (60 mL). The organic layer was separated and dried ($MgSO_4$), filtered and evaporated on the rotary to viscous oil. Chromatography on the chromatotron eluting with EtOAc-hexane 5:95 gave an oil. 0.67 g. NMR $CDCl_3$ δ 7.70-7.7.58 (m, 3H), 2.62(S, 3H).

Step C

5-Chloro-3-methyl-benzofuran-2-sulfonic acid (2-hydroxy-propyl)-propyl-amide

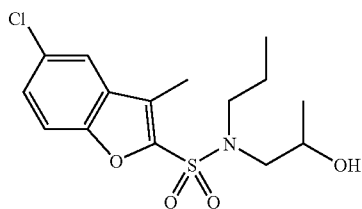

A solution of 5-chloro-3-methyl-benzofuran-2-sulfonyl chloride (268 mg, 1.01 mmol, 1 equiv) in anhydrous $CH_2Cl_2$ (5 mL) was added to a solution of 1-amino-2-propanol (95 µL, 92 mg, 1.2 mmol, 1.2 equiv) and triethylamine (280 µL, 200 mg, 2.0 mmol, 2.0 equiv) in anhydrous $CH_2Cl_2$ (5 mL) cooled to 0° C. After stirring for 30 min, the solution was washed with 1 M aq HCl (5 mL), dried (anhydrous $MgSO_4$), and rotary evaporated (50° C.) giving 242 mg (79%) of the secondary amide as a light-yellow crystalline solid, which was then dissolved in anhydrous DMF (5 mL). Cesium carbonate (430 mg, 1.3 mmol, 1.3 equiv) was added to the solution followed by 1-iodopropane (130 µL, 230 mg, 1.3 mmol, 1.3 equiv). The mixture was stirred at 50° C., and after 1 h, it was poured into 1 M aq HCl (25 mL) and extracted with $Et_2O$ (25 mL). The organic layer was dried (anhydrous $MgSO_4$) and rotary evaporated (50° C.) giving 246 mg (70%) of tertiary amide as a light-yellow crystalline solid. The solid was eluted (150 mL 30% EtOAc/hex) through a chromatotron (1 mm plate) yielding 154 mg (44%) of the purified material as a white crystalline solid.

Calculated for $C_{15}H_{20}ClNNaO_4S$: m/z 368.0699. Found: 368.0701.

Step D (4-{2-[(5-Chloro-3-methyl-benzofuran-2-sulfonyl)-propyl-amino]-1-methyl-ethoxy}-2-methyl-phenoxy)-acetic acid Diisopropyl azodicarboxylate (26 µL, 27 mg, 0.13 mmol, 1.0 equiv) over a period of 1 min was added to a solution of (4-hydroxy-2-methyl-phenoxy)-acetic acid methyl ester (26 mg, 0.13 mmol, 1 equiv), 5-chloro-3-methyl-benzofuran-2-sulfonic acid (2-hydroxy-propyl)-propyl-amide (46 mg, 0.13 mmol. 1.0 equiv), and triphenylphosphine (35 mg, 0.13 mmol, 1.0 equiv) in anhydrous toluene (3 mL). The solution was stirred for 22 h, and the mixture was rotary evaporated. The resultant yellow oil was eluted (200 mL 5% EtOAc/hex, 200 mL 10% EtOAc/hex) through a chromatotron (1 mm plate) yielding 40 mg (58%) of the methyl ester as a colorless oil, which was dissolved in EtOH (4 mL) and 5 M aq NaOH (0.4 mL). After stirring 15 h, the solution was rotary evaporated, the residue was acidified with 5 M aq HCl (2 mL) and then extracted with $CH_2Cl_2$ (5 mL). The organic layer was dried (anhydrous $MgSO_4$) and rotary evaporated (50° C.) to afford about 32 mg (47%) of the acid as a colorless oil. Calculated for $C_{24}H_{28}ClNNaO_7S$: m/z 532.1173. Found: 532.1160.

EXAMPLE 204

(4-{2-[(5-Chloro-3-methyl-benzofuran-2-sulfonyl)-propyl-amino]-1-methyl-ethylsulfanyl}-2-methyl-phenoxy)-acetic acid

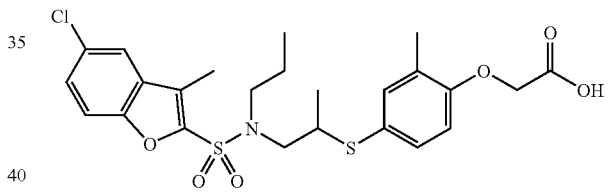

Step A

5-Chloro-3-methyl-benzofuran-2-sulfonic acid (2-bromo-propyl)-propyl-amide

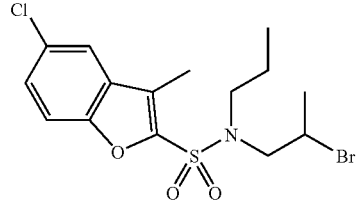

Triphenylphosphine (93 mg. 0.35 mmol, 1.5 equiv) was added to a solution of 5-chloro-3-methyl-benzofuran-2-sulfonic acid (2-hydroxy-propyl)-propyl-amide (82 mg, 0.24 mmol, 1 equiv) and carbon tetrabromide (120 mg, 0.36 mmol, 1.5 equiv) in dichloromethane (3 mL). The solution was stirred for 21 hours and rotary evaporated, and the resultant yellow oil was eluted (200 mL 5% EtOAc/hex) through a chromatotron (1 mm plate) to afford about 79 mg (82%) of the product as a white crystalline solid. Calculated for $C_{15}H_{20}ClNNaO_4S$: m/z 368.0699. Found: 368.0701.

Step B (4-{2-[(5-Chloro-3-methyl-benzofuran-2-sulfonyl)-propyl-amino]-1-methyl-ethylsulfanyl}-2-methyl-phenoxy)-acetic acid A mixture of 5-chloro-3-methyl-benzofuran-2-sulfonic acid (2-bromo-propyl)-propyl-amide (48 mg, 0.12 mmol. 1 equiv), (4-mercapto-2-methyl-phenoxy)-acetic acid ethyl ester (27 mg, 0.12 mmol, 1.0 equiv), and cesium carbonate (1.0 mg, 0.34 mmol, 2.9 equiv) in anhydrous DMF (5 mL) was stirred at 60° C. for 18 h. The mixture was poured into H$_2$O (30 mL) and extracted with Et$_2$O (4×15 mL). The organic layer was dried (anhydrous MgSO$_4$) and rotary evaporated (50° C.) giving 58 mg of a yellow oil, which was eluted (100 mL 5% EtOAc/hex, 100 mL 0% EtOAc/hex) through a chromatotron (1 mm plate) yielding 11 mg of the ethyl ester as a colorless film. The material was dissolved in EtOH (1 mL) and 5 M aq NaOH (0.1 mL). After stirring 16 h, the solution was evaporated. The resultant residue was acidified with 1 M aq HCl (2 mL) and then extracted with CH$_2$Cl$_2$ (5 mL). Dry the organic layer was dried (anhydrous MgSO$_4$) and rotary evaporated (50° C.) to yield about 3.3 mg (5%) of the desired acid as a colorless film. Calculated for C$_{24}$H$_{28}$ClNNaO$_6$S$_2$: m/z 548.0944. Found: 548.0940.

EXAMPLE 205

3-(4-{2-[(5-Chloro-3-methyl-benzo[b]thiophene-2-sulfonyl)-propyl-amino]-1-methyl-ethylsulfanyl}-2-methyl-phenyl)-propionic acid

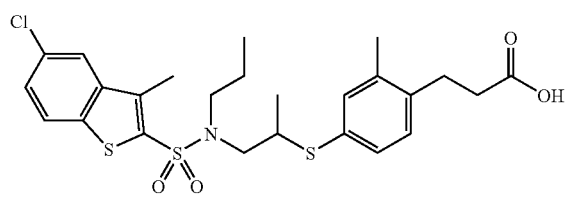

Step A 3-(4-{2-[(5-Chloro-3-methyl-benzo[b]thiophene-2-sulfonyl)-propyl-amino]-1-methyl-ethylsulfanyl}-2-methyl-phenyl)-propionic acid methyl ester

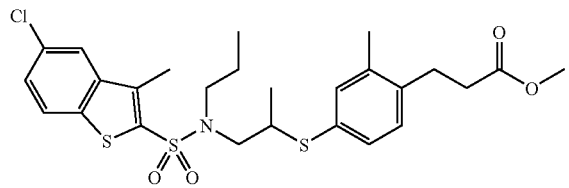

The compound of 4,4-dimethyl-2-(triphenyl-λ$^5$-phosphanyl)-[1,2,5]thiadiazolidine 1,1-dioxide (190 mg. 0.46 mmol, 1.5 eq.) was added to a solution of 3-(4-{2-[(5-chloro-3-methyl-benzo[b]thiophene-2-sulfonyl)-propyl-amino]-ethylsulfanyl}-2-methyl-phenyl)-propionic acid (69 mg. 0.33 mmol, 1.1 eq.) and 5-chloro-3-methyl-benzo[b]thiophene-2-sulfonic acid (2-hydroxy-propyl)-propyl-amide (109 mg, 0.30 mmol, 1 eq.) in anhydrous toluene (3 mL). The mixture was stirred for 17 h and rotary evaporated. The resultant material was eluted (100 mL 5% EtOAc/hex, 100 mL 10% EtOAc/hex, 100 mL 20% EtOAc/hex) through a chromatotron (1 mm plate) to yield about 21 mg (13%) of the methyl ester as a colorless oil;

Step B 3-(4-{2-[(5-Chloro-3-methyl-benzo[b]thiophene-2-sulfonyl)-propyl-amino]-1-methyl-ethylsulfanyl}-2-methyl-phenyl)-propionic acid The compound of 3-(4-{2-[(5-chloro-3-methyl-benzo[b]thiophene-2-sulfonyl)-propyl-amino]-1-methyl-ethylsulfanyl}-2-methyl-phenyl)-propionic acid methyl ester (21 mg, 3.8 mmol) was dissolved in EtOH (2 mL) and 5 M aq NaOH (0.2 mL). After stirring for 17 h, the mixture was rotary evaporated. The resultant residue was acidified with 1 M aq HCl (5 mL) and then extracted with CH$_2$Cl$_2$ (5 mL). The organic layer was dried (anhydrous MgSO$_4$) and rotary evaporated (50° C.) yielding the crude acid as a colorless film. The material was divided into two samples. Each sample was chromatographed by reverse-phase (10 mL 0.1% TFA in 65% CH$_3$CN/H$_2$O, 10 mL CH$_3$CN) through 500-mg C$_{18}$ cartridges to yield about 11 mg (54%) of the purified acid. Calculated for C$_{25}$H$_{30}$ClNNaO$_4$S$_3$: m/z 562.0923. Found: 562.0914.

EXAMPLE 206

(4-{2-[(5-Chloro-3-ethyl-benzo[b]thiophene-2-sulfonyl)-propyl-amino]-1-methyl-ethylsulfanyl}-2-methyl-phenoxy)-acetic acid

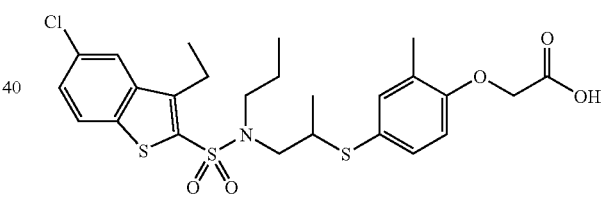

Step A

3-Bromo-5-chloro-benzo[b]thiophene

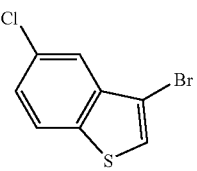

A solution of bromine (2.2 mL, 6.9 g, 43 mmol, 1.1 equiv) in AcOH (20 mL) was added to a solution 5-chloro-benzo[b]thiophene (6.65 g, 39.4 mmol, 1 equiv) in AcOH (20 mL), and the mixture was heated at 50° C. for 1 h and the volatiles were removed by rotary evaporation (50° C.). The resultant material was dissolved in CH$_2$Cl$_2$ (80 mL), washed with saturated aq. NaHCO$_3$ (80 mL), dried (anhydrous Na$_2$SO$_4$), and rotary evaporated (50° C.) to give about 9.23 g (94.6%) of crude product as a light-brown solid.

Step B

3-Bromo-5-chloro-benzo[b]thiophene-2-sulfonyl chloride

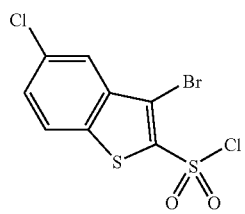

Chlorosulfonic acid (1.91 g, 3 equiv) was added to a solution of 3-bromo-5-chloro-benzo[b]thiophene (1 g, 0.004 mol, 1 equiv) in 1,2-dichloroethane (20 mL) at 0° C. and warmed to room temperature, and then added to a mixture of EtOAc (100 mL) and saturated aq NaCl (100 mL). The organic layer was dried (anhydrous $Na_2SO_4$) and rotary evaporated giving 3.2 g of the crude material. The material was eluted (10-70% EtOAc/hex) on chromatotron to yield about 0.88 g of the title compound.

Step C

3-Bromo-5-chloro-benzo[b]thiophene-2-sulfonic acid (2-hydroxy-propyl)-propyl-amide

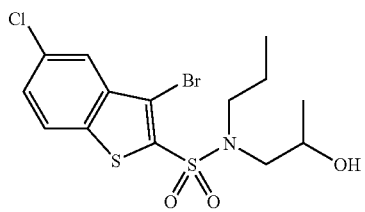

A solution of 3-bromo-5-chloro-benzo[b]thiophene-2-sulfonyl chloride (0.88 g, 2.5 mmol, 1 equiv) in anhydrous $CH_2Cl_2$ (10 mL) was added to a solution of 1-amino-2-propanol (0.24 mL, 0.23 g, 3.1 mmol. 1.2 equiv) and triethylamine (0.72 mL, 0.52 g, 5.2 mmol, 2.0 equiv) in anhydrous $CH_2Cl_2$ (15 mL) cooled to 0° C. The solution was washed with 1 M aq HCl (10 mL), dried (anhydrous $Na_2SO_4$), and rotary evaporated (50° C.) to give about 0.80 g (82%) of the secondary amide as a light-yellow solid. The solid was dissolved in anhydrous DMF (15 mL) and cesium carbonate (1.1 g, 3.4 mmol, 1.3 equiv) was added followed by 1-iodopropane (0.32 mL, 0.56 g, 3.3 mmol, 1.3 equiv). The reaction mixture was stirred at 50° C. After 1 h, the mixture was poured into 1 M aq HCl (25 mL), and extracted with $Et_2O$ (2×25 mL). The organic layer was dried (anhydrous $Na_2SO_4$) and rotary evaporated (50° C.) to give about 0.85 g (78%) of tertiary amide as a yellow oil. The solid was eluted (200 mL 30% EtOAc/hex) through a chromatotron (2 mm plate) yielding about 0.62 g (57%) of the title compound as an off-white crystalline solid. Calculated for $C_{14}H_{18}BrClNO_3S_2$: m/z 425.9600. Found: 425.9618.

Step D

3-Bromo-5-chloro-benzo[b]thiophene-2-sulfonic acid[2-(tert-butyl-dimethyl-silanyloxy)-propyl]-propyl-amide

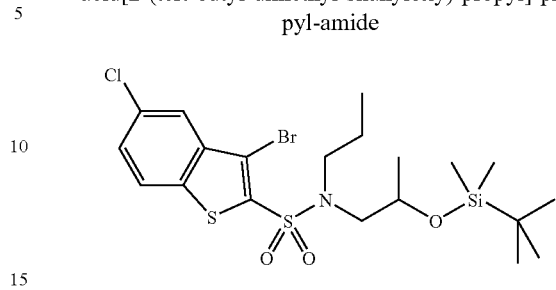

The compound of tert-butyldimethylsilyl chloride (0.39 g, 2.6 mmol, 2.0 equiv) was added to a solution of 3-bromo-5-chloro-benzo[b]thiophene-2-sulfonic acid (2-hydroxy-propyl)-propyl-amide (0.55 g. 1.3 mmol, 1 equiv) and imidazole (0.18 g, 2.6 mmol, 2.1 equiv) in anhydrous $CH_2CO_2$ (15 mL). After stirring for about 71 h, the mixture was rotary evaporated, which was then taken up in $Et_2O$ (30 mL) and washed with saturated aq $NH_4Cl$ (2×15 mL) and $NaHCO_3$ (15 mL). The organic layer was dried (anhydrous $Na_2SO_4$) and rotary evaporated (50° C.) giving 0.73 g (100%) of the crude product as a yellow oil. The solid was eluted (100 mL hexanes, 300 mL 5% EtOAc/hex) through a chromatotron (4 mm plate) yielding about 0.59 g (85%) of the title compound as a yellow crystalline solid. Calculated for $C_{20}H_{32}BrClNO_3S_2Si$: m/z 540.0465. Found: 540.0430.

Step E

5-Chloro-3-ethyl-benzo[b]thiophene-2-sulfonic acid [2-(tert-butyl-dimethyl-silanyloxy)-propyl]-propyl-amide

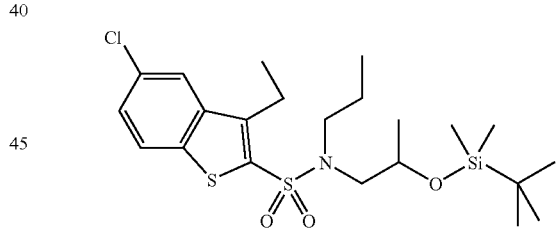

Under argon, butyllithium (1.6 M in hexanes; 350 µL, 0.56 mmol, 1.1 equiv) was added over a period of 2 min to a solution of 3-bromo-5-chloro-benzo[b]thiophene-2-sulfonic acid[2-(tert-butyl-dimethyl-silanyloxy)-propyl]-propyl-amide (277 mg, 0.512 mmol, 1 equiv) in anhydrous THF (15 mL) cooled to −78° C. After stirring for 60 min, iodoethane (filtered through alumina; 200 µL, 390 mg, 2.5 mmol, 4.9 equiv) was added to the reaction solution and allow the reaction solution to warm slowly. After stirring for 2 h, the solution was quenched with saturated aq $NaHCO_3$ (10 mL). $Et_2O$ (10 mL) was added and the organic layer was separated, dried (anhydrous $MgSO_4$), and rotary evaporated (50° C.) to give about 239 mg of a brown oil. The material was purified by chromatography (50% $CH_2Cl_2$/hex) to yield about 94 mg (37%) of the desired compound as an oil. Calculated for $C_{22}H_{37}ClNO_3S_2Si$: m/z 490.1673. Found: 490.1666.

Step F

5-Chloro-3-ethyl-benzo[b]thiophene-2-sulfonic acid (2-hydroxy-propyl)-propyl-amide

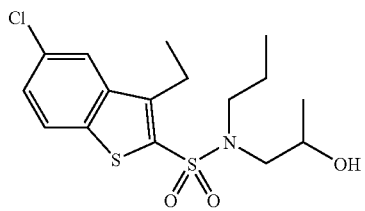

About 5 M aq HCl (5 mL) was added to a solution of 5-chloro-3-ethyl-benzo[b]thiophene-2-sulfonic acid[2-(tert-butyl-dimethyl-silanyloxy)-propyl]-propyl-amide (94 mg) in EtOH (5 mL) and the mixture was stirred for 63 h. The mixture was rotary evaporated (75° C.; azeotroping with MeOH and then $CH_2CH_2$) to yield about 75 mg of the title compound as an oil. Calculated for $C_{16}H_{22}ClNNaO_3S_2$: m/z 398.0627. Found: 398.0602.

Step G

(4-{2-[(5-Chloro-3-ethyl-benzo[b]thiophene-2-sulfonyl)-propyl-amino]-1-methyl-ethylsulfanyl}-2-methyl-phenoxy)-acetic acid The compound of 4,4-dimethyl-2-(triphenyl-$\lambda^5$-phosphanyl)-[1,2,5]thiadiazolidine 1,1-dioxide (120 mg, 0.29 mmol, 1.5 equiv) was added to a solution of (4-mercapto-2-methyl-phenoxy)-acetic acid ethyl ester (48 mg, 0.21 mmol, 1.1 equiv) and 5-chloro-3-ethyl-benzo[b]thiophene-2-sulfonic acid (2-hydroxy-propyl)-propyl-amide (73 mg, 0.19 mmol, 1 equiv) in anhydrous toluene (3 mL). The mixture was stirred for 16 h and rotary evaporated. The resultant material was eluted (100 mL 5% EtOAc/hex, 200 mL 10% EtOAc/hex, 150 mL 20% EtOAc/hex) through a chromatotron (1 mm plate) yielding 6.1 mg (5.4%) of the ethyl ester as a colorless oil, which was dissolved in EtOH (1 mL) and 5 M aq NaOH (1 mL). After stirring for 40 min, the reaction solution was evaporated, and the resultant residue was acidified with 1 M aq HCl (5 mL) and then extracted with $CH_2Cl_2$ (2×5 mL). The organic layer was dried (anhydrous $MgSO_4$) and rotary evaporated (50° C.) to yield about 4.8 mg (4.4%) of the product. Calculated for $C_{25}H_{30}ClNO_5S_3$: m/z 555.0975. Found: 555.0964.

EXAMPLE 207

(4-{2-[(5-Chloro-benzo[b]thiophene-2-sulfonyl)-propyl-amino]-1-methyl-ethoxy}-2-methyl-phenoxy)-acetic acid

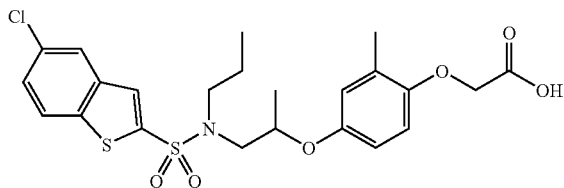

Step A

5-Chloro-benzo[b]thiophene-2-sulfonic acid (2-hydroxy-propyl)-propyl-amide

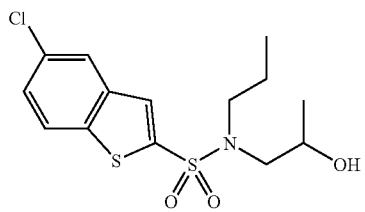

Under argon, butyllithium (1.6 M in hexanes: 1.3 mL, 2.1 mmol, 2.3 equiv) was added over a period of 2 min to a solution of 3-bromo-5-chloro-benzo[b]thiophene-2-sulfonic acid (2-hydroxy-propyl)-propyl-amide (381 mg, 0.893 mmol, 1 equiv) in anhydrous THF (20 mL) cooled to −78° C. After stirring for 60 min, MeOH (200 µL,) was added to quench the reaction solution. The solution (50° C.) was evaporated, and the resultant residue was taken up in $Et_2O$ (10 mL) and washed with saturated aq $NH_4Cl$ (10 mL). The organic layer was separated, dried (anhydrous $MgSO_4$), and rotary evaporated (50° C.) giving 297 mg (96%) of an orange-yellow oil. The oil was eluted (50 mL 1:1 $CH_2Cl_2$/hex, 50 mL 1% EtOH in 1:1 $CH_2Cl_2$/hex, 100 mL 2% EtOH in 1:1 $CH_2Cl_2$/hex,) through a chromatotron (1 mm plate) to yield about 250 mg (80.5%) of the product as a light orange-red oil. Calculated for $C_{14}H_{19}ClNO_3S_2$: m/z 368.0495. Found: 368.0491.

Step B

(4-{2-[(5-Chloro-benzo[b]thiophene-2-sulfonyl)-propyl-amino]-1-methyl-ethoxy}-2-methyl-phenoxy)-acetic acid Diisopropyl azodicarboxylate (24 µL, 25 mg, 0.12 mmol, 1.0 equiv) was added over a period of 1 min to a solution of (4-hydroxy-2-methyl-phenoxy)-acetic acid methyl ester (24 mg, 0.12 mmol, 1 equiv), 5-chloro-benzo[b]thiophene-2-sulfonic acid (2-hydroxy-propyl)-propyl-amide (43 mg, 0.12 mmol, 1.0 equiv), and triphenylphosphine (32 mg, 0.12 mmol, 1.0 equiv) in anhydrous toluene (3 mL). The solution was stirred for 4.5 h and rotary evaporated. The resultant yellow oil was eluted (200 mL 5% EtOAc/hex, 200 mL 10% EtOAc/hex) through a chromatotron (1 mm plate) yielding 13 mg (20%) of the methyl ester as a colorless oil, which was dissolved in EtOH (2 mL) and 5 M aq NaOH (0.2 mL). After stirring for 62 h, solution was rotary evaporated, and the resultant residue was acidified with 1 M aq HCl (10 mL) and then extracted with $CH_2Cl_2$ (2×5 mL). The organic layer was dried (anhydrous $MgSO_4$) and rotary evaporated (50° C.) to yield about 13 mg (21%) of the desired acid as a colorless film. Calculated for $C_{23}H_{26}ClNO_6S_2$: m/z 512.0968. Found: 512.0948.

EXAMPLE 208

(2-Methyl-4-{1-methyl-2-[(3-methyl-benzo[b]thiophene-2-sulfonyl)-propyl-amino]-ethoxy}-phenoxy)-acetic acid

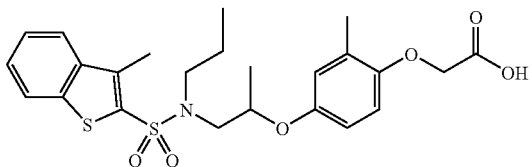

Step A

5-Chloro-3-methyl-benzo[b]thiophene-2-sulfonic acid[2-(tert-butyl-dimethyl-silanyloxy)-propyl]-propyl-amide

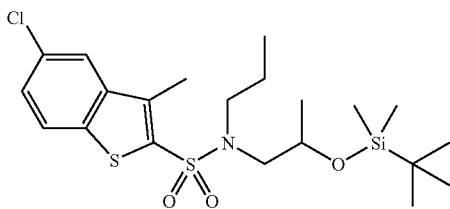

The compound of tert-butyldimethylsilyl chloride (318 mg, 2.11 mmol, 2.0 equiv) was added to a solution of 5-chloro-3-methyl-benzo[b]thiophene-2-sulfonic acid (2-hydroxy-propyl)-propyl-amide (382 mg, 1.06 mmol, 1 equiv) and imidazole (144 mg, 2.12 mmol, 2.1 equiv) in $CH_2Cl_2$ (10 mL). After stirring for 17 h, the mixture was evaporated and the resultant material was taken up in $Et_2O$ (20 mL) and washed with saturated aq $NH_4Cl$ (10 mL) and $NaHCO_3$ (10 mL). The organic layer was dried (anhydrous $MgSO_4$) and rotary evaporated giving 575 mg (114%) of the crude product as a colorless oil. The solid was eluted (100 mL hexanes, 150 mL 5% EtOAc/hex) through a chromatotron (2 mm plate) to yield about 478 mg (95.1%) of the purified material as a colorless crystalline solid. Calculated for $C_{21}H_{35}ClNO_3S_2Si$: m/z 476.1516. Found: 476.1508.

Step B

3-Methyl-benzo[b]thiophene-2-sulfonic acid[2-(tert-butyl-dimethyl-silanyloxy)-propyl]-propyl-amide

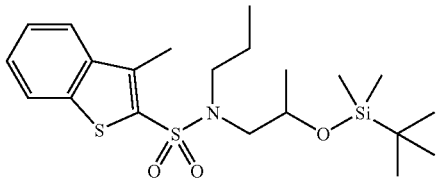

A mixture of 5-chloro-3-methyl-benzo[b]thiophene-2-sulfonic acid[2-(tert-butyl-dimethyl-silanyloxy)-propyl]-propyl-amide (395 mg, 0.830 mmol), palladium on carbon (5% Pd; 49 mg), and triethylamine (2 mL) was shaken under 60 psig $H_2$ for 30 h. The mixture was filtered and the filtrate was rotary evaporated (50° C.) yielding 366 mg (100%) of the product as a colorless crystalline solid. Calculated for $C_{21}H_{36}NO_3S_2Si$: m/z 442.1906. Found: 442.1895.

Step C

3-Methyl-benzo[b]thiophene-2-sulfonic acid (2-hydroxy-propyl)-propyl-amide

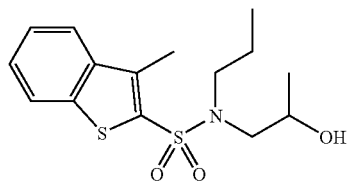

A solution of 3-methyl-benzo[b]thiophene-2-sulfonic acid [2-(tert-butyl-dimethyl-silanyloxy)-propyl]-propyl-amide (350 mg, 0.79 mmol) and trifluoroacetic acid (2 mL) in $CH_2Cl_2$ (10 mL) was stirred for 15 min. and the mixture was rotary evaporated. The resultant residue was chromatographed (100 mL hexanes, 100 mL 50% EtOAc/hex) through flash silica gel (35 mm×35 mm dia.) to yield about 213 mg (82%) of the product as a yellow oil. Calculated for $C_{15}H_{22}NO_3S_2$: m/z 328.1041. Found: 328.1037.

Step D (2-Methyl-4-{1-methyl-2-[(3-methyl-benzo[b]thiophene-2-sulfonyl)-propyl-amino]-ethoxy}-phenoxy)-acetic acid Diisopropyl azodicarboxylate (30 μL, 31 mg, 0.15 mmol, 1.0 equiv) was added over a period of 1 min to a solution of (4-hydroxy-2-methyl-phenoxy)-acetic acid methyl ester (30 mg, 0.15 mmol, 1.0 equiv), 3-methyl-benzo[b]thiophene-2-sulfonic acid (2-hydroxy-propyl)-propyl-amide (50 mg, 0.15 mmol, 1 equiv), and triphenylphosphine (40 mg, 0.15 mmol, 1.0 equiv) in anhydrous toluene (3 mL). The solution was stirred for 17 h., and the mixture was rotary evaporated. The resultant yellow oil was eluted (200 mL 5% EtOAc/hex, 200 mL 10% EtOAc/hex) through a chromatotron (1 mm plate) yielding 20 mg (26%) of the methyl ester as a colorless oil. The oil was dissolved in EtOH (2 mL) and 5 M aq NaOH (0.2 mL) was added. After stirring for 2 h, the reaction solution was evaporated, and the resultant residue was acidified with 1 M aq HCl (10 mL) and then extracted with $CH_2Cl_2$ (2×5 mL). The organic layer was dried (anhydrous $MgSO_4$) and rotary evaporated (50° C.) yielding 18 mg (24%) of the desired acid as a colorless film. Calculated for $C_{24}H_{29}NO_6S_2$: m/z 492.1515. Found: 492.1532.

EXAMPLE 209

(4-{2-[(5-Chloro-2-methyl-benzo[b]thiophene-3-sulfonyl)-propyl-amino]-ethylsulfanyl}-2-methyl-phenoxy)-acetic acid

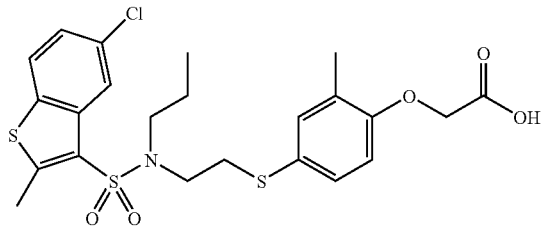

Step A

5-Chloro-2-methyl-benzo[b]thiophene-3-sulfony) chloride

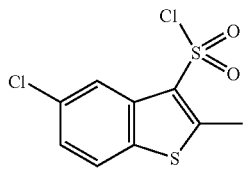

Chlorosulfonic acid (72 µL, 130 mg, 1.18 mmol, 3.0 equiv) was added to a solution of 5-chloro-2-methyl-benzo[b]thiophene (66 mg. 0.36 mmol, 1 equiv) in 1.2-dichloroethane (1 mL) cooled to 0° C. After stirring for an 1 h, the mixture was poured into a mixture of EtOAc (5 mL) and saturated aq NaCl (5 mL). The organic layer was separated, dried (anhydrous $Na_2SO_4$), and rotary evaporated (40° C.) to yield about 82 mg (81%) of the product.

Step B

[2-Methyl-4-(2-propylamino-ethylsulfanyl)-phenoxy]-acetic acid ethyl ester

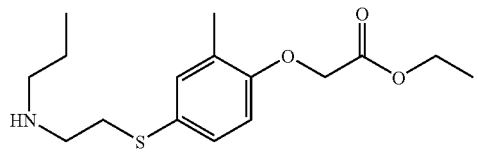

Trifluoroacetic acid (2.0 mL, 3.0 g, 26 mmol, 22 equiv) was added to a solution of {4-[2-(tert-butoxycarbonyl-propyl-amino)-ethylsulfanyl]-2-methyl-phenoxy}-acetic acid ethyl ester (490 mg, 1.19 mmol, 1 equiv) in $CH_2Cl_2$ (20 mL), the reaction solution was stirred for an 1 h. The solution (40° C.) was evaporated to yield 713 mg (140%) of the trifluoroacetate salt as a colorless oil. The oil was dissolved in $CH_2Cl_2$ (50 mL) and saturated aq $NaHCO_3$ (20 mL) was added. The organic layer was separated, dried (anhydrous $Na_2SO_4$), and rotary evaporated (40° C.) to yield about 349 mg (94.1%) of the free-base amine as a colorless oil. Calculated for $C_{16}H_{26}NO_3S$: m/z 312.1633. Found: 312.1652.

Step C (4-{2-[(5-Chloro-2-methyl-benzo[b]thiophene-3-sulfonyl)-propyl-amino]-ethylsulfanyl}-2-methyl-phenoxy)-acetic acid ethyl ester

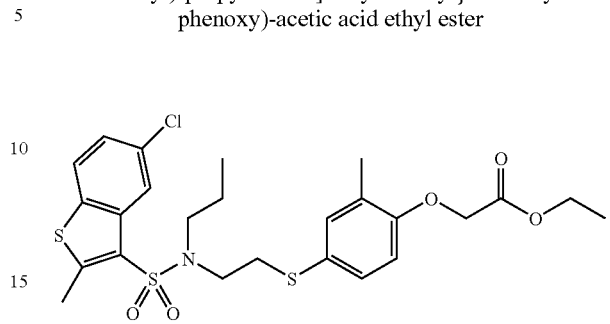

A solution of 5-chloro-2-methyl-benzo[b]thiophene-3-sulfonyl chloride (33 mg, 0.12 mmol, 1 equiv) in anhydrous $CH_2Cl_2$ (1 mL) was added to a solution of[2-methyl-4-(2-propylamino-ethylsulfanyl)-phenoxy]-acetic acid ethyl ester (40 mg, 0.13 mmol. 1.1 equiv) and triethylamine (35 µL, 25 mg, 0.25 mmol 2.1 equiv) in anhydrous $CH_2Cl_2$ (1 mL) cooled to 0° C. After stirring for an 1 h, the solution was diluted with $CH_2Cl_2$ (3 mL), washed with 0.2 M aq HCl (5 mL), dried (anhydrous $MgSO_4$), and rotary evaporated (50° C.) to give 72 mg (110%) of the sulfonamide as a yellow oil. The oil was eluted (50 mL 10% EtOAc/hex, 100 µL 20% EtOAc/hex) through a chromatotron (1 mm plate) to yield 44 mg (67%) of the purified material as a colorless film. Calculated for $C_{25}H_{31}ClNO_5S_3$: m/z 556.1053. Found: 556.1072.

Step D (4-{2-[(5-Chloro-2-methyl-benzo[b]thiophene-3-sulfonyl)-propyl-amino]-ethylsulfanyl}-2-methyl-phenoxy)-acetic acid The compound of (4-{2-[(5-chloro-2-methyl-benzo[b]thiophene-3-sulfonyl)-propyl-amino]-ethylsulfanyl}-2-methyl-phenoxy)-acetic acid ethyl ester (43 mg, 0.077 mmol, 1 equiv) was dissolved in EtOH (4 mL) and 5 M aq NaOH (0.4 mL) was added. After stirring for 2 h, the reaction solution was rotary evaporated. The resultant residue was acidified with 1 M aq HCl (10 mL) and then extracted with $CH_2Cl_2$ (2×5 mL). The combined organic layers were dried (anhydrous $MgSO_4$) and rotary evaporated (50° C.) to yield about 38 mg (93%) of the acid as a yellow film. Calculated for $C_{23}H_{27}ClNO_5S_3$: m/z 528.0740. Found: 528.0746.

EXAMPLE 210

(4-{2-[(6-Chloro-3-methyl-benzo[b]thiophene-2-sulfonyl)-propyl-amino]-ethylsulfanyl}-2-methyl-phenoxy)-acetic acid

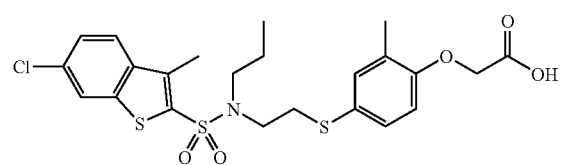

Step A

4-Chloro-2-fluoro-N-methoxy-N-methyl benzamide

2-Fluoro-4-chloro benzoic acid (2.00 g, 11.5 mmol) was added to SOCl₂ (25 mL) and the mixture was heated at reflux for an hour. The excess SOCl₂ was removed on the rotary evaporator and the resulting oil was dissolved in CH₂Cl₂ (2 omL) and added to a stirred mixture of N-methylN-methoxy hydrochloride (1.25 g, 12.8 mmol) and pyridine (2.50 mL, 30 mmol) in CH₂Cl₂ (50 mL) at 0° C. under N₂. The mixture was stirred overnight, diluted with fresh CH₂Cl₂ (100 mL) and extracted with H₂O (3×100 mL), 1 N HCl (100 mL) and saturated NaHCO₃ (100 mL), and then washed with brine and dried (MgSO₄). The mixture was filtered and evaporated to give about 2.06 g (82%) of the title compound as a pale yellow liquid. NMR (CDCl₃) δ 7.4 (m, 1H), 7.2 (m, 1H), 7.15 (m, 1H), 3.5 (broad s, 3H), 2.4 (s, 3H).

Step B 1-(4-Chloro-2-fluoro-phenyl) ethanone

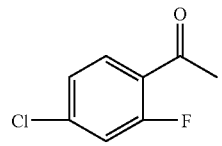

CH₃Li (4.30 mL, 6.0 mmol) was added dropwise to a stirring solution of 4-chloro-2-fluoro-N-methoxy-n-methyl benzamide (1.09 g, 5.0 mmol) in THF (30 mL) under N₂ at −70° C. The mixture was stirred for 1 hour at −70° C., and then at 0° C. for 1 hour. The mixture was quenched with a saturated solution of NH₄Cl at 10° C. and extracted with Et₂O (100 mL). The organic layer was dried (MgSO₄), filtered and evaporated to give a pale yellow liquid (0.84 g), which was chromatographed on the chromatotron using a 4 mm plate and then eluted with EtOAc-hexane (10:90) to afford about 0.52 g (60%) of a pale yellow liquid. NMR CDCl₃ δ 7.9 (t, 1H), 7.25-1.5 (m, 2H), 2.6 (s, 3H).

Step C

6-Chloro-3-methyl-benzo[b]thiophene-2-carboxylic acid ethyl ester

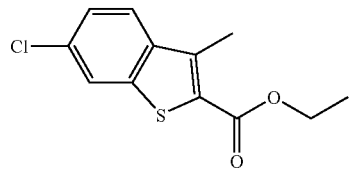

Cesium carbonate (4.5 g, 14 mmol, 2.0 equiv) was added to a solution of 1-(4-chloro-2-fluoro-phenyl)-ethanone (1.25 g, 7.24 mmol, 1.1 equiv) and ethyl 2-mercaptoacetate (0.75 mL. 0.82 g, 6.8 mmol. 1 equiv) in anhydrous DMF (5 mL). The mixture was stirred at 80° C. for 1 h and then stirred at 20 DC for 14 h. The mixture was poured into 320 (75 mL) and extracted with Et₂O (2×50 mL). The combined organic layers were dried (anhydr Na₂SO₄) and rotary evaporated (90° C.) 0 yield 1.43 g (82%) of product as a orange-yellow solid.

Step D

6-Chloro-3-methyl-benzo[b]thiophene

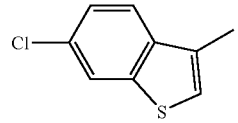

The compound of 6-chloro-3-methyl-benzo[b]thiophene-2-carboxylic acid ethyl ester (1.40 g, 5.50 mmol, 1 equiv) was dissolved in hot EtOH (30 mL) and 5 M NaOH (3 mL) was added. The solution was stirred for an hour and then rotary evaporated. The resultant solid was suspended in 0.2 M aq HCl (50 mL) and extracted with EtOAc (50 mL). The EtOAc layer was dried (anhydr Na₂SO₄) and rotary evaporated (50° C.) yielding 1.15 g (92.3%) of acid as a light yellow solid. The acid and copper powder (210 mg, 3.3 mmol, 0.60 equiv) was suspended in quinoline (60 mL), and the mixture was heated at 200° C. for 20 min and then allowed to cool. The mixture was diluted with Et₂O (300 mL) and filtered through Celite. The filtrate was washed with 5 M aq HCl (4×100 mL) to remove quinoline. The organic layer was dried (anhydrous Na₂SO₄) and rotary evaporated (50° C.) to yield 1.62 g (161%) of crude product as a brown liquid. The liquid was eluted (200 mL hexanes) through a chromatotron (4 mm plate) to afford about 961 mg (95.7%) of the product as a colorless liquid.

Step E

6-Chloro-3-methyl-benzo[b]thiophene-2-sulfonyl chloride

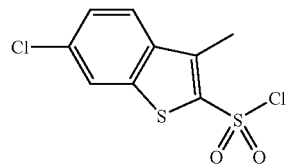

Butyllithium (1.6 M in hexanes. 830 μL, 1.3 mmol, 1.2 equiv) was added to a solution of 6-chloro-3-methyl-benzo [b]thiophene (203 mg, 1.1 mmol, 1 equiv) in anhydrous THF (5 mL) cooled to −40° C. in an acetonitrile/dry ice bath. The reaction solution was transferred to a regular ice bath (0° C.). After stirring for 30 min. the reaction solution was added to a solution of sulfuryl chloride (180 μL, 300 mg, 2.2 mmol 2.0 equiv) in hexanes (2 mL) cooled to −40° C. Then the solution was then transferred to a regular ice bath (0° C.). After stirring for 30 min, the solution was quenched with MeOH, and saturated aq NaHCO₃ was added to neutralize the acidic mixture. The organic layer was separated, dried (anhydrous MgSO₄), and rotary evaporated. The resultant brown oil was eluted (50 mL hexanes, 50 mL 10% EtOAc/hex) through a chromatotron (1 mm plate) to yield 51 mg (16%) of product as yellow-orange needles.

Step F (4-{2-[(6-Chloro-3-methyl-benzo[b]thiophene-2-sulfonyl)-propyl-amino]-ethylsulfanyl}-2-methyl-phenoxy)-acetic acid A solution of 6-chloro-3-methyl-benzo[b]thiophene-2-sulfonyl chloride (47 mg, 0.17 mmol, 1 equiv) in anhydrous $CH_2Cl_2$ (1 mL) was added to a solution of[2-methyl-4-(2-propylamino-ethylsulfanyl)-phenoxy]-acetic acid ethyl ester (57 mg, 0.18 mmol, 1.1 equiv) and triethylamine (47 µL, 34 mg, 0.34 mmol, 2.0 equiv) in anhydrous $CH_2Cl_2$ (1 mL) cooled to 0° C. in an ice bath. After about 30 min, the solution was removed from the ice bath. After stirring for 2.5 h, the solution was diluted with $CH_2Cl_2$ (3 mL), washed with 0.2 M aq HCl (5 mL), dried (anhydrous $MgSO_4$), and rotary evaporated (50° C.) to give 101 mg (110%) of the sulfonamide as a brown oil. The oil was eluted (50 mL 10% EtOAc/hex, 100 mL 20% EtOAc/hex) through a chromatotron (1 mm plate) to yield 55 mg (59%) of the purified sulfonamide ester as a colorless film, which was then dissolved in EtOH (5 mL) and 5 M aq NaOH (0.5 mL) was added. After stirring for 1 h, the solution was evaporated and the resultant residue was acidified with 1 M aq HCl (10 mL) and extracted with $CH_2Cl_2$ (2×5 mL). The combined organic layers were dried (anhydrous $MgSO_4$) and rotary evaporated (50° C.) to yield bout 52 mg (59%) of the acid as a yellow glass. Calculated for $C_{23}H_{27}ClNO_5S_3$: m/z 528.0740. Found: 528.0746.

EXAMPLE 211

(4-{2-[(7-Chloro-3-methyl-benzo[b]thiophene-2-sulfonyl)-propyl-amino]-ethylsulfanyl}-2-methyl-phenoxy)-acetic acid

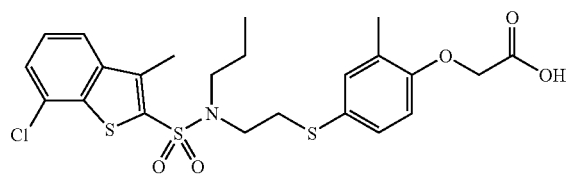

Step A

3-Chloro-2-fluoro-N-methoxy-N-methyl benzamide

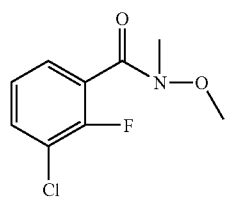

The compound of 3-chloro-2-fluoro benzoyl chloride (3.50 g, 17.1 mmol) in $CH_2Cl_2$ (20 mL) was added dropwise to a stirring solution of N-methoxy-N-methyl hydroxylamine hydrochloride (1.95 g, 20 mmol) and pyridine (3.60 mL, 44.5 mmol) in $CH_2Cl_2$ (80 mL) at 0° C. The mixture was stirred over the weekend and worked up as described in Example 210, Step A to give the title compound 3.56 g (96%) as a colorless oil. MS (M/E): 218(m+1), 220(m+1).

Step B 1-(3-Chloro-2-fluoro-phenyl) ethanone

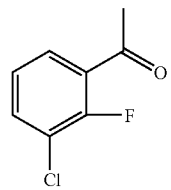

$CH_3Li$ (12.00 mL, 1.68 mmol) was added to a stirring solution of 3-chloro-2-fluoro-N-methoxy-N-methyl benzamide (3.26 g, 15.0 mmol) in THF (70 mL) under $N_2$ at −60° C. The mixture was stirred at 60° C. for 3 h, and then warmed to −40° C. and quenched with a saturated solution of $NH_4Cl$. The mixture was worked up as described in Example 210, Step B. Chromatography on the chromatron using a 4 mm plate and eluting with EtOAc-hexane (5-95) affords about 1.20 g (46%) of the title compound. NMR ($CDCl_3$) δ 7.68 (m, 1H), 7.45 (m, 1H), 7.18 (m, 1H), 7.65 (d, 3H).

Step C

7-Chloro-3-methyl-benzo[b]thiophene-2-carboxylic acid ethyl ester

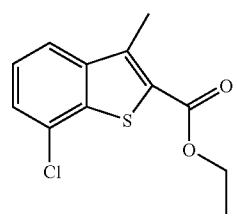

The compound of 1-(3-Chloro-2-fluoro-phenyl) ethanone (1.18 g, 6.8 mmol) was added to a stirring suspension of $Cs_2CO_3$ (4.17 g, 12.8 mmol) in day DMF (20 mL) and then 2-mercapto ethyl acetate (0.77 g, 6.4 mmol) was added. The mixture was heated at 80° C. for 1 hour. The mixture was stirred under $N_2$ overnight, and then poured into $H_2O$ (100 mL) and extracted with $Et_2O$ (150 mL). The $Et_2O$ was extracted with $H_2O$ (3×200 mL), washed with brine, dried ($MgSO_4$) and filtered. A light brown solid was obtained upon evaporation. NMR ($CDCl_3$) δ 7.65 (d, 1H), 7.45 (d, 1H), 7.4 (t, 1H), 4.40 (q, 2H), 2.68 (S, 3H), 1.44 (t, 3H).

Step D

7-Chloro-3-methyl benzo[b]thiophene-2-carboxylic acid

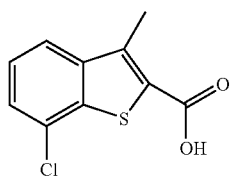

The compound of 7-Chloro-3-methyl-benzo[b]thiophene-2-carboxylic acid ethyl ester (1.10 g, 4.3 mmol) was added to a stirring solution of 5M NaOH (30 mL) and EtOH (30 mL) under $N_2$, and the mixture was heated at reflux for 30 minutes. The mixture was acidified to pH 4.0 with 37% HCl and extracted with $Et_2O$ (300 mL). The $Et_2O$ was washed with $H_2O$ (2×200 mL) and brine, and then dried ($MgSO_4$), filtered and evaporated to give about 0.96 g of a light brown solid. NMR (DMSO-$d_6$) $\delta$ 7.85 (d, 1H), 7.64 (d 1H), 7.45 (t, 3H).

Step E

7-Chloro-3-methyl-benzo[b]thiophene

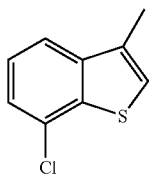

A solution of 7-chloro-3-methyl benzo[b]thiophene-2-carboxylic acid (0.41 g, 1.49 mmol) and Cu powder (0.069 g. 1.09 mmol) in quinoline (20 mL) was stirred and heated at 200° C. for 20 minutes. The mixture was cooled to ambient temperature and diluted with $Et_2O$ (100 mL), and then extracted with 2 M HCl (5×100 mL), washed with brine, dried ($MgSO_4$) and filtered through celite. The filtrate was concentrated to a brown oil and chromatographed on a 4 mm plate eluting with EtOAc-hexane (5-95) to afford about 0.19 g of oil. NMR (CDCl$_3$) $\delta$ 7.62 (m, 2H), 7.35 (m, 2H), 7.05 (s, 1H), 2.42 (s, 3H).

Step F

7-Chloro-3-methyl-benzo[b]thiophene-2-sulfonyl chloride

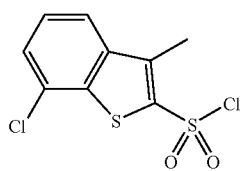

Butyllithium (1.6 M in hexanes, 1.8 mL, 2.9 mmol, 1.2 equiv) was added to a solution of 7-chloro-3-methyl-benzo[b]thiophene (442 mg, 2.42 mmol, 1 equiv) in anhydrous THF (5 mL) cooled in an acetonitrile/dry ice bath (−40° C.). The solution was transferred to an ice bath (0° C.). After stirring for 20 min, the solution was added to a solution of sulfuryl chloride (390 µL, 660 mg. 4.9 mmol, 2.0 equiv) in hexanes (5 mL) cooled in an acetonitrile/dry ice bath (−40° C.) (do not warm above −17° C. during the addition). Then the reaction solution was transferred to a regular ice bath (0° C.). After stirring for 1 h. saturated aq NaHCO$_3$ (5 mL) was added to quench the reaction. The organic layer was separated, dried (anhydrous MgSO$_4$), and rotary evaporated (50° C.) to give 542 mg (79.7%) of crude product as a tan crystalline solid. The solid was eluted (50 mL hexanes. 150 mL 10% EtOAc/hex) through a chromatotron (2 mm plate) to yield 187 mg (27.5%) of product as a light-yellow crystalline solid.

Step G (4-{2-[(7-Chloro-3-methyl-benzo[b]thiophene-2-sulfonyl)-propyl-amino]-ethylsulfanyl}-2-methyl-phenoxy)-acetic acid A solution of 7-chloro-3-methyl-benzo[b]thiophene-2-sulfonyl chloride (54 mg, 0.19 mmol, 1 equiv) in anhydrous CH$_2$Cl$_2$ (1 mL) was added to a solution of [2-methyl-4-(2-propyl amino-ethylsulfanyl)-phenoxy]-acetic acid ethyl ester (66 mg, 0.21 mmol, 1.1 equiv) and triethylamine (54 µL, 39 mg, 0.39 mmol, 2.0 equiv) in anhydrous CH$_2$Cl$_2$ (1 mL) cooled in an ice bath (0° C.). The solution was removed from the ice bath. After stirring for 2 h, the solution was diluted with CH$_2$Cl$_2$ (3 mL), washed with 0.2 M aq HCl (5 mL), dried (anhydrous MgSO$_4$), and rotary evaporated (50° C.) to give 109 mg (100%) of the sulfonamide as a yellow oil. The oil was eluted (50 mL 10% EtOAc/hex, 100 mL 20% EtOAc/hex) through a chromatotron (1 mm plate) to yield 82 mg (77%) of the purified ester as a colorless film, which was then dissolved in EtOH (8 mL) and 5 M aq NaOH (0.8 mL) was added. After stirring for 3 h, the solution was concentrated, and the resultant residue was acidified with 1 M aq HCl (10 mL) and then extracted with CH$_2$Cl$_2$ (2×5 mL). The combined organic layers were dried (anhydrous MgSO$_4$) and rotary evaporated (50° C.) to yield 65 mg (64%) of the acid as a white crystalline solid. Calculated for $C_{23}H_{27}ClNO_5S_3$: m/z 528.0740. Found: 528.0730.

EXAMPLE 212

(4-{2-[(4-Chloro-3-methyl-benzo[b]thiophene-2-sulfonyl)-propyl-amino]-ethylsulfanyl}-2-methyl-phenoxy)-acetic acid

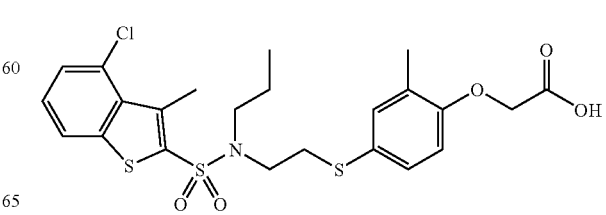

Step A

4-Chloro-3-methyl-benzo[b]thiophene-2-sulfonyl chloride

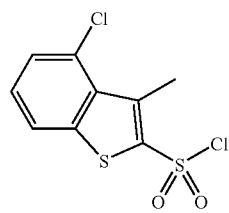

Butyllithium (1.6 M in hexanes; 4.2 mL, 6.7 mmol, 1.1 equiv) was added to a solution of 4-chloro-3-methyl-benzo [b]thiophene (1.1 g, 6.02 mmol, 1 equiv) in anhydrous THF (10 mL) cooled in an acetonitrile/dry ice bath (–40° C.). The reaction solution was transferred to a regular ice bath (0° C.). After stirring for 20 min, the reaction solution was added to a solution of sulfuryl chloride (1.5 mL, 2.5 g, 19 mmol, 3.1 equiv) in hexanes (10 mL) cooled in an acetonitrile/dry ice bath (–40° C.) (do not warm above –3° C. during the addition). The reaction solution was transferred to a regular ice bath (0° C.). After stirring for 1 h, a saturated aq NaHCO₃ (10 mL) was added to quench the reaction. The organic layer was separated, dried (anhydrous Na₂SO₄), and rotary evaporated (40° C.) to give 1.37 g (80.9%) of crude product as a tan crystalline solid. The material was eluted (150 mL hexanes, 150 mL 10% EtOAc/hex 150 mL 20% EtOAc/hex) through a chromatotron (4 mm plate) to yield 746 mg (44.1%) of product as a cream-colored crystalline solid.

Step B

(4-{2-[(4-Chloro-3-methyl-benzo[b]thiophene-2-sulfonyl)-propyl-amino]-ethylsulfanyl}-2-methyl-phenoxy)-acetic acid A solution of 4-chloro-3-methyl-benzo[b]thiophene-2-sulfonyl chloride (54 mg, 0.19 mmol, 1 equiv) in anhydrous CH₂Cl₂ (1 mL) was added to a solution of [2-methyl-4-(2-propylamino-ethylsulfanyl)-phenoxy]-acetic acid ethyl ester (66 mg, 0.21 mmol, 1.1 equiv) and triethylamine (54 μL, 39 mg. 0.39 mmol, 2.0 equiv) in anhydrous CH₁₂C₂ (1 μL). After stirring for 13 h. the solution (50° C.) was concentrated to give a yellow film. The material was eluted (50 mL 10% EtOAc/hex, 50 mL 20% EtOAc/hex) through a chromatotron (1 mm plate) to yield 84 mg (79%) of the purified ester as a colorless film, which was then dissolved in EtOH (8 mL) and 5 M aq NaOH (0.8 mL) was added. After stirring for 1 h, the reaction solution was rotary evaporated and the resultant residue was acidified with 1 M aq HCl (10 mL) and extracted with CH₂Cl₂ (2×5 mL). The combined organic layers were dried (anhydrous MgSO₄) and rotary evaporated (50° C.) to yield about 83 mg (82%) of the acid as a light-yellow crystalline solid. Calculated for $C_{23}H_{27}ClNO_5S_3$: m/z 528.0740. Found: 528.0755.

EXAMPLE 213

(4-{2-[(3-Methyl-benzo[b]thiophene-2-sulfonyl)-propyl-amino]-ethylsulfanyl}-2-methyl-phenoxy)-acetic acid

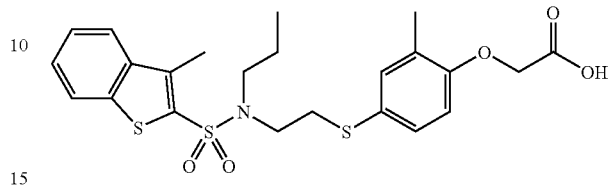

Step A

3-Methyl-benzo[b]thiophene-2-sulfonyl chloride

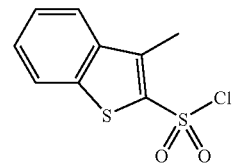

Butyllithium (1.6 M in hexanes: 5.3 mL, 8.5 mmol, 1.1 equiv) was added to a solution of 3-methyl-benzo[b] thiophene (1.15 g. 7.76 mmol, 1 equiv) in anhydrous THF (10 mL) cooled in an acetonitrile/dry ice bath (–40° C.). The reaction solution was transferred to a regular ice bath (0° C.). After stirring for 20 min, the reaction solution was added over a period of 90 seconds to a solution of sulfuryl chloride (1.9 mL, 3.2 g, 24 mmol, 3.0 equiv) in anhydrous THF (10 mL) cooled in an acetonitrile/dry ice bath (–40° C.) never warmed above –6° C. during the addition. The reaction solution was then transferred to a regular ice bath (0° C.). After stirring for 1 h, a saturated aq NaHCO₃ (10 mL) was slowly added to quench the reaction. The organic layer was separated, dried (anhydr Na₂SO₄), and rotary evaporated (50° C.) to give 1.39 g (72.6%) of crude product as an orange-yellow crystalline solid. The material was eluted (150 mL hexanes, 100 mL 10% EtOAc/hex, 400 mL 20% EtOAc/hex) through a chromatotron (4 mm plate) to yield 737 mg (38.5%) of product as a yellow crystalline solid.

Step B

(4-{2-[(3-Methyl-benzo[b]thiophene-2-sulfonyl)-propyl-amino]-ethylsulfanyl}-2-methyl-phenoxy)-acetic acid A solution of 3-methyl-benzo[b]thiophene-2-sulfonyl chloride (50 mg, 0.20 mmol, 1 equiv) in anhydrous CH₂Cl₂ (1 mL) was added to a solution of [2-methyl-4-(2-propylamino-ethylsulfanyl)-phenoxy]-acetic acid ethyl ester (70 mg, 0.22 mmol, 1.1 equiv) and triethylamine (56 μL, 41 mg, 0.40 mmol, 2.0 equiv) in anhydrous CH₂Cl₂ (1 mL). After stirring for 1.5 h, the solution was rotary evaporated to give a yellow film. The material was eluted (50 mL 10% EtOAc/hex, 100 mL 20% EtOAc/hex) through a chromatotron (1 mm plate) to yield 72 mg (68%) of the purified ester as a colorless film, which was then dissolve in EtOH (7 mL) and 5 M aq NaOH (0.7 mL) was added. After stirring for 16 h, the solution was concentrated, and the resultant residue was acidified with 1 M aq HCl (10 mL) and then extracted with CH$_2$Cl$_2$ (2×5 mL). The combined organic layers were dried (anhydrous MgSO$_4$) and rotary evaporated (50° C.) to yield 65 mg (65.0%) of the acid as a colorless film.

Calculated for C$_{23}$H$_{28}$NO$_5$S$_3$: m/z 494.1130. Found: 494.1134.

EXAMPLE 214

(4-{2-[(5-Chloro-benzo[b]thiophene-2-sulfony)-propyl-amino]-ethylsulfanyl}-2-methyl-phenoxy)-acetic acid

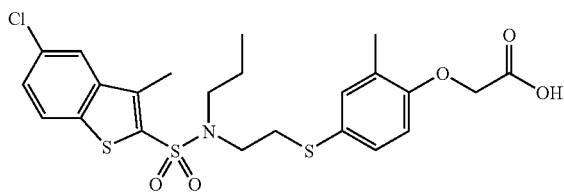

Step A

5-Chloro-benzo[b]thiophene-2-sulfonyl chloride

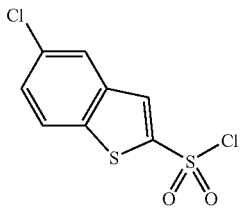

Butyllithium (1.6 M in hexanes; 8.4 mL, 13 mmol, 1.1 equiv) was added to a solution of 5-chloro-benzo[b]thiophene (2.05 g, 12.2 mmol, 1 equiv) in anhydrous THF (20 mL) cooled in an acetonitrile/dry ice bath (−40° C.). The reaction solution was transferred to a regular ice bath (0° C.). After stirring for 15 min. the reaction solution was added over a period of 2 min to a solution of sulfuryl chloride (2.0 mL, 3.4 g, 25 mmol, 2.0 equiv) in hexanes (20 mL) cooled in an acetonitrile/dry ice bath (−40° C.) never warming above −9° C. during the addition. The reaction solution was transferred to a regular ice bath (0° C.). After stirring for 1 h, a saturated aq NaHCO$_3$ (20 mL) was added slowly to quench the reaction. The organic layer was separated, dried (anhydrous Na$_2$SO$_4$), and rotary evaporated (50° C.) to give 2.72 g (83.8%) of crude product as a brown oil with brown crystals. The material was eluted (200 mL hexanes, 300 mL 10% EtOAc/hex) through a chromatotron (6 mm plate) to yield 1.37 g (42.2%) of product as a tan crystalline solid.

Step B (4-{2-[(5-Chloro-benzo[b]thiophene-2-sulfonyl)-propyl-amino]-ethylsulfanyl}-2-methyl-phenoxy)-acetic acid A solution of 5-chloro-benzo[b]thiophene-2-sulfonyl chloride (53 mg, 0.20 mmol. 1 equiv) in anhydrous CH$_2$Cl$_2$ (1 mL) was added to a solution of [2-methyl-4-(2-propylamino-ethylsulfanyl)-phenoxy]-acetic acid ethyl ester trifluoroacetate (94 mg, 0.22 mmol, 1.1 equiv) and triethylamine (83 μL, 60 mg, 0.60 mmol 3.0 equiv) in anhydrous CH$_2$Cl$_2$ (1 mL). After stirring for 1.5 h, the reaction solution was concentrated to give a yellow film. The material was eluted (50 mL 10% EtOAc/hex, 100 mL 20% EtOAc/hex) through a chromatotron (1 mm plate) to yield 92 mg (86%) of the purified ester as a colorless film. The material was dissolved in EtOH (9 mL) and 5 M aq NaOH (0.9 mL) was added. After stirring for 63 h. the reaction solution rotary evaporated, and the resultant residue was acidified with 1 M aq HCl (10 mL) and then extracted, with CH$_2$Cl$_2$ (2×5 mL). The combined organic layers were dried (anhydrous MgSO$_4$) and rotary evaporated (50° C.) to yield 67 mg (66%) of the acid as an off-white crystalline solid. Calculated for C$_{22}$H$_{25}$ClNO$_5$S$_3$: m/z 514.0583. Found: 514.0583.

EXAMPLE 215

(4-{1-[(5-Chloro-3-methyl-benzo[b]thiophene-2-sulfonylamino)-methyl]-butoxy}-2-methyl-phenoxy)-acetic acid

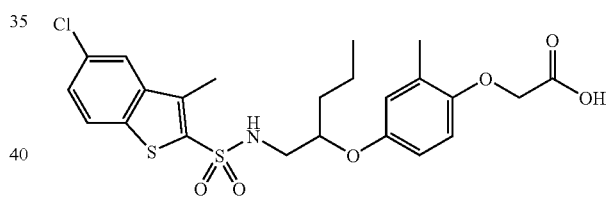

Step A (2-Oxo-pentyl)-carbamic acid tert-butyl ester

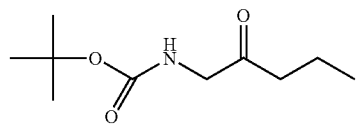

n-PrMgBr 2.0 M (12.5 mL, 25 mmol) was added to a stirring solution of n-(tert-butoxy carbonyl)glycine N-methoxy-N-methylamide (2.18 g, 10.7 mmol) in dry THF (30 mL) at −10 to 0° C. The resulting pale yellow solution was stirred at ambient temperature for 72 hours and then at reflux for 2.5 hours. The mixture was quenched at 0° C. with a saturated solution of NH$_4$Cl. The Et$_2$O was added, and the organic layer was separated, washed with brine, dried (MgSO$_4$) and filtered. The filtrate was evaporated to give 1.93 g of a pale yellow oil. NMR CDCl$_3$ δ 5.24 (b s, 1H), 4.00 (m, 2H), 2.40 (t, 2H), 1.65 (m, 2H), 1.25 (s, 9H), 0.90 (t, 3H).

Step B

(2-Hydroxy-pentyl)-carbamic acid tert butyl ester

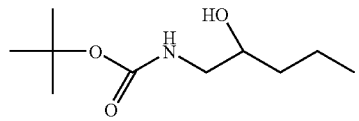

NaBH₄ 0.380 g. 10 mmol) was added portion wise to a stirring solution of 2-oxo-pentyl)-carbamic acid tert-butyl ester (1.50 g. 7.45 mmol) in dry THF (50 mL) at ambient temperature. The resulting suspension was stirred overnight and quenched with CH₃OH. The mixture was evaporated to a semisolid residue, which was partitioned between H₂O and CH₂Cl₂ (200 mL). The organic layer was separated, washed with brine, dried (MgSO₄) and filtered. The filtrate was evaporated to give 1.09 g (72%) of a viscous liquid. MS(FAB⁺) 204.1.

Step C

{4-[1-(tert-Butoxycarbonylamino-methyl)-butoxy]-2-methyl-phenoxy}-acetic acid methyl ester

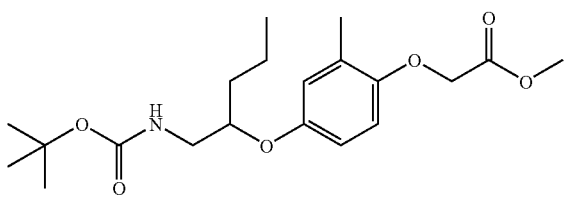

Diisopropyl azodicarboxylate (0.64 mL, 0.66 g, 3.3 mmol, 1.0 equiv) was added over a period of 3 min to a solution of (4-hydroxy-2-methyl-phenoxy)-acetic acid methyl ester (633 mg, 3.23 mmol, 1 equiv), (2-hydroxy-pentyl)-carbamic acid tert-butyl ester (656 g, 3.23 mmol, 1.0 equiv), and triphenylphosphine (846 g, 3.23 mmol, 1.0 equiv) in anhydr toluene (60 mL). The solution was stirred for 14 h and the mixture was rotary evaporated. The resultant yellow oil was eluted (50 mL 5% EtOAc/hex, 100 mL 10% EtOAc/hex, 100 mL 20% EtOAc/hex, 300 mL 30% EtOAc/hex) through a chromatotron (6 mm plate) to yield 757 mg (61.5%) of product as nearly colorless oil. Calculated for $C_{10}H_{31}NNaO_6$: m/z 404.2049. Found: 404.2042.

Step D

[4-(1-Aminomethyl-butoxy)-2-methyl-phenoxy]-acetic acid methyl ester

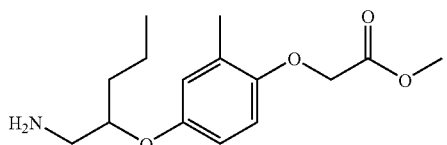

Trifluoroacetic acid (2.9 mL, 4.3 g, 38 mmol. 20 equiv) was added to a solution of {4-[1-(tert-butoxycarbonylamino-methyl)-butoxy]-2-methyl-phenoxy}-acetic acid methyl ester (Example 210, Step C) (722 mg, 1.89 mmol. 1 equiv) in CH₂Cl₂ (20 mL). The colorless solution was stirred for 2 h. The reaction solution (50° C.) yielding 1.04 g (140%) of the trifluoroacetate salt was rotary evaporated as an orange oil. The oil was dissolved in CH₂Cl₂ (50 mL) and saturated aq NaHCO₃ (20 mL) was added. The organic layer was separated, dried (anhydrous Na₂SO₄), and rotary evaporated (40° C.) to yield 492 mg (92.4%) of the free-base amine as an orange oil. Calculated for $C_{15}H_{24}NO_4$: m/z 282.1705. Found: 282.1703.

Step E

(4-{1-[(5-Chloro-3-methyl-benzo[b]thiophene-2-sulfonylamino)-methyl]-butoxy}-2-methyl-phenoxy)-acetic acid A solution of 5-chloro-3-methylbenzo[b]thiophene-2-sulfonyl chloride (Oakwood; 237 mg, 0.843 mmol, 1 equiv) in anhydrous CH₂Cl₂ (4 mL) was added to a solution of [4-(1-aminomethyl-butoxy)-2-methyl-phenoxy]-acetic acid methyl ester (249 mg, 0.885 mmol, 1.05 equiv) and triethylamine (360 µL, 260 mg, 2.6 mmol, 3.0 equiv) in anhydrous CH₂Cl₂ (4 mL). After 20 h, the reaction solution was rotary evaporated. The resultant material was eluted (50 mL 10% EtOAc/hex, 100 mL 20% EtOAc/hex, 150 mL 30% EtOAc/hex) through a chromatotron (2 mm plate) to yield 201 mg (45.3%) of the purified ester as a light-yellow film. The material was dissolved in EtOH (2 mL) and 5 M aq NaOH (0.2 mL) was added. After stirring for 16 h, the reaction solution was rotary evaporated, and the resultant residue was acidified with 1 M aq HCl (10 mL) and then extracted with CH₂Cl₂ (2×5 mL). The combined organic layers were dried (anhydrous MgSO₄) and rotary evaporated (50° C.) to yield about 188 mg (43.6%) of the acid as an off-white solid. Calculated for $C_{23}H_{27}ClNO_6S_2$: m/z 512.0968. Found: 512.0967.

EXAMPLE 216

(4-{1-[(5-Fluoro-3-methyl-benzo[b]thiophene-2-sulfonylamino)-methyl]-butoxy}-2-methyl-phenoxy)-acetic acid

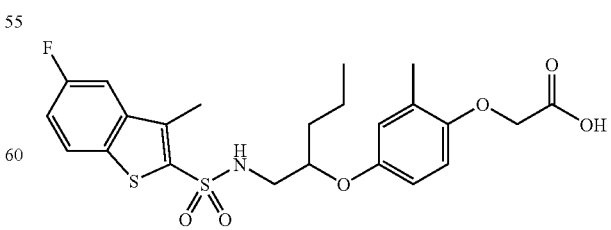

A suspension of 5-fluoro-3-methylbenzo[b]thiophene-2-sulfonyl chloride (211 mg, 0.797 mmol, 1 equiv) in anhydrous CH₂Cl₂ (4 mL) was added to a solution of [4-(1-aminomethyl-butoxy)-2-methyl-phenoxy]-acetic acid methyl ester (236 mg, 0.839 mmol. 1.05 equiv) and triethylamine (330 μL. 240 mg, 2.4 mmol, 3.0 equiv) in anhydrous CH$_2$Cl$_2$ (4 mL). After stirring for 17 h, the reaction solution was rotary evaporated. The resultant material was eluted (50 mL 10% EtOAc/hex, 100 mL 20% EtOAc/hex) through a chromatotron (2 mm plate) to yield 117 mg (28.8%) of the purified ester as a colorless film. The material was dissolved in EtOH (2 mL) and 5 M aq NaOH (0.2 mL) was added. After stirring for 16 h, the reaction solution was rotary evaporated, and the resultant residue was acidified with 1 M aq HCl (10 mL) and then extracted with CH$_2$Cl$_2$ (2×5 mL). The combined organic layers were dried (anhydrous MgSO$_4$) and rotary evaporated (50° C.) to yield 105 mg (26.6%) of the acid as a white foam. Calculated for C$_{23}$H$_{27}$FNO$_6$S$_2$: m/z 496.1264. Found: 496.1264.

EXAMPLE 217

(4-{2-[(5-Chloro-3-trifluoromethyl-benzo[b]thiophene-2-sulfonyl)-propyl-amino]-ethylsulfanyl}-2-methyl-phenoxy)-acetic acid

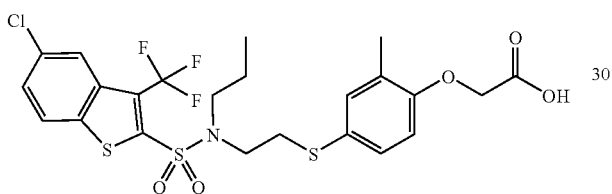

Step A 1-(5-Chloro-2-fluorophenyl)-2,2,2-trifluoro ethanone

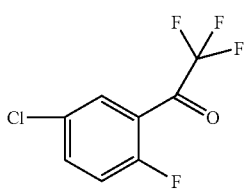

LDA 1.5 m (7.3 mL, 1.0 mmol) was added dropwise to a stirring solution of p-fluorochlorobenzene (1.30 g, 10 mmol) in anhydrous THF (15.0 mL) under N$_2$ at −70° C. The mixture was stirred at −70° C. for 1 hour and then ethyl trifluoro acetate (1.56 g, 11 mmol) in THF (5.0 mL) was added dropwise. The resulting mixture was stirred at ambient temperature under N$_2$ overnight and quenched at 0° C. with a saturated solution of NH$_4$Cl. The mixture was diluted with Et$_2$O, and the organic layer was separated, dried (MgSO$_4$), filtered, evaporated and chromatographed using a 4 mm plate and eluting with EtOAc-hexane (6:94) to give 0.98 g (43%) of a yellow liquid. NMR CDCl$_3$ δ 7.85 (m, 1H), 7.65 (m, 1H), 7.25 (m, 1H).

Step B

5-Chloro-3-trifluoromethyl-benzo[b]thiophene-2-carboxylic acid ethyl ester

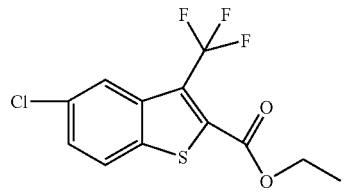

A solution of 1-(5-Chloro-2-fluorophenyl)-2,2,2-trifluoro ethanone 0.95 g, 4.20 mmol) in CH$_3$CN (4.0 mL) was added to a stirring solution ethylthioacetate (0.51 mL, 4.60 mmol) and Et$_3$N (0.77 mL, 5.50 mmol) in CH$_3$CN (20 mL) at ambient temperature. The resulting yellow solution was heated at 80° C. for 18 hours. After cooling to ambient temperature, the solvent was evaporated and the mixture was partitioned between Et$_2$O (100 mL) and 1 M NaOH (50 mL). The organic layer was separated, dried (MgSO$_4$) and filtered. The filtrate was evaporated, chromatographed on the chromatron using a 4 mm plate and eluted with EtOAc-hexane (10:90) to give the ester as a white crystalline solid, 0.80 g (62%). NMR CDCl$_3$ δ 8.05 (s, 1H), 8.80 (d, 1H), 7.45 (d, 1H), 4.42 (q, 2H), 1.42 (t, 3H).

Step C

5-Chloro-3-trifluoromethyl-benzo[b]thiophene-2-carboxylic acid

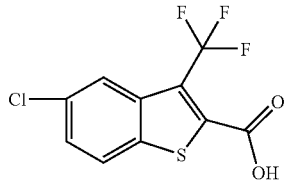

2 M NaOH (40 mL) was added to a stirring solution of 5-Chloro-3-trifluoromethyl-benzo[b]thiophene-2-carboxylic acid ethyl ester (1.75 g, 5.7 mmol) in EtOH (40 mL), and the mixture was heated under reflux for 2 hours. EtOH was evaporated on the rotary evaporator and the resulting suspension was diluted with 120 (100 mL), acidified to pH 1 with 37% HCl. The resulting precipitate was extracted into EtOAc (250 mL), washed with brine, dried (MgSO$_4$), filtered and concentrated to give a white solid, 1.45 g.

Step D

5-Chloro-3-trifluoromethylbenzo[b]thiophene

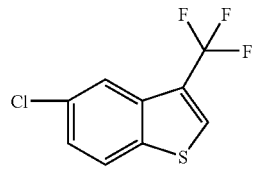

Copper powder (0.200 g, 3.15 mmol) was added to a stirring solution of 5-chloro-3-trifluoromethyl-benzo[b]

thiophene-2-carboxylic acid (1.45 g, 5.18 mmol) in quinoline (14.0 mL), and the mixture was heat under $N_2$ at 200° C. for 20 minutes. The mixture was diluted with $Et_2O$ (20 mL) and filtered through celite. The filtrate was extracted with 1M HCl (3×100 mL), washed with brine, dried ($MgSO_4$), filtered and evaporated to a brown liquid. The liquid was chromatographed on the chromatron on a 4 mm plate eluting with hexane to give the title compound 1.10 g as a clear liquid. Calculated for $C_9H_4F_3SCl$: 235.9674; Found 235.9659.

Step E

5-Chloro-3-trifluoromethyl-benzo[b]thiophene-2-sulfonyl chloride

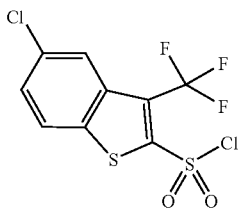

Butyllithium (1.6 M in hexanes; 3.2 mL, 5.1 mmol, 1.1 equiv) was added to a solution of 5-chloro-3-trifluoromethyl-benzo[b]thiophene (1.09 g, 4.61 mmol, 1 equiv) in anhydrous THF (20 mL) cooled in an acetonitrile/dry ice bath (−40° C.). The reaction solution was transferred to a regular ice bath (0° C.). After stirring for 10 min, the reaction solution was added over a period of 1 min to a solution of sulfuryl chloride (750 μL, 1.3 g, 9.3 mmol, 2.0 equiv) in anhydrous THF (20 mL) in an acetonitrile/dry ice bath (−40° C.) never warming above −8° C. during the addition. The reaction solution was transferred to a regular ice bath (0° C.). After stirring for 1 h, a saturated aq $NaHCO_3$ (20 mL) was slowly added to quench the reaction. The organic layer was separated, dried (anhydrous $Na_2SO_4$), and rotary evaporated (50° C.) to give 1.23 g (79.7%) of a crude to product as an orange-brown oil. The material was eluted (200 mL hexanes. 100 mL 5% EtOAc/hex, 100 mL 10% EtOAc/hex) through a chromatotron (4 mm plate) to yield 355 mg (23.0%) of product as an off-white crystalline solid.

Step F

[2-Methyl-4-(2-propylamino-ethylsulfanyl)-phenoxy]-acetic acid ethyl ester

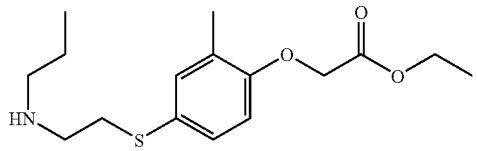

The compound of [2-methyl-4-(2-propylamino-ethylsulfanyl)-phenoxy]-acetic acid ethyl ester trifluoroacetate (545 mg. 1.28 mmol) was dissolved in $CH_2Cl_2$ (30 mL) and then saturated aq $NaHCO_3$ (20 mL) was added. The organic layer was separated, dried (anhydrous $Na_2SO_4$), and rotary evaporated (40° C.) to yield 235 mg (58.9%) of the free-base amine as a colorless oil.

Step G (4-{2-[(5-Chloro-3-trifluoromethyl-benzo[b]thiophene-2-sulfonyl)-propyl-amino]-ethylsulfanyl}-2-methyl-phenoxy)-acetic acid ethyl ester

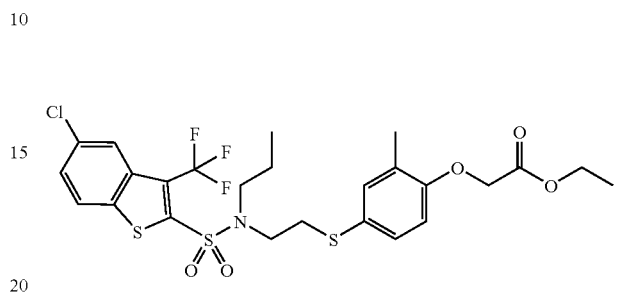

The compound of 5-chloro-3-trifluoromethyl-benzo[b]thiophene-2-sulfonyl chloride (100 mg, 0.298 mmol. 1 equiv) was added to a solution of [2-methyl-4-(2-propylamino-ethylsulfanyl)-phenoxy]-acetic acid ethyl ester (100 mg, 0.321 mmol, 1.1 equiv) and triethylamine (85 μL, 62 mg. 0.61 mmol, 2.0 equiv) in anhydrous $CH_2Cl_2$ (2 mL). After stirring for 1 h, the reaction solution was transferred to a chromatotron (1 mm plate) and eluted (100 mL hexanes. 100 mL 10% EtOAc/hex, 50 mL 20% EtOAc/hex) to yield 133 mg (73.1%) of the purified ester as a colorless film.

Step H (4-{2-[(5-Chloro-3-trifluoromethyl-benzo[b]thiophene-2-sulfonyl)-propyl-amino]-ethylsulfanyl}-2-methyl-phenoxy)-acetic acid The compound of (4-{2-[(5-chloro-3-trifluoromethyl-benzo[b]thiophene-2-sulfonyl)-propyl-amino]-ethylsulfanyl}-2-methyl-phenoxy)-acetic acid ethyl ester (156 mg, 0.256 mmol) was dissolved in EtOH (16 mL) and 5 M aq NaOH (1.6 mL) was added. After stirring for 14 h. the reaction solution was rotary evaporated. The resultant residue was acidified with 1 M aq HCl (15 mL) and then extracted with $CH_2Cl_2$ (2×10 mL). The combined organic layers were dried (anhydrous $MgSO_4$), rotary evaporated (40° C.), and placed under high vacuum (8 mtorr) for 4 hours to yield 104 mg (69.9%) of the acid as a white crystalline solid. Calculated for $C_{23}H_{24}ClF_3NO_5S_3$: m/z 582.0457. Found: 582.0443.

Elemental analysis for $C_{23}H_{23}ClF_3NO_5S_3$: calculated: C, 47.46; H, 3.98; N, 2.41; found: C, 47.57; H, 3.87; N, 2.29.

EXAMPLE 218

(2-Hydroxy-1-methyl-propyl)-carbamic acid tert-butyl ester

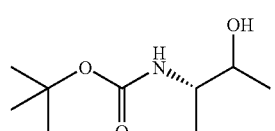

Step A

(1-Methyl-2-oxo-ethyl)-carbamic acid tert-butyl ester

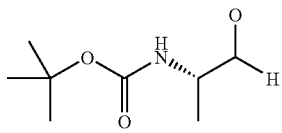

A solution of [1-(methoxy-methyl-carbamoyl)-ethyl]-carbamic acid tert-butyl ester (2 g, 8.6 mmol) in 20 mL dry THF was cooled to −78° C. DIBAL (2 eq, 8.6 mL of 1M in toluene) was added and the reaction was stirred at −78° C. for 30 minutes. The reaction was quenched with 10 mL MeOH and 10 mL water. The reaction was worked up in 50 mL EtOAc and 50 mL sat NaCl. The organics were dried with sodium sulfate and the organic layer was rotovaped to give 2.2 g of the desired product. MS [EI+] 174 (M+H)$^+$.

Step B

(2-Hydroxy-1-methyl-propyl)-carbamic acid tert-butyl ester

A solution of (1-methyl-2-oxo-ethyl)-carbamic acid tert-butyl ester (2 g, 11.5 mmol) in 20 mL dry THF was cooled to −78° C. MeLi (3 eq, 24.6 mL of 1.4M solution in ether) was added and the reaction was stirred at −78° C. for 30 minutes. The reaction was allowed to slowly warm to RT. The mixture was added to 200 mL EtOAc and washed with brine. The organics were dried with sodium sulfate and rotovaped to give 2.2 g of the desired alcohol. MS [EI+] 190 (M+H)$^+$.

EXAMPLE 219

Procedure A: General Procedure Used for Mitsunobu Reactions

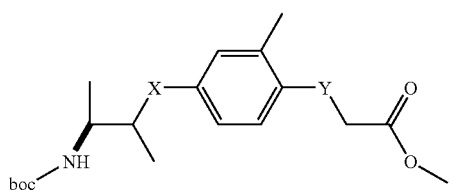

To a solution of primary or secondary alcohol in 25 mL toluene was added phenol headpiece (1 eq), DIAD (1 eq.), PPh3 (1 eq.). The reaction was stirred overnight at RT. The reaction mixture was added to 100 mL EtOAc. The organic layer was washed with brine and water (100 mL each). The organics were dried with sodium sulfate and rotovaped to give crude material. The materials were separated on chromatotron (10-70% EtOAc/hex) to give desired product.

EXAMPLE 220

3-Bromo-5-chloro-benzo[b]thiophene-2-sulfonyl chloride

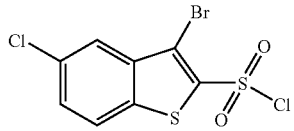

To a solution of 3-bromo-5-chloro-benzo[b]thiophene (1 g, 0.004 mol. 1 eq) in 20 mL of 1,2-dichloroethane at 0° C. was added chlorosulfonic acid (3 eq. 1.91 g). The solution was warmed to room temperature. The solution was added to 100 mL EtOAc and 100 mL brine for workup. The organic layer was dried with sodium sulfate and rotovaped to give 3.2 g of the crude material. The material was separated on the chromatatron (10-70% EtOAc/hex). The desired spot was rotovaped to give 0.88 g of product. MS [EI+] 347 (M+H)$^+$

EXAMPLE 221

Procedure B: General Procedure Used for Deprotection, Sulfonyl Chloride Displacement, and Hydrolysis

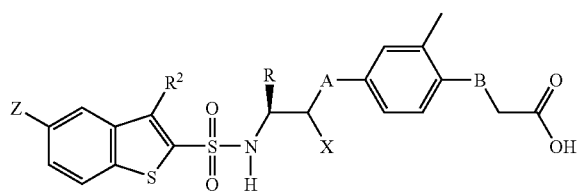

BOC-protected amines (Procedure A, Example 219) were added to a solution of trifluoroacetic acid (10 mL). The reaction mixtures were stirred overnight at RT. The mixtures were added to 50 mL EtOAc and washed with brine twice. The organic layers were dried with sodium sulfate and rotovaped. The materials were dissolved in 20 mL DMF and sulfonyl chloride was added (1 eq.). The reaction mixture was stirred overnight at RT. The reaction mixtures were each added to 50 mL EtOAc and washed with brine twice. The organic layers were dried with sodium sulfate and rotovaped to give the desired esters. Some of these esters were held aside and used in Procedure C as described in Example 217. The materials were dissolved in EtOH (5 mL) along with 5 mL 5N NaOH. The reaction mixtures were stirred overnight at RT. The reaction mixtures were added to 25 mL EtOAc, and the solution was acidified with 10 mL 5N HCl. The organic layer was dried with sodium sulfate and rotovaped to give the desired acid product. The compounds were characterized with MS.

EXAMPLE 222

Procedure C: Genera Procedure for N-alkylation and Hydrolysis

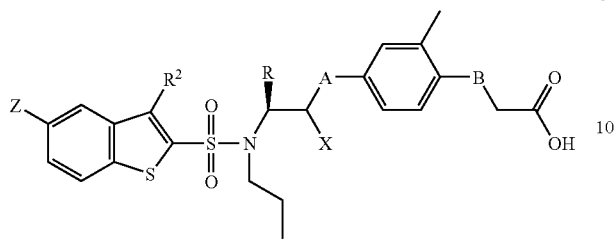

To a solution of ester (Procedure B. Example 221) in 20 mL DMF at 0° C. was added 3 eq. of propyl iodide along with 2 eq. of NaH (mineral oil). The mixtures were heated and stirred at 80° C. overnight. The reaction mixtures were added to 50 mL EtOAc and washed with brine twice. The organic layers were dried with sodium sulfate and rotovaped to give crude material. The material was separated on chromatotron (10-70% EtOAc/hex elution). The desired esters were isolated and identified with MS. The materials were dissolved in EtOH (5 mL) along with 5 mL 5N NaOH. The reactions where stirred overnight at RT. The mixtures were added to 25 mL EtOAc and acidified with 10 mL 5N HCl. The organic layer was dried with sodium sulfate and rotovaped to give the desired carboxylic acids. The compounds were characterized with MS.

EXAMPLE 223

S-Chloro-3-trifluoromethyl-benzo[b]thiophene

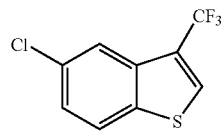

To 3-bromo-5-chloro-benzo[b]thiophene (1 g, 0.004 mol, 1 eq) was added copper powder (2.5 eq, 0.010 mmol. 0.64 g) added along with 50 mL DMSO. To this solution was slowly bubbled trifluoromethyl iodide. The reaction was stirred overnight at 120° C. The reaction mixture was filtered through celite. The filtrate was added to 100 mL EtOAc for workup. The solution was washed with saturated NaCl twice. The organic layer was removed and dried with sodium sulfate. The solution was concentrated to give 500 mg of crude material. The material was added to chromatotron and eluted with 10-70% EtOAc/hexanes. The product spot was identified with MS. About 200 mg was isolated. MS [EI+] 237 (M+H)$^+$.

EXAMPLE 224

(2-Hydroxy-pentyl)-carbamic acid tert-butyl ester

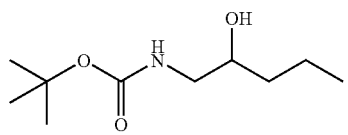

(2-Oxo-ethyl)-carbamic acid tert-butyl ester 2 g, 12.5 mmol) was dissolved in 20 mL dry THF. The solution was cooled to −78° C. N-propyl magnesium bromide (3 eq. 37.7 mmol, 5.55 g, 17.2 mL of 30% solution in THF) was added, and the reaction was stirred at −78° C. for 30 minutes. The reaction was quenched with 20 mL MeOH. The organics were removed and about 1.5 g of product was identified by MS.
MS [EI+] 204 (M+H)$^+$.

EXAMPLE 225

5-Chloro-3-trifluoromethyl-benzo[b]thiophene-2-sulfonic acid[2-(tert-butyl-dimethyl-silanyloxy)-propyl]-propyl-amide

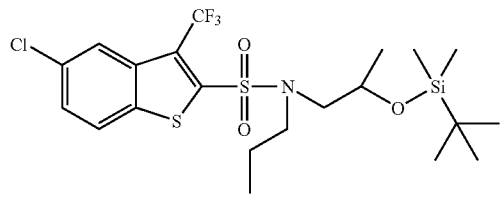

The compound of 3-bromo-5-chloro-benzo[b]thiophene-2-sulfonic acid[2-(tert-butyl-dimethyl-silanyloxy)-propyl]-propyl-amide (0.100 g, 0.18 mmol, 1 eq) was added to a 3-necked flask. Copper powder (2.5 eq, 0.46 mmol. 0.030 g) was added along with 50 mL DMSO. To this solution was slowly bubbled trifluoromethyl iodide. The reaction was stirred overnight at 120° C. The reaction mixture was filtered through celite. The filtrate was added to 100 mL EtOAc for workup and washed with saturated NaCl twice. The organic layer was removed and dried with sodium sulfate. The solution was concentrated to give 500 mg of crude material. The material was added to a chromatotron and eluted with 10-70% EtOAc/hexanes. About 32 mg of product was isolated. MS [EI+] 530 (M+H)$^+$.

EXAMPLE 226

(4-{2-[(3-Bromo-5-chloro-benzo[b]thiophene-2-sulfonyl)-propyl-amino]-ethylsulfanyl}-2-methyl-phenoxy)-acetic acid ethyl ester

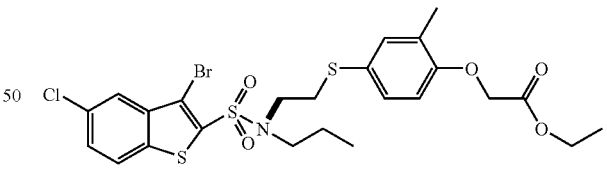

{4-[2-(tert-Butoxycarbonyl-propyl-amino)-ethylsulfanyl]-2-methyl-phenoxy}-acetic acid ethyl ester (250 mg, 0.6 mmol) was dissolved in 5 mL of dichloromethane. Dimethyldiethylsilane (3 eq. 1.8 mmol 160 mg) was added along with 2 mL TFA. The reaction was stirred at RT for 1 hr. The solvent was removed and material dissolved in 5 mL dichloromethane. Triethylamine (6 eq, 5 mL) was added along with 3-Bromo-5-chloro-benzo[b]thiophene-2-sulfonyl chloride (1 eq, 210 mg). The reaction mixture was filtered through celite. The filtrate was added to 100 mL EtOAc for workup. The solution was washed with saturated NaCl twice. The organic layer was removed and dried with sodium sulfate. The solution was concentrated to give 500 mg of crude material. The

EXAMPLE 227

(4-{2-[(5-Chloro-3-trifluoromethyl-benzo[b]thiophene-2-sulfonyl)-propyl-amino]-1-methyl-ethoxy}-2-methyl-phenoxy)-acetic acid

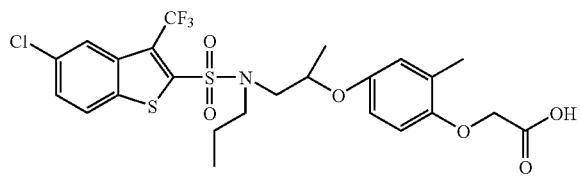

5-Chloro-3-trifluoromethyl-benzo[b]thiophene-2-sulfonic acid (2-hydroxy-propyl)-propyl-amide (0.030 g, 1 eq, 0.07 mmol) was added to 50 mL toluene. (4-Hydroxy-2-methyl-phenoxy)-acetic acid methyl ester (1 eq, 0.07 mmol), DIAD (0.014 mL, 202.21 amu, 1 eq.), PPh3 (0.07 mmol, 0.018 g, 1 eq.) were added to the solution. The reaction was stirred overnight at RT. The mixture was added to 100 mL EtOAc. The solution was washed with brine and water (100 mL each). The organics were dried with sodium sulfate and rotovaped to give 35 mg of crude material. The material was separated on a chromatotron (10-70% EtOAc/hex) to give 15 mg of material. MS [EI+] 581 (M+H)+.

EXAMPLE 228

(4-{2-[(3-Bromo-5-chloro-benzo[b]thiophene-2-sulfonyl)-propyl-amino]-ethylsulfanyl}-2-methyl-phenoxy)-acetic acid

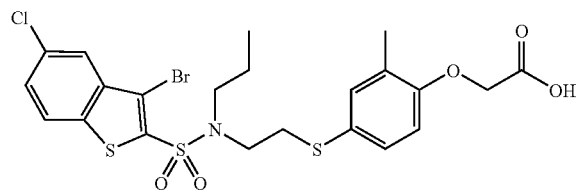

The compound of (4-{2-[(3-bromo-5-chloro-benzo[b]thiophene-2-sulfonyl)-propyl-amino]-ethylsulfanyl}-2-methyl-phenoxy)-acetic acid ethyl ester (10 mg) was dissolved in 10 mL EtOH. To the solution was added 10 mL of 5N NaOH and the reaction was stirred overnight at RT. The solution was added to 100 mL EtOAc and acidified with 20 mL of 5N HCl. The organic layer was removed, dried with magnesium sulfate, and rotovaped to give 9.2 g of material. MS [EI+] 594 (M+H)+.

EXAMPLE 229

(4-{2-[(5-Chloro-3-trifluoromethyl-benzo[b]thiophene-2-sulfonyl)-propyl-amino]-ethylsulfanyl}-2-methyl-phenoxy)-acetic acid

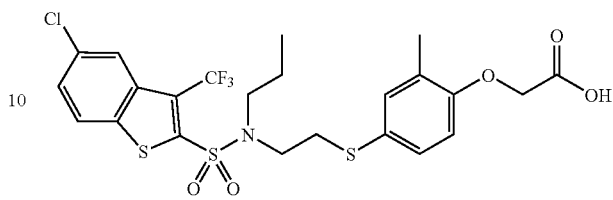

The compound of (4-{2-[(3-bromo-5-chloro-benzo[b]thiophene-2-sulfonyl)-propyl-amino]-ethylsulfanyl}-2-methyl-phenoxy)-acetic acid ethyl ester (150 mg, 0.24 mmol, 1 eq) was added to a 3-necked flask. Copper powder (2.5 eq, 0.038 g) was added along with 50 mL DMSO. To this solution was slowly bubbled trifluoromethyl iodide. The mixture was stirred overnight at 120° C. and then filtered through celite. The filtrate was added to 100 mL EtOAc for workup. The solution was washed with saturated NaCl twice. The organic layer was removed and dried with sodium sulfate. The solution was concentrated to give 100 mg of crude material. The material was added to a chromatotron and eluted with 10-70% EtOAc/hexanes. About 15 mg of material was isolated. The material was dissolved in 10 mL 5N HCl/10 mL EtOH and stirred overnight at RT. The solvent was removed and about 9.5 mg of the title compound was isolated.

MS [EI+] 583 (M+H)+.

EXAMPLE 230

(4-{2-[(5-Chloro-3-methyl-benzo[b]thiophene-2-sulfonyl)-propyl-amino]-ethylsulfanyl}-2-propyl-phenoxy)-acetic acid

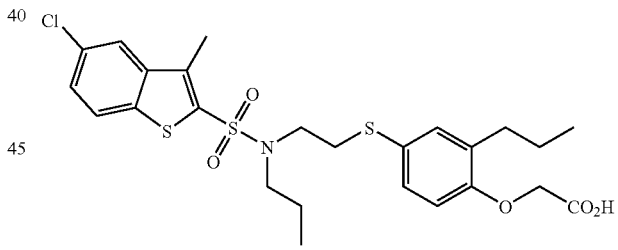

A mixture of toluene-4-sulfonic acid 2-[(5-chloro-3-methyl-benzo[b]thiophene-2-sulfonyl)-propyl-amino]-ethyl ester (200 mg, 0.40 mmol), (4-mercapto-2-propyl-phenoxy)-acetic acid ethyl ester (111 mg, 0.44 mmol) and Cs$_2$CO$_3$ (195 mg, 0.60 mmol) in 10 mL of dry DMF was heated to 45° C. for 2 h. The mixture was diluted with Et$_2$O and 1 N HCl. The organic layer was washed with 1 N HCl (3×10 mL) and brine and then dried over Na$_2$SO$_4$. Organic solvent was removed under the vacuum. Crude material was purified by chromatography (Hexanes/Acetone=12/1) to provide 141 mg of (4-{2-[(5-chloro-3-methyl-benzo[b]thiophene-2-sulfonyl)-propyl-amino]-ethylsulfanyl}-2-propyl-phenoxy)-acetic acid ethyl ester. The ethyl ester was then dissolved in 10 mL of THF/H$_2$O (1:1 by volume) with 0.8 mL of 1N aqueous LiOH. The mixture was allowed to stand at r.t. for 5 h. The mixture was diluted with Et$_2$O and 1N HCl. The organic layer was washed with 1N HCl (3×10 mL) and brine and then dried over Na$_2$SO$_4$. The organic solvent was removed under the vacuum to give 133 mg of the title compound as white solid. $^1$H NMR (400 MHz, CDCl$_3$); MS (ES$^+$) 177/mass calculated for C$_{25}$H$_{30}$ClNO$_5$S$_3$ 555, found 556 (M+1, 100%).

EXAMPLE 231

(4-{2-[(5-Chloro-3-methyl-benzo[b]thiophene-2-sulfonyl)-propyl-amino]-ethylsulfanyl}-phenoxy)-acetic acid

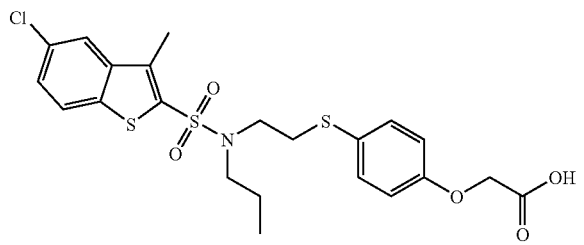

A mixture of toluene-4-sulfonic acid 2-[(5-chloro-3-methyl-benzo[b]thiophene-2-sulfonyl)-propyl-amino]-ethyl ester (116 mg, 0.23 mmol), (4-Mercapto-phenoxy)-acetic acid ethyl ester (54 mg, 0.25 mmol) and Cs$_2$CO$_3$ (112 mg, 0.35 mmol) in 10 mL of dry DMF was heated to 45° C. for 2 h. The mixture was diluted with Et$_2$O and 1N HCl. The organic layer was washed with 1N HCl (3×10 mL) and brine and then dried over Na$_2$SO$_4$. The organic solvent was removed under the vacuum. Crude material was purified by chromatography (hexanes/acetone=6/1) to provide 94 mg of (4-{2-[(5-chloro-3-methyl-benzo[b]thiophene-2-sulfonyl)-propyl-amino]-ethylsulfanyl}-phenoxy)-acetic acid ethyl ester. The ethyl ester was then dissolved in 10 mL of THF/H$_2$O (1:1 by volume) with 0.8 mL of 1N aqueous LiOH. The mixture was allowed to stand at r.t. for 5 h. The mixture was diluted with Et$_2$O and 1N HCl. The organic layer was washed with 1N HCl (3×10 mL) and brine and then dried over Na$_2$SO$_4$. The organic solvent was removed under the vacuum to give 89 mg of the title compound as white solid. $^1$H NMR (400 MHz, CDCl$_3$): MS (ES$^+$) m/z mass calculated for C$_{22}$H$_{24}$ClNO$_5$S$_3$ 513, found 514 (M+1, 100%).

EXAMPLE 232

(4-{2-[(5-Chloro-3-methyl-benzo[b]thiophene-2-sulfonyl)-propyl-amino]-ethylsulfanyl}-2-trifluoromethyl-phenoxy)-acetic acid

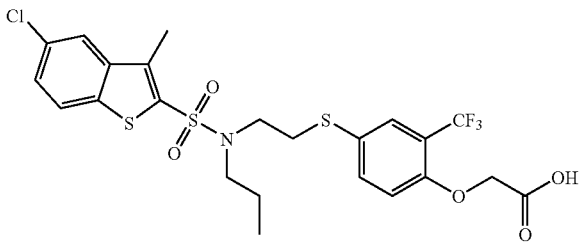

A mixture of toluene-4-sulfonic acid 2-[(5-chloro-3-methyl-benzo[b]thiophene-2-sulfonyl)-propyl-amino]-ethyl ester (361 mg, 0.72 mmol), (4-Mercapto-2-trifluoromethyl-phenoxy)-acetic acid ethyl ester (200 mg, 0.72 mmol) and Cs$_2$CO$_3$ (468 mg, 1.44 mmol) in 15 mL of dry DMF was heated to 45° C. for 4 h. The mixture was diluted with Et$_2$O and 1N HCl. The organic layer was washed with 1N HCl (3×10 mL), brine and dried over Na$_2$SO$_4$. The organic solvent was removed under the vacuum. The crude material was purified by chromatography (hexanes/acetone=7/1) to provide 355 mg of (4-{2-[(5-chloro-3-methyl-benzo[b]thiophene-2-sulfonyl)-propyl-amino]-ethylsulfanyl}-2-trifluoromethyl-phenoxy)-acetic acid ethyl ester. The ethyl ester was then dissolved in 10 mL of EtOH with 0.3 mL of 5N aqueous NaOH. The mixture was allowed to stand at r.t. for 1 h. The mixture was diluted with Et$_2$O and 1N HCl. The organic layer was washed with 1N HCl (3×100 mL) and brine and then dried over Na$_2$SO$_4$. The organic solvent was removed under the vacuum to give 388 mg of the title compound as white solid.) $^1$H NMR (400 MHz, CDCl$_3$); MS (ES$^+$) m/z mass calculated for C$_{23}$H$_{23}$ClF$_3$NO$_5$S$_3$ 581, found 582 (M+1, 100%).

EXAMPLE 233

(S)-{2-Methyl-4-[1-(4-trifluoromethyl-benzenesulfonyl)-pyrrolidin-2-ylmethylsulfanyl]-phenoxy}-acetic acid

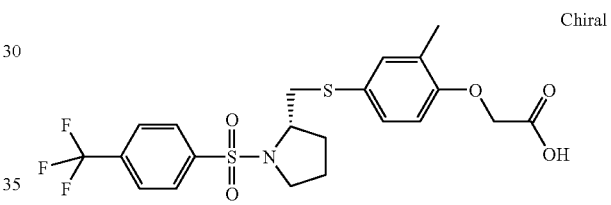

Step A

[2-Methyl-4-(pyrrolidin-2-ylmethylsulfanyl)-phenoxy]-acetic acid ethyl ester, TFA salt

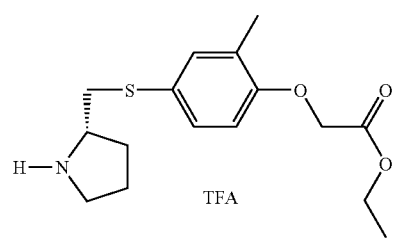

To a solution of (S)-2-hydroxymethyl-pyrrolidine-1-carboxylic acid tert-butyl ester (2.4 g, 11.9 mmol) in toluene (50 mL) were added ADDP (4.6 g, 18.2 mmol) and n-Bu3P (4.6 mL, 18.5 mmol) under nitrogen at 0~5° C., followed by the addition of (4-Mercapto-2-methyl-phenoxy)-acetic acid ethyl ester (2.6 g, 11.5 mmol). The reaction mixture was allowed to warm to room temperature and stirred overnight. The mixture was loaded on silica gel column and eluted with hexanes and ethyl acetate giving (s)-2-(4-ethoxycarbonylmethoxy-3-methyl-phenylsulfanylmethyl)-pyrrolidine-1-carboxylic acid tert-butyl ester (4.33 g, 88.7%). The product was taken into methylene chloride (30 mL, treated with trifluoroacetic acid (5 mL) at 0~5° C. and stirred for 2 h. Concentration of the mixture gives the title compound that was used for next step without further purification.

Step B (S)-{2-Methyl-4-[1-(4-trifluoromethyl-benzenesulfonyl)-pyrrolidin-2-ylmethylsulfanyl]-phenoxy}-acetic acid

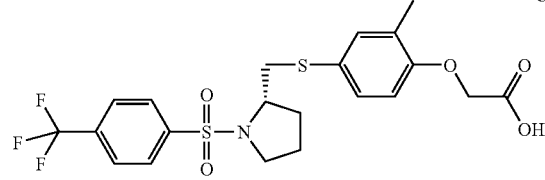

To a solution of [2-methyl-4-(pyrrolidin-2-ylmethylsulfanyl)-phenoxy]-acetic acid ethyl ester, TFA salt (210 mg, 05 mmol) in methylene chloride (5 mL) was added triethyl amine (1 mL) and 4-trifluoromethyl-benzenesulfonyl chloride (122 mg, 0.5 mmol) at 0~5° C. After stirred for 2 h, the mixture was concentrated and the residue was treated with NaOH (5N, 1 mL) in ethanol (1 mL) for 2 h. The mixture was concentrated and acidified with 5 N HCl (1 mL) and extracted with ethyl acetate. The extracts were dried and concentrated, and the crude product was purified by reversed phase HPLC (water-acetonitrile-0.1% TFA) giving the title compound. MS (ES): 490.2 (M$^+$+1).

The following Examples 234 to 239 were prepared by following the procedure as described in Example 233.

EXAMPLE 234

(s)-{4-[1-(5-Chloro-3-methyl-benzo[b]thiophene-2-sulfonyl)-pyrrolidin-2-ylmethylsulfanyl]-2-methyl-phenoxy}-acetic acid

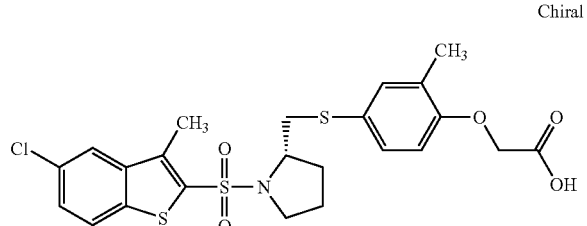

MS (ES): 528.2 ($^{37}$Cl, M$^+$+1), 526.2 ($^{35}$Cl, M$^+$+1).

EXAMPLE 235

(R)-{2-Methyl-4-[1-(4-trifluoromethyl-benzenesulfonyl)-pyrrolidin-2-ylmethylsulfanyl]-phenoxy}-acetic acid

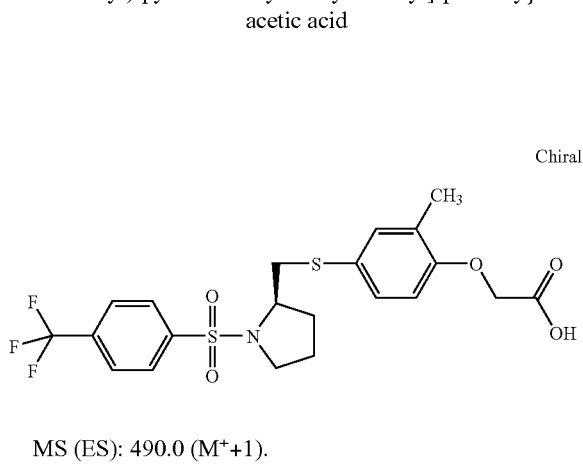

MS (ES): 490.0 (M$^+$+1).

EXAMPLE 236

(s{4-[1-(5-Bromo-6-ethoxy-pyridine-3-sulfonyl)-pyrrolidin-2-ylmethylsulfanyl]-2-methyl-phenoxy}-acetic acid

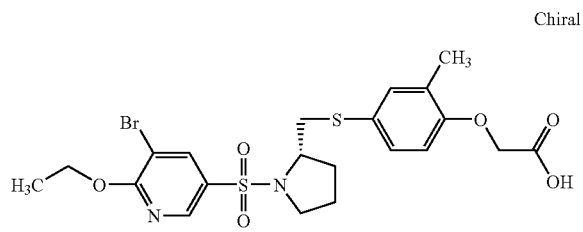

MS (ES): 545.4 ($^{79}$Br, M$^+$+1), 547.2 ($^{81}$Br, M$^+$+1)

EXAMPLE 237

(R)-{4-[1-(5-Bromo-6-ethoxy-pyridine-3-sulfonyl)-pyrrolidin-2-ylmethylsulfanyl]-2-methyl-phenoxy}-acetic acid

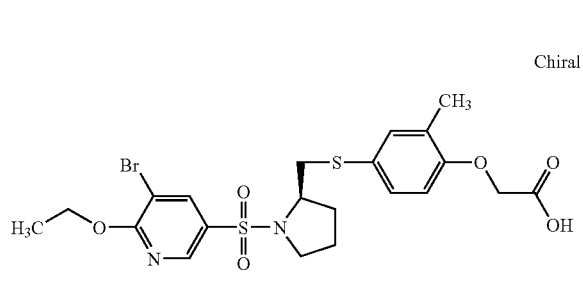

MS (ES): 545.4 ($^{79}$Br, M$^+$1), 547.2 ($^{81}$Br, M$^+$+1).

EXAMPLE 238

(S)-{2-Methyl-4-[1-(4-trifluoromethoxy-benzene-sulfonyl)-pyrrolidin-2-ylmethylsulfanyl]-phenoxy}-acetic acid

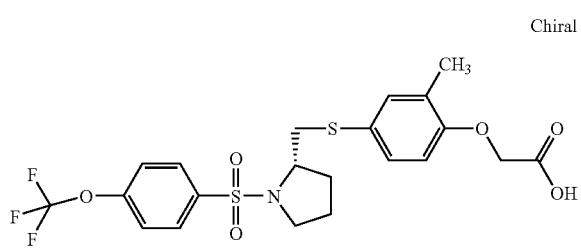

MS (ES): 506.3 (M$^+$+1).

EXAMPLE 239

(R)-{2-Methyl 4-[1-(4-trifluoromethoxy-benzene-sulfonyl)-pyrrolidin-2-ylmethylsulfanyl]-phenoxy}-acetic acid

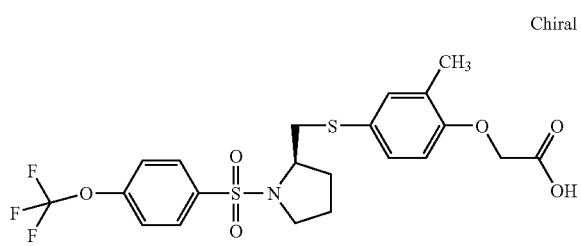

MS (ES): 506.3 (M$^+$+1).

EXAMPLE 240

(3-Chloro-4-{2-[(5-chloro-3-methyl-benzo[b]thiophene-2-sulfonyl)-propyl-amino]-ethylsulfanyl}-phenyl)-acetic acid

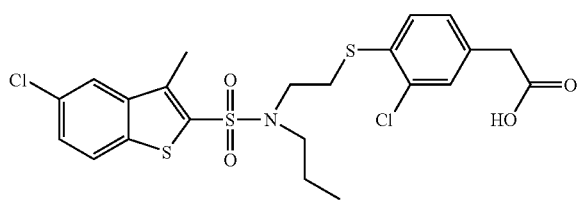

Step A

5-Chloro-3-methyl-benzo[b]thiophene-2-sulfonic acid (2-hydroxy-ethyl)-propyl-amide To a solution of 2-propylamino-ethanol (0.35 g, 3.44 mmol) in methylene chloride (34 mL) was added triethyl amine (7.2 mL) and 5-chloro-3-methyl-benzo[b]thiophene-2-sulfonyl chloride (0.97 mg. 3.44 mmol) at 0~5° C. After stirring for 2 h, the reaction mixture was concentrated and the residue was purified by column chromatography on silica gel (1.0 g).

Step B (3-Chloro-4-{2-[(5-chloro-3-methyl-benzo[b]thiophene-2-sulfonyl)-propyl-amino]-ethylsulfanyl}-phenyl)-acetic acid To a solution of 5-chloro-3-methyl-benzo[b]thiophene-2-sulfonic acid (2-hydroxy-ethyl)-propyl-amide (180 mg, 0.5 mmol) in toluene (4 mL) were added ADDP (240 mg, 1 mmol) and n-Bu3P (0.24 mL, 1 mmol) under nitrogen at 0~5° C. Then (3-chloro-4-mercapto-phenyl)-acetic acid (110 mg, 0.5 mmol) was added. The mixture was warmed to room temperature and stirred overnight. The mixture was loaded on silica gel column and eluted with hexanes and ethyl acetate giving (3-chloro-4-{2-[(5-chloro-3-methyl-benzo[b]thiophene-2-sulfonyl)-propyl-amino]-ethylsulfanyl}-phenyl)-acetic acid methyl ester (310 mg). The compound was then treated with NaOH (5N, 1 mL) in ethanol (1 mL) for 2 h at 50° C. The mixture was concentrated and acidified with 5 N HCl (1 mL) and extracted with ethyl acetate. The extracts were dried and concentrated, and the crude product was purified by reversed phase HPLC (water-acetonitrile-0.1% TFA) giving the title compound. MS (ES): 532.2(M$^+$+1).

The following Examples 241 to 243 were prepared according to a procedure described in Example 240.

EXAMPLE 241

(4-{2-[(5-Bromo-6-ethoxy-pyridine-3-sulfonyl)-propyl-amino]-ethylsulfanyl}-3-chloro-phenyl)-acetic acid

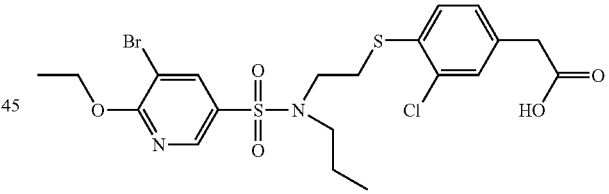

MS (ES): 551.2 (M$^+$+1).

EXAMPLE 242

(4-{2-[(5-Bromo-6-ethoxy-pyridine-3-sulfonyl)-propyl-amino]-ethylsulfanyl}-2-methyl phenoxy)-acetic acid

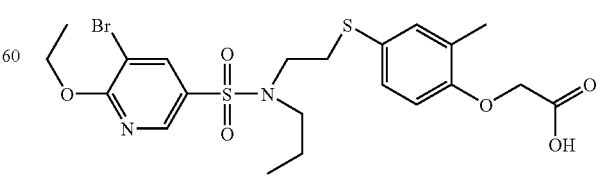

MS (ES): 547.3 (M$^+$+1).

EXAMPLE 243

(4-{2-[(5-Bromo-6-chloro-pyridine-3-sulfonyl)-propyl-amino]-ethylsulfanyl}-2-methyl-phenoxy)-acetic acid

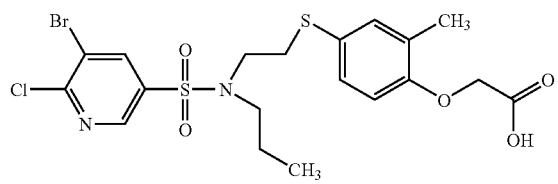

MS (ES): 537.1 (M$^+$+1).

EXAMPLE 244

[3-Chloro-4-(1-{[propyl-(4-trifluoromethoxybenzenesulfonyl)amino]-methyl}-propylsulfanyl)-phenyl]acetic acid

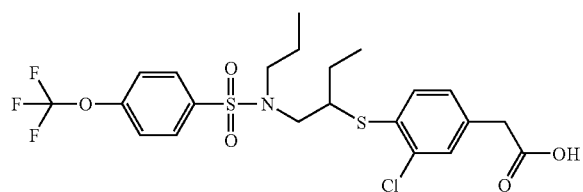

To a solution of (3-chloro-4-mercaptophenyl)acetic acid methyl ester (110 mg. 0.51 mmol) in DMF (3 mL) was added K$_2$CO$_3$ (104 mg, 0.75 mmol), followed by the addition of N-2-bromo-butyl)-N-propyl-4-trifluoromethoxy-benzenesulfonamide (217 mg 0.5 mmol) in DMF (2 mL). After the mixture was stirred overnight, NaOH (5 N, 2 mL) and ethanol (1 mL) were added, and then healed at 60° C. for 2 h. The mixture was concentrated, acidified by 5N HCl (2 mL), extracted with ethyl acetate, dried and concentrated. Reversed phase HPLC purification (water-acetonitrile-0.1% TFA) afforded the title compound. MS (ES): 540.3 (M$^+$+1).

EXAMPLE 245

(R)-(3-Chloro-4-{2-[(5-chloro-3-methyl-benzo[b]thiophene-2-sulfonyl)-propyl-amino]-1-methyl-ethylsulfanyl}-phenyl)-acetic acid Chiral

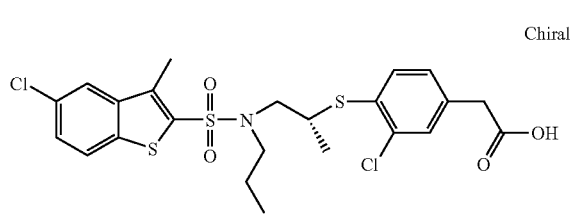

To a solution of (3-chloro-4-mercapto-phenyl)-acetic acid methyl ester (240 mg, 1.11 mmol) in DMF (6 mL) was added K$_2$CO$_3$ (240 mg, 1.7 mmol), followed by the addition of methanesulfonic acid 2-[(5-chloro-3-methyl-benzo[b]thiophene-2-sulfonyl)-propyl-amino]-1-methyl-ethyl ester (442 mg, 1 mmol) in DMF (4 mL). After stirring at room temperature over a week, the mixture was diluted with ethyl acetate, washed with water, dried and concentrated. Column chromatography on silica gel afforded (R)-(3-chloro-4-{2-[(5-chloro-3-methyl-benzo[b]thiophene-2-sulfonyl)-propyl-amino]-1-methyl-ethylsulfanyl}-phenyl)-acetic acid methyl ester. This product was treated with NaOH (5 N. 1 mL) in ethanol (1 mL) at 60° C. for 2 h. The mixture was then concentrated, acidified by 5N HCl (2 mL), extracted with ethyl acetate, dried and concentrated. Reversed phase HPLC purification (water-acetonitrile-0.1% TFA) gave the title compound (90 mg). MS (ES): 547.3 (M$^+$–1).

The following Examples 246 to 249 were prepared by following the procedure as described in Example 245.

EXAMPLE 246

(2-Methyl-4-{2-[(naphthalene-2-sulfonyl)-propyl-amino]-ethylsulfanyl}-phenoxy)-acetic acid

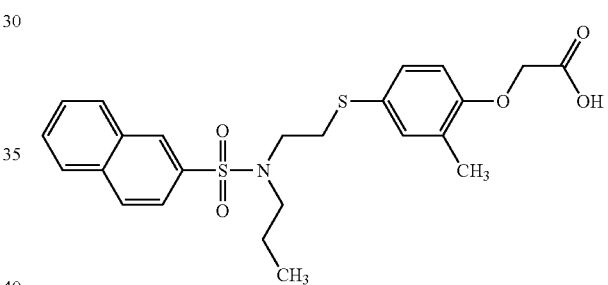

MS (ES): 472.1 (M$^+$–1).

EXAMPLE 247

(4-{2-[(5-Fluoro-3-methyl-benzo[b]thiophene-2-sulfonyl)-propyl-amino]-ethylsulfanyl}-2-methyl-phenoxy)-acetic acid

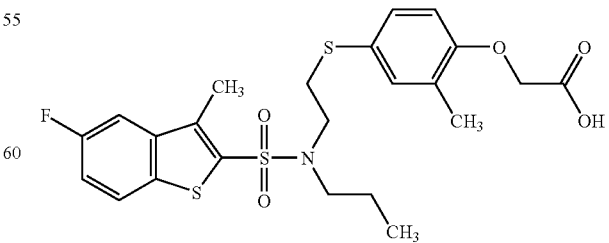

MS (ES): 510.1(M$^+$–1).

EXAMPLE 248

(4-{2-[(6-Fluoro-3-methyl-benzo[b]thiophene-2-sulfonyl)-propyl-amino]-ethanesulfinyl}-2-methyl-phenoxy)-acetic acid

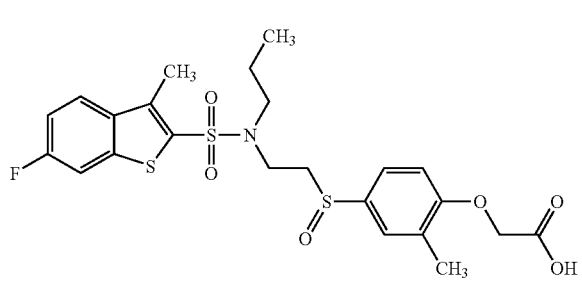

MS (ES): 526.06(M$^+$−1).

EXAMPLE 249

(5-{2-[(Naphthalene-2-sulfonyl)-propyl-amino]-ethoxy}-indol-1-yl)-acetic acid

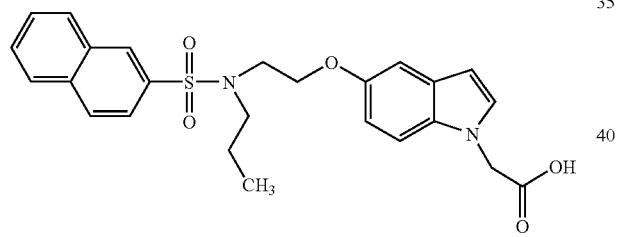

MS (ES): 465.0(M$^+$−1).

EXAMPLE 250

[4-(1-{[(5-Chloro-3-methyl-benzo[b]thiophene-2-sulfonyl)-propyl-amino]-methyl}-propylsulfanyl)-2-methyl-phenoxy]-acetic acid

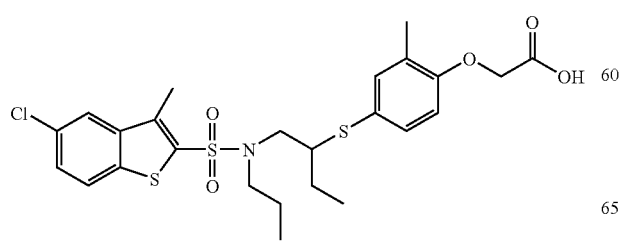

Step A

5-Chloro-3-methyl-benzo[b]thiophene-2-sulfonyl chloride

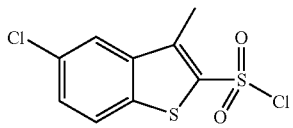

Chlorosulphonic acid (21.8 mL, 0.328 mol) was added via syringe to 0° C. dichloroethane (118 mL). The compound of 5-chloro-3-methylbenzothiophene (20.0 g, 0.109 mol) in dichloroethane (32 mL) was added dropwise to the solution. The resulting cranberry-colored solution thickened to a slurry and was stirred at room temperature. After 2 h, the reaction slurry was poured over an ice/water bath. The resulting precipitate was washed with copious amounts of water and dried overnight in a vacuum oven to provide 26.0 g (84%) of the title compound. $^1$H NMR (400 MHz. CDCl$_3$) δ 7.88 (d, 1H, J=8.6 Hz), 7.75 (d, 1H, J=2.0 Hz), 7.35 (dd, 1H, J=8.6 Hz, 2.0 Hz), 2.45 (s, 3H). R$_f$=0.53 in 33% acetone in hexanes.

Step B

5-Chloro-3-methyl-benzo[b]thiophene-2-sulfonic acid (2-hydroxy-butyl)-amide

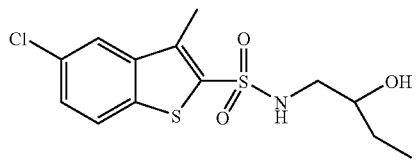

Dropwise, add 5-chloro-3-methyl-benzo[b]thiophene-2-sulfonyl chloride (2.03 g, 7.22 mmol) in dichloromethane (20 mL) to a 0° C. solution of 1-amino-2-butanol (0.8 mL, 9.94 mmol) and triethylamine (2.0 mL, 14.4 mmol) in dichloromethane (80 mL). The resulting solution was stirred at ambient temperature for 1 h, then diluted with dichloromethane and washed with water. The organic layer was dried over Na$_2$SO$_4$ and concentrated in vacuo to provide a quantitative yield of the title compound. $^1$H NMR (400 MHz, CDCl$_3$) δ 7.79 (d, 1H, J=8.0 Hz), 7.45 (dd, 1H, J=8.0 Hz, 1.8 Hz), 3.69-3.64 (m, 1H), 3.24 (dd, 1H, J=13.3 Hz, 3.1 Hz), 3.92 (dd, 1H, J=13.3 Hz, 8.0 Hz), 2.66 (s, 3H), 1.53-1.41 (m, 2H), 0.91 (t, 3H, J=7.1 Hz). MS (EI+) 334 (M+H)$^+$. R$_f$=0.52 in 50% acetone in hexanes.

Step C

5-Chloro-3-methyl-benzo[b]thiophene-2-sulfonic acid (2-hydroxy-butyl)-propyl-amide

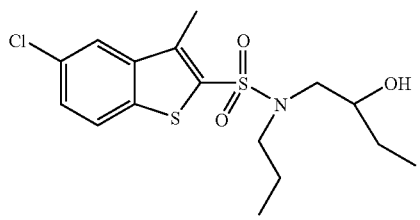

A solution of 5-chloro-3-methyl-benzo[b]thiophene-2-sulfonic acid (2-hydroxy-butyl)-amide (2.41 g. 7.22 mmol) and 1-iodopropane (0.92 mL, 9.38 mmol) in dimethylformamide (120 mL) was treated with cesium carbonate (3.06 g, 9.38 mmol). The resulting mixture was healed to 50° C. under N, until all of the 5-chloro-3-methyl-benzo[b]thiophene-2-sulfonic acid (2-hydroxy-butyl)-amide was consumed. The reaction mixture was cooled to ambient temperature, and diluted with diethyl ether. The organic layer was washed with 1N HCl and water, dried over $Na_2SO_4$, and concentrated in vacuo. The crude material was purified by flash chromatography, using 20% acetone in hexanes as eluent to provide 2.43 g (90%) of the title compound. $^1$H NMR (400 MHz, $CDCl_3$) δ 7.79 (d, 1 h, J=2.3 Hz), 7.74 (d, 1H, J=8.7 Hz), 7.46 (dd, 1H J=8.7 Hz, 2.3 Hz), 3.83-3.76 (m, 1H), 3.35-3.16 (m, 4H), 2.69 (s, 3H), 2.33 (d, 1H, J=3.6 Hz), 1.67-1.57 (m, 2H), 1.53-1.42 (m, 2H), 0.98 (t, 3H, J=7.3 Hz), 0.82 (t, 3H, J=7.3 Hz). MS [EI+] 376 (M+H)$^+$. $R_f$=0.23 in 20% acetone in hexanes.

Step D

5-Chloro-3-methyl-benzo[b]thiophene-2-sulfonic acid (2-bromo-butyl)-propyl-amide

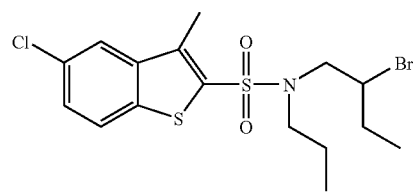

A solution of 5-chloro-3-methyl-benzo[b]thiophene-2-sulfonic acid (2-hydroxy-butyl)-propyl-amide (3.34 g, 8.88 mmol) and carbon tetrabromide (4.42 g, 13.33 mmol) in dichloromethane (60 mL) was treated with triphenylphosphine (3.50 g, 13.33 mmol). The resulting mixture was stirred at ambient temperature overnight, and then concentrated in vacuo. The residue was diluted with diethyl ether and filtered. The filtrate was adsorbed onto silica gel and purified by flash chromatography, using 10% acetone in hexanes as eluent, to provide 2.34 g (60%) of the title compound. $^1$ H NMR (400 MHz, $CDCl_3$) δ 7.79 (d, 1H, J=1.9 Hz), 7.74 (d, 1H, J=8.6 Hz), 7.45 (d, 1H, J=8.6 Hz. 1.9 Hz), 4.17-4.10 (m, 1H), 3.73, 3.47 ($AB_q$, 1H, J=7.2 Hz), 3.69, 3.51 ($AB_q$, 1H, J=7.2 Hz), 3.37-3.30 (m, 1H), 3.23-3.15 (m, 1H), 2.68 (s, 3H), 2.13-2.08 (m, 1H), 1.78-1.51 (m, 3H), 1.08 (t, 3H, J=7.2 Hz), 0.87 (t, 3H, J=7.2 Hz).

Step E

[4-(1-{[(5-Chloro-3-methyl-benzo[b]thiophene-2-sulfonyl)-propyl-amino]-methyl}-propylsulfanyl)-2-methyl-phenoxy]-acetic acid ethyl ester

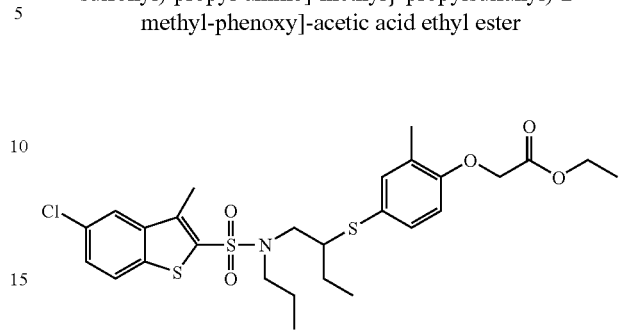

A 0° C. suspension of sodium hydride (0.17 g 4.29 mmol and (4-Mercapto-2-methyl-phenoxy)-acetic acid ethyl ester (0.97 g, 4.29 mmol) in dry DMF (26 mL) was treated with a solution of 5-chloro-3-methyl-benzo[b]thiophene-2-sulfonic acid (2-bromo-butyl)-propyl-amide (1.31 g, 2.98 mmol) in DMF (6 mL). The resulting solution was stirred at ambient temperature for 5 h, and then quenched with 1N HCl (49 mL). The reaction mixture was diluted with diethyl ether and washed with water. The organic layer was dried over sodium sulphate and adsorbed onto silica gel. The crude material was purified by flash chromatography, using 14% ethyl acetate in hexanes, to obtain 0.68 g (39%) of the title compound. $R_f$=0.18 in 20% acetone in hexanes. $^1$H NMR (400 MHz, $CDCl_3$) δ 7.77 (d, 1H, J=2.2 Hz), 7.73 (d, 1H, J=8.6 Hz), 7.44 (dd, 1H, J=8.6 Hz, 2.2 Hz), 7.22 (d, 1H J=1.4 Hz), 7.18 (dd, 1H, J=8.6 Hz, 2.9 Hz), 6.59 (d, 1H, J=8.6 Hz), 4.62 (s, 2H), 4.26 (q, 2H, J=7.2 Hz), 3.38 (dd, 1H, J=14.4 Hz, 9.4 Hz), 3.24 (dd, 1H, J=14.4 Hz, 5.8 Hz), 3.20-3.06 (m, 3H), 2.56 (s, 3H), 2.24 (s, 3H), 1.97-1.87 (m, 1H), 1.52-1.35 (m, 3H), 1.29 (t, 3H, J=7.2 Hz), 1.29 (t, 3H, J=7.2 Hz), 1.09 (t, 3H, J=7.2 Hz), 0.81 (t, 3H, J=7.2 Hz).

Step F

[4-(1-{[(5-Chloro-3-methyl-benzo[b]thiophene-2-sulfonyl)-propyl-amino]-methyl}-propylsulfanyl)-2-methyl-phenoxy]-acetic acid A solution of [4-(1-{[(5-chloro-3-methyl-benzo[b]thiophene-2-sulfonyl)-propyl-amino]-methyl}-propylsulfanyl)-2-methyl-phenoxy]-acetic acid ethyl ester (0.68 g, 1.16 mmol) and 5N NaOH (0.7 mL) in a solution of dioxane (1 mL) and ethanol (8 mL) was stirred at ambient temperature under nitrogen for 2 h, and then concentrated in vacuo. The residue was diluted with 1N HCl, extracted with $CH_2Cl_2$, dried over $Na_2SO_4$, and concentrated in vacuo to provide 0.60 g (93%) of the title compound. $^1$H NMR (400 MHz, $CDCl_3$) δ 7.74 (s, 1H), 7.71 (d, 1H, J=8.8 Hz. 1.5 Hz), 7.42 (d, 1H, J=8.8 Hz), 7.22 (s, 1H), 7.19 (d, 1H, J=8.8 Hz), 6.61 (d, 1H, J=8.8 Hz), 5.29 (d, 1H, J=2.2 Hz), 4.68 (s, 2H), 3.39 (dd, 1H, J=13.9 Hz, 8.8 Hz), 3.25 (dd, 1H, J=15.4 Hz, 4.4 Hz), 3.20-3.07 (m, 3H), 2.57 (s, 3H), 2.22 (s, 3H), 1.96-1.86 (m, 1H), 1.53-1.35 (m, 3H), 1.09 (t, 3H, J=7.3 Hz), 0.81 (t, 3H, J=7.3 Hz). MS (ES$^-$) m/z mass calculated for $C_{21}H_{30}O_5NS_3Cl$ 555, found 554 (M−1) and 556 (M+1).

EXAMPLE 251

[4-(1-{[(5-Chloro-3-methyl-benzo[b]thiophene-2-sulfonyl)-propyl-amino]-methyl}-propylsulfanyl)-2-methyl-phenoxy]-acetic acid

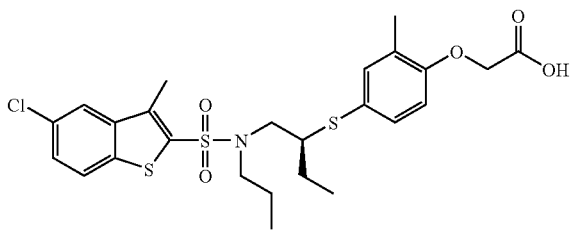

The compound of [4-(1-{[(5-Chloro-3-methyl-benzo[b]thiophene-2-sulfonyl)-propyl-amino]-methyl}-propylsulfanyl)-2-methyl-phenoxy]-acetic acid was resolved using chiral HPLC (Chiral Pak AD 4.6×250 mm, 90/10 heptane/3A EtOH, 1 ml/min, 240 nm UV setting) to give enantiomers of isomer 1 (0.301 g, isomer 1, 100% ee) and isomer 2 (0.297 g, isomer 2, 97.5% ee). $^1$H NMR (400 MHz, CDCl$_3$) δ 7.74 (s, 1H), 7.71 (d, 1H, J=8.8 Hz, 1.5 Hz), 7.42 (d, 1H, J=8.8 Hz), 7.22 (s, 1H), 7.19 (d, 1H, J=8.8 Hz), 6.61 (d, 1H, J=8.8 Hz), 5.29 (d, 1H, J=2.2 Hz), 4.68 (s, 2H), 3.39 (dd, 1H, J=13.9 Hz, 8.8 Hz), 3.25 (dd, 1H, J=15.4 Hz, 4.4 Hz), 3.20-3.07 (m, 3H), 2.57 (s, 3H), 2.22 (s, 3H), 1.96-1.86 (m, 1H), 1.53-1.35 (m, 3H), 1.09 (t, 3H, J=7.3 Hz), 0.81 (t, 3H, J=7.3 Hz).

EXAMPLE 252

No Example with Example Number 252

Standard synthesis procedures were used in preparing many of the exemplified compounds or intermediates of the present invention. These standard procedures are described below:

EXAMPLE 253

Standard Procedure (A): A mixture of 0.35 mmol sulfonyl chloride, 0.3 mmol 2-methyl-2-[4-(3-propyl amino-propyl)-phenoxy]-propionic acid ethyl ester in 1 mL CH$_2$Cl$_2$ and 200 μL triethyl amine were placed in a 1 dram screw cap vial. The mixture was shaken for 18 h at an ambient temperature. The solvent was removed from the vial by evaporation, and the residue was dissolved in 1 mL ethanol and then 250 μL 5N NaOH was added. The mixture was heated at 50° C. for 1 h, which was then cooled and acidified with 350 μL 5N HCl. The crude reaction was poured onto a Varian ChemElut 1003 cartridge and eluted with 10 mL CH$_2$Cl$_2$. After evaporation, the crude compound was purified using mass-guided reverse phase HPLC.

EXAMPLE 254

Standard Procedure (B): A solution of 0.265 mmol sulfonamide (see Standard Procedure (F)) in ethanol (1 mL) and 0.22 mmol tosylate derivative (e.g. 2-methyl-2-{4-[3-(toluene-4-sulfonyloxy)-propyl]-phenoxy}-propionic acid ethyl ester or 2-methyl-2-{3-[3-(toluene-4-sulfonyloxy)-propyl]-phenoxy}-propionic acid ethyl ester) in ethanol (1 mL) with approximately 50 mg potassium carbonate, were placed in a 1 dram vial and sealed. The mixture was heated at 75° C. for 48 h, which was then cooled and filtered through a plug of cotton. The filtrate was charged with 0.5 mL 5N NaOH and warmed at 60° C. for 2 h. After acidification with 0.7 mL 5N HCl, the crude reaction was poured onto a Varian ChemElut 1003 cartridge and eluted with 10 mL CH$_2$Cl$_2$. After evaporation, the crude compound was purified using mass guided reverse-phase HPLC.

EXAMPLE 255

Standard Procedure (C): Into a 1 dram vial was placed a solution of 0.265 mmol sulfonamide (see Standard Procedure (F)), 0.22 mmol of the appropriate bromoethyl derivative (e.g. 2-[4-(2-bromo-ethoxy)-phenoxy]-2-methyl-propionic acid ethyl ester), ethanol (1 mL), and polystyrene bound 1,5,7-triazabicyclo[4.4.0]dec-5-ene (200 mg, 2.6 mmol/g). The vial was tightly closed and heated in a block heater for 24-48 hours at 55° C. The reaction was filtered through a plug of cotton. The filtrate was charged with 0.5 mL 5N NaOH and warmed at 60° C. for 2 h. After acidification with 0.7 mL 5N HCl, the crude reaction was poured onto a Varian ChemElut 1003 cartridge and eluted with 10 mL CH$_2$Cl$_2$. After evaporation, the crude compound was purified using mass-guided reverse phase HPLC.

EXAMPLE 256

Standard Procedure (D): Into a 1 dram vial was placed 0.1 mmol of the appropriate aryl bromide derivative (e.g. 2-(4-{3-[(3-bromo-benzenesulfonyl)-propyl-amino]-propyl}-phenoxy)-2-methyl-propionic acid ethyl ester or 2-(4-{3-[(2-bromo-benzenesulfonyl)-propyl-amino]-propyl}-phenoxy)-2-methyl-propionic acid ethyl ester), 0.13 mmol of a boronic acid, 15 mg cesium fluoride, and dioxane (1 mL). About 100 mg of PdCl$_2$(dppf) was added, and the vials were sealed. The reactions were heated at 85° C. for 18 h, which were then filtered and concentrated. The residue was dissolved in 0.8 mL ethanol, and 0.5 mL 5N NaOH were added, which was then warmed at 60° C. for 2 h. After acidification with 0.7 mL 5N HCl, the crude reaction was poured onto Varian ChemElut 1003 cartridge and eluted with 10 mL CH$_2$Cl$_2$. After evaporation, the crude compound was purified using mass guided reverse-phase HPLC.

EXAMPLE 257

Standard Procedure (E): General Sulfonyl Chloride Preparation

The following procedure, adopted from S. L. Graham et. al, *J. Med. Chem.*, 2548-2554 (1989), was used to prepare sulfonyl chlorides that were not commercially available. A solution of 3-methylbenzothiophene (Lancaster) (4.35 g, 29.3 mmol) in THF (80 mL) was cooled to 0° C. and n-BuLi (1.6M in hexanes, 21 mL, 33 mmol) was added slowly. The mixture was stirred for 15 min, and sulfuryl chloride (4.8 g, 36 mmol) was added slowly while maintaining the temperature at 0° C. The mixture was warmed to ambient temperature and then shaken with ethyl acetate/water. The 3-methyl-benzo[b]thiophene-2-sulfonyl chloride was purified using a flash chromatography (hexane, then 5% EtOAc/hexane) to give 1.63 g (23%) product as a light yellow solid.

An alternate procedure was used to prepare some of the sulfonyl chlorides that were not commercially available.

5-Chloro-3-methyl-benzo[b]thiophene-2-sulfonyl chloride

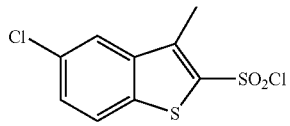

A solution of chlorosulfonic acid (5.5 mL, 82.7 mmol, 3 eq.) in 1,2-dichloroethane (30 mL) at 0° C. was treated dropwise over 10 min with a solution of 5-chloro-3-methyl-benzo[b]thiophene (5 g, 27.37 mmol, 1 eq.) in 1,2-dichloroethane (10 mL) while keeping the temperature at 0 to 5° C. Some solids were formed during the addition. After the addition, the purple mixture was stirred for 1 h without the cooling bath and monitored by TLC. The mixture was transferred with $CH_2Cl_2$ and added cautiously to 100 g of ice water with stirring. The mixture was extracted with $CH_2Cl_2$ (3×100 mL). The cloudy extract was diluted with 100 mL of MTBE until clear. The dried ($Na_2SO_4$) solution was concentrated to afford about 6 g (78%) of the sulfonyl chloride as an off-white solid. $R_f$=0.45 (9.5:0.5 hexane/EtOAc). $^1$H NMR (300 MHz, $CDCl_3$) δ 2.80 (s, 3H), 7.56 (dd, 1H, J=2.1 Hz, 8.7 Hz), 7.80 (d, 1H, J=8.7 Hz), 7.90 (d, 1H, J=2.1 Hz).

EXAMPLE 258

Standard Procedure (F): General sulfonamide preparation Naphthalene-2-sulfonic acid propylamide

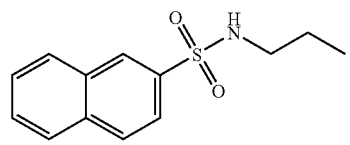

A mixture of propylamine (19 mL, 233 mmol), pyridine (19 mL, 233 mmol) and 2-naphthalenesulfonyl chloride (10.6 g, 46.8 mmol) in THF (140 mL) was stirred overnight. The mixture was quenched with water, and the THF was removed under reduced pressure. The residue was shaken with ethyl acetate/water. After drying ($MgSO_4$) the organic layer and concentration, a white solid was obtained. Trituration with hexane gave about 6.31 g (72%) white crystals (mp 76° C.).

The following compounds were prepared using the standard procedure as described above:
Naphthalene-2-sulfonic acid isopropylamide; mp 115.8° C.
Naphthalene-2-sulfonic acid cyclopropylamide; mp 99.9° C.
Naphthalene-2-sulfonic acid methylamide; mp 109° C.
Naphthalene-2-sulfonic acid ethylamide; mp 84.4° C.
Naphthalene-2-sulfonic acid butylamide; mp 63.6° C.
Naphthalene-2-sulfonic acid pentylamide; mp 72.6° C.
Naphthalene-2-sulfonic acid benzylamide; mp 122.7° C.
Naphthalene-2-sulfonic acid (2,2,2-trifluoro-ethyl)-amide; mp 187.9° C.
Naphthalene-2-sulfonic acid isobutylamide; mp 118.3° C.
Naphthalene-2-sulfonic acid sec-butylamide; mp 122.8° C.
5-Chloro-3-methyl-benzo[b]thiophene-2-sulfonic acid (2,2,2-trifluoro-ethyl)-amide; mp 180.1° C.

EXAMPLE 259

Standard Synthesis of Fibrate Portion (G)

2-[4-(3-Hydroxypropyl)phenoxy]-2-methylpropanoic acid ethyl ester

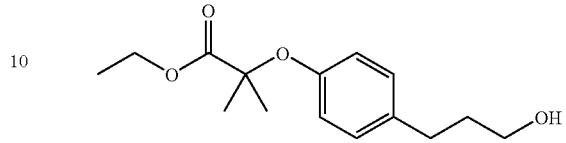

A mixture of 3-(4-hydroxyphenyl)-1-propanol (20 g, 131.4 mmol, 1 eq.), potassium carbonate (33 g, 238.8 mmol, 1.8 eq.), and magnesium sulfate (13 g) in ethanol (260 mL) was heated to 40° C. while stirring under nitrogen. Ethyl bromoisobutyrate (46 mL, 313.4 mmol, 2.4 eq.) was added. The mixture was heated to 80-81° C. for 14 h. An aliquot of the mixture was periodically filtered and concentrated for HPLC (0.05% TFA, MeCN, 230 nm, 1 ml/min, Hitachi L7100). After 14 hrs, 0.61% of the starting phenol was remained. Upon cooling to room temperature, inorganic salts were removed by filtration and rinsed three times with a total of 100 mL ethanol. The filtrate was diluted with 1:1 MTBE/heptane (300 mL) and washed with water (400 mL). The aqueous layer was extracted with 1:1 MTBE/heptane (150 mL). The combined organic solution was washed three times with saturated aqueous $NaHCO_3$ (300 mL) and once with brine (300 mL). The solution was dried ($Na_2SO_4$) and concentrated at a reduced pressure to afford about 32.5 g (95%) of yellow oil. $R_f$=0.45 (3:2 hexane/EtOAc). $^1$H NMR (300 MHz, $CDCl_3$) δ 1.25 (t, 3H, J=7.2 Hz), 1.44 (br s, 1H), 1.58 (s, 6H), 1.84 (m, 2H), 2.63 (t, 2H, J=7.8 Hz), 3.65 (t, 2H, J=6.3 Hz), 4.23 (q, 2H, J=7.2 Hz), 6.76 (m, 2H), 7.04 (m, 2H).

EXAMPLE 260

Standard Procedure (H): Bromoethyloxyfibrate Preparation

2-[4-(2-Bromo-ethoxy)-3-propyl-phenoxy]-2-methyl-propionic acid ethyl ester

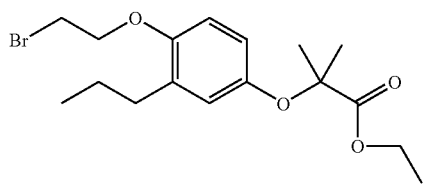

A mixture of 2-(4-hydroxy-3-propyl-phenoxy)-2-methyl-propionic acid ethyl ester (13.4 g, 50.3 mmol), $Na_2SO_4$ (7 g), $K_2CO_3$ (9.3 g, 67 mmol), 1,2-dibromoethane (65 mL, 750 mmol), and ethanol (200 mL) was refluxed for 48 h. The cooled reaction was filtered, and the solvent was removed. The residue was purified by short path filtration through 200 g silica gel using 10% ethyl acetate/hexane to give 10.2 g (54%) title compound as a pale tan oil. $^1$H NMR ($CDCl_3$) δ 0.93 (t, 3H), 1.30 (t, 3H), 1.56 (s, 6H), 1.61 (m, 2H), 2.57 (t, 2H), 3.65 (t, 3H), 4.23 (t, 2H), 4.27 (q, 2H), 6.67 (m, 2H), 6.74 (m, 1H). MS [EI+] 375 (M+H).

Using the standard procedure as described above, the following compounds were prepared:

2-[4-(2-Bromo-ethoxy)-phenoxy]-2-methyl-propionic acid ethyl ester

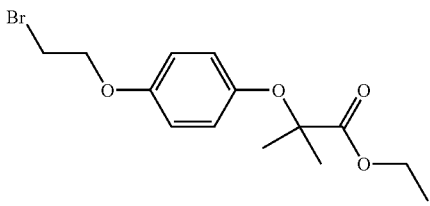

2-[4-(2-Bromo-ethoxy)-2-propyl-phenoxy]-2-methyl-propionic acid ethyl ester

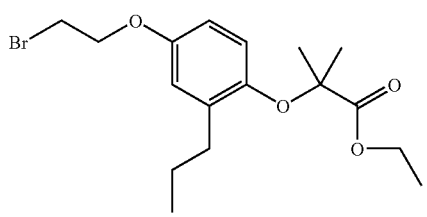

2-[3-(2-Bromo-ethoxy)-phenoxy]-2-methyl-propionic acid ethyl ester

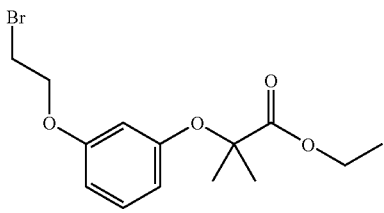

EXAMPLE 261

Standard Procedure (I): Tosylate Preparation

2-Methyl-2-[4-[3-[(methylphenyl)sulfonyl]oxyl propyl]phenoxy]propanoic acid ethyl ester

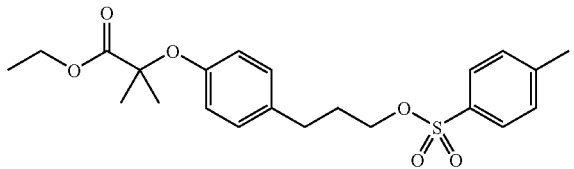

To 2-[4-(3-hydroxypropyl)phenoxy]-2-methylpropanoic acid ethyl ester (67.73 g, 0.25 mol) in dichloromethane (300 mL) at 5° C. was added p-toluenesulfonyl chloride (53.63 g, 0.28 mol), triethylamine (39 mL, 28.13 g, 0.28 mol), and 4-dimethylaminopyridine (2.15 g, 0.026 mol). The resulting solution was held at 10° C. for 6 h, and then filtered and concentrated to an oil. The oil was reconstituted in THF (300 mL) and then water (10 mL) and triethylamine (10 mL) were added. The resulting mixture was stirred at room temperature overnight. The mixture was partitioned between ethyl acetate and 1 N HCl. The organic layer was washed with saturated aqueous NaHCO$_3$ and NaCl, and then dried (MgSO$_4$), filtered and concentrated to an oil. Purification of a 29.96 g portion of the oil was effected via silica gel chromatography (4:1 hexanes:ethyl acetate) to obtain about 17.3 g of the title compound. $^1$H NMR (CDCl$_3$) δ 1.25 (t, 3H, J=7 Hz), 1.56 (s, 6H), 1.91 (m, 2H), 2.46 (s, 3H), 2.57 (t, 21, J=7 Hz) 4.00 (t, 2H, J=6 Hz, 4.23 (q, 2H, J=7 Hz), 6.71 (d, 2H, J=8.4 Hz), 6.91 (d, 2H, J=8.1 Hz), 7.34 (d, 2H, J=8.1 Hz), 7.77 (d, 2H, J=8.4 Hz). MS [EI+] 438 (M+H+NH$_3$).

2-Methyl-2-[3-[3-[(methylphenyl)sulfonyl]oxy]propyl]phenoxypropanoic acid ethyl ester

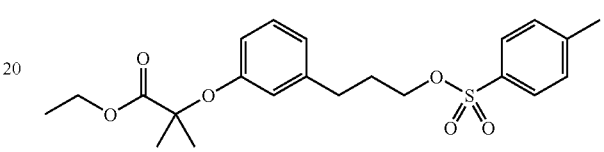

Using the compound of 2-[3-(3-hydroxy-propyl)-phenoxy]-2-methyl-propionic acid ethyl ester as a stating material gave the compound of 2-methyl-2-[3-[3-[(methylphenyl) sulfonyl]oxy]propyl]phenoxypropanoic acid ethyl ester. $^1$H NMR (CDCl$_3$) δ 1.24 (t, 3H), 1.57 (s, 6H), 1.92 (m, 2H), 2.45 (s, 3H), 2.58 (t, 2H), 4.01 (t, 2H), 4.21 (q, 2H), 6.63 (s, 1H), 6.68 (d, 1H), 7.08 (m, 1H), 7.34 (d, 2H), 7.78 (d, 2H).

The compound of 2-[4-(3-chloro-propyl)-phenoxy]-2-methyl-propionic acid ethyl ester can be used an alternative to the tosylate.

2-[4-(3-Chloro-propyl)-phenoxy]-2-methyl-propionic acid ethyl ester

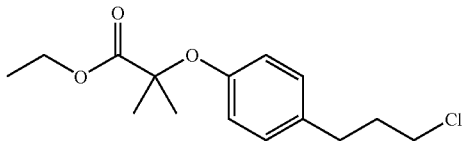

A solution of 2-[4-(3-hydroxypropyl)phenoxy]-2-methyl-propanoic acid ethyl ester (34.5 g, 81% by HPLC, 0.105 mol) in 1,2-dichloroethane (142 mL) was treated dropwise but quickly with thionyl chloride (11.4 mL, 0.056 mol) and then DMF (0.1 mL) was added. The solution was stirred for 0.5 h at room temperature, heated at reflux for 1 h, and then stirred 14 h at room temperature until the starting material was consumed (as determined by TLC of concentrated aliquot). The solvent was removed at reduced pressure. The residue was taken up in MTBE (200 mL) and washed successively with 100 mL of water, saturated aqueous NaHCO$_3$ and brine. The dried (Na$_2$SO$_4$) solution was concentrated to afford about 36 g of title compound. R$_f$=0.66 (9:1 hexanes/EtOAc). $^1$H NMR (300 MHz, CDCl$_3$) δ 1.25 (t, 3H, J=7.2 Hz), 1.57 (s, 6H), 2.03 (m, 2H), 2.70 (t, 2H, J=7.2 Hz), 3.50 (t, 2H, J=6.6 Hz), 4.23 (q, 2H, J=7.2 Hz), 6.77 (m, 2H), 7.05 (m, 2H).

EXAMPLE 262

Standard Procedure (J): Fibrate Alkylamino Preparation

2-Methyl-2-[4-[3-(n-propylamino)propyl]phenoxy]propanoic acid ethyl ester

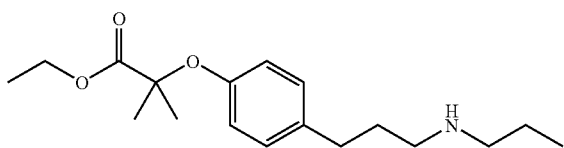

To 2-methyl-2-[4-[3-[(methylphenyl)sulfonyl]oxy]propyl]phenoxy]propanoic acid ethyl ester (9.81 go 23.3 mmol) was added ethanol (75 mL) and n-propylamine (75 mL). The resulting solution was heated at reflux for 1 h, then cooled and concentrated to a solid. The solid was partitioned between ethyl acetate (150 mL) and saturated aqueous $NaHCO_3$ (100 mL). The organic layer washed with saturated aqueous NaCl (75 mL), dried ($MgSO_4$), filtered, and concentrated to an oil. The oil was further purified by re-dissolving in ethyl acetate (150 mL) and by washing sequentially with saturated aqueous $NaHCO_3$ (2×), water (2×), and saturated aqueous NaCl. The organic layer was dried ($MgSO_4$), filtered and concentrated to afford title compound (6.22 g, 20.25 mmol, 87%) as an oil. $^1$H NMR ($CDCl_3$) δ 0.89 (t, 3H), 1.23 (t, 3H), 1.59 (s, 6H), 1.62 (m, 2H), 1.91 (m, 2H), 2.59 (t, 2H), 2.69 (m, 4H), 4.22 (q, 2H), 6.76 (d, 2H), 7.02 (d, 2H). MS [EI+] 308 (M+H).

2-{4-[3-(2-M ethoxy-ethylamino)-propyl]-phenoxy}-2-methyl-propionic acid ethyl ester

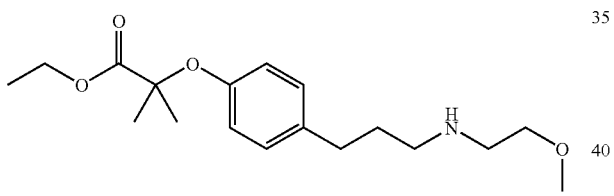

The title compound was prepared by following the procedure detailed above and by using methoxyethyl amine. The reaction afforded the title compound as a light yellow oil. $^1$H NMR ($CDCl_3$) δ 1.27 (t, 3H), 1.54 (s, 6H), 2.86 (t, 2H), 3.00 (t, 2H), 3.37 (s, 3H), 3.03 (t, 2H), 4.02 (t, 2H), 4.25 (q, 2H), 6.75 (m, 4H), MS [EI+] 326 (M+H).

2-[4-(3-Amino-propyl)-phenoxy]-2-methyl-propionic acid ethyl ester

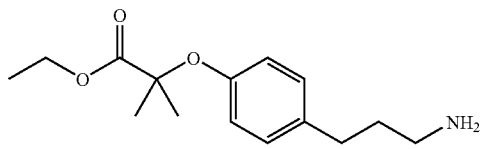

In a Carius tube was placed 2-methyl-2-[4-[3-[(methylphenyl)sulfonyl]oxy]propyl]phenoxy]propanoic acid ethyl ester (3.0 g, 7.1 mmol) and 2N $NH_3$/MeOH (15 mL). The tube was sealed and the solution was heated at 60° C. for 20 h. The cooled solution was concentrated, and the residue was partitioned between water and ethyl acetate. After drying ($MgSO_4$), the solution was concentrated to yield about 1.78 g (94%) white waxy semi-solid. The product can be further purified by a flash chromatography (15% MeOH/ethyl acetate with 1% $NH_4OH$). $^1$H NMR (DMSO-$d_6$) δ1.07 (t, 3H), 1.42 (s, 6H), 1.63 (qn, 2H), 2.46 (t, 2H), 2.59 (t, 2H), 4.07 (q, 2H), 7.00 (m, 4H). MS [EI+] 266 (M+H).

2-[4-(3-Amino-propyl)-phenoxy]-2-methyl-propionic acid ethyl ester

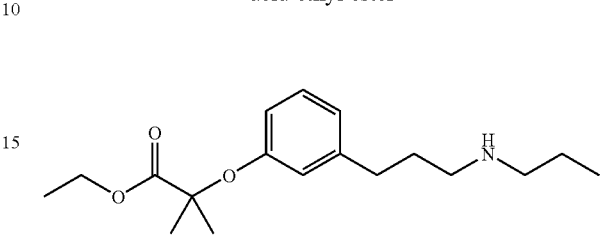

The title compound was prepared by reacting with 2-methyl-2-[3-[3-[(methylphenyl)sulfonyl]oxy]propyl]phenoxy]propanoic acid ethyl ester by following the procedure detailed above. $^1$H NMR ($CDCl_3$) δ 0.91 (t, 3H), 1.22 (t, 3H), 1.58 (s, 6H), 1.59 (m, 2H), 1.88 (m, 2H), 2.65 (m, 6H), 4.23 (q, 2H), 6.64 (dd, 1H), 6.69 (s, 1H), 6.81 (d, 1H), 7.12 (m, 1H).

2-Methyl-2-[4-(2-propylamino-ethyl)-phenoxy]-propionic acid ethyl ester

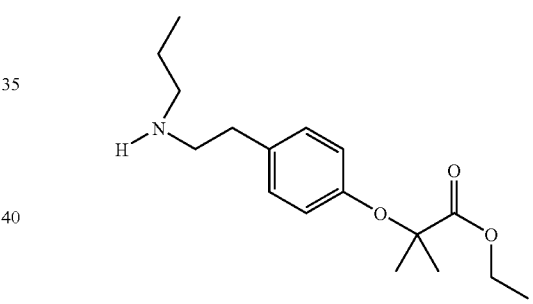

A mixture of 2-methyl-2-{4-[2-(toluene-4-sulfonyloxy)-ethyl]-phenoxyl}-propionic acid ethyl ester (2.26 g. 5.35 mmol) (M. Kitazawa, et al, WO 9813333 A1 19980402) and n-propylamine (50 mL) in ethanol (40 mL) was stirred overnight at ambient temperature. The solution was concentrated, and the residue was partitioned between ethyl acetate/water. After drying ($MgSO_4$), the organic layer and the solvent was removed under reduced pressure to yield 1.36 g (87%) of the title compound as a waxy semi-solid. $^1$H NMR ($CDCl_3$) δ 0.81 (t, 3H), 1.17 (t, 3H), 1.48 (s, 6H), 2.57 (t, 2H), 2.76 (m, 4H), 3.74 (t, 2H), 4.16 (q, 2H), 6.67 (d, 2H), 6.96 (d, 2H). MS [EI+] 294 (M+H).

2-{4-[2-(2-Methoxy-ethylamino)-ethoxy]-phenoxy}-2-methyl-propionic acid ethyl ester

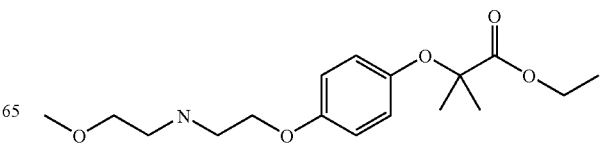

A mixture of 2-[4-(2-bromo-ethoxy)-phenoxy]-2-methyl-propionic acid ethyl ester (2.77 g, 8.36 mmol), and 2-methoxyethylamine (10 mL) in ethanol (40 mL) was stirred at ambient temperature for 18 h. The mixture was concentrated under reduced pressure. The residue was dissolved in ethyl acetate and shaken with water. The organic layer was dried (MgSO$_4$) and concentrated to yield about 2.18 g (80%) of the title compound as a tan oil. $^1$H NMR (CDCl$_3$) δ 1.27 (t 3H), 1.56 (s, 6H), 2.08 (br s, 1H), 2.89 (t, 2H), 3.03 (t, 2H), 3.39 (s, 3H), 3.04 (t, 2H), 4.04 (t, 2H), 4.24 (q, 2H), 6.82 (m, 4H). MS [EI+] 326 (M+H).

EXAMPLE 263

2-methyl-2-[4-[3-(n-propylamino)propyl]phenoxy]propanoic acid ethyl ester

Alternately, the amines could be prepared from 2-[4-(3-chloro-propyl)-phenoxy]-2-methyl-propionic acid ethyl ester as described below. A solution of 2-[4-(3-chloro-propyl)-phenoxy]-2-methyl-propionic acid ethyl ester (36 g, 0.126 mol) in 1:1 EtOH/propylamine (144 mL) was heated at reflux for 24 h under nitrogen until starting material was consumed. After cooling to room temperature, the solvent was removed at reduced pressure. The residual oil was taken up in 1:1 EtOAc/heptane (300 mL) and washed three times with 200 mL of 10% aqueous K$_2$CO$_3$, and then with 200 mL brine. The dried (Na$_2$SO$_4$) solution was concentrated to afford about 38.2 g (98%) of 2-methyl-2-[4-[3-(n-propylamino)propyl]phenoxy]propanoic acid ethyl ester as yellow oil. R$_f$=0.52 (8.9:1.1 CH$_2$Cl$_2$/MeOH). $^1$H NMR (300 MHz, CDCl$_3$) δ 0.89 (t, 3H, J=7.2 Hz), 1.24 (t, 3H, J=7.2 Hz), 1.47 (m, 3H), 1.56 (s, 6H), 1.77 (m, 2H), 2.57 (m, 6H), 4.22 (q, 2H. 3=7.2 Hz), 6.75 (m, 2H), 7.03 (m, 2H).

3-[4-(3-Propylamino-propyl)-phenyl]-propionic acid methyl ester

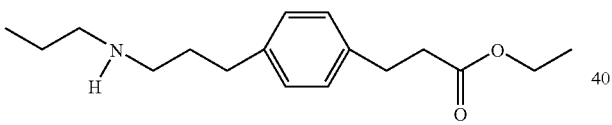

Step A

3-[4-(3-hydroxy-prop-1-ynyl)-phenyl]-propionic acid methyl ester

Under argon, in a flame dried flask, was placed 3-(4-trifluoromethanesulfonyloxy-phenyl)-propionic acid methyl ester (1.0 g, 7.2 mmol) (G. R. Brown et al., WO 94-GB910 19940428, CAS[166959-38-2]), propargyl alcohol (1.12 mL, 19.2 mmol) and DMF (6 mL). Lastly, triethylamine (1.78 mL. 12.8 mmol) and Pd(Ph$_3$P)Cl$_2$ (112 mg. 0.16 mmol) were added. The reaction was heated at 90° C. for 2 h and then cooled and concentrated under vacuum. The residue was diluted with ethyl acetate (200 mL) and brine (100 mL). The aqueous layer was extracted a second time with ethyl acetate. The combined organic layers were dried (Na$_2$SO$_4$) and concentrated to give 1.1 g crude product as a dark oil. The product was purified by a radial chromatography using a gradient of 25-35% EtOAc/hexanes. The pure fractions were concentrated to yield about 0.29 g (42%) of 3-[4-(3-hydroxy-prop-1-ynyl)-phenyl]-propionic acid methyl ester as a yellow oil. $^1$H NMR (300 MHz. CDCl$_3$) □ 2.62 (t, 2H), 2.94 (t, 2H), 3.66 (s, 3H), 4.49 (d, 2H), 7.14 (d, 2H), 7.30 (d, 2H). MS [EI] 218 (M).

Step B

3-[4-(3-hydroxy-propyl)-phenyl]-propionic acid methyl ester

The compound of 3-[4-(3-hydroxy-prop-1-ynyl)-phenyl]-propionic acid methyl ester (1.0 g, 4.58 mmol) was dissolved in THF (20 mL), and 10% Pd/C (100 mg) was added. The slurry was stirred under a hydrogen atmosphere for 16 h, and then filtered through Celite and concentrated to give about 0.97 g (95%) of 3-[4-(3-hydroxy-propyl)-phenyl]-propionic acid methyl ester as an off-white solid. $^1$H NMR (CDCl$_3$) δ 1.25 (br s, 1H), 1.88 (m 2H), 2.64 (m, 4H), 2.92 (t, 2H), 3.67 (s and m, 5H), 7.12 (s, 4H).

MS [EI+] 223 (M+1).

Step C

3-[4-(3-benzenesulfonyloxy-propyl)-phenyl]-propionic acid methyl ester

A mixture of 3-[4-(3-hydroxy-propyl)-phenyl]-propionic acid methyl ester (0.95 g, 4.27 mmol), DMAP (0.156 g, 1.28 mmol), tosic anhydride (1.67 g, 5.12 mmol), pyridine (1.17 mL), and dichloromethane (17 mL) was stirred at ambient temperature for 18 h. The reaction was charged with 1N HCl (16 mL), stirred vigorously for 1 h, and then the layers were separated. The organic layer was washed with brine, dried (Na$_2$SO$_4$) and concentrated to give about 1.6 g (100%) of 3-[4-(3-benzenesulfonyloxy-propyl)-phenyl]-propionic acid methyl ester as a colorless oil. 3H NMR (CDCl$_3$) δ 1.93 (qn, 2H), 2.46 (s, 3H), 2.60 (m, 4H), 2.90 (t, 2H), 3.66 (s, 3H), 4.02 (t, 2H), 7.00 (d, 2H), 7.07 (d, 2H), 7.33 (d, 2H), 7.79 (d, 2H). MS [EI+] 377 (M+1).

Step D

3-[4-(3-propylamino-propyl)-phenyl]-propionic acid methyl ester

A solution of 3-[4-(3-benzenesulfonyloxy-propyl)-phenyl]-propionic acid methyl ester (1.82 mL, 4.83 mmol) in DMF (54 mL) and n-propylamine (1.99 mL, 24.2 mmol) was stirred at room temperature for 18 h. The reaction was partitioned between water (50 mL) and ethyl acetate (100 mL). The aqueous layer was extracted with ethyl acetate. The combined organic layers were washed with brine, dried (Na$_2$SO$_4$), and concentrated to give about 1.3 g (100%) of 3-[4-(3-propylamino-propyl)-phenyl]-propionic acid methyl ester as a thin oil. $^1$H NMR (CDCl$_3$) δ 0.91 (t, 3H), 1.84 (m, 2H), 2.20 (qn, 2H), 2.61 (m, 4H), 2.90 (m, 6H), 3.66 (s, 6H), 7.26 (s, 4H), 9.40 (br s, 1H). MS [EI+] 264 (M+1).

EXAMPLE 264

2-(3-{3-[(5-Chloro-3-methyl-benzo[b]thiophene-2-sulfonyl)-propyl-amino]-propyl}-phenoxy)-2-methyl-propionic acid

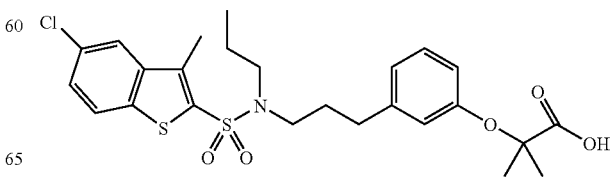

A mixture of 2-methyl-2-[3-(3-propylamino-propyl)-phenoxy]-propionic acid ethyl ester (550 mg. 1.79 mmol), 5-chloro-3-methyl-benzo[b]thiophene-2-sulfonyl chloride (503 mg, 1.79 mmol) and 3 mL triethylamine was dissolved in 40 mL dichloromethane and stirred for 18 h at room temperature. The reaction was shaken with dilute HCl, dried (MgSO$_4$) and concentrated to give 750 mg crude product. The ester was purified by a flash chromatography using 12% EtOAc/hexane. After concentration of the fractions containing pure product, about 390 mg (39%) ester was obtained as a colorless oil. $^1$H NMR (300 MHz, CDCl$_3$): δ 0.80 (t, 3H), 1.17 (t, 3H), 1.45 (m, 2H), 1.51 (s, 6H), 1.79 (m, 2H), 2.47 (t, 2H), 2.55 (s, 3H), 3.13 (m, 4H), 4.14 (q, 2H), 6.55 (m, 2H), 6.67 (br d, 1H), 7.04 (t, 1H), 7.36 (dd, 1H), 7.66 (m, 2H). MS [EI+] 552 (M+H), 569 (M+NH$_3$).

The ester obtained above (390 mg, 0.71 mmol) was dissolved in EtOH (10 mL), and then 5 N NaOH (5 mL) was added. The solution was warned at 50° C. for 1.5 h. The cooled hydrolysis reaction was concentrated to remove most of the ethanol, acidified with HCl, and extracted with ethyl acetate. The organic layer was dried (MgSO$_4$) and concentrated to give 275 mg (74%) of the title compound as a light pink oil, which slowly crystallized. $^1$H NMR (300 MHz, CDCl$_3$) δ 0.94 (t, 3H), 1.60 (m, 2H), 1.55 (s, 6H), 1.94 (m, 2H), 2.65 (t, 2H), 2.67 (s, 3H), 3.27 (m, 4H), 6.85 (m, 3H), 7.22 (m, 1H), 7.48 (dd, 1H), 7.79 (m, 2H). MS [ES+] 524 (M+H), [EI−] 522 (M−H).

EXAMPLE 265

2-(4-{3-[(5-Chloro-3-methyl-benzo[b]thiophene-2-sulfonyl)-propyl-amino]-propyl}-phenoxy)-2-methyl-propionate, sodium salt

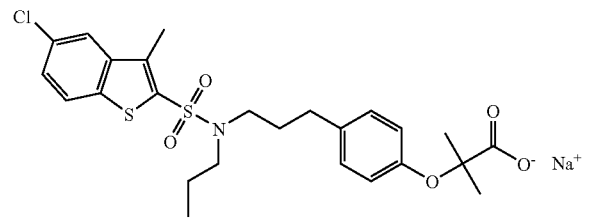

Step A 2-(4-{3-[(5-Chloro-3-methyl-benzo[b]thiophene-2-sulfonyl)-propyl-amino]-propyl}-phenoxy)-2-methyl-propionic acid ethyl ester

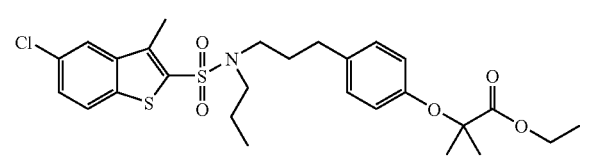

A mixture of 2-methyl-2-[4-(3-propylamino-propyl)-phenoxy]-propionic acid ethyl ester (2.25 g. 7.3 mmol), 5-chloro-3-methyl-benzo[b]thiophene-2-sulfonyl chloride (2.06 g. 7.3 mmol), triethylamine (5 mL) and dichloromethane (50 mL) was stirred for 18 h. at room temperature. The mixture was shaken with 1N HCl, dried (MgSO$_4$) and concentrated to give 3.3 g crude product. The ester was purified by a flash chromatography (15% ethyl acetate/hexane) to yield 990 mg of pure ester. $^1$H NMR (300 MHz, CDCl$_3$): δ 0.79 (t, 3H), 1.17 (t, 3H), 1.47 (m, 2H), 1.49 (s, 6H), 1.78 (m, 2H), 2.46 (t, 2H), 3.12 (q, 2H), 4.15 (q, 2H), 6.66 (d, 2H), 6.91 (d, 2H), 7.36 (dd, 1H), 7.65 (m, 3H). MS [EI+] 552 (M+H), 569 (M+NH$_3$).

Step B 2-(4-{3-[(5-Chloro-3-methyl-benzo[b]thiophene-2-sulfonyl)-propyl-amino]-propyl}-phenoxy)-2-methyl-propionic acid

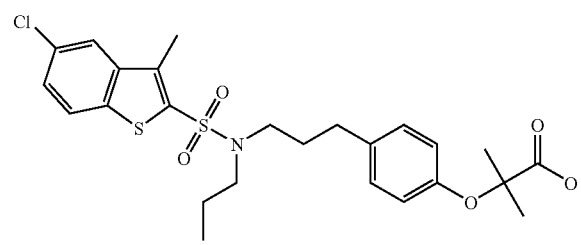

A solution of 2-(4-{3-[(5-chloro-3-methyl-benzo[b]thiophene-2-sulfonyl)-propyl-amino]-propyl}-phenoxy)-2-methyl-propionic acid ethyl ester (990 mg, 1.79 mmol) in ethanol (30 mL) was treated with 5N NaOH (3 mL) and warmed at 50° C. for 2 h. The cooled mixture was diluted with water and most of the ethanol was removed under reduced pressure. After acidification with aqueous HCl, the product was extracted into ethyl acetate. The organic layer was dried (MgSO$_4$) and concentrated to give 810 mg (86%) of the title compound as a viscous oil. $^1$H NMR (300 MHz. CDCl$_3$): δ 0.82 (t, 3H), 1.48 (s, 6H), 1.49 (m, 2H), 3.81 (m, 2H), 2.52 (m, 2H), 2.56 (s, 3H), 3.18 (m, 4H), 6.78 (d, 2H), 7.00 (d, 2H), 7.37 (dd, 1H), 7.66 (m, 3H). MS [EI+] 524 (M=H), [EI−] 522 (M−H)

Step C 2-(4-{3-[(5-Chloro-3-methyl-benzo[b]thiophene-2-sulfonyl)-propyl-amino]-propyl}-phenoxy)-2-methyl-propionate, sodium salt

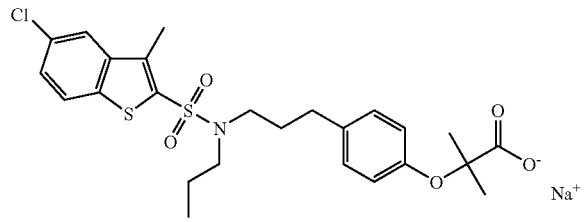

A solution of 2-(4-{3-[(5-chloro-3-methyl-benzo[b]thiophene-2-sulfonyl)-propyl-amino]-propyl}-phenoxy)-2-methyl-propionic (80 mg, 0.15 mmol) in ethyl acetate (1 mL) under nitrogen was treated with sodium 2-ethylhexanoate (28 mg, 0.17 mmol), and the reaction was stirred at room temperature. After 8 h, the precipitate was collected and dried to give 71 mg (87%) of the title compound as an off-white solid. $^1$H NMR (300 MHz, DMSO-d$_6$): δ 0.81 (t, 3H), 1.35 (s, 6H), 1.49 (m, 2H), 1.72 (m, 2H), 2.42 (t, 2H), 2.58 (s, 3H), 3.17 (m, 4H), 6.70 (d, 2H), 6.87 (d, 2H), 7.59 (dd, 1H), 8.06 (d, 1H), 8.15 (d, 1H). MS [EI+] 524 (M+1), [EI−] 522 (M−H).

EXAMPLE 266

2-(4-{3-[(5-Chloro-3-methyl-benzo[b]thiophene-2-sulfonyl)-propyl-amino]-propyl}-phenoxy)-2-methyl-propionic acid 2-morpholin-4-yl-ethyl ester, HCl salt

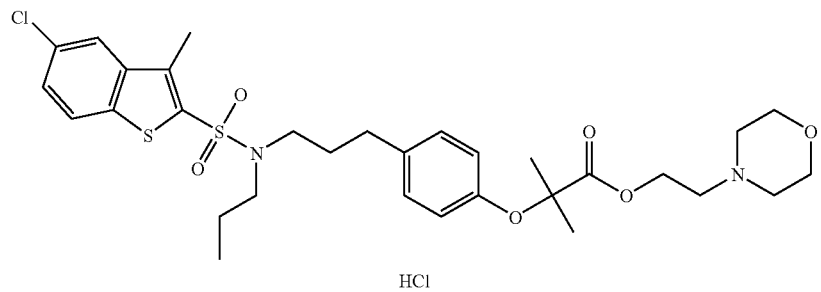

2-(4-{3-[(5-Chloro-3-methyl-benzo[b]thiophene-2-sulfonyl)-propyl-amino]-propyl}-phenoxy)-2-methyl-propionic acid (330 mg, 0.63 mmol) was dissolved in dichloromethane (3 mL), and 2M oxalyl chloride in $CH_2Cl_2$ (400 µL, 0.8 mmol) was added. One drop of DMF was added, and the reaction was stirred for 1 h. The mixture was concentrated and the residue was redissolved in $CH_2Cl_2$. The compound of 2-(2-hydroxyethyl)morpholine (121 µL, 1 mmol), triethylamine (131 µL, 1 mmol), and a catalytic amount of DMAP were added. The mixture was stirred for 18 h, concentrated, and purified by a flash chromatography (60% ethyl acetate/hexane). The colorless oil (180 mg) was dissolved in diethyl ether, and 1 M HCl/ether (500 µL) was added. The resulting oil was dissolved in EtOAc, and the solution was concentrated. The residue was dissolved in dichloromethane, and the mixture was concentrated to yield 124 mg (31%) of the title compound as a white hygroscopic foam. $^1$H NMR (300 MHz, $CDCl_3$): δ 0.8 (t, 3H), 1.50 (m, 6H), 1.54 (s, 6H), 1.81 (m, 2H), 2.47 (m, 2H), 2.55 (s, 3H), 3.05 (m, 2H), 3.14 (m, 4H), 3.65 (m, 2H), 4.01 (m, 2H), 4.67 (m, 2H), 6.62 (d, 2H), 6.95 (d, 2H), 7.37 (dd, 1H), 7.66 (m, 3H), 13.35 (br s, 1H). MS [EI+] 637 (M+H).

EXAMPLES 267-385

Examples 267 to 385 were prepared according to the indicated Standard Procedures as described in Examples 253 to 262.

| Example No. | Structure | MS(ES) | Standard Procedure |
|---|---|---|---|
| 267 | 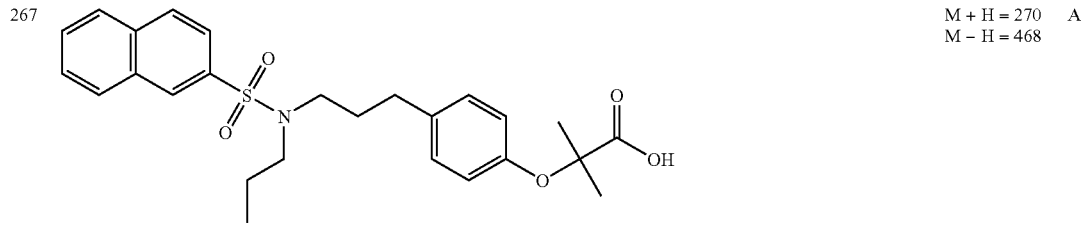 | M + H = 270<br>M − H = 468 | A |
| 268 | 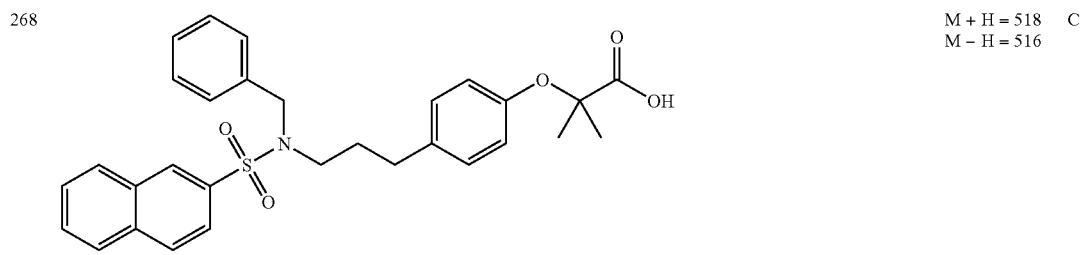 | M + H = 518<br>M − H = 516 | C |

-continued

| Example No. | Structure | MS(ES) | Standard Procedure |
|---|---|---|---|
| 269 | 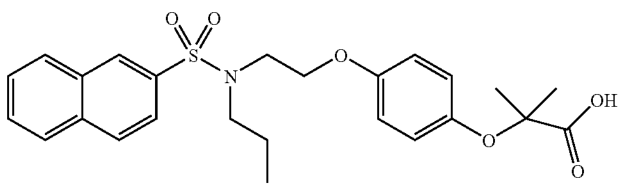 | M + H = 472<br>M − H = 470 | C |
| 270 | 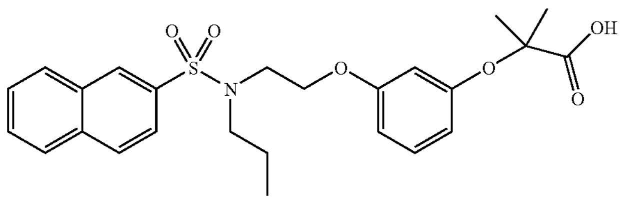 | M + H = 472<br>M − H = 470 | C |
| 271 | 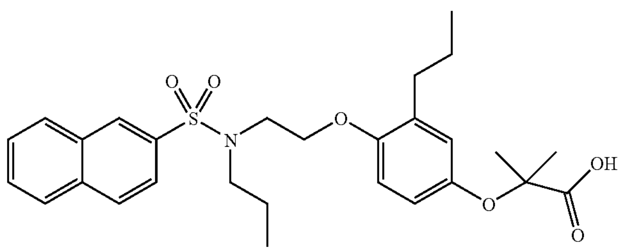 | M + H = 514<br>M − H = 512 | C |
| 272 | 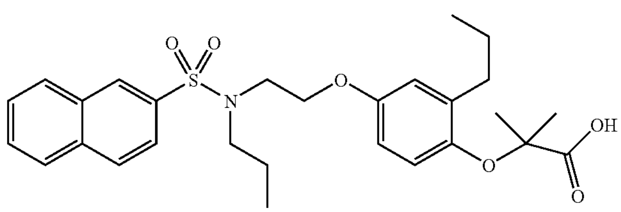 | M + H = 514<br>M − H = 512 | C |
| 273 | 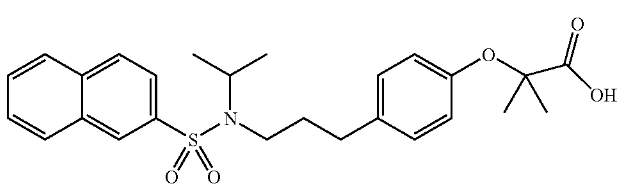 | M + H = 470<br>M − H = 469 | B |
| 274 | 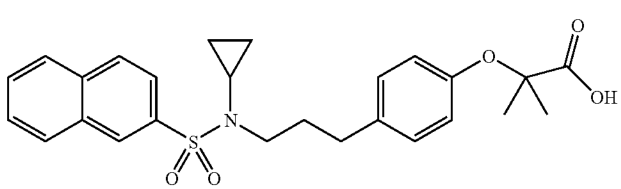 | M + H = 420<br>M − H = 418 | B |
| 275 | 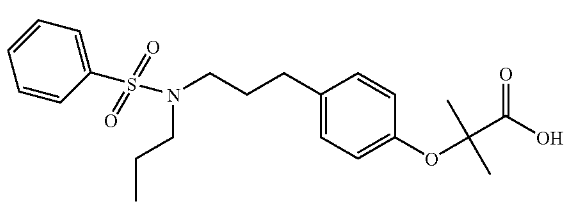 | M + H = 454<br>M − H = 452 | A |

-continued

| Example No. | Structure | MS(ES) | Standard Procedure |
|---|---|---|---|
| 276 | 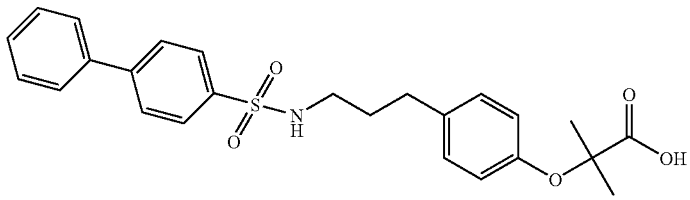 | M + H = 468<br>M − H = 466 | A |
| 277 | 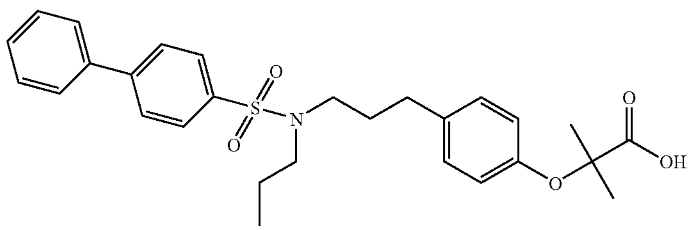 | M + H = 469<br>M − H = 494 | A |
| 278 | 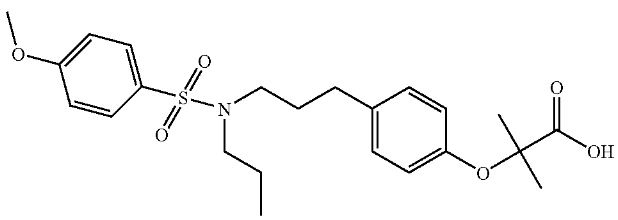 | M + H = 450<br>M − H = 448 | A |
| 279 | 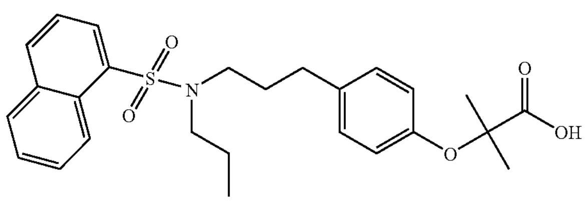 | M + H = 470<br>M − H = 468 | A |
| 280 | 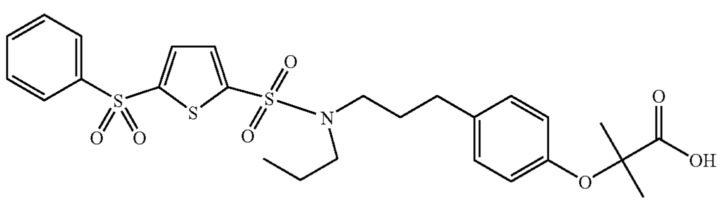 | M + H = 566<br>M − H = 564 | A |
| 281 | 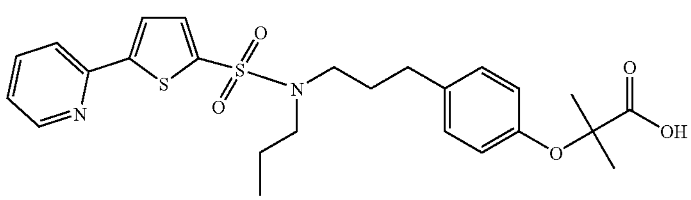 | M + H = 503<br>M − H = 501 | A |
| 282 | 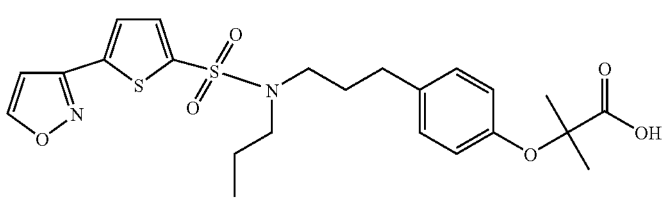 | M + H = 493<br>M − H = 491 | A |

-continued

| Example No. | Structure | MS(ES) | Standard Procedure |
|---|---|---|---|
| 283 | 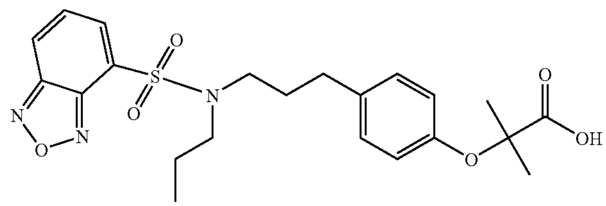 | M + H = 462<br>M − H = 460 | A |
| 284 | 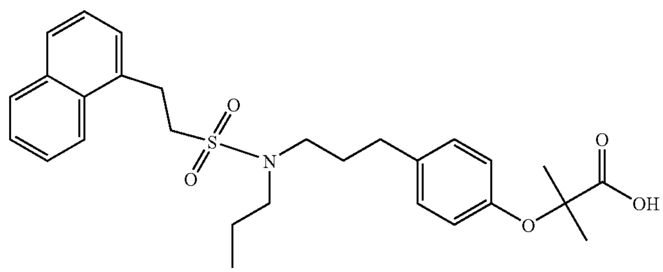 | M + H = 498<br>M − H = 496 | A |
| 285 | 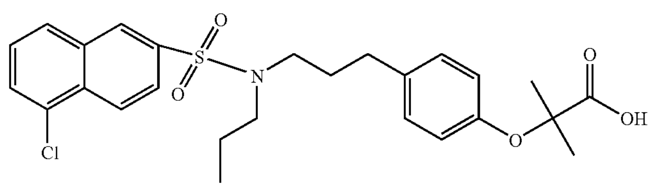 | M + H = 504<br>M − H = 502 | A |
| 286 | 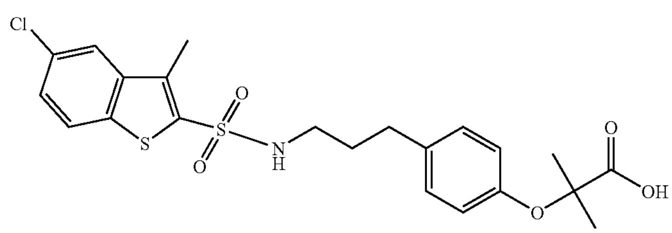 | M + H = 482<br>M − H = 480 | A |
| 287 | 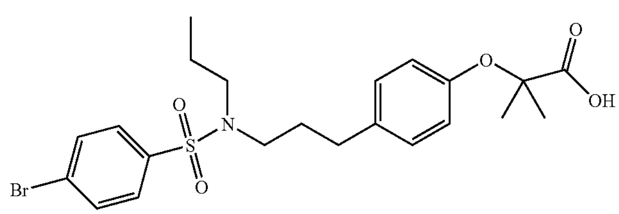 | M + H = 500<br>M − H = 498 | A |
| 288 | 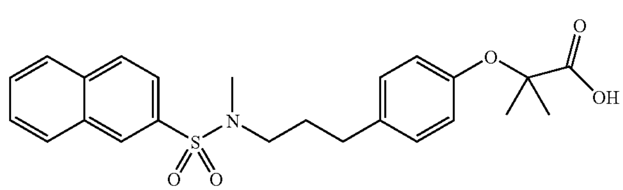 | M + H = 442<br>M − H = 440 | B |
| 289 | 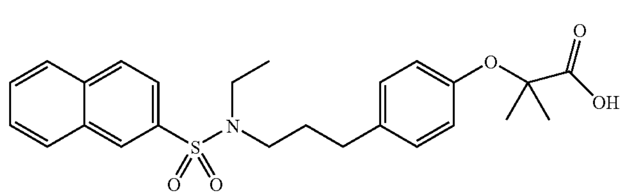 | M + H = 456<br>M − H = 454 | B |

-continued

| Example No. | Structure | MS(ES) | Standard Procedure |
|---|---|---|---|
| 290 | 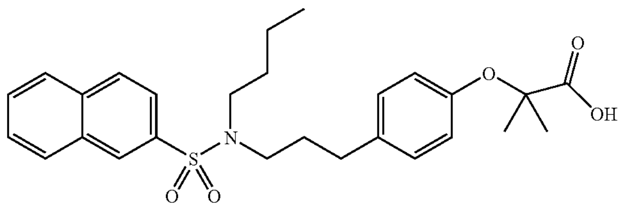 | M + H = 484<br>M − H = 482 | B |
| 291 | 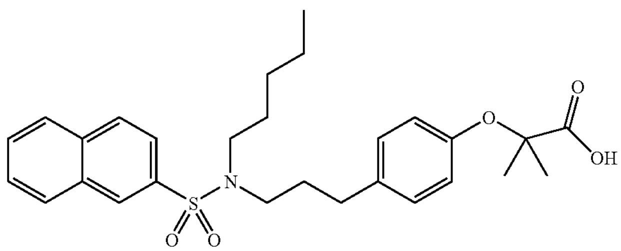 | M + H = 498<br>M − H = 496 | B |
| 292 | 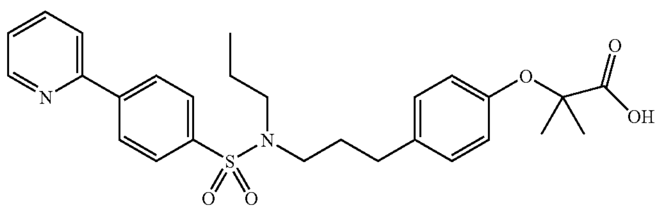 | M + H = 497<br>M − H = 495 | D |
| 293 | 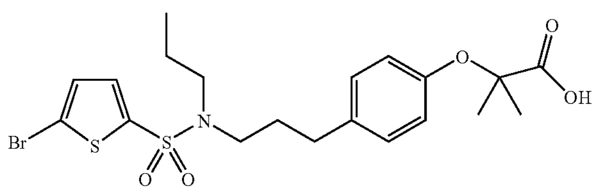 | M + H = 506<br>M − H = 504 | A |
| 294 | 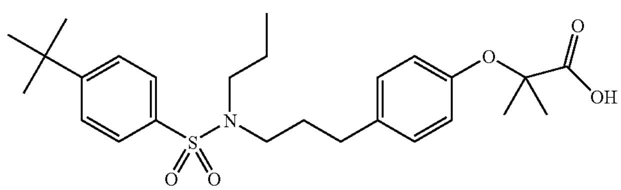 | M + H = 476<br>M − H = 474 | A |
| 295 | 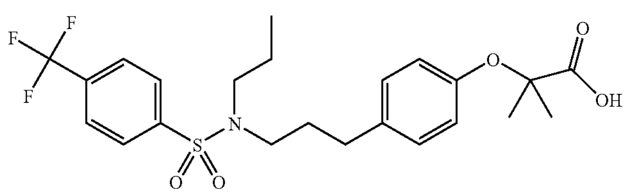 | M + H = 488<br>M − H = 486 | A |
| 296 | 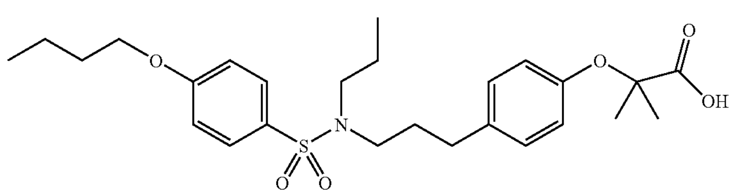 | M + H = 492<br>M − H = 490 | A |

-continued

| Example No. | Structure | MS(ES) | Standard Procedure |
|---|---|---|---|
| 297 | 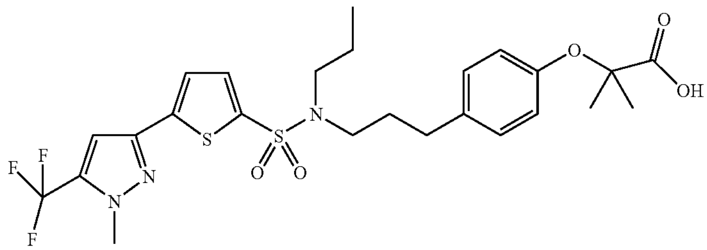 | M + H = 574<br>M − H = 572 | A |
| 299 | | M + H = 550<br>M − H = 548 | A |
| 299 | | M + H = 456<br>M − H = 454 | A |
| 300 | 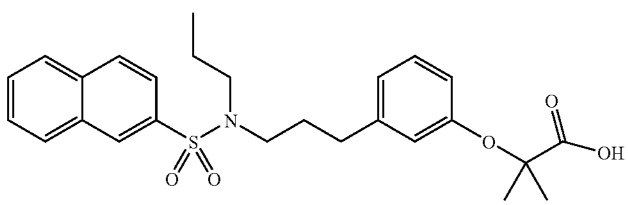 | M + H = 470<br>M − H = 468 | A |
| 301 | 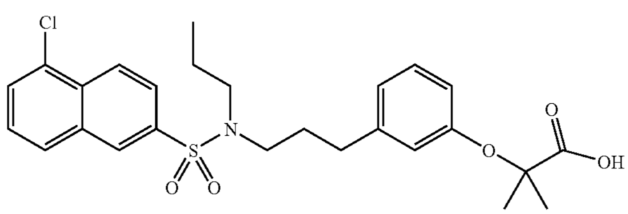 | M + H = 504<br>M − H = 502 | A |
| 302 | 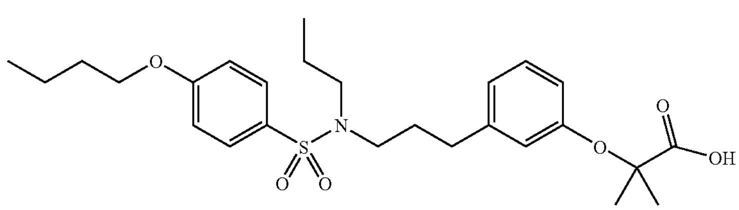 | M + H = 492<br>M − H = 490 | A |
| 303 | 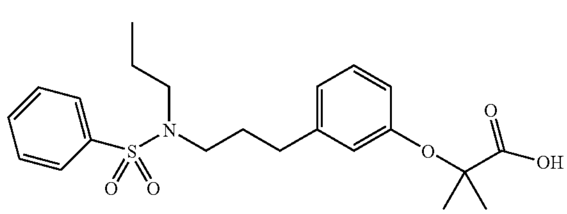 | M + H = 450<br>M − H = 448 | A |

-continued

| Example No. | Structure | MS(ES) | Standard Procedure |
|---|---|---|---|
| 304 | 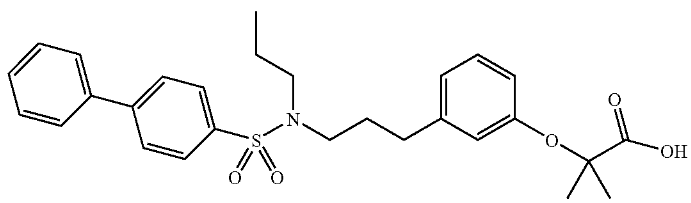 | M + H = 496<br>M − H = 494 | A |
| 305 | 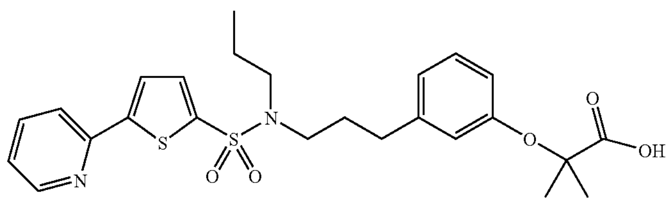 | M + H = 503<br>M − H = 501 | A |
| 306 | 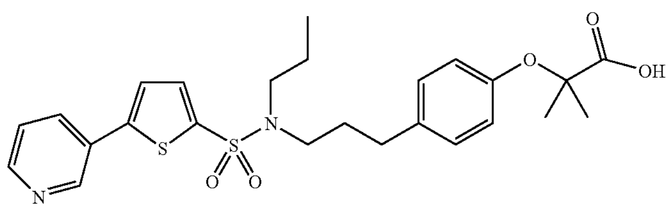 | M + H = 503<br>M − H = 501 | D |
| 307 | 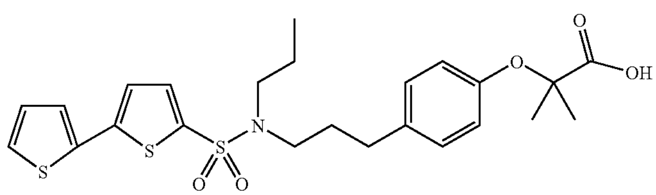 | M + H = 508<br>M − H = 506 | D |
| 308 | 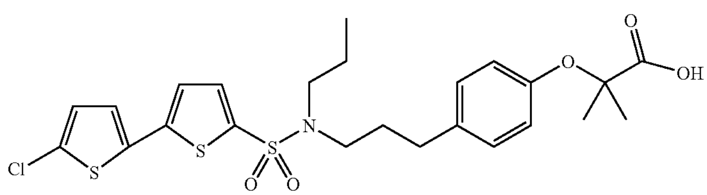 | M + H = 542<br>M − H = 540 | D |
| 309 | 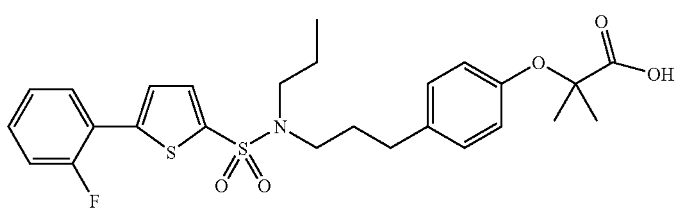 | M + H = 520<br>M − H = 518 | D |
| 310 | 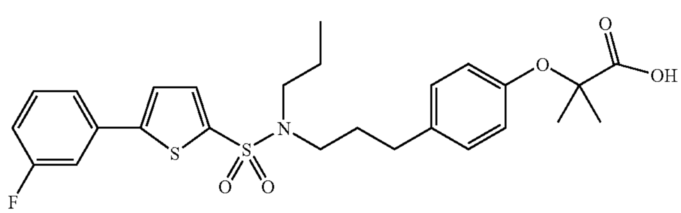 | M + H = 520<br>M − H = 518 | D |

-continued

| Example No. | Structure | MS(ES) | Standard Procedure |
|---|---|---|---|
| 311 | 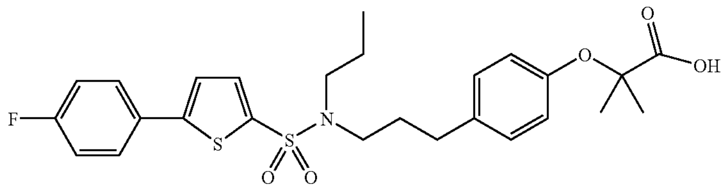 | M + H = 520<br>M − H = 518 | D |
| 312 | 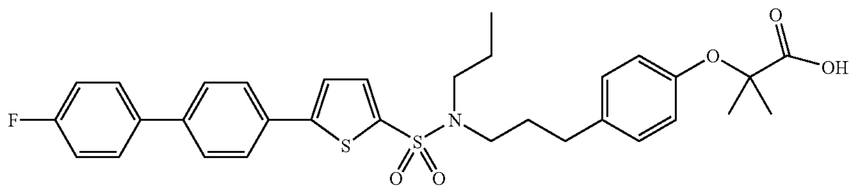 | M + H = 596<br>M − H = 594 | D |
| 313 | 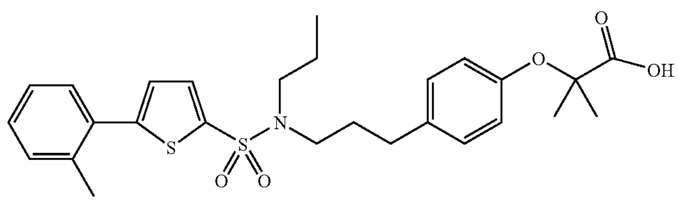 | M + H = 516<br>M − H = 514 | D |
| 314 | 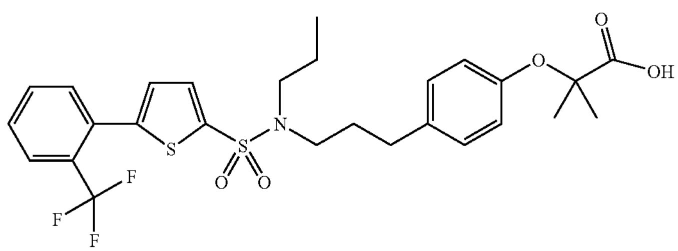 | M + H = 570<br>M − H = 568 | D |
| 315 | 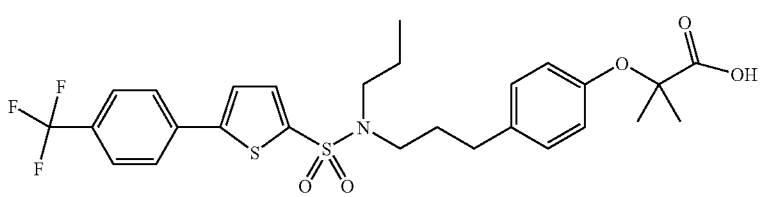 | M + H = 570<br>M − H = 568 | D |
| 316 | 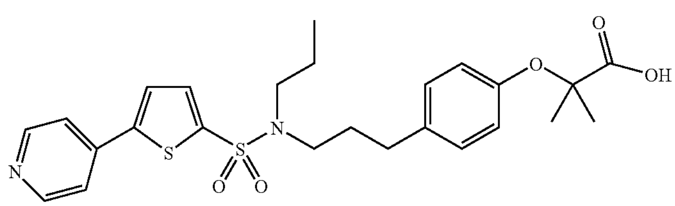 | M + H = 503<br>M − H = 501 | D |
| 317 | 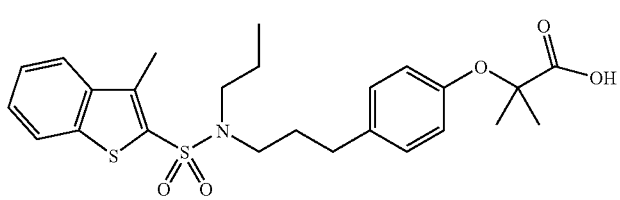 | M + H = 500<br>M − H = 498 | A |

-continued

| Example No. | Structure | MS(ES) | Standard Procedure |
|---|---|---|---|
| 318 | 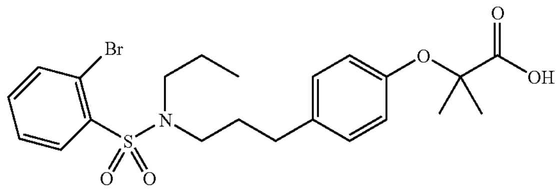 | M + H = 490<br>M − H = 488 | A |
| 319 | 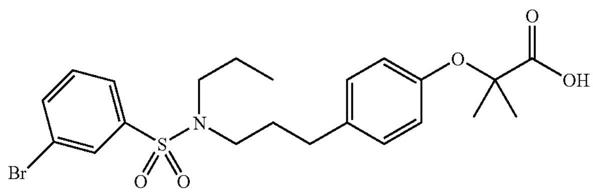 | M + H = 490<br>M − H = 488 | A |
| 320 | 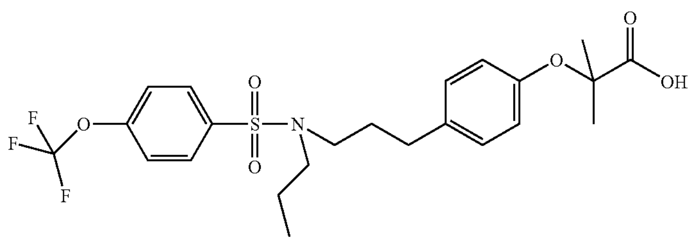 | M + H = 504 | A |
| 321 | 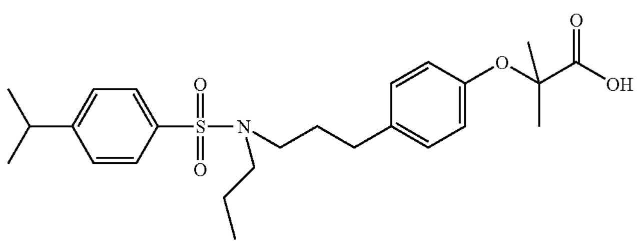 | M + H = 462 | A |
| 322 | 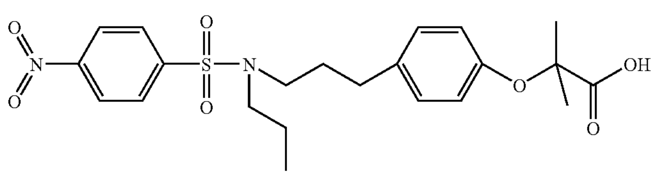 | M + H = 465 | A |
| 323 | 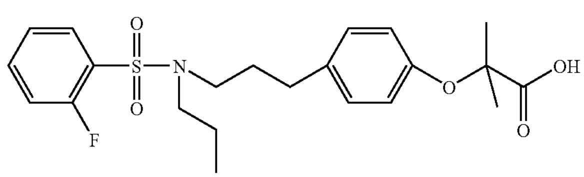 | M + H = 438 | A |
| 324 | 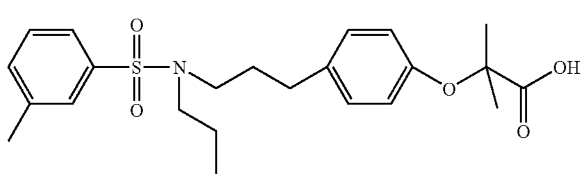 | M + H = 484 | A |

-continued

| Example No. | Structure | MS(ES) | Standard Procedure |
|---|---|---|---|
| 325 | 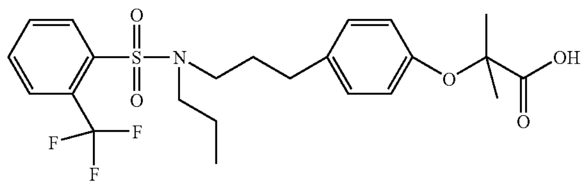 | M + H = 488 | A |
| 326 | 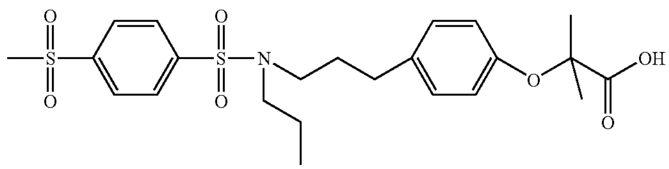 | M + H = 498 | A |
| 327 | 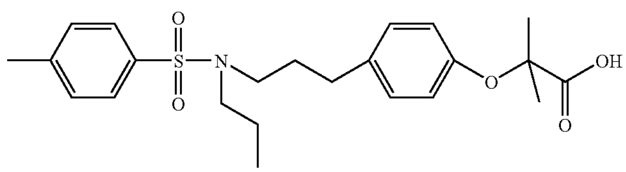 | M + H = 434 | A |
| 328 | 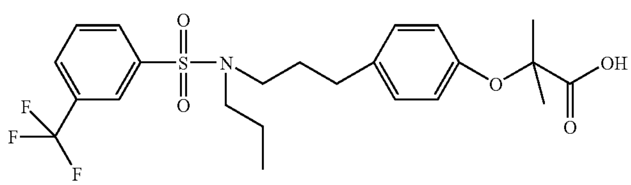 | M + H = 488 | A |
| 329 | 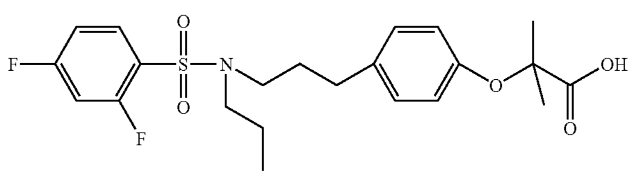 | M + H = 456 | A |
| 330 | 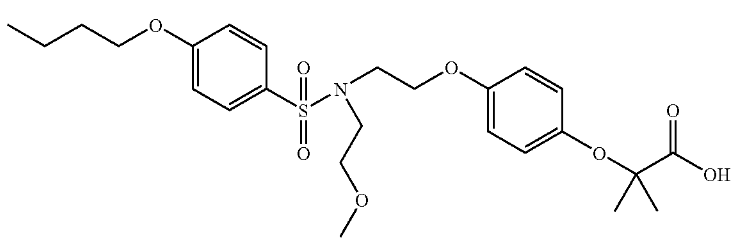 | M + H = 510<br>M − H = 508 | A |
| 331 | 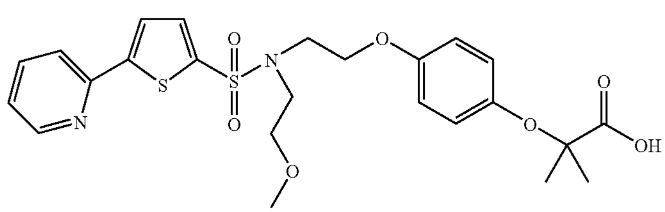 | M + H = 521<br>M − H = 519 | A |

-continued

| Example No. | Structure | MS(ES) | Standard Procedure |
|---|---|---|---|
| 332 | 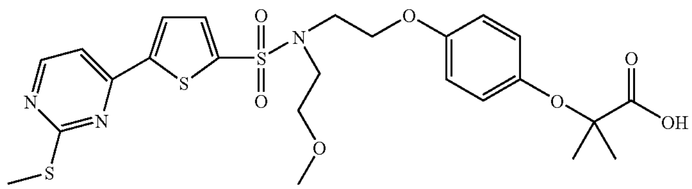 | M + H = 568<br>M − H = 566 | A |
| 333 | 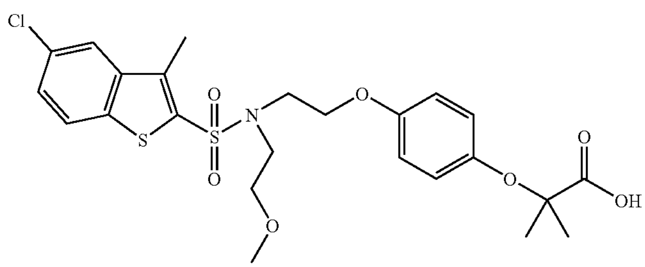 | M + H = 542<br>M − H = 540 | A |
| 334 | 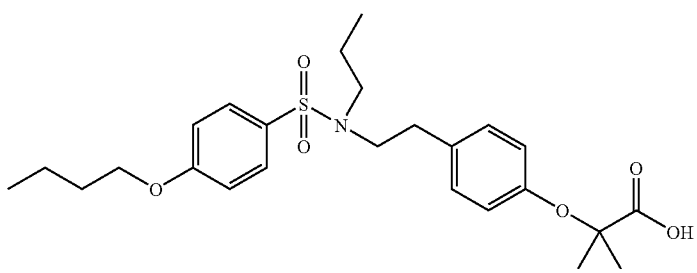 | M + H = 478<br>M − H = 476 | A |
| 335 | 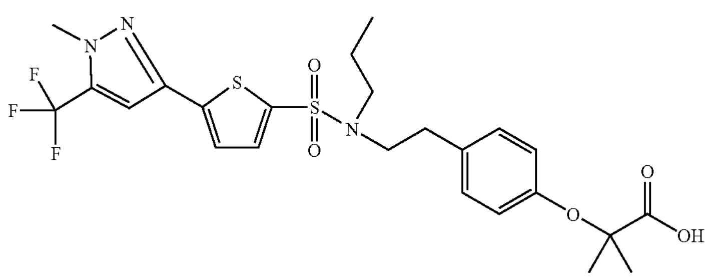 | M + H = 550<br>M − H = 558 | A |
| 336 | 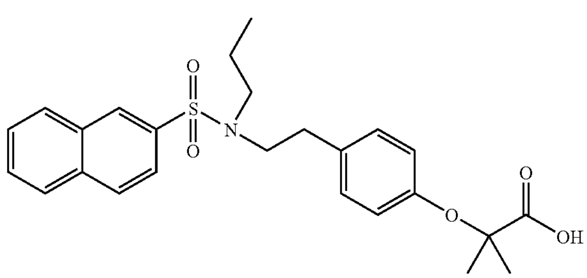 | M + H = 456<br>M − H = 454 | A |

-continued

| Example No. | Structure | MS(ES) | Standard Procedure |
|---|---|---|---|
| 337 | 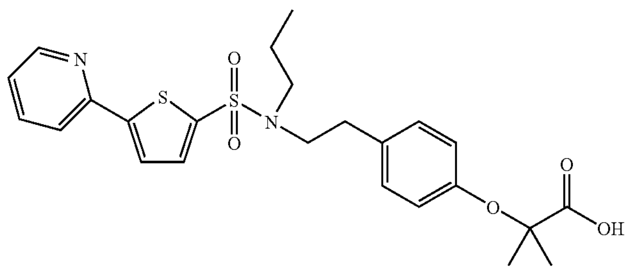 | M + H = 489<br>M − H = 487 | A |
| 338 | 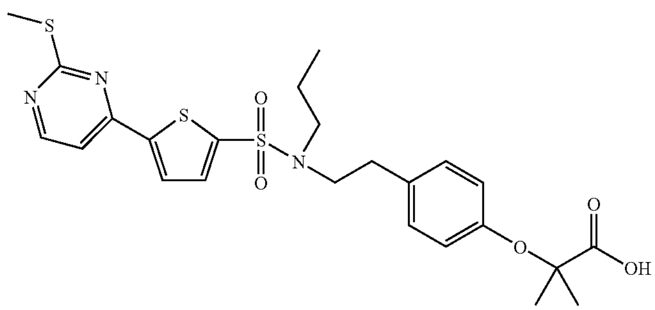 | M + H = 536<br>M − H = 534 | A |
| 339 | 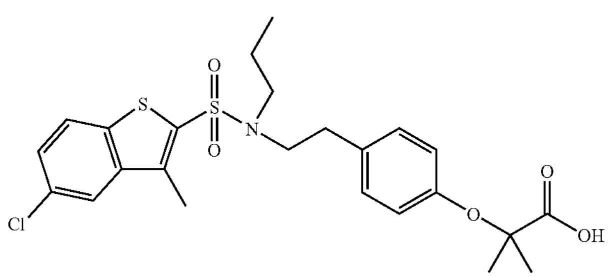 | M + H = 510<br>M − H = 508 | A |
| 340 | 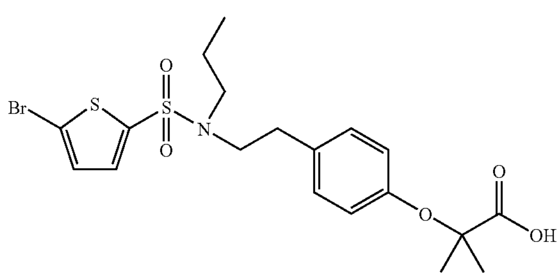 | M + H = 492<br>M − H = 490 | A |
| 341 | 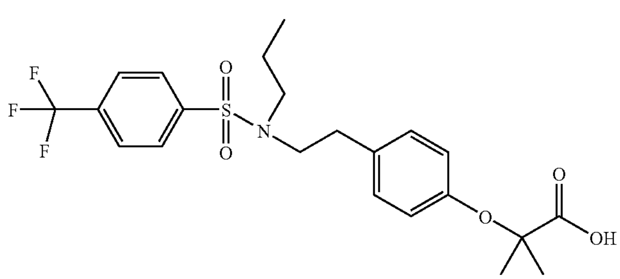 | M + H = 474<br>M − H = 472 | A |

-continued

| Example No. | Structure | MS(ES) | Standard Procedure |
|---|---|---|---|
| 342 | 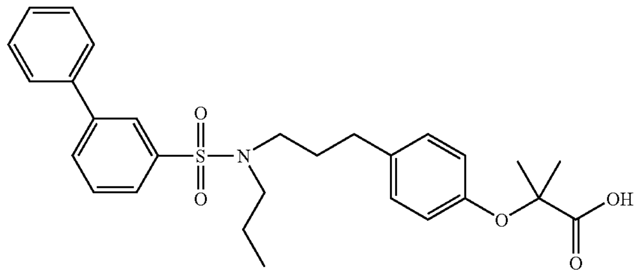 | M + H = 496<br>M − H = 494 | D |
| 343 | 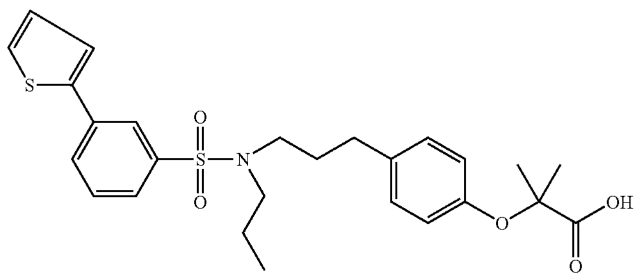 | M + H = 500<br>M − H = 498 | D |
| 344 | 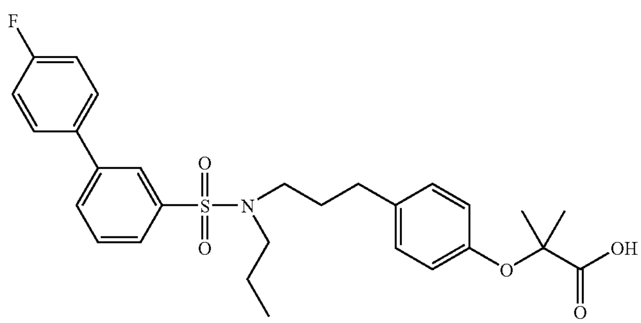 | M + H = 514<br>M − H = 512 | D |
| 345 | 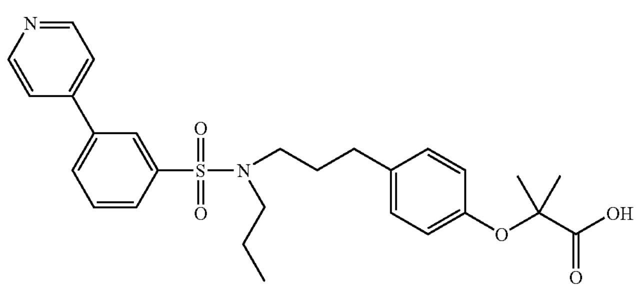 | M + H = 497<br>M − H = 495 | D |
| 346 | 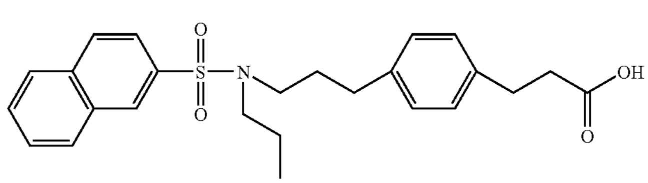 | M + H = 440 | A |

-continued

| Example No. | Structure | MS(ES) | Standard Procedure |
|---|---|---|---|
| 347 | 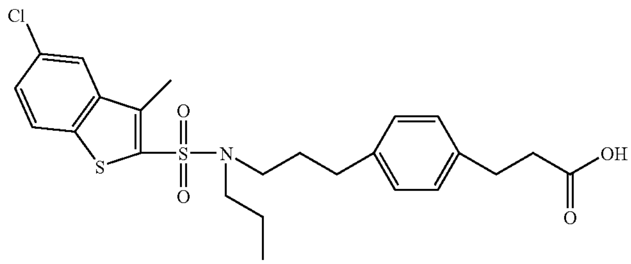 | M + H = 495 | A |
| 348 | 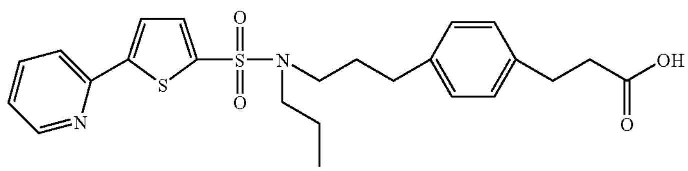 | M + H = 473 | A |
| 349 | 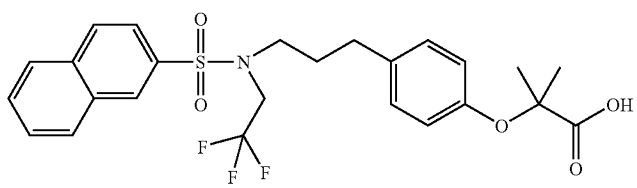 | M + H = 510<br>M − H = 508 | B |
| 350 | 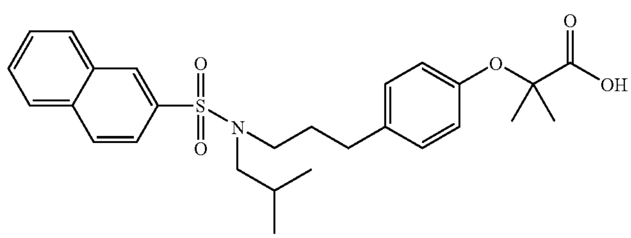 | M + H = 484<br>M − H = 482 | B |
| 351 | 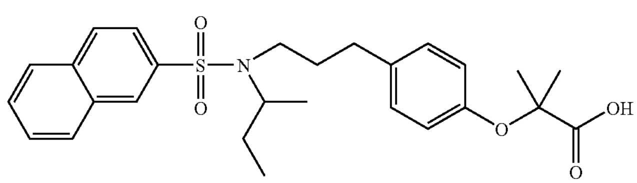 | M + H = 484<br>M − H = 482 | B |
| 352 | 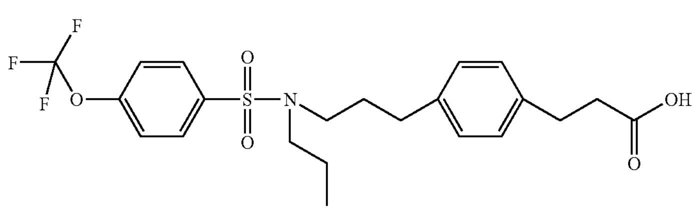 | M + H = 474 | A |
| 353 | 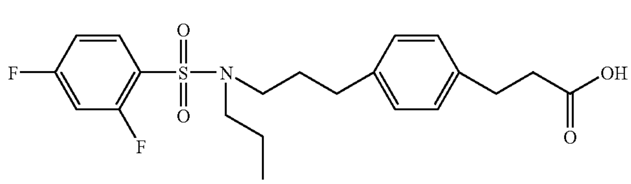 | M + H = 426 | A |

-continued

| Example No. | Structure | MS(ES) | Standard Procedure |
|---|---|---|---|
| 354 | 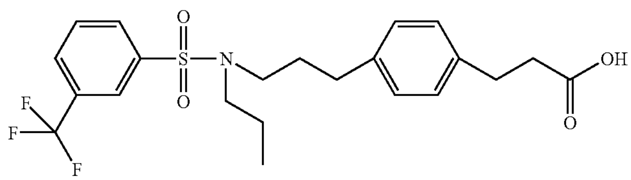 | M + H = 458 | A |
| 355 | 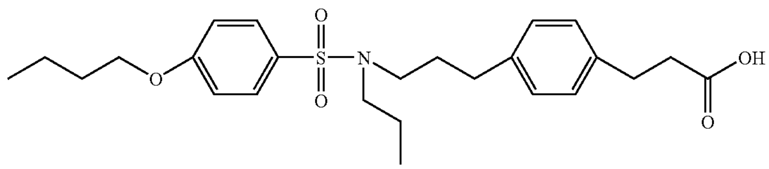 | M + H = 462 | A |
| 356 | 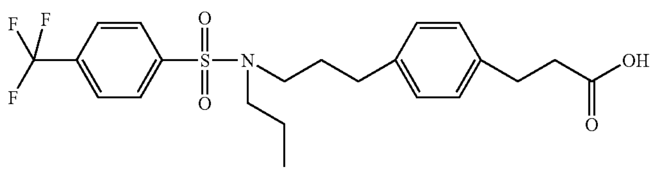 | M + H = 458 | A |
| 357 | 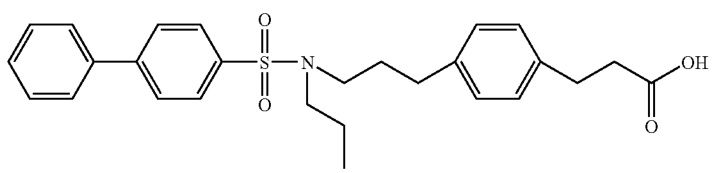 | M + H = 466 | A |
| 358 | 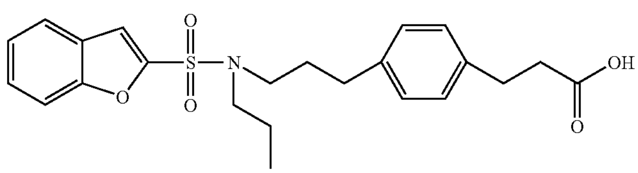 | M + H = 430 | A |
| 359 | 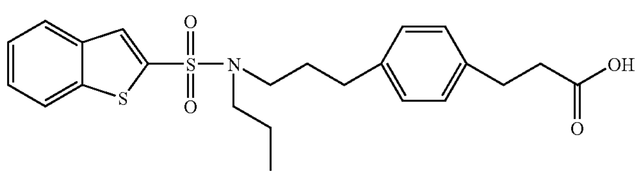 | M + H = 446 | A |
| 360 | 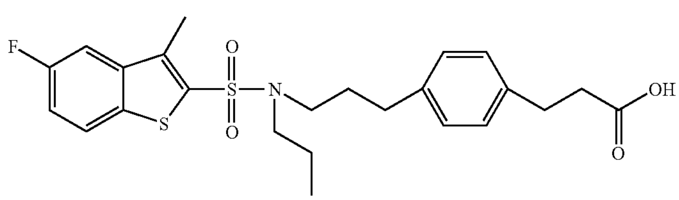 | M + H = 478 | A |
| 361 | 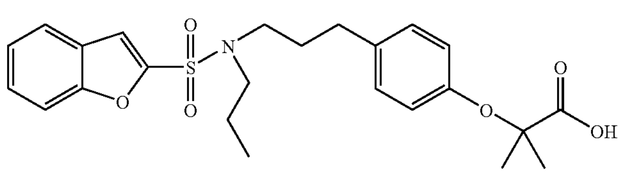 | M + H = 460<br>M − H = 458 | A |

-continued

| Example No. | Structure | MS(ES) | Standard Procedure |
|---|---|---|---|
| 362 | 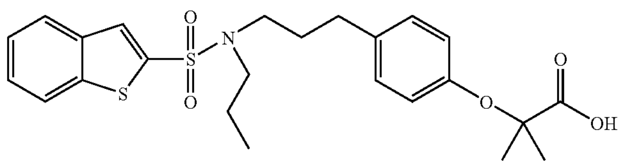 | M + H = 476<br>M − H = 474 | A |
| 363 | 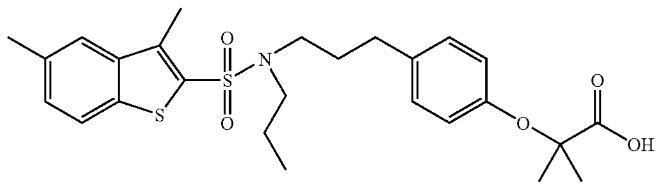 | M + H = 504<br>M − H = 502 | A |
| 364 | 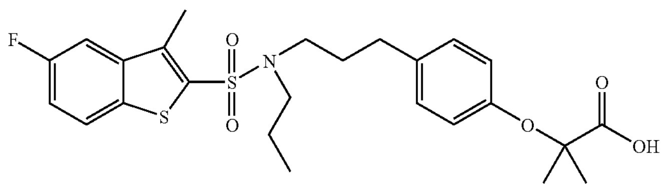 | M + H = 508<br>M − H = 506 | A |
| 365 | 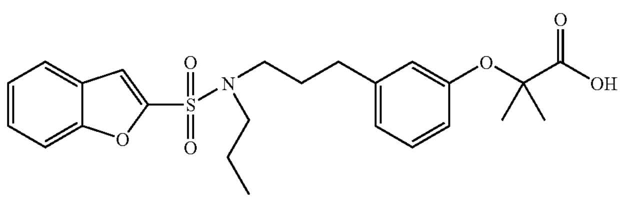 | M + H = 460<br>M − H = 458 | A |
| 366 | 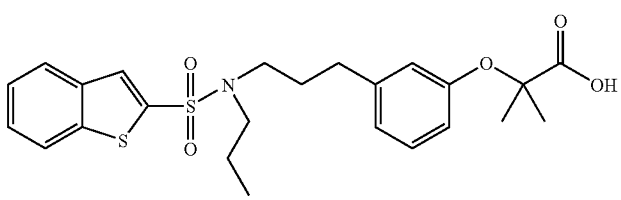 | M + H = 476<br>M − H = 474 | A |
| 367 | 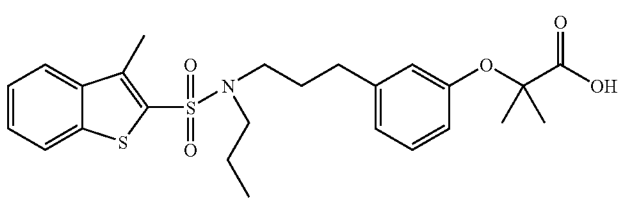 | M + H = 490<br>M − H = 488 | A |
| 368 | 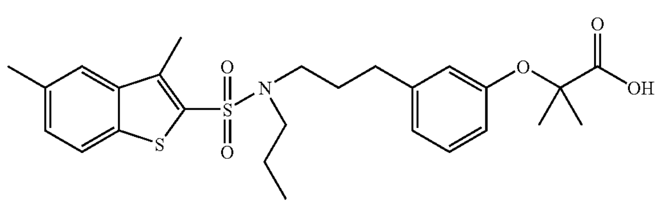 | M + H = 504<br>M − H = 502 | A |

-continued

| Example No. | Structure | MS(ES) | Standard Procedure |
|---|---|---|---|
| 369 | 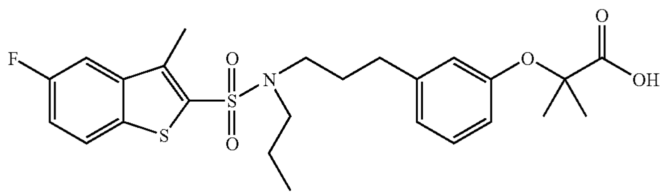 | M + H = 508<br>M − H = 506 | A |
| 370 | 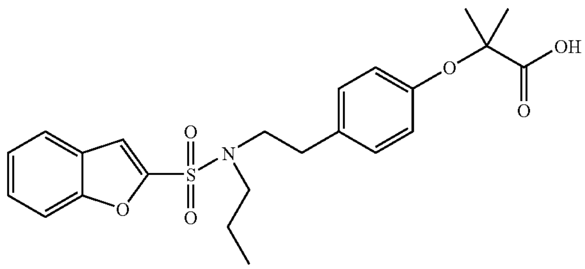 | M + H = 446<br>M − H = 444 | A |
| 371 | 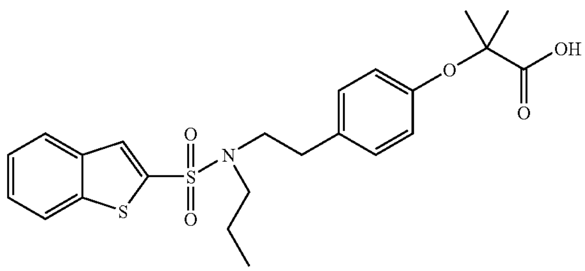 | M + H = 462<br>M − H = 460 | A |
| 372 | 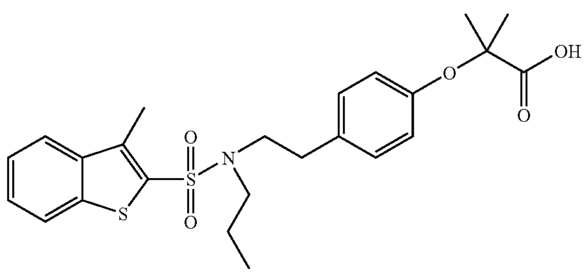 | M + H = 476<br>M − H = 474 | A |
| 373 | 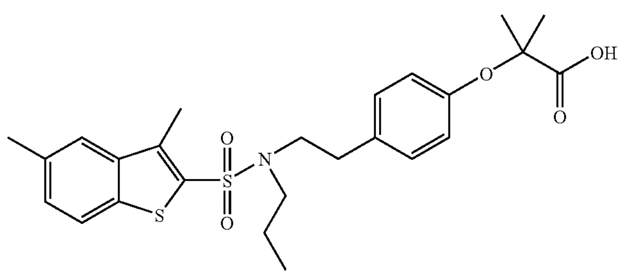 | M + H = 490<br>M − H = 488 | A |
| 374 | 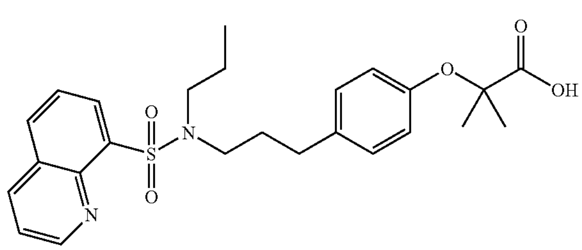 | M + H = 471<br>M − H = 469 | A |

-continued

| Example No. | Structure | MS(ES) | Standard Procedure |
|---|---|---|---|
| 375 | 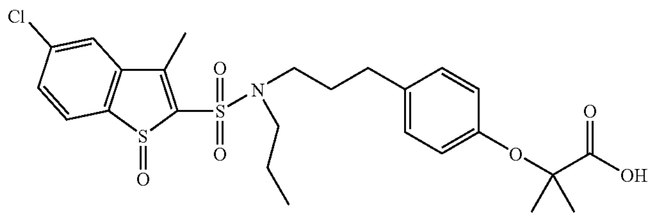 | M + NH$_3$ = 557 | MCPBA oxidation |
| 376 | 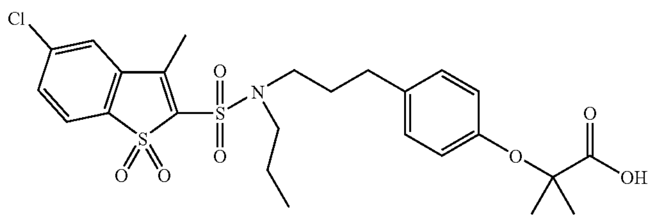 | M + H = 557<br>M − H = 554 | MCPBA oxidation |
| 377 | 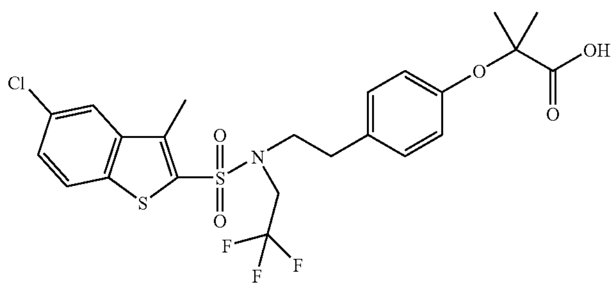 | M + NH$_3$ = 567<br>M − H = 548 | B |
| 378 | 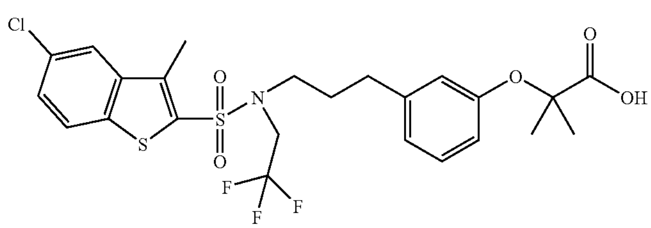 | M + NH$_3$ = 551<br>M − H = 562 | B |
| 379 | 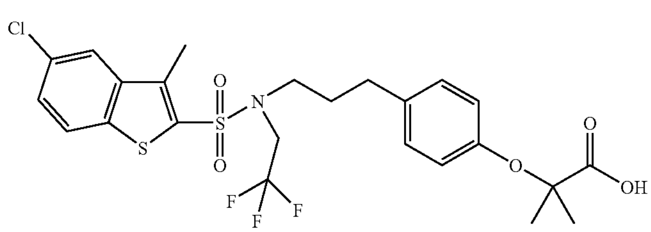 | M + NH$_3$ = 581<br>M − H = 562 | B |
| 380 | 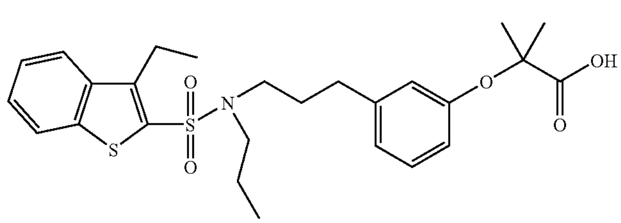 | M + NH$_3$ = 565<br>M − H = 546 | A |

-continued
| Example No. | Structure | MS(ES) | Standard Procedure |
|---|---|---|---|
| 381 | 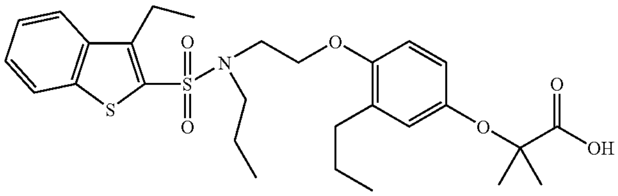 | M + NH₃ = 521<br>M − H = 502 | A |
| 382 | 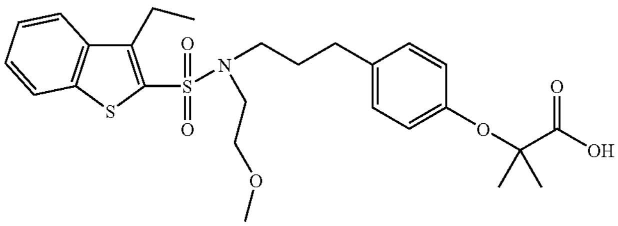 | M + NH₃ = 537<br>M − H = 518 | A |
| 383 | 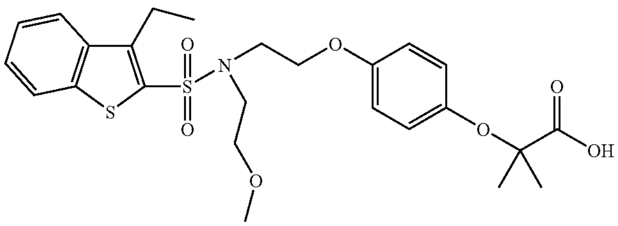 | M + NH₃ = 539<br>M − H = 520 | A |
| 384 | 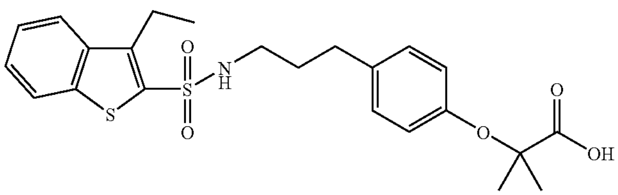 | M + NH₃ = 479<br>M − H = 460 | A |
| 385 | 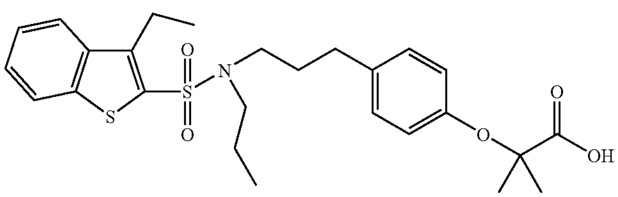 | M + NH₃ = 521<br>M − H = 502 | A |
EXAMPLE 386
(R)-(6-{1-Methyl-2-[(3-methyl-5-trifluoromethyl-benzo[b]thiophene-2-sulfonyl)-propyl-amino]-ethoxy}-1-propyl-1H-indol-3-yl)-acetic acid
Step A
(6-Benzyloxy-1H-indol-3-yl)-oxo-acetic acid methyl ester
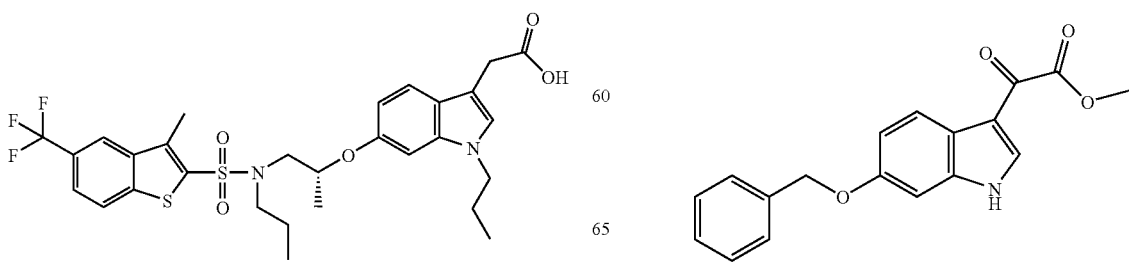

To a solution of 6-benzoxyindole (25 g. 112 mmol) in diethylether (300 mL) was added oxalyl chloride (10.7 mL, 123 mmol) at 0~5° C., and the mixture was stirred for 2 hrs. The mixture was cooled to −78° C. and sodium methoxide (25% w/v in methanol, 31 mL) was added over one hour. The mixture was warmed to room temperature, and then quenched with water. The solid product is collected by filtration, washed with water and dried under vacuum.

Step B (6-Benzyloxy-1-propyl-1H-indol-3-yl)-oxo-acetic acid methyl ester

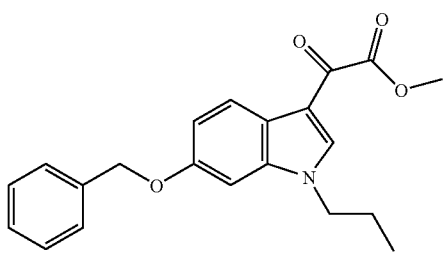

To a solution of (6-benzyloxy-1H-indol-3-yl)-oxo-acetic acid methyl ester (3.0 g, 9.7 mmol) in anhydrous dimethyl formamide (50 mL) at 0° C. under nitrogen was added sodium hydride (0.600 g, 14.5 mmol) in small portions. The reaction was allowed to warm to room temperature and stirred for 2 hours. The mixture as cooled to 0° C. and n-propyl iodide (1.9 mL, 20 mmol) was slowly added to the slurry. The reaction was allowed to warm slowly to room temperature and monitored by TLC. After complete consumption of the starting material, the reaction as quenched with water, then diluted with ethyl acetate, and the two phases were separated. The organic layer was washed, dried, filtered and concentrated. The crude (6-benzyloxy-1-propyl-1H-indol-3-yl)-oxo-acetic acid ethyl ester (0.840 g, 2.20 mmol). 25% yield, was further purified using flash column chromatography.

Step C (6-Hydroxy-1-propyl-1H-indol-3-yl)-acetic acid methyl ester

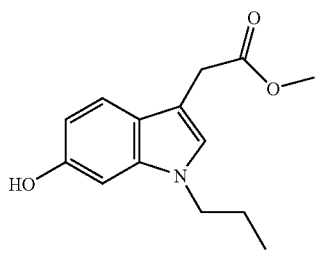

The compound of (6-benzyloxy-1-propyl-1H-indol-3-yl)-oxo-acetic acid methyl ester (0.810 g, 2.20 mmol) was dissolved in anhydrous dioxane (10 mL) and 10% palladium on carbon (200 mg) was added. The mixture was purged and back filled with nitrogen several times, and then replaced with an atmosphere of hydrogen. The reaction mixture was heated to reflux and a saturated solution of sodium hypophosphite (1 ml) was added over one hour, and then the mixture heated at reflux temperature overnight. After the starting material was completely consumed, the reaction was allowed to cool to room temperature, diluted with dichloromethane and celite was added. The mixture was filtered through a plug of celite and the two phases were separated. The organic layer was washed with water and brine, and dried over sodium sulfate and then concentrated. The residue was purified using flash column chromatography to afford the title compound.

Step D (R)-(6-{1-Methyl-2-[(3-methyl-5-trifluoromethyl-benzo[b]thiophene-2-sulfonyl)-propyl-amino]-ethoxy}-1-propyl-1H-indol-3-yl)-acetic acid methyl ester

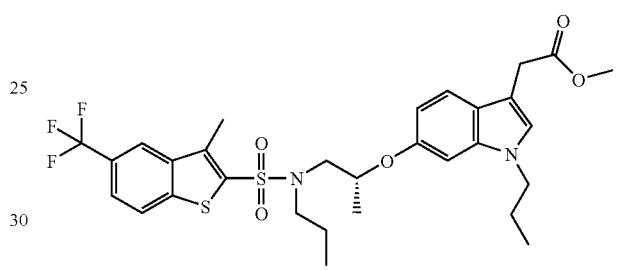

To a cooled solution of (6-hydroxy-1-propyl-1-indol-3-yl)-acetic acid methyl ester (112 mg, 0.45 mmol) and (S)-3-methyl-5-trifluoromethyl-benzo[b]thiophene-2-sulfonic acid (2-hydroxy-propyl)-propyl-amide (150 mg, 0.37 mmol) in toluene (2 ml) at 0° C. was added tri-n-butylphosphine (0.11 ml, 0.45 mmol) over 1 minute followed by the dropwise addition of a solution of 1,1'-(azodicarbonyl) dipiperidine (113 mg, 0.45 mmol) in toluene (1.5 ml) over 5 minutes. The suspension was stirred in at 0° C. for 15 minutes, and then stirred at room temperature for 18 hours. The mixture was diluted with hexanes (4 ml), filtered, and the filtrate was concentrated to give an oil. Purification by silica chromatography using 8:1 hexanes:ethyl acetate provided the title compound as an oil, 33 mg.

Step E (R)-(6-{1-Methyl-2-[(3-methyl-5-trifluoromethyl-benzo[b]thiophene-2-sulfonyl)-propyl-amino]-ethoxy}-1-propyl-1H-indol-3-yl)-acetic acid To a solution of (R)-(6-{1-methyl-2-[(3-methyl-5-trifluoromethyl-benzo[b]thiophene-2-sulfonyl)-propyl-amino]-ethoxy}-1-propyl-1H indol-3-yl)-acetic acid methyl ester (33 mg. 0.052 mmol) in methanol (2 ml) at room temperature was added aqueous 5N NaOH (0.5 ml. 2.5 mmol), and the mixture was stirred for 18 hours. The mixture was concentrated to give a residue, which was dissolved in water (10 ml) and ethyl acetate (15 ml), and then the mixture was adjusted to pH 3 with 5N HCl. After extracting the aqueous layer with ethyl acetate (10 ml), the combined organic extracts were washed

EXAMPLE 387

3-(4-{3-[(2,4-Difluorobenzenesulfonyl)propylamino]propyl}phenyl) propionic acid

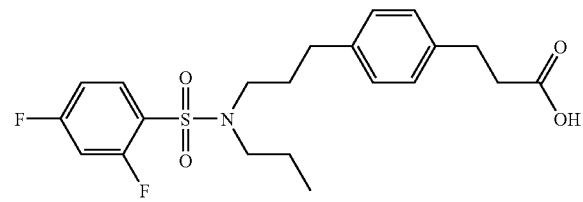

The compound of 3-(4-{3-[(2,4-difluorobenzenesulfonyl)propylamino]propyl}, phenyl) propionic acid was prepared according to the scheme provided below:

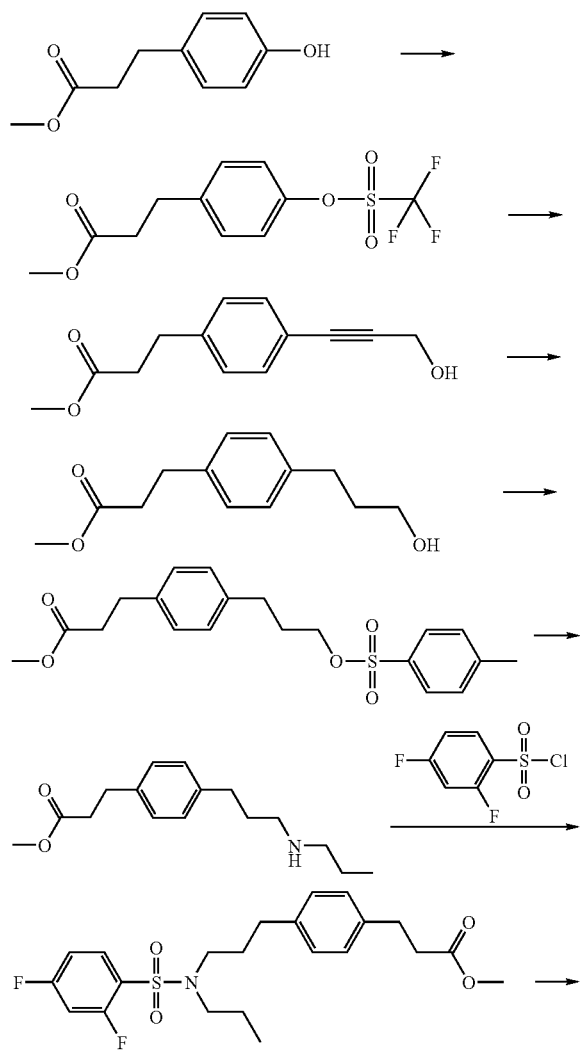

-continued

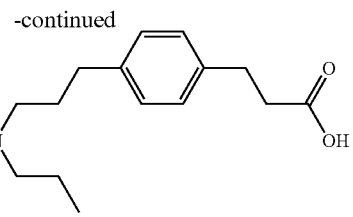

Step A 3-(4-Trifluoromethanesulfonyloxyphenyl)propionic acid methyl ester

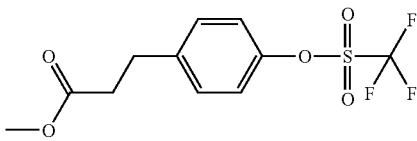

To a 500 mL round bottom flask under a nitrogen atmosphere were charged with methyl 3-(4-hydroxyphenyl propionate (10.0 g, 55.5 mmol) and phenyl N-phenyltriflimide (20.4 g, 57.2 mmol) dissolved in 150 mL anhydrous MeCl$_2$ (JOC, 55, 906-910, 1990). The stirred solution was cooled to 0° C. for 1 h and triethylamine was added dropwise (8.3 mL, 59.9 mmol). The reaction was allowed to warm up to ambient temperature and diluted with 500 mL ether, which was washed with water and brine, and then dried over Na$_2$SO$_4$ and concentrated. The crude material was purified by medium pressure HPLC normal phase silica gel chromatography utilizing a Biotage 65M cartridge eluting with 10:90 EtOAc:Hex to give a colorless oil (13.4 g, 77%). $^1$H NMR (400 MHz, CDCl$_3$) δ 2.64 (t, J=7.6 Hz, 2H), 2.98 (t, J=7.6 Hz. 2H), 3.67 (s, 3H), 7.19 (d, J=8.8 Hz, 2H), 7.28 (d, J=8.8 Hz, 2H), MS (ES) m/e 330 (M+NH$_4$).

Step B

3-[4-(3-Hydroxyprop-1-ynyl)phenyl]propionic acid methyl ester

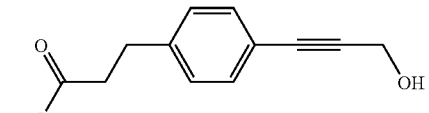

To a flame-dried 50 mL round bottom flask under an argon atmosphere were charged with 3-(4-trifluoromethanesulfonyloxyphenyl)propionic acid methyl ester (1.0 g (3.20 mmol), and propargyl alcohol (1.12 mL. 19.2 μmol) dissolved in anhydrous DMF, followed by the addition of triethylamine (1.78 mL. 12.8 mmol) and dichloridobis(triphenylphospine)-palladium (II) (0.112 g 0.16 mmol) (Heterocycles. 38, 2463-2472, 1994). The mixture was heated to 90° C. for 2 h. The mixture was concentrated, diluted with 200 mL EtOAc, washed with brine, dried over Na$_2$SO$_4$, and concentrated. The crude residue was purified using radial chromatography (25:

75 to 35:65 EtOAc:Hex) 10 give a yellow oil (0.29 g. 42%). $^1$H NMR (400 MHz, CDCl$_3$) δ 1.64 (t, J=6.1 Hz. 1H), 2.62 (t, J=7.8 Hz, 2H), 2.94 (t, J=7.8 Hz, 2H), 3.67 (s, 3H), 4.49 (d, J=5.9 Hz, 2H), 7.15 (d, J=8.3 Hz, 2H), 7.36 (d, J=8.3 Hz, 2H). MS (ES) m/e 219 (M+1).

Step C

3-[4-(3-Hydroxypropyl)phenyl]propionic acid methyl ester

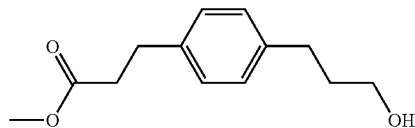

To a 100 mL round bottom flask was charged with 3-[4-(3-hydroxyprop-1-ynyl)phenyl]propionic acid methyl ester (1.0 g, 4.58 mmol) dissolved in 20 mL of THF. Pd/C (10%) was added and the reaction mixture was stirred under a balloon containing hydrogen for 16 h. The catalyst was filtered through celite, and the filtrate was concentrated to give a white solid (0.97 g, 97%). $^1$H NMR (400 MHz, CDCl$_3$) δ 1.25 (br s, 1H), 1.85-1.92 (m, 2H), 2.60-2.70 (m, 4H), 2.92 (t, J=7.8 Hz, 2H), 3.67 (s, 51), 7.12 (s, 4H). MS (ES) m/e 223 (M+1).

Step D

3-{4-[3-(Toluene-4-sulfonyloxy)propyl]phenyl}propionic acid methyl ester

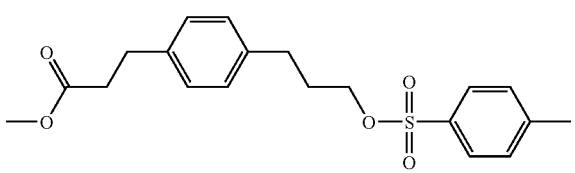

To a 250 round bottom flask was charged with 3-[4-(3-hydroxypropyl) phenyl]-propionic acid methyl ester (1.42 g. 6.39 mmol) dissolved in 25 mL of anhydrous MeCl$_2$, followed by the addition of 4-dimethylaminopyridine (0.23 g. 1.92 mmol) and pyridine (1.76 mL, 21.7 mmol). The compound of p-toluenesulfonic anhydride (2.50 g, 7.67 mmol) was added. The reaction mixture was stirred at ambient temperature for 16 h and treated with 25 mL 1N HCl and stirred vigorously for 1 h. The layers were separated and the MeCl$_2$ was washed with brine, dried over Na$_2$SO$_4$ and concentrated. The crude material was purified by medium pressure HPLC normal phase silica gel chromatography utilizing a Biotage 40L cartridge eluting with 15:85 EtOAc:Hex to give a yellow oil (1.95 g. 81%). $^1$H NMR (400 MHz. CDCl$_3$) δ 1.90-1.97 (m, 2H), 2.46 (s, 3H), 2.58-2.63 (m, 4H), 2.90 (t, J=7.8 Hz, 2H), 3.67 (s, 3H), 4.02 (t, J=6.4 Hz, 2H), 6.99 (d, J=7.8 Hz, 2H), 7.07 (d, J=7.8 Hz, 2H), 7.35 (d, J=7.8 Hz, 2H), 7.80 (d, J=8.3 Hz, 2H). MS (ES) m/e 377 (M+1).

Step E

3-[4-(3-Propylaminopropyl)phenyl]propionic acid methyl ester

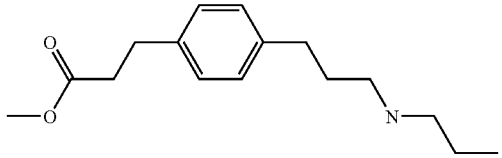

To a 250 mL round bottom flask was charged 3-{4-[3-(toluene-4-sulfonyloxy) propyl]phenyl}propionic acid methyl ester (1.82 g, 4.83 mmol) dissolved in 54 mL of anhydrous DMF, followed by the slow addition of n-propylamine (1.99 mL 24.17 mmol). The reaction mixture was stirred at ambient temperature for 18 h and then poured into 100 mL EtOAc and 50 mL water. The aqueous layer was washed with fresh EtOAc. The organic layers were combined washed with brine, dried over Na$_2$SO$_4$ and concentrated to give a thin yellow oil (1.3 g. quantitative). $^1$H NMR (400 MHz, CDCl$_3$) δ 0.91 (t, J=7.6 Hz, 3H), 1.85 (q, J=7.8 Hz, 2H), 2.19 (q, J=7.7 Hz, 2H), 2.57-2.65 (m, 4H), 2.78-2.91 (m, 6H), 3.67 (s, 3H), 7.09 (s, 4H), 9.40 (br s, 1H). MS (ES) m/e 264 (M+1).

Step F 3-(4-{3-[(2,4-Difluorobenzenesulfonyl)propylamino]propyl}phenyl)propionic acid To a 1 dram screw capped vial were charged with 3-[4-(3-propylaminopropyl) phenyl]propionic acid methyl ester (0.092 g, 0.30 mmol), triethylamine (0.42 mL, 3.0 mmol), and 2,4-difluorobenzenesulfonyl chloride (0.096 g, 0.17 mmol) in 1 mL anhydrous MeCl$_2$. The mixture was shaken at ambient temperature for 18 h. Next N,N-dimethylethylamine was added (0.033 mL. 0.30 mmol) and the vial was shaken for 1 h. After diluting with 1 mL MeOH, the reaction was poured into a 5 g SCX cartridge and eluted with 1:1 MeCl$_2$:MeOH. The solvent was removed under a stream of nitrogen, and the residue was transferred to a 50 mL Dyna Vac carousel glass tube with screw cap. The residue was dissolved in 1 mL EtOH, treated with 0.3 mL 5N NaOH. and heated to 55° C. for 2 h. After removing the solvent under a stream of nitrogen, the residue was diluted with 1 mL MeCl$_2$ and 0.5 mL 5N HCl and poured into a Varian ChemElut 1003 cartridge. The cartridge was eluted with MeCl$_2$. The eluent was concentrated under a stream of nitrogen. The crude residue was purified by mass-directed reverse phase HPLC to provide 0.041 g (32%) of the acid compound. MS (ES) m/e 513 (M+1).

The following Examples 388 to 392 were prepared according to the procedure described above in Example 387.

EXAMPLE 388

3-(4-{3-[(5-Chloro-3-methylbenzo[b]thiophene-2-sulfonyl)propylamino]propyl}phenyl) propionic acid

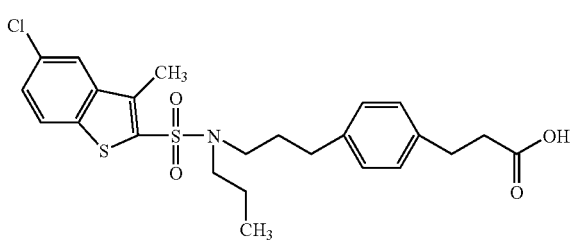

MS (ES) m/e 495 (M+1).

EXAMPLE 389

3-(4-{3-[Propyl(5-pyridin-2-ylthiophene-2-sulfonyl)amino]propyl}phenyl)propionic acid

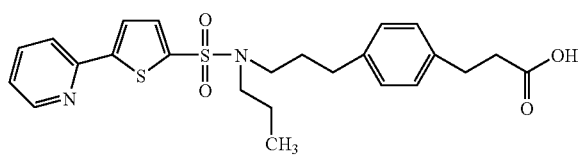

MS (ES) m/e 473 (M+1).

EXAMPLE 390

3-(4-{3-[Propyl(4-trifluoromethoxybenzenesulfonyl)amino]propyl}phenyl)propionic acid

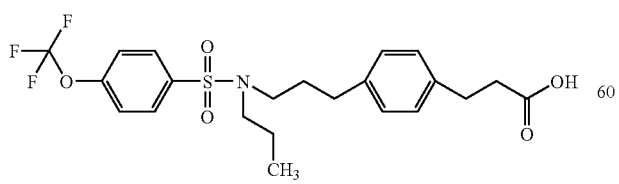

Ms (ES) m/e 474 (M+1).

EXAMPLE 391

3-(4-{3-[Propyl(4-trifluoromethylbenzenesulfonyl)amino]propyl}phenyl)propionic acid

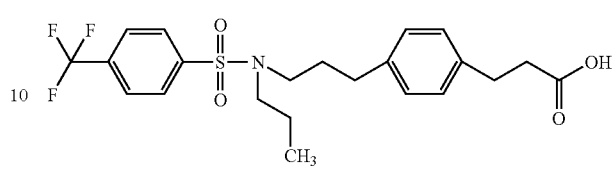

MS (ES) m/e 458 (M+1).

EXAMPLE 392

3-(4-{3-[(5-Fluoro-3-methylbenzo[b]thiophene-2-sulfonyl)propylamino]propyl}phenyl) propionic acid

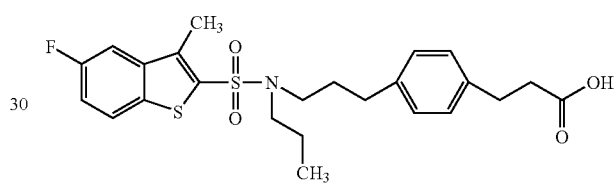

MS (ES) m/e 478 (M+1).

EXAMPLE 393

3-(4-{2-[(Biphenyl-4-sulfonyl)propylamino]ethyl}phenyl)propionic acid

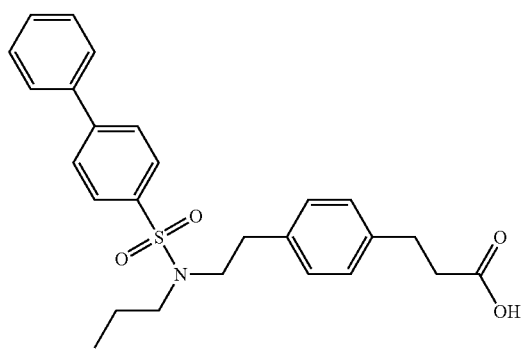

The compound of 3-(4-{2-[(biphenyl-4-sulfonyl)propylamino]ethyl}phenyl)propionic acid was prepared according to the scheme provided below:

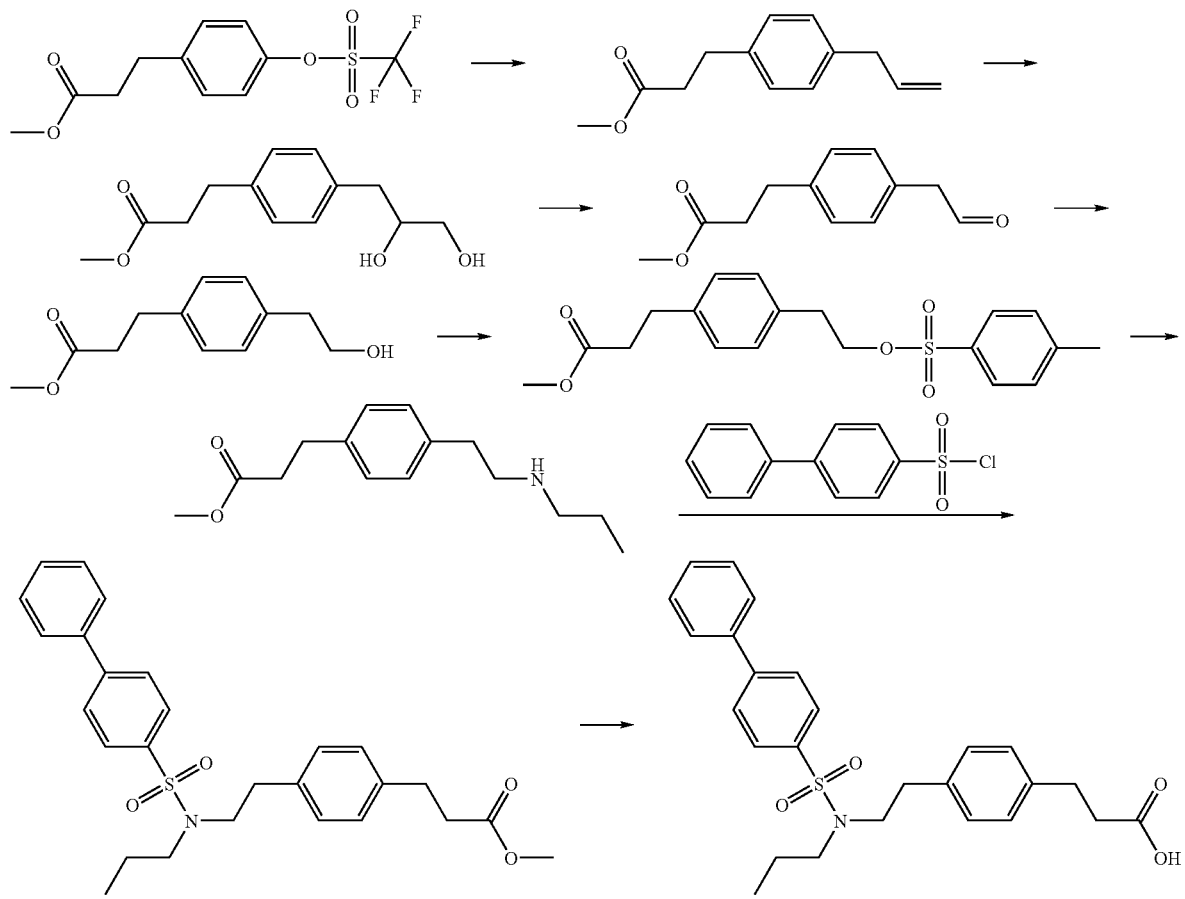

Step A

3-(4-Allylphenyl)propionic acid methyl ester

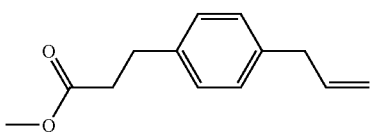

To a flame dried 250 mL round bottom flask under an argon atmosphere in 50 mL of anhydrous DMF were charged with 3-(4-trifluoromethanesulfonyloxyphenyl)-propionic acid methyl ester (2.0 g. 6.40 mmol), lithium chloride (2.28 g, 53.8 mmol), triphenyphosphine (1.01 g, 3.84 mmol), dichlorobis(triphenylphospine)palladium (II) (0.54 g, 0.77 mmol) and then allyltributylin (3.97 mL. 12.8 mmol) (JOC, 57, 678-685, 1992). The reaction was heated to 95° C. for 2.5 h. The solvent was concentrated, and the residue was dissolved in 300 mL EtOAc and washed with 200 mL 2N HCl (4×), 100 mL 5% KF (1×). brine, dried over Na$_2$ $_{SO4}$ and concentrated. The crude material was purified by medium pressure HPLC normal phase silica gel chromatography using a Biotage 65M cartridge eluting with 5:95 EtOAc:Hex. This oil was treated further with a saturated KF/ether trituration followed by an EtOAc extraction. The organic layer was washed with brine, dried over Na$_2$SO$_4$, and concentrated to give a colorless oil (0.56 g. 42%). MS (ES) m/e 205 (M+1).

Step B

3-[4-(2,3-Dihydroxypropyl)phenyl]propionic acid methyl ester

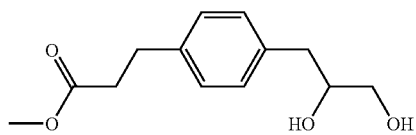

To a 250 mL round bottom flask was charged with 3-(4-allylphenyl)propionic acid methyl ester (10.2 g, 49.9 mmol) dissolved in 100 mL acetone followed by the addition of 4-methylmorpholine N-oxide (8.1 g, 59.9 mmol) and water (10 mL). Osmium tetroxide (3 chips) was added and the reaction was stirred at ambient temperature for 4 h. The reaction was poured into 500 mL EtOAc and washed twice with Na$_2$S$_2$O$_3$, brine, dried over Na$_2$SO$_4$ and concentrated to give a soft off-white solid (9.75 g, 81%). MS (ES) m/e 256 (M+NH$_4$).

Step C

3-[4-(2-Oxoethyl)phenyl]propionic acid methyl ester

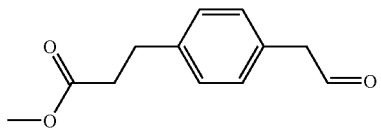

To a 100 mL round bottom flask was charged 3-[4-(2,3-dihydroxypropyl)phenyl]propionic acid methyl ester (0.82 g, 2.45 mmol) dissolved in 12 mL each of THF and water. Sodium periodate (1.57 g, 7.35 mmol) was added, and the reaction was stirred at ambient temperature for 2 h. The reaction was poured into 50 mL EtOAc and 25 mL brine. The organic layer was washed with $Na_2S_2O_3$ solution, brine, dried over $Na_2SO_4$ and concentrated to give a colorless oil (0.42 g, 83%). MS (ES) m/e 207 (M+1).

Step D

3-[4-(2-Hydroxyethyl)phenyl]propionic acid methyl ester

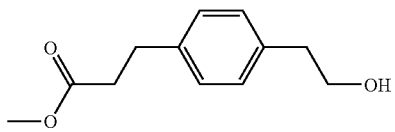

To a 250 mL round bottom flask was charged with 3-[4-(2-oxoethyl)phenyl]propionic acid methyl ester (2.11 g. 10.2 mmol) dissolved in 35 mL anhydrous THF and 25 mL anhydrous MeOH. The solution was cooled down in an ice bath followed by the portion-wise addition of sodium borohydride (0.58 g, 15.3 mmol). The cooling bath was removed, and the reaction mixture was stirred at ambient temperature for 2 h. The mixture was poured into 200 mL EtOAc and 100 mL ice water, and then 1N HCl (50 mL) was added slowly. The aqueous layer was discarded, and the organic layer was washed with brine, dried over $Na_2SO_4$ and concentrated. The crude residue was purified using radial chromatography (2:98 to 5:95 MeOH:$MeCl_2$) to give a white solid (0.89 g, 42%). MS (ES) m/e 226 (M+$NH_4$).

Step E

3-{4-[2-(Toluene-4-sulfonyloxy)ethyl]phenylpropionic acid methyl ester

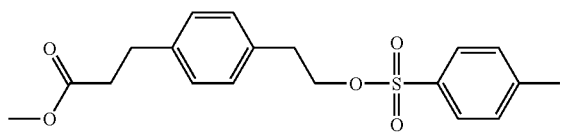

To a 100 round bottom flask was charged with 3-[4-(2-hydroxyethyl)phenyl]propionic acid methyl ester (0.89 g. 4.27 mmol) dissolved in 16 mL of anhydrous $MeCl_2$, followed by the addition of 4-dimethylaminopyridine (0.156 g, 1.28 mmol) and pyridine (1.17 mL, 14.5 mmol). The compound of p-toluenesulfonic anhydride (1.67 g. 5.13 mmol) was added, and the reaction was stirred at ambient temperature for 16 h. The reaction was treated with 15 mL 1N HCl and stirred vigorously for 1 h. The layers were separated, and the $MeCl_2$ was washed with brine, dried over $Na_2SO_4$ and concentrated. The crude residue was purified using radial chromatography (5:95 to 25:75 EtOAc:Hex) to give a yellow oil (1.3 g. 84%). MS (ES) m/e 380 (M+$NH_4$).

Step F

3-[4-(2-Propylaminoethyl)phenyl]propionic acid methyl ester

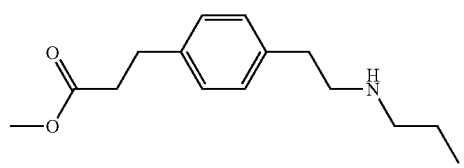

To a 250 mL round bottom flask was charged 3-{4-[2-(toluene-4-sulfonyloxy)ethyl]phenylpropionic acid methyl ester (1.28 g, 3.53 mmol) dissolved in 40 mL of anhydrous DMF. followed by the slow addition of n-propylamine (1.45 mL 17.66 mmol). The reaction was stirred at ambient temperature for 30 h and poured into 100 mL EtOAc and 50 mL water. The aqueous layer was washed with fresh EtOAc. The organic layers were combined, washed with brine, dried over $Na_2SO_4$ and concentrated to give a yellow oil (0.88 g, quantitative). MS (ES) m/e 250 (M+1).

Step G 3-(4-{2-[(Biphenyl-4-sulfonyl)propylamino]ethyl}phenyl)propionic acid A 50 mL glass tube with screw cap and nitrogen inlet was charged with sequentially with 3-[4-(3-propylaminopropyl)phenyl]propionic acid methyl ester (0.0 g, 0.40 mmol), anhydrous $MeCl_2$ (1.5 mL), triethylamine (0.17 mL, 1.2 mmol), and 4-biphenylsulfony) chloride (0.152 g, 0.60 mmol). The mixture was stirred at ambient temperature for 18 h and concentrated under a stream of $N_2$. The residue was dissolved in EtOH (1.5 mL), treated with 2N NaOH (0.40 mL, 2.0 mmol), and heated at 55° C. for 3 h. The mixture was concentrated under a stream of $N_2$. The residue was treated with $MeCl_2$ (2 mL), water (0.5 mL), and 5N HCl (0.64 mL, 3.2 mmol). The mixture was poured into a Varian ChemElut 1003 drying cartridge and was eluted with $MeCl_2$. The crude residue was purified by mass-directed reverse phase HPLC to provide 0.12 g (68%) of the final acid compound. MS (ES) m/e 513 (M+1).

The following Examples 394 and 395 were prepared according to the procedure described above in Example 393.

EXAMPLE 394

3-(4-{2-[(5-Chloro-3-methylbenzo[b]thiophene-2-sulfonyl)propylamino]ethyl}phenyl) propionic acid

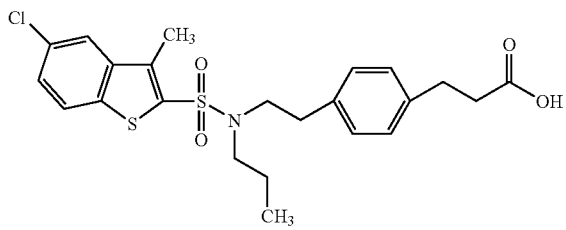

MS (ES) m/e 481 (M+1).

EXAMPLE 395

3-(4-{2-[(5-Fluoro-3-methylbenzo[b]thiophene-2-sulfonyl)propylaminoethyl}phenyl) propionic acid

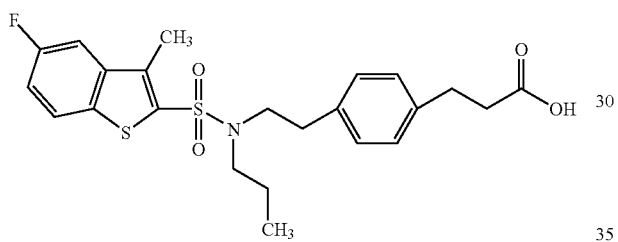

MS (ES) m/e 464 (M+1).

EXAMPLE 396

3-[4-hydroxy-2-(isopropoxycarbonylamino-methyl)-phenyl]-propionic acid tert-butyl ester

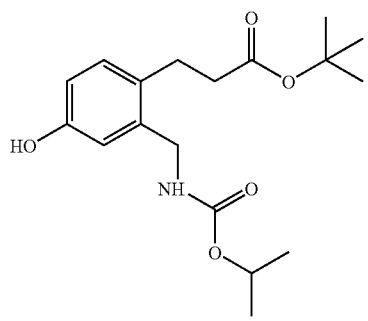

Slurry of 3-(2-aminomethyl-4-hydroxy-phenyl)-propionic acid tert-butyl ester (75.4 g. 0.3 mol) in CH$_2$Cl$_2$ (900 mL) at 1° C. was treated with triethylamine (60.7 g, 0.6 mol). Isopropyl chloroformate (300 mL. 0.3 mol. 1M in toluene) was added while maintaining the temperature less than 12° C. The resulting solution was stirred 16 h at ambient temperature. After 16 h. additional isopropyl chloroformate (15 mL, 0.015 mol, 1.0M in toluene) was added, and the reaction was stirred for 1 h. The reaction mixture was washed with 1N HCl (2×200 mL) and saturated NaHCO$_3$ solution (2×200 mL). The organic layer was dried (Na$_2$SO$_4$) and concentrated. The residue was purified by filtration through Merck silica gel 62 (750 grams. CH$_2$Cl$_2$/MeOH 100/0 to 96/4) to give the title compound (95.48 g, 94.3%). $^1$H NMR (300 MHz, CDCl$_3$): δ 1.20-1.24 (d, 6H), 1.40 (s, 9H), 2.46-2.52 (t, 2H), 2.81-2.86 (t, 2H), 4.29-4.32 (d, 2H), 4.86-4.97 (m, 1H), 5.19-5.28 (m, 1H), 6.67-6.72 (dd, 2H), 6.76 (s, 1H) 6.97-7.00 (d, 1H). MS (ES) m/z 336.1 [M−H]$^−$.

EXAMPLE 397

3-(2-{[(2,5-dichloro-thiophene-3-carbonyl)-amino]-methyl}-4-hydroxy-phenyl)-propionic acid tert-butyl ester

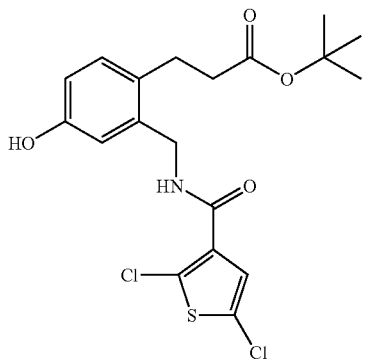

Step A 2,5-Dichloro-thiophene-3-carboxylic acid

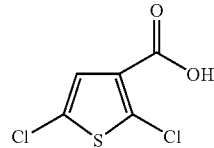

A mixture of the 1-(2,5-dichloro-thiophen-3-yl)-ethanone (10 g, 51.26 mmol) and 9.5% NaOCl (150 mL. 230 mmol, 4.5 eq., commercial bleach) was treated with 5N NaOH (1 mL, 5 mmol, 0.1 eq.). The mixture was stirred vigorously and heated to 55° C. The internal temperature was monitored closely and heat was removed to control the exotherm. After 6 h at 61° C., starting material was completely consumed. The mixture was cooled to 0° C. and carefully quenched with 20% aq. NaHSO$_3$ solution (20 mL). At 0° C., 6M HCl (12 mL) was added to adjust the pH to 1.5. The mixture was extracted with EtOAc (300 mL and 3×50 mL). The combined organic layers were washed with brine (200 mL), dried (Na$_2$SO$_4$), and concentrated to a white solid (8.8 g).

Step B 3-(2-{[(2,5-dichloro-thiophene-3-carbonyl)-amino]-methyl}-4-hydroxy-phenyl)-propionic acid tert-butyl ester A solution of the 2,5-dichloro-thiophene-3-carboxylic acid (12.9 g. 65.5 mmol) and 4-methylmorpholine (7.17 mL, 65.2 mmol) in dry THF (400 mL) was cooled to −15° C. Isobutyl chloroformate (8.46 mL, 65.2 mmol) was added. The mixture was stirred 3 min and triethylamine (9.1 mL. 65 mmol) was added. A solution of 3-(2-aminomethyl-4-hydroxy-phenyl)-propionic acid tert-butyl ester (16.4 g. 65.3 mmol) in DMF (130 mL) pre-cooled to −15° C. was added via cannula over 15 min. After stirring 1 h, TLC indicated complete reaction. The reaction mixture was allowed to warm to ambient temperature. Solids were removed by filtration and washed with THF (100 mL). The filtrate was diluted with Et$_2$O (500 mL) and washed with water (250 mL) then brine (150 mL). The organic layer was dried (Na$_2$SO$_4$) and concentrated. The crude brown oil was purified by silica gel chromatography (hexanes/EtOAc 2/1) and recrystallization (toluene) to afford the title compound as a white crystalline solid (22.3 g, 79.6%). MS (ES$^+$) m/z 430.1 [M+H]$^+$.

EXAMPLE 398

3-[2-(1,3-Dioxo-1,3-dihydro-isoindol-2-ylmethyl)-4-hydroxy-phenyl]-propionic acid tert-butyl ester

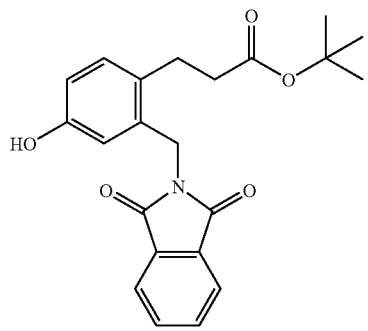

Step A (4-Bromo-3-methyl-phenoxy)-tert-butyl-dimethyl-silane

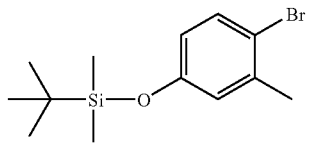

A 12 L flask was charged with 4-bromo-3-methyl phenol (428 g, 2.29 mol). CH$_2$Cl$_2$ (7.5 L). triethylamine (480 mL. 3.45 mol). and tert-butyldimethylsilyl chloride (324 g. 2.15 mol). To the solution was added 4-dimethylaminopyridine (15.0 g. 0.123 mol). The reaction mixture was stirred at ambient temperature overnight. The reaction was washed with saturated ammonium chloride (2.2 L) and then DI water (0.9 L). The organic layer was dried (Na$_2$SO$_4$), filtered, and concentrated to crude product (699 g). This material was purified by silica gel chromatography (heptane) to give the title compound (637 g. 98.5%).

Step B (4-Bromo-3-bromomethyl-phenoxy)-tert-butyl-dimethyl-silane

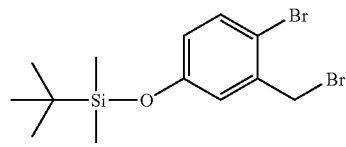

The compounds of (4-bromo-3-methyl-phenoxy)-tert-butyl-dimethyl-silane (255 g, 0.846 mol), dichloroethane (2.5 L), N-bromosuccinimide (165 g, 0.927 mol) and 2,2'-azobisisobutyronitrile (19.0 g, 0.116 mol) were combined in a 5 L flask. The mixture was degassed by evacuating and purging with N$_2$ (5×). The reaction mixture was heated to 47° C., and the heat was shut off. An exotherm to 76° C. occurred. GC analysis showed 6.5% unreacted starting material. The heat was applied again, and the reaction was held at reflux (83° C.) for 15 min. After cooling to 8° C., heptane (1.0 L) was added. The resulting slurry was stirred at 4° C. for 30 min and filtered. The filtrate was evaporated to dryness. The residue was treated with heptane (1 L), placed in the freezer overnight, and filtered. The filtrate was concentrated to the title compound (326 g, 101%).

Step C

2-[2-Bromo-5-(tert-butyl-dimethyl-silanyloxy)-benzyl]-isoindole-1,3-dione

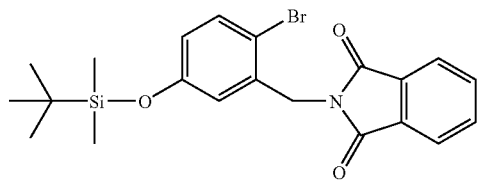

A 12 L flask was charged with (4-bromo-3-bromomethyl-phenoxy)-tert-butyl-dimethyl-silane (568 g 1.49 mol), DMF (3.1 L), and potassium phthalimide (316 g 1.71 mol). An exotherm to 34° C. occurred. After 40 min, the reaction mixture was cooled to 18° C. Ether (6.2 L) and DI water (4.9 L) were added, and the layers were separated. The organic layer was washed with saturated NaCl solution (2 L). dried (Na$_2$SO$_4$), filtered. and concentrated. The residue was recrystallized from heptane (1.5 L) to give the title compound (454 g 68%).

Step D

3-[2-(1,3-Dioxo-1,3-dihydro-isoindol-2-ylmethyl)-4-hydroxy-phenyl]-acrylic acid tert-butyl ester

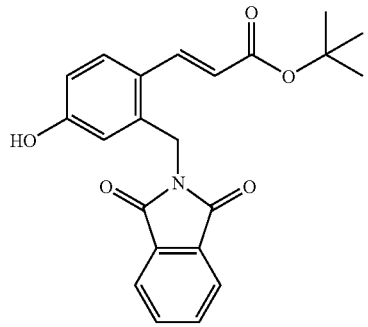

A 12 L flask was charged with 2-[2-bromo-5-(tert-butyl-dimethyl-silanyloxy)-benzyl]-isoindole-1,3-dione (461 g, 1.03 mol), propionitrile (7 L), tri-ortho-tolyl phosphine (76.0 g, 0.250 mol) and diisopropyl ethyl amine (365 mL, 2.10 mol). The reaction mixture was degassed/purged with $N_2$ (3×), and tert-butyl acrylate (465 mL, 3.17 mol) was added. After degassing/purging one time, palladium (II) acetate (28.0 g, 0.125 mol) was added. The stirred mixture was degassed/purged with $N_2$ three times and heated to 95° C. for 20 h. The mixture was filtered through a hyflo cake, washed with acetonitrile, and concentrated to a brown oil (841 g). The residue was dissolved in THF (3.5 L), and tetrabutylammonium fluoride (TBAF. 650 mL, 0.65 mol. 1M in THF) was added. After 1 h, additional TBAF (95 mL) was added. The mixture was rotated on the rotary evaporator for 10 min and was concentrated to crude product (987 g). This material was purified by silica gel chromatography (toluene/ethyl acetate, 100/0 to 75/25) to give the title compound (340 go 86.8%).

Step E

3-[2-(1,3-Dioxo-1,3-dihydro-isoindol-2-ylmethyl)-4-hydroxy-phenyl]-propionic acid tert-butyl ester A 1 gallon autoclave was charged with 3-[2-(1,3-dioxo-1,3-dihydro-isoindol-2-ylmethyl)-4-hydroxy-phenyl]-acrylic acid tert-butyl ester (196 g, 0.517 mol), ethyl acetate (2.6 L) and 5% palladium on carbon (75 g). The autoclave was kept at 25° C. under 60 psi of hydrogen for 21 h. The temperature of the reaction was increased to 40° C. and the pressure was increased to 75 psi for 5 h. The mixture was filtered through a pad of hyflo and concentrated to the title compound (186 g, 94.4%). MS (ESI) m/z 380.2 (M−H)⁻.

EXAMPLE 399

3-[4-{2-[(5-Chloro-3-methyl-benzo[b]thiophene-2-sulfonyl)-propyl-amino]-ethoxy}-2-(isopropoxycarbonylamino-methyl)-phenyl]-propionic acid

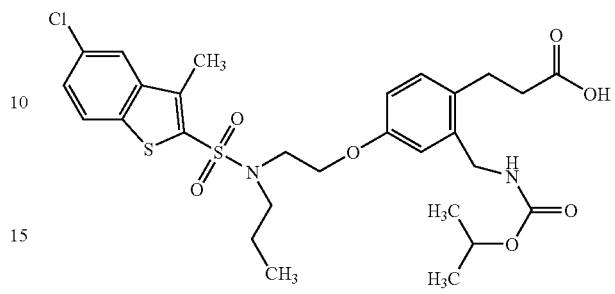

A mixture of 3-[4-hydroxy-2-(isopropoxycarbonylamino-methyl)-phenyl]-propionic acid tert-butyl ester (34 mg, 0.10 mmol) (see Example 396), toluene-4-sulfonic acid 2-[(5-chloro-3-methyl-benzo[b]thiophene-2-sulfonyl)-propyl-amino]-ethyl ester (55 mg, 0.110 mmol), and potassium carbonate (100 mg, 0.725 mmol, 100 mesh) in DMF (1 mL) was heated to 65° C. for 18 h. The mixture was quenched with water (15 mL) and extracted with EtOAc (2×15 mL). The organic layer was dried ($Na_2SO_4$) and concentrated. The crude product was purified by silica gel chromatography (20-40% EtOAc/Hex). The ester was dissolved in $CH_2Cl_2$ (1 mL), treated with TFA (0.3 mL) and water (0.05 mL), and stirred at ambient temperature for 2 h. The solution was concentrated to give the title compound. MS (ESI) m/z 611.2 (M+H)⁺.

The following Examples 400 to 404 were prepared according to the procedure described above in Example 399 by using an appropriate headpiece as described in Examples 396 to 398.

EXAMPLE 400

3-(2-{[(2,5-Dichloro-thiophene-3-carbonyl)-amino]-methyl}-4-{2-[propyl-(4-trifluoromethyl-benzene-sulfonyl)-amino]-ethoxy}-phenyl)-propionic acid

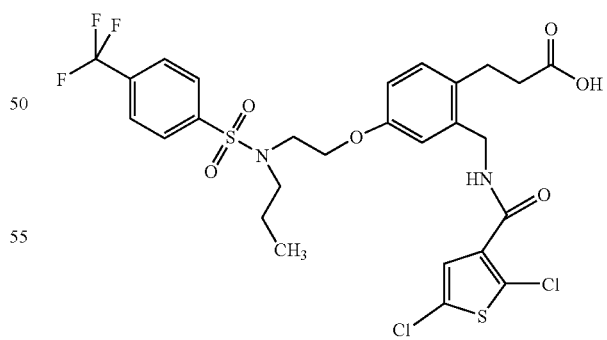

¹H NMR (400 MHz, CDCl₃) δ 0.78 (t, J=7.3 Hz, 3H), 1.51-1.56 (m, 2H), 2.60 (t, J=7.6 Hz, 2H), 2.89 (t, J=7.3 Hz, 2H), 3.13 (apparent t, J=7.6 Hz, 2H), 3.44 (t, J=5.9 Hz, 2H), 4.01 (t, J=6.1 Hz, 2H), 4.52 (d, J=5.4 Hz. 2H), 6.60 (dd, J=2.6, 8.1 Hz, 1H), 6.70-6.74 (m, 1H), 6.73 (d, J=2.9 Hz, 1H), 7.03 (d, J=8.3 Hz, 1H), 7.12 (s, 1H), 7.65 (d, J=8.3 Hz, 2H), 7.85 (d, J=8.3 Hz, 2H).

EXAMPLE 401

3-(2-(Isopropoxycarbonylamino-methyl)-4-{2-[propyl-(4-trifluoromethyl-benzenesulfonyl)-amino]-ethoxy}-phenyl)-propionic acid

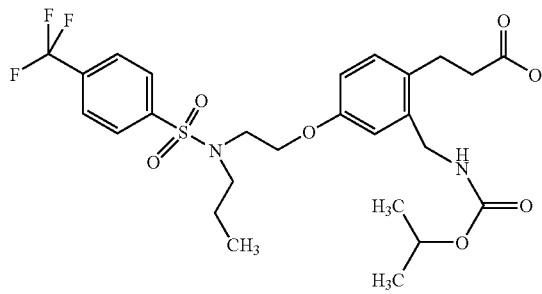

MS (ESI) m/z 575.3 (M+H)+.

EXAMPLE 402

3-(2-{[(2,5-Dichloro-thiophene-3-carbonyl)-amino]-methyl}-4-{2-[(naphthalene-2-sulfonyl)-propyl-amino]-ethoxy}-phenyl)-propionic acid

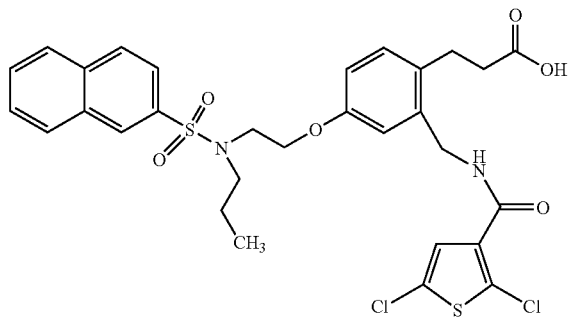

MS (ESI) m/Z 649.1 (M+H)+.

EXAMPLE 403

3-(4-{2-[Biphenyl-4-sulfonyl)-propyl-amino]-ethoxy}-2-{[(2,5-dichloro-thiophene-3-carbonyl)-amino]-methyl}-phenyl)-propionic acid

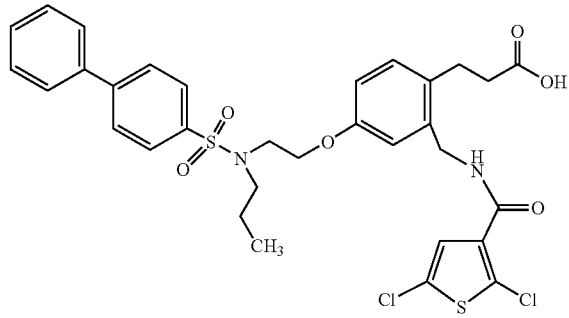

MS (ESI) m/z 675.2 (M+H)+.

EXAMPLE 404

3-[4-{2-[(4-Butoxy-benzenesulfonyl)-propyl-amino]-ethoxy}-2-(1,3-dioxo-1,3-dihydro-isoindol-2-ylmethyl)-phenyl]-propionic acid

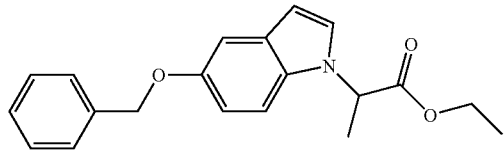

MS (ESI) m/z 623.2 (M+H)+.

EXAMPLE 405

2-(5-{2-[(5-Fluoro-3-methyl-benzo[b]thiophene-2-sulfonyl)-propyl-amino]ethoxy}-indol-1-yl)-propionic acid

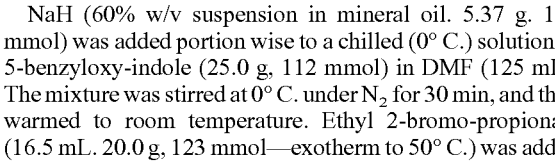

Step A 2-(5-Benzyloxy-indol-1-yl)-propionic acid ethyl ester

NaH (60% w/v suspension in mineral oil. 5.37 g. 134 mmol) was added portion wise to a chilled (0° C.) solution of 5-benzyloxy-indole (25.0 g, 112 mmol) in DMF (125 mL). The mixture was stirred at 0° C. under $N_2$ for 30 min, and then warmed to room temperature. Ethyl 2-bromo-propionate (16.5 mL. 20.0 g, 123 mmol—exotherm to 50° C.) was added and the mixture was headed to 70° C. overnight. The mixture was cooled to 0° C. and NaH (2.5 g, 62.5 mmol) and DMF (90 mL) were added. The mixture was warmed to room temperature for 30 min, and ethyl 2-bromo-propionate (8 mL, 11.2 g, 60 mmol) was added. The mixture was heated to 70° C.

overnight, cooled to room temperature, and diluted with ethyl acetate (300 mL). Organics were washed twice with 1.00N HCl (200 mL), dried (MgSO4), filtered, and concentrated. Crude material was purified by silica gel chromatography (800 g) eluting with 92:8 hexanes:EtOAc to afford 10.2 g (28%) of the title compound as a pink oil. $^1$H-NMR (CDCl$_3$) δ 1.25 (t, 3H), 1.83 (d, 3H), 4.20 (g, 2H), 5.09 (q, 1H), 5.15 (s, 2H), 6.52 (d, 1H), 7.00 (dd, 1H), 7.20 (d, 1H), 7.27 (d, 2H), 7.33-7.46 (m, 3H), 7.51 (dd, 2H); MS [ES] 324 (M+H).

Step B 2-(5-Hydroxy-indol-1-yl)-propionic acid ethyl ester

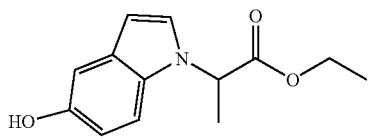

To a solution of 2-(5-benzyloxy-indol-1-yl)-propionic acid ethyl ester (7.0 g, 21 mmol) in EtOH (90 mL) was added 5% Pd/C (875 mg). The resulting mixture was shaken for 6 h at room temperature under H$_2$ (60 psi), which was then filtered and concentrated to afford 4.0 g (87%) of the title compound as a tan oil.) $^1$H-NMR (CDCl$_3$) δ 1.12 (t, 3H), 1.71 (d, 3H), 4.08 (q, 2H), 4.97 (q, 1H) 6.35 (d, 1H), 6.69 (dd, 1H), 6.94 (d, 1H), 7.08 (d, 1H), 7.16 (d, 1H); MS [ES] 234 (M+H).

Step C

2-[5-(2-Hydroxy-ethoxy)-indol-1-yl]-propionic acid ethyl ester

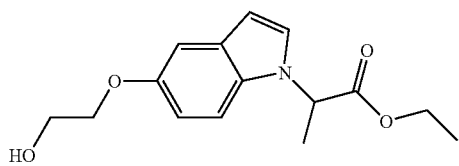

A mixture of 2-(5-hydroxy-indol-1-yl)-propionic acid ethyl ester (3.75 g, 16.1 mmol), ethylene carbonate (7.08 g, 80.4 mmol). DABCO (270 mg, 2.4 mmol), Na$_2$SO$_4$ (2 g, 14 mmol), and tert-butanol (30 mL) was heated 10 reflux for 45 min and stirred at room temperature overnight. The mixture was concentrated in-vacuo, and diluted with 1.00N HCl and water, which was then extracted into ethyl acetate, dried (MgSO$_4$), filtered, and concentrated. The resulting material was purified on silica gel (600 g) by eluting with 80:20 hexanes:EtOAc to afford 3.16 g (71%) of the title compound as a yellow oil. MS [ES] 278 (M+H).

Step D

2-{5-[2-(Toluene-4-sulfonyloxy)-ethoxy]-indol-1-yl}-propionic acid ethyl ester

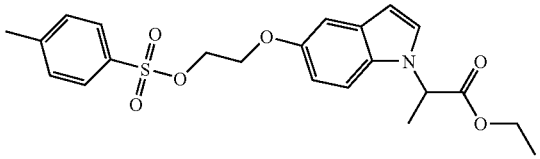

Standard Procedure (I), which described in Example 261 was utilized with 2-[5-(2-hydroxy-ethoxy)-indol-1-yl]-propionic acid ethyl ester to afford the title compound as a colorless oil. $^1$H-NMR (CDCl$_3$) δ 1.23 (t, 3H), 1.83 (d, 3H), 2.48 (s, 3H), 4.19 (m, 4H), 4.42 (t, 2H), 5.08 (q, 1H), 6.48 (d, 1H), 6.78 (dd, 1H), 7.00 (d, 1H), 7.21 (d, 1H), 7.28 (d, 1H), 7.36 (d, 2H), 7.86 (d, 2H); MS [ES] 432 (M+H).

Step E

2-[5-(2-Propylamino-ethoxy)-indol-1-yl]-propionic acid ethyl ester

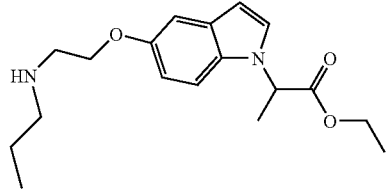

Standard Procedure (J) which described in Example 262 was utilized with 2-{5-[2-(toluene-4-sulfonyloxy)-ethoxy]-indol-1-yl}-propionic acid ethyl ester to afford the title compound as a tan oil. $^1$H-NMR (CDCl$_3$) δ 0.88 (t, 3H), 1.14 (t, 3H), 1.50 (m, 2H), 1.73 (d, 3H), 2.20 (br s, 1H), 2.61 (t, 2H), 2.99 (t, 2H), 4.07 (m, 4H), 5.00 (q, 1H), 6.41 (d, 1H), 6.80 (dd, 1H), 7.03 (d, 1H), 7.16 (m, 2H); MS [ES] 319 (M+H).

Step F 2-(5-{2-[(5-Fluoro-3-methyl-benzo[b]thiophene-2-sulfonyl)-propyl-amino]-ethoxy}-indol-1-yl)-propionic acid Standard Procedure (A) which described in Example 253 was utilized with 2-[5-(2-propylamino-ethoxy)-indol-1-yl]-propionic acid ethyl ester and 5-fluoro-3-methyl-benzo[b]thiophene-2-sulfonyl chloride to prepare the title compound. $^1$H-NMR; MS [ES] 519 (M+H), 517 (M–H).

The following Examples 406 and 407 were prepared according to the procedure described above in Example 405 by using the appropriate sulfonyl chlorides.

EXAMPLE 406

2-(5-{2-[Propyl-(5-pyridin-2-yl-thiophene-2-sulfonyl)-amino]-ethoxy}-indol-1-yl)-propionic acid

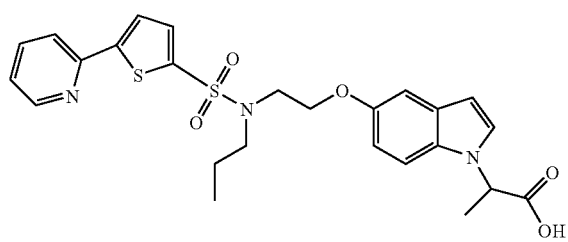

¹H-NMR: MS [ES] 514 (M+H), 512 (M–H).

EXAMPLE 407

2-(5-{2-[(3-Methyl-benzo[b]thiophene-2-sulfonyl)-propyl-amino]-ethoxy}-indol-1-yl)-propionic acid

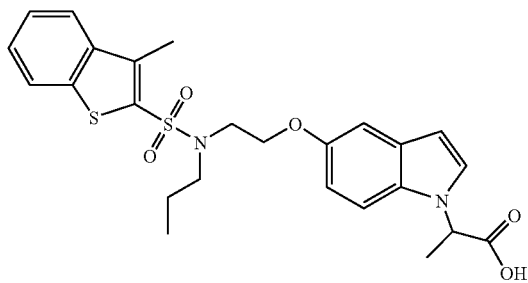

¹H-NMR: MS [ES] 501 (M+H), 499 (M–H)

EXAMPLE 408

2-(5-{2-[(5-Fluoro-3-methyl-benzo[b]thiophene-2-sulfonyl)-propyl-amino]-ethoxy}-indol-1-yl)-2-methyl-propionic acid

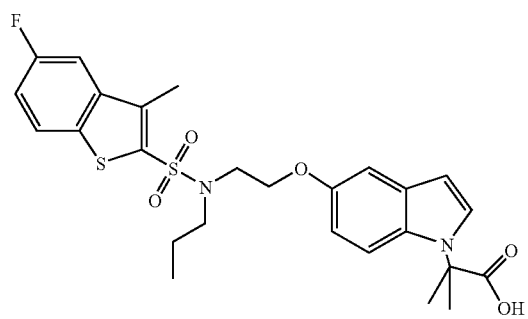

Step A 2-(5-Benzyloxy-indol-1-yl)-2-methyl-propionic acid ethyl ester

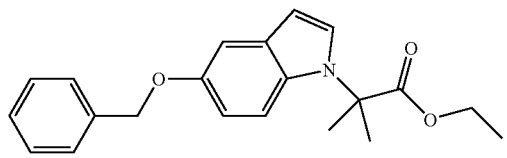

LDA (2M in THF, 18.9 mL, 37.9 mmol) was added slowly (exothermic) to a chilled (−78° C.) solution of 2-(5-benzyloxy-indol-1-yl)-propionic acid ethyl ester (10.2 g, 31.5 mmol) in THF (90 mL) under $N_2$. The reaction mixture was stirred for 30 min under $N_2$ at −78° C., and $CH_3I$ (3.93 mL. 8.95 g. 63.1 mmol) was added. The mixture was warmed up to room temperature and concentrated in vacuo. The residue was diluted with $H_2O$ and extracted into EtOAc, which was then dried ($MgSO_4$), filtered, and concentrated. The material was purified by silica gel chromatography (300 g) by eluting with 90:10 hexanes/EtOAc to afford 7.28 g (68%) of the title compound as a yellow oil. ¹H-NMR (CDCl₃) δ 1.03 (t, 3H), 1.79 (s, 6H), 4.07 (q, 2H), 5.02 (s, 2H), 6.38 (d, 1H), 6.81 (dd, 1H), 7.02 (d, 1H), 7.09 (d, 1H), 7.16 (t, 1H), 7.22-7.35 (m, 3H), 7.40 (d, 2H); MS [ES] 338 (M+H).

Step B 2-(5-Hydroxy-indol-1-yl)-2-methyl-propionic acid ethyl ester

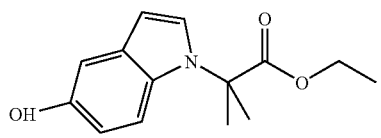

The procedure described in Example 405, Step B was used with 2-(5-benzyloxy-indol-1-yl)-2-methyl-propionic acid ethyl ester to afford the title compound as a yellow oil. ¹H-NMR (CDCl₃) δ 1.04 (t, 3H), 1.78 (s, 6H), 4.07 (q, 2H), 4.69 (br s, 1H), 6.31 (d, 1H), 6.65 (dd, 1H), 6.95 (d, 1H), 7.17 (d, 1H), 7.19 (s, 1H); MS [ES] 248 (M+H).

Step C

2-[5-(2-Bromo-ethoxy)-indol-1-yl]-2-methyl-propionic acid ethyl ester

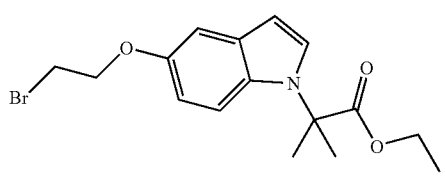

Standard Procedure (H) which described in Example 260 was utilized with 2-(5-hydroxy-indol-1-yl)-2-methyl-propionic acid ethyl ester to prepare the title compound as a colorless oil. $^1$H-NMR (CDCl$_3$) δ 1.14 (t, 3H), 1.89 (s, 1H), 3.78 (t, 2H), 4.18 (q, 2H), 4.46 (t, 2H), 6.46 (d, 1H), 6.86 (dd, 1H), 7.13 (d, 1H), 7.29 (d, 1H), 7.30 (s, 1H); MS [ES] 354, 356 (M+H).

Step D

2-Methyl-2-[5-(2-propylamino-ethoxy)-indol-1-yl]-propionic acid ethyl ester

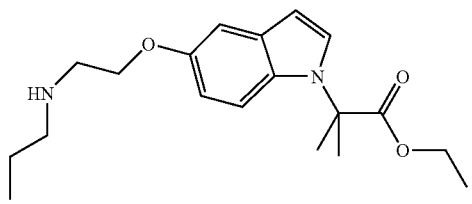

Standard Procedure (J) which described in Example 262 was utilized with 2-[5-(2-bromo-ethoxy)-indol-1-yl]-2-methyl-propionic acid ethyl ester to prepare the title compound as a yellow oil. $^1$H-NMR (CDCl$_3$) δ 0.87 (t, 3H), 1.03 (t, 3H), 1.52 (m, 2H), 1.80 (s, 6H), 2.16 (br s, 1H), 2.64 (t, 2H), 2.98 (t, 2H), 4.06 (m, 4H), 6.36 (d, 1H), 6.74 (dd, 1H), 7.00 (d, 1H), 7.13 (d, 1H), 7.18 (d, 1H): MS [ES] 333 (M+H).

Step E 2-(5-{2-[(5-Fluoro-3-methyl-benzo[b]thiophene-2-sulfonyl)-propyl-amino]-ethoxy}-indol-1-yl)-2-methyl-propionic acid Standard Procedure (A) which described in Example 253 was utilized with 2-methyl-2-[5-(2-propylamino-ethoxy)-indol-1-yl]-propionic acid ethyl ester and 5-fluoro-3-methyl-benzo[b]thiophene-2-sulfonyl chloride to prepare the title compound. $^1$H-NMR: MS [ES] 533 (M+H), 531 (M−H).

The following Examples 409 to 41 were prepared according to the procedure described above in Example 408.

EXAMPLE 409

2-Methyl-2-(5-{2-[(3-methylbenzo[b]thiophene-2-sulfonyl)-propyl-amino]-ethoxy}-indol-1-yl)-propionic acid

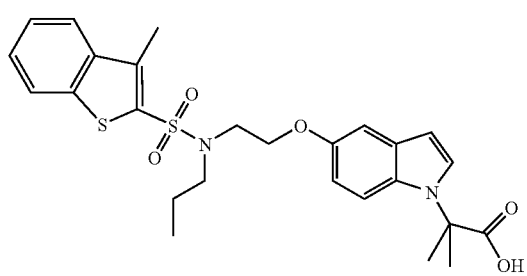

$^1$H-NMR; MS [ES] 515 (M+H), 513 (M−H).

EXAMPLE 410

2-Methyl-2-(5-{2-[propyl-(5-pyridin-2-yl-thiophene-2-sulfonyl)-amino]-ethoxy}-indol-1-yl)-propionic acid

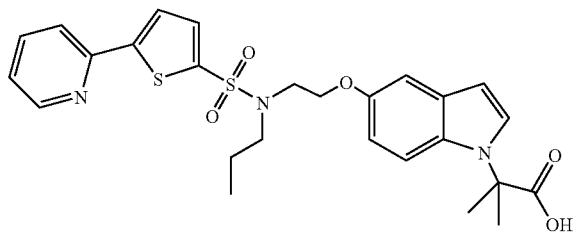

$^1$H-NMR; MS [ES] 528 (M+H), 526 (M−H).

EXAMPLE 411

2-Methyl-2-(5-{2-[(naphthalene-2-sulfonyl)-propyl-amino]-ethoxy}-indol-1-yl)-propionic acid

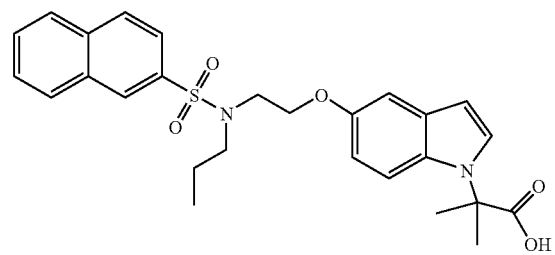

$^1$H-NMR: MS [ES] 495 (M+H), 493 (M−H).

EXAMPLE 412

2-(5-{2-[(5-Chloro-3-methyl-benzo[b]thiophene-2-sulfonyl)-propyl-amino]-ethoxy}-indol-1-yl)-2-methyl-propionic acid

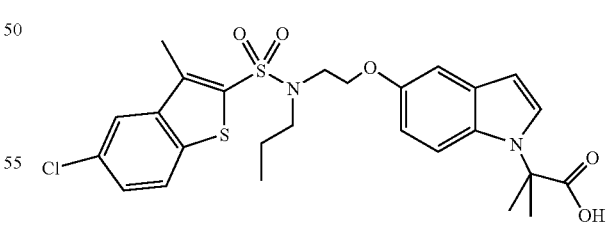

The title compound was prepared by following the procedure described in Example 74, Step C by using 2-(5-hydroxy-indol-1-yl)-2-methyl-propionic acid ethyl ester to afford the compound as a white solid. $^1$H-NMR (CDCl$_3$) δ 0.85 (t, 3H), 1.63 (m, 2H), 1.84 (s, 6H), 2.60 (s, 3H), 3.30 (m, 2H), 3.61 (t, 2H), 4.08 (t, 2H), 6.33 (d, 1H), 6.62 (dd, 1H), 6.89 (d, 1H), 7.03 (d, 1H), 7.19 (d, 1H), 7.36 (dd, 1H), 7.66 (m, 2H); MS [ES] 549 (M+H), 547 (M−H).

EXAMPLE 413

2-(5-{3-[(5-Fluoro-3-methyl-benzo[b]thiophene-2-sulfonyl)-propyl-amino]-propyl}-indol-1-yl)-propionic acid

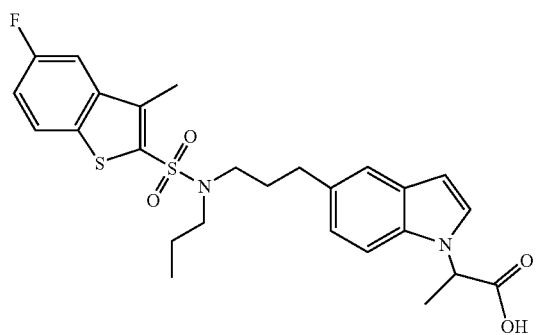

Step A 2-(5-Iodo-indol-1-yl)-propionic acid ethyl ester

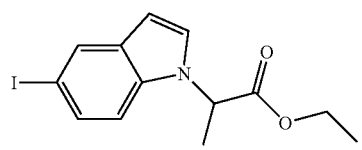

The title compound was prepared by following the procedure described in Example 387. Step A by using 5-iodoindole to prepare the title compound as a colorless oil. $^1$H-NMR (CDCl$_3$) δ 1.23 (t, 3H), 1.84 (d, 3H), 4.19 (q, 2H), 5.10 (q, 1H), 6.52 (d, 1H), 7.12 (d, 1H), 7.26 (d, 1H), 7.47 (dd, 1H), 7.99 (d, 1H): MS [ES] 344 (M+H).

Step B

2-[5-(3-Hydroxy-prop-1-ynyl)-indol-1-yl]-propionic acid ethyl ester

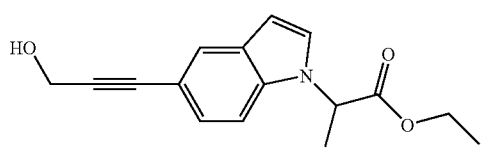

Propargyl alcohol (6.11 mL, 5.88 g, 105 mmol) in DMF (10 mL) was added slowly to a mixture of 2-(5-iodo-indol-1-yl)-propionic acid ethyl ester (6.00 g, 17.5 mmol), Et$_3$N (9.75 mL, 7.08 g, 70.0 mmol), and Pd(PPh$_3$)$_2$Cl$_2$ (614 mg, 0.87 mmol) in DMF (35 mL). The mixture was stirred at room temperature under N$_2$ for 40 h, and concentrated in-vacuo, which was then diluted with 0.1 N HCl and extracted into ethyl acetate. The material was dried (MgSO$_4$), filtered, and concentrated. Crude product was purified on silica gel (500 g) by eluting with 75:25 hexanes:EtOAc to afford 620 mg (13%) of the title compound as a brown oil. $^1$H-NMR (CDCl$_3$) δ 1.23 (t, 3H), 1.84 (d, 3H), 4.20 (q, 2H), 4.55 (d, 2H), 5.14 (q, 1H), 6.57 (d, 1H), 7.30 (m, 3H), 7.77 (s, 1H); MS [ES] 272 (M+H).

Step C

2-[5-(3-Hydroxy-propyl)-indol-1-yl]-propionic acid ethyl ester

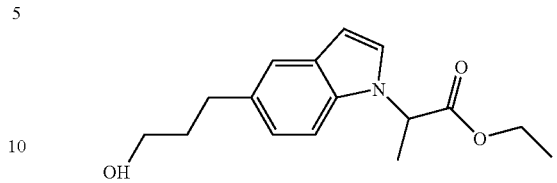

Palladium on carbon (10%, Pd/C) (50 mg) was added to a solution of 2-[5-(3-hydroxy-prop-1-ynyl)-indol-1-yl]-propionic acid ethyl ester (1.16 g, 4.26 mmol) in EtOH (30 mL) and the mixture was stirred at room temperature overnight under a balloon of H$_2$. The mixture was filtered and concentrated to afford 940 mg (80%) of the title compound as a brown oil. $^1$H-NMR (CDCl$_3$) δ 1.14 (t, 3H), 0.73 (d, 3H), 1.86 (m, 2H), 2.73 (t, 2H), 3.62 (t, 2H), 4.10 (q, 2H), 5.02 (q, 1H), 6.44 (d, 1H), 6.98 (dd, 1H), 7.16 (d 1H), 7.37 (d, 1H); MS [ES] 276 (M+H).

Step D

2-{5-[3-(Toluene-4-sulfonyloxy)-propyl]-indol-1-yl}-propionic acid ethyl ester

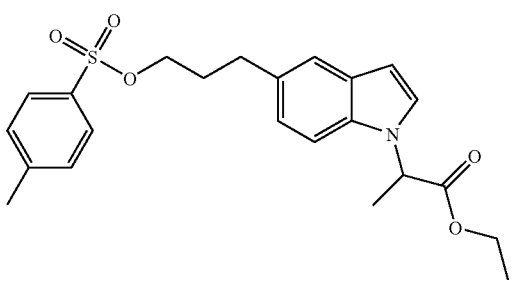

Standard Procedure (I) which described in Example 261 was utilized with 2-[5-(3-hydroxy-propyl)-indol-1-yl]-propionic acid ethyl ester to afford the title compound as a yellow oil. $^1$H-NMR (CDCl$_3$) δ 1.23 (t, 3H), 1.81 (d, 3H), 2.01 (m, 2H), 2.47 (s, 3H), 2.75 (t, 2H), 4.07 (t, 2H), 4.18 (q, 2H), 5.10 (q, 1H), 6.48 (d, 1H), 6.95 (dd, 1H), 7.23 (d, 1H), 7.26 (d, 1H), 7.29 (s, 1H), 7.35 (d, 2H), 7.82 (d, 2H); MS [ES] 430 (M+H).

Step E

2-[5-(3-Propylamino-propyl)-indol-1-yl]-propionic acid ethyl ester

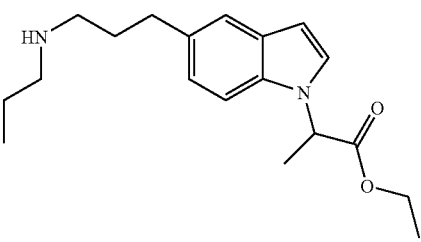

Standard Procedure (J) described in Example 262 was utilized with 2-{5-[3-(toluene-4-sulfonyloxy)-propyl]-indol-1-yl}-propionic acid ethyl ester to afford the title compound as a yellow solid. $^1$H-NMR (CDCl$_3$) δ 0.80 (t, 3H), 1.14 (t, 3H), 1.50 (m, 2H), 1.72 (d, 3H), 1.87 (m, 2H), 2.56 (t, 2H), 2.65 (m, 4H), 3.10 (br s, 1H), 4.08 (q, 2H), 5.02 (q, 1H), 6.41 (d, 1H), 6.94 (dd, 1H), 7.18 (d, 1H), 7.32 (d, 1H), 7.67 (d, 1H); MS [ES] 317 (M+H).

Step F 2-(5-{3-[(5-Fluoro-3-methyl-benzo[b]thiophene-2-sulfonyl)-propyl-amino]-propyl}-indol-1-yl)-propionic acid Standard Procedure (A) which described in Example 253 was utilized with 2-[5-(3-ropylamino-propyl)-indol-1-yl]-propionic acid ethyl ester and 5-fluoro-3-methyl-benzo[b]thiophene-2-sulfonyl chloride to prepare the title compound. $^1$H-NMR; MS [ES] 517 (M+H), 515 (M−H).

The following Examples 414 to 417 were prepared according to the procedure described above in Example 413.

EXAMPLE 414

2-(5-{3-[(Naphthalene-2-sulfonyl)-propyl-amino]-propyl}-indol-1-yl)-propionic acid

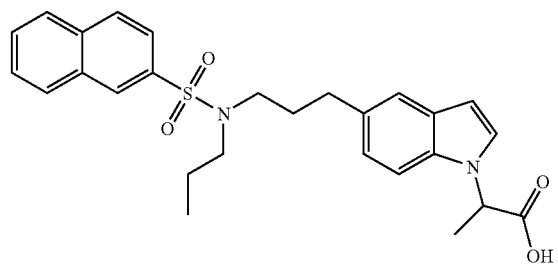

$^1$H-NMR; MS [ES] 479 (M+H), 477 (M−H).

EXAMPLE 415

2-(5-{3-[Propyl-(5-pyridin-2-yl-thiophene-2-sulfonyl)-amino]-propyl}-indol-1-yl)-propionic acid

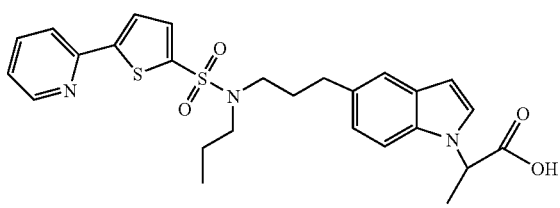

$^1$H-NMR: MS [ES] 512 (M+H), 510 (M−H).

EXAMPLE 416

2-(5-{3-[(5-Chloro-3-methyl-benzo[b]thiophene-2-sulfonyl)-propyl-amino]-propyl}-indol-1-yl)-propionic acid

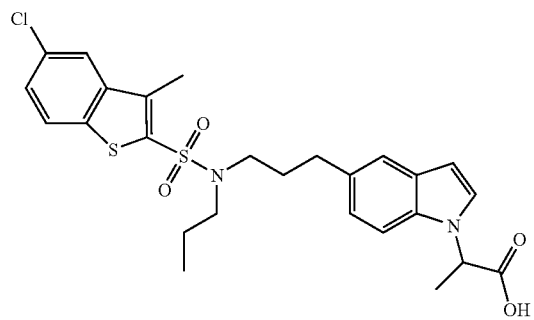

$^1$H-NMR MS [ES] 533 (M+H), 531 (M−H).

EXAMPLE 417

2-(5-{3-[(3-Methyl-benzo[b]thiophene-2-sulfonyl)-propyl-amino]-propyl}-indol-1-yl)-propionic acid

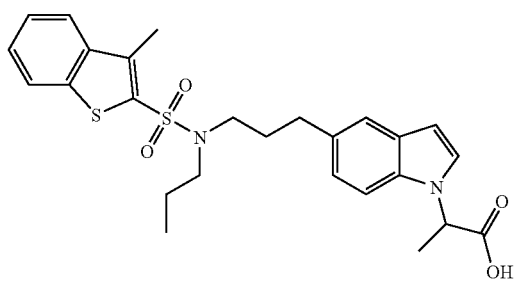

$^1$H-NMR: MS [ES] 499 (M+H), 497 (M−H).

EXAMPLE 418

2-(5-{3-[(5-Fluoro-3-methyl-benzo[b]thiophene-2-sulfonyl)-propyl-amino]-propyl}-indol-1-yl)-2-methyl-propionic acid

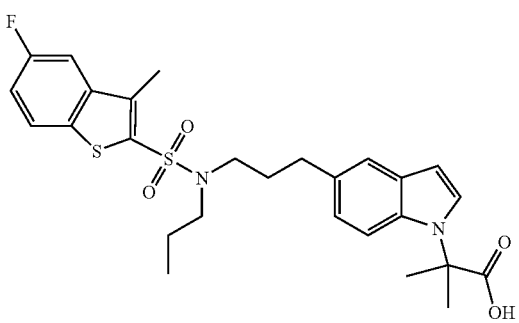

Step A

2-(5-Iodo-indol-1-yl)-2-methyl-propionic acid ethyl ester

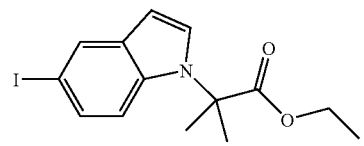

The title compound was prepared by following the procedure described in Example 390, Step A by utilizing 2-(5-iodo-indol-1-yl)-propionic acid ethyl ester to afford the compound as a yellow oil. $^1$H-NMR (CDCl$_3$) δ 1.14 (t, 3H), 1.90 (s, 6H), 4.18 (q, 2H), 6.47 (d, 1H), 6.99 (d, 1H), 7.28 (d, 1H), 7.41 (dd, 1H), 7.99 (d, 1H); MS [ES] 358 (M+H).

Step B

2-[5-(3-Hydroxy-prop-1-ynyl)-indol-1-yl]-2-methyl-propionic acid ethyl ester

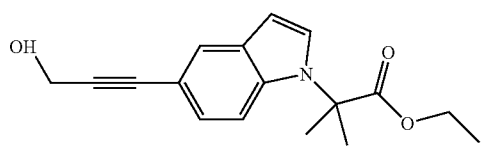

The title compound was prepared by following the procedure described in Example 395, Step B by using 2-(5-iodo-indol-1-yl)-2-methyl-propionic acid ethyl ester to afford the title compound as a brown solid. $^1$H-NMR (CDCl$_3$) δ 1.01 (t, 3H), 1.82 (s, 6H), 4.08 (q, 2H), 4.46 (d, 2H), 6.44 (d, 1H), 7.04 (d, 1H), 7.15 (dd, 1H), 7.24 (d, 1H), 7.67 (s, 1H); MS [ES] 286 (M+H).

Step C

2-[5-(3-Hydroxy-propyl)-indol-1-yl]-2-methyl-propionic acid ethyl ester

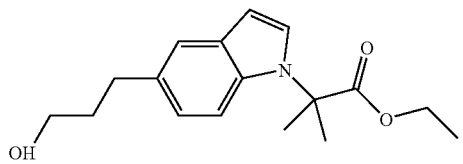

The title compound was prepared by using 2-[5-(3-hydroxy-prop-1-ynyl)-indol-1-yl]-2-methyl-propionic acid ethyl ester to afford the title compound as a brown oil. $^1$H-NMR (CDCl$_3$) δ 1.14 (t, 3H), 1.90 (s, 6H), 1.96 (m, 2H), 2.82 (t, 2H), 3.72 (t, 2H), 4.18 (q, 2H), 6.48 (d, 1H), 7.01 (dd, 1H), 7.13 (d, 1H), 7.29 (d, 1H), 7.46 d, 1H); MS [ES] 290 (M+H).

Step D

2-Methyl-2-{5-[3-(toluene-4-sulfonyloxy)-propyl]-indol-1-yl}-propionic acid ethyl ester

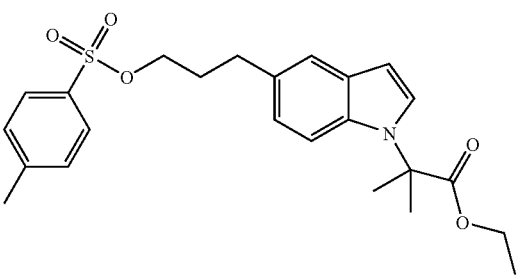

Standard Procedure (I) which described in Example 261 was utilized with 2-[5-(3-hydroxy-propyl)-indol-1-yl]-2-methyl-propionic acid ethyl ester to afford the title compound as a brown oil. MS [ES] 444 (M+H).

Step E

2-Methyl-2-[5-(3-propylamino-propyl)-indol-1-yl]-propionic acid ethyl ester

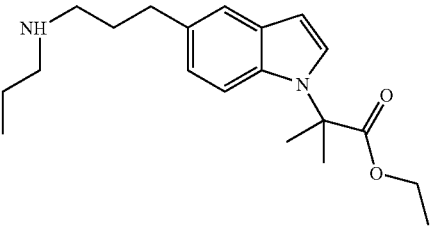

Standard Procedure (J) described in Example 262 was utilized with 2-methyl-2-{5-[3-(toluene-4-sulfonyloxy)-propyl]-indol-1-yl}-propionic acid ethyl ester to afford the title compound as a brown oil. MS [ES] 331 (M+H).

Step F

2-(5-{3-[(5-Fluoro-3-methyl-benzo[b]thiophene-2-sulfonyl)-propyl-amino]-propyl}-indol-1-yl)-2-methyl-propionic acid

Standard Procedure (A) which described in Example 253 was utilized with 2-methyl-2-[5-(3-propylamino-propyl)-indol-1-yl]-propionic acid ethyl ester and 5-fluoro-3-methyl-benzo[b]thiophene-2-sulfonyl chloride to prepare the title compound. $^1$H-NMR; MS [ES] 531 (M+H), 529 (M−H).

The following Examples 419 and 420 were prepared according to the procedure described above in Example 418.

EXAMPLE 419

2-(5-{3-[(Benzo[b]thiophene-2-sulfonyl)-propyl-amino]-propyl}-indol-1-yl)-2-methyl-propionic acid

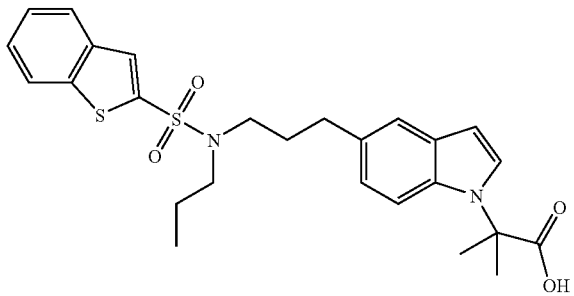

$^1$H-NMR: MS [ES] 499 (M+H), 497 (M−H).

EXAMPLE 420

2-(5-{3-[(5-Chloro-3-methyl-benzo[b]thiophene-2-sulfonyl)-propyl-amino]-propyl}-indol-1-yl)-2-methyl-propionic acid

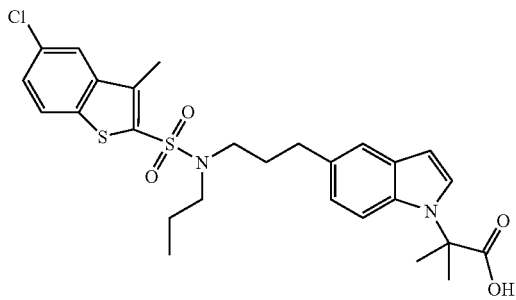

$^1$H-NMR: MS [ES] 547 (M+H), 545 (M−H).

What is claimed is:
1. A compound having a structural Formula I,

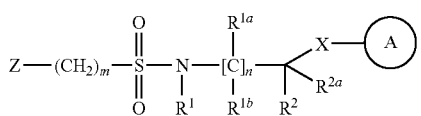

or pharmaceutically acceptable salts or stereoisomers thereof,
wherein:

A is:

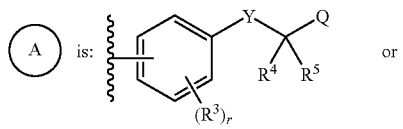

or

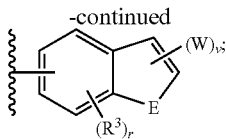

E is selected from the group consisting of O, S and $NR^{14}$;
W is selected from the group consisting of

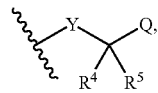

hydrogen, $C_1$-$C_6$ alkyl, $(CH_2)_n C_3$-$C_6$ cycloalkyl, haloalkyl and acyl;
Q is: —C(O)O$R^6$ or $R^{6A}$;
X is selected from the group consisting of a bond, $CH_2$, O, S and $S[O]_p$;
Y is selected from the group consisting of a bond, S, $CH_2$ and O;
Z is: benzothiophene;
   wherein the benzothiophene is optionally substituted with one or more groups independently selected from $R^{15}$;
m and n' are each independently selected from the group consisting of 0, 1, 2, 3 and 4;
n is selected from the group consisting of 0, 1, 2 and 3;
p is: 1 or 2;
r is selected from the group consisting of 1, 2, 3 and 4;
v is: 1 or 2;
$R^1$ is selected from the group consisting of hydrogen,
   haloalkyl,
   $C_1$-$C_6$ alkyl,
   $C_1$-$C_6$ alkyl-$C_1$-$C_6$ alkoxy,
   $C_1$-$C_6$ alkyl-aryl,
   $C_2$-$C_6$ alkenyl,
   $C_2$-$C_6$ alkynyl,
   $(CH_2)_n C_3$-$C_6$ cycloalkyl,
   $C_1$-$C_6$ alkoxy,
   aryl, and
   $R^1$ and $R^2$ together being a 5- to 8-membered heterocyclyl ring;
   wherein alkyl, aryl, alkenyl, alkynyl, cycloalkyl and alkoxy being optionally substituted with one or more groups independently selected from $R^{15}$;
$R^{1a}$ and $R^{1b}$ are each independently is selected from the group consisting of
   hydrogen,
   $C_1$-$C_6$ alkyl, and
   $R^1$ and $R^{1a}$, $R^1$ and $R^{1b}$, $R^2$ and $R^{1a}$, $R^2$ and $R^{1b}$ or $R^{1a}$ and $R^{1b}$ together being a 3- to 6-membered heterocyclyl or carbocyclyl ring wherein at least one of $R^{1a}$ and $R^{1b}$ is not hydrogen;
$R^2$ is selected from the group consisting of hydrogen,
   haloalkyl,
   $C_1$-$C_6$ alkyl,
   $C_1$-$C_6$ alkyl-$C_1$-$C_6$ alkoxy,
   $C_1$-$C_6$ alkyl-aryl,
   $C_2$-$C_6$ alkenyl,
   $C_2$-$C_6$ alkynyl,
   $(CH_2)_n C_3$-$C_6$ cycloalkyl,
   $C_1$-$C_6$ alkoxy,
   aryl, and R$^1$ and R$^2$ together being a 5- to 8-membered heterocyclyl ring;
  wherein alkyl, aryl, alkenyl, alkynyl, cycloalkyl and alkoxy being optionally substituted with one or more groups independently selected from R$^{15}$;
R$^{2a}$ is selected from the group consisting of hydrogen, halo, C$_1$-C$_6$ alkyl and wherein R$^2$ and R$^{2a}$ together being a 3- to 8-membered ring; wherein alkyl being optionally substituted with one or more groups independently selected from R$^{15}$;
R$^3$ is selected from the group consisting of hydrogen,
  halo,
  cyano,
  haloalkyl,
  C$_1$-C$_6$ alkyl,
  (CH$_2$)$_n$C$_3$-C$_6$ cycloalkyl,
  (C$_1$-C$_4$ alkyl)-heterocyclyl, and
  (C$_1$-C$_4$ alkyl)-NR$^7$C(O)$_p$R$^9$;
  wherein alkyl, cycloalkyl and heterocyclyl being optionally substituted with one or more groups independently selected from R$^{15}$;
R$^4$ and R$^5$ are each independently selected from the group consisting of
  hydrogen,
  halo,
  C$_1$-C$_6$ alkyl
  C$_1$-C$_6$ alkoxy;
  aryloxy;
  N(R$^8$)$_2$,
  SR$^8$ and
  R$^4$ and R$^5$ together being a 3- to 8-membered ring;
R$^6$ is selected from the group consisting of hydrogen, C$_1$-C$_6$ alkyl and aminoalkyl;
R$^{6A}$ is selected from the group consisting of carboxamide, C$_1$-C$_3$ alkylnitrile, sulfonamide, acylsulfonamide and tetrazole;
R$^7$ is selected from the group consisting of hydrogen and C$_1$-C$_6$ alkyl;
R$^8$ and R$^9$ are each independently selected from the group consisting of
  hydrogen, C$_1$-C$_6$ alkyl, aryl, heteroaryl, and heterocyclyl;
  wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, C$_1$-C$_6$ alkyl and C$_1$-C$_6$ alkoxy;
R$^{14}$ is selected from the group consisting of hydrogen, aryl, C$_1$-C$_6$ alkyl, and C$_1$-C$_6$ alkyl -COOR$^6$,
  wherein aryl and alkyl being optionally substituted with one or more groups independently selected from R$^{15}$; and
R$^{15}$ is selected from the group consisting of hydrogen, nitro, cyano, hydroxyl, halo, haloalkyl, haloalkyloxy, aryloxy, oxo, C$_1$-C$_6$ alkyl, C$_1$-C$_6$ alkoxy, (CH$_2$)$_n$C$_3$-C$_6$ cycloalkyl, N(R$^8$)$_2$, NR$^8$S(O)$_2$R$^9$, NR$^8$C(O)$_p$R$^9$, C(O)NR$^8$R$^9$, C(O)$_p$R$^8$, SR$^8$, S(O)$_p$R$^8$ and S(O)$_2$NR$^8$R$^9$.

2. The compound claim 1, wherein X and Y are respectively S and O; S and CH$_2$; or CH$_2$ and O.

3. The compound of claim 1, wherein R$^1$ is C$_3$-C$_6$ alkyl or (CH$_2$)$_n$C$_3$-C$_6$ cycloalkyl; R$^2$ and R$^3$ are each independently C$_1$-C$_3$ alkyl; and r is 1.

4. The compound claim 3, wherein X is positioned para to Y; and R$^3$ is positioned ortho to Y.

5. A compound having a structural Formula II,

II

Z—(CH$_2$)$_m$—S(O)$_2$—N(R$^1$)—[C]$_n$(R$^{1a}$)(R$^{1b}$)(R$^2$)(R$^{2a}$)—X—[aryl(R$^3$)$_r$]—Y—Q(R$^4$)(R$^5$)

or pharmaceutically acceptable salts or stereoisomers thereof,
wherein:
  Q is: —C(O)OR$^6$ or R$^{6A}$;
  X is selected from the group consisting of a bond, CH$_2$, O, S and S[O]$_p$;
  Y is selected from the group consisting of a bond, S, CH$_2$ and O;
  Z is benzothiopene;
    wherein the benzothiophene is optionally substituted with one or more groups independently selected from R$^{15}$;
  m and n' are each independently selected from the group consisting of 0, 1, 2, 3 and 4;
  n is selected from the group consisting of 0, 1, 2 and 3;
  p is: 1 or 2;
  r is selected from the group consisting of 1, 2, 3 and 4;
  R$^1$ is selected from the group consisting of aryl,
    haloalkyl,
    C$_1$-C$_6$ alkyl,
    C$_1$-C$_6$ alkyl-C$_1$-C$_6$ alkoxy,
    C$_1$-C$_6$ alkyl-aryl,
    C$_2$-C$_6$ alkenyl,
    C$_2$-C$_6$ alkynyl,
    (CH$_2$)$_n$C$_3$-C$_6$ cycloalkyl,
    C$_1$-C$_6$ alkoxy and
    R$^1$ and R$^2$ together being a 5- to 8-membered heterocyclyl ring;
    wherein alkyl, aryl, alkenyl, alkynyl, cycloalkyl and alkoxy being optionally substituted with one or more groups independently selected from R$^{15}$;
  R$^{1a}$ and R$^{1b}$ are each independently selected from the group consisting of
    hydrogen,
    C$_1$-C$_6$ alkyl, and,
    R$^1$ and R$^{1a}$, R$^1$ and R$^{1b}$, R$^2$ and R$^{1a}$, R$^2$ and R$^{1b}$ or R$^{1a}$ and R$^{1b}$ together being a 3- to 6-membered heterocyclyl or carbocyclyl ring where at least one of R$^{1a}$ and R$^{1b}$ is not hydrogen;
  R$^2$ is selected from the group consisting of hydrogen,
    haloalkyl,
    C$_1$-C$_6$ alkyl,
    C$_1$-C$_6$ alkyl-C$_1$-C$_6$ alkoxy,
    C$_1$-C$_6$ alkyl-aryl,
    C$_2$-C$_6$ alkenyl,
    C$_2$-C$_6$ alkynyl,
    (CH$_2$)$_n$C$_3$-C$_6$ cycloalkyl,
    C$_1$-C$_6$ alkoxy,
    aryl, and
    R$^1$ and R$^2$ together being a 5- to 8-membered heterocyclyl ring;
    wherein alkyl, aryl, alkenyl, alkynyl, cycloalkyl and alkoxy being optionally substituted with one or more groups independently selected from R$^{15}$;

$R^{2a}$ is selected from the group consisting of hydrogen, halo or $C_1$-$C_6$ alkyl and wherein $R^2$ and $R^{2a}$ together being a 3- to 8-membered ring; wherein alkyl being optionally substituted with one or more groups independently selected from $R^{15}$;

$R^3$ is selected from the group consisting of hydrogen,
  halo,
  cyano,
  haloalkyl,
  $C_1$-$C_6$ alkyl,
  $(CH_2)_n$$C_3$-$C_6$ cycloalkyl,
  ($C_1$-$C_4$ alkyl)-heterocyclyl, and
  ($C_1$-$C_4$ alkyl)-$NR^7C(O)_pR^9$;
  wherein alkyl, cycloalkyl and heterocyclyl being optionally substituted with one or more groups independently selected from $R^{15}$;

$R^4$ and $R^5$ are each independently selected from the group consisting of hydrogen,
  halo,
  $C_1$-$C_6$ alkyl
  $C_1$-$C_6$ alkoxy;
  aryloxy;
  $N(R^8)_2$,
  $SR^8$ and
  $R^4$ and $R^5$ together being a 3- to 8-membered ring;

$R^6$ is selected from the group consisting of hydrogen, $C_1$-$C_6$ alkyl and aminoalkyl;

$R^{6A}$ is selected from the group consisting of carboxamide, $C_1$-$C_3$ alkylnitrile, sulfonamide, acylsulfonamide and tetrazole;

$R^7$ is selected from the group consisting of hydrogen and $C_1$-$C_6$ alkyl;

$R^8$ and $R^9$ are each independently selected from the group consisting of
  hydrogen, $C_1$-$C_6$ alkyl, aryl, heteroaryl, and heterocyclyl;
  wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy;

$R^{15}$ is selected from the group consisting of hydrogen, nitro, cyano, hydroxyl, halo, haloalkyl, haloalkyloxy, aryloxy, oxo, $C_1$-$C_6$ alkyl, $C_1$-$C_6$ alkoxy, $(CH_2)_n$$C_3$-$C_6$ cycloalkyl, $N(R^8)_2$, $NR^8S(O)_2R^9$, $NR^8C(O)_pR^9$, $C(O)NR^8R^9$, $C(O)_pR^8$, $SR^8$, $S(O)_pR^8$ and $S(O)_2NR^8R^9$.

6. The compound of claim 5, wherein X and Y are respectively S and O; S and $CH_2$; or $CH_2$ and O.

7. The compound of claim 6, wherein $R^1$ is $C_3$-$C_6$ alkyl or $(CH_2)_n$$C_3$-$C_6$ cycloalkyl; $R^2$ and $R^3$ are each independently $C_1$-$C_3$ alkyl; and r is 1.

8. The compound claim 7, wherein X is positioned para to Y; and $R^3$ is positioned ortho to Y.

9. The compound of claim 5, wherein the compound having a structural Formula III,

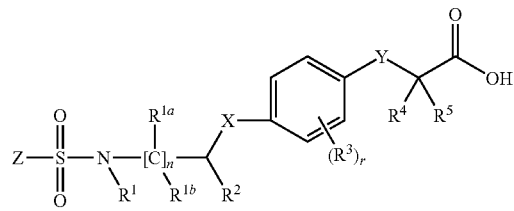

or pharmaceutically acceptable salts or stereoisomers thereof, wherein:
  n is: 1 or 2;
  r is: 1, 2, 3, or 4;
  X is: S or $CH_2$;
  Y is: $CH_2$ or O;
  Z is: benzothiophene;
  wherein the benzothiophene is optionally substituted with one or more groups independently selected from $R^{15}$;
  $R^1$ and $R^2$ are each independently selected from the group consisting of $C_1$-$C_6$ alkyl and $(CH_2)_n$$C_3$-$C_6$ cycloalkyl; and
  $R^{1a}$ and $R^{1b}$, $R^3$, $R^4$ and $R^5$ are each independently selected from the group consisting of hydrogen and $C_1$-$C_6$ alkyl.

10. A compound having a structural Formula VI,

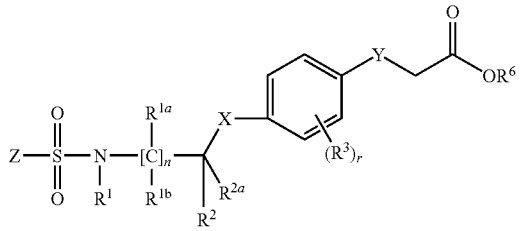

or pharmaceutically acceptable salts or stereoisomers thereof, wherein:
  X is selected from the group consisting of a bond, $CH_2$, O, S and $S[O]_p$;
  Y is selected from the group consisting of a bond, S, $CH_2$ and O;
  Z is benzothiophene; wherein the benzotihophene is optionally substituted with one or more groups selected from $R^{15}$;
  n is: 0, 1, 2 or 3;
  n' is: 0, 1, 2, 3 or 4;
  p is: 1 or 2;
  r is: 1, 2, 3 or 4;
  $R^1$ is selected from the group consisting of hydrogen,
    haloalkyl,
    $C_1$-$C_6$ alkyl,
    $C_1$-$C_6$ alkyl-$C_1$-$C_6$ alkoxy,
    $C_1$-$C_6$ alkyl-aryl,
    $C_2$-$C_6$ alkenyl,
    $C_2$-$C_6$ alkynyl,
    $(CH_2)_n$$C_3$-$C_6$ cycloalkyl,
    $C_1$-$C_6$ alkoxy,
    aryl, and
    $R^1$ and $R^2$ together being a 5- to 8-membered heterocyclyl ring;

wherein alkyl, aryl, alkenyl, alkynyl, cycloalkyl and alkoxy being optionally substituted with one or more groups independently selected from $R^{15}$;

$R^{1a}$ and $R^{1b}$ are each independently selected from the group consisting of hydrogen, $C_1$-$C_6$ alkyl, and $R^1$ and $R^{1a}$, $R^1$ and $R^{1b}$, $R^2$ and $R^{1a}$, $R^2$ and $R^{1b}$ or $R^{1a}$ and $R^{1b}$ together being a 3- to 6-membered heterocyclyl or carbocyclyl ring; wherein at least one of $R^{1a}$ and $R^{1b}$ is not hydrogen;

$R^2$ is selected from the group consisting of hydrogen, haloalkyl, $C_1$-$C_6$ alkyl, $C_1$-$C_6$ alkyl-$C_1$-$C_6$ alkoxy, $C_1$-$C_6$ alkyl-aryl, $C_2$-$C_6$ alkenyl, $C_2$-$C_6$ alkynyl, $(CH_2)_n C_3$-$C_6$ cycloalkyl, $C_1$-$C_6$ alkoxy, aryl, and $R^1$ and $R^2$ together being a 5- to 8-membered heterocyclyl ring;

wherein alkyl, aryl, alkenyl, alkynyl, cycloalkyl and alkoxy being optionally substituted with one or more groups independently selected from $R^{15}$;

$R^{2a}$ is selected from the group consisting of hydrogen, halo and $C_1$-$C_6$ alkyl; wherein $R^2$ and $R^{2a}$ together being a 3- to 8-membered ring; wherein alkyl being optionally substituted with one or more groups independently selected from $R^{15}$;

$R^3$ is selected from the group consisting of hydrogen, halo, cyano, haloalkyl, $C_1$-$C_6$ alkyl, $(CH_2)_n C_3$-$C_6$ cycloalkyl, $(C_1$-$C_4$ alkyl)-heterocyclyl, and $(C_1$-$C_4$ alkyl)-$NR^7C(O)_pR^9$, wherein alkyl, cycloalkyl and heterocyclyl being optionally substituted with one or more groups independently selected from $R^{15}$;

$R^6$ is selected from the group consisting of hydrogen, $C_1$-$C_6$ alkyl and aminoalkyl;

$R^7$ is selected from the group consisting of hydrogen and $C_1$-$C_6$alkyl;

$R^8$ and $R^9$ are each independently selected from the group consisting of hydrogen, $C_1$-$C_6$ alkyl, aryl, heteroaryl, and heterocyclyl;

wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy; and $R^{15}$ is selected from the group consisting of hydrogen, nitro, cyano, hydroxyl, halo, haloalkyl, haloalkyloxy, aryloxy, oxo, $C_1$-$C_6$ alkyl, $C_1$-$C_6$ alkoxy, $N(R^8)_2$, $NR^8S(O)_2R^9$, $NR^8C(O)_pR^9$, $C(O)NR^8R^9$, $C(O)_pR^8$, $SR^8$, $S(O)_pR^8$ and $S(O)_2NR^8R^9$.

11. The compound of claim 10, wherein the compound having a structural Formula VII,

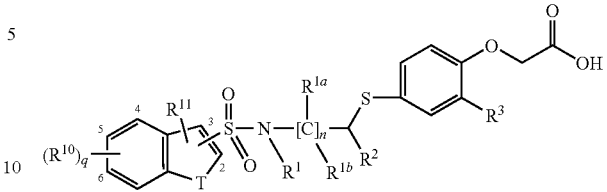

or pharmaceutically acceptable salts or stereoisomers thereof, wherein:

q is: 1, 2, 3, or 4;

T is S;

$R^{10}$ and $R^{11}$ are each independently selected from the group consisting of hydrogen, nitro, cyano, hydroxyl, halo, haloalkyl, haloalkyloxy, aryloxy, $C_1$-$C_6$ alkyl and $C_1$-$C_6$ alkoxy;

wherein alkyl, aryloxy, and alkoxy being optionally substituted with one or more groups independently selected from $R^{15}$.

12. The compound of claim 11, wherein the compound having a structural Formula VIII,

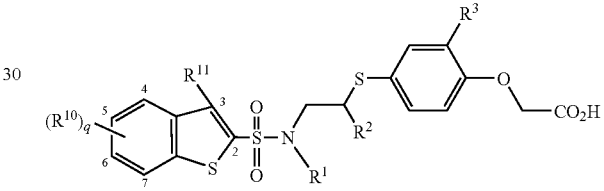

or pharmaceutically acceptable salts or stereoisomers thereof, wherein:

q is: 1 or 2;

$R^1$ is selected from the group consisting of $C_3$-$C_5$ alky and $(CH_2)_n C_3$-$C_6$ cycloalkyl;

$R^2$ and $R^3$ are each independently: $C_1$-$C_3$ alkyl;

$R^{10}$ is selected from the group consisting of halo, haloalkyl and $C_1$-$C_3$ alkyl; wherein $R^{10}$ being substituted at a position 5, or 6, or both 5 and 6 of benzothiophenyl ring; and $R^{11}$ is selected from the group consisting of hydrogen and $C_1$-$C_6$ alkyl.

13. The compound of claim 12, wherein $R^{10}$ is Cl, F, Br, $CH_3$ or $CF_3$ being substituted at a position 5 of benzothiophenyl ring.

14. A compound having a structural Formula IX,

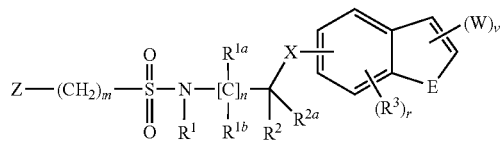

or pharmaceutically acceptable salts or stereoisomers thereof, wherein:

E is selected from the group consisting of O, S and $NR^{14}$;

W is selected from the group consisting of

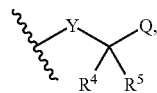

hydrogen, $C_1$-$C_6$ alkyl, $(CH_2)_n$$C_3$-$C_6$ cycloalkyl, haloalkyl and acyl;

Q is selected from the group consisting of —C(O)OR$^6$ and R$^{6A}$;

X is selected from the group consisting of a bond, C, O, S and S[O]$_p$;

Y is selected from the group consisting of a bond, S, CH$_2$ and O;

Z is benzothiopene: and:
  wherein the benzothiophene is optionally substituted with one or more groups independently selected from R$^{15}$;

m and n' are each independently: 0, 1, 2, 3 or 4;

n is: 0, 1, 2 or 3;

p is: 1 or 2;

r is: 1, 2, 3 or 4;

v is: 1 or 2;

R$^1$ is selected from the group consisting of hydrogen,
  haloalkyl,
  $C_1$-$C_6$ alkyl,
  $C_1$-$C_6$ alkyl-$C_1$-$C_6$ alkoxy,
  $C_1$-$C_6$ alkyl-aryl,
  $C_2$-$C_6$ alkenyl,
  $C_2$-$C_6$ alkynyl,
  $(CH_2)_n$$C_3$-$C_6$ cycloalkyl,
  $C_1$-$C_6$ alkoxy,
  aryl, and
  R$^1$ and R$^2$ together being a 5- to 8-membered heterocyclyl ring:
  wherein alkyl, aryl, alkenyl, alkynyl, cycloalkyl and alkoxy being optionally substituted with one or more groups independently selected from R$^{15}$;

R$^{1a}$ and R$^{1b}$ are each independently selected from the group consisting of
  hydrogen,
  $C_1$-$C_6$ alkyl, and
  R$^1$ and R$^{1a}$, R$^1$ and R$^{1b}$, R$^2$ and R$^{1a}$, R$^2$ and R$^{1b}$ or R$^{1a}$ and R$^{1b}$ together being a 3- to 6-membered heterocyclyl or carbocyclyl ring wherein at least one of R$^{1a}$ and R$^{1b}$ is not hydrogen;

R$^2$ is selected from the group consisting of hydrogen,
  haloalkyl,
  $C_1$-$C_6$ alkyl,
  $C_1$-$C_6$ alkyl-$C_1$-$C_6$ alkoxy,
  $C_1$-$C_6$ alkyl-aryl,
  $C_2$-$C_6$ alkenyl,
  $C_2$-$C_6$ alkynyl,
  $(CH_2)_n$$C_3$-$C_6$ cycloalkyl,
  $C_1$-$C_6$ alkoxy,
  aryl, and
  R$^1$ and R$^2$ together being a 5- to 8-membered heterocyclyl ring;
  wherein alkyl, aryl, alkenyl, alkynyl, cycloalkyl and alkoxy being optionally substituted with one or more groups independently selected from R$^{15}$;

R$^{2a}$ is selected from the group consisting of hydrogen, halo and $C_1$-$C_6$ alkyl and wherein R$^2$ and R$^{2a}$ together being a 3- to 8-membered ring; wherein alkyl being optionally substituted with one or more groups independently selected from R$^{15}$;

R$^3$ is selected from the group consisting of hydrogen,
  halo,
  cyano,
  haloalkyl,
  $C_1$-$C_6$ alkyl,
  $(CH_2)_n$$C_3$-$C_6$ cycloalkyl,
  ($C_1$-$C_4$ alkyl)-heterocyclyl, and
  ($C_1$-$C_4$ alkyl)-NR$^7$C(O)$_p$R$^9$:

wherein alkyl, cycloalkyl and heterocyclyl being optionally substituted with one or more groups independently selected from R$^{15}$;

R$^4$ and R$^5$ are each independently selected from the group consisting of
  hydrogen,
  halo,
  $C_1$-$C_6$ alkyl
  $C_1$-$C_6$ alkoxy;
  aryloxy;
  N(R$^8$)$_2$,
  SR$^8$ and
  R$^4$ and R$^5$ together being a 3- to 8-membered ring;

R$^6$ is selected from the group consisting of hydrogen, $C_1$-$C_6$ alkyl and aminoalkyl;

R$^{6A}$ is selected from the group consisting of carboxamide, $C_1$-$C_3$ alkylnitrile, sulfonamide, acylsulfonamide and tetrazole;

R$^7$ is selected from the group consisting of hydrogen and $C_1$-$C_6$alkyl;

R$^8$ and R$^9$ are each independently selected from the group consisting of
  hydrogen, $C_1$-$C_6$ alkyl, aryl, heteroaryl, and heterocyclyl;
  wherein aryl, heteroaryl and heterocyclyl being optionally substituted with one or more substituents selected from the group consisting of hydrogen, nitro, cyano, hydroxyl, halo, haloalkyl, haloalkyloxy, aryloxy, oxo, $C_1$-$C_6$ alkyl and $C_1$-$C_6$ alkoxy;

R$^{14}$ is selected from the group consisting of hydrogen, aryl, $C_1$-$C_6$ alkyl, and $C_1$-$C_6$ alkyl -COOR$^6$;
  wherein aryl and alkyl being optionally substituted with one or more groups independently selected from R$^{15}$; and R$^{15}$ is selected from the group consisting of hydrogen, nitro, cyano, hydroxyl, halo, haloalkyl, haloalkyloxy, aryloxy, oxo, $C_1$-$C_6$ alkyl, $C_1$-$C_6$ alkoxy, $(CH_2)_n$$C_3$-$C_6$ cycloalkyl, N(R$^8$)$_2$, NR$^8$S(O)$_2$R$^9$, NR$^8$C(O)$_p$R$^9$, C(O)NR$^8$R$^9$, C(O)$_p$R$^8$, SR$^8$, S(O)$_p$R$^8$ and S(O)$_2$NR$^8$R$^9$.

15. The compound of claim 14, wherein the compound having a structural Formula X:

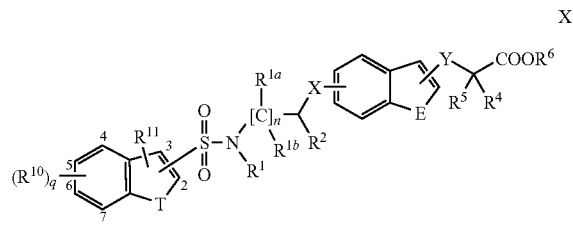

X and pharmaceutically acceptable salts, solvates, hydrates or stereoisomers thereof,
wherein:
  n and q are each independently: 1, 2, 3 or 4;
  T is S;
  X is selected from the group consisting of CH$_2$, O and S;
  R$^1$ is selected from the group consisting of hydrogen, $C_1$-$C_6$ alkyl and $(CH_2)_n$$C_3$-$C_6$ cycloalkyl;
  R$^{1a}$, R$^{1b}$, R$^{1c}$ and R$^2$ are each independently selected from the group consisting of hydrogen and $C_1$-$C_6$ alkyl; and
  R$^{10}$ and R$^{11}$ are each independently selected from the group consisting of hydrogen, nitro, cyano, hydroxyl, halo, haloalkyl, haloalkyloxy, aryloxy, $C_1$-$C_6$ alkyl and $C_1$-$C_6$ alkoxy; wherein alkyl, alkoxy and aryloxy being optionally substituted with one or more groups selected from $R^{15}$.

16. The compound of claim 15, wherein the compound having a structural Formula XI:

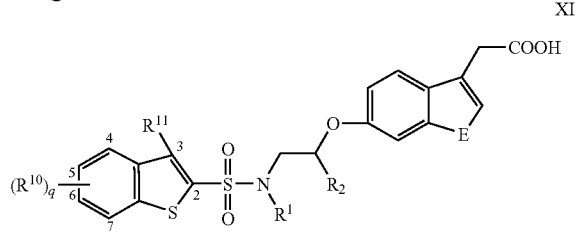

XI or pharmaceutically acceptable salts or stereoisomers thereof, wherein:

q is 1 or 2;

E is selected from the group consisting of O, S and $NR^{14}$;

$R^1$, $R^2$ and $R^{11}$ are each independently selected from the group consisting of $C_1$-$C_4$ alkyl;

$R^{10}$ is selected from the group consisting of Cl, F, Br, $CH_3$ and $CF_3$; wherein $R^{10}$ being substituted at a position 5, or 6, or both 5 and 6 of benzothiophenyl ring; and $R^{14}$ is selected from the group consisting of hydrogen, $C_1$-$C_6$ alkyl and aryl.

17. A compound selected from the group consisting of

| No. | Structure | Name |
|---|---|---|
| 1 | 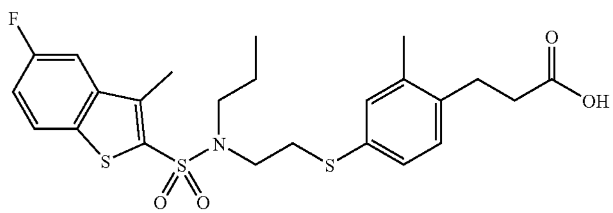 | 3-(4-{2-[(5-Fluoro-3-methyl-benzo[b]thiophene-2-sulfonyl)-propyl-amino]-ethylsulfanyl}-2-methyl-phenyl)-propionic acid |
| 2 | 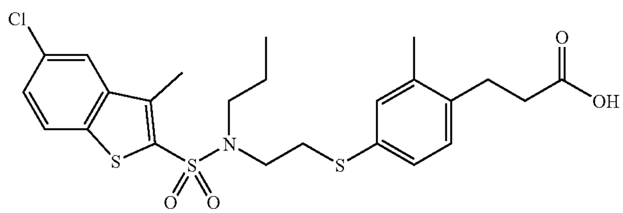 | 3-(4-{2-[(5-Chloro-3-methyl-benzo[b]thiophene-2-sulfonyl)-propyl-amino]-ethylsulfanyl}-2-methyl-phenyl)-propionic acid |
| 5 | 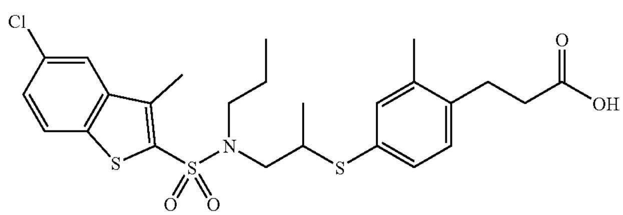 | 3-(4-{2-[(5-Chloro-3-methyl-benzo[b]thiophene-2-sulfonyl)-propyl-amino]-1-methyl-ethylsulfanyl}-2-methyl-phenyl)-propionic acid |
| 6 | 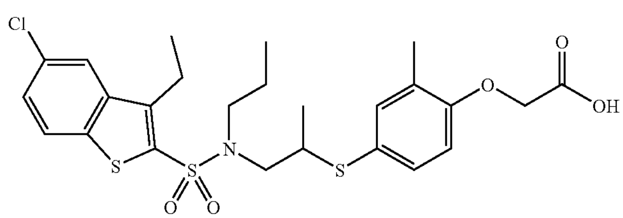 | (4-{2-[(5-Chloro-3-ethyl-benzo[b]thiophene-2-sulfonyl)-propyl amino]-1-methyl-ethylsulfanyl}-2-methyl-phenoxy)-acetic acid |
| 7 | 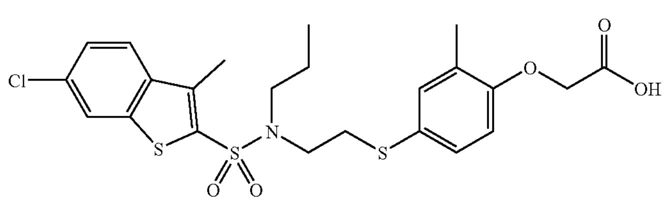 | 4-{2-[(6-Chloro-3-methyl-benzo[b]thiophene-2-sulfonyl)-propyl-amino]-ethylsulfanyl}-2-methyl-phenoxy)-acetic acid |

-continued

| No. | Structure | Name |
|---|---|---|
| 8 | 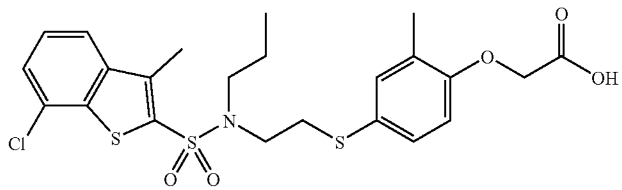 | 4-{2-[(7-Chloro-3-methyl-benzo[b]thiophene-2-sulfonyl)-propyl-amino]-ethylsulfanyl}-2-methyl-phenoxy)-acetic acid |
| 9 | 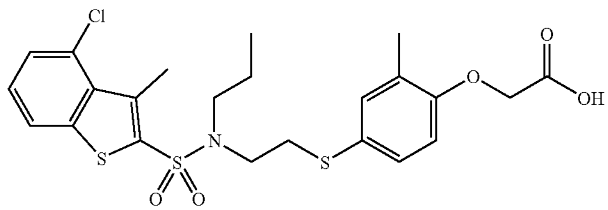 | (4-{2-[(4-Chloro-3-methyl-benzo[b]thiophene-2-sulfonyl)-propyl-amino]-ethylsulfanyl}-2-methyl-phenoxy)-acetic acid |
| 10 | 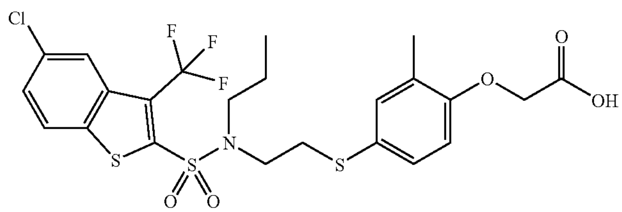 | (4-{2-[(5-Chloro-3-trifluoromethyl-benzo[b]thiophene-2-sulfonyl)-propyl-amino]-ethylsulfanyl}-2-methyl-phenoxy)-acetic acid |
| 11 | 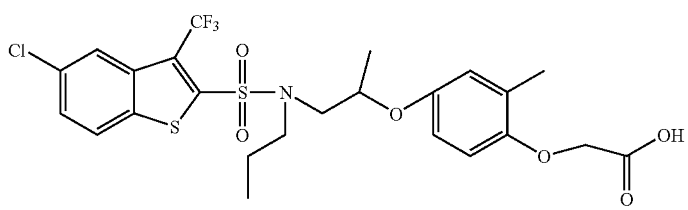 | (4-{2-[(5-Chloro-3-trifluoromethyl-benzo[b]thiophene-2-sulfonyl)-propyl-amino]-1-methyl-ethoxy}-2-methyl-phenoxy)-acetic acid |
| 13 | 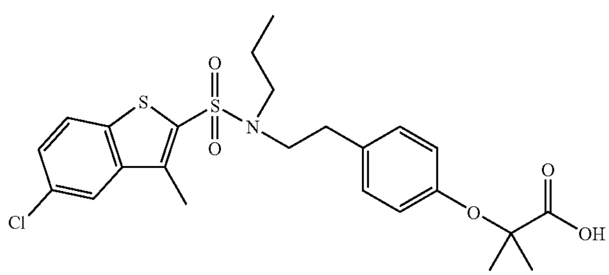 | 2-(4-{2-[(5-Chloro-3-methyl-benzo[b]thiophene-2-sulfonyl)-propy]-amino]-ethyl}-phenoxy)-2-methyl-propionic acid |
| 14 | 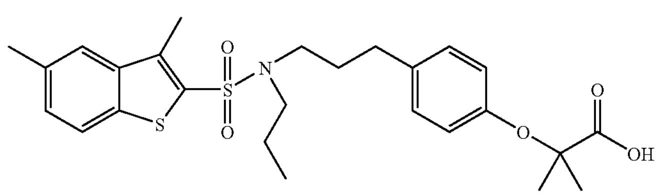 | 2-(4-{3-[(3,5-Dimethyl-benzo[b]thiophene-2-sulfonyl)-propyl-amino]-propyl}-phenoxy)-2-methyl-propionic acid |
| 15 | 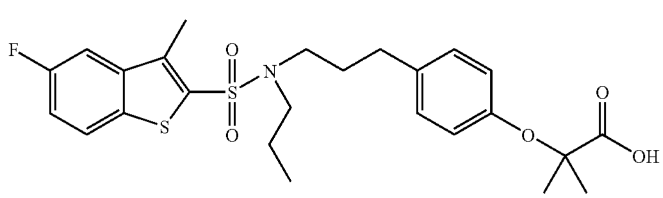 | 2-(4-{3-[(5-Fluoro-3-methyl-benzo[b]thiophene-2-sulfonyl)-propyl-amino]-propyl}-phenoxy)-2-methyl-propionic acid |

-continued

| No. | Structure | Name |
|---|---|---|
| 16 | 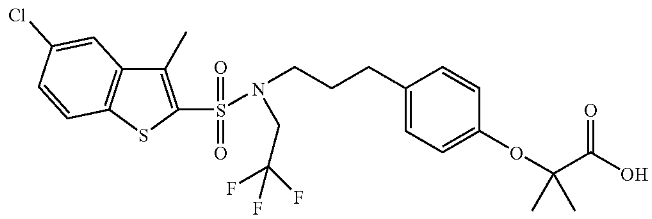 | 2-(4-{3-[(5-Chloro-3-methyl-benzo[b]thiophene-2-sulfonyl)-(2,2,2-trifluoro-ethyl)-amino]-propyl}-phenoxy)-2-methyl-propionic acid |
| 17 | 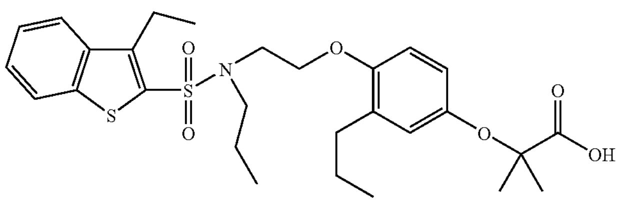 | 2-(4-{2-[(3-Ethyl-benzo[b]thiophene-2-sulfonyl)-propyl-amino]-ethoxy}-3-propyl-phenoxy)-2-methyl-propionic acid |
| 18 | 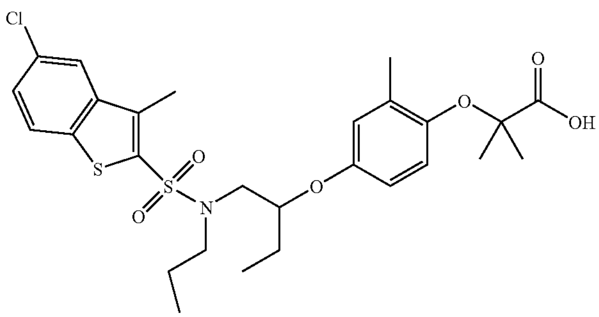 | 2-[4-(1-{[(5-Chloro-3-methyl-benzo[b]thiophene-2-sulfonyl)-propyl-amino]-methyl}-propoxy)-2-methyl-phenoxy]-2-methyl-propionic acid |
| 19 | 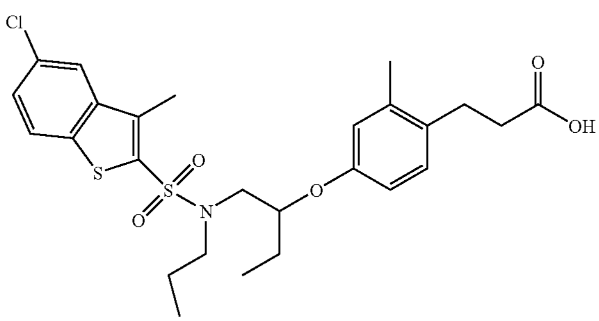 | 3-[4-(1-{[(5-Chloro-3-methyl-benzo[b]thiophene-2-sulfonyl)-propyl-amino]-methyl}-propoxy)-2-methyl-phenyl]-propionic acid |
| 20 | 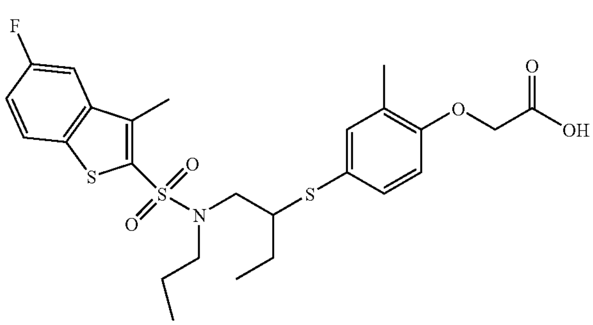 | [4-(1-{[(5-Fluoro-3-methyl-benzo[b]thiophene-2-sulfonyl)-propyl-amino]-methyl}-propylsulfanyl)-2-methyl-phenoxy]-acetic acid |

-continued

| No. | Structure | Name |
|---|---|---|
| 21 | 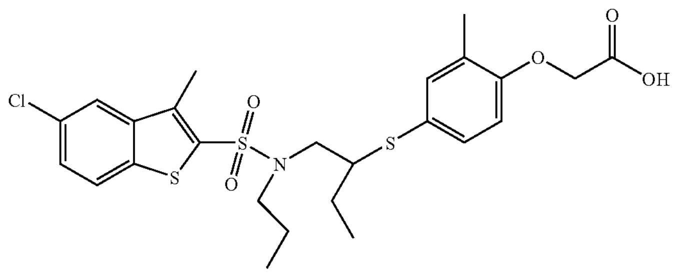 | [4-(1-{[(5-Chloro-3-methyl-benzo[b]thiophene-2-sulfonyl)-propyl-amino]-methyl}-propylsulfanyl)-2-methyl-phenoxy]-acetic acid |
| 22 | 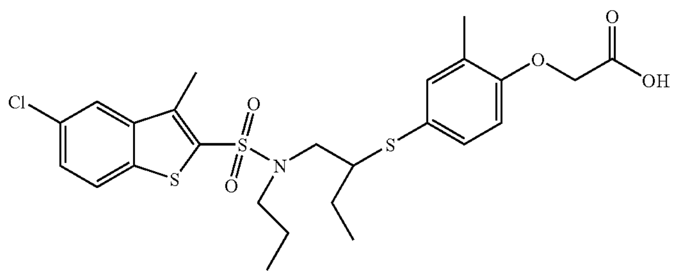 | [4-(1-{[(5-Chloro-3-methyl-benzo[b]thiophene-2-sulfonyl)-propyl-amino]-methyl}-propylsulfanyl)-2-methyl-phenoxy]-acetic acid |
| 34 | 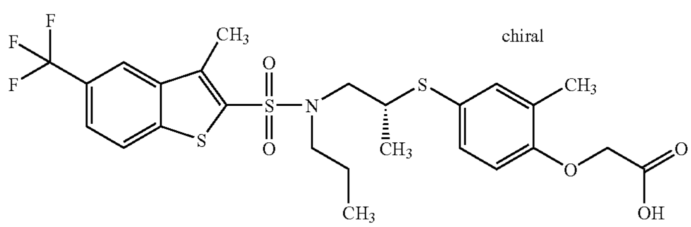 | (R)-(2-Methyl-4-{1-methyl-2-[(3-methyl-5-trifluoromethyl-benzo[b]thiophene-2-sulfonyl)-propyl-amino]-ethylsulfanyl}-phenoxy)-acetic acid |
| 35 | 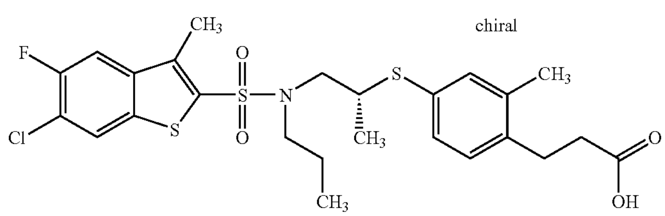 | (R)-3-(4-{2-[(6-Chloro-5-fluoro-3-methyl-benzo[b]thiophene-2-sulfonyl)-propyl-amino]-1-methyl-ethylsulfanyl}-2-methyl-phenyl)-propionic acid |
| 36 | 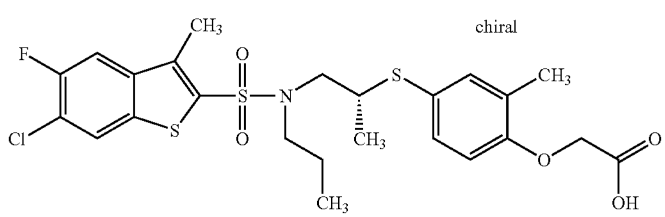 | (R)-(4-{2-[(6-Chloro-5-fluoro-3-methyl-benzo[b]thiophene-2-sulfony])-propyl-amino]-1-methyl-ethylsulfanyl}-2-methyl-phenoxy)-acetic acid |
| 79 | 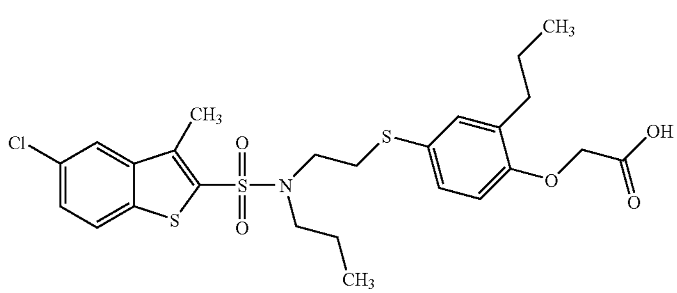 | (4-{2-[(5-Chloro-3-methyl-benzo[b]thiophene-2-sulfonyl)-propyl-amino]-ethylsulfanyl}-2-propyl-phenoxy)-acetic acid |

-continued

| No. | Structure | Name |
|---|---|---|
| 80 | 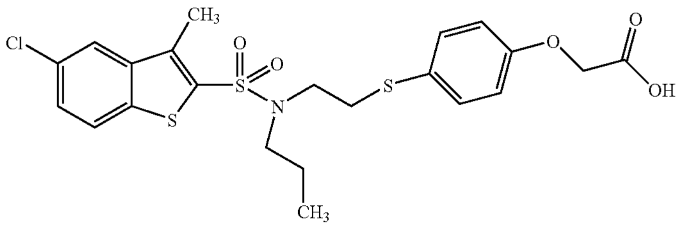 | (4-{2-[(5-Chloro-3-methyl-benzo[b]thiophene-2-sulfonyl)-propyl-amino]-ethylsulfanyl}-phenoxy)-acetic acid |
| 81 | 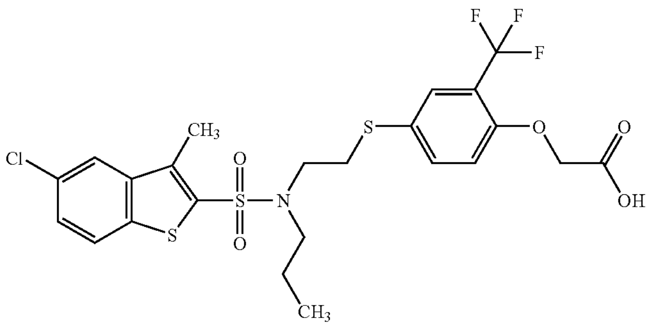 | (4-{2-[(5-Chloro-3-methyl-benzo[b]thiophene-2-sulfonyl)-propyl-amino]-ethylsulfanyl}-2-trifluoromethyl-phenoxy)-acetic acid |
| 83 | 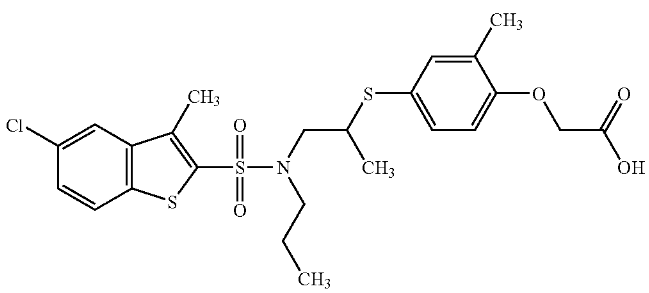 | (4-{2-[(5-Chloro-3-methyl-benzo[b]thiophene-2-sulfonyl)-propyl-amino]-1-methyl-ethylsulfanyl}-2-methyl-phenoxy)-acetic acid |
| 84 | 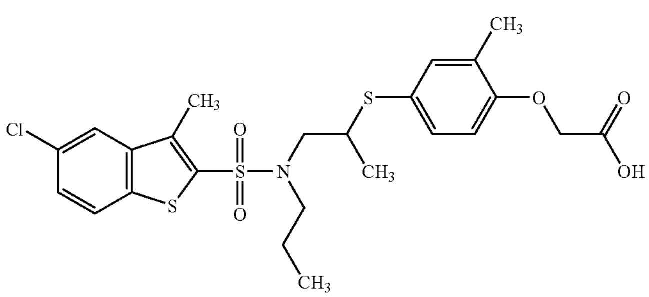 | (4-{2-[(5-Chloro-3-methyl-benzo[b]thiophene-2-sulfonyl)-propyl-amino]-1-methyl-ethylsulfanyl}-2-methyl-phenoxy)-acetic acid |
| 85 | 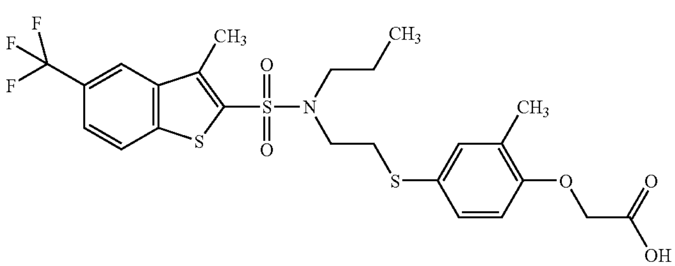 | (2-Methyl-4-{2-[(3-methyl-5-trifluoromethyl-benzo[b]thiophene-2-sulfonyl)-propyl-amino]-ethylsulfanyl}-phenoxy)-acetic acid |

-continued

| No. | Structure | Name |
|---|---|---|
| 90 | 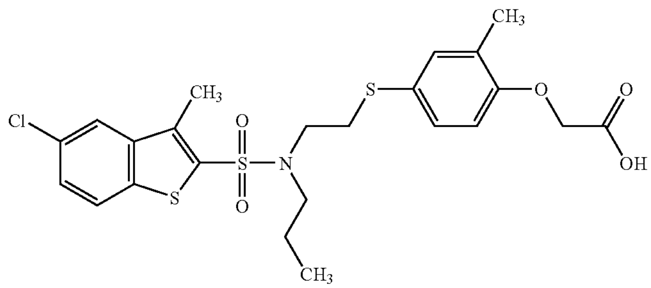 | (4-{2-[(5-Chloro-3-methyl-benzo[b]thiophene-2-sulfonyl)-propyl-amino]-ethylsulfanyl}-2-methyl-phenoxy)-acetic acid |
| 91 | 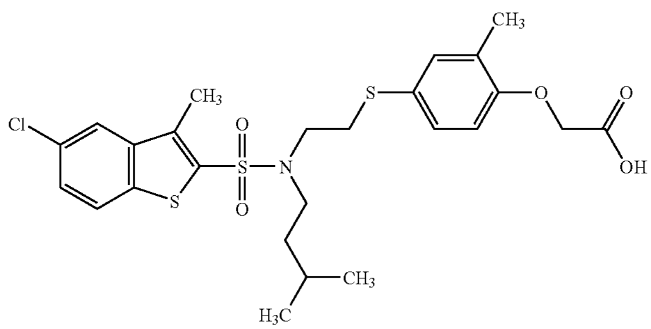 | (4-{2-[(5-Chloro-3-methyl-benzo[b]thiophene-2-sulfonyl)-(3-methyl-butyl)-amino]-ethylsulfanyl}-2-methyl-phenoxy)-acetic acid |
| 92 | 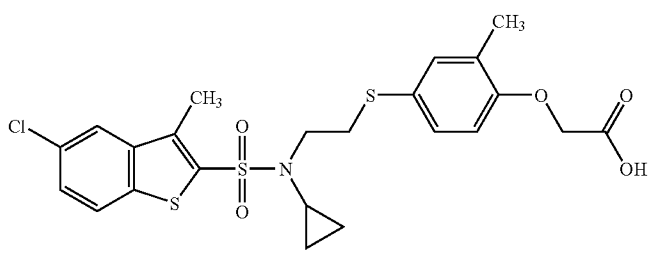 | (4-{2-[(5-Chloro-3-methyl-benzo[b]thiophene-2-sulfonyl)-cyclopropyl-amino]-ethylsulfanyl}-2-methyl-phenoxy)-acetic acid |
| 93 | 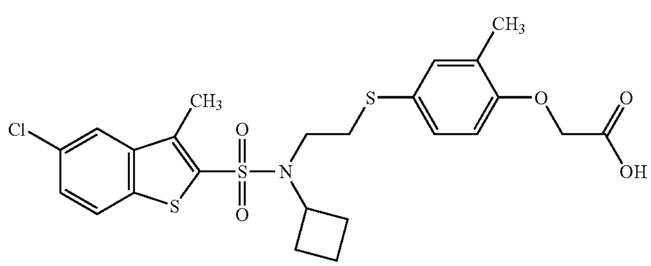 | (4-{2-[(5-Chloro-3-methyl-benzo[b]thiophene-2-sulfonyl)-cyclobutyl-amino]-ethylsulfanyl}-2-methyl-phenoxy)-acetic acid |
| 94 | 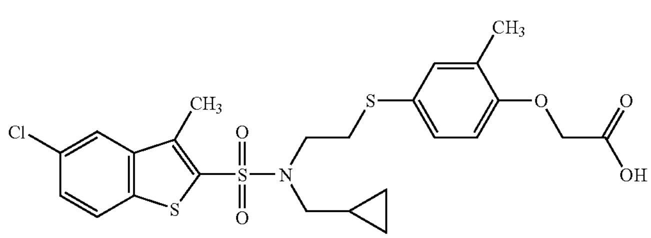 | (4-{2-[(5-Chloro-3-methyl-benzo[b]thiophene-2-sulfonyl)-cyclopropylmethyl-amino]-ethylsulfanyl}-2-methyl-phenoxy)-acetic acid |

-continued

| No. | Structure | Name |
|---|---|---|
| 95 | 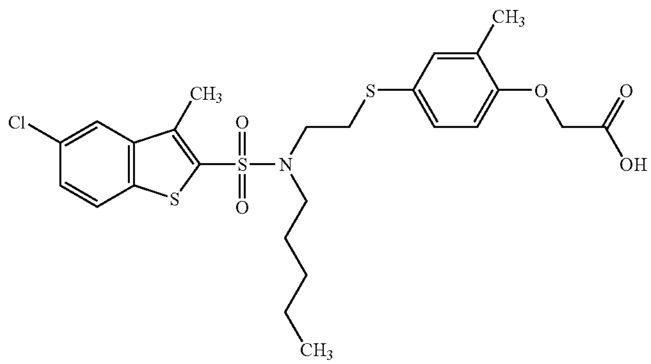 | (4-{2-[(5-Chloro-3-methyl-benzo[b]thiophene-2-sulfonyl)-pentyl-amino]-ethylsulfanyl}-2-methyl-phenoxy)-acetic acid |
| 96 | 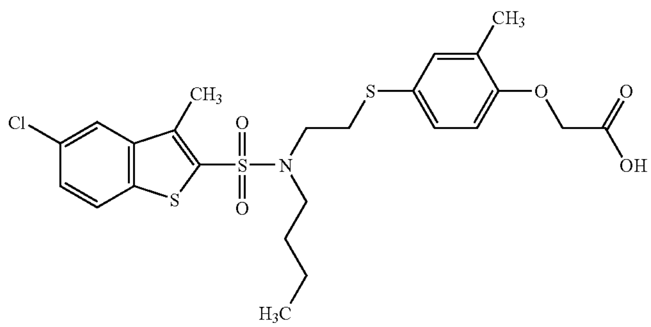 | (4-{2-[Butyl-(5-chloro-3-methyl-benzo[b]thiophene-2-sulfonyl)-amino]-ethylsulfanyl}-2-methyl-phenoxy)-acetic acid |
| 98 | 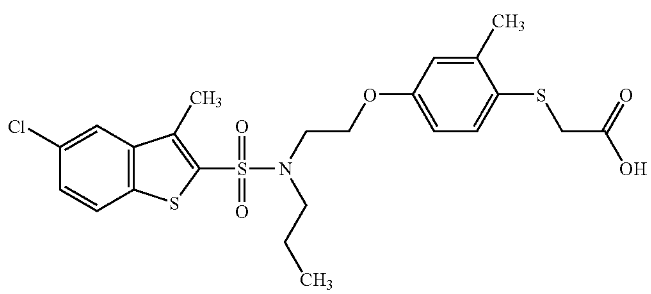 | (4-{2-[(5-Chloro-3-methyl-benzo[b]thiophene-2-sulfonyl)-propyl-amino]-ethoxy}-2-methyl-phenylsulfanyl)-acetic acid |
| 99 | 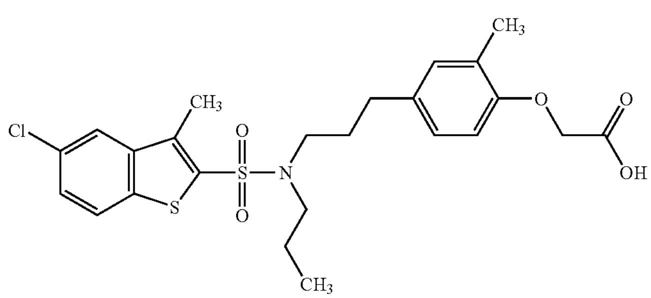 | (4-{3-[(5-Chloro-3-methyl-benzo[b]thiophene-2-sulfonyl)-propyl-amino]-propyl}-2-methyl-phenoxy)-acetic acid |
| 100 | 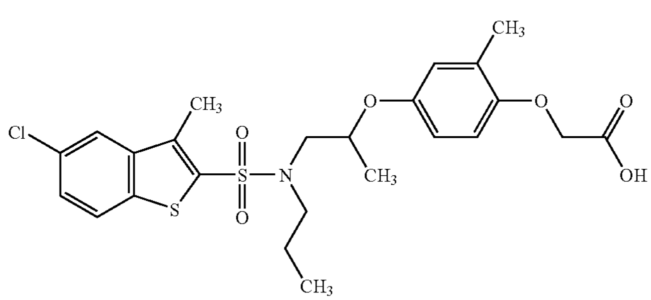 | (4-{2-[(5-Chloro-3-methyl-benzo[b]thiophene-2-sulfonyl)-propyl-amino]-1-methyl-ethoxy}-2-methyl-phenoxy)-acetic acid |

-continued

| No. | Structure | Name |
|---|---|---|
| 101 | 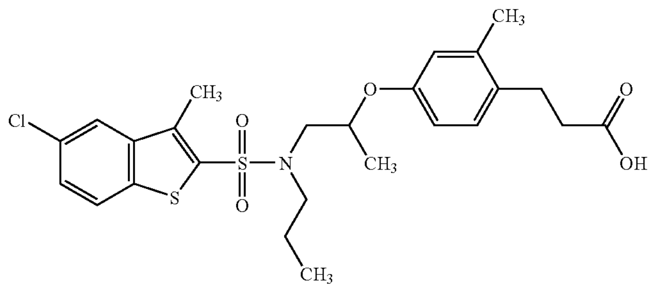 | 3-(4-{2-[(5-Chloro-3-methyl-benzo[b]thiophene-2-sulfonyl)-propyl-amino]-1-methyl-ethoxy}-2-methyl-phenyl)-propionic acid |
| 102 | 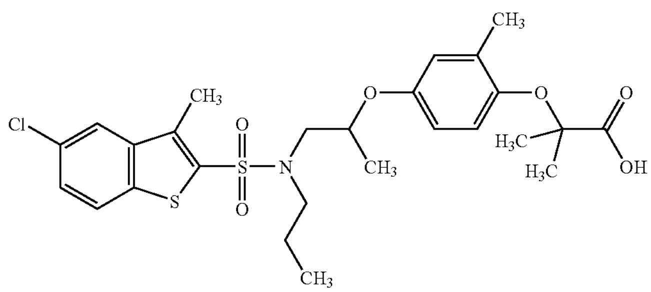 | 2-(4-{2-[(5-Chloro-3-methyl-benzo[b]thiophene-2-sulfonyl)-propyl-amino]-1-methyl-ethoxy}-2-methyl-phenoxy)-2-methyl-propionic acid |
| 103 | 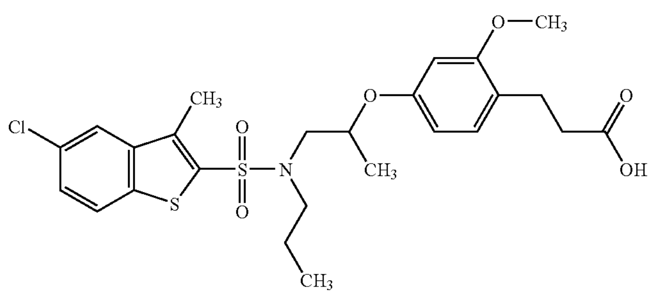 | 3-(4-{2-[(5-Chloro-3-methyl-benzo[b]thiophene-2-sulfonyl)-propyl-amino]-1-methyl-ethoxy}-2-methoxy-phenyl)-propionic acid |
| 104 | 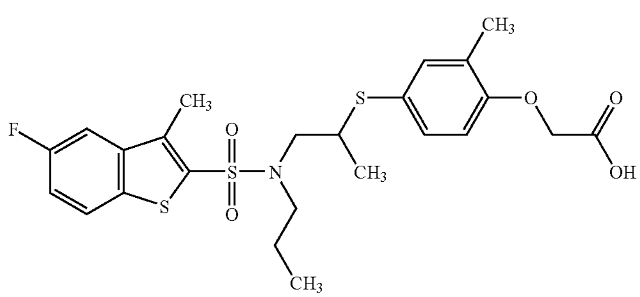 | (4-{2-[(5-Fluoro-3-methyl-benzo[b]thiophene-2-sulfonyl)-propyl-amino]-1-methyl-ethylsulfanyl}-2-methyl-phenoxy)-acetic acid |
| 105 | 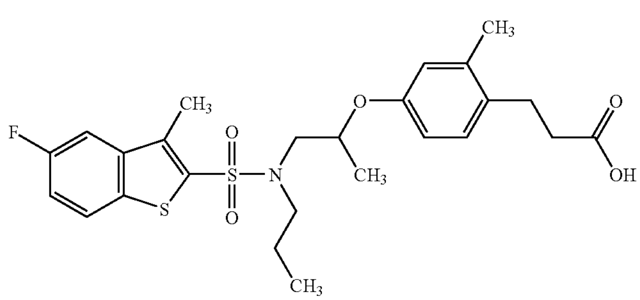 | 3-(4-{2-[(5-Fluoro-3-methyl-benzo[b]thiophene-2-sulfonyl)-propyl-amino]-1-methyl-ethoxy}-2-methyl-phenyl)-propionic acid |

-continued

| No. | Structure | | Name |
|---|---|---|---|
| 106 | 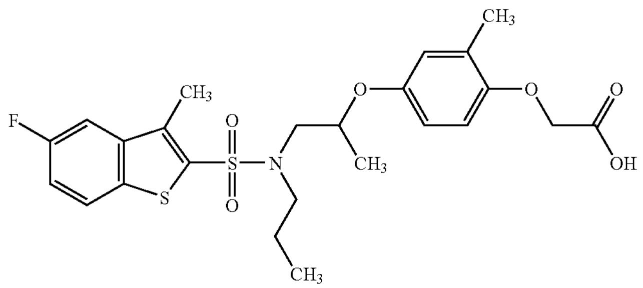 | | (4-{2-[(5-Fluoro-3-methyl-benzo[b]thiophene-2-sulfonyl)-propyl-amino]-1-methyl-ethoxy}-2-methyl-phenoxy)-acetic acid |
| 107 | 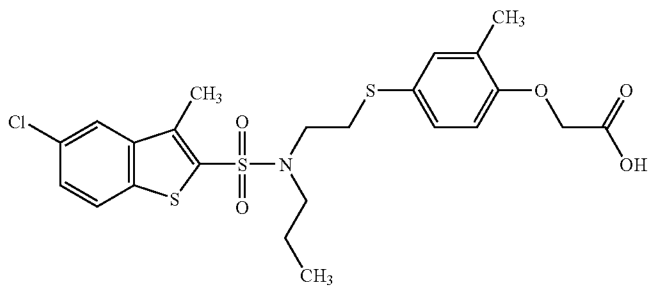 | | (2-Chloro-4-{2-[(5-chloro-3-methyl-benzo[b]thiophene-2-sulfonyl)-propyl-amino]-ethylsulfanyl}-phenoxy)-acetic acid |
| 108 | 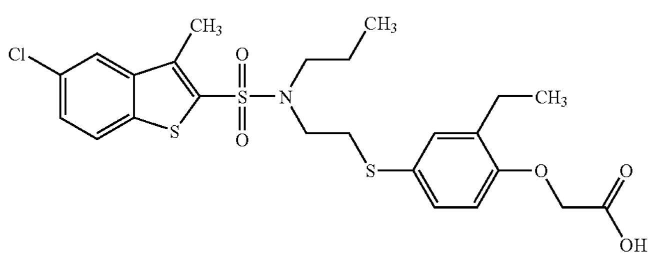 | | (4-{2-[(5-Chloro-3-methyl-benzo[b]thiophene-2-sulfonyl)-propyl-amino]-ethylsulfanyl)-2-ethyl-phenoxy)-acetic acid |
| 112 | 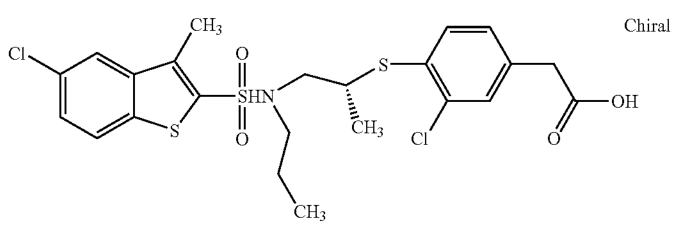 | Chiral | (R)-(3-Chloro-4-{2-[(5-chloro-3-methyl-benzo[b]thiophene-2-sulfonyl)-propyl-amino]-1-methyl-ethylsulfanyl}-phenyl)-acetic acid |
| 113 | 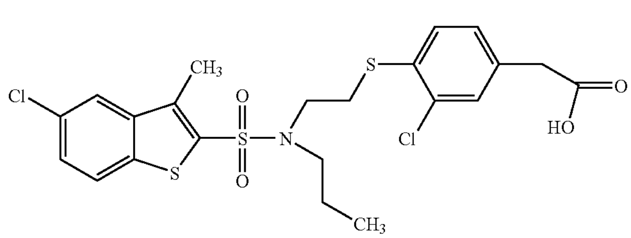 | | (3-Chloro-4-{2-[(5-chloro-3-methyl-benzo[b]thiophene-2-sulfonyl)-propyl-amino]-ethylsulfanyl}-phenyl)-acetic acid |

-continued

| No. | Structure | Name |
|---|---|---|
| 114 | 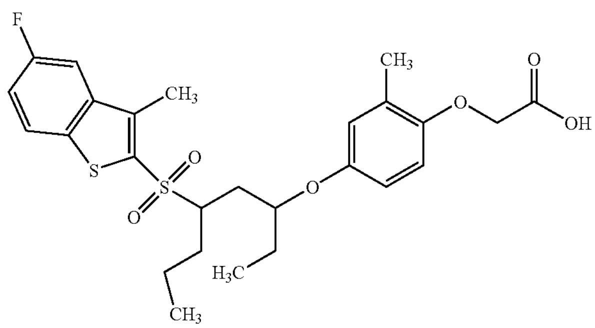 | [4-(1-{[(5-Fluoro-3-methyl-benzo[b]thiophene-2-sulfonyl)-propyl-amino]-methyl}-propoxy)-2-methyl-phenoxy]-acetic acid |
| 115 | 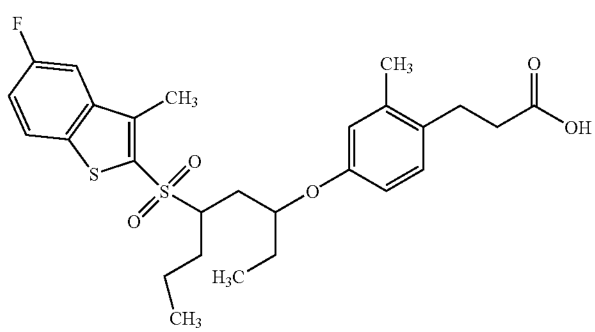 | 3-[4-(1-{[(5-Fluoro-3-methyl-benzo[b]thiophene-2-sulfonyl)-propyl-amino]-methyl}-propoxy)-2-methyl-phenyl]-propionic acid |
| 116 | 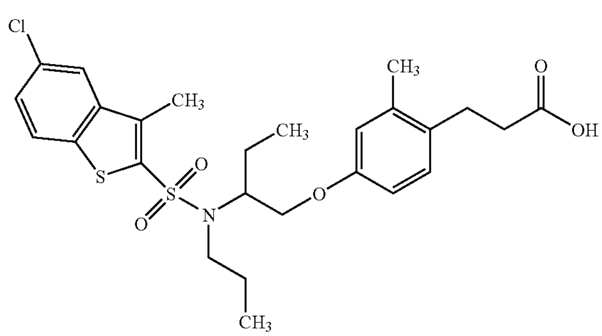 | 3-(4-{2-[(5-Chloro-3-methyl-benzo[b]thiophene-2-sulfonyl)-propyl-amino]-butoxy}-2-methyl-phenyl)-propionic acid |
| 117 | 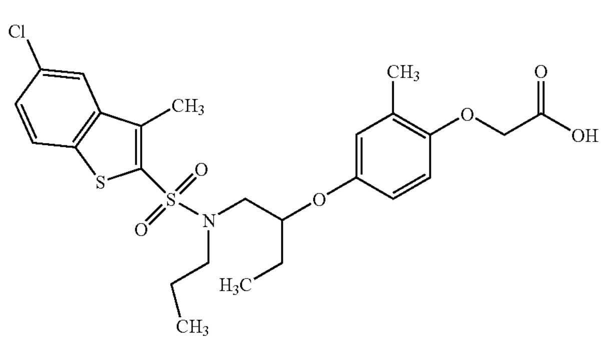 | [4-(1-{[(5-Chloro-3-methyl-benzo[b]thiophene-2-sulfonyl)-propyl-amino]-methyl}-propoxy)-2-methyl-phenoxy]-acetic acid |

-continued

| No. | Structure | Name |
|---|---|---|
| 118 | 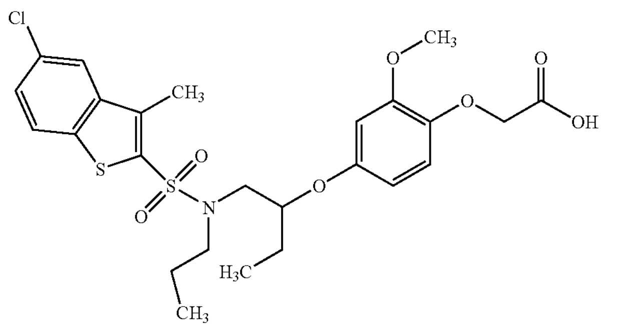 | [4-(1-{[(5-Chloro-3-methyl-benzo[b]thiophene-2-sulfonyl)-propyl-amino]-methyl}-propoxy)-2-methoxy-phenoxy]-acetic acid |
| 119 | 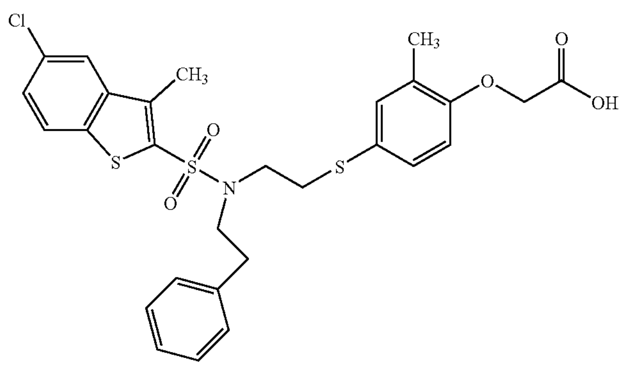 | (4-{2-[(5-Chloro-3-methyl-benzo[b]thiophene-2-sulfonyl)-phenethyl-amino]-ethylsulfanyl}-2-methyl-phenoxy)-acetic acid |
| 120 | 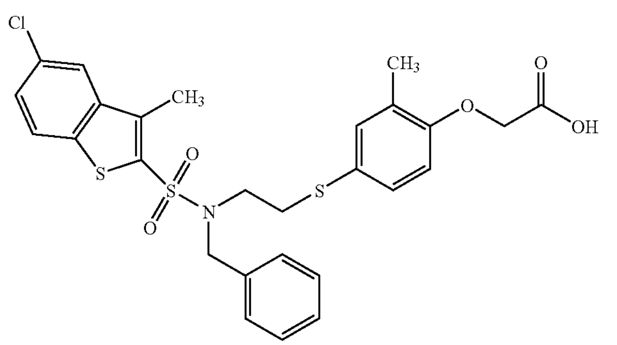 | (4-{2-[Benzyl-(5-chloro-3-methyl-benzo[b]thiophene-2-sulfonyl)-amino]-ethylsulfanyl}-2-methyl-phenoxy)-acetic acid |
| 121 | 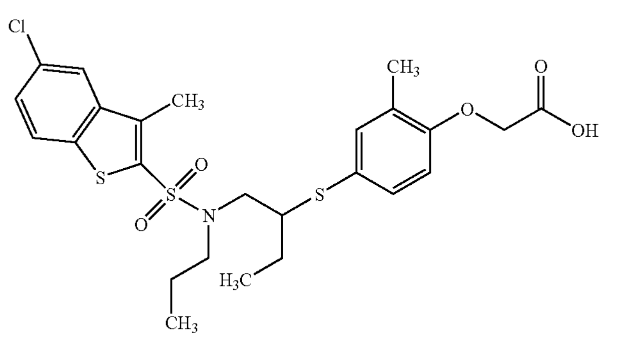 | [4-(1-{[(5-Chloro-3-methyl-benzo[b]thiophene-2-sulfonyl)-propyl-amino]-methyl}-propylsulfanyl)-2-methyl-phenoxy]-acetic acid. |

18. A pharmaceutical composition comprising a pharmaceutically acceptable carrier and at least one compound of claim 1 or pharmaceutically acceptable salts thereof.

19. A method for lowering blood-glucose in a mammal comprising the step of administering an effective amount of at least one compound of claim 1.

* * * * *